United States Patent
Bilotta et al.

(10) Patent No.: US 9,693,997 B2
(45) Date of Patent: Jul. 4, 2017

(54) ANTIVIRAL COMPOUNDS

(71) Applicant: Hoffmann-La Roche Inc., Nutley, NJ (US)

(72) Inventors: Joseph Anthony Bilotta, Nutley, NJ (US); Zhi Chen, Livingston, NJ (US); Feng Chi, Basking Ridge, NJ (US); Elbert Chin, San Mateo, CA (US); Qingjie Ding, Bridgewater, NJ (US); Shawn David Erickson, Leonia, NJ (US); Stephen Deems Gabriel, Morristown, NJ (US); Nan Jiang, Pine Brook, NJ (US); Buelent Kocer, Maulburg (DE); Eric Mertz, Fair lawn, NJ (US); Jean-Marc Plancher, Hagenthal-le-Bas (FR); Robert J. Weikert, Basel (CH); Jing Zhang, Parsippany, NJ (US); Qiang Zhang, East Brunswick, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/768,915

(22) PCT Filed: Mar. 3, 2014

(86) PCT No.: PCT/EP2014/054069
§ 371 (c)(1),
(2) Date: Aug. 19, 2015

(87) PCT Pub. No.: WO2014/135495
PCT Pub. Date: Sep. 12, 2014

(65) Prior Publication Data
US 2016/0000760 A1    Jan. 7, 2016

Related U.S. Application Data

(60) Provisional application No. 61/773,221, filed on Mar. 6, 2013.

(51) Int. Cl.
| | |
|---|---|
| *C07D 249/14* | (2006.01) |
| *C07D 401/12* | (2006.01) |
| *C07D 403/12* | (2006.01) |
| *C07D 405/12* | (2006.01) |
| *C07D 417/12* | (2006.01) |
| *C07D 491/107* | (2006.01) |
| *C07D 495/04* | (2006.01) |
| *A61K 31/4196* | (2006.01) |
| *A61K 31/454* | (2006.01) |
| *A61K 31/428* | (2006.01) |
| *A61K 31/496* | (2006.01) |
| *A61K 31/5377* | (2006.01) |
| *A61K 31/538* | (2006.01) |
| *A61K 31/541* | (2006.01) |
| *A61K 31/5415* | (2006.01) |
| *A61K 45/06* | (2006.01) |

(Continued)

(52) U.S. Cl.
CPC ........ *A61K 31/4196* (2013.01); *A61K 31/428* (2013.01); *A61K 31/454* (2013.01); *A61K 31/496* (2013.01); *A61K 31/538* (2013.01); *A61K 31/5377* (2013.01); *A61K 31/541* (2013.01); *A61K 31/5415* (2013.01); *A61K 45/06* (2013.01); *C07D 249/14* (2013.01); *C07D 401/12* (2013.01); *C07D 403/12* (2013.01); *C07D 405/12* (2013.01); *C07D 411/12* (2013.01); *C07D 413/12* (2013.01); *C07D 417/12* (2013.01); *C07D 491/107* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 6,924,302 B2 * | 8/2005 | Lin | A61K 31/4178 514/383 |
| 8,871,790 B2 | 10/2014 | Oslob et al. | |
| 9,428,469 B2 * | 8/2016 | Ding | C07D 403/12 |

(Continued)

FOREIGN PATENT DOCUMENTS

| | | | | |
|---|---|---|---|---|
| WO | WO 02/057240 | * | 7/2002 | ........... C07D 249/14 |
| WO | 02094814 | | 11/2002 | |

(Continued)

OTHER PUBLICATIONS

"Guidance for Industry: Q3C—Tables and List" (Nov. 2003).*
http://www.cdc.gov/hepatitis/hcv/cfaq.htm, Accessed Nov. 19, 2016.*
The International Search Report and Written Opinion, mailed on Apr. 4, 2014, in the related PCT Appl. No. PCT/EP14/54069.
The Chinese Office Action, mailed on Aug. 23, 2016, in the related Chinese Patent Appl. No. 201480012392.1.
The European Communication, issued on Mar. 9, 2017, in the related European Application No. 14708234.1.

Primary Examiner — Alicia L Otton

(57) ABSTRACT

The present invention discloses compounds of Formula I: wherein the variables in Formula I are defined as described herein. Also disclosed are pharmaceutical compositions containing such compounds and methods for using the compounds of Formula I in the prevention or treatment of HCV infection.

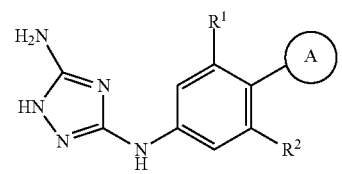

19 Claims, No Drawings

(51) Int. Cl.
*C07D 411/12* (2006.01)
*C07D 413/12* (2006.01)

(56) References Cited

U.S. PATENT DOCUMENTS

2004/0077878 A1 4/2004 Liu
2012/0039847 A1 2/2012 Zhao

FOREIGN PATENT DOCUMENTS

| WO | 2004046120 | 6/2004 |
| WO | 20058012263 | 2/2005 |
| WO | 2014006066 | 1/2014 |
| WO | 2014/135422 | 9/2014 |
| WO | 2014/135471 | 9/2014 |

\* cited by examiner

ANTIVIRAL COMPOUNDS

This application is a National Stage Application of PCT/EP2014/054069 filed Mar. 3, 2014, which claims priority from U.S. Provisional Patent Application No. 61/773,221, filed on Mar. 6, 2013. The priority of both said PCT and U.S. Provisional Patent Application are claimed. Each of the prior mentioned applications is hereby incorporated by reference herein in its entirety.

The present invention provides compounds of Formula I useful as inhibitors of hepatitis C virus (HCV), as inhibitors of HCV infection, and for the prevention and treatment of hepatitis C infection.

Hepatitis C virus (HCV) infection is a major health problem that affects 170 million people worldwide and 3-4 million people in the United States (Armstrong, G. L., et al., Ann. Intern. Med. 2006, 144:705-714; Lauer, G. M., et al., N. Eng. J. Med. 2001, 345:41-52). HCV infection leads to chronic liver disease, such as cirrhosis and hepatocellular carcinoma in a substantial number of infected individuals. Chronic HCV infection associated liver cirrhosis and hepatocellular carcinoma are also the leading cause of liver transplantation in the United States. Current treatments for HCV infection include immunotherapy with pegylated interferon-α in combination with the nucleoside-analog ribavirin. Pegylated interferon-α in combination with ribavirin and one of the two recently approved HCV NS3 protease inhibitors Incivek or Victrelis is the current standard of care for the treatment of genotype 1 HCV infected patients, the most difficult to treat patient population. However, current HCV treatments are compromised by suboptimal sustained virological response rates and associated with severe side effects, as well as resistance to the protease inhibitors. Therefore there is a clear need for improved antiviral drugs with better efficacy, safety, and resistance profiles.

The infection of human hepatocytes by HCV, also known as HCV entry, is mediated by the functional interactions of virally-encoded envelope glycoproteins E1 and E2 and host cell co-receptors, followed by a receptor-mediated endocytosis processes. This HCV entry step is a putative target for therapeutic intervention. Several virally-encoded enzymes are also putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

Systems have been developed to study the biology of HCV entry into host cells. Pseudotyping systems where the E1 and E2 glycoproteins are used to functionally replace the glycoproteins of retroviruses have been developed (Bartosch, B., Dubuisson, J. and Cosset, F.-L. J. Exp. Med. 2003, 197:633-642; Hsu, M. et al. Proc. Natl. Acad. Sci. USA. 2003, 100:7271-7276). These systems yield HCV pseudoparticles that bind to and enter host cells in a manner which is believed to be analogous to the natural virus, thus making them a convenient tool to study the viral entry steps as well as to identify inhibitors blocking this process.

There is a clear and long-felt need to develop effective therapeutics for treatment of HCV infection. Specifically, there is a need to develop compounds that selectively inhibit HCV viral entry and replication and that are useful for treating HCV-infected patients and protecting liver transplant patients from HCV re-infection. This application discloses novel compounds that are effective in prevention of HCV infection. Additionally, the disclosed compounds provide advantages for pharmaceutical uses, for example, with respect to their mechanism of action, binding, prevention of infection, inhibition efficacy, and target selectivity.

SUMMARY OF THE INVENTION

The application provides compound of formula I

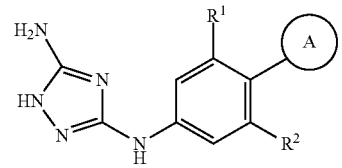

wherein:

A is pheny, naphthyl, or bicyclic unsaturated or partially saturated heteroaryl, optionally substituted with one or more A';

each A' is independently lower alkyl, halo, lower alkoxy, $S(=O)_2(CH_2)_mA''$, $C(=O)NHA''$, $NHC(=O)A''$, $-O(CH_2)_mA''$, $(CHA^1)_mNHS(=O)_2A^1$; or $S(=O)_2NHA''$;

each A" is independently lower alkyl, heterocycloalkyl or heteroaryl, optionally substituted with one or more A''';

each A''' is independently hydroxy, lower alkyl, oxo, $C(=O)OA^1$, halo loweralkyl, each $A^1$ is independently H, lower alkyl, halo loweralkyl, amino, lower alkoxy, each m is independently 0, 1, 2, or 3;

$R^1$ is H, halo, lower alkyl, halo loweralkyl, $SF_5$, $R^2$ is H, halo, lower alkyl, halo loweralkyl, or a pharmaceutically acceptable salt thereof.

The application provides a method for preventing a Hepatitis C Virus (HCV) infection comprising administering to a patient in need thereof a therapeutically effective amount of a compound of Formula I.

The application provides a method for treating a Hepatitis C Virus (HCV) infection comprising administering to a patient in need thereof a therapeutically effective amount of a compound of Formula I.

The application provides a composition comprising a compound of Formula I and a pharmaceutically acceptable excipient.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "- - - - - -" drawn through a bond each refer to the point of attachment of a functional group or other chemical moiety to the rest of the molecule of which it is a part. Thus, for example:

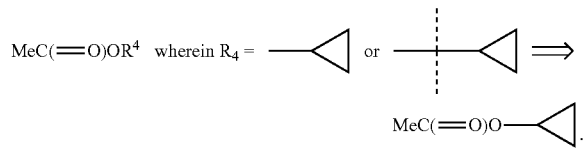

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

If a substituent is designated to be "absent", the substituent is not present.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-☐-C(—OH)=CH—), amide/imidic acid (—C(=O)—NH-☐-C(—OH)=N—) and amidine (—C(=NR)—NH-☐-C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "carbonyl" or "acyl" as used herein denotes a group of formula —C(=O)R wherein R is hydrogen or lower alkyl as defined herein.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —$CH_2CH(i-Pr)CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The terms "haloalkoxy" or "halo lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The term "sulfinyl" as used herein denotes a —SO— group.

The term "sulfonyl" as used herein denotes a —$SO_2$— group.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "lower alkyl sulfonylamido" as used herein refers to a group of formula —S(=O)$_2$NR$_2$ wherein each R is independently hydrogen or $C_{1-3}$ alkyl, and lower alkyl is as defined herein.

The term "trifluoromethyl sulfonyl" as used herein refers to a group of formula —S(=O)$_2$CF$_3$.

The term "trifluoromethyl sulfinyl" as used herein refers to a group of formula —S(=O)CF The term "trifluoromethyl sulfanyl" as used herein refers to a group of formula —SCF$_3$.

The term "nitro" as used herein refers to a group of formula —N$^+$(=O)O$^-$.

The term "carboxyl" as used herein refers to a group of formula —C(=O)R$_2$ wherein each R is independently hydrogen or $C_{1-3}$ alkyl, and lower alkyl is as defined herein.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "amino" as used herein denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "amido" as used herein denotes a group of the formula —C(=O)NR'R" or —NR'C(=O)R" wherein R' and R" are independently hydrogen, alkyl, alkoxy, cycloalkyl, heterocycloalkyl, aryl or heteroaryl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

Inhibitors of HCV Entry

The application provides a compound of formula I

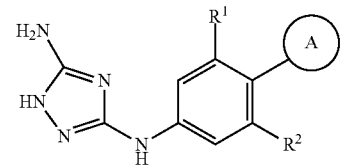

wherein:

A is pheny, naphthyl, or bicyclic unsaturated or partially saturated heteroaryl, optionally substituted with one or more A';

each A' is independently lower alkyl, halo, lower alkoxy, $S(=O)_2(CH_2)_mA''$, $C(=O)NHA''$, $NHC(=O)A''$, $-O(CH_2)_mA''$, $(CHA^1)_mNHS(=O)_2A^1$; or $S(=O)_2NHA''$;

each A" is independently lower alkyl, heterocycloalkyl or heteroaryl, optionally substituted with one or more A''';

each A''' is independently hydroxy, lower alkyl, oxo, $C(=O)OA^1$, halo loweralkyl, each $A^1$ is independently H, lower alkyl, halo loweralkyl, amino, lower alkoxy, each m is independently 0, 1, 2, or 3;

$R^1$ is H, halo, lower alkyl, halo loweralkyl, $SF_5$, $R^2$ is H, halo, lower alkyl, halo loweralkyl, or a pharmaceutically acceptable salt thereof.

The application provides a compound of formula I, wherein A is phenyl.

The application provides a compound of formula I, wherein $R^1$ is halo loweralkyl.

The application provides a compound of formula I, wherein $R^2$ is halo.

The application provides a compound of formula I, wherein $R^1$ is halo.

The application provides a compound of formula I, wherein $R^2$ is halo.

The application provides a compound of formula I, wherein A' is $S(=O)_2(CH_2)_mA''$ or $(CH_2)_mS(=O)_2A''$.

The application provides a compound of formula I, wherein A' is lower alkyl, halo, or lower alkoxy.

The application provides a compound of formula I, wherein A' is $C(=O)NHA''$ or $NHC(=O)A''$.

The application provides a compound of formula I, wherein A' is $(CHA^1)_mNHS(=O)_2A^1$ or $S(=O)_2NHA''$.

The application provides a compound of formula I, wherein A' is $O(CH_2)_mA''$.

The application provides a compound of formula I, selected from the group consisting of:

4-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester;

3-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester;

(S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid tert-butyl ester;

$N^3$-{6-Chloro-2-trifluoromethyl-4'-[1-(3,3,3-trifluoro-propyl)-piperidine-4-sulfonyl]-biphenyl-4-yl}-1H-[1,2,4]triazole-3,5-diamine;

$N^3$-{6-Chloro-4'-[1-(3,3-dimethyl-butyl)-piperidine-4-sulfonyl]-2-trifluoromethyl-biphenyl-4-yl}-1H-[1,2,4]triazole-3,5-diamine;

3-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester;

4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester;

4'-(5-Amino-1H-[1,2,4]triazol-3-ylamino)-2',6'-dichloro-biphenyl-4-carboxylic acid tert-butyl amide;

Pentanoic acid [4'-(5-amino-1H-[1,2,4]triazol-3-ylamino)-2',6'-dichloro-biphenyl-4-yl]-amide;

$N^3$-[4-(2-tert-Butyl-1,1-dioxo-2,3-dihydro-1H-1$\lambda^6$-benzo[d]isothiazol-6-yl)-3-chloro-5-trifluoromethyl-phenyl]-1H-[1,2,4]triazole-3,5-diamine;

$N^3$-{6-Chloro-2-trifluoromethyl-4'-[1-(3,3,3-trifluoro-propyl)-piperidine-3-sulfonyl]-biphenyl-4-yl}-1H-[1,2,4]triazole-3,5-diamine;

N-[4'-(5-Amino-1H-[1,2,4]triazol-3-ylamino)-2',6'-dichloro-biphenyl-4-ylmethyl]-methanesulfonamide;

N—{(S)-1-[4'-(5-Amino-1H-[1,2,4]triazol-3-ylamino)-2'-chloro-6'-trifluoromethyl-biphenyl-4-yl]-ethyl}-methanesulfonamide;

$N^3$-(2,6-Dichloro-4'-methanesulfonyl-3'-trifluoromethyl-biphenyl-4-yl)-1H-[1,2,4]triazole-3,5-diamine;

$N^3$-[3,5-Dichloro-4-(1-methanesulfonyl-1H-indol-4-yl)-phenyl]-1H-[1,2,4]triazole-3,5-diamine;

4-[4'-(5-Amino-1H-[1,2,4]triazol-3-ylamino)-2'-chloro-6'-trifluoromethyl-biphenyl-4-sulfonyl]-piperazine-1-carboxylic acid tert-butyl ester;

$N^3$-{6-Chloro-4'-[1-(3,3-dimethyl-butyl)-piperidine-3-sulfonyl]-2-trifluoromethyl-biphenyl-4-yl}-1H-[1,2,4]triazole-3,5-diamine;

4'-(5-Amino-1H-[1,2,4]triazol-3-ylamino)-2'-chloro-4-methyl-6'-trifluoromethyl-biphenyl-3-sulfonic acid tert-butylamide;

$N^3$-[2-Chloro-4'-methoxy-3'-(propane-2-sulfonyl)-6-trifluoromethyl-biphenyl-4-yl]-1H-[1,2,4]triazole-3,5-diamine;

$N^3$-[2-Chloro-4'-(piperidine-4-sulfonyl)-6-trifluoromethyl-biphenyl-4-yl]-1H-[1,2,4]triazole-3,5-diamine;

4-[4'-(5-Amino-1H-[1,2,4]triazol-3-ylamino)-2'-chloro-6'-trifluoromethyl-biphenyl-3-yloxy]-piperidine-1-carboxylic acid tert-butyl ester;

$N^3$-[2-Chloro-4'-(4-methyl-piperazine-1-sulfonyl)-6-trifluoromethyl-biphenyl-4-yl]-1H-[1,2,4]triazole-3,5-diamine;

N-[2-Chloro-6-fluoro-4'-(propane-2-sulfonyl)-biphenyl-4-yl]-1H-[1,2,4]triazole-3,5-diamine;

N—{(R)-1-[4'-(5-Amino-1H-[1,2,4]triazol-3-ylamino)-2'-chloro-6'-trifluoromethyl-biphenyl-4-yl]-ethyl}-methanesulfonamide;

$N^3$-[2-Chloro-4'-(piperidin-3-ylmethanesulfonyl)-6-trifluoromethyl-biphenyl-4-yl]-1H-[1,2,4]triazole-3,5-diamine;

4-[4'-(5-Amino-1H-[1,2,4]triazol-3-ylamino)-2',6'-dichloro-biphenyl-4-yloxy]-butyronitrile;

4'-(5-Amino-1H-[1,2,4]triazol-3-ylamino)-2'-chloro-6'-trifluoromethyl-biphenyl-4-sulfonic acid ((S)-1-pyrolidin-2-ylmethyl)-amide;

N-[4'-(5-Amino-1H-[1,2,4]triazol-3-ylamino)-2',6'-dichloro-2-fluoro-biphenyl-4-yl]-methanesulfonamide;

$N^3$-[2-Chloro-4'-(piperidine-3-sulfonyl)-6-trifluoromethyl-biphenyl-4-yl]-1H-[1,2,4]triazole-3,5-diamine;

$N^3$-(2-Chloro-6-fluoro-4'-methanesulfonyl-biphenyl-4-yl)-1H-[1,2,4]triazole-3,5-diamine;

$N^3$-(2,6-Dichloro-4'-methanesufonylmethyl-biphenyl-4-yl)-1H-[1,2,4]triazole-3,5-diamine;

$N^3$-[4'-(Azetidin-3-ylmethoxy)-2,6-dichloro-biphenyl-4-yl]-1H-[1,2,4]triazole-3,5-diamine;

$N^3$-[2-Chloro-4'-(piperazine-1-sulfonyl)-6-trifluoromethyl-biphenyl-4-yl]-1H-[1,2,4]triazole-3,5-diamine;

4'(5-Amino-1H-[1,2,4]triazol-3-ylamino)-2'-chloro-6'-fluoro-biphenyl-4-sulfonic acid dimethylamide;

$N^3$-[2-Chloro-4'-((S)-1-pyrrolidin-2-ylmethanesulfonyl)-6-trifluoromethyl-biphenyl-4-yl]-1H-[1,2,4]triazole-3,5-diamine;

$N^3$-[2-Chloro-4'-(morpholine-4-sulfonyl)-6-trifluoromethyl-biphenyl-4-yl]-1H-[1,2,4]triazole-3,5-diamine;

$N^3$-[4'-(Azetidin-3-ylmethoxy)-2-chloro-6-trifluoromethyl-biphenyl-4-yl]-1H-[1,2,4]triazole-3,5-diamine;

N-{2-[4'-(5-Amino-1H-[1,2,4]triazol-3-ylamino)-2'-chloro-6'-trifluoromethyl-biphenyl-4-yl]-ethyl}-methanesulfonamide;

5-((3aR,6S,6aS)-2-Oxo-hexahydro-thieno[3,4-d]imidazol-6-yl)-pentanoic acid [4'-(5-amino-1H-[1,2,4]triazol-3-ylamino)-2',6'-dichloro-biphenyl-4-yl]-amide;

$N^3$-[2-Chloro-4'-(piperidin-4-ylmethanesulfonyl)-6-trifluoromethyl-biphenyl-4-yl]-1H-[1,2,4]triazole-3,5-diamine;

$N^3$-[2-Chloro-3'-(piperidin-4-yloxy)-6-trifluoromethyl-biphenyl-4-yl]-1H-[1,2,4]triazole-3,5-diamine;

$N^3$-[3,5-Dichloro-4-(1-methanesulfonyl-1H-indol-5-yl)-phenyl]-1H-[1,2,4]triazole-3,5-diamine;

1-[4'-(5-Amino-1H-[1,2,4]triazol-3-ylamino)-2',6'-dichloro-biphenyl-4-yl]-pyrrolidin-2-one;

$N^3$-[3-Chloro-4-(4-methanesulfonyl-3,4-dihydro-2H-benzo[1,4]oxazin-6-yl)-5-trifluoromethyl-phenyl]-1H-[1,2,4]triazole-3,5-diamine;

$N^3$-[2-Chloro-4'-(1,1-dioxo-1$\lambda^6$-thiomorpholine-4-sulfonyl)-6-trifluoromethyl-biphenyl-4-yl]-1H-[1,2,4]triazole-3,5-diamine;

N-[4'-(5-Amino-1H-[1,2,4]triazol-3-ylamino)-2',6'-dichloro-3-fluoro-biphenyl-4-yl]-methanesulfonamide;

6-[4-(5-Amino-1H-[1,2,4]triazol-3-ylamino)-2-chloro-6-trifluoromethyl-phenyl]-4H-benzo[1,4]oxazin-3-one;

$N^3$-(2,6-Dichloro-biphenyl-4-yl)-1H-[1,2,4]triazole-3,5-diamine;

$N^3$-[4'-(4-Amino-butoxy)-2,6-dichloro-biphenyl-4-yl]-1H-[1,2,4]triazole-3,5-diamine;
compound with trifluoro-acetic acid;

$N^3$-(4'-Amino-2,6-dichloro-biphenyl-4-yl)-1H-[1,2,4]triazole-3,5-diamine;

(S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid;

$N^3$-[3,5-Dichloro-4-(2,2-dimethyl-4,4-dioxo-3,4-dihydro-2H-4$\lambda^6$-benzo[1,4]oxathiin-6-yl)-phenyl]-1H-[1,2,4]triazole-3,5-diamine;

Pentanoic acid [4'-(5-amino-1H-[1,2,4]triazol-3-ylamino)-biphenyl-4-yl]-amide;

5-((3aR,6S,6aS)-2-Oxo-hexahydro-thieno[3,4-d]imidazol-6-yl)-pentanoic acid [4'-(5-amino-1H-[1,2,4]triazol-3-ylamino)-biphenyl-4-yl]-amide;

$N^3$-Biphenyl-4-yl-1H-[1,2,4]triazole-3,5-diamine;

$N^3$-{6-Chloro-4'-[1-(3,3-dimethyl-butyl)-piperidin-3-ylmethanesulfonyl]-2-trifluoromethyl-biphenyl-4-yl}-1H-[1,2,4]triazole-3,5-diamine;

$N^3$-{6-Chloro-4'-[1-(3,3-dimethyl-butyl)-piperidin-4-ylmethanesulfonyl]-2-trifluoromethyl-biphenyl-4-yl}-1H-[1,2,4]triazole-3,5-diamine;

$N^3$-[4'-(tert-Butyl amino-methyl)-2-chloro-6-trifluoromethyl-biphenyl-4-yl]-1H-[1,2,4]triazole-3,5-diamine;

3-[4'-(5-Amino-1H-[1,2,4]triazol-3-ylamino)-6'-cloro-2'-trifluoromethyl-biphenyl-4-sulfonyl]-azetidine-1-carboxylic acid tert-butyl ester;

4'-(5-Amino-1H-[1,2,4]triazol-3-ylamino)-6'-chloro-2'-trifluoromethyl-biphenyl-4-sulfonic acid (3-methyl-oxetan-3-yl)-amide;

$N^3$-[6-Chloro-4'-(3-methyl-butane-1-sulfonyl)-2-trifluoromethyl-biphenyl-4-yl]-1H-[1,2,4]triazole-3,5-diamine;

$N^3$-[6-Chloro-4'-(3,3-difluoro-pyrrolidine-1-sulfonyl)-2-trifluoromethyl-biphenyl-4-yl]-1H-[1,2,4]triazole-3,5-diamine;

1-[4'-(5-Amino-1H-[1,2,4]triazol-3-ylamino)-6'-chloro-2'-trifluoromethyl-biphenyl-4-sulfonyl]-3-methyl-azetidin-3-ol;

$N^3$-(6-Chloro-4'-cyclopropylmethanesulfonyl-2-trifluoromethyl-biphenyl-4-yl)-1H-[1,2,4]triazole-3,5-diamine;

$N^3$-[6-Chloro-4'-(2-methyl-propane-1-sulfonyl)-2-trifluoromethyl-biphenyl-4-yl]-1H-[1,2,4]triazole-3,5-diamine;

1-[4'-(5-Amino-1H-[1,2,4]triazol-3-ylamino)-6'-chloro-2'-trifluoromethyl-biphenyl-4-sulfonyl]-4-methyl-piperidin-4-ol;

$N^3$-[4'-(Azetidine-3-sulfonyl)-6-chloro-2-trifluoromethyl-biphenyl-4-yl]-1H-[1,2,4]triazole-3,5-diamine;

1-[4'-(5-Amino-1H-[1,2,4]triazol-3-ylamino)-6'-chloro-2'-trifluoromethyl-biphenyl-4-sulfonyl]-3-methyl-pyrrolidin-3-ol;

$N^3$-[6-Chloro-4'-(2-oxa-6-aza-spiro[3.3]heptane-6-sulfonyl)-2-trifluoromethyl-biphenyl-4-yl]-1H-[1,2,4]triazole-3,5-diamine;

$N^5$-(2-Fluoro-4'-methanesulfonyl-6-trifluoromethyl-biphenyl-4-yl)-1H-[1,2,4]triazole-3,5-diamine;

$N^5$-[2-Fluoro-4'-(propane-2-sulfonyl)-6-trifluoromethyl-biphenyl-4-yl]-1H-[1,2,4]triazole-3,5-diamine;

4'-(5-Amino-2H-[1,2,4]triazol-3-ylamino)-2'-fluoro-6'-trifluoromethyl-biphenyl-4-sulfonic acid methylamide;

N-[4'-(5-Amino-1H-[1,2,4]triazol-3-ylamino)-2',6'-dichloro-biphenyl-4-yl]-2-methoxy-acetamide;

$N^5$-(2-Fluoro-3'-methanesulfonyl-6-trifluoromethyl-biphenyl-4-yl)-1H-[1,2,4]triazole-3,5-diamine;

4'-(5-Amino-2H-[1,2,4]triazol-3-ylamino)-2'-fluoro-6'-trifluoromethyl-biphenyl-4-sulfonic acid dimethylamide;

$N^5$-(2,6-Difluoro-4'-methanesulfonyl-biphenyl-4-yl)-1H-[1,2,4]triazole-3,5-diamine;

$N^5$-[2,6-Difluoro-4'-(morpholine-4-sulfonyl)-biphenyl-4-yl]-1H-[1,2,4]triazole-3,5-diamine;

$N^5$-[2-Fluoro-4'-(morpholine-4-sulfonyl)-6-trifluoromethyl-biphenyl-4-yl]-1H-[1,2,4]triazole-3,5-diamine;

4'-(5-Amino-2H-[1,2,4]triazol-3-ylamino)-2'-fluoro-6'-trifluoromethyl-biphenyl-4-carbonitrile;

$N^5$-(2,6-Difluoro-3'-methanesulfonyl-biphenyl-4-yl)-1H-[1,2,4]triazole-3,5-diamine;

4'-(5-Amino-2H-[1,2,4]triazol-3-ylamino)-2'-fluoro-6'-trifluoromethyl-biphenyl-3-sulfonic acid methylamide;

Tetrahydro-pyran-4-carboxylic acid [4'-(5-amino-1H-[1,2,4]triazol-3-ylamino)-2',6'-dichloro-biphenyl-4-yl]-amide;

$N^3$-(2,6-Dichloro-4'-nitro-biphenyl-4-yl)-1H-[1,2,4]triazole-3,5-diaminetrifluoro-acetic acid;

4'-(5-Amino-2H-[1,2,4]triazol-3-ylamino)-2'-fluoro-6'-trifluoromethyl-biphenyl-3-sulfonic acid dimethylamide;

4'-(5-Amino-2H-[1,2,4]triazol-3-ylamino)-2'-fluoro-6'-trifluoromethyl-biphenyl-4-carboxylic acid dimethylamide;

$N^5$-(2-Fluoro-4'-methoxy-6-trifluoromethyl-biphenyl-4-yl)-1H-[1,2,4]triazole-3,5-diamine;

4'-(5-Amino-2H-[1,2,4]triazol-3-ylamino)-2',6'-difluoro-biphenyl-4-carbonitrile;

$N^5$-(2-Fluoro-4'-trifluoromethanesulfonyl-6-trifluoromethyl-biphenyl-4-yl)-1H-[1,2,4]triazole-3,5-diamine;

4'-(5-Amino-2H-[1,2,4]triazol-3-ylamino)-2'-fluoro-6'-trifluoromethyl-biphenyl-3-carbonitrile;

$N^3$-(4-Methanesulfonyl-2-trifluoromethyl-biphenyl-4-yl)-1H-[1,2,4]triazole-3,5-diamine;

$N^3$-(2,6-Dichloro-4'-trifluoromethoxy-biphenyl-4-yl)-1H-[1,2,4]triazole-3,5-diamine;

$N^3$-(2,6,3'-Trichloro-biphenyl-4-yl)-1H-[1,2,4]triazole-3,5-diamine;

4'-(5-Amino-1H-[1,2,4]triazol-3-ylamino)-2',6'-dichloro-biphenyl-4-carbonitrile;

$N^3$-(2,6-Dichloro-4'-methanesulfonyl-biphenyl-4-yl)-1H-[1,2,4]triazole-3,5-diamine;

$N^3$-(3,5-Dichloro-4-naphthalen-1-yl-phenyl)-1H-[1,2,4]triazole-3,5-diamine;

$N^3$-(2,6,4'-Trichloro-biphenyl-4-yl)-1H-[1,2,4]triazole-3,5-diamine;

$N^3$-(2,6-Dichloro-4'-methyl-biphenyl-4-yl)-1H-[1,2,4]triazole-3,5-diamine;

N³-(2,6-Dichloro-4'-methoxy-biphenyl-4-yl)-1H-[1,2,4]triazole-3,5-diamine;
N³-(2,6-Dichloro-4'-trifluoromethyl-biphenyl-4-yl)-1H-[1,2,4]triazole-3,5-diamine;
N³-(2,6-Dichloro-3'-methoxy-biphenyl-4-yl)-1H-[1,2,4]triazole-3,5-diamine;
N³-(2,6,2'-Trichloro-biphenyl-4-yl)-1H-[1,2,4]triazole-3,5-diamine;
N³-(2,6,3',4'-Tetrachloro-biphenyl-4-yl)-1H-[1,2,4]triazole-3,5-diamine;
4'-(5-Amino-1H-[1,2,4]triazol-3-ylamino)-2',6'-dichloro-biphenyl-3-carbonitrile;
4'-(5-Amino-1H-[1,2,4]triazol-3-ylamino)-2',6'-dichloro-biphenyl-2-carbonitrile;
4'-(5-Amino-1H-[1,2,4]triazol-3-ylamino)-4,2',6'-trichloro-biphenyl-3-carbonitrile;
4'-(5-Amino-1H-[1,2,4]triazol-3-ylamino)-2',6'-dichloro-biphenyl-3-carboxylic acid;
1-[4'-(5-Amino-1H-[1,2,4]triazol-3-ylamino)-2',6'-dichloro-biphenyl-4-yl]-ethanone;
N³-(2,6-Dichloro-3'-trifluoromethyl-biphenyl-4-yl)-1H-[1,2,4]triazole-3,5-diamine;
N³-(2,6,2',3'-Tetrachloro-biphenyl-4-yl)-1H-[1,2,4]triazole-3,5-diamine;
4'-(5-Amino-1H-[1,2,4]triazol-3-ylamino)-2',6'-dichloro-biphenyl-4-carboxylic acid methyl ester;
N-[4'-(5-Amino-1H-[1,2,4]triazol-3-ylamino)-2',6'-dichloro-biphenyl-4-yl]-methanesulfonamide;
N-[4'-(5-Amino-1H-[1,2,4]triazol-3-ylamino)-2',6'-dichloro-biphenyl-3-yl]-methanesulfonamide;
4'-(5-Amino-1H-[1,2,4]triazol-3-ylamino)-2',6'-dichloro-biphenyl-4-carboxylic acid dimethylamide;
N³-(2,6-Dichloro-3'-methanesulfonyl-biphenyl-4-yl)-1H-[1,2,4]triazole-3,5-diamine;
4'-(5-Amino-1H-[1,2,4]triazol-3-ylamino)-2',6'-dichloro-biphenyl-3-carboxylic acid dimethylamide;
4'-(5-Amino-1H-[1,2,4]triazol-3-ylamino)-2',6'-dichloro-biphenyl-4-carboxylic acid methylamide;
4'-(5-Amino-1H-[1,2,4]triazol-3-ylamino)-2',6'-dichloro-biphenyl-3-carboxylic acid methylamide;
4'-(5-Amino-1H-[1,2,4]triazol-3-ylamino)-2',6'-dichloro-biphenyl-4-sulfonic acid methylamide;
4'-(5-Amino-1H-[1,2,4]triazol-3-ylamino)-2',6'-dichloro-biphenyl-3-sulfonic acid methylamide;
N³-(2,6-Dichloro-2'-methoxy-biphenyl-4-yl)-1H-[1,2,4]triazole-3,5-diamine;
N³-(2,6-Dichloro-3'-fluoro-4'-methanesulfonyl-biphenyl-4-yl)-1H-[1,2,4]triazole-3,5-diamine;
N³-[2,6-Dichloro-4'-(propane-2-sulfonyl)-biphenyl-4-yl]-1H-[1,2,4]triazole-3,5-diamine;
4'-(5-Amino-1H-[1,2,4]triazol-3-ylamino)-2',6'-dichloro-biphenyl-4-sulfonic acid dimethylamide;
N³-(2,6,2',4'-Tetrachloro-biphenyl-4-yl)-1H-[1,2,4]triazole-3,5-diamine;
{2-[4'-(5-Amino-1H-[1,2,4]triazol-3-ylamino)-6'-chloro-2'-trifluoromethyl-biphenyl-4-yloxy]-ethyl}-methyl-carbamic acid tert-butyl ester;
N³-[6-Chloro-4'-(2-methylamino-ethoxy)-2-trifluoromethyl-biphenyl-4-yl]-1H-[1,2,4]triazole-3,5-diamine;
N³-[6-Chloro-4'-(1,2,2,6,6-pentamethyl-piperidin-4-ylsulfanyl)-2-trifluoromethyl-biphenyl-4-yl]-1H-[1,2,4]triazole-3,5-diamine;
{2-[4'-(5-Amino-1H-[1,2,4]triazol-3-ylamino)-6'-cloro-2'-trifluoromethyl-biphenyl-4-yloxy]-1,1-dimethyl-ethyl}-methyl-carbamic acid tert-butyl ester;
3-[4'-(5-Amino-1H-[1,2,4]triazol-3-ylamino)-6'-chloro-2'-trifluoromethyl-biphenyl-4-yloxy]-piperidine-1-carboxylic acid tert-butyl ester;
N³-[6-Chloro-4'-(piperidin-3-yloxy)-2-trifluoromethyl-biphenyl-4-yl]-1H-[1,2,4]triazole-3,5-diamine;
N³-{6-Chloro-4'-[1-(3,3-dimethyl-butyl)-piperidin-3-yloxy]-2-trifluoromethyl-biphenyl-4-yl}-1H-[1,2,4]triazole-3,5-diamine;
N³-[6-Chloro-4'-(1-methyl-piperidin-3-yloxy)-2-trifluoromethyl-biphenyl-4-yl]-1H-[1,2,4]triazole-3,5-diamine;
N³-{6-Chloro-2-trifluoromethyl-4'-[1-(3,3,3-trifluoro-propyl)-piperidin-3-yloxy]-biphenyl-4-yl}-1H-[1,2,4]triazole-3,5-diamine;
{2-[4'-(5-Amino-1H-[1,2,4]triazol-3-ylamino)-6'-chloro-2'-trifluoromethyl-biphenyl-4-yloxy]-ethyl}-carbamic acid tert-butyl ester;
N³-[4'-(2-Amino-ethoxy)-6-chloro-2-trifluoromethyl-biphenyl-4-yl]-1H-[1,2,4]triazole-3,5-diamine;
N³-{6-Chloro-4'-[2-(3,3-dimethyl-butylamino)-ethoxy]-2-trifluoromethyl-biphenyl-4-yl}-1H-[1,2,4]triazole-3,5-diamine;
N³-(4'-{2-[Bis-(3,3-dimethyl-butyl)-amino]-ethoxy}-6-chloro-2-trifluoromethyl-biphenyl-4-yl)-1H-[1,2,4]triazole-3,5-diamine;
4-[4'-(5-Amino-1H-[1,2,4]triazol-3-ylamino)-6'-chloro-2'-trifluoromethyl-biphenyl-4-yloxy]-piperidine-1-carboxylic acid tert-butyl ester;
N³-[6-Chloro-4'-(piperidin-4-yloxy)-2-trifluoromethyl-biphenyl-4-yl]-1H-[1,2,4]triazole-3,5-diamine;
N³-{6-Chloro-2-trifluoromethyl-4'-[1-(3,3,3-trifluoro-propyl)-piperidin-4-yloxy]-biphenyl-4-yl}-1H-[1,2,4]triazole-3,5-diamine;
N³-{6-Chloro-4'-[1-(2-methanesulfonyl-ethyl)-piperidin-4-yloxy]-2-trifluoromethyl-biphenyl-4-yl}-1H-[1,2,4]triazole-3,5-diamine;
N³-{6-Chloro-4'-[1-(3-methanesulfonyl-propyl)-piperidin-4-yloxy]-2-trifluoromethyl-biphenyl-4-yl}-1H-[1,2,4]triazole-3,5-diamine;
N³-{6-Chloro-4'-[1-(2-methoxy-ethyl)-piperidin-4-yloxy]-2-trifluoromethyl-biphenyl-4-yl}-1H-[1,2,4]triazole-3,5-diamine;
N³-(2-Chloro-biphenyl-4-yl)-1H-[1,2,4]triazole-3,5-diamine;
N³-(2-Chloro-4'-fluoro-biphenyl-4-yl)-1H-[1,2,4]triazole-3,5-diamine;
N³-(2-Chloro-2'-fluoro-biphenyl-4-yl)-1H-[1,2,4]triazole-3,5-diamine;
N³-(2-Chloro-3',4'-difluoro-biphenyl-4-yl)-1H-[1,2,4]triazole-3,5-diamine;
N³-(2-Chloro-3'-fluoro-biphenyl-4-yl)-1H-[1,2,4]triazole-3,5-diamine;
N³-(2-Trifluoromethyl-biphenyl-4-yl)-1H-[1,2,4]triazole-3,5-diamine;
N³-(2'-Fluoro-2-trifluoromethyl-biphenyl-4-yl)-1H-[1,2,4]triazole-3,5-diamine;
N³-(4'-Fluoro-2-trifluoromethyl-biphenyl-4-yl)-1H-[1,2,4]triazole-3,5-diamine;
N³-(3',4'-Difluoro-2-trifluoromethyl-biphenyl-4-yl)-1H-[1,2,4]triazole-3,5-diamine;
N³-(2'-Chloro-2-trifluoromethyl-biphenyl-4-yl)-1H-[1,2,4]triazole-3,5-diamine;
N³-(2-Chloro-4'-methanesulfonyl-biphenyl-4-yl)-1H-[1,2,4]triazole-3,5-diamine;
N³-(2,2'-Dichloro-biphenyl-4-yl)-1H-[1,2,4]triazole-3,5-diamine;
N³-(2-Chloro-2'-fluoro-4'-methylsulfanyl-biphenyl-4-yl)-H-[1,2,4]triazole-3,5-diamine;

N³-(2-Chloro-2'-fluoro-4'-methanesulfonyl-biphenyl-4-yl)-1H-[1,2,4]triazole-3,5-diamine;
4'-(5-Amino-1H-[1,2,4]triazol-3-ylamino)-2',6'-dichloro-biphenyl-3-carboxylic acid amide;
4'-(5-Amino-1H-[1,2,4]triazol-3-ylamino)-2',6'-dichloro-biphenyl-4-carboxylic acid amide;
4'-(5-Amino-1H-[1,2,4]triazol-3-ylamino)-2',6'-dichloro-biphenyl-4-sulfonic acid (2-hydroxy-ethyl)-amide;
4'-(5-Amino-1H-[1,2,4]triazol-3-ylamino)-2'-chloro-6'-trifluoromethyl-biphenyl-4-sulfonic acid (2-hydroxy-ethyl)-amide;
2-[4'-(5-Amino-1H-[1,2,4]triazol-3-ylamino)-2'-chloro-6'-trifluoromethyl-biphenyl-4-sulfonyl]-ethanol;
4-[4'-(5-Amino-1H-[1,2,4]triazol-3-ylamino)-6'-chloro-3-methoxy-2'-trifluoromethyl-biphenyl-4-sulfonyl amino]-piperidine-1-carboxylic acid tert-butyl ester;
4'-(5-Amino-1H-[1,2,4]triazol-3-ylamino)-2',6'-dichloro-biphenyl-4-sulfonic acid tert-butylamide;
4'-(5-Amino-1H-[1,2,4]triazol-3-ylamino)-6'-chloro-2'-trifluoromethyl-biphenyl-4-sulfonic acid (2,2,2-trifluoro-1,1-dimethyl-ethyl)-amide;
4-[4'-(5-Amino-1H-[1,2,4]triazol-3-ylamino)-6'-chloro-4-methoxy-2'-trifluoromethyl-biphenyl-3-sulfonyl]-piperazine-1-carboxylic acid tert-butyl ester;
4'-(5-Amino-1H-[1,2,4]triazol-3-ylamino)-6'-chloro-3-methoxy-2'-trifluoromethyl-biphenyl-4-sulfonic acid (4-hydroxy-cyclohexyl)-amide;
4'-(5-Amino-1H-[1,2,4]triazol-3-ylamino)-6'-chloro-4-methoxy-2'-trifluoromethyl-biphenyl-3-sulfonic acid (tetrahydro-pyran-4-yl)-amide;
4'-(5-Amino-1H-[1,2,4]triazol-3-ylamino)-6'-chloro-2'-trifluoromethyl-biphenyl-4-sulfonic acid cyclopropylamide;
N³-[6-Chloro-4'-(pyrrolidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-2'-trifluoromethyl-biphenyl-4-sulfonic acid amide;
4'-(5-Amino-1H-[1,2,4]triazol-3-ylamino)-6'-chloro-2'-trifluoromethyl-biphenyl-4-sulfonic acid (3-hydroxy-cyclobutyl)-amide;
4'-(5-Amino-1H-[1,2,4]triazol-3-ylamino)-6'-chloro-2'-trifluoromethyl-biphenyl-4-sulfonic acid (3-hydroxy-cyclobutyl)-amide;
4'-(5-Amino-1H-[1,2,4]triazol-3-ylamino)-6'-chloro-2'-trifluoromethyl-biphenyl-4-sulfonic acid (3-hydroxy-cyclobutyl)-amide;
4'-(5-amino-1H-1,2,4-triazol-3-ylamino)-2'-chloro-N-(2-hydroxyethyl)-4-methoxy-6'-(trifluoromethyl)biphenyl-3-sulfonamide
4'-(5-Amino-1H-[1,2,4]triazol-3-ylamino)-6'-chloro-4-methoxy-2'-trifluoromethyl-biphenyl-3-sulfonic acid (2-hydroxy-ethyl)-amide;
4'-(5-Amino-1H-[1,2,4]triazol-3-ylamino)-6'-chloro-2'-trifluoromethyl-biphenyl-3-sulfonic acid tert-butylamide;
N³-[6-Chloro-4'-methoxy-3'-(morpholine-4-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-3-methoxy-2'-trifluoromethyl-biphenyl-4-sulfonic acid piperidin-4-ylamide;
4'-(5-Amino-1H-[1,2,4]triazol-3-ylamino)-6'-chloro-4-methoxy-2'-trifluoromethyl-biphenyl-3-sulfonic acid amide;
N³-[6-Chloro-4'-(propane-2-sulfonyl)-2-trifluoromethyl-biphenyl-4-yl]-1H-[1,2,4]triazole-3,5-diamine;
N³-[6-Chloro-4'-methoxy-3'-(piperazine-1-sulfonyl)-2-trifluoromethyl-biphenyl-4-yl]-1H-[1,2,4]triazole-3,5-diamine;
N³-[6-Chloro-4'-(4,4-difluoro-piperidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-2'-trifluoromethyl-biphenyl-4-sulfonic acid (4-hydroxy-cyclohexyl)-amide;
4'-(5-Amino-1H-[1,2,4]triazol-3-ylamino)-6'-chloro-2'-trifluoromethyl-biphenyl-4-sulfonic acid dimethylamide;
N-[4'-(5-Amino-1H-[1,2,4]triazol-3-ylamino)-6'-chloro-2'-trifluoromethyl-biphenyl-4-ylmethyl]-methanesulfonamide;
N³-(6-Chloro-4'-methanesulfonyl-2-trifluoromethyl-biphenyl-4-yl)-1H-[1,2,4]triazole-3,5-diamine;
N³-(6-Chloro-4'-cyclopropanesulfonyl-2-trifluoromethyl-biphenyl-4-yl)-1H-[1,2,4]triazole-3,5-diamine;
4'-(5-Amino-1H-[1,2,4]triazol-3-ylamino)-6'-chloro-2'-trifluoromethyl-biphenyl-4-carboxylic acid methylamide;
4'-(5-Amino-1H-[1,2,4]triazol-3-ylamino)-6'-chloro-4-methoxy-2'-trifluoromethyl-biphenyl-3-sulfonic acid (4-hydroxy-cyclohexyl)-amide;
1-[4'-(5-Amino-1H-[1,2,4]triazol-3-ylamino)-6'-chloro-2'-trifluoromethyl-biphenyl-4-sulfonyl]-azetidin-3-ol;
N³-[6-Chloro-3'-(pyrrolidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-4-trifluoromethoxy-2'-trifluoromethyl-biphenyl-3-sulfonic acid tert-butylamide;
1-[4'-(5-Amino-1H-[1,2,4]triazol-3-ylamino)-6'-chloro-2'-trifluoromethyl-biphenyl-4-sulfonyl]-piperidin-4-ol;
N³-(6-Chloro-3'-methanesulfonyl-2-trifluoromethyl-biphenyl-4-yl)-H-[1,2,4]triazole-3,5-diamine;
4'-(5-Amino-1H-[1,2,4]triazol-3-ylamino)-6'-chloro-2'-trifluoromethyl-biphenyl-3-sulfonic acid tert-butyl-methyl-amide;
4'-(5-Amino-1H-[1,2,4]triazol-3-ylamino)-6'-chloro-2'-trifluoromethyl-biphenyl-3-sulfonic acid amide;
4'-(5-Amino-1H-[1,2,4]triazol-3-ylamino)-6'-chloro-2'-trifluoromethyl-biphenyl-3-sulfonic acid dimethylamide;
N-[4'-(5-Amino-1H-[1,2,4]triazol-3-ylamino)-6'-chloro-2'-trifluoromethyl-biphenyl-3-ylmethyl]-methanesulfonamide;
4'-(5-Amino-1H-[1,2,4]triazol-3-ylamino)-6'-chloro-2'-trifluoromethyl-biphenyl-4-carboxylic acid tert-butyl ester;
N³-(6-Chloro-2-trifluoromethyl-biphenyl-4-yl)-1H-[1,2,4]triazole-3,5-diamine;
4'-(5-Amino-1H-[1,2,4]triazol-3-ylamino)-6'-chloro-2'-trifluoromethyl-biphenyl-4-carboxylic acid;
N³-[6-Chloro-4'-methoxy-3'-(pyrrolidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-4-methoxy-2'-trifluoromethyl-biphenyl-3-sulfonic acid piperidin-4-ylamide
3-[4'-(5-Amino-1H-[1,2,4]triazol-3-ylamino)-6'-chloro-2'-trifluoromethyl-biphenyl-4-sulfonylamino]-3-methyl-azetidine-1-carboxylic acid tert-butyl ester;
4'-(5-Amino-1H-[1,2,4]triazol-3-ylamino)-6'-chloro-2'-trifluoromethyl-biphenyl-4-sulfonic acid (1-methyl-cyclopropyl)-amide;
4'-(5-Amino-1H-[1,2,4]triazol-3-ylamino)-6'-chloro-2'-trifluoromethyl-biphenyl-4-sulfonic acid (3-methyl-azetidin-3-yl)-amide;
4-[4'-(5-Amino-1H-[1,2,4]triazol-3-ylamino)-6'-chloro-2'-trifluoromethyl-biphenyl-4-sulfonyl]-4,7-diaza-spiro[2.5]octane-7-carboxylic acid tert-butyl ester;

{2-[4'-(5-Amino-1H-[1,2,4]triazol-3-ylamino)-6'-chloro-2'-trifluoromethyl-biphenyl-4-sulfonylamino]-ethyl}-methyl-carbamic acid tert-butyl ester;
4'-(5-Amino-1H-[1,2,4]triazol-3-ylamino)-6'-chloro-2'-trifluoromethyl-biphenyl-4-sulfonic acid (1-isopropyl-3-methyl-azetidin-3-yl)-amide;
4'-(5-Amino-1H-[1,2,4]triazol-3-ylamino)-6'-chloro-2'-trifluoromethyl-biphenyl-4-sulfonic acid (1-isopropyl-3-methyl-azetidin-3-yl)-amide;
3-[4'-(5-Amino-1H-[1,2,4]triazol-3-ylamino)-6'-chloro-4-methoxy-2'-trifluoromethyl-biphenyl-3-sulfonylamino]-3-methyl-azetidine-1-carboxylic acid tert-butyl ester;
4'-(5-Amino-1H-[1,2,4]triazol-3-ylamino)-6'-chloro-2'-trifluoromethyl-biphenyl-4-sulfonic acid (2-methylamino-ethyl)-amide;
$N^3$-[6-Chloro-4'-(4,7-diaza-spiro[2.5]octane-4-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-4-methoxy-2'-trifluoromethyl-biphenyl-3-sulfonic acid (3-methyl-azetidin-3-yl)-amide;
4'-(5-Amino-1H-[1,2,4]triazol-3-ylamino)-6'-chloro-4-methoxy-2'-trifluoromethyl-biphenyl-3-sulfonic acid tert-butylamide;
4'-(5-Amino-1H-[1,2,4]triazol-3-ylamino)-6'-chloro-3-trifluoromethoxy-2'-trifluoromethyl-biphenyl-4-sulfonic acid tert-butylamide;
4'-(5-Amino-1H-[1,2,4]triazol-3-ylamino)-6'-chloro-4-methoxy-2'-trifluoromethyl-biphenyl-3-sulfonic acid (2-hydroxy-1,1-dimethyl-ethyl)-amide;
4'-(5-Amino-1H-[1,2,4]triazol-3-ylamino)-2'-chloro-6'-trifluoromethyl-biphenyl-4-sulfonic acid tert-butylamide;
$N^3$-[2,6-Dichloro-4'-(pyrrolidine-1-sulfonyl)-biphenyl-4-yl]-1H-[1,2,4]triazole-3,5-diamine;
4-[4'-(5-Amino-1H-[1,2,4]triazol-3-ylamino)-6'-chloro-4-methoxy-2'-trifluoromethyl-biphenyl-3-sulfonylamino]-piperidine-1-carboxylic acid tert-butyl ester;
4'-(5-Amino-1H-[1,2,4]triazol-3-ylamino)-2'-chloro-4-methoxy-6'-trifluoromethyl-biphenyl-3-sulfonic acid piperidin-4-ylamide;
4'-(5-Amino-1H-[1,2,4]triazol-3-ylamino)-6'-chloro-2'-trifluoromethyl-biphenyl-4-sulfonic acid tert-butyl-(2,2,2-trifluoro-ethyl)-amide;
$N^3$-[6-Chloro-4'-(3,3-difluoro-azetidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-4-methoxy-2'-trifluoromethyl-biphenyl-3-sulfonic acid (1-cyano-cyclopropyl)-amide;
4'-(5-Amino-1H-[1,2,4]triazol-3-ylamino)-6'-chloro-2'-trifluoromethyl-biphenyl-4-sulfonic acid (2-hydroxy-1,1-dimethyl-ethyl)-amide;
4'-(5-Amino-1H-[1,2,4]triazol-3-ylamino)-2'-chloro-4-methoxy-6'-trifluoromethyl-biphenyl-3-sulfonic acid (1-acetyl-piperidin-4-yl)-amide;
N*3*-[6-Chloro-4'-(propane-2-sulfonyl)-2-trifluoromethyl-biphenyl-4-yl]-1H-[1,2,4]triazole-3,5-diamine
$N^3$-(6-Chloro-3'-isopropoxy-4'-methoxy-2-trifluoromethyl-biphenyl-4-yl)-1H-[1,2,4]triazole-3,5-diamine;
$N^3$-(4'-tert-Butoxy-6-chloro-2-trifluoromethyl-biphenyl-4-yl)-1H-[1,2,4]triazole-3,5-diamine;
$N^3$-(6-Chloro-4'-methoxy-2,3'-bis-trifluoromethyl-biphenyl-4-yl)-1H-[1,2,4]triazole-3,5-diamine;
$N^3$-[6'-Chloro-4,4''-bis-(pyrrolidine-1-sulfonyl)-[1,1';2',1'']terphenyl-4'-yl]-1H-[1,2,4]triazole-3,5-diamine;
$N^3$-[6-Chloro-4'-(3-fluoro-azetidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-4-methoxy-2'-trifluoromethyl-biphenyl-3-sulfonic acid piperidin-4-yl-(2,2,2-trifluoro-ethyl)-amide;
4,4-Difluoro-cyclohexanecarboxylic acid [4'-(5-amino-1H-[1,2,4]triazol-3-ylamino)-6'-chloro-2'-trifluoromethyl-biphenyl-4-yl]-amide;
[4'-(5-Amino-1H-[1,2,4]triazol-3-ylamino)-6'-chloro-2'-trifluoromethyl-biphenyl-4-yl]-carbamic acid 1-tert-butyl-azetidin-3-yl ester;
[4'-(5-Amino-1H-[1,2,4]triazol-3-ylamino)-6'-chloro-2'-trifluoromethyl-biphenyl-4-yl]-carbamic acid propyl ester;
N-[4'-(5-Amino-1H-[1,2,4]triazol-3-ylamino)-6'-chloro-2'-trifluoromethyl-biphenyl-4-yl]-3-(tetrahydro-pyran-4-yl)-propionamide;
1,1-Dioxo-hexahydro-1$\lambda^6$-thiopyran-4-carboxylic acid [4'-(5-amino-1H-[1,2,4]triazol-3-ylamino)-6'-chloro-2'-trifluoromethyl-biphenyl-4-yl]-amide;
N-[4'-(5-Amino-1H-[1,2,4]triazol-3-ylamino)-6'-chloro-2'-trifluoromethyl-biphenyl-4-yl]-2-(1,1-dioxo-1$\lambda^6$-thiomorpholin-4-yl)-acetamide;
N-[4'-(5-Amino-1H-[1,2,4]triazol-3-ylamino)-6'-chloro-2'-trifluoromethyl-biphenyl-4-yl]-2-morpholin-4-yl-acetamide;
N-[4'-(5-Amino-2H-[1,2,4]triazol-3-ylamino)-6'-fluoro-2'-trifluoromethyl-biphenyl-4-yl]-methanesulfonamide;
N-[4'-(5-Amino-2H-[1,2,4]triazol-3-ylamino)-6'-fluoro-2'-trifluoromethyl-biphenyl-3-yl]-methanesulfonamide;
$N^5$-(6,3'-Difluoro-2-trifluoromethyl-biphenyl-4-yl)-H-[1,2,4]triazole-3,5-diamine;
$N^5$-(6,4'-Difluoro-2-trifluoromethyl-biphenyl-4-yl)-1H-[1,2,4]triazole-3,5-diamine;
$N^5$-(6-Fluoro-2,4'-bis-trifluoromethyl-biphenyl-4-yl)-1H-[1,2,4]triazole-3,5-diamine;
$N^5$-(6-Fluoro-4'-methyl-2-trifluoromethyl-biphenyl-4-yl)-1H-[1,2,4]triazole-3,5-diamine;
4'-(5-Amino-2H-[1,2,4]triazol-3-ylamino)-6'-fluoro-2'-trifluoromethyl-biphenyl-3-carboxylic acid methylamide;
$N^5$-(3-Fluoro-4-naphthalen-2-yl-5-trifluoromethyl-phenyl)-1H-[1,2,4]triazole-3,5-diamine;
4,4-Difluoro-cyclohexanecarboxylic acid [4'-(5-amino-1H-[1,2,4]triazol-3-ylamino)-2',6'-dichloro-biphenyl-4-yl]-amide;
N-[4'-(5-Amino-1H-[1,2,4]triazol-3-ylamino)-2',6'-dichloro-biphenyl-4-yl]-isobutyramide;
N-[4'-(5-Amino-1H-[1,2,4]triazol-3-ylamino)-2',6'-dichloro-biphenyl-3-yl]-isobutyramide;
4'-(5-Amino-1H-[1,2,4]triazol-3-ylamino)-2',6'-dichloro-biphenyl-4-sulfonic acid amide;
5-[4-(5-Amino-2H-[1,2,4]triazol-3-ylamino)-2,6-dichloro-phenyl]-1,3-dihydro-indol-2-one;
5-[4-(5-Amino-2H-[1,2,4]triazol-3-ylamino)-2,6-dichloro-phenyl]-1,3-dihydro-benzoimidazol-2-one;
6-[4-(5-Amino-2H-[1,2,4]triazol-3-ylamino)-2,6-dichloro-phenyl]-1,3-dihydro-indol-2-one;
$N^5$-[3,5-Dichloro-4-(1H-indazol-5-yl)-phenyl]-1H-[1,2,4]triazole-3,5-diamine;
$N^3$-(2',6'-Dichloro-biphenyl-4-yl)-1H-[1,2,4]triazole-3,5-diamine;
$N^5$-[2,6-Dichloro-4'-(piperidin-3-yloxy)-biphenyl-4-yl]-1H-[1,2,4]triazole-3,5-diamine;
3-[4'-(5-Amino-1H-[1,2,4]triazol-3-ylamino)-2',6'-dichloro-biphenyl-4-yloxymethyl]-azetidine-1-carboxylic acid tert-butyl ester;
{2-[4'-(5-Amino-1H-[1,2,4]triazol-3-ylamino)-2',6'-dichloro-biphenyl-4-yloxy]-ethyl}-methyl-carbamic acid tert-butyl ester;

N³-[2,6-Dichloro-4'-(piperidin-4-yloxy)-biphenyl-4-yl]-1H-[1,2,4]triazole-3,5-diamine;
N³-[2,6-Dichloro-4'-(2-methylamino-ethoxy)-biphenyl-4-yl]-1H-[1,2,4]triazole-3,5-diamine;
N³-[2,6-Dichloro-4'-(2-pyrrolidin-2-yl-ethoxy)-biphenyl-4-yl]-1H-[1,2,4]triazole-3,5-diamine;
N³-[2,6-Dichloro-4'-((S)-1-pyrrolidin-2-ylmethoxy)-biphenyl-4-yl]-1H-[1,2,4]triazole-3,5-diamine;
2-{2-[4'-(5-Amino-1H-[1,2,4]triazol-3-ylamino)-2',6'-dichloro-biphenyl-4-yloxy]-ethyl}-pyrrolidine-1-carboxylic acid tert-butyl ester;
(R)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester;
4-[4'-(5-Amino-1H-[1,2,4]triazol-3-ylamino)-2',6'-dichloro-biphenyl-4-yloxy]-piperidine-1-carboxylic acid tert-butyl ester;
N³-[2,6-Dichloro-4'-(2-dimethylamino-ethoxy)-biphenyl-4-yl]-1H-[1,2,4]triazole-3,5-diamine;
N³-[6-Chloro-4'-((S)-1-pyrrolidin-2-ylmethoxy)-2-trifluoromethyl-biphenyl-4-yl]-1H-[1,2,4]triazole-3,5-diamine;
N³-[2,6-Dichloro-4'-((S)-pyrrolidin-3-yloxy)-biphenyl-4-yl]-1H-[1,2,4]triazole-3,5-diamine;
N³-[2,6-Dichloro-4'-((R)-1-pyrrolidin-2-ylmethoxy)-biphenyl-4-yl]-1H-[1,2,4]triazole-3,5-di amine;
(S)-3-[4'-(5-Amino-1H-[1,2,4]triazol-3-ylamino)-2',6'-dichloro-biphenyl-4-yloxy]-pyrrolidine-1-carboxylic acid tert-butyl ester;
N³-[2,6-Dichloro-4'-(2,2-dimethyl-[1,3]dioxolan-4-ylmethoxy)-biphenyl-4-yl]-1H-[1,2,4]triazole-3,5-diamine;
(R)-2-[4'-(5-Amino-1H-[1,2,4]triazol-3-ylamino)-2',6'-dichloro-biphenyl-4-yloxymethy]-pyrrolidine-1-carboxylic acid tert-butyl ester;
[4'-(5-Amino-1H-[1,2,4]triazol-3-ylamino)-2',6'-dichloro-biphenyl-4-yloxy]-acetic acid tert-butyl ester;
(S)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester;
N³-[2,6-Dichloro-4'-(2-methoxy-ethoxy)-biphenyl-4-yl]-1H-[1,2,4]triazole-3,5-diamine
N³-[6-Chloro-4'-((R)-1-pyrrolidin-2-ylmethoxy)-2-trifluoromethyl-biphenyl-4-yl]-1H-[1,2,4]triazole-3,5-diamine;
(S)-2-[4'-(5-Amino-1H-[1,2,4]triazol-3-ylamino)-2',6'-dichloro-biphenyl-4-yloxymethyl]-pyrrolidine-1-carboxylic acid tert-butyl ester;
N³-[2,6-Dichloro-4'-(2-morpholin-4-yl-ethoxy)-biphenyl-4-yl]-1H-[1,2,4]triazole-3,5-diamine;
3-[4'-(5-Amino-1H-[1,2,4]triazol-3-ylamino)-2',6'-dichloro-biphenyl-4-yloxy]-propane-1,2-diol;
N³-[2,6-Dichloro-4'-(3-morpholin-4-yl-propoxy)-biphenyl-4-yl]-1H-[1,2,4]triazole-3,5-diamine;
N³-[2,6-Dichloro-4'-(pyridin-2-ylmethoxy)-biphenyl-4-yl]-1H-[1,2,4]triazole-3,5-diamine;
[4'-(5-Amino-1H-[1,2,4]triazol-3-ylamino)-2',6'-dichloro-biphenyl-4-yloxy]-acetic acid;
N³-(2,6-Dichloro-4'-fluoro-biphenyl-4-yl)-1H-[1,2,4]triazole-3,5-diamine;
N³-(2,6-Dichloro-2'-fluoro-biphenyl-4-yl)-1H-[1,2,4]triazole-3,5-diamine;
N*3*-(4'-Methanesulfonyl-2-pentafluorosulfur-biphenyl-4-yl)-1H-[1,2,4]triazole-3,5-diamine
N³-[2,6-Dichloro-4'-(1,1-dioxo-λ⁶-isothiazolidin-2-yl)-biphenyl-4-yl]-H-[1,2,4]triazole-3,5-diamine;
N-[4'-(5-Amino-1H-[1,2,4]triazol-3-ylamino)-6'-chloro-2'-trifluoromethyl-biphenyl-3-yl]-methanesulfonamide;
4'-(5-Amino-1H-[1,2,4]triazol-3-ylamino)-6'-chloro-3-fluoro-2'-trifluoromethyl-biphenyl-4-carboxylic acid methylamide;
4'-(5-Amino-1H-[1,2,4]triazol-3-ylamino)-6'-chloro-4-fluoro-2'-trifluoromethyl-biphenyl-3-carboxylic acid methylamide;
4'-(5-Amino-1H-[1,2,4]triazol-3-ylamino)-6'-chloro-3-fluoro-2'-trifluoromethyl-biphenyl-4-carboxylic acid (2-hydroxy-ethyl)-amide;
4'-(5-Amino-1H-[1,2,4]triazol-3-ylamino)-6'-chloro-4-fluoro-2'-trifluoromethyl-biphenyl-3-carboxylic acid (2-hydroxy-ethyl)-amide;
4'-(5-Amino-1H-[1,2,4]triazol-3-ylamino)-2'-chloro-6'-trifluoromethyl-biphenyl-4-sulfonic acid oxetan-3-ylamide; and
4'-(5-Amino-1H-[1,2,4]triazol-3-ylamino)-6'-chloro-4-methoxy-2'-trifluoromethyl-biphenyl-3-sulfonic acid (1-isopropyl-piperidin-4-yl)-amide.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering a combination of antiviral agents that inhibits replication of HCV.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

The application provides a composition comprising a compound of Formula I and a pharmaceutically acceptable excipient.

The application provides the use of the compound of Formula I in the preparation of a medicament for the prevention of HCV.

The application provides the use of the compound of Formula I in the preparation of a medicament for the treatment of HCV.

The application provides any compound, composition, method or use as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I:

TABLE I

| # | Nomenclature | Structure |
|---|---|---|
| 1 | 4-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester; | 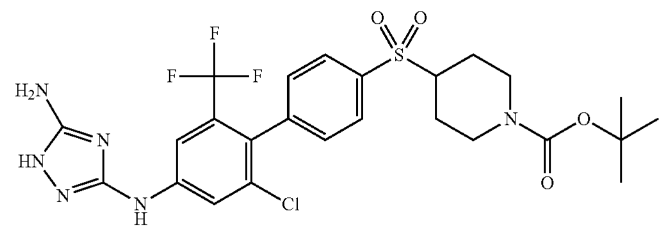 [SMILES: CC(C)(C)OC(=O)N1CCC(S(=O)(=O)c2ccc(-c3c(Cl)cc(Nc4n[nH]c(N)n4)cc3C(F)(F)F)cc2)CC1] |
| 2 | 3-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester; | 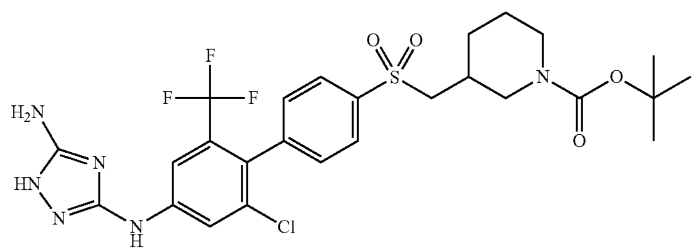 [SMILES: CC(C)(C)OC(=O)N1CCCC(CS(=O)(=O)c2ccc(-c3c(Cl)cc(Nc4n[nH]c(N)n4)cc3C(F)(F)F)cc2)C1] |
| 3 | (S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid tert-butyl ester; | 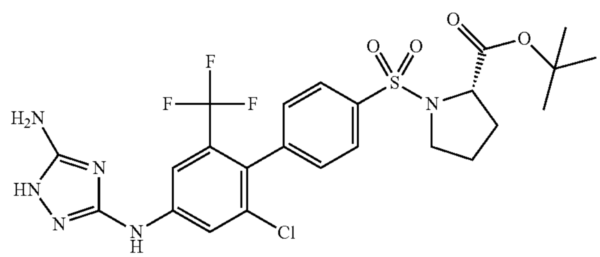 [SMILES: CC(C)(C)OC(=O)[C@@H]1CCCN1S(=O)(=O)c1ccc(-c2c(Cl)cc(Nc3n[nH]c(N)n3)cc2C(F)(F)F)cc1] |
| 4 | $N^3$-{6-Chloro-2-trifluoromethyl-4'-[1-(3,3,3-trifluoropropyl)-piperidine-4-sulfonyl]-biphenyl-4-yl}-1H-[1,2,4]triazole-3,5-diamine; | 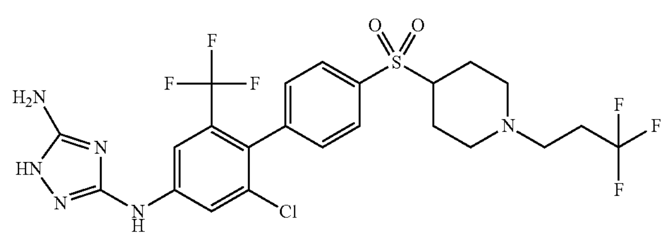 [SMILES: Nc1nc(Nc2cc(Cl)c(-c3ccc(S(=O)(=O)C4CCN(CCC(F)(F)F)CC4)cc3)c(C(F)(F)F)c2)n[nH]1] |
| 5 | $N^3$-{6-Chloro-4'-[1-(3,3-dimethyl-butyl)-piperidine-4-sulfonyl]-2-trifluoromethyl-biphenyl-4-yl}-1H-[1,2,4]triazole-3,5-diamine; | 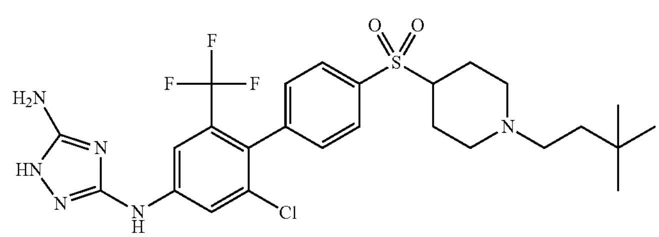 [SMILES: CC(C)(C)CCN1CCC(S(=O)(=O)c2ccc(-c3c(Cl)cc(Nc4n[nH]c(N)n4)cc3C(F)(F)F)cc2)CC1] |
| 6 | 3-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester; | 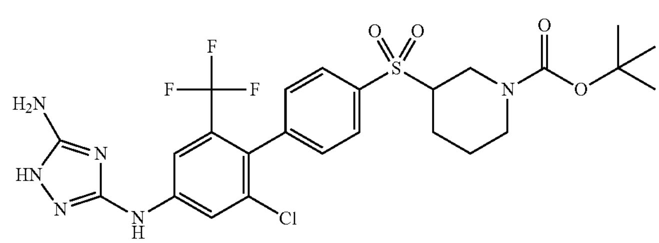 [SMILES: CC(C)(C)OC(=O)N1CCCC(S(=O)(=O)c2ccc(-c3c(Cl)cc(Nc4n[nH]c(N)n4)cc3C(F)(F)F)cc2)C1] |

TABLE I-continued

| # | Nomenclature | Structure |
|---|---|---|
| 7 | 4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester; | 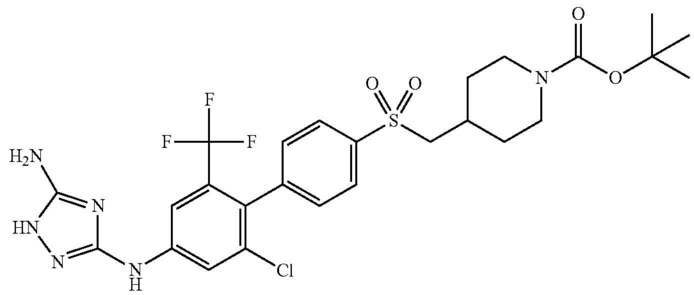 [SMILES: CC(C)(C)OC(=O)N1CCC(CS(=O)(=O)c2ccc(-c3c(Cl)cc(Nc4n[nH]c(N)n4)cc3C(F)(F)F)cc2)CC1] |
| 8 | 4'-(5-Amino-1H-[1,2,4]triazol-3-ylamino)-2',6'-dichloro-biphenyl-4-carboxylic acid tert-butylamide; | 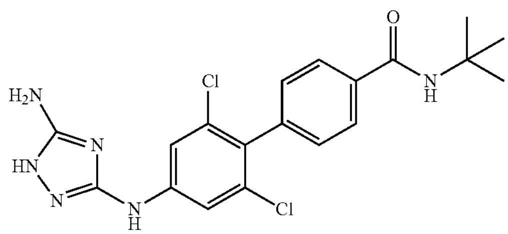 [SMILES: CC(C)(C)NC(=O)c1ccc(-c2c(Cl)cc(Nc3n[nH]c(N)n3)cc2Cl)cc1] |
| 9 | Pentanoic acid [4'-(5-amino-1H-[1,2,4]triazol-3-ylamino)-2',6'-dichloro-biphenyl-4-yl]-amide; | 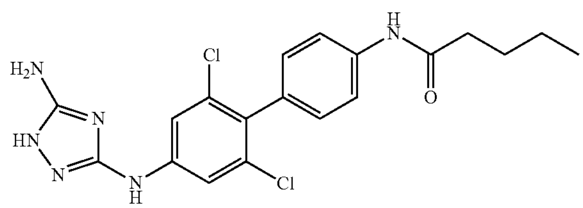 [SMILES: CCCCC(=O)Nc1ccc(-c2c(Cl)cc(Nc3n[nH]c(N)n3)cc2Cl)cc1] |
| 10 | $N^3$-[4-(2-tert-Butyl-1,1-dioxo-2,3-dihydro-1H-1$\lambda^6$-benzo[d]isothiazol-6-yl)-3-chloro-5-trifluoromethyl-phenyl]-1H-[1,2,4]triazole-3,5-diamine; | 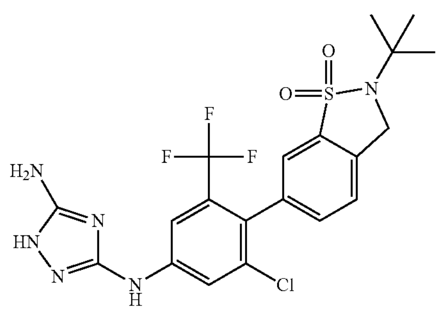 [SMILES: CC(C)(C)N1Cc2ccc(-c3c(Cl)cc(Nc4n[nH]c(N)n4)cc3C(F)(F)F)cc2S1(=O)=O] |
| 11 | $N^3$-{6-Chloro-2-trifluoromethyl-4'-[1-(3,3,3-trifluoro-propyl)-piperidine-3-sulfonyl]-biphenyl-4-yl}-1H-[1,2,4]triazole-3,5-diamine; | 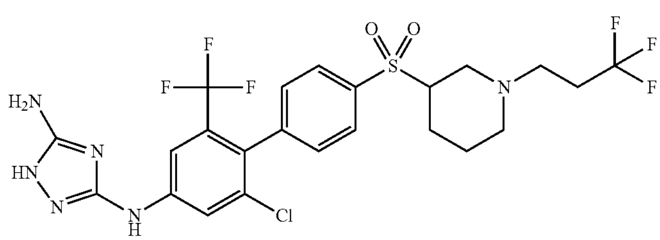 [SMILES: Nc1nc(Nc2cc(Cl)c(-c3ccc(S(=O)(=O)C4CCCN(CCC(F)(F)F)C4)cc3)c(C(F)(F)F)c2)n[nH]1] |
| 12 | N-[4'-(5-Amino-1H-[1,2,4]triazol-3-ylamino)-2',6'-dichloro-biphenyl-4-ylmethyl]-methane-sulfonamide; | 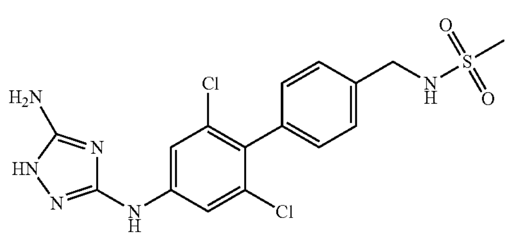 [SMILES: CS(=O)(=O)NCc1ccc(-c2c(Cl)cc(Nc3n[nH]c(N)n3)cc2Cl)cc1] |

TABLE I-continued

| # | Nomenclature | Structure |
|---|---|---|
| 13 | N-{(S)-1-[4'-(5-Amino-1H-[1,2,4]triazol-3-ylamino)-2'-chloro-6'-trifluoromethyl-biphenyl-4-yl]-ethyl}-methane-sulfonamide; | 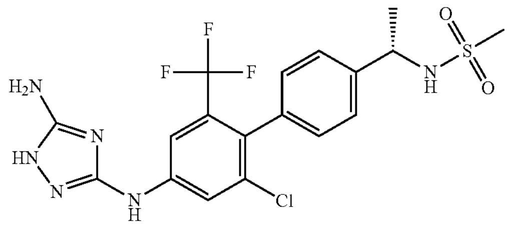 [SMILES: C[C@H](NS(C)(=O)=O)c1ccc(-c2c(Cl)cc(Nc3n[nH]c(N)n3)cc2C(F)(F)F)cc1] |
| 14 | N³-(2,6-Dichloro-4'-methane-sulfonyl-3'-trifluoromethyl-biphenyl-4-yl)-1H-[1,2,4]triazole-3,5-diamine; | 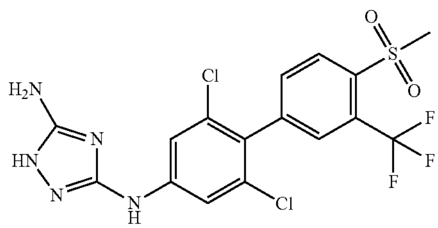 [SMILES: CS(=O)(=O)c1ccc(-c2c(Cl)cc(Nc3n[nH]c(N)n3)cc2Cl)cc1C(F)(F)F] |
| 15 | N³-[3,5-Dichloro-4-(1-methane-sulfonyl-1H-indol-4-yl)-phenyl]-1H-[1,2,4]triazole-3,5-diamine; | 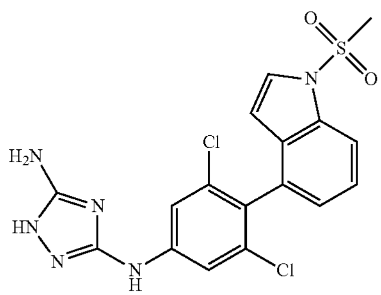 [SMILES: CS(=O)(=O)n1ccc2c(-c3c(Cl)cc(Nc4n[nH]c(N)n4)cc3Cl)cccc21] |
| 16 | 4-[4'-(5-Amino-1H-[1,2,4]triazol-3-ylamino)-2'-chloro-6'-trifluoromethyl-biphenyl-4-sulfonyl]-piperazine-1-carboxylic acid tert-butyl ester; | 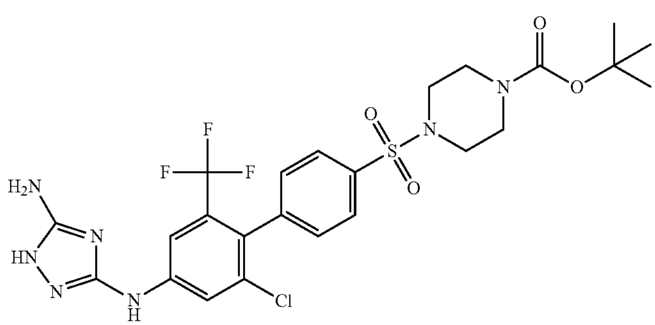 [SMILES: CC(C)(C)OC(=O)N1CCN(S(=O)(=O)c2ccc(-c3c(Cl)cc(Nc4n[nH]c(N)n4)cc3C(F)(F)F)cc2)CC1] |
| 17 | N³-{6-Chloro-4'-[1-(3,3-dimethyl-butyl)-piperidine-3-sulfonyl]-2-trifluoromethyl-biphenyl-4-yl}-1H-[1,2,4]triazole-3,5-diamine; | 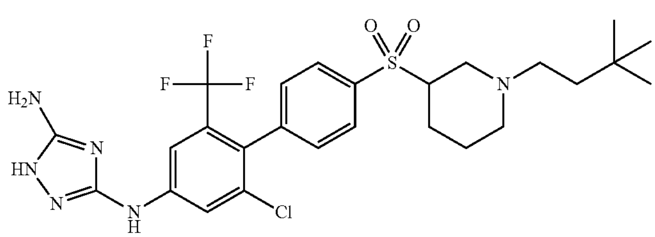 [SMILES: CC(C)(C)CCN1CCCC(S(=O)(=O)c2ccc(-c3c(Cl)cc(Nc4n[nH]c(N)n4)cc3C(F)(F)F)cc2)C1] |

TABLE I-continued

| # | Nomenclature | Structure |
|---|---|---|
| 18 | 4'-(5-Amino-1H-[1,2,4]triazol-3-ylamino)-2'-chloro-4-methyl-6'-trifluoromethyl-biphenyl-3-sulfonic acid tert-butylamide; | 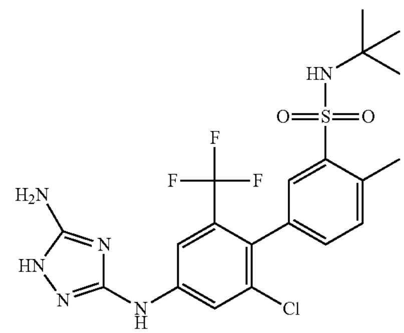 [SMILES: Cc1ccc(-c2c(Cl)cc(Nc3n[nH]c(N)n3)cc2C(F)(F)F)cc1S(=O)(=O)NC(C)(C)C] |
| 19 | $N^3$-[2-Chloro-4'-methoxy-3'-(propane-2-sulfonyl)-6-trifluoromethyl-biphenyl-4-yl]-1H-[1,2,4]triazole-3,5-diamine; | 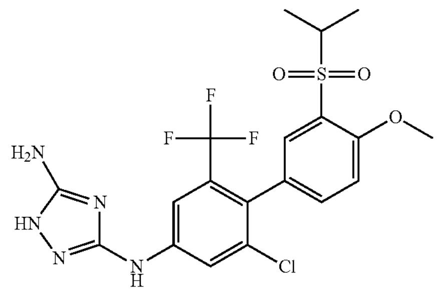 [SMILES: COc1ccc(-c2c(Cl)cc(Nc3n[nH]c(N)n3)cc2C(F)(F)F)cc1S(=O)(=O)C(C)C] |
| 20 | $N^3$-[2-Chloro-4'-(piperidine-4-sulfonyl)-6-trifluoromethyl-biphenyl-4-yl]-1H-[1,2,4]triazole-3,5-diamine; | 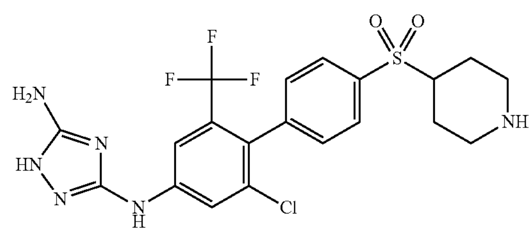 [SMILES: Nc1nc(Nc2cc(Cl)c(-c3ccc(S(=O)(=O)C4CCNCC4)cc3)c(C(F)(F)F)c2)n[nH]1] |
| 21 | 4-[4'-(5-Amino-1H-[1,2,4]triazol-3-ylamino)-2'-chloro-6'-trifluoromethyl-biphenyl-3-yloxy]-piperidine-1-carboxylic acid tert-butyl ester; | 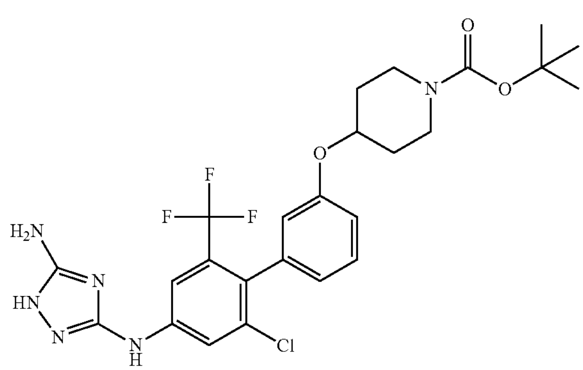 [SMILES: CC(C)(C)OC(=O)N1CCC(Oc2cccc(-c3c(Cl)cc(Nc4n[nH]c(N)n4)cc3C(F)(F)F)c2)CC1] |
| 22 | $N^3$-[2-Chloro-4'-(4-methyl-piperazine-1-sulfonyl)-6-trifluoromethyl-biphenyl-4-yl]-1H-[1,2,4]triazole-3,5-diamine; | 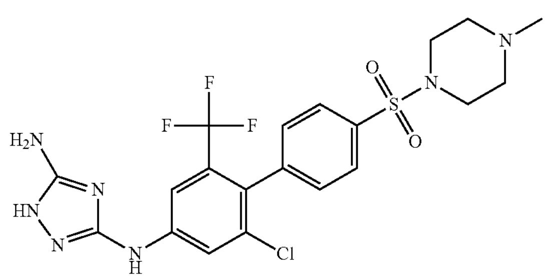 [SMILES: CN1CCN(S(=O)(=O)c2ccc(-c3c(Cl)cc(Nc4n[nH]c(N)n4)cc3C(F)(F)F)cc2)CC1] |

TABLE I-continued

| # | Nomenclature | Structure |
|---|---|---|
| 23 | N³-[2-Chloro-6-fluoro-4'-(propane-2-sulfonyl)-biphenyl-4-yl]-1H-[1,2,4]triazole-3,5-diamine; | 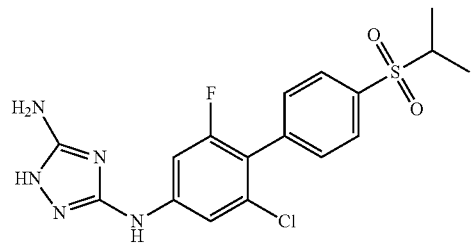 |
| 24 | N-{(R)-1-[4'-(5-Amino-1H-[1,2,4]triazol-3-ylamino)-2'-chloro-6'-trifluoromethyl-biphenyl-4-yl]-ethyl}-methane-sulfonamide; | 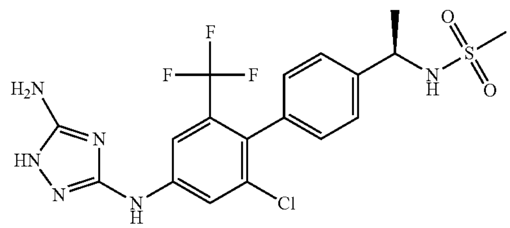 [SMILES: C[C@@H](NS(C)(=O)=O)c1ccc(-c2c(Cl)cc(Nc3n[nH]c(N)n3)cc2C(F)(F)F)cc1] |
| 25 | N³-[2-Chloro-4'-(piperidin-3-ylmethane-sulfonyl)-6-trifluoromethyl-biphenyl-4-yl]-1H-[1,2,4]triazole-3,5-diamine; | 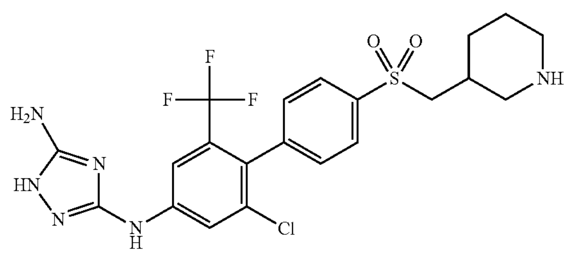 [SMILES: Nc1nc(Nc2cc(Cl)c(-c3ccc(S(=O)(=O)CC4CCCNC4)cc3)c(C(F)(F)F)c2)n[nH]1] |
| 26 | 4-[4'-(5-Amino-1H-[1,2,4]triazol-3-ylamino)-2',6'-dichloro-biphenyl-4-yloxy]-butyronitrile; | 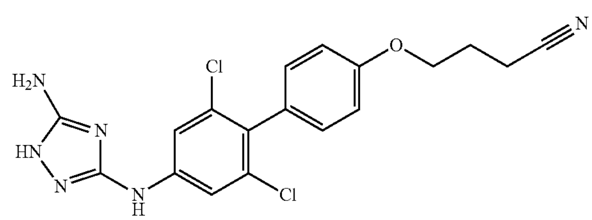 [SMILES: N#CCCCOc1ccc(-c2c(Cl)cc(Nc3n[nH]c(N)n3)cc2Cl)cc1] |
| 27 | 4'-(5-Amino-1H-[1,2,4]triazol-3-ylamino)-2'-chloro-6'-trifluoromethyl-biphenyl-4-sulfonic acid ((S)-1-pyrrolidin-2-ylmethyl)-amide; | 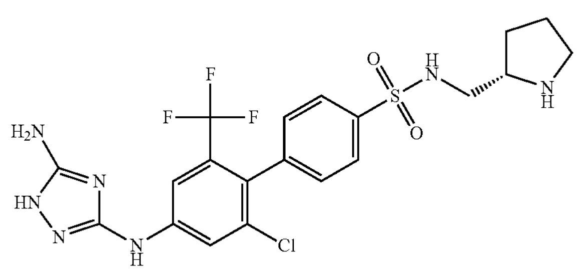 [SMILES: Nc1nc(Nc2cc(Cl)c(-c3ccc(S(=O)(=O)NC[C@@H]4CCCN4)cc3)c(C(F)(F)F)c2)n[nH]1] |
| 28 | N-[4'-(5-Amino-1H-[1,2,4]triazol-3-ylamino)-2',6'-dichloro-2-fluoro-biphenyl-4-yl]-methane-sulfonamide; | 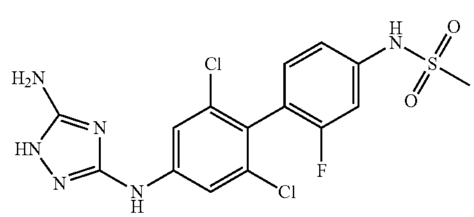 [SMILES: CS(=O)(=O)Nc1ccc(-c2c(Cl)cc(Nc3n[nH]c(N)n3)cc2Cl)c(F)c1] |

TABLE I-continued

| # | Nomenclature | Structure |
|---|---|---|
| 29 | N³-[2-Chloro-4'-(piperidine-3-sulfonyl)-6-trifluoromethyl-biphenyl-4-yl]-1H-[1,2,4]triazole-3,5-diamine; | 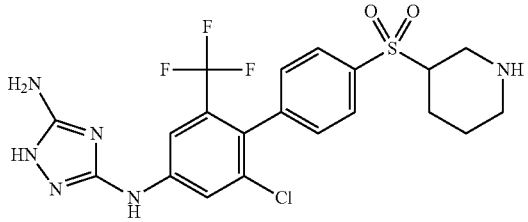 [SMILES: Nc1nc(Nc2cc(Cl)c(-c3ccc(S(=O)(=O)C4CCCNC4)cc3)c(C(F)(F)F)c2)n[nH]1] |
| 30 | N³-(2-Chloro-6-fluoro-4'-methanesulfonyl-biphenyl-4-yl)-1H-[1,2,4]triazole-3,5-diamine; | 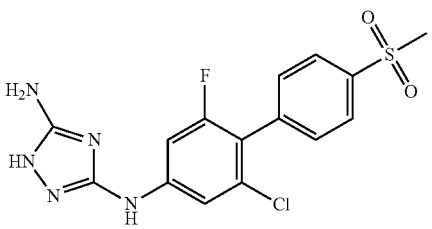 [SMILES: CS(=O)(=O)c1ccc(-c2c(F)cc(Nc3n[nH]c(N)n3)cc2Cl)cc1] |
| 31 | N³-(2,6-Dichloro-4'-methane-sulfonylmethyl-biphenyl-4-yl)-1H-[1,2,4]triazole-3,5-diamine; | 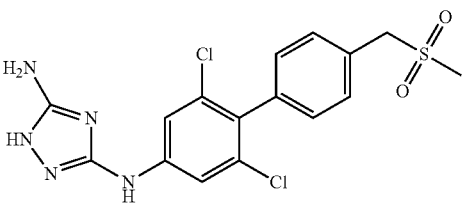 [SMILES: CS(=O)(=O)Cc1ccc(-c2c(Cl)cc(Nc3n[nH]c(N)n3)cc2Cl)cc1] |
| 32 | N³-[4'-(Azetidin-3-ylmethoxy)-2,6-dichloro-biphenyl-4-yl]-1H-[1,2,4]triazole-3,5-diamine; | 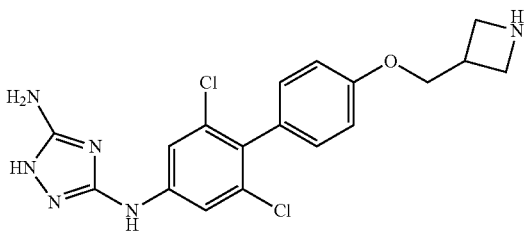 [SMILES: Nc1nc(Nc2cc(Cl)c(-c3ccc(OCC4CNC4)cc3)c(Cl)c2)n[nH]1] |
| 33 | N³-[2-Chloro-4'-(piperazine-1-sulfonyl)-6-trifluoromethyl-biphenyl-4-yl]-1H-[1,2,4]triazole-3,5-diamine; | 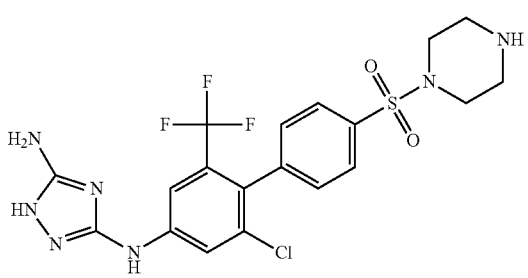 [SMILES: Nc1nc(Nc2cc(Cl)c(-c3ccc(S(=O)(=O)N4CCNCC4)cc3)c(C(F)(F)F)c2)n[nH]1] |
| 34 | 4'-(5-Amino-1H-[1,2,4]triazol-3-ylamino)-2'-chloro-6'-fluoro-biphenyl-4-sulfonic acid dimethylamide; | 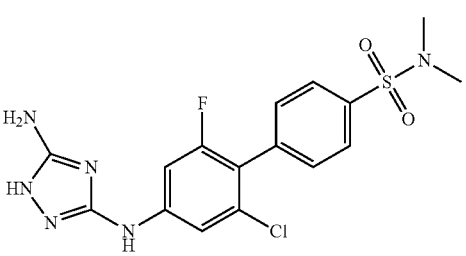 [SMILES: CN(C)S(=O)(=O)c1ccc(-c2c(F)cc(Nc3n[nH]c(N)n3)cc2Cl)cc1] |

TABLE I-continued

| # | Nomenclature | Structure |
|---|---|---|
| 35 | N³-[2-Chloro-4'-((S)-1-pyrrolidin-2-ylmethane-sulfonyl)-6-trifluoromethyl-biphenyl-4-yl]-1H-[1,2,4]triazole-3,5-diamine; | 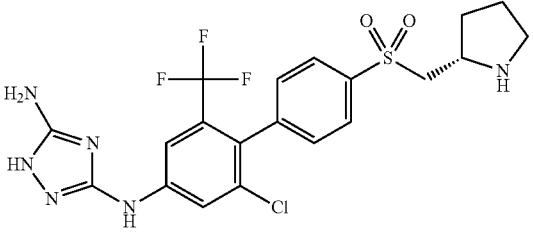 [SMILES: Nc1nc(Nc2cc(Cl)c(-c3ccc(S(=O)(=O)C[C@@H]4CCCN4)cc3)c(C(F)(F)F)c2)n[nH]1] |
| 36 | N³-[2-Chloro-4'-(morpholine-4-sulfonyl)-6-trifluoromethyl-biphenyl-4-yl]-1H-[1,2,4]triazole-3,5-diamine; | 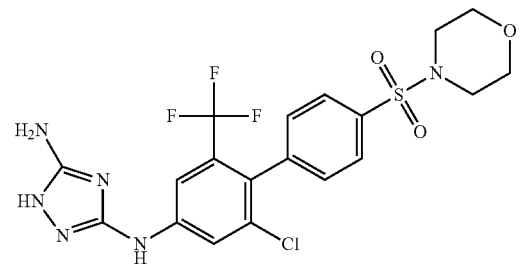 [SMILES: Nc1nc(Nc2cc(Cl)c(-c3ccc(S(=O)(=O)N4CCOCC4)cc3)c(C(F)(F)F)c2)n[nH]1] |
| 37 | N³-[4'-(Azetidin-3-ylmethoxy)-2-chloro-6-trifluoromethyl-biphenyl-4-yl]-1H-[1,2,4]triazole-3,5-diamine; | 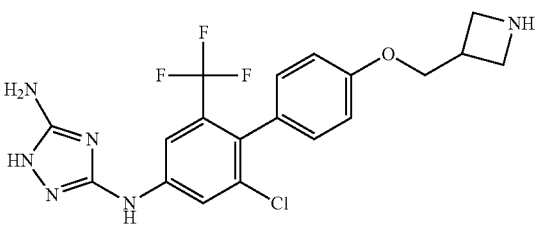 [SMILES: Nc1nc(Nc2cc(Cl)c(-c3ccc(OCC4CNC4)cc3)c(C(F)(F)F)c2)n[nH]1] |
| 38 | N-{2-[4'-(5-Amino-1H-[1,2,4]triazol-3-ylamino)-2'-chloro-6'-trifluoromethyl-biphenyl-4-yl]-ethyl}-methane-sulfonamide; | 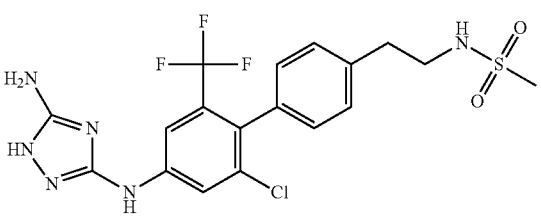 [SMILES: CS(=O)(=O)NCCc1ccc(-c2c(Cl)cc(Nc3n[nH]c(N)n3)cc2C(F)(F)F)cc1] |
| 39 | 5-((3aR,6S,6aS)-2-Oxo-hexahydro-thieno[3,4-d]imidazol-6-yl)-pentanoic acid [4'-(5-amino-1H-[1,2,4]triazol-3-ylamino)-2',6'-dichloro-biphenyl-4-yl]-amide; | 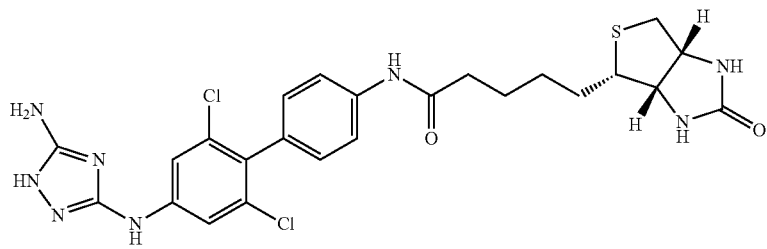 [SMILES: Nc1nc(Nc2cc(Cl)c(-c3ccc(NC(=O)CCCC[C@@H]4SC[C@@H]5NC(=O)N[C@@H]54)cc3)c(Cl)c2)n[nH]1] |
| 40 | N³-[2-Chloro-4'-(piperidin-4-ylmethane-sulfonyl)-6-trifluoromethyl-biphenyl-4-yl]-1H-[1,2,4]triazole-3,5-diamine; | 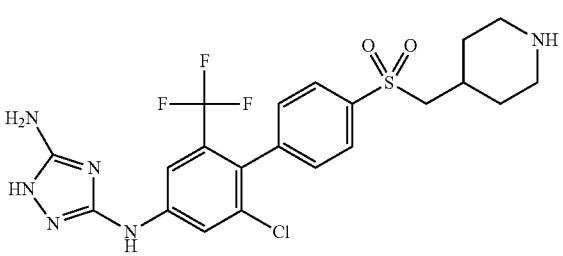 [SMILES: Nc1nc(Nc2cc(Cl)c(-c3ccc(S(=O)(=O)CC4CCNCC4)cc3)c(C(F)(F)F)c2)n[nH]1] |

TABLE I-continued

| # | Nomenclature | Structure |
|---|---|---|
| 41 | N³-[2-Chloro-3'-(piperidin-4-yloxy)-6-trifluoromethyl-biphenyl-4-yl]-1H-[1,2,4]triazole-3,5-diamine; | 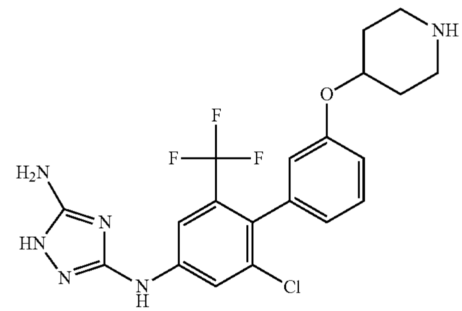 [SMILES: Nc1nc(Nc2cc(Cl)c(-c3cccc(OC4CCNCC4)c3)c(C(F)(F)F)c2)n[nH]1] |
| 42 | N³-[3,5-Dichloro-4-(1-methane-sulfonyl-1H-indol-5-yl)-phenyl]-1H-[1,2,4]triazole-3,5-diamine; | 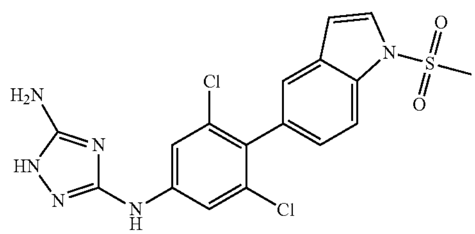 [SMILES: CS(=O)(=O)n1ccc2cc(-c3c(Cl)cc(Nc4n[nH]c(N)n4)cc3Cl)ccc21] |
| 43 | 1-[4'-(5-Amino-1H-[1,2,4]triazol-3-ylamino)-2',6'-dichloro-biphenyl-4-yl]-pyrrolidin-2-one; | 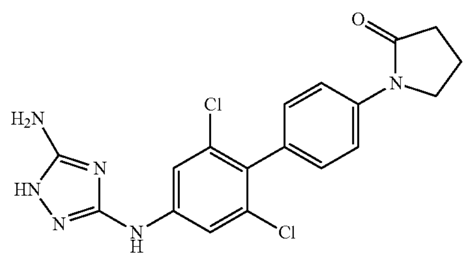 [SMILES: Nc1nc(Nc2cc(Cl)c(-c3ccc(N4CCCC4=O)cc3)c(Cl)c2)n[nH]1] |
| 44 | N³-[3-Chloro-4-(4-methane-sulfonyl-3,4-dihydro-2H-benzo[1,4]oxazin-6-yl)-5-trifluoro-methyl-phenyl]-1H-[1,2,4]triazole-3,5-diamine; | 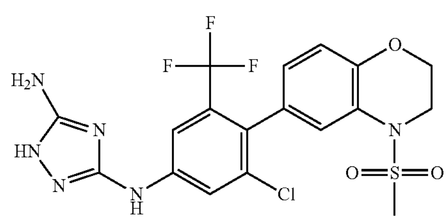 [SMILES: CS(=O)(=O)N1CCOc2ccc(-c3c(Cl)cc(Nc4n[nH]c(N)n4)cc3C(F)(F)F)cc21] |
| 45 | N³-[2-Chloro-4'-(1,1-dioxo-1λ⁶-thio-morpholine-4-sulfonyl)-6-trifluoromethyl-biphenyl-4-yl]-1H-[1,2,4]triazole-3,5-diamine; | 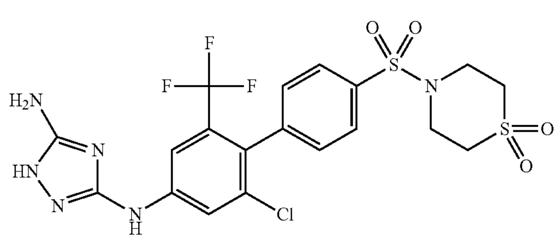 [SMILES: Nc1nc(Nc2cc(Cl)c(-c3ccc(S(=O)(=O)N4CCS(=O)(=O)CC4)cc3)c(C(F)(F)F)c2)n[nH]1] |
| 46 | N-[4'-(5-Amino-1H-[1,2,4]triazol-3-ylamino)-2',6'-dichloro-3-fluoro-biphenyl-4-yl]-methane-sulfonamide; | 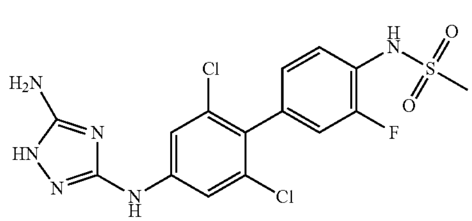 [SMILES: CS(=O)(=O)Nc1ccc(-c2c(Cl)cc(Nc3n[nH]c(N)n3)cc2Cl)cc1F] |

TABLE I-continued

| # | Nomenclature |
|---|---|
| 47 | 6-[4-(5-Amino-1H-[1,2,4]triazol-3-ylamino)-2-chloro-6-trifluoromethyl-phenyl]-4H-benzo[1,4]oxazin-3-one; |
| 48 | N³-(2,6-Dichloro-biphenyl-4-yl)-1H-[1,2,4]triazole-3,5-diamine; |
| 49 | N³-[4'-(4-Amino-butoxy)-2,6-dichloro-biphenyl-4-yl]-1H-[1,2,4]triazole-3,5-diamine; compound with trifluoro-acetic acid; |
| 50 | N³-(4'-Amino-2,6-dichloro-biphenyl-4-yl)-1H-[1,2,4]triazole-3,5-diamine; |
| 51 | (S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid; |
| 52 | N³-[3,5-Dichloro-4-(2,2-dimethyl-4,4-dioxo-3,4-dihydro-2H-4λ⁶-benzo[1,4]oxathiin-6-yl)-phenyl]-1H-[1,2,4]triazole-3,5-diamine; |
| 53 | Pentanoic acid [4'-(5-amino-1H-[1,2,4]triazol-3-ylamino)-biphenyl-4-yl]-amide; |

TABLE I-continued

| # | Nomenclature | Structure |
|---|---|---|
| 54 | 5-((3aR,6S,6aS)-2-Oxo-hexahydro-thieno[3,4-d]imidazol-6-yl)-pentanoic acid [4'-(5-amino-1H-[1,2,4]triazol-3-ylamino)-biphenyl-4-yl]-amide; | 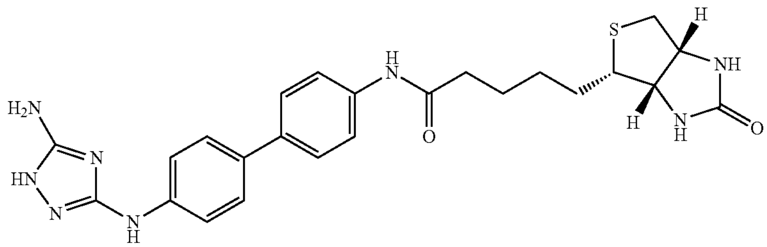 [SMILES: Nc1nc(Nc2ccc(-c3ccc(NC(=O)CCCC[C@@H]4SC[C@@H]5NC(=O)N[C@@H]54)cc3)cc2)n[nH]1] |
| 55 | N³-Biphenyl-4-yl-1H-[1,2,4]triazole-3,5-diamine; | 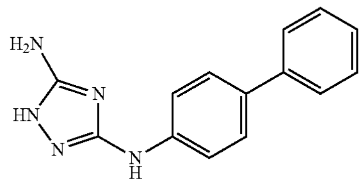 [SMILES: Nc1nc(Nc2ccc(-c3ccccc3)cc2)n[nH]1] |
| 56 | N³-{6-Chloro-4'-[1-(3,3-dimethyl-butyl)-piperidin-3-ylmethane-sulfonyl]-2-trifluoromethyl-biphenyl-4-yl}-1H-[1,2,4]triazole-3,5-diamine; | 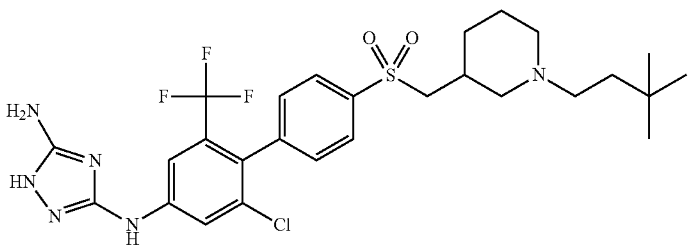 [SMILES: CC(C)(C)CCN1CCCC(CS(=O)(=O)c2ccc(-c3c(Cl)cc(Nc4n[nH]c(N)n4)cc3C(F)(F)F)cc2)C1] |
| 57 | N³-{6-Chloro-4'-[1-(3,3-dimethyl-butyl)-piperidin-4-ylmethane-sulfonyl]-2-trifluoromethyl-biphenyl-4-yl}-1H-[1,2,4]triazole-3,5-diamine; | 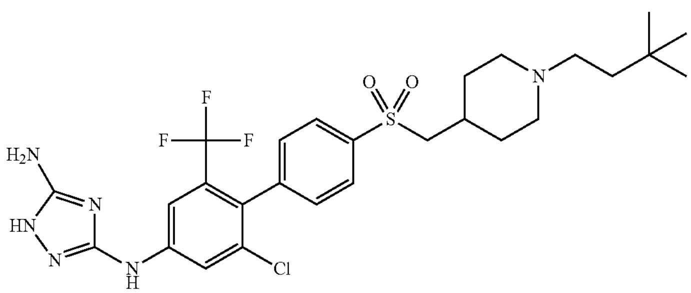 [SMILES: CC(C)(C)CCN1CCC(CS(=O)(=O)c2ccc(-c3c(Cl)cc(Nc4n[nH]c(N)n4)cc3C(F)(F)F)cc2)CC1] |
| 58 | N³-[4'-(tert-Butylamino-methyl)-2-chloro-6-trifluoromethyl-biphenyl-4-yl]-1H-[1,2,4]triazole-3,5-diamine; | 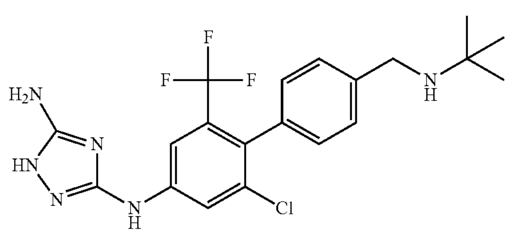 [SMILES: CC(C)(C)NCc1ccc(-c2c(Cl)cc(Nc3n[nH]c(N)n3)cc2C(F)(F)F)cc1] |
| 59 | 3-[4'-(5-Amino-1H-[1,2,4]triazol-3-ylamino)-6'-chloro-2'-trifluoromethyl-biphenyl-4-sulfonyl]-azetidine-1-carboxylic acid tert-butyl ester; | 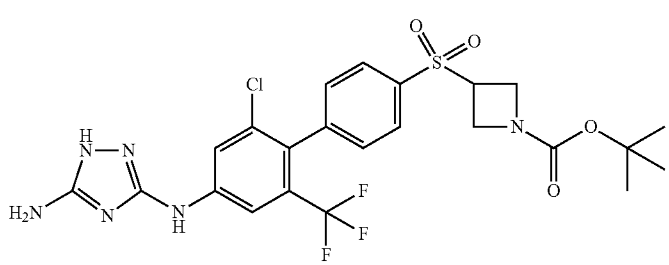 [SMILES: CC(C)(C)OC(=O)N1CC(S(=O)(=O)c2ccc(-c3c(Cl)cc(Nc4n[nH]c(N)n4)cc3C(F)(F)F)cc2)C1] |

TABLE I-continued

| # | Nomenclature | Structure |
|---|---|---|
| 60 | 4'-(5-Amino-1H-[1,2,4]triazol-3-ylamino)-6'-chloro-2'-trifluoromethyl-biphenyl-4-sulfonic acid (3-methyl-oxetan-3-yl)-amide; | 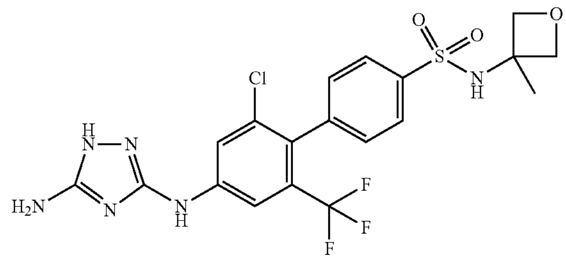 [SMILES: CC1(NS(=O)(=O)c2ccc(-c3c(Cl)cc(Nc4n[nH]c(N)n4)cc3C(F)(F)F)cc2)COC1] |
| 61 | $N^3$-[6-Chloro-4'-(3-methyl-butane-1-sulfonyl)-2-trifluoromethyl-biphenyl-4-yl]-1H-[1,2,4]triazole-3,5-diamine; | 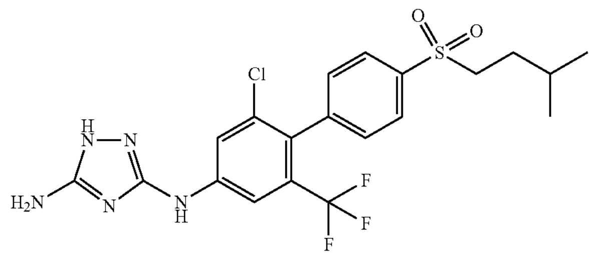 [SMILES: CC(C)CCS(=O)(=O)c1ccc(-c2c(Cl)cc(Nc3n[nH]c(N)n3)cc2C(F)(F)F)cc1] |
| 62 | $N^3$-[6-Chloro-4'-(3,3-difluoro-pyrrolidine-1-sulfonyl)-2-trifluoromethyl-biphenyl-4-yl]-1H-[1,2,4]triazole-3,5-diamine; | 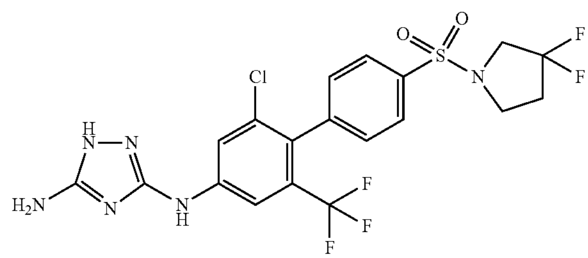 [SMILES: Nc1nc(Nc2cc(Cl)c(-c3ccc(S(=O)(=O)N4CCC(F)(F)C4)cc3)c(C(F)(F)F)c2)n[nH]1] |
| 63 | 1-[4'-(5-Amino-1H-[1,2,4]triazol-3-ylamino)-6'-chloro-2'-trifluoromethyl-biphenyl-4-sulfonyl]-3-methyl-azetidin-3-ol; | 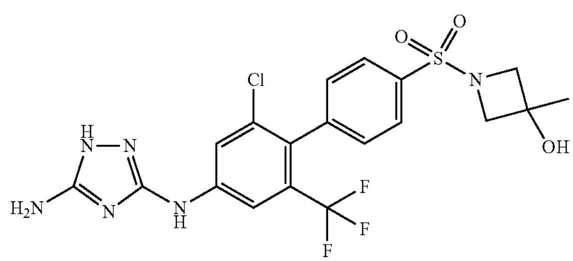 [SMILES: CC1(O)CN(S(=O)(=O)c2ccc(-c3c(Cl)cc(Nc4n[nH]c(N)n4)cc3C(F)(F)F)cc2)C1] |
| 64 | $N^3$-(6-Chloro-4'-cyclopropyl-methanesulfonyl-2-trifluoromethyl-biphenyl-4-yl)-1H-[1,2,4]triazole-3,5-diamine; | 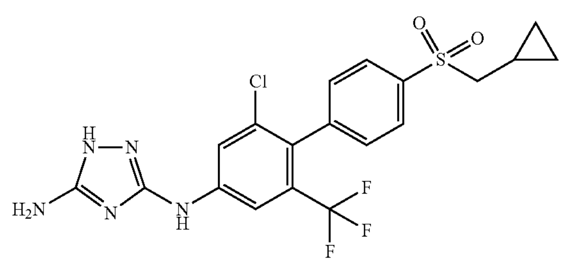 [SMILES: Nc1nc(Nc2cc(Cl)c(-c3ccc(S(=O)(=O)CC4CC4)cc3)c(C(F)(F)F)c2)n[nH]1] |
| 65 | $N^3$-[6-Chloro-4'-(2-methyl-propane-1-sulfonyl)-2-trifluoromethyl-biphenyl-4-yl]-1H-[1,2,4]triazole-3,5-diamine; | 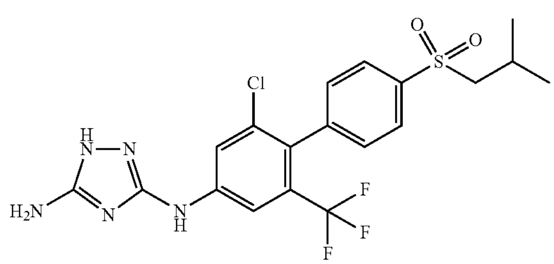 [SMILES: CC(C)CS(=O)(=O)c1ccc(-c2c(Cl)cc(Nc3n[nH]c(N)n3)cc2C(F)(F)F)cc1] |

TABLE I-continued

| # | Nomenclature | Structure |
|---|---|---|
| 66 | 1-[4'-(5-Amino-1H-[1,2,4]triazol-3-ylamino)-6'-chloro-2'-trifluoromethyl-biphenyl-4-sulfonyl]-4-methyl-piperidin-4-ol; | 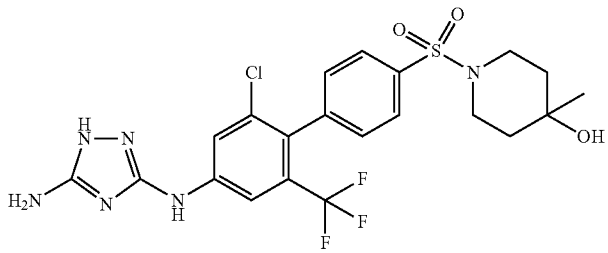 [SMILES: CC1(O)CCN(S(=O)(=O)c2ccc(-c3c(Cl)cc(Nc4n[nH]c(N)n4)cc3C(F)(F)F)cc2)CC1] |
| 67 | N³-[4'-(Azetidine-3-sulfonyl)-6-chloro-2-trifluoromethyl-biphenyl-4-yl]-1H-[1,2,4]triazole-3,5-diamine; | 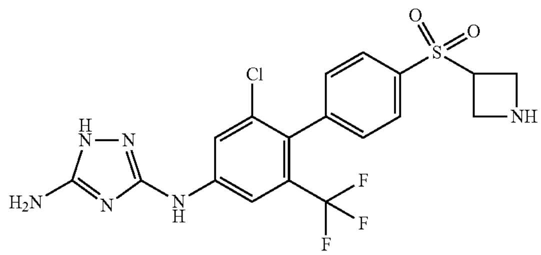 [SMILES: Nc1nc(Nc2cc(Cl)c(-c3ccc(S(=O)(=O)C4CNC4)cc3)c(C(F)(F)F)c2)n[nH]1] |
| 68 | 1-[4'-5-Amino-1H-[1,2,4]triazol-3-ylamino)-6'-chloro-2'-trifluoromethyl-biphenyl-4-sulfonyl]-3-methyl-pyrrolidin-3-ol; | 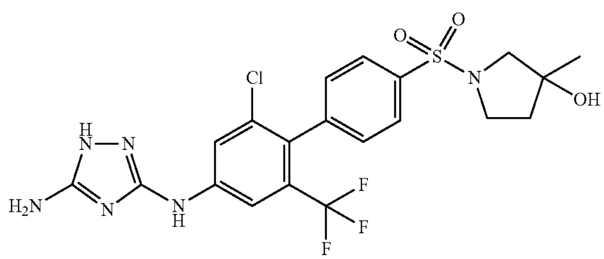 [SMILES: CC1(O)CCN(S(=O)(=O)c2ccc(-c3c(Cl)cc(Nc4n[nH]c(N)n4)cc3C(F)(F)F)cc2)C1] |
| 69 | N³-[6-Chloro-4'-(2-oxa-6-aza-spiro[3.3]heptane-6-sulfonyl)-2-trifluoromethyl-biphenyl-4-yl]-1H-[1,2,4]triazole-3,5-diamine; | 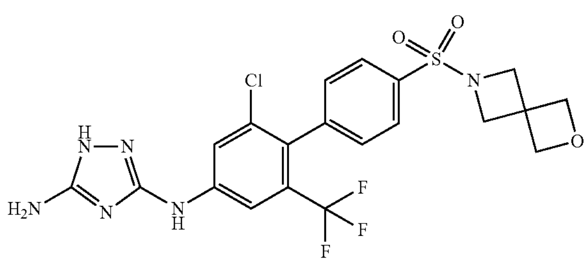 [SMILES: Nc1nc(Nc2cc(Cl)c(-c3ccc(S(=O)(=O)N4CC5(COC5)C4)cc3)c(C(F)(F)F)c2)n[nH]1] |
| 70 | N⁵-(2-Fluoro-4'-methane-sulfonyl-6-trifluoromethyl-biphenyl-4-yl)-1H-[1,2,4]triazole-3,5-diamine; | 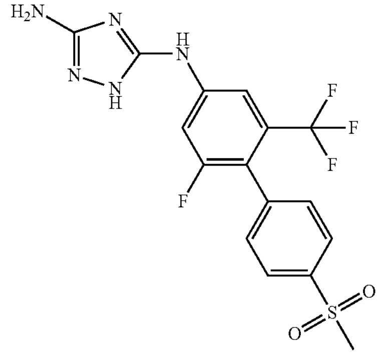 [SMILES: CS(=O)(=O)c1ccc(-c2c(F)cc(Nc3nc(N)n[nH]3)cc2C(F)(F)F)cc1] |

TABLE I-continued
| # | Nomenclature | Structure |
|---|---|---|
| 71 | N[5]-[2-Fluoro-4'-(propane-2-sulfonyl)-6-trifluoromethyl-biphenyl-4-yl]-1H-[1,2,4]triazole-3,5-diamine; | 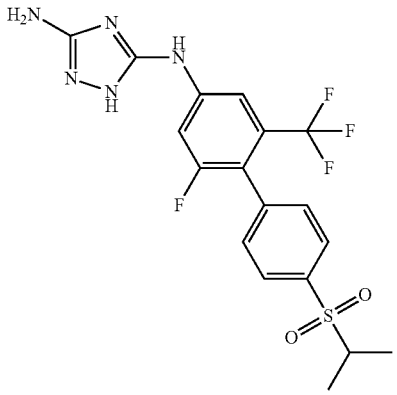 [SMILES: CC(C)S(=O)(=O)c1ccc(-c2c(F)cc(Nc3nc(N)n[nH]3)cc2C(F)(F)F)cc1] |
| 72 | 4'-(5-Amino-2H-[1,2,4]triazol-3-ylamino)-2'-fluoro-6'-trifluoromethyl-biphenyl-4-sulfonic acid methylamide; | 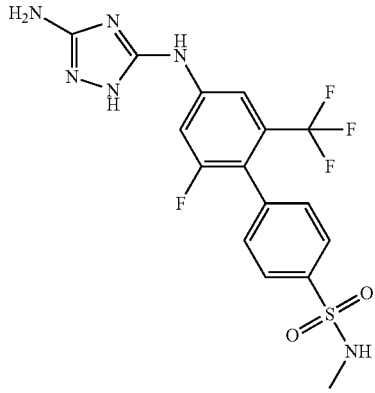 [SMILES: CNS(=O)(=O)c1ccc(-c2c(F)cc(Nc3nc(N)n[nH]3)cc2C(F)(F)F)cc1] |
| 73 | N-[4'-(5-Amino-1H-[1,2,4]triazol-3-ylamino)-2',6'-dichloro-biphenyl-4-yl]-2-methoxy-acetamide; | 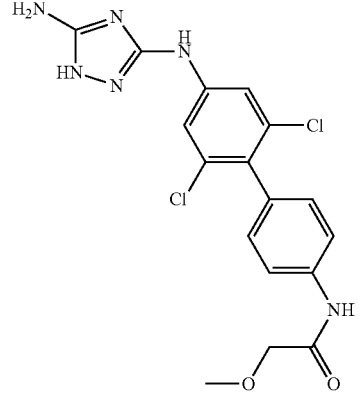 [SMILES: COCC(=O)Nc1ccc(-c2c(Cl)cc(Nc3n[nH]c(N)n3)cc2Cl)cc1] |
| 74 | N[5]-(2-Fluoro-3'-methane-sulfonyl-6-trifluoromethyl-biphenyl-4-yl)-1H-[1,2,4]triazole-3,5-diamine; | 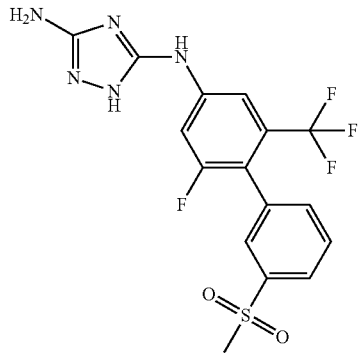 [SMILES: CS(=O)(=O)c1cccc(-c2c(F)cc(Nc3nc(N)n[nH]3)cc2C(F)(F)F)c1] |

TABLE I-continued
| # | Nomenclature | Structure |
|---|---|---|
| 75 | 4'-(5-Amino-2H-[1,2,4]triazol-3-ylamino)-2'-fluoro-6'-trifluoromethyl-biphenyl-4-sulfonic acid dimethylamide; | 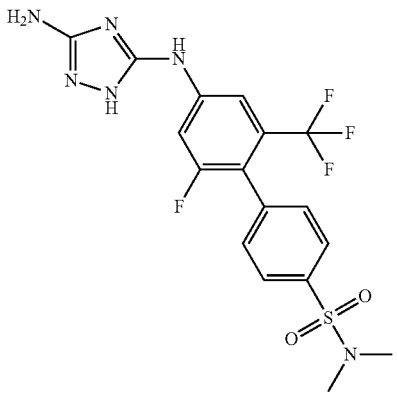 [SMILES: CN(C)S(=O)(=O)c1ccc(-c2c(F)cc(Nc3nc(N)n[nH]3)cc2C(F)(F)F)cc1] |
| 76 | $N^5$-(2,6-Difluoro-4'-methane-sulfonyl-biphenyl-4-yl)-1H-[1,2,4]triazole-3,5-diamine; | 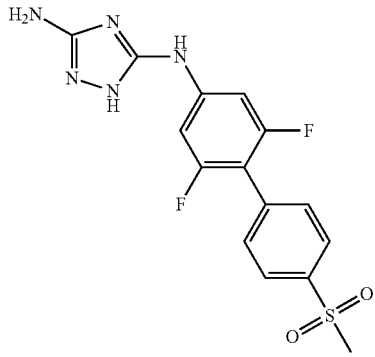 [SMILES: CS(=O)(=O)c1ccc(-c2c(F)cc(Nc3nc(N)n[nH]3)cc2F)cc1] |
| 77 | $N^5$-[2,6-Difluoro-4'-(morpholine-4-sulfonyl)-biphenyl-4-yl]-1H-[1,2,4]triazole-3,5-diamine; | 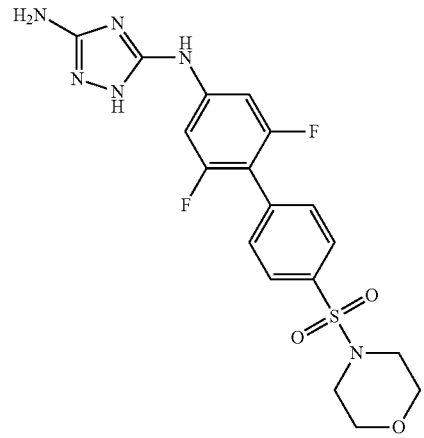 [SMILES: Nc1n[nH]c(Nc2cc(F)c(-c3ccc(S(=O)(=O)N4CCOCC4)cc3)c(F)c2)n1] |

TABLE I-continued

| # | Nomenclature | Structure |
|---|---|---|
| 78 | N⁵-[2-Fluoro-4'-(morpholine-4-sulfonyl)-6-trifluoromethyl-biphenyl-4-yl]-1H-[1,2,4]triazole-3,5-diamine; | 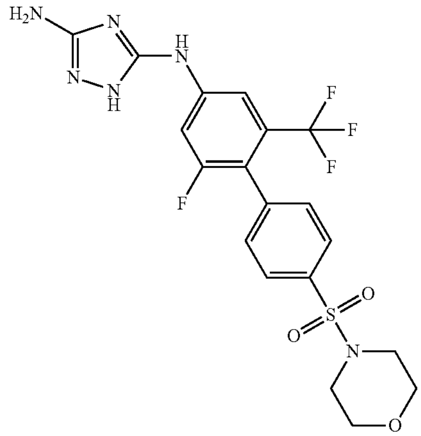 [SMILES: Nc1n[nH]c(Nc2cc(F)c(-c3ccc(S(=O)(=O)N4CCOCC4)cc3)c(C(F)(F)F)c2)n1] |
| 79 | 4'-(5-Amino-2H-[1,2,4]triazol-3-ylamino)-2'-fluoro-6'-trifluoromethyl-biphenyl-4-carbonitrile; | 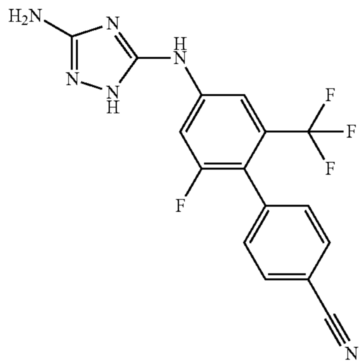 [SMILES: N#Cc1ccc(-c2c(F)cc(Nc3nc(N)n[nH]3)cc2C(F)(F)F)cc1] |
| 80 | N⁵-(2,6-Difluoro-3'-methane-sulfonyl-biphenyl-4-yl)-1H-[1,2,4]triazole-3,5-diamine; | 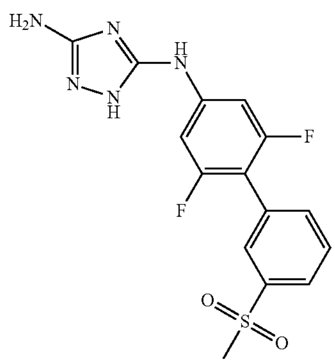 [SMILES: CS(=O)(=O)c1cccc(-c2c(F)cc(Nc3nc(N)n[nH]3)cc2F)c1] |
| 81 | 4'-(5-Amino-2H-[1,2,4]triazol-3-ylamino)-2'-fluoro-6'-trifluoromethyl-biphenyl-3-sulfonic acid methylamide; | 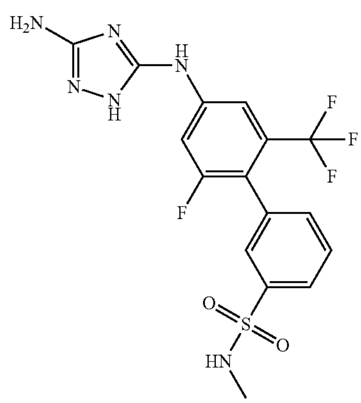 [SMILES: CNS(=O)(=O)c1cccc(-c2c(F)cc(Nc3nc(N)n[nH]3)cc2C(F)(F)F)c1] |

TABLE I-continued

| # | Nomenclature |
|---|---|
| 82 | Tetrahydro-pyran-4-carboxylic acid [4'-(5-amino-1H-[1,2,4]triazol-3-ylamino)-2',6'-dichloro-biphenyl-4-yl]-amide; |
| 83 | N³-(2,6-Dichloro-4'-nitro-biphenyl-4-yl)-1H-[1,2,4]triazole-3,5-diaminetrifluoro-acetic acid; |
| 84 | 4'-(5-Amino-2H-[1,2,4]triazol-3-ylamino)-2'-fluoro-6'-trifluoromethyl-biphenyl-3-sulfonic acid dimethylamide; |
| 85 | 4'-(5-Amino-2H-[1,2,4]triazol-3-ylamino)-2'-fluoro-6'-trifluoromethyl-biphenyl-4-carboxylic acid dimethylamide; |

TABLE I-continued
| # | Nomenclature | Structure |
|---|---|---|
| 86 | N⁵-(2-Fluoro-4'-methoxy-6-trifluoromethyl-biphenyl-4-yl)-1H-[1,2,4]triazole-3,5-diamine; | 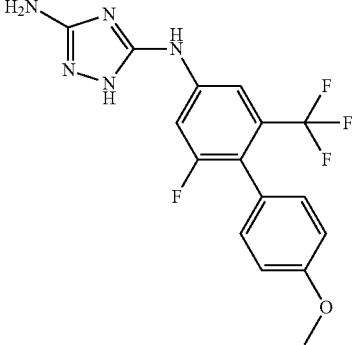 [SMILES: COc1ccc(-c2c(F)cc(Nc3nc(N)n[nH]3)cc2C(F)(F)F)cc1] |
| 87 | 4'-(5-Amino-2H-[1,2,4]triazol-3-ylamino)-2',6'-difluoro-biphenyl-4-carbonitrile; | 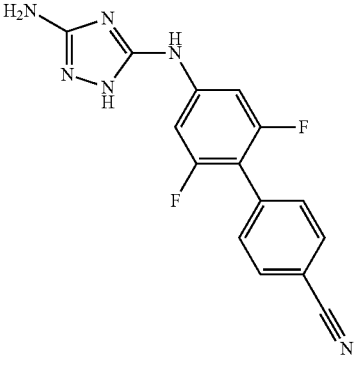 [SMILES: N#Cc1ccc(-c2c(F)cc(Nc3nc(N)n[nH]3)cc2F)cc1] |
| 88 | N⁵-(2-Fluoro-4'-trifluoromethane-sulfonyl-6-trifluoromethyl-biphenyl-4-yl)-1H-[1,2,4]triazole-3,5-diamine; | 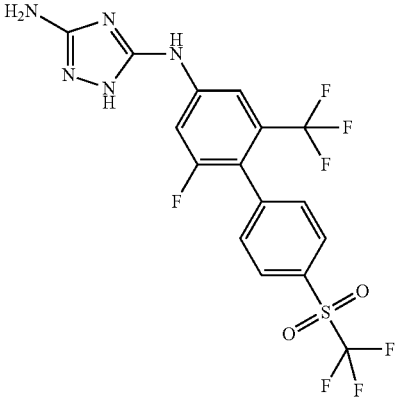 [SMILES: Nc1n[nH]c(Nc2cc(F)c(-c3ccc(S(=O)(=O)C(F)(F)F)cc3)c(C(F)(F)F)c2)n1] |
| 89 | 4'-(5-Amino-2H-[1,2,4]triazol-3-ylamino)-2'-fluoro-6'-trifluoromethyl-biphenyl-3-carbonitrile; | 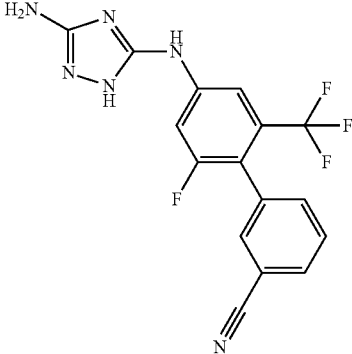 [SMILES: N#Cc1cccc(-c2c(F)cc(Nc3nc(N)n[nH]3)cc2C(F)(F)F)c1] |

TABLE I-continued

| # | Nomenclature | Structure |
|---|---|---|
| 90 | N³-(4'-Methane-sulfonyl-2-trifluoromethyl-biphenyl-4-yl)-1H-[1,2,4]triazole-3,5-diamine; | 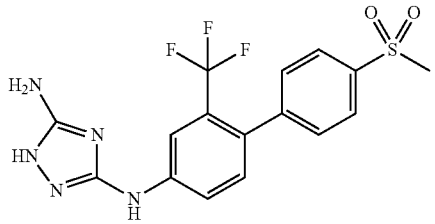 [SMILES: CS(=O)(=O)c1ccc(-c2ccc(Nc3n[nH]c(N)n3)cc2C(F)(F)F)cc1] |
| 91 | N³-(2,6-Dichloro-4'-trifluoro-methoxy-biphenyl-4-yl)-1H-[1,2,4]triazole-3,5-diamine; | 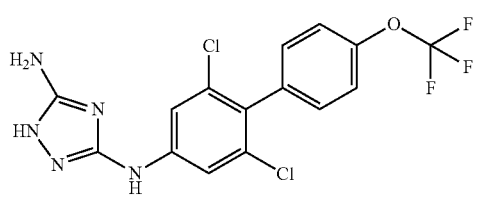 [SMILES: Nc1nc(Nc2cc(Cl)c(-c3ccc(OC(F)(F)F)cc3)c(Cl)c2)n[nH]1] |
| 92 | N³-(2,6,3'-Trichloro-biphenyl-4-yl)-1H-[1,2,4]triazole-3,5-diamine; | 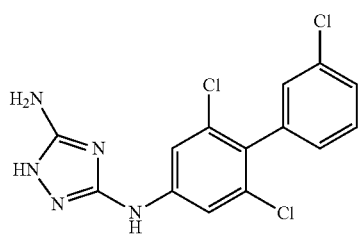 [SMILES: Nc1nc(Nc2cc(Cl)c(-c3cccc(Cl)c3)c(Cl)c2)n[nH]1] |
| 93 | 4'-(5-Amino-1H-[1,2,4]triazol-3-ylamino)-2',6'-dichloro-biphenyl-4-carbonitrile; | 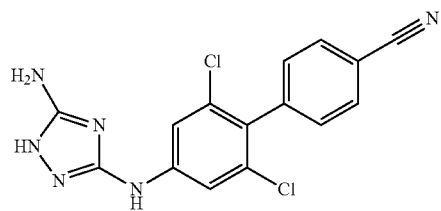 [SMILES: N#Cc1ccc(-c2c(Cl)cc(Nc3n[nH]c(N)n3)cc2Cl)cc1] |
| 94 | N³-(2,6-Dichloro-4'-methane-sulfonyl-biphenyl-4-yl)-1H-[1,2,4]triazole-3,5-diamine; | 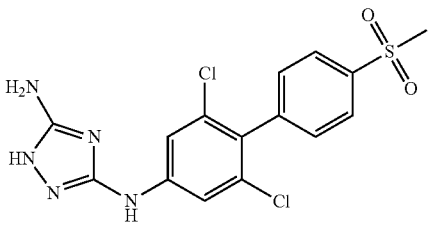 [SMILES: CS(=O)(=O)c1ccc(-c2c(Cl)cc(Nc3n[nH]c(N)n3)cc2Cl)cc1] |
| 95 | N³-(3,5-Dichloro-4-naphthalen-1-yl-phenyl)-1H-[1,2,4]triazole-3,5-diamine; | 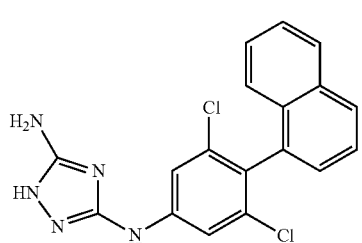 |
| 96 | N³-(2,6,4'-Trichloro-biphenyl-4-yl)-1H-[1,2,4]triazole-3,5-diamine; | 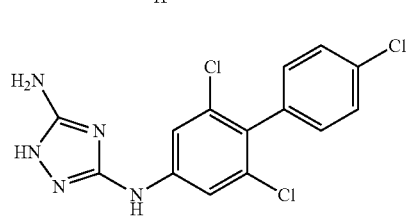 |

TABLE I-continued

| # | Nomenclature | Structure |
|---|---|---|
| 97 | N³-(2,6-Dichloro-4'-methyl-biphenyl-4-yl)-1H-[1,2,4]triazole-3,5-diamine; | 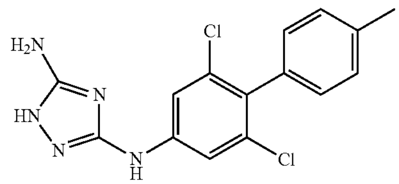 [SMILES: Cc1ccc(-c2c(Cl)cc(Nc3n[nH]c(N)n3)cc2Cl)cc1] |
| 98 | N³-(2,6-Dichloro-4'-methoxy-biphenyl-4-yl)-1H-[1,2,4]triazole-3,5-diamine; | 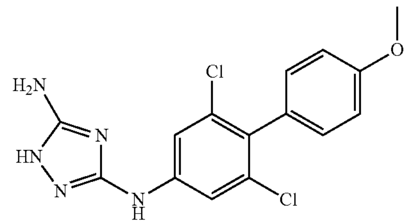 [SMILES: COc1ccc(-c2c(Cl)cc(Nc3n[nH]c(N)n3)cc2Cl)cc1] |
| 99 | N³-(2,6-Dichloro-4'-trifluoromethyl-biphenyl-4-yl)-1H-[1,2,4]triazole-3,5-diamine; | 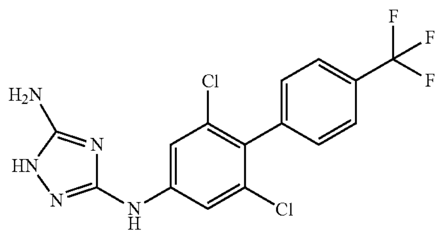 [SMILES: Nc1nc(Nc2cc(Cl)c(-c3ccc(C(F)(F)F)cc3)c(Cl)c2)n[nH]1] |
| 100 | N³-(2,6-Dichloro-3'-methoxy-biphenyl-4-yl)-1H-[1,2,4]triazole-3,5-diamine; | 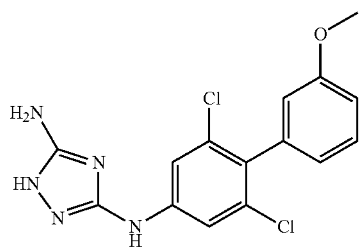 [SMILES: COc1cccc(-c2c(Cl)cc(Nc3n[nH]c(N)n3)cc2Cl)c1] |
| 101 | N³-(2,6,2'-Trichloro-biphenyl-4-yl)-1H-[1,2,4]triazole-3,5-diamine; | 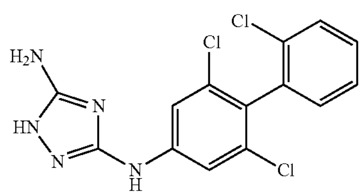 [SMILES: Nc1nc(Nc2cc(Cl)c(-c3ccccc3Cl)c(Cl)c2)n[nH]1] |
| 102 | N³-(2,6,3',4'-Tetrachloro-biphenyl-4-yl)-1H-[1,2,4]triazole-3,5-diamine; | 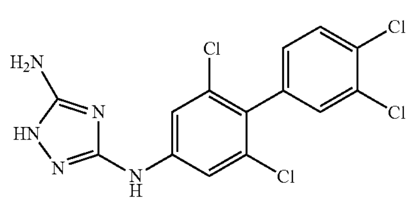 [SMILES: Nc1nc(Nc2cc(Cl)c(-c3ccc(Cl)c(Cl)c3)c(Cl)c2)n[nH]1] |
| 103 | 4'-(5-Amino-1H-[1,2,4]triazol-3-ylamino)-2',6'-dichloro-biphenyl-3-carbonitrile; | 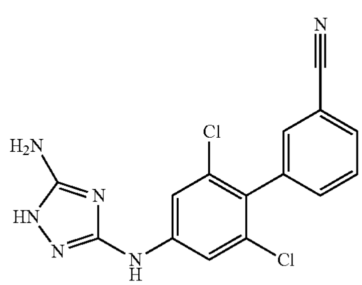 [SMILES: N#Cc1cccc(-c2c(Cl)cc(Nc3n[nH]c(N)n3)cc2Cl)c1] |

TABLE I-continued

| # | Nomenclature | Structure |
|---|---|---|
| 104 | 4'-(5-Amino-1H-[1,2,4]triazol-3-ylamino)-2',6'-dichloro-biphenyl-2-carbonitrile; | 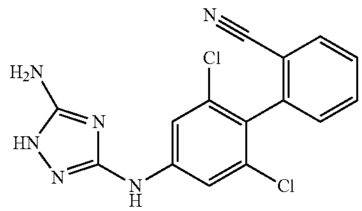 [SMILES: N#Cc1ccccc1-c1c(Cl)cc(Nc2n[nH]c(N)n2)cc1Cl] |
| 105 | 4'-(5-Amino-1H-[1,2,4]triazol-3-ylamino)-4,2',6'-trichloro-biphenyl-3-carbonitrile; | 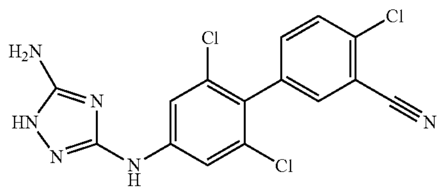 [SMILES: N#Cc1cc(-c2c(Cl)cc(Nc3n[nH]c(N)n3)cc2Cl)ccc1Cl] |
| 106 | 4'-(5-Amino-1H-[1,2,4]triazol-3-ylamino)-2',6'-dichloro-biphenyl-3-carboxylic acid; | 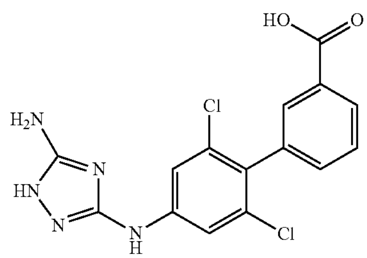 [SMILES: Nc1nc(Nc2cc(Cl)c(-c3cccc(C(=O)O)c3)c(Cl)c2)n[nH]1] |
| 107 | 1-[4'-(5-Amino-1H-[1,2,4]triazol-3-ylamino)-2',6'-dichloro-biphenyl-4-yl]-ethanone; | 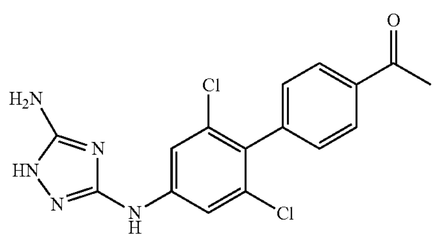 [SMILES: CC(=O)c1ccc(-c2c(Cl)cc(Nc3n[nH]c(N)n3)cc2Cl)cc1] |
| 108 | $N^3$-(2,6-Dichloro-3'-trifluoromethyl-biphenyl-4-yl)-1H-[1,2,4]triazole-3,5-diamine; | 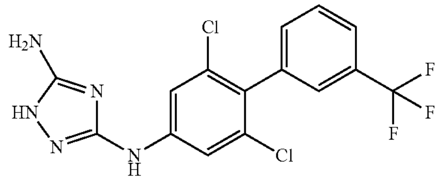 [SMILES: Nc1nc(Nc2cc(Cl)c(-c3cccc(C(F)(F)F)c3)c(Cl)c2)n[nH]1] |
| 109 | $N^3$-(2,6,2',3'-Tetrachloro-biphenyl-4-yl)-1H-[1,2,4]triazole-3,5-diamine; | 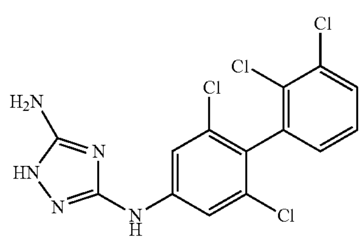 [SMILES: Nc1nc(Nc2cc(Cl)c(-c3cccc(Cl)c3Cl)c(Cl)c2)n[nH]1] |
| 110 | 4'-(5-Amino-1H-[1,2,4]triazol-3-ylamino)-2',6'-dichloro-biphenyl-4-carboxylic acid methyl ester; | 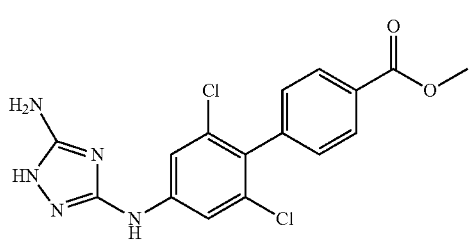 [SMILES: COC(=O)c1ccc(-c2c(Cl)cc(Nc3n[nH]c(N)n3)cc2Cl)cc1] |

TABLE I-continued

| # | Nomenclature | Structure |
|---|---|---|
| 111 | N-[4'-(5-Amino-1H-[1,2,4]triazol-3-ylamino)-2',6'-dichloro-biphenyl-4-yl]-methane-sulfonamide; | 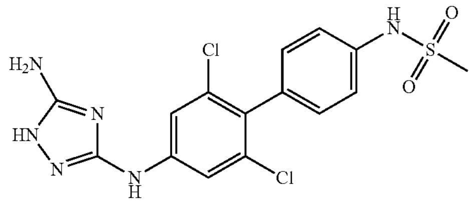 [SMILES: CS(=O)(=O)Nc1ccc(-c2c(Cl)cc(Nc3n[nH]c(N)n3)cc2Cl)cc1] |
| 112 | N-[4'-(5-Amino-1H-[1,2,4]triazol-3-ylamino)-2',6'-dichloro-biphenyl-3-yl]-methane-sulfonamide; | 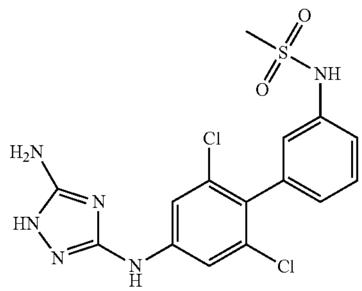 [SMILES: CS(=O)(=O)Nc1cccc(-c2c(Cl)cc(Nc3n[nH]c(N)n3)cc2Cl)c1] |
| 113 | 4'-(5-Amino-1H-[1,2,4]triazol-3-ylamino)-2',6'-dichloro-biphenyl-4-carboxylic acid dimethylamide; | 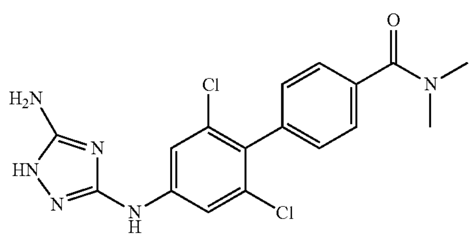 [SMILES: CN(C)C(=O)c1ccc(-c2c(Cl)cc(Nc3n[nH]c(N)n3)cc2Cl)cc1] |
| 114 | $N^3$-(2,6-Dichloro-3'-methane-sulfonyl-biphenyl-4-yl)-1H-[1,2,4]triazole-3,5-diamine; | 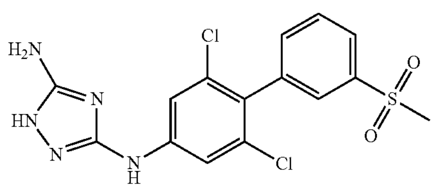 [SMILES: CS(=O)(=O)c1cccc(-c2c(Cl)cc(Nc3n[nH]c(N)n3)cc2Cl)c1] |
| 115 | 4'-(5-Amino-1H-[1,2,4]triazol-3-ylamino)-2',6'-dichloro-biphenyl-3-carboxylic acid dimethylamide; | 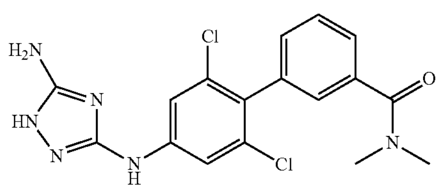 [SMILES: CN(C)C(=O)c1cccc(-c2c(Cl)cc(Nc3n[nH]c(N)n3)cc2Cl)c1] |
| 116 | 4'-(5-Amino-1H-[1,2,4]triazol-3-ylamino)-2',6'-dichloro-biphenyl-4-carboxylic acid methylamide; | 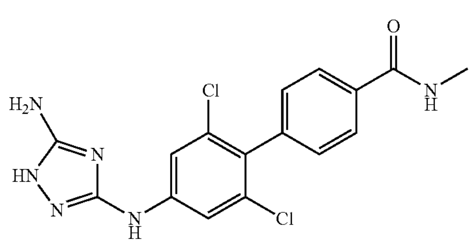 [SMILES: CNC(=O)c1ccc(-c2c(Cl)cc(Nc3n[nH]c(N)n3)cc2Cl)cc1] |
| 117 | 4'-(5-Amino-1H-[1,2,4]triazol-3-ylamino)-2',6'-dichloro-biphenyl-3-carboxylic acid methylamide; | 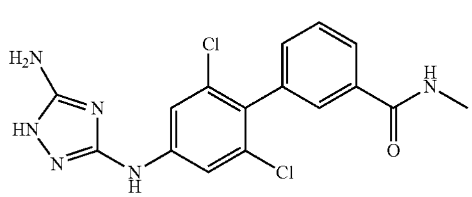 [SMILES: CNC(=O)c1cccc(-c2c(Cl)cc(Nc3n[nH]c(N)n3)cc2Cl)c1] |

TABLE I-continued

| # | Nomenclature | Structure |
|---|---|---|
| 118 | 4'-(5-Amino-1H-[1,2,4]triazol-3-ylamino)-2',6'-dichloro-biphenyl-4-sulfonic acid methylamide; | 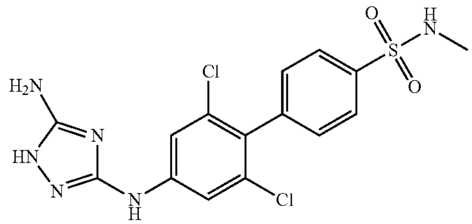 [SMILES: CNS(=O)(=O)c1ccc(-c2c(Cl)cc(Nc3n[nH]c(N)n3)cc2Cl)cc1] |
| 119 | 4'-(5-Amino-1H-[1,2,4]triazol-3-ylamino)-2',6'-dichloro-biphenyl-3-sulfonic acid methylamide; | 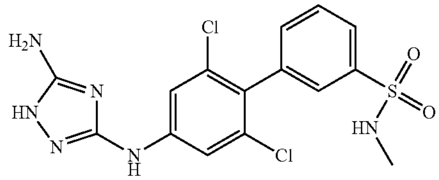 [SMILES: CNS(=O)(=O)c1cccc(-c2c(Cl)cc(Nc3n[nH]c(N)n3)cc2Cl)c1] |
| 120 | N³-(2,6-Dichloro-2'-methoxy-biphenyl-4-yl)-1H-[1,2,4]triazole-3,5-diamine; | 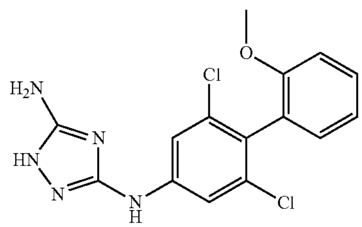 [SMILES: COc1ccccc1-c1c(Cl)cc(Nc2n[nH]c(N)n2)cc1Cl] |
| 121 | N³-(2,6-Dichloro-3'-fluoro-4'-methanesulfonyl-biphenyl-4-yl)-1H-[1,2,4]triazole-3,5-diamine; | 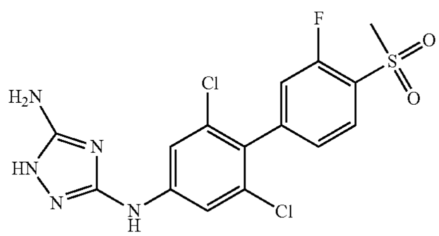 [SMILES: CS(=O)(=O)c1ccc(-c2c(Cl)cc(Nc3n[nH]c(N)n3)cc2Cl)cc1F] |
| 122 | N³-[2,6-Dichloro-4'-(propane-2-sulfonyl)-biphenyl-4-yl]-1H-[1,2,4]triazole-3,5-diamine; | 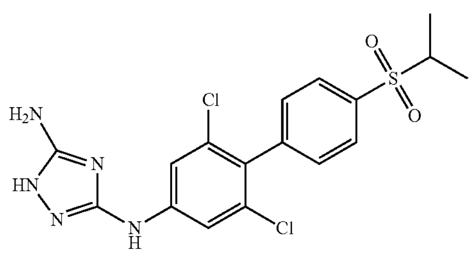 [SMILES: CC(C)S(=O)(=O)c1ccc(-c2c(Cl)cc(Nc3n[nH]c(N)n3)cc2Cl)cc1] |
| 123 | 4'-(5-Amino-1H-[1,2,4]triazol-3-ylamino)-2',6'-dichloro-biphenyl-4-sulfonic acid dimethylamide; | 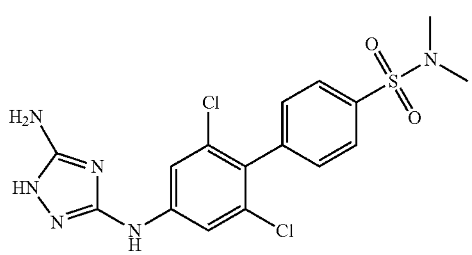 [SMILES: CN(C)S(=O)(=O)c1ccc(-c2c(Cl)cc(Nc3n[nH]c(N)n3)cc2Cl)cc1] |
| 124 | N³-(2,6,2',4'-Tetrachloro-biphenyl-4-yl)-1H-[1,2,4]triazole-3,5-diamine; | 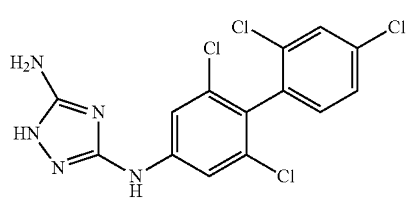 [SMILES: Nc1nc(Nc2cc(Cl)c(-c3ccc(Cl)cc3Cl)c(Cl)c2)n[nH]1] |

TABLE I-continued

| # | Nomenclature | Structure |
|---|---|---|
| 125 | {2-[4'-(5-Amino-1H-[1,2,4]triazol-3-ylamino)-6'-chloro-2'-trifluoromethyl-biphenyl-4-yloxy]-ethyl}-methyl-carbamic acid tert-butyl ester; | 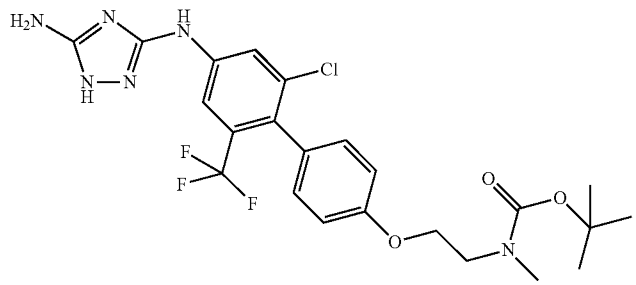 [SMILES: CN(CCOc1ccc(-c2c(Cl)cc(Nc3n[nH]c(N)n3)cc2C(F)(F)F)cc1)C(=O)OC(C)(C)C] |
| 126 | $N^3$-[6-Chloro-4'-(2-methyl-amino-ethoxy)-2-trifluoro-methyl-biphenyl-4-yl]-1H-[1,2,4]triazole-3,5-diamine; | 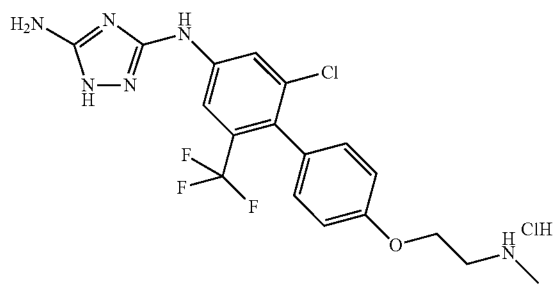 [SMILES: CNCCOc1ccc(-c2c(Cl)cc(Nc3n[nH]c(N)n3)cc2C(F)(F)F)cc1 ; Cl] |
| 127 | $N^3$-[6-Chloro-4'-(1,2,2,6,6-pentamethyl-piperidin-4-ylsulfanyl)-2-trifluoromethyl-biphenyl-4-yl]-1H-[1,2,4]triazole-3,5-diamine; | 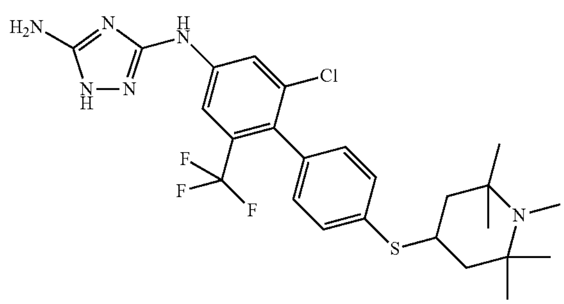 |
| 128 | {2-[4'-(5-Amino-1H-[1,2,4]triazol-3-ylamino)-6'-chloro-2'-trifluoromethyl-biphenyl-4-yloxy]-1,1-dimethyl-ethyl}-methyl-carbamic acid tert-butyl ester; | 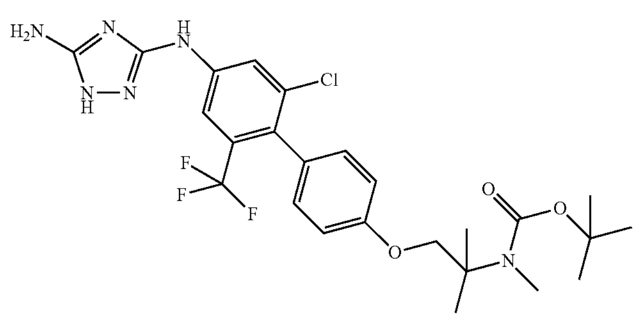 [SMILES: CN(C(=O)OC(C)(C)C)C(C)(C)COc1ccc(-c2c(Cl)cc(Nc3n[nH]c(N)n3)cc2C(F)(F)F)cc1] |

TABLE I-continued

| # | Nomenclature | Structure |
|---|---|---|
| 129 | 3-[4'-(5-Amino-1H-[1,2,4]triazol-3-ylamino)-6'-chloro-2'-trifluoromethyl-biphenyl-4-yloxy]-piperidine-1-carboxylic acid tert-butyl ester; | 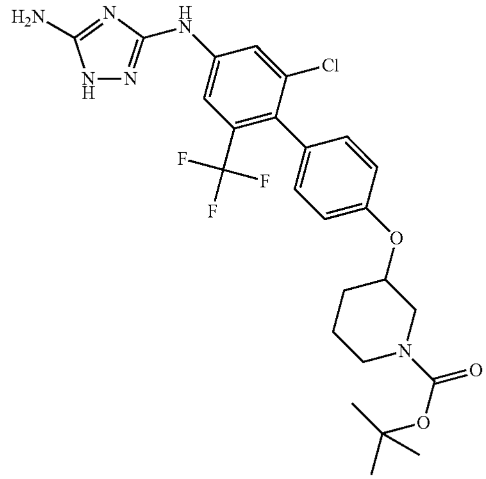 [SMILES: CC(C)(C)OC(=O)N1CCCC(Oc2ccc(-c3c(Cl)cc(Nc4n[nH]c(N)n4)cc3C(F)(F)F)cc2)C1] |
| 130 | $N^3$-[6-Chloro-4'-(piperidin-3-yloxy)-2-trifluoromethyl-biphenyl-4-yl]-1H-[1,2,4]triazole-3,5-diamine; | 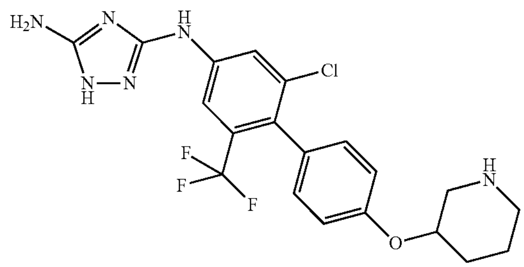 [SMILES: Nc1nc(Nc2cc(Cl)c(-c3ccc(OC4CCCNC4)cc3)c(C(F)(F)F)c2)n[nH]1] |
| 131 | $N^3$-{6-Chloro-4'-[1-(3,3-dimethyl-butyl)-piperidin-3-yloxy]-2-trifluoromethyl-biphenyl-4-yl}-1H-[1,2,4]triazole-3,5-diamine; | 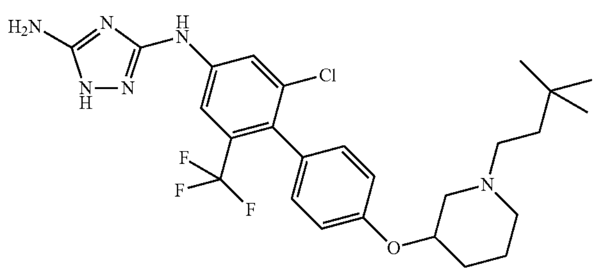 [SMILES: CC(C)(C)CCN1CCCC(Oc2ccc(-c3c(Cl)cc(Nc4n[nH]c(N)n4)cc3C(F)(F)F)cc2)C1] |
| 132 | $N^3$-[6-Chloro-4'-(1-methyl-piperidin-3-yloxy)-2-trifluoromethyl-biphenyl-4-yl]-1H-[1,2,4]triazole-3,5-diamine; | 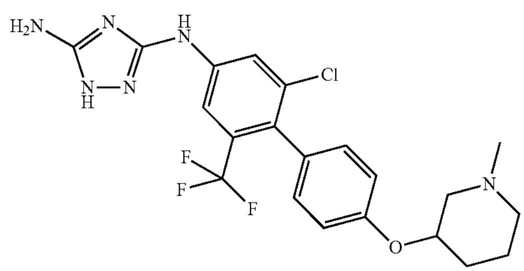 [SMILES: CN1CCCC(Oc2ccc(-c3c(Cl)cc(Nc4n[nH]c(N)n4)cc3C(F)(F)F)cc2)C1] |
| 133 | $N^3$-{6-Chloro-2-trifluoromethyl-4'-[1-(3,3,3-trifluoro-propyl)-piperidin-3-yloxy]-biphenyl-4-yl}-1H-[1,2,4]triazole-3,5-diamine; | 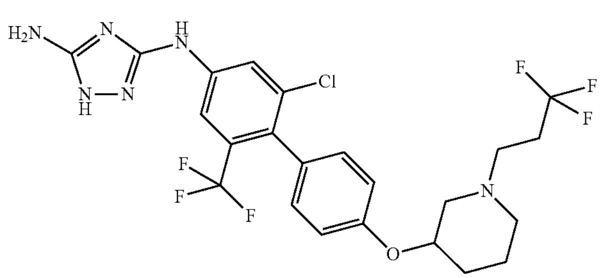 [SMILES: Nc1nc(Nc2cc(Cl)c(-c3ccc(OC4CCCN(CCC(F)(F)F)C4)cc3)c(C(F)(F)F)c2)n[nH]1] |

TABLE I-continued

| # | Nomenclature | Structure |
|---|---|---|
| 134 | {2-[4'-(5-Amino-1H-[1,2,4]triazol-3-ylamino)-6'-chloro-2'-trifluoromethyl-biphenyl-4-yloxy]-ethyl}-carbamic acid tert-butyl ester; | 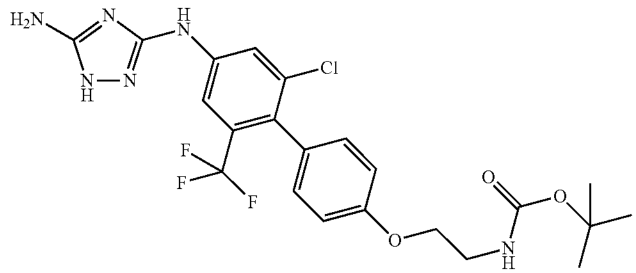 [SMILES: CC(C)(C)OC(=O)NCCOc1ccc(-c2c(Cl)cc(Nc3n[nH]c(N)n3)cc2C(F)(F)F)cc1] |
| 135 | N³-[4'-(2-Amino-ethoxy)-6-chloro-2-trifluoromethyl-biphenyl-4-yl]-1H-[1,2,4]triazole-3,5-diamine; | 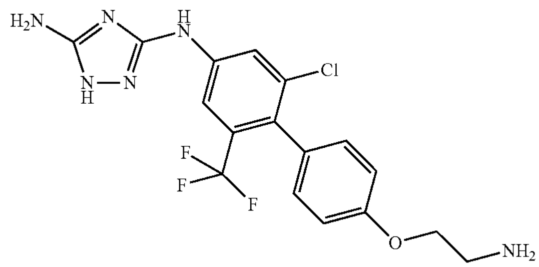 [SMILES: NCCOc1ccc(-c2c(Cl)cc(Nc3n[nH]c(N)n3)cc2C(F)(F)F)cc1] |
| 136 | N³-{6-Chloro-4'-[2-(3,3-dimethyl-butylamino)-ethoxy]-2-trifluoromethyl-biphenyl-4-yl}-1H-[1,2,4]triazole-3,5-diamine; | 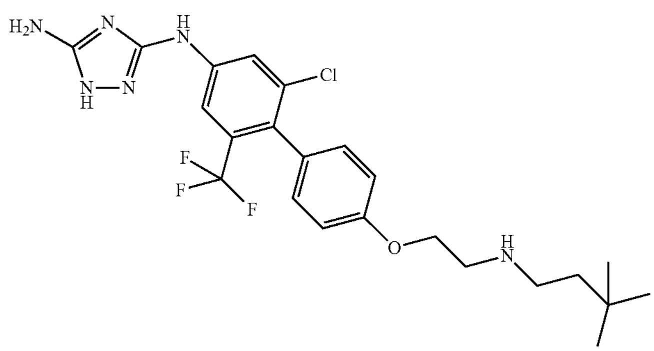 [SMILES: CC(C)(C)CCNCCOc1ccc(-c2c(Cl)cc(Nc3n[nH]c(N)n3)cc2C(F)(F)F)cc1] |
| 137 | N³-(4'-{2-[Bis-(3,3-dimethyl-butyl)-amino]-ethoxy}-6-chloro-2-trifluoromethyl-biphenyl-4-yl)-1H-[1,2,4]triazole-3,5-diamine; | 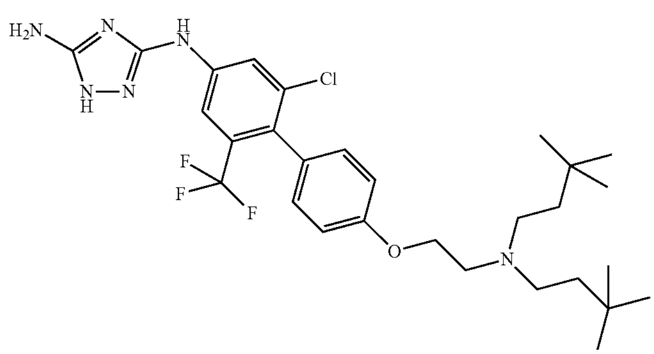 [SMILES: CC(C)(C)CCN(CCOc1ccc(-c2c(Cl)cc(Nc3n[nH]c(N)n3)cc2C(F)(F)F)cc1)CCC(C)(C)C] |

TABLE I-continued

| # | Nomenclature | Structure |
|---|---|---|
| 138 | 4-[4'-(5-Amino-1H-[1,2,4]triazol-3-ylamino)-6'-chloro-2'-trifluoromethyl-biphenyl-4-yloxy]-piperidine-1-carboxylic acid tert-butyl ester; | 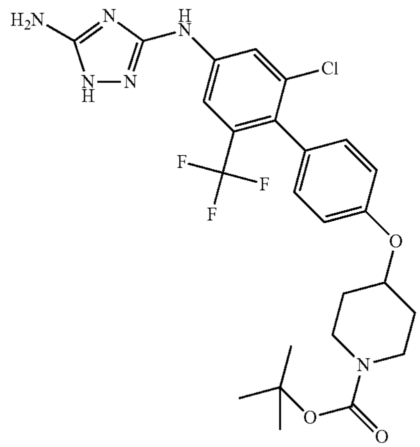 [SMILES: CC(C)(C)OC(=O)N1CCC(Oc2ccc(-c3c(Cl)cc(Nc4n[nH]c(N)n4)cc3C(F)(F)F)cc2)CC1] |
| 139 | N³-[6-Chloro-4'-(piperidin-4-yloxy)-2-trifluoromethyl-biphenyl-4-yl]-1H-[1,2,4]triazole-3,5-diamine; | 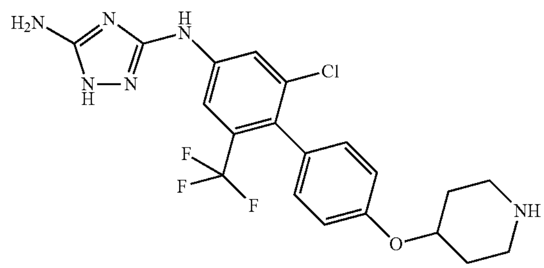 [SMILES: Nc1nc(Nc2cc(Cl)c(-c3ccc(OC4CCNCC4)cc3)c(C(F)(F)F)c2)n[nH]1] |
| 140 | N³-{6-Chloro-2-trifluoromethyl-4'-[1-(3,3,3-trifluoro-propyl)-piperidin-4-yloxy]-biphenyl-4-yl}-1H-[1,2,4]triazole-3,5-diamine; | 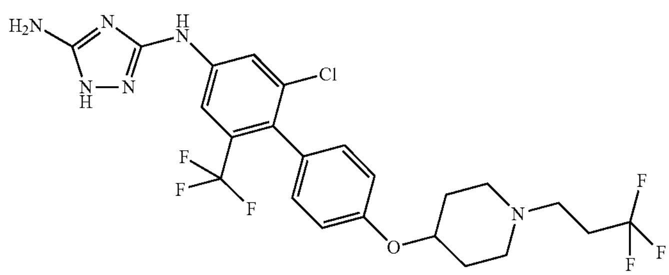 [SMILES: Nc1nc(Nc2cc(Cl)c(-c3ccc(OC4CCN(CCC(F)(F)F)CC4)cc3)c(C(F)(F)F)c2)n[nH]1] |
| 141 | N³-{6-Chloro-4'-[1-(2-methane-sulfonyl-ethyl)-piperidin-4-yloxy]-2-trifluoromethyl-biphenyl-4-yl}-1H-[1,2,4]triazole-3,5-diamine; | 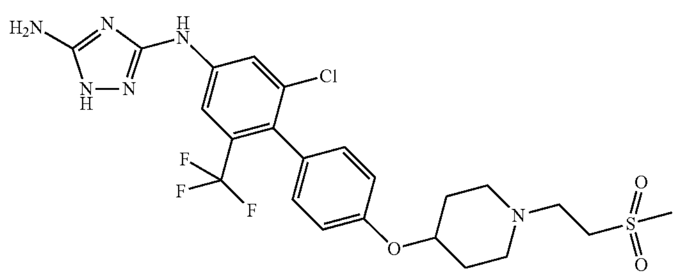 [SMILES: CS(=O)(=O)CCN1CCC(Oc2ccc(-c3c(Cl)cc(Nc4n[nH]c(N)n4)cc3C(F)(F)F)cc2)CC1] |
| 142 | N³-{6-Chloro-4'-[1-(3-methane-sulfonyl-propyl)-piperidin-4-yloxy]-2-tri-fluoromethyl-biphenyl-4-yl}-1H-[1,2,4]triazole-3,5-diamine; | 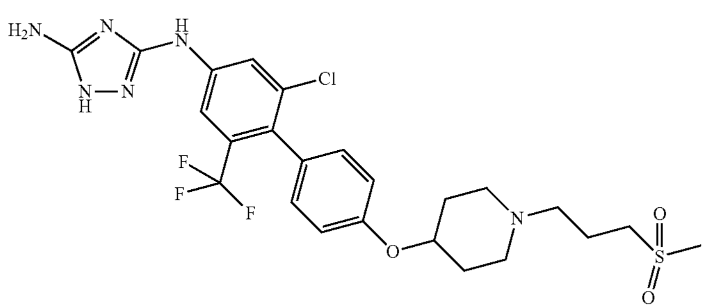 [SMILES: CS(=O)(=O)CCCN1CCC(Oc2ccc(-c3c(Cl)cc(Nc4n[nH]c(N)n4)cc3C(F)(F)F)cc2)CC1] |

TABLE I-continued

| # | Nomenclature | Structure |
|---|---|---|
| 143 | N³-{6-Chloro-4'-[1-(2-methoxy-ethyl)-piperidin-4-yloxy]-2-trifluoromethyl-biphenyl-4-yl}-1H-[1,2,4]triazole-3,5-diamine; | 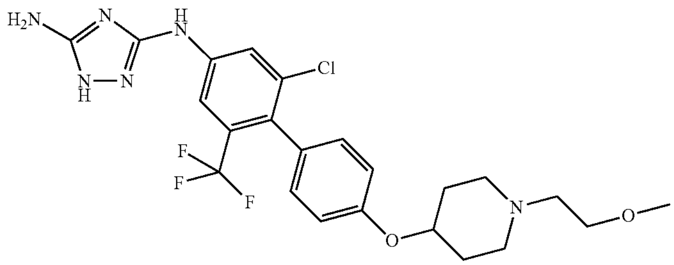 [SMILES: COCCN1CCC(Oc2ccc(-c3c(Cl)cc(Nc4n[nH]c(N)n4)cc3C(F)(F)F)cc2)CC1] |
| 144 | N³-(2-Chloro-biphenyl-4-yl)-1H-[1,2,4]triazole-3,5-diamine; | 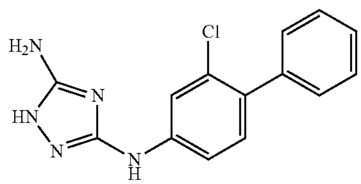 [SMILES: Nc1nc(Nc2ccc(-c3ccccc3)c(Cl)c2)n[nH]1] |
| 145 | N³-(2-Chloro-4'-fluoro-biphenyl-4-yl)-1H-[1,2,4]triazole-3,5-diamine; | 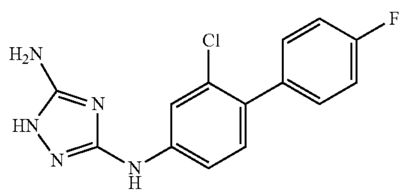 [SMILES: Nc1nc(Nc2ccc(-c3ccc(F)cc3)c(Cl)c2)n[nH]1] |
| 146 | N³-(2-Chloro-2'-fluoro-biphenyl-4-yl)-1H-[1,2,4]triazole-3,5-diamine; | 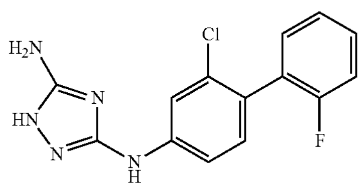 [SMILES: Nc1nc(Nc2ccc(-c3ccccc3F)c(Cl)c2)n[nH]1] |
| 147 | N³-(2-Chloro-3',4'-difluoro-biphenyl-4-yl)-1H-[1,2,4]triazole-3,5-diamine; | 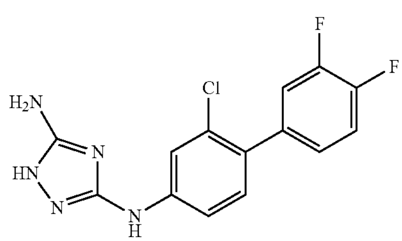 [SMILES: Nc1nc(Nc2ccc(-c3ccc(F)c(F)c3)c(Cl)c2)n[nH]1] |
| 148 | N³-(2-Chloro-3'-fluoro-biphenyl-4-yl)-1H-[1,2,4]triazole-3,5-diamine; | 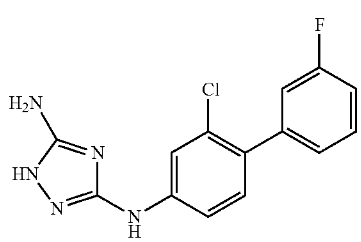 [SMILES: Nc1nc(Nc2ccc(-c3cccc(F)c3)c(Cl)c2)n[nH]1] |
| 149 | N³-(2-Trifluoromethyl-biphenyl-4-yl)-1H-[1,2,4]triazole-3,5-diamine; | 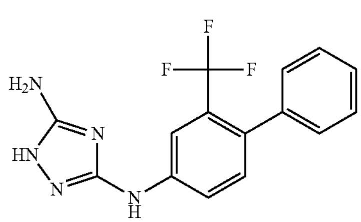 [SMILES: Nc1nc(Nc2ccc(-c3ccccc3)c(C(F)(F)F)c2)n[nH]1] |

TABLE I-continued

| # | Nomenclature | Structure |
|---|---|---|
| 150 | N³-(2'-Fluoro-2-trifluoromethyl-biphenyl-4-yl)-1H-[1,2,4]triazole-3,5-diamine; | 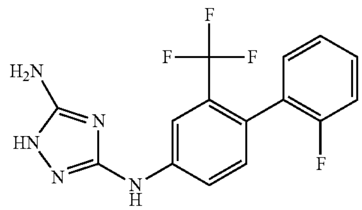 [SMILES: Nc1nc(Nc2ccc(-c3ccccc3F)c(C(F)(F)F)c2)n[nH]1] |
| 151 | N³-(4'-Fluoro-2-trifluoromethyl-biphenyl-4-yl)-1H-[1,2,4]triazole-3,5-diamine; | 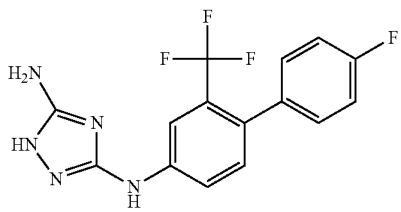 [SMILES: Nc1nc(Nc2ccc(-c3ccc(F)cc3)c(C(F)(F)F)c2)n[nH]1] |
| 152 | N³-(3',4'-Difluoro-2-trifluoromethyl-biphenyl-4-yl)-1H-[1,2,4]triazole-3,5-diamine; | 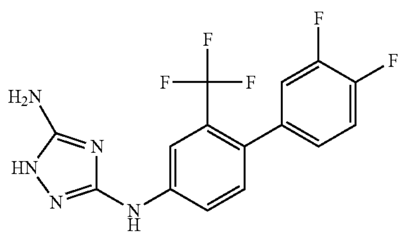 [SMILES: Nc1nc(Nc2ccc(-c3ccc(F)c(F)c3)c(C(F)(F)F)c2)n[nH]1] |
| 153 | N³-(2'-Chloro-2-trifluoromethyl-biphenyl-4-yl)-1H-[1,2,4]triazole-3,5-diamine; | 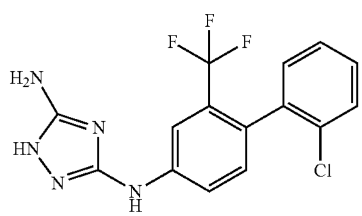 [SMILES: Nc1nc(Nc2ccc(-c3ccccc3Cl)c(C(F)(F)F)c2)n[nH]1] |
| 154 | N³-(2-Chloro-4'-methane-sulfonyl-biphenyl-4-yl)-1H-[1,2,4]triazole-3,5-diamine; | 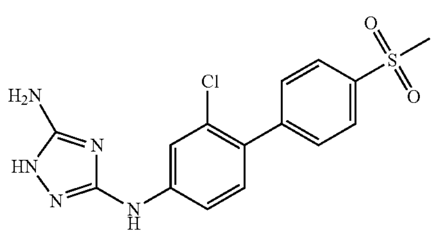 [SMILES: CS(=O)(=O)c1ccc(-c2ccc(Nc3n[nH]c(N)n3)cc2Cl)cc1] |
| 155 | N³-(2,2'-Dichloro-biphenyl-4-yl)-1H-[1,2,4]triazole-3,5-diamine; | 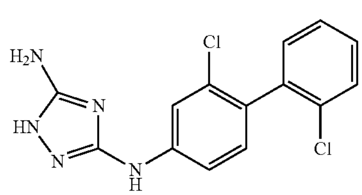 [SMILES: Nc1nc(Nc2ccc(-c3ccccc3Cl)c(Cl)c2)n[nH]1] |
| 156 | N³-(2-Chloro-2'-fluoro-4'-methylsulfanyl-biphenyl-4-yl)-1H-[1,2,4]triazole-3,5-diamine; | 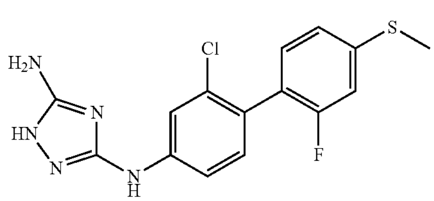 [SMILES: CSc1ccc(-c2ccc(Nc3n[nH]c(N)n3)cc2Cl)c(F)c1] |

| # | Nomenclature | Structure |
|---|---|---|
| 157 | N$^3$-(2-Chloro-2'-fluoro-4'-methanesulfonyl-biphenyl-4-yl)-1H-[1,2,4]triazole-3,5-diamine; | 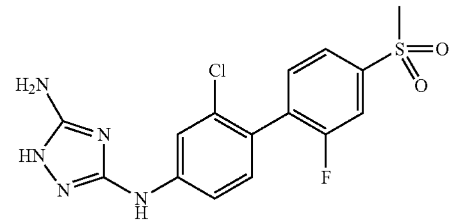 [SMILES: CS(=O)(=O)c1ccc(-c2ccc(Nc3n[nH]c(N)n3)cc2Cl)c(F)c1] |
| 158 | 4'-(5-Amino-1H-[1,2,4]triazol-3-ylamino)-2',6'-dichloro-biphenyl-3-carboxylic acid amide; | 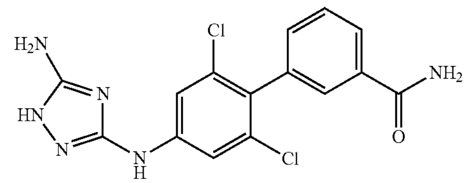 [SMILES: NC(=O)c1cccc(-c2c(Cl)cc(Nc3n[nH]c(N)n3)cc2Cl)c1] |
| 159 | 4'-(5-Amino-1H-[1,2,4]triazol-3-ylamino)-2',6'-dichloro-biphenyl-4-carboxylic acid amide; | 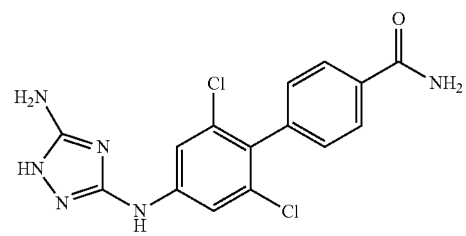 [SMILES: NC(=O)c1ccc(-c2c(Cl)cc(Nc3n[nH]c(N)n3)cc2Cl)cc1] |
| 160 | 4'-(5-Amino-1H-[1,2,4]triazol-3-ylamino)-2',6'-dichloro-biphenyl-4-sulfonic acid (2-hydroxy-ethyl)-amide; | 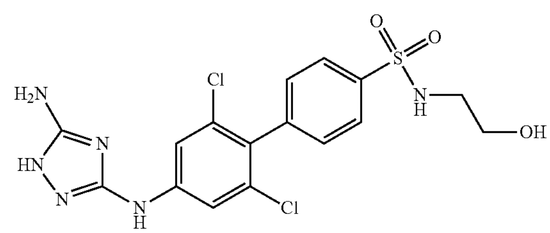 [SMILES: Nc1nc(Nc2cc(Cl)c(-c3ccc(S(=O)(=O)NCCO)cc3)c(Cl)c2)n[nH]1] |
| 161 | 4'-(5-Amino-1H-[1,2,4]triazol-3-ylamino)-2'-chloro-6'-trifluoromethyl-biphenyl-4-sulfonic acid (2-hydroxy-ethyl)-amide; | 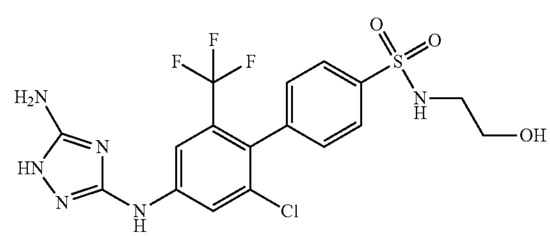 [SMILES: Nc1nc(Nc2cc(Cl)c(-c3ccc(S(=O)(=O)NCCO)cc3)c(C(F)(F)F)c2)n[nH]1] |
| 162 | 2-[4'-(5-Amino-1H-[1,2,4]triazol-3-ylamino)-2'-chloro-6'-trifluoromethyl-biphenyl-4-sulfonyl]-ethanol; | 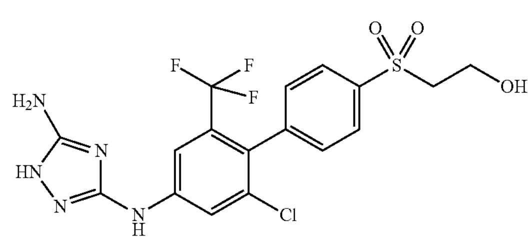 [SMILES: Nc1nc(Nc2cc(Cl)c(-c3ccc(S(=O)(=O)CCO)cc3)c(C(F)(F)F)c2)n[nH]1] |

TABLE I-continued

| # | Nomenclature | Structure |
|---|---|---|
| 163 | 4-[4'-(5-Amino-1H-[1,2,4]triazol-3-ylamino)-6'-chloro-3-methoxy-2'-trifluoromethyl-biphenyl-4-sulfonylamino]-piperidine-1-carboxylic acid tert-butyl ester; | 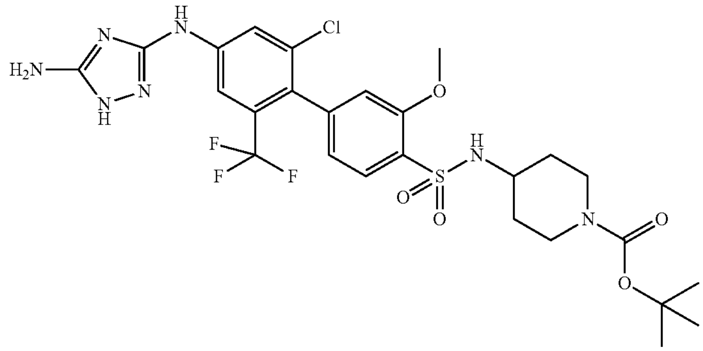 [SMILES: COc1cc(-c2c(Cl)cc(Nc3n[nH]c(N)n3)cc2C(F)(F)F)ccc1S(=O)(=O)NC1CCN(C(=O)OC(C)(C)C)CC1] |
| 164 | 4'-(5-Amino-1H-[1,2,4]triazol-3-ylamino)-2',6'-dichloro-biphenyl-4-sulfonic acid tert-butylamide; | 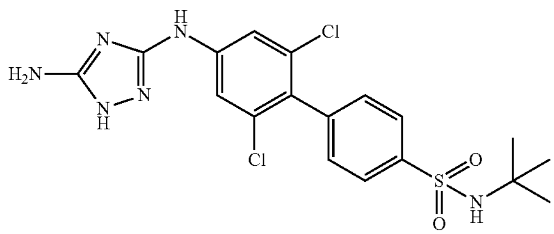 [SMILES: CC(C)(C)NS(=O)(=O)c1ccc(-c2c(Cl)cc(Nc3n[nH]c(N)n3)cc2Cl)cc1] |
| 165 | 4'-(5-Amino-1H-[1,2,4]triazol-3-ylamino)-6'-chloro-2'-trifluoromethyl-biphenyl-4-sulfonic acid (2,2,2-trifluoro-1,1-dimethyl-ethyl)-amide; | 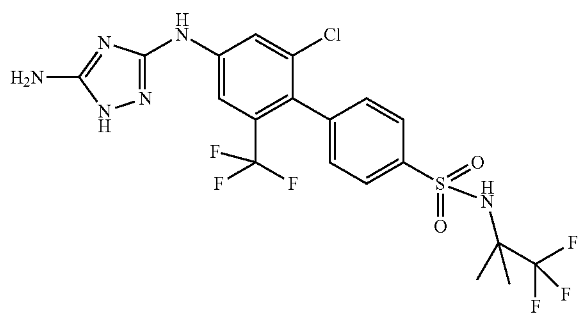 [SMILES: CC(C)(NS(=O)(=O)c1ccc(-c2c(Cl)cc(Nc3n[nH]c(N)n3)cc2C(F)(F)F)cc1)C(F)(F)F] |
| 166 | 4-[4'-(5-Amino-1H-[1,2,4]triazol-3-ylamino)-6'-chloro-4-methoxy-2'-trifluoromethyl-biphenyl-3-sulfonyl]-piperazine-1-carboxylic acid tert-butyl ester; | 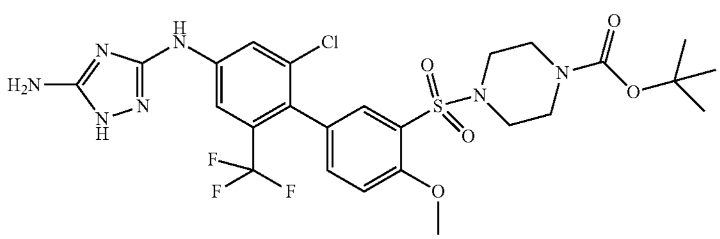 [SMILES: COc1ccc(-c2c(Cl)cc(Nc3n[nH]c(N)n3)cc2C(F)(F)F)cc1S(=O)(=O)N1CCN(C(=O)OC(C)(C)C)CC1] |
| 167 | 4'-(5-Amino-1H-[1,2,4]triazol-3-ylamino)-6'-chloro-3-methoxy-2'-trifluoromethyl-biphenyl-4-sulfonic acid (4-hydroxy-cyclohexyl)-amide; | 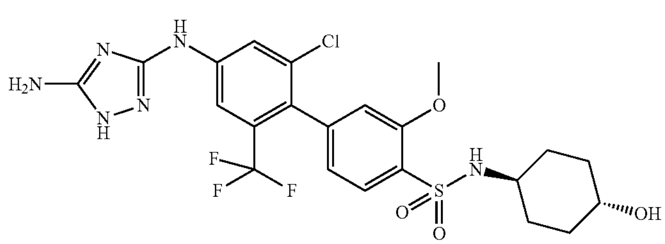 [SMILES: COc1cc(-c2c(Cl)cc(Nc3n[nH]c(N)n3)cc2C(F)(F)F)ccc1S(=O)(=O)N[C@H]1CC[C@H](O)CC1] |

TABLE I-continued

| # | Nomenclature | Structure |
|---|---|---|
| 168 | 4'-(5-Amino-1H-[1,2,4]triazol-3-ylamino)-6'-chloro-4-methoxy-2'-trifluoromethyl-biphenyl-3-sulfonic acid (tetrahydro-pyran-4-yl)-amide; | 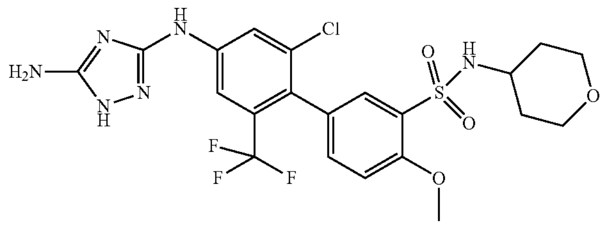 [SMILES: COc1ccc(-c2c(Cl)cc(Nc3n[nH]c(N)n3)cc2C(F)(F)F)cc1S(=O)(=O)NC1CCOCC1] |
| 169 | 4'-(5-Amino-1H-[1,2,4]triazol-3-ylamino)-6'-chloro-2'-trifluoromethyl-biphenyl-4-sulfonic acid cyclopropyl-amide; | 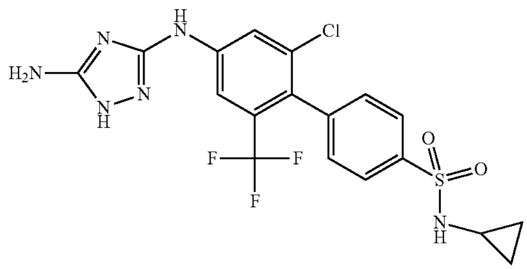 [SMILES: Nc1nc(Nc2cc(Cl)c(-c3ccc(S(=O)(=O)NC4CC4)cc3)c(C(F)(F)F)c2)n[nH]1] |
| 170 | $N^3$-[6-Chloro-4'-(pyrrolidine-1-sulfonyl)-2-trifluoromethyl-biphenyl-4-yl]-1H-[1,2,4]triazole-3,5-diamine; | 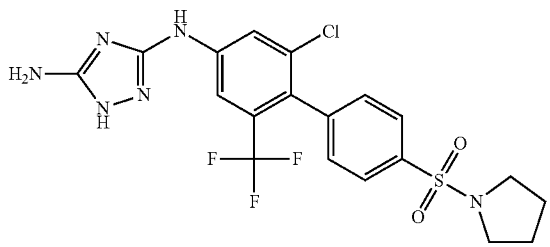 [SMILES: Nc1nc(Nc2cc(Cl)c(-c3ccc(S(=O)(=O)N4CCCC4)cc3)c(C(F)(F)F)c2)n[nH]1] |
| 171 | 4'-(5-Amino-1H-[1,2,4]triazol-3-ylamino)-6'-chloro-2'-trifluoromethyl-biphenyl-4-sulfonic acid amide; | 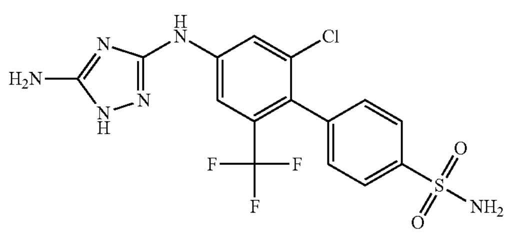 [SMILES: Nc1nc(Nc2cc(Cl)c(-c3ccc(S(N)(=O)=O)cc3)c(C(F)(F)F)c2)n[nH]1] |
| 172 | 4'-(5-Amino-1H-[1,2,4]triazol-3-ylamino)-6'-chloro-2'-trifluoromethyl-biphenyl-4-sulfonic acid (3-hydroxy-cyclobutyl)-amide; | 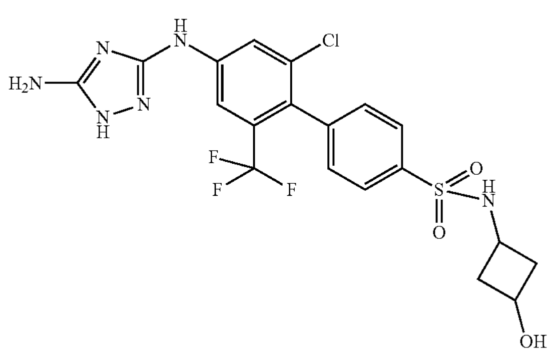 [SMILES: Nc1nc(Nc2cc(Cl)c(-c3ccc(S(=O)(=O)NC4CC(O)C4)cc3)c(C(F)(F)F)c2)n[nH]1] |

TABLE I-continued

| # | Nomenclature | Structure |
|---|---|---|
| 173 | 4'-(5-Amino-1H-[1,2,4]triazol-3-ylamino)-6'-chloro-2'-trifluoromethyl-biphenyl-4-sulfonic acid (3-hydroxy-cyclobutyl)-amide; | 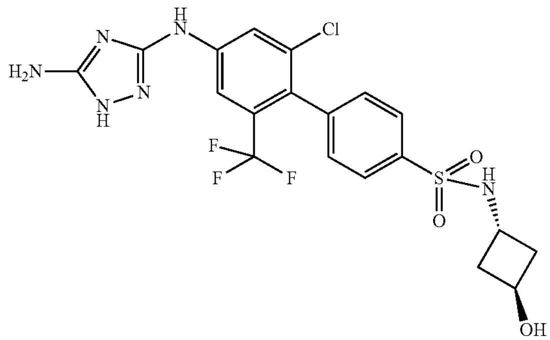 [SMILES: Nc1nc(Nc2cc(Cl)c(-c3ccc(S(=O)(=O)N[C@H]4C[C@H](O)C4)cc3)c(C(F)(F)F)c2)n[nH]1] |
| 174 | 4'-(5-Amino-1H-[1,2,4]triazol-3-ylamino)-6'-chloro-2'-trifluoromethyl-biphenyl-4-sulfonic acid (3-hydroxy-cyclobutyl)-amide; | 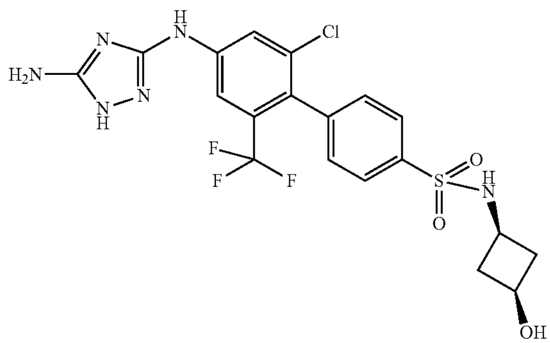 [SMILES: Nc1nc(Nc2cc(Cl)c(-c3ccc(S(=O)(=O)N[C@H]4C[C@@H](O)C4)cc3)c(C(F)(F)F)c2)n[nH]1] |
| 175 | 4'-(5-amino-1H-1,2,4-triazol-3-ylamino)-2'-chloro-N-(2-hydroxyethyl)-4-methoxy-6'-(trifluoromethyl)biphenyl-3-sulfonamide | 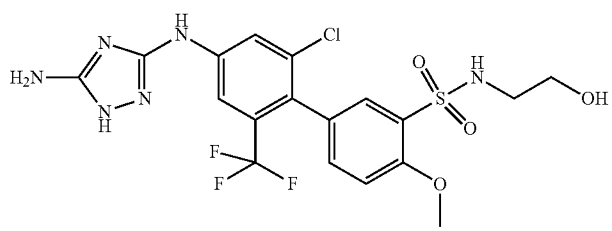 [SMILES: COc1ccc(-c2c(Cl)cc(Nc3n[nH]c(N)n3)cc2C(F)(F)F)cc1S(=O)(=O)NCCO] |
| 176 | 4'-(5-Amino-1H-[1,2,4]triazol-3-ylamino)-6'-chloro-4-methoxy-2'-trifluoromethyl-biphenyl-3-sulfonic acid (2-hydroxy-ethyl)-amide; | 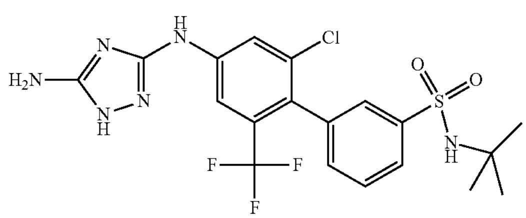 [SMILES: CC(C)(C)NS(=O)(=O)c1cccc(-c2c(Cl)cc(Nc3n[nH]c(N)n3)cc2C(F)(F)F)c1] |
| 177 | 4'-(5-Amino-1H-[1,2,4]triazol-3-ylamino)-6'-chloro-2'-trifluoromethyl-biphenyl-3-sulfonic acid tert-butylamide; | 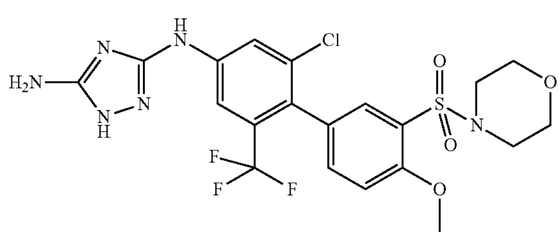 [SMILES: COc1ccc(-c2c(Cl)cc(Nc3n[nH]c(N)n3)cc2C(F)(F)F)cc1S(=O)(=O)N1CCOCC1] |

TABLE I-continued

| # | Nomenclature | Structure |
|---|---|---|
| 178 | N³-[6-Chloro-4'-methoxy-3'-(morpholine-4-sulfonyl)-2-trifluoromethyl-biphenyl-4-yl]-1H-[1,2,4]triazole-3,5-diamine; | 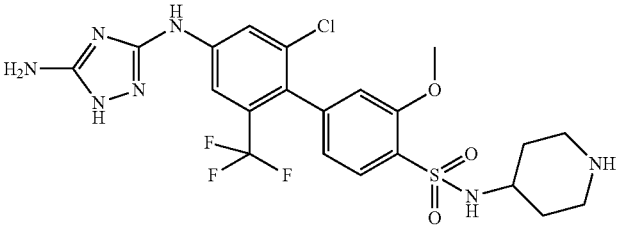 [SMILES: COc1cc(-c2c(Cl)cc(Nc3n[nH]c(N)n3)cc2C(F)(F)F)ccc1S(=O)(=O)NC1CCNCC1] |
| 179 | 4'-(5-Amino-1H-[1,2,4]triazol-3-ylamino)-6'-chloro-3-methoxy-2'-trifluoromethyl-biphenyl-4-sulfonic acid piperidin-4-ylamide; | 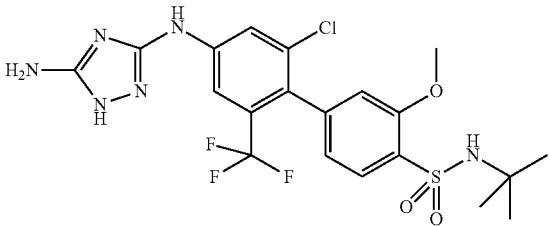 [SMILES: COc1cc(-c2c(Cl)cc(Nc3n[nH]c(N)n3)cc2C(F)(F)F)ccc1S(=O)(=O)NC(C)(C)C] |
| 180 | 4'-(5-Amino-1H-[1,2,4]triazol-3-ylamino)-6'-chloro-4-methoxy-2'-trifluoromethyl-biphenyl-3-sulfonic acid amide; | 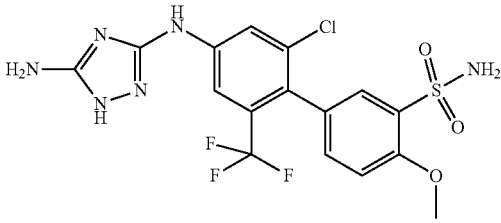 [SMILES: COc1ccc(-c2c(Cl)cc(Nc3n[nH]c(N)n3)cc2C(F)(F)F)cc1S(N)(=O)=O] |
| 181 | N³-[6-Chloro-4'-(propane-2-sulfonyl)-2-trifluoromethyl-biphenyl-4-yl]-1H-[1,2,4]triazole-3,5-diamine; | 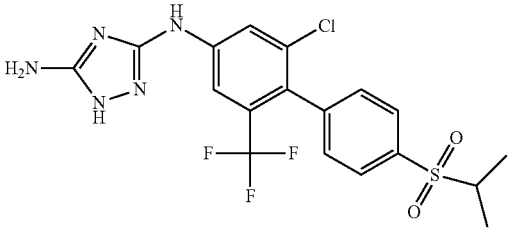 [SMILES: CC(C)S(=O)(=O)c1ccc(-c2c(Cl)cc(Nc3n[nH]c(N)n3)cc2C(F)(F)F)cc1] |
| 182 | N³-[6-Chloro-4'-methoxy-3'-(piperazine-1-sulfonyl)-2-trifluoromethyl-biphenyl-4-yl]-1H-[1,2,4]triazole-3,5-diamine; | 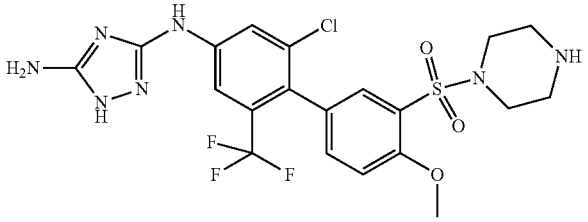 [SMILES: COc1ccc(-c2c(Cl)cc(Nc3n[nH]c(N)n3)cc2C(F)(F)F)cc1S(=O)(=O)N1CCNCC1] |
| 183 | N³-[6-Chloro-4'-(4,4-difluoro-piperidine-1-sulfonyl)-2-trifluoromethyl-biphenyl-4-yl]-1H-[1,2,4]triazole-3,5-diamine; | 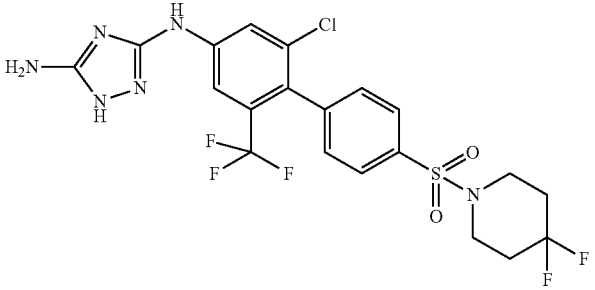 [SMILES: Nc1nc(Nc2cc(Cl)c(-c3ccc(S(=O)(=O)N4CCC(F)(F)CC4)cc3)c(C(F)(F)F)c2)n[nH]1] |

TABLE I-continued

| # | Nomenclature | Structure |
|---|---|---|
| 184 | 4'-(5-Amino-1H-[1,2,4]triazol-3-ylamino)-6'-chloro-2'-trifluoromethyl-biphenyl-4-sulfonic acid (4-hydroxy-cyclohexyl)-amide; | 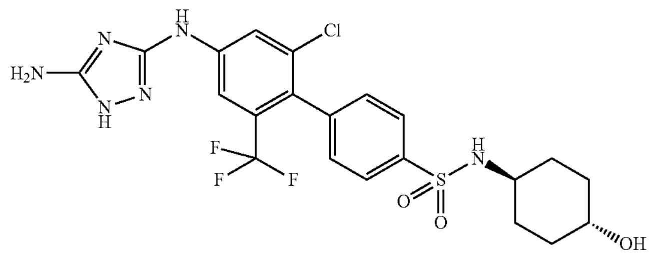 [SMILES: Nc1nc(Nc2cc(Cl)c(-c3ccc(S(=O)(=O)N[C@H]4CC[C@H](O)CC4)cc3)c(C(F)(F)F)c2)n[nH]1] |
| 185 | 4'-(5-Amino-1H-[1,2,4]triazol-3-ylamino)-6'-chloro-2'-trifluoromethyl-biphenyl-4-sulfonic acid dimethylamide; | 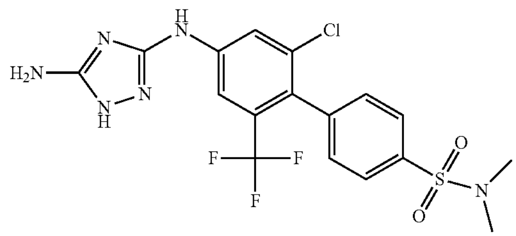 [SMILES: CN(C)S(=O)(=O)c1ccc(-c2c(Cl)cc(Nc3n[nH]c(N)n3)cc2C(F)(F)F)cc1] |
| 186 | N-[4'-(5-Amino-1H-[1,2,4]triazol-3-ylamino)-6'-chloro-2'-trifluoromethyl-biphenyl-4-ylmethyl]-methane-sulfonamide; | 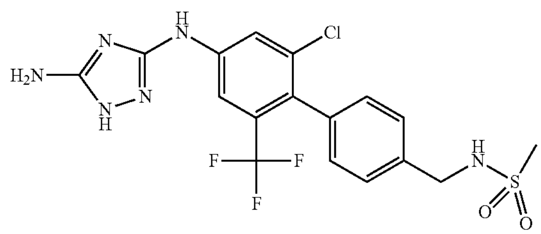 [SMILES: CS(=O)(=O)NCc1ccc(-c2c(Cl)cc(Nc3n[nH]c(N)n3)cc2C(F)(F)F)cc1] |
| 187 | $N^3$-(6-Chloro-4'-methane-sulfonyl-2-trifluoromethyl-biphenyl-4-yl)-1H-[1,2,4]triazole-3,5-diamine; | 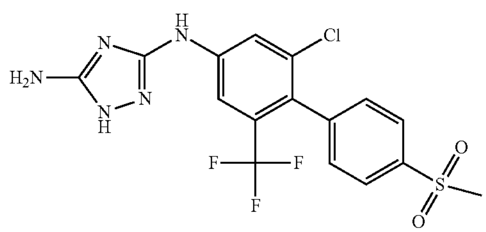 [SMILES: CS(=O)(=O)c1ccc(-c2c(Cl)cc(Nc3n[nH]c(N)n3)cc2C(F)(F)F)cc1] |
| 188 | $N^3$-(6-Chloro-4'-cyclopropane-sulfonyl-2-trifluoromethyl-biphenyl-4-yl)-1H-[1,2,4]triazole-3,5-diamine; | 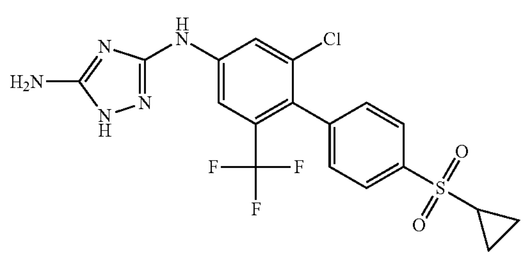 [SMILES: Nc1nc(Nc2cc(Cl)c(-c3ccc(S(=O)(=O)C4CC4)cc3)c(C(F)(F)F)c2)n[nH]1] |
| 189 | 4'-(5-Amino-1H-[1,2,4]triazol-3-ylamino)-6'-chloro-2'-trifluoromethyl-biphenyl-4-carboxylic acid methylamide; | 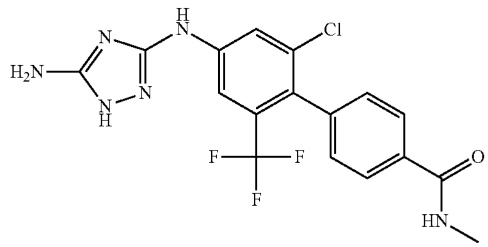 [SMILES: CNC(=O)c1ccc(-c2c(Cl)cc(Nc3n[nH]c(N)n3)cc2C(F)(F)F)cc1] |

TABLE I-continued

| # | Nomenclature | Structure |
|---|---|---|
| 190 | 4'-(5-Amino-1H-[1,2,4]triazol-3-ylamino)-6'-chloro-4-methoxy-2'-trifluoromethyl-biphenyl-3-sulfonic acid (4-hydroxy-cyclohexyl)-amide; | 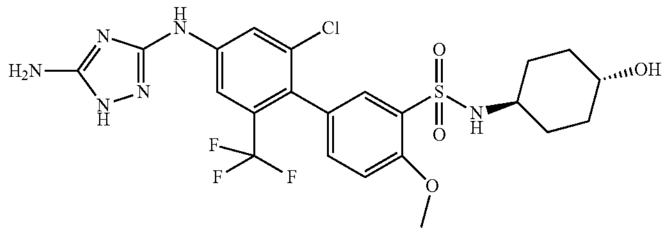 [SMILES: COc1ccc(-c2c(Cl)cc(Nc3n[nH]c(N)n3)cc2C(F)(F)F)cc1S(=O)(=O)N[C@H]1CC[C@H](O)CC1] |
| 191 | 1-[4'-(5-Amino-1H-[1,2,4]triazol-3-ylamino)-6'-chloro-2'-trifluoromethyl-biphenyl-4-sulfonyl]-azetidin-3-ol; | 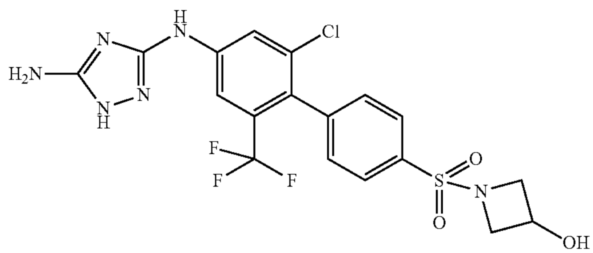 [SMILES: Nc1nc(Nc2cc(Cl)c(-c3ccc(S(=O)(=O)N4CC(O)C4)cc3)c(C(F)(F)F)c2)n[nH]1] |
| 192 | $N^3$-[6-Chloro-3'-(pyrrolidine-1-sulfonyl)-2-trifluoromethyl-biphenyl-4-yl]-1H-[1,2,4]triazole-3,5-diamine; | 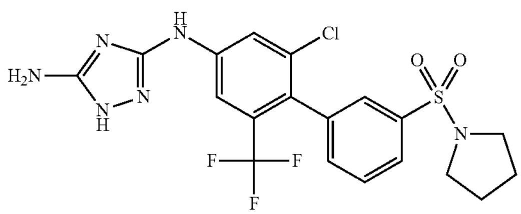 [SMILES: Nc1nc(Nc2cc(Cl)c(-c3cccc(S(=O)(=O)N4CCCC4)c3)c(C(F)(F)F)c2)n[nH]1] |
| 193 | 4'-(5-Amino-1H-[1,2,4]triazol-3-ylamino)-6'-chloro-4-trifluoromethoxy-2'-trifluoromethyl-biphenyl-3-sulfonic acid tert-butylamide; | 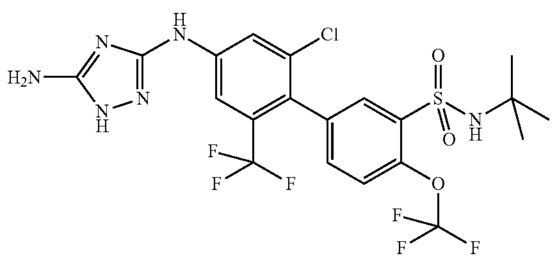 [SMILES: CC(C)(C)NS(=O)(=O)c1cc(-c2c(Cl)cc(Nc3n[nH]c(N)n3)cc2C(F)(F)F)ccc1OC(F)(F)F] |
| 194 | 1-[4'-(5-Amino-1H-[1,2,4]triazol-3-ylamino)-6'-chloro-2'-trifluoromethyl-biphenyl-4-sulfonyl]-piperidin-4-ol; | 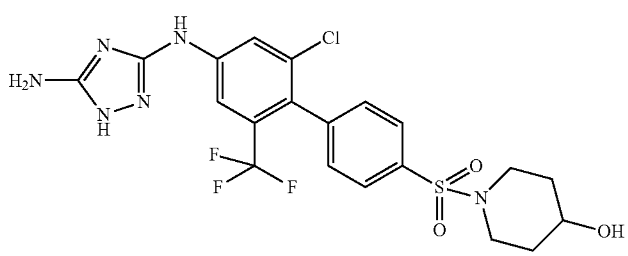 [SMILES: Nc1nc(Nc2cc(Cl)c(-c3ccc(S(=O)(=O)N4CCC(O)CC4)cc3)c(C(F)(F)F)c2)n[nH]1] |
| 195 | $N^3$-(6-Chloro-3'-methane-sulfonyl-2-trifluoromethyl-biphenyl-4-yl)-1H-[1,2,4]triazole-3,5-diamine; | 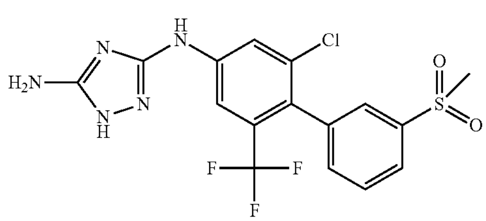 [SMILES: CS(=O)(=O)c1cccc(-c2c(Cl)cc(Nc3n[nH]c(N)n3)cc2C(F)(F)F)c1] |

TABLE I-continued

| # | Nomenclature | Structure |
|---|---|---|
| 196 | 4'-(5-Amino-1H-[1,2,4]triazol-3-ylamino)-6'-chloro-2'-trifluoromethyl-biphenyl-3-sulfonic acid tert-butyl-methyl-amide; | 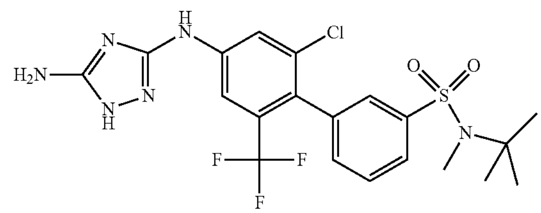 [SMILES: CN(C(C)(C)C)S(=O)(=O)c1cccc(-c2c(Cl)cc(Nc3n[nH]c(N)n3)cc2C(F)(F)F)c1] |
| 197 | 4'-(5-Amino-1H-[1,2,4]triazol-3-ylamino)-6'-chloro-2'-trifluoromethyl-biphenyl-3-sulfonic acid amide; | 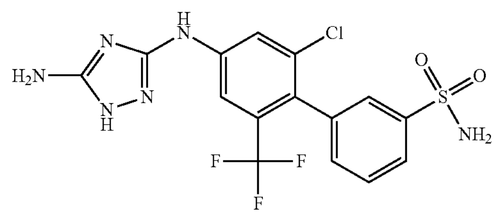 [SMILES: Nc1nc(Nc2cc(Cl)c(-c3cccc(S(N)(=O)=O)c3)c(C(F)(F)F)c2)n[nH]1] |
| 198 | 4'-(5-Amino-1H-[1,2,4]triazol-3-ylamino)-6'-chloro-2'-trifluoromethyl-biphenyl-3-sulfonic acid dimethylamide; | 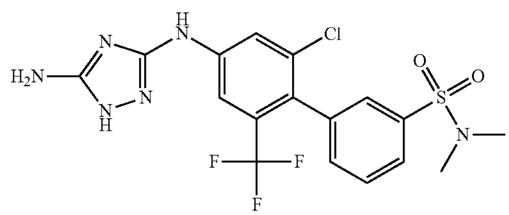 [SMILES: CN(C)S(=O)(=O)c1cccc(-c2c(Cl)cc(Nc3n[nH]c(N)n3)cc2C(F)(F)F)c1] |
| 199 | N-[4'-(5-Amino-1H-[1,2,4]triazol-3-ylamino)-6'-chloro-2'-trifluoromethyl-biphenyl-3-ylmethyl]-methane-sulfonamide; | 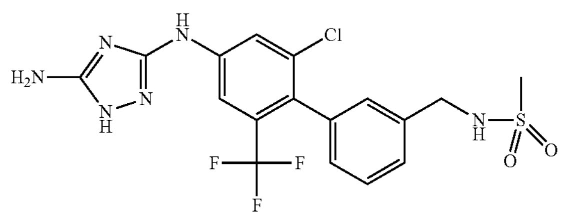 [SMILES: CS(=O)(=O)NCc1cccc(-c2c(Cl)cc(Nc3n[nH]c(N)n3)cc2C(F)(F)F)c1] |
| 200 | 4'-(5-Amino-1H-[1,2,4]triazol-3-ylamino)-6'-chloro-2'-trifluoromethyl-biphenyl-4-carboxylic acid tert-butyl ester; | 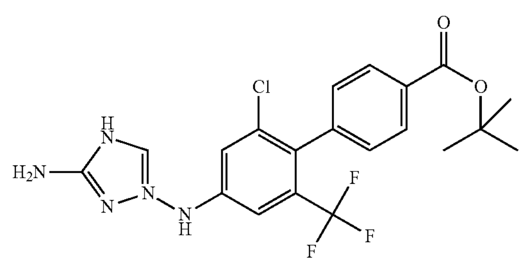 |
| 201 | $N^3$-(6-Chloro-2-trifluoromethyl-biphenyl-4-yl)-1H-[1,2,4]triazole-3,5-diamine; | 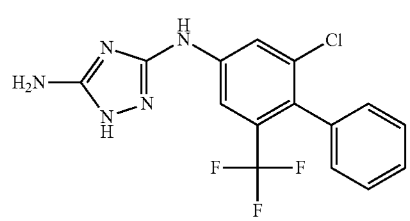 [SMILES: Nc1nc(Nc2cc(Cl)c(-c3ccccc3)c(C(F)(F)F)c2)n[nH]1] |
| 202 | 4'-(5-Amino-1H-[1,2,4]triazol-3-ylamino)-6'-chloro-2'-trifluoromethyl-biphenyl-4-carboxylic acid; | 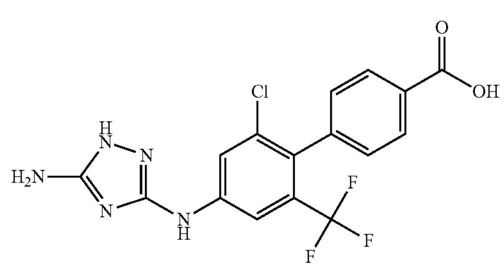 [SMILES: Nc1nc(Nc2cc(Cl)c(-c3ccc(C(=O)O)cc3)c(C(F)(F)F)c2)n[nH]1] |

TABLE I-continued

| # | Nomenclature |
|---|---|
| 203 | N³-[6-Chloro 4'-methoxy-3'-(pyrrolidine-1-sulfonyl)-2-trifluoromethyl-biphenyl-4-yl]-1H-[1,2,4]triazole-3,5-diamine; |
| 204 | 4'-(5-Amino-1H-[1,2,4]triazol-3-ylamino)-6'-chloro-4-methoxy-2'-trifluoromethyl-biphenyl-3-sulfonic acid piperidin-4-ylamide |
| 205 | 3-[4'-(5-Amino-1H-[1,2,4]triazol-3-ylamino)-6'-chloro-2'-trifluoromethyl-biphenyl-4-sulfonylamino]-3-methyl-azetidine-1-carboxylic acid tert-butyl ester; |
| 206 | 4'-(5-Amino-1H-[1,2,4]triazol-3-ylamino)-6'-chloro-2'-trifluoromethyl-biphenyl-4-sulfonic acid (1-methyl-cyclopropyl)-amide; |
| 207 | 4'-(5-Amino-1H-[1,2,4]triazol-3-ylamino)-6'-chloro-2'-trifluoromethyl-biphenyl-4-sulfonic acid (3-methyl-azetidin-3-yl)-amide; |
| 208 | 4-[4'-(5-Amino-1H-[1,2,4]triazol-3-ylamino)-6'-chloro-2'-trifluoromethyl-biphenyl-4-sulfonyl]-4,7-diaza-spiro[2.5]octane-7-carboxylic acid tert-butyl ester; |

TABLE I-continued

| # | Nomenclature | Structure |
|---|---|---|
| 209 | {2-[4'-(5-Amino-1H-[1,2,4]triazol-3-ylamino)-6'-chloro-2'-trifluoromethyl-biphenyl-4-sulfonylamino]-ethyl}-methyl-carbamic acid tert-butyl ester; | 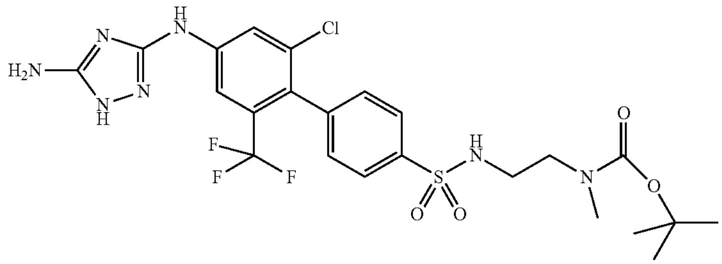 [SMILES: CN(CCNS(=O)(=O)c1ccc(-c2c(Cl)cc(Nc3n[nH]c(N)n3)cc2C(F)(F)F)cc1)C(=O)OC(C)(C)C] |
| 210 | 4'-(5-Amino-1H-[1,2,4]triazol-3-ylamino)-6'-chloro-2'-trifluoromethyl-biphenyl-4-sulfonic acid (1-isopropyl-3-methyl-azetidin-3-yl)-amide; | 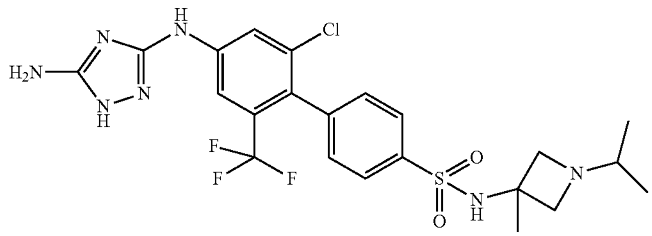 [SMILES: CC(C)N1CC(C)(NS(=O)(=O)c2ccc(-c3c(Cl)cc(Nc4n[nH]c(N)n4)cc3C(F)(F)F)cc2)C1] |
| 211 | 4'-(5-Amino-1H-[1,2,4]triazol-3-ylamino)-6'-chloro-2'-trifluoromethyl-biphenyl-4-sulfonic acid (1-isopropyl-3-methyl-azetidin-3-yl)-amide; | 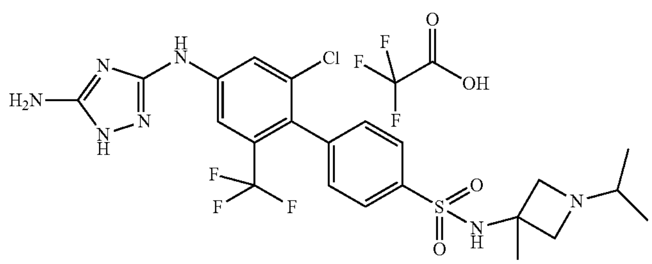 |
| 212 | 3-[4'-(5-Amino-1H-[1,2,4]triazol-3-ylamino)-6'-chloro-4-methoxy-2'-trifluoromethyl-biphenyl-3-sulfonylamino]-3-methyl-azetidine-1-carboxylic acid tert-butyl ester; | 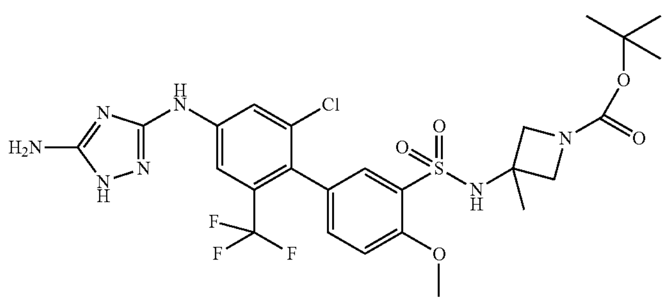 [SMILES: COc1ccc(-c2c(Cl)cc(Nc3n[nH]c(N)n3)cc2C(F)(F)F)cc1S(=O)(=O)NC1(C)CN(C(=O)OC(C)(C)C)C1] |
| 213 | 4'-(5-Amino-1H-[1,2,4]triazol-3-ylamino)-6'-chloro-2'-trifluoromethyl-biphenyl-4-sulfonic acid (2-methylamino-ethyl)-amide; | 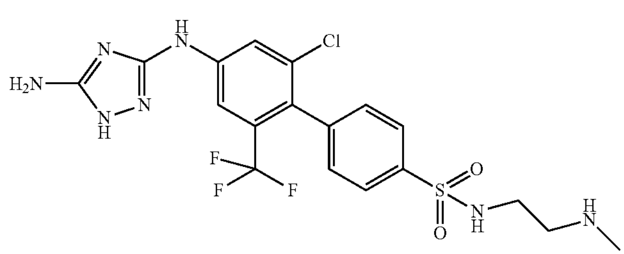 [SMILES: CNCCNS(=O)(=O)c1ccc(-c2c(Cl)cc(Nc3n[nH]c(N)n3)cc2C(F)(F)F)cc1] |

TABLE I-continued

| # | Nomenclature | Structure |
|---|---|---|
| 214 | N³-[6-Chloro-4'-(4,7-diaza-spiro[2.5]octane-4-sulfonyl)-2-trifluoromethyl-biphenyl-4-yl]-1H-[1,2,4]triazole-3,5-diamine; | 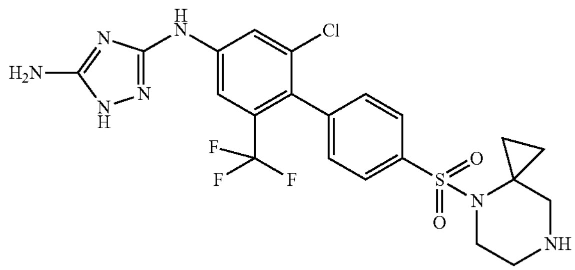 [SMILES: Nc1nc(Nc2cc(Cl)c(-c3ccc(S(=O)(=O)N4CCNCC45CC5)cc3)c(C(F)(F)F)c2)n[nH]1] |
| 215 | 4'-(5-Amino-1H-[1,2,4]triazol-3-ylamino)-6'-chloro-4-methoxy-2'-trifluoromethyl-biphenyl-3-sulfonic acid (3-methyl-azetidin-3-yl)-amide; | 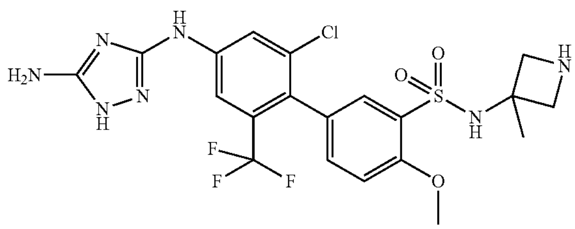 [SMILES: COc1ccc(-c2c(Cl)cc(Nc3n[nH]c(N)n3)cc2C(F)(F)F)cc1S(=O)(=O)NC1(C)CNC1] |
| 216 | 4'-(5-Amino-1H-[1,2,4]triazol-3-ylamino)-6'-chloro-4-methoxy-2'-trifluoromethyl-biphenyl-3-sulfonic acid tert-butylamide; | 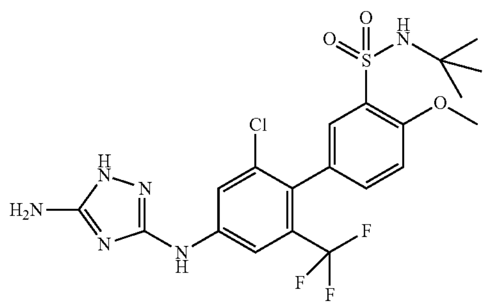 [SMILES: COc1ccc(-c2c(Cl)cc(Nc3n[nH]c(N)n3)cc2C(F)(F)F)cc1S(=O)(=O)NC(C)(C)C] |
| 217 | 4'-(5-Amino-1H-[1,2,4]triazol-3-ylamino)-6'-chloro-3-trifluoromethoxy-2'-trifluoromethyl-biphenyl-4-sulfonic acid tert-butylamide; | 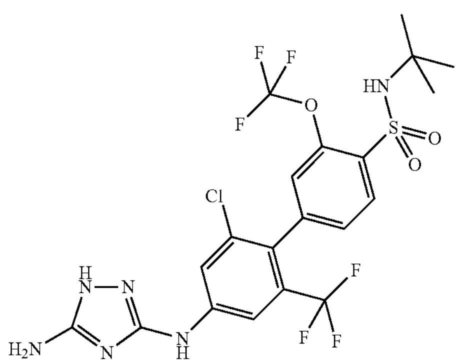 [SMILES: CC(C)(C)NS(=O)(=O)c1ccc(-c2c(Cl)cc(Nc3n[nH]c(N)n3)cc2C(F)(F)F)cc1OC(F)(F)F] |
| 218 | 4'-(5-Amino-1H-[1,2,4]triazol-3-ylamino)-6'-chloro-4-methoxy-2'-trifluoromethyl-biphenyl-3-sulfonic acid (2-hydroxy-1,1-dimethyl-ethyl)-amide; | 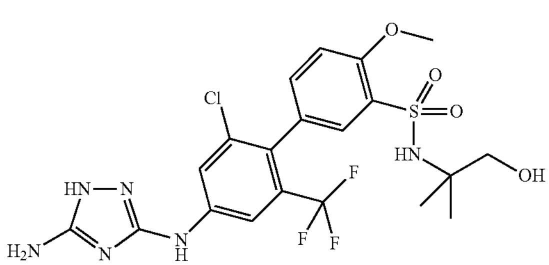 [SMILES: COc1ccc(-c2c(Cl)cc(Nc3n[nH]c(N)n3)cc2C(F)(F)F)cc1S(=O)(=O)NC(C)(C)CO] |

TABLE I-continued

| # | Nomenclature | Structure |
|---|---|---|
| 219 | 4'-(5-Amino-1H-[1,2,4]triazol-3-ylamino)-2'-chloro-6'-trifluoromethyl-biphenyl-4-sulfonic acid tert-butylamide; | 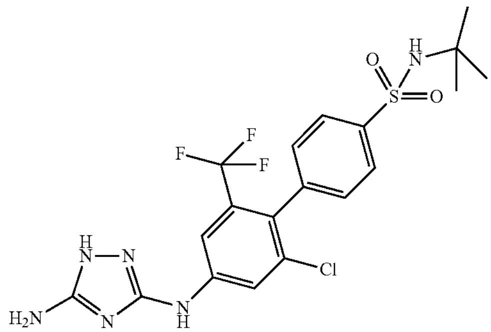 [SMILES: CC(C)(C)NS(=O)(=O)c1ccc(-c2c(Cl)cc(Nc3n[nH]c(N)n3)cc2C(F)(F)F)cc1] |
| 220 | $N^3$-[2,6-Dichloro-4'-(pyrrolidine-1-sulfonyl)-biphenyl-4-yl]-1H-[1,2,4]triazole-3,5-diamine; | 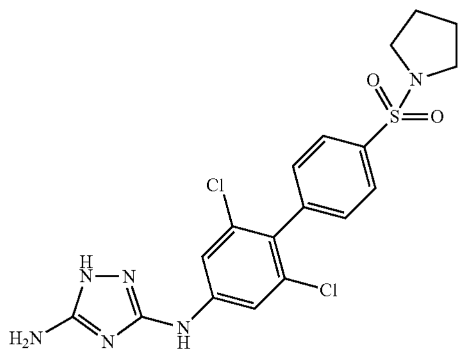 [SMILES: Nc1nc(Nc2cc(Cl)c(-c3ccc(S(=O)(=O)N4CCCC4)cc3)c(Cl)c2)n[nH]1] |
| 221 | 4-[4'-(5-Amino-1H-[1,2,4]triazol-3-ylamino)-6'-chloro-4-methoxy-2'-trifluoromethyl-biphenyl-3-sulfonylamino]-piperidine-1-carboxylic acid tert-butyl ester; | 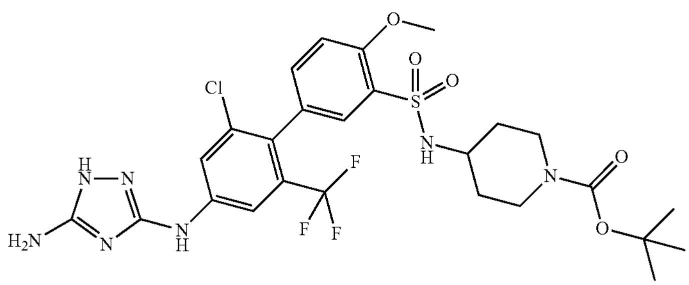 [SMILES: COc1ccc(-c2c(Cl)cc(Nc3n[nH]c(N)n3)cc2C(F)(F)F)cc1S(=O)(=O)NC1CCN(C(=O)OC(C)(C)C)CC1] |
| 222 | 4'-(5-Amino-1H-[1,2,4]triazol-3-ylamino)-2'-chloro-4-methoxy-6'-trifluoromethyl-biphenyl-3-sulfonic acid piperidin-4-ylamide; | 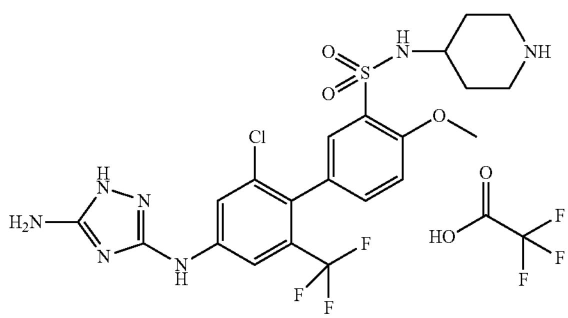 |
| 223 | 4'-(5-Amino-1H-[1,2,4]triazol-3-ylamino)-6'-chloro-2'-trifluoromethyl-biphenyl-4-sulfonic acid tert-butyl-(2,2,2-trifluoro-ethyl)-amide; | 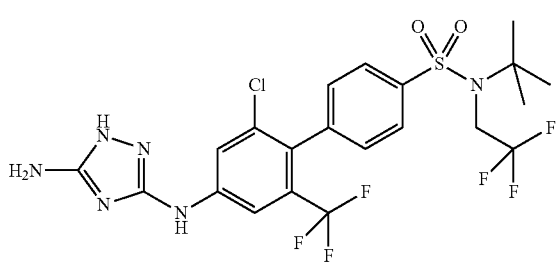 [SMILES: CC(C)(C)N(CC(F)(F)F)S(=O)(=O)c1ccc(-c2c(Cl)cc(Nc3n[nH]c(N)n3)cc2C(F)(F)F)cc1] |

| # | Nomenclature | Structure |
|---|---|---|
| 224 | N³-[6-Chloro-4'-(3,3-difluoro-azetidine-1-sulfonyl)-2-trifluoromethyl-biphenyl-4-yl]-1H-[1,2,4]triazole-3,5-diamine; | 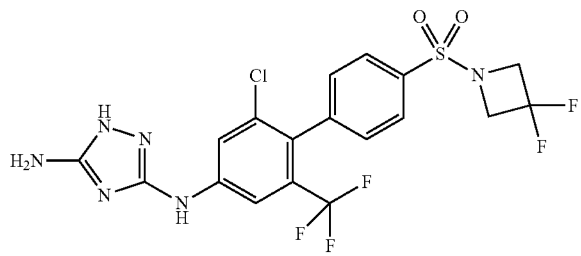 [SMILES: Nc1nc(Nc2cc(Cl)c(-c3ccc(S(=O)(=O)N4CC(F)(F)C4)cc3)c(C(F)(F)F)c2)n[nH]1] |
| 225 | 4'-(5-Amino-1H-[1,2,4]triazol-3-ylamino)-6'-chloro-4-methoxy-2'-trifluoromethyl-biphenyl-3-sulfonic acid (1-cyano-cyclopropyl)-amide; | 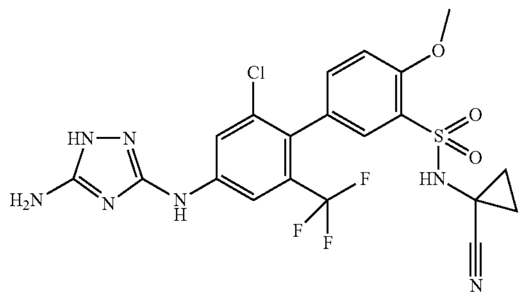 [SMILES: COc1ccc(-c2c(Cl)cc(Nc3n[nH]c(N)n3)cc2C(F)(F)F)cc1S(=O)(=O)NC1(C#N)CC1] |
| 226 | 4'-(5-Amino-1H-[1,2,4]triazol-3-ylamino)-6'-chloro-2'-trifluoromethyl-biphenyl-4-sulfonic acid (2-hydroxy-1,1-dimethyl-ethyl)-amide; | 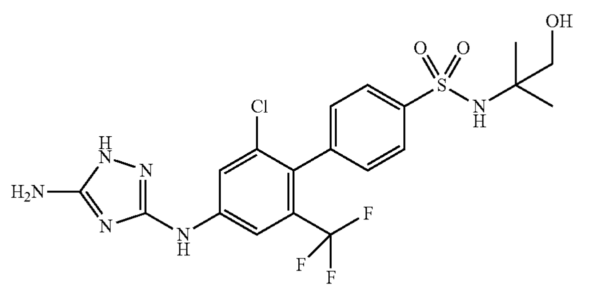 [SMILES: CC(C)(CO)NS(=O)(=O)c1ccc(-c2c(Cl)cc(Nc3n[nH]c(N)n3)cc2C(F)(F)F)cc1] |
| 227 | 4'-(5-Amino-1H-[1,2,4]triazol-3-ylamino)-2'-chloro-4-methoxy-6'-trifluoromethyl-biphenyl-3-sulfonic acid (1-acetyl-piperidin-4-yl)-amide; | 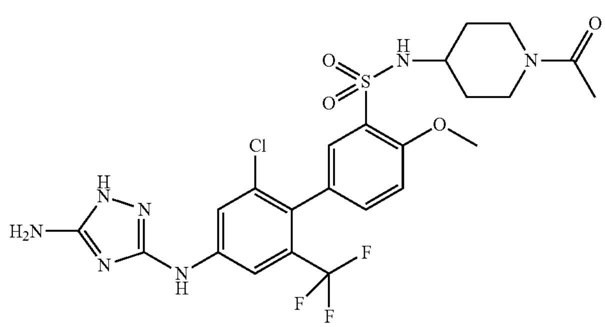 [SMILES: COc1ccc(-c2c(Cl)cc(Nc3n[nH]c(N)n3)cc2C(F)(F)F)cc1S(=O)(=O)NC1CCN(C(C)=O)CC1] |
| 228 | N*3*-[6-Chloro-4'-(propane-2-sulfonyl)-2-trifluoromethyl-biphenyl-4-yl]-1H-[1,2,4]triazole-3,5-diamine | 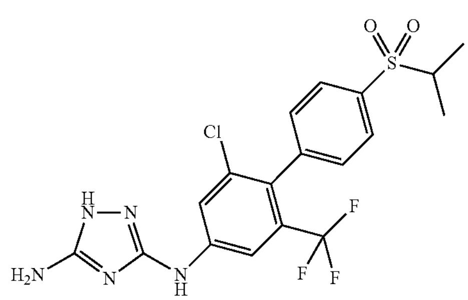 [SMILES: CC(C)S(=O)(=O)c1ccc(-c2c(Cl)cc(Nc3n[nH]c(N)n3)cc2C(F)(F)F)cc1] |

TABLE I-continued

| # | Nomenclature |
|---|---|
| 229 | N³-(6-Chloro-3'-isopropoxy-4'-methoxy-2-trifluoromethyl-biphenyl-4-yl)-1H-[1,2,4]triazole-3,5-diamine; |
| 230 | N³-(4'-tert-Butoxy-6-chloro-2-trifluoromethyl-biphenyl-4-yl)-1H-[1,2,4]triazole-3,5-diamine; |
| 231 | N³-(6-Chloro-4'-methoxy-2,3'-bis-trifluoromethyl-biphenyl-4-yl)-1H-[1,2,4]triazole-3,5-diamine; |
| 232 | N³-[6'-Chloro-4,4''-bis-(pyrrolidine-1-sulfonyl)-[1,1';2',1'']terphenyl-4'-yl]-1H-[1,2,4]triazole-3,5-diamine; |
| 233 | N³-[6-Chloro-4'-(3-fluoro-azetidine-1-sulfonyl)-2-trifluoromethyl-biphenyl-4-yl]-1H-[1,2,4]triazole-3,5-diamine; |

TABLE I-continued

| # | Nomenclature | Structure |
|---|---|---|
| 234 | 4'-(5-Amino-1H-[1,2,4]triazol-3-ylamino)-6'-chloro-4-methoxy-2'-trifluoromethyl-biphenyl-3-sulfonic acid piperidin-4-yl-(2,2,2-trifluoro-ethyl)-amide; | 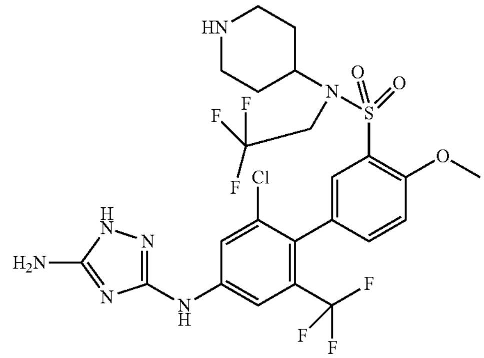 [SMILES: COc1ccc(-c2c(Cl)cc(Nc3n[nH]c(N)n3)cc2C(F)(F)F)cc1S(=O)(=O)N(CC(F)(F)F)C1CCNCC1] |
| 235 | 4,4-Difluoro-cyclohexane-carboxylic acid [4'-(5-amino-1H-[1,2,4]triazol-3-ylamino)-6'-chloro-2'-trifluoromethyl-biphenyl-4-yl]-amide; | 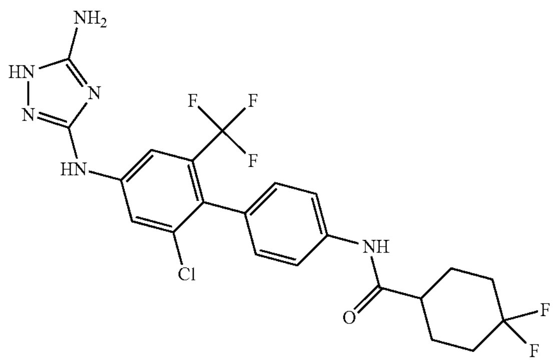 [SMILES: Nc1nc(Nc2cc(Cl)c(-c3ccc(NC(=O)C4CCC(F)(F)CC4)cc3)c(C(F)(F)F)c2)n[nH]1] |
| 236 | [4'-(5-Amino-1H-[1,2,4]triazol-3-ylamino)-6'-chloro-2'-trifluoromethyl-biphenyl-4-yl]-carbamic acid 1-tert-butyl-azetidin-3-yl ester; | 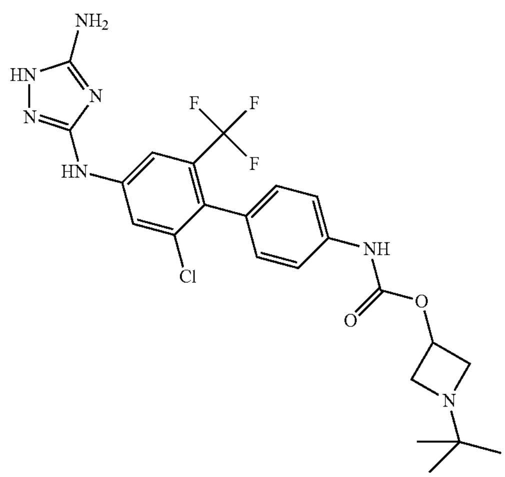 [SMILES: CC(C)(C)N1CC(OC(=O)Nc2ccc(-c3c(Cl)cc(Nc4n[nH]c(N)n4)cc3C(F)(F)F)cc2)C1] |
| 237 | [4'-(5-Amino-1H-[1,2,4]triazol-3-ylamino)-6'-chloro-2'-trifluoromethyl-biphenyl-4-yl]-carbamic acid propyl ester; | 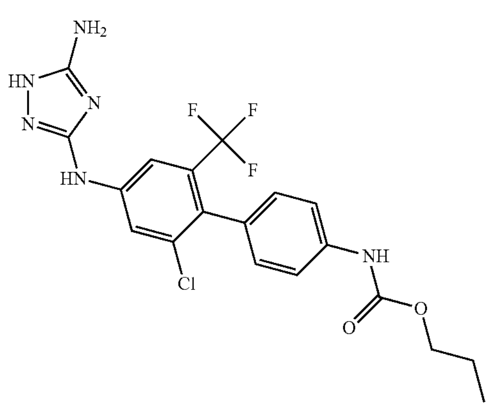 [SMILES: CCCOC(=O)Nc1ccc(-c2c(Cl)cc(Nc3n[nH]c(N)n3)cc2C(F)(F)F)cc1] |

TABLE I-continued

| # | Nomenclature | Structure |
|---|---|---|
| 238 | N-[4'-(5-Amino-1H-[1,2,4]triazol-3-ylamino)-6'-chloro-2'-trifluoromethyl-biphenyl-4-yl]-3-(tetrahydro-pyran-4-yl)-propionamide; | 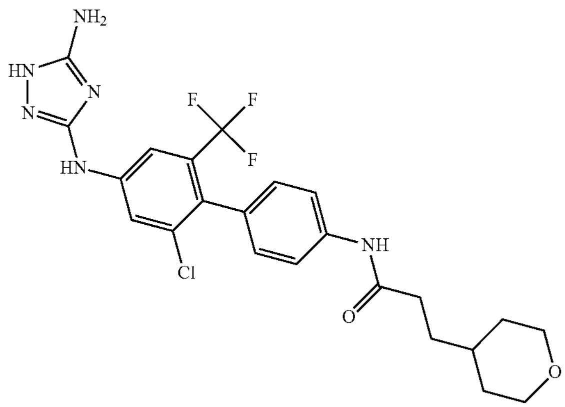 [SMILES: Nc1nc(Nc2cc(Cl)c(-c3ccc(NC(=O)CCC4CCOCC4)cc3)c(C(F)(F)F)c2)n[nH]1] |
| 239 | 1,1-Dioxo-hexahydro-1$\lambda^6$-thiopyran-4-carboxylic acid [4'-(5-amino-1H-[1,2,4]triazol-3-ylamino)-6'-chloro-2'-trifluoromethyl-biphenyl-4-yl]-amide; | 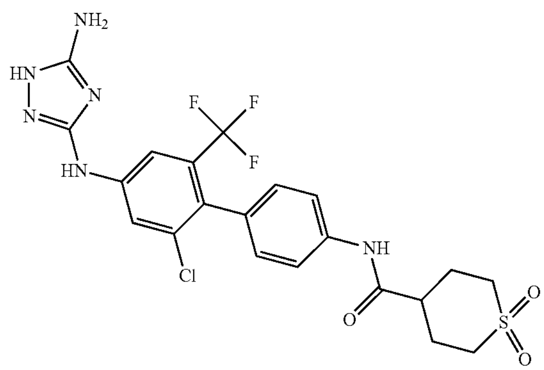 [SMILES: Nc1nc(Nc2cc(Cl)c(-c3ccc(NC(=O)C4CCS(=O)(=O)CC4)cc3)c(C(F)(F)F)c2)n[nH]1] |
| 240 | N-[4'-(5-Amino-1H-[1,2,4]triazol-3-ylamino)-6'-chloro-2'-trifluoromethyl-biphenyl-4-yl]-2-(1,1-dioxo-1$\lambda^6$-thio-morpholin-4-yl)-acetamide; | 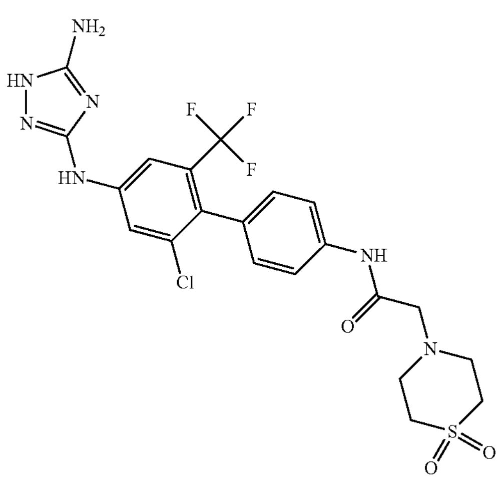 [SMILES: Nc1nc(Nc2cc(Cl)c(-c3ccc(NC(=O)CN4CCS(=O)(=O)CC4)cc3)c(C(F)(F)F)c2)n[nH]1] |

TABLE I-continued

| # | Nomenclature | Structure |
|---|---|---|
| 241 | N-[4'-(5-Amino-1H-[1,2,4]triazol-3-ylamino)-6'-chloro-2'-trifluoromethyl-biphenyl-4-yl]-2-morpholin-4-yl-acetamide; | 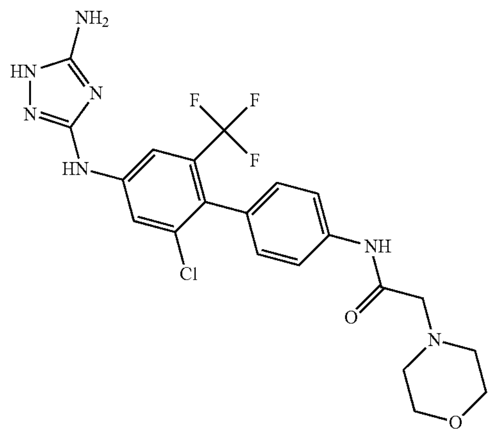 [SMILES: Nc1nc(Nc2cc(Cl)c(-c3ccc(NC(=O)CN4CCOCC4)cc3)c(C(F)(F)F)c2)n[nH]1] |
| 242 | N-[4'-(5-Amino-2H-[1,2,4]triazol-3-ylamino)-6'-fluoro-2'-trifluoromethyl-biphenyl-4-yl]-methane-sulfonamide; | 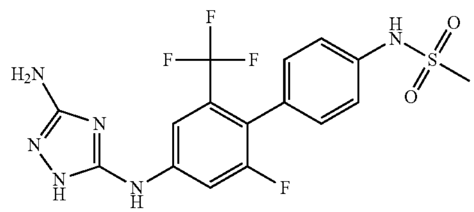 [SMILES: CS(=O)(=O)Nc1ccc(-c2c(F)cc(Nc3nc(N)n[nH]3)cc2C(F)(F)F)cc1] |
| 243 | N-[4'-(5-Amino-2H-[1,2,4]triazol-3-ylamino)-6'-fluoro-2'-trifluoromethyl-biphenyl-3-yl]-methane-sulfonamide; | 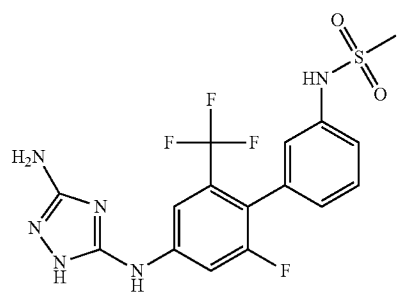 [SMILES: CS(=O)(=O)Nc1cccc(-c2c(F)cc(Nc3nc(N)n[nH]3)cc2C(F)(F)F)c1] |
| 244 | $N^5$-(6,3'-Difluoro-2-trifluoromethyl-biphenyl-4-yl)-1H-[1,2,4]triazole-3,5-diamine; | 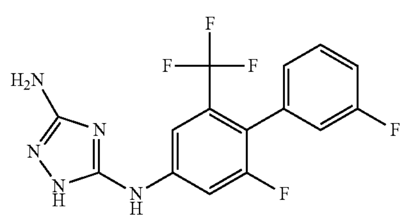 [SMILES: Nc1n[nH]c(Nc2cc(F)c(-c3cccc(F)c3)c(C(F)(F)F)c2)n1] |
| 245 | $N^5$-(6,4'-Difluoro-2-trifluoromethyl-biphenyl-4-yl)-1H-[1,2,4]triazole-3,5-diamine; | 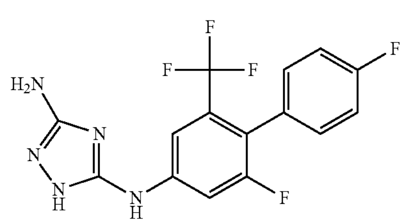 [SMILES: Nc1n[nH]c(Nc2cc(F)c(-c3ccc(F)cc3)c(C(F)(F)F)c2)n1] |
| 246 | $N^5$-(6-Fluoro-2,4'-bis-trifluoromethyl-biphenyl-4-yl)-1H-[1,2,4]triazole-3,5-diamine; | 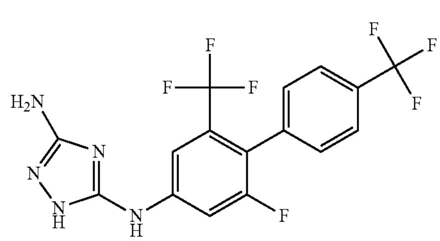 [SMILES: Nc1n[nH]c(Nc2cc(F)c(-c3ccc(C(F)(F)F)cc3)c(C(F)(F)F)c2)n1] |

… TABLE I-continued

| # | Nomenclature |
|---|---|
| 247 | N⁵-(6-Fluoro-4'-methyl-2-trifluoromethyl-biphenyl-4-yl)-1H-[1,2,4]triazole-3,5-diamine; |
| 248 | 4'-(5-Amino-2H-[1,2,4]triazol-3-ylamino)-6'-fluoro-2'-trifluoromethyl-biphenyl-3-carboxylic acid methylamide; |
| 249 | N⁵-(3-Fluoro-4-naphthalen-2-yl-5-trifluoromethyl-phenyl)-1H-[1,2,4]triazole-3,5-diamine; |
| 250 | 4,4-Difluoro-cyclohexane-carboxylic acid [4'-(5-amino-1H-[1,2,4]triazol-3-ylamino)-2',6'-dichloro-biphenyl-4-yl]-amide; |
| 251 | N-[4'-(5-Amino-1H-[1,2,4]triazol-3-ylamino)-2',6'-dichloro-biphenyl-4-yl]-isobutyramide; |
| 252 | N-[4'-(5-Amino-1H-[1,2,4]triazol-3-ylamino)-2',6'-dichloro-biphenyl-3-yl]-isobutyramide; |

TABLE I-continued

| # | Nomenclature | Structure |
|---|---|---|
| 253 | 4'-(5-Amino-1H-[1,2,4]triazol-3-ylamino)-2',6'-dichloro-biphenyl-4-sulfonic acid amide; | 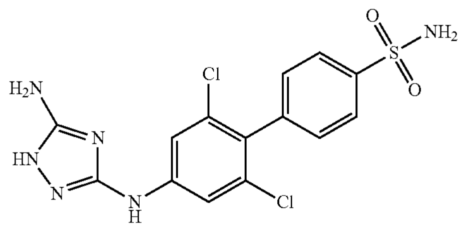 [SMILES: Nc1nc(Nc2cc(Cl)c(-c3ccc(S(N)(=O)=O)cc3)c(Cl)c2)n[nH]1] |
| 254 | 5-[4-(5-Amino-2H-[1,2,4]triazol-3-ylamino)-2,6-dichloro-phenyl]-1,3-dihydro-indol-2-one; | 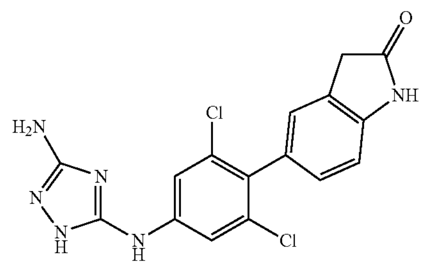 [SMILES: Nc1n[nH]c(Nc2cc(Cl)c(-c3ccc4c(c3)CC(=O)N4)c(Cl)c2)n1] |
| 255 | 5-[4-(5-Amino-2H-[1,2,4]triazol-3-ylamino)-2,6-dichloro-phenyl]-1,3-dihydro-benzoimidazol-2-one; | 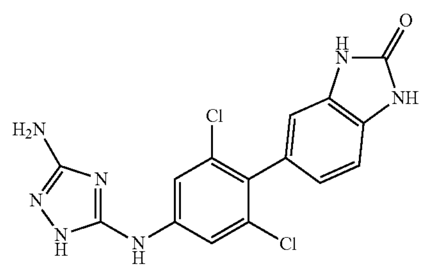 [SMILES: Nc1n[nH]c(Nc2cc(Cl)c(-c3ccc4[nH]c(=O)[nH]c4c3)c(Cl)c2)n1] |
| 256 | 6-[4-(5-Amino-2H-[1,2,4]triazol-3-ylamino)-2,6-dichloro-phenyl]-1,3-dihydro-indol-2-one; | 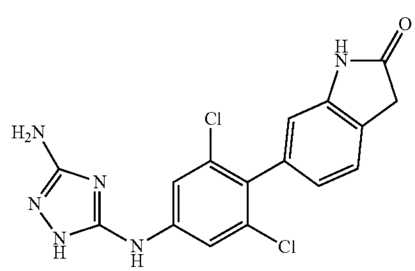 [SMILES: Nc1n[nH]c(Nc2cc(Cl)c(-c3ccc4c(c3)NC(=O)C4)c(Cl)c2)n1] |
| 257 | $N^5$-[3,5-Dichloro-4-(1H-indazol-5-yl)-phenyl]-1H-[1,2,4]triazole-3,5-diamine; | 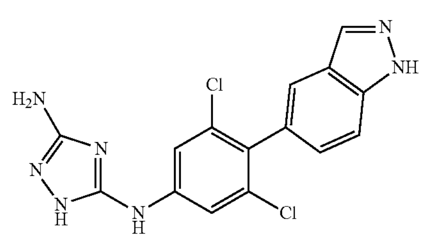 [SMILES: Nc1n[nH]c(Nc2cc(Cl)c(-c3ccc4[nH]ncc4c3)c(Cl)c2)n1] |
| 258 | $N^3$-(2',6'-Dichloro-biphenyl-4-yl)-1H-[1,2,4]triazole-3,5-diamine; | 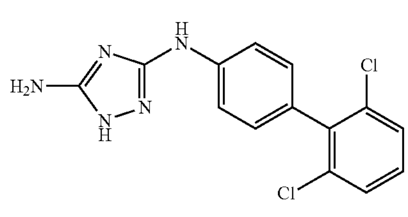 [SMILES: Nc1nc(Nc2ccc(-c3c(Cl)cccc3Cl)cc2)n[nH]1] |

TABLE I-continued

| # | Nomenclature | Structure |
|---|---|---|
| 259 | $N^5$-[2,6-Dichloro-4'-(piperidin-3-yloxy)-biphenyl-4-yl]-1H-[1,2,4]triazole-3,5-diamine; | 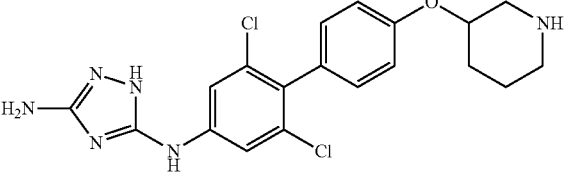 |
| 260 | 3-[4'-(5-Amino-1H-[1,2,4]triazol-3-ylamino)-2',6'-dichloro-biphenyl-4-yloxymethyl]-azetidine-1-carboxylic acid tert-butyl ester; | 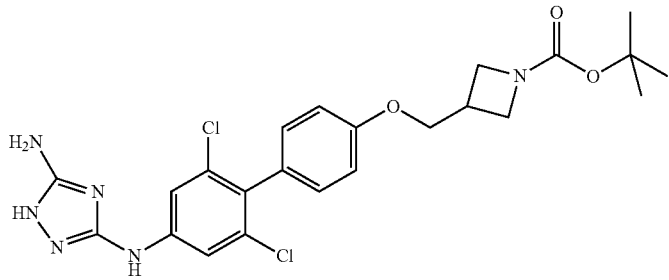 [SMILES: CC(C)(C)OC(=O)N1CC(COc2ccc(-c3c(Cl)cc(Nc4n[nH]c(N)n4)cc3Cl)cc2)C1] |
| 261 | {2-[4'-(5-Amino-1H-[1,2,4]triazol-3-ylamino)-2',6'-dichloro-biphenyl-4-yloxy]-ethyl}-methyl-carbamic acid tert-butyl ester; | 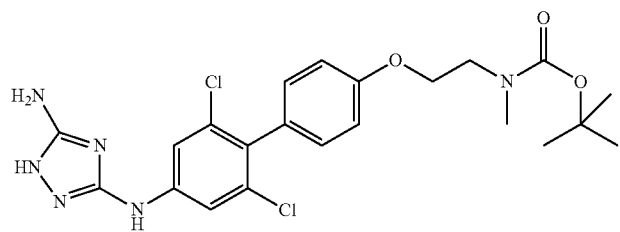 [SMILES: CN(CCOc1ccc(-c2c(Cl)cc(Nc3n[nH]c(N)n3)cc2Cl)cc1)C(=O)OC(C)(C)C] |
| 262 | $N^3$-[2,6-Dichloro-4'-(piperidin-4-yloxy)-biphenyl-4-yl]-1H-[1,2,4]triazole-3,5-diamine; | 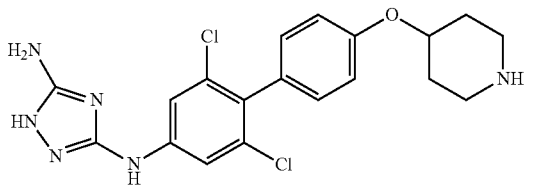 [SMILES: Nc1nc(Nc2cc(Cl)c(-c3ccc(OC4CCNCC4)cc3)c(Cl)c2)n[nH]1] |
| 263 | $N^3$-[2,6-Dichloro-4'-(2-methylamino-ethoxy)-biphenyl-4-yl]-1H-[1,2,4]triazole-3,5-diamine; | 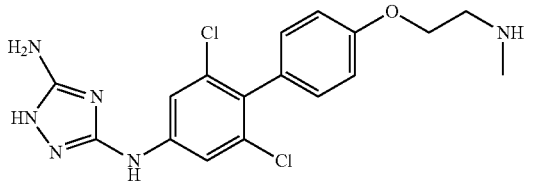 [SMILES: CNCCOc1ccc(-c2c(Cl)cc(Nc3n[nH]c(N)n3)cc2Cl)cc1] |
| 264 | $N^3$-[2,6-Dichloro-4'-(2-pyrrolidin-2-yl-ethoxy)-biphenyl-4-yl]-1H-[1,2,4]triazole-3,5-diamine; | 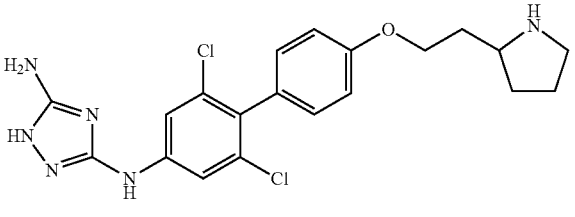 [SMILES: Nc1nc(Nc2cc(Cl)c(-c3ccc(OCCC4CCCN4)cc3)c(Cl)c2)n[nH]1] |
| 265 | $N^3$-[2,6-Dichloro-4'-((S)-1-pyrrolidin-2-ylmethoxy)-biphenyl-4-yl]-1H-[1,2,4]triazole-3,5-diamine; | 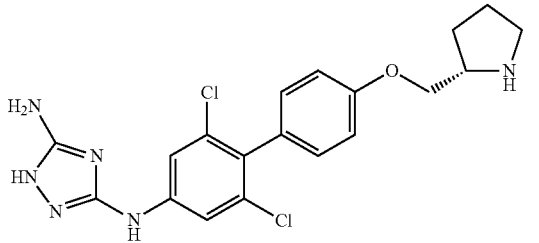 [SMILES: Nc1nc(Nc2cc(Cl)c(-c3ccc(OC[C@@H]4CCCN4)cc3)c(Cl)c2)n[nH]1] |

TABLE I-continued

| # | Nomenclature |
|---|---|
| 266 | 2-{2-[4'-(5-Amino-1H-[1,2,4]triazol-3-ylamino)-2',6'-dichloro-biphenyl-4-yloxy]-ethyl}-pyrrolidine-1-carboxylic acid tert-butyl ester; |
| 267 | (R)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester; |
| 268 | 4-[4'-(5-Amino-1H-[1,2,4]triazol-3-ylamino)-2',6'-dichloro-biphenyl-4-yloxy]-piperidine-1-carboxylic acid tert-butyl ester; |
| 269 | $N^3$-[2,6-Dichloro-4'-(2-dimethyl-amino-ethoxy)-biphenyl-4-yl]-1H-[1,2,4]triazole-3,5-diamine; |
| 270 | $N^3$-[6-Chloro-4'-((S)-1-pyrrolidin-2-ylmethoxy)-2-trifluoromethyl-biphenyl-4-yl]-1H-[1,2,4]triazole-3,5-diamine; |
| 271 | $N^3$-[2,6-Dichloro-4'-((S)-pyrrolidin-3-yloxy)-biphenyl-4-yl]-1H-[1,2,4]triazole-3,5-diamine; |

TABLE I-continued

| # | Nomenclature | Structure |
|---|---|---|
| 272 | N³-[2,6-Dichloro-4'-((R)-1-pyrrolidin-2-ylmethoxy)-biphenyl-4-yl]-1H-[1,2,4]triazole-3,5-diamine; | 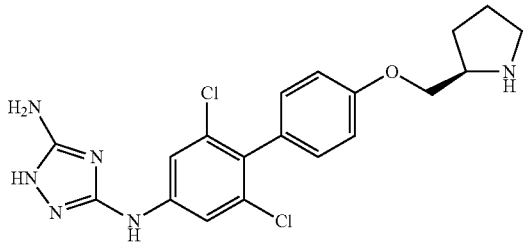 [SMILES: Nc1nc(Nc2cc(Cl)c(-c3ccc(OC[C@H]4CCCN4)cc3)c(Cl)c2)n[nH]1] |
| 273 | (S)-3-[4'-(5-Amino-1H-[1,2,4]triazol-3-ylamino)-2',6'-dichloro-biphenyl-4-yloxy]-pyrrolidine-1-carboxylic acid tert-butyl ester; | 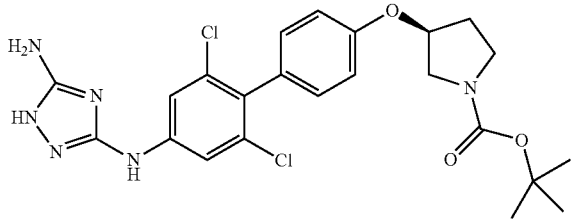 [SMILES: CC(C)(C)OC(=O)N1CC[C@H](Oc2ccc(-c3c(Cl)cc(Nc4n[nH]c(N)n4)cc3Cl)cc2)C1] |
| 274 | N³-[2,6-Dichloro-4'-(2,2-dimethyl-[1,3]dioxolan-4-ylmethoxy)-biphenyl-4-yl]-1H-[1,2,4]triazole-3,5-diamine; | 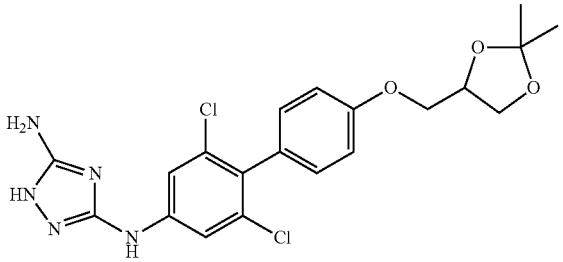 [SMILES: CC1(C)OCC(COc2ccc(-c3c(Cl)cc(Nc4n[nH]c(N)n4)cc3Cl)cc2)O1] |
| 275 | (R)-2-[4'-(5-Amino-1H-[1,2,4]triazol-3-ylamino)-2',6'-dichloro-biphenyl-4-yloxymethyl]-pyrrolidine-1-carboxylic acid tert-butyl ester; | 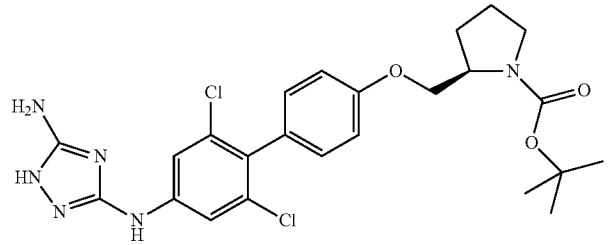 [SMILES: CC(C)(C)OC(=O)N1CCC[C@@H]1COc1ccc(-c2c(Cl)cc(Nc3n[nH]c(N)n3)cc2Cl)cc1] |
| 276 | [4'-(5-Amino-1H-[1,2,4]triazol-3-ylamino)-2',6'-dichloro-biphenyl-4-yloxy]-acetic acid tert-butyl ester; | 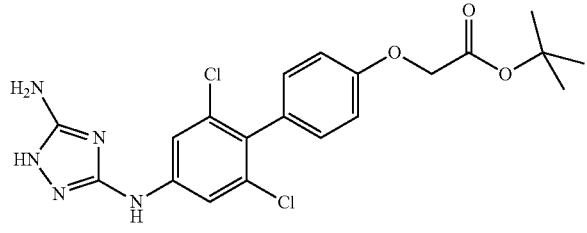 [SMILES: CC(C)(C)OC(=O)COc1ccc(-c2c(Cl)cc(Nc3n[nH]c(N)n3)cc2Cl)cc1] |
| 277 | (S)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester; | 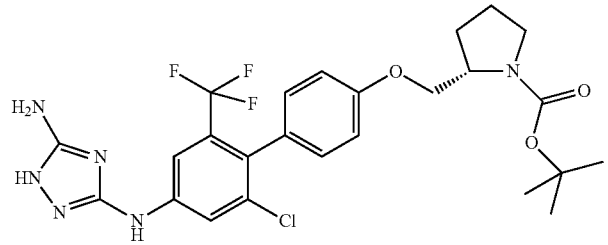 [SMILES: CC(C)(C)OC(=O)N1CCC[C@H]1COc1ccc(-c2c(Cl)cc(Nc3n[nH]c(N)n3)cc2C(F)(F)F)cc1] |

TABLE I-continued

| # | Nomenclature | Structure |
|---|---|---|
| 278 | N³-[2,6-Dichloro-4'-(2-methoxy-ethoxy)-biphenyl-4-yl]-1H-[1,2,4]triazole-3,5-diamine | 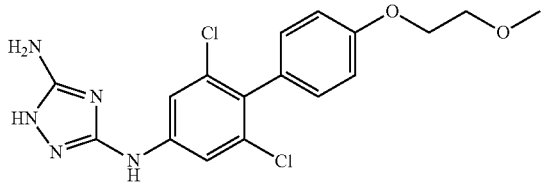 [SMILES: COCCOc1ccc(-c2c(Cl)cc(Nc3n[nH]c(N)n3)cc2Cl)cc1] |
| 279 | N³-[6-Chloro-4'-((R)-1-pyrrolidin-2-ylmethoxy)-2-trifluoromethyl-biphenyl-4-yl]-1H-[1,2,4]triazole-3,5-diamine; | 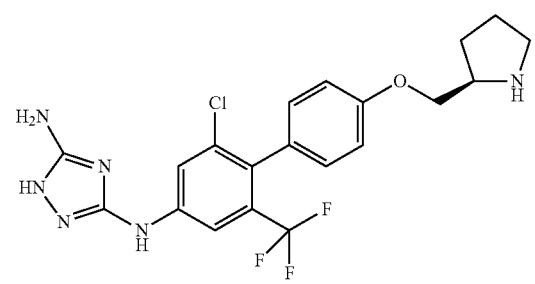 [SMILES: Nc1nc(Nc2cc(Cl)c(-c3ccc(OC[C@H]4CCCN4)cc3)c(C(F)(F)F)c2)n[nH]1] |
| 280 | (S)-2-[4'-(5-Amino-1H-[1,2,4]triazol-3-ylamino)-2',6'-dichloro-biphenyl-4-yloxymethyl]-pyrrolidine-1-carboxylic acid tert-butyl ester; | 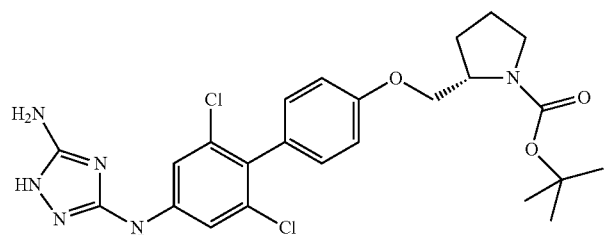 |
| 281 | N³-[2,6-Dichloro-4'-(2-morpholin-4-yl-ethoxy)-biphenyl-4-yl]-1H-[1,2,4]triazole-3,5-diamine; | 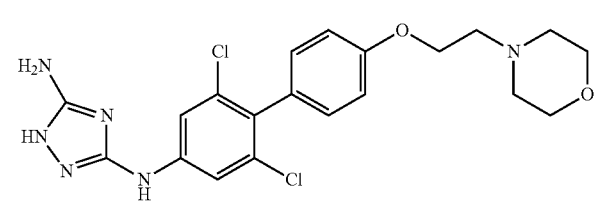 [SMILES: Nc1nc(Nc2cc(Cl)c(-c3ccc(OCCN4CCOCC4)cc3)c(Cl)c2)n[nH]1] |
| 282 | 3-[4'-(5-Amino-1H-[1,2,4]triazol-3-ylamino)-2',6'-dichloro-biphenyl-4-yloxy]-propane-1,2-diol; | 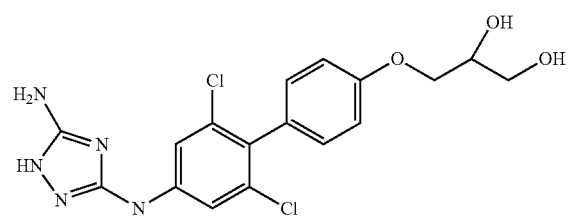 |
| 283 | N³-[2,6-Dichloro-4'-(3-morpholin-4-yl-propoxy)-biphenyl-4-yl]-1H-[1,2,4]triazole-3,5-diamine; | 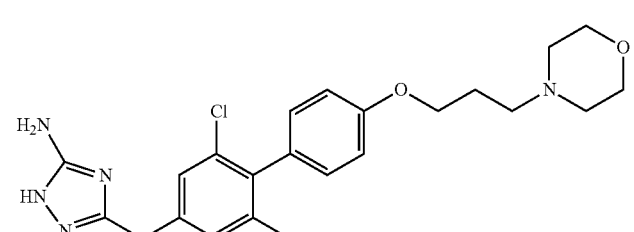 |

TABLE I-continued

| # | Nomenclature | Structure |
|---|---|---|
| 284 | N³-[2,6-Dichloro-4'-(pyridin-2-ylmethoxy)-biphenyl-4-yl]-1H-[1,2,4]triazole-3,5-diamine; | 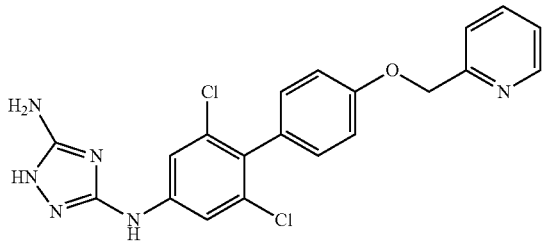 [SMILES: Nc1nc(Nc2cc(Cl)c(-c3ccc(OCc4ccccn4)cc3)c(Cl)c2)n[nH]1] |
| 285 | [4'-(5-Amino-1H-[1,2,4]triazol-3-ylamino)-2',6'-dichloro-biphenyl-4-yloxy]-acetic acid; | 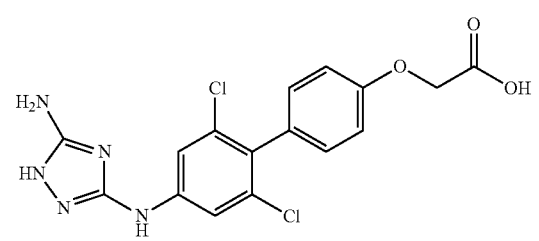 [SMILES: Nc1nc(Nc2cc(Cl)c(-c3ccc(OCC(=O)O)cc3)c(Cl)c2)n[nH]1] |
| 286 | N³-(2,6-Dichloro-4'-fluoro-biphenyl-4-yl)-1H-[1,2,4]triazole-3,5-diamine; | 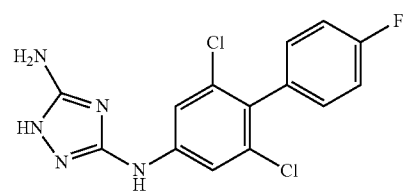 [SMILES: Nc1nc(Nc2cc(Cl)c(-c3ccc(F)cc3)c(Cl)c2)n[nH]1] |
| 287 | N³-(2,6-Dichloro-2'-fluoro-biphenyl-4-yl)-1H-[1,2,4]triazole-3,5-diamine; | 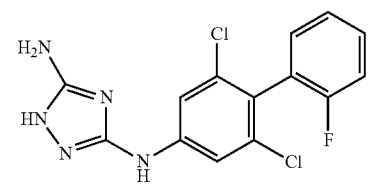 [SMILES: Nc1nc(Nc2cc(Cl)c(-c3ccccc3F)c(Cl)c2)n[nH]1] |
| 288 | N*3*-(4'-Methanesulfonyl-2-pentafluoro-sulfur-biphenyl-4-yl)-1H-[1,2,4]triazole-3,5-diamine | 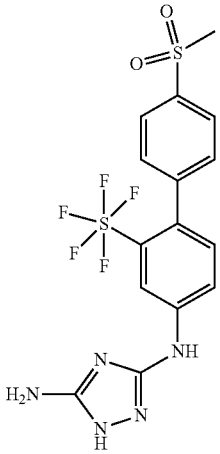 [SMILES: CS(=O)(=O)c1ccc(-c2ccc(Nc3n[nH]c(N)n3)cc2S(F)(F)(F)(F)F)cc1] |
| 289 | N³-[2,6-Dichloro-4'-(1,1-dioxo-1λ⁶-isothiazolidin-2-yl)-biphenyl-4-yl]-1H-[1,2,4]triazole-3,5-diamine; | 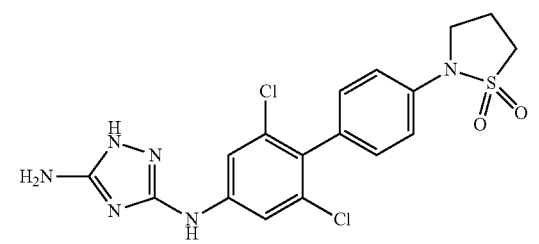 [SMILES: Nc1nc(Nc2cc(Cl)c(-c3ccc(N4CCCS4(=O)=O)cc3)c(Cl)c2)n[nH]1] |

TABLE I-continued

| # | Nomenclature | Structure |
|---|---|---|
| 290 | N-[4'-(5-Amino-1H-[1,2,4]triazol-3-ylamino)-6'-chloro-2'-trifluoromethyl-biphenyl-3-yl]-methanesulfonamide; | 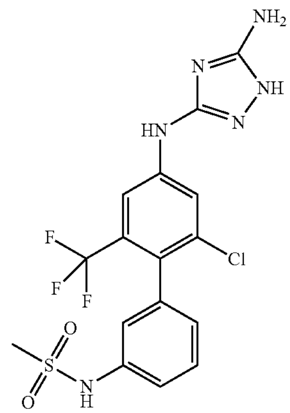 [SMILES: CS(=O)(=O)Nc1cccc(-c2c(Cl)cc(Nc3n[nH]c(N)n3)cc2C(F)(F)F)c1] |
| 291 | 4'-(5-Amino-1H-[1,2,4]triazol-3-ylamino)-6'-chloro-3-fluoro-2'-trifluoromethyl-biphenyl-4-carboxylic acid methyl amide; | 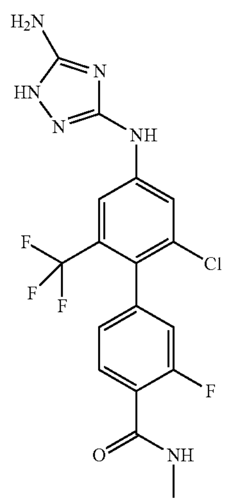 [SMILES: CNC(=O)c1ccc(-c2c(Cl)cc(Nc3n[nH]c(N)n3)cc2C(F)(F)F)cc1F] |
| 292 | 4'-(5-Amino-1H-[1,2,4]triazol-3-ylamino)-6'-chloro-4-fluoro-2'-trifluoromethyl-biphenyl-3-carboxylic acid methylamide; | 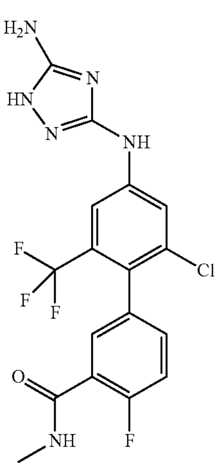 [SMILES: CNC(=O)c1cc(-c2c(Cl)cc(Nc3n[nH]c(N)n3)cc2C(F)(F)F)ccc1F] |

TABLE I-continued

| # | Nomenclature | Structure |
|---|---|---|
| 293 | 4'-(5-Amino-1H-[1,2,4]triazol-3-ylamino)-6'-chloro-3-fluoro-2'-trifluoromethyl-biphenyl-4-carboxylic acid (2-hydroxy-ethyl)-amide; | 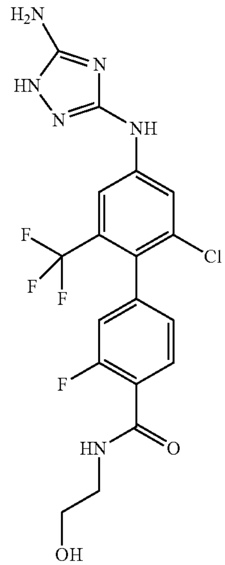 [SMILES: Nc1nc(Nc2cc(Cl)c(-c3ccc(C(=O)NCCO)c(F)c3)c(C(F)(F)F)c2)n[nH]1] |
| 294 | 4'-(5-Amino-1H-[1,2,4]triazol-3-ylamino)-6'-chloro-4-fluoro-2'-trifluoromethyl-biphenyl-3-carboxylic acid (2-hydroxy-ethyl)-amide; and | 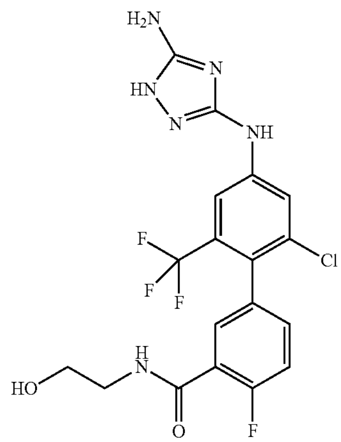 [SMILES: Nc1nc(Nc2cc(Cl)c(-c3ccc(F)c(C(=O)NCCO)c3)c(C(F)(F)F)c2)n[nH]1] |
| 295 | 4'-(5-Amino-1H-[1,2,4]triazol-3-ylamino)-2'-chloro-6'-trifluoromethyl-biphenyl-4-sulfonic acid oxetan-3-ylamide. | 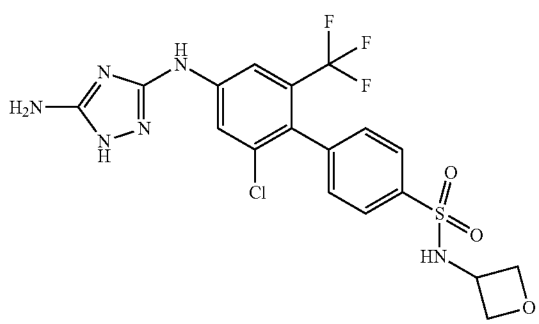 [SMILES: Nc1nc(Nc2cc(Cl)c(-c3ccc(S(=O)(=O)NC4COC4)cc3)c(C(F)(F)F)c2)n[nH]1] |
| 296 | 4'-(5-Amino-1H-[1,2,4]triazol-3-ylamino)-6'-chloro-4-methoxy-2'-trifluoromethyl-biphenyl-3-sulfonic acid (1-isopropyl-piperidin-4-yl)-amide | 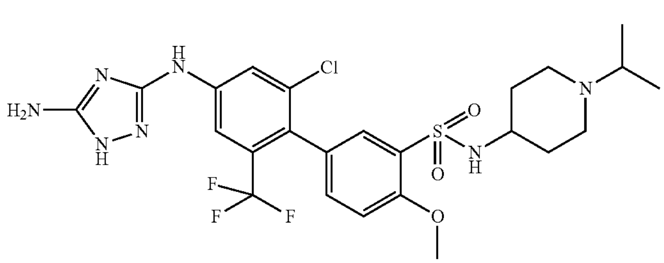 [SMILES: COc1ccc(-c2c(Cl)cc(Nc3n[nH]c(N)n3)cc2C(F)(F)F)cc1S(=O)(=O)NC1CCN(C(C)C)CC1] |

Synthesis
General Schemes
The following schemes depict general methods for obtaining compounds of Formula I.
Procedure 1
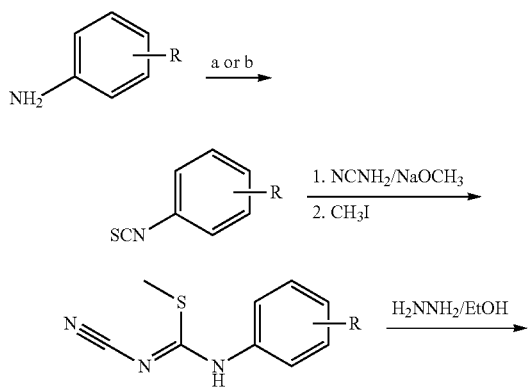
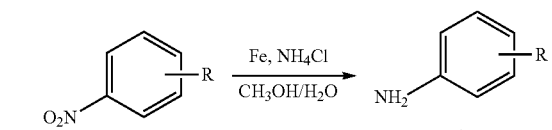
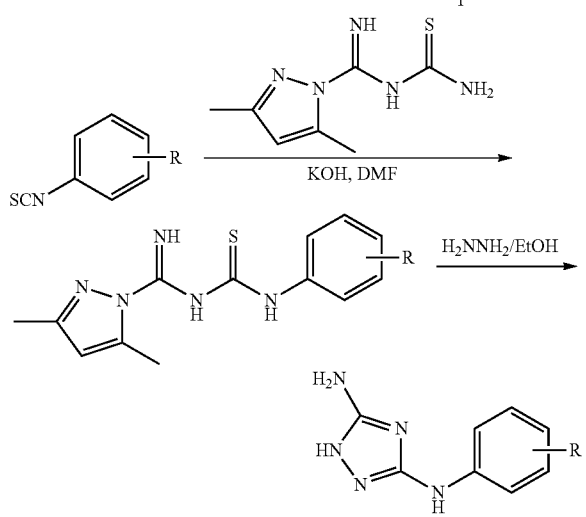
Procedure 2
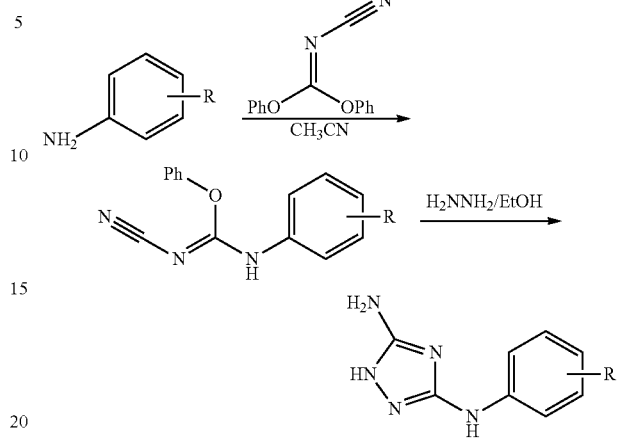
Procedure 3
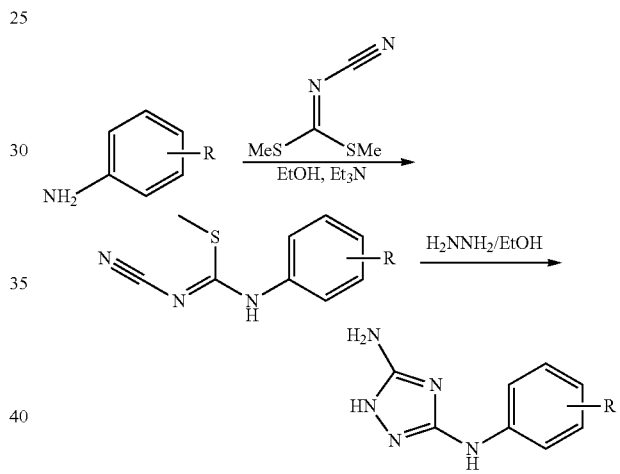
Procedure 4
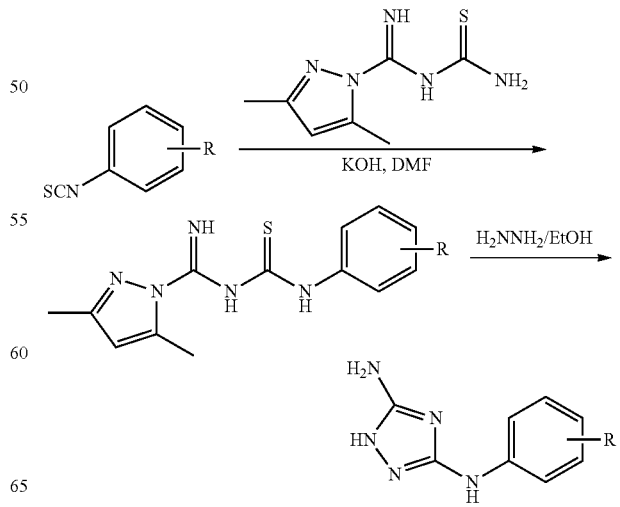

Procedure 5

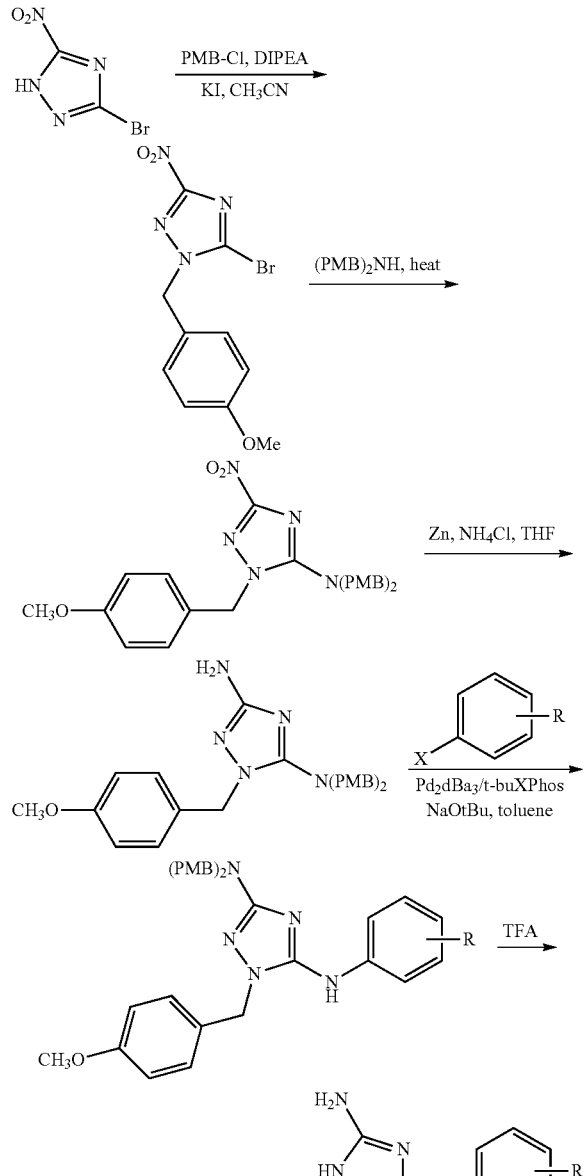

Procedure 6

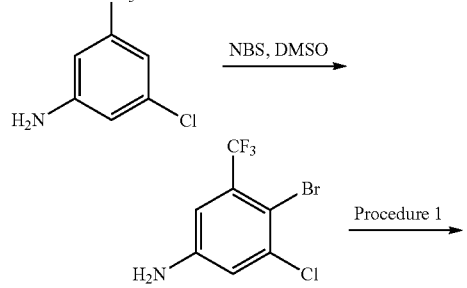

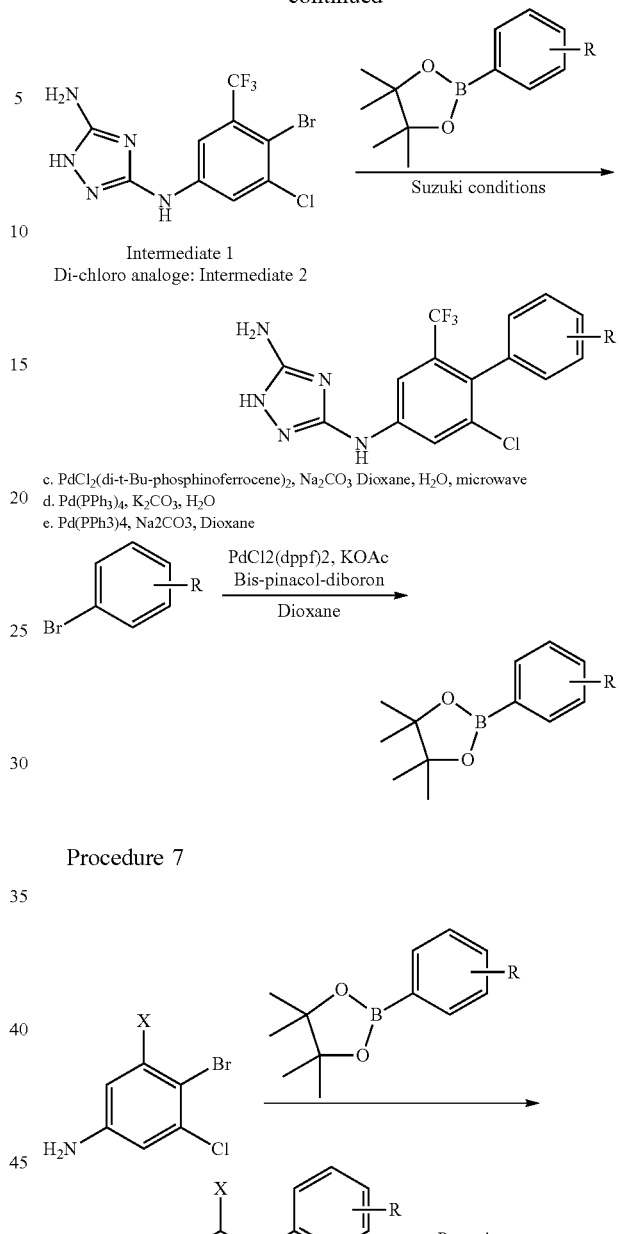

Procedure 7

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment
Indications

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors, NS5A inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-813, PHX-1766, PHX2054, IDX-136, IDX-316, ABT-450 EP-0 13420 (and congeners) and VBY-376; the Nucleosidic HCV polymerase (replicase) inhibitors useful in the invention include, but are not limited to, R7128, PSI-7851, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/40381; WO00/56331, WO02/04425; WO03/

007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927. Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for preventing a Hepatitis C Virus (HCV) infection comprising administering to a patient in need thereof a therapeutically effective amount of a compound of Formula I.

The application provides the above method, further comprising administering to a patient in need thereof a therapeutically effective amount of an immune system suppressant.

The application provides a method for treating a Hepatitis C Virus (HCV) infection comprising administering to a patient in need thereof a therapeutically effective amount of a compound of Formula I.

The application provides any of the above methods, further comprising administering an immune system modulator or an antiviral agent that inhibits replication of HCV, or a combination thereof.

The application provides the above method, wherein the immune system modulator is an interferon or a chemically derivatized interferon.

The application provides any of the above methods, further comprising administering an immune system modulator or an antiviral agent that inhibits replication of HCV, or a combination thereof, wherein the antiviral agent is selected from the group consisting of a HCV protease inhibitor, a HCV polymerase inhibitor, a HCV helicase inhibitor, a HCV NS5A inhibitor, or any combination thereof.

EXAMPLES

Abbreviations

Commonly used abbreviations include: acetyl (Ac), azobis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) (Pd(dppf)$Cl_2$), palladium(II) acetate (Pd(OAc)$_2$), tris(dibenzylideneacetone)dipalladium(0) ($Pd_2(dba)_3$), pyridinium dichromate (PDC), phenyl (Ph), propyl (Pr), isopropyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-$C_6H_4SO_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

PREPARATIVE EXAMPLES

Intermediate 1

Procedure 1

N*3*-(4-Bromo-3-chloro-5-trifluoromethyl-phenyl)-1H-[1,2,4]triazole-3,5-diamine (Intermediate 1)

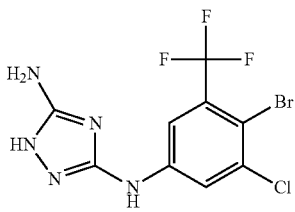 [SMILES: Nc1nc(Nc2cc(Cl)c(Br)c(C(F)(F)F)c2)n[nH]1]

2-bromo-1-chloro-5-isothiocyanato-3-(trifluoromethyl)benzene

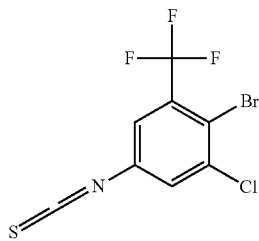 [SMILES: FC(F)(F)c1cc(N=CC=S)cc(Cl)c1Br]

To a suspension of 4-bromo-3-chloro-5-(trifluoromethyl) aniline (15 g, 54.7 mmol, Eq: 1.00) in dichloromethane (13.2 g, 10.0 ml, 155 mmol, Eq: 25.3) at 0, was added 1,1'-thiocarbonyldiimidazole (11.7 g, 65.6 mmol, Eq: 1.2) The reaction was gradually warmed to room temperature and stirred overnight. The reaction was concentrated and chromatographed (220 g Redisep, 5 to 15% dichloromethane/hexane) to give 13.84 g (80%) pale yellow oil.

(Z)-methyl N-4-bromo-3-chloro-5-(trifluoromethyl) phenyl-N'-cyanocarbamimidothioate

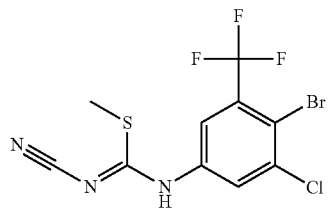 [SMILES: CS/C(=N\C#N)Nc1cc(Cl)c(Br)c(C(F)(F)F)c1]

To a solution of 2-bromo-1-chloro-5-isothiocyanato-3-(trifluoromethyl)benzene (13.84 g, 43.7 mmol, Eq: 1.00) in dimethoxyethane (100 mL) was added sodium hydrogen cyanamide (3.36 g, 52.5 mmol, Eq: 1.2) and methanol (10 mL). After 30 minutes, methyl iodide (15.9 g, 7 ml, 112 mmol, Eq: 2.56) was added to the magenta-colored soln and the reaction was stirred overnight at room temperature. The reaction mixture was concentrated to dryness and dissolved in ~50 mL acetonitrile. Added 100 mL water to give a white precipitate. Filtered white solid, rinsed with water and air-dried o/n to give 16.0 g (99%) of white solid.

N*3*-(4-Bromo-3-chloro-5-trifluoromethyl-phenyl)-1H-[1,2,4]triazole-3,5-diamine (Intermediate 1)

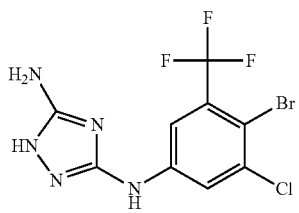 [SMILES: Nc1nc(Nc2cc(Cl)c(Br)c(C(F)(F)F)c2)n[nH]1]

In a 500 mL round-bottomed flask, (Z)-methyl N-4-bromo-3-chloro-5-(trifluoromethyl)phenyl-N'-cyanocarbamimidothioate (1.45 g, 3.89 mmol, Eq: 1.00) was combined with ethanol (15 ml) to give a white suspension. Hydrazine (1.25 g, 1.22 ml, 38.9 mmol, Eq: 10) was added and the reaction mixture was heated to 70° C. and stirred for 3 h. The reaction was cooled and water (~40 mL) was added to the reaction with shaking. The resulting suspension was filtered, washed with water and vacuum oven dried at 45 C over weekend. Obtained a white solid as desired product (1.12 g, 81% yield). Another sample was collected from mother liquor as an pink solid (148 mg, ~90 pure, 9.6% yield)

MS m/z 356 [M+H]

Intermediate 2

Procedure 1

N*3*-(4-Bromo-3,5-dichloro-phenyl)-1H-[1,2,4]triazole-3,5-diamine (Intermediate 2)

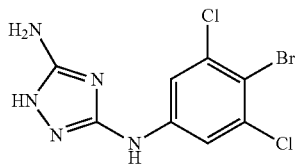

(Z)-methyl N-4-bromo-3,5-dichlorophenyl-N'-cyanocarbamimidothioate

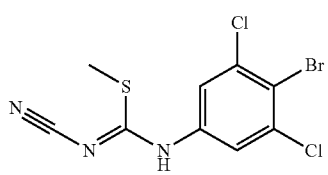 [SMILES: CS/C(=N\C#N)Nc1cc(Cl)c(Br)c(Cl)c1]

A solution of sodium methoxide (2.6 ml, 1.3 mmol, Eq: 1.23) was added to cyanamide (50 mg, 1.19 mmol, Eq: 1.12) and stirred at room temperature for 15 minutes. 2-bromo-1,3-dichloro-5-isothiocyanatobenzene (300 mg, 1.06 mmol, Eq: 1.00) was added to the reaction mixture and stirred for 1 hr. Iodomethane (331 mg, 146 µl, 2.33 mmol, Eq: 2.2) was added and the pale yellow solution was stirred overnight at room temperature. The resulting suspension was filtered and air dried to give 154 mg (43%) of desired product as a light brown solid.

N*3*-(4-Bromo-3,5-dichloro-phenyl)-1H-[1,2,4]triazole-3,5-diamine (Intermediate 2)

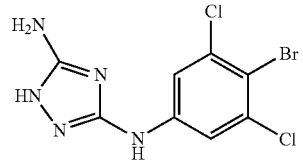

A solution of (Z)-methyl N-4-bromo-3,5-dichlorophenyl-N'-cyanocarbamimidothioate (154 mg, 454 µmol, Eq: 1.00) and hydrazine (153 mg, 150 µl, 4.78 mmol, Eq: 10.5) in ethanol (5 mL) was heated at 65° C. After 3 hr, LCMS ok, no sm. Cooled to rt and stirred solution over weekend. The reaction mixture was concentrated and chromatographed (11 g Supelco, 0 to 10% MeOH/CH2Cl2) to give 80 mg (55%) of desired product as an off-white solid.

$^1$H NMR (300 MHz, DMSO) δ: 11.35 (s, 1H), 9.33 (s, 1H), 7.75 (s, 2H), 6.05 (s, 2H) ppm Intermediate 3

Procedure 1

N$^5$-(4-bromo-3-fluoro-5-trifluoromethylphenyl)-1H-[1,2,4]-triazole-3,5-diamine (Intermediate 3)

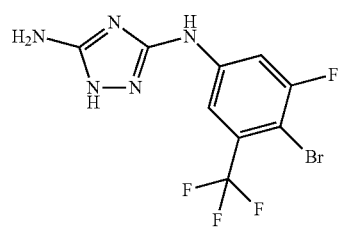 [SMILES: Nc1nc(Nc2cc(F)c(Br)c(C(F)(F)F)c2)n[nH]1]

2-bromo-1-fluoro-5-isothiocyanato-3-trifluoromethylbenzene

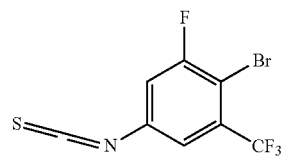 [SMILES: Fc1cc(N=CC=S)cc(C(F)(F)F)c1Br]

4-bromo-3-fluoro-5-trifluoromethylaniline (4.22 g, 16.4 mmol, Eq: 1.00) and calcium carbonate (3.44 g, 1.17 ml, 34.3 mmol, Eq: 2.1) were suspended in 50% aqueous dichlormethane (20 ml) mixture. The thick suspension was stirred vigorously at 0° C. Thiophosgene (2.07 g, 1.38 ml, 18.0 mmol, Eq: 1.1) was added slowly dropwise to the mixture. After the addition the mixture was stirred at 0° C. for 1.5 hr then stirred overnight at room temperature. The solids were filtered and the filtrate was extracted with dichloromethane. The combined organic phases were washed with water, brine, dried over sodium sulfate and concentrated in vacuo to afford 4.71 g (96%) of the desired material as a light brown solid.

$^1$H NMR (300 MHz, DMSO-d$_6$) δ ppm 7.84 (s, 1H) 7.96 (dd, J=9.06, 2.27 Hz, 1H)

(4-Bromo-3-fluoro-5-trifluoromethyl-phenylamino)-(methyl-λ$^4$sulfanylidene)-methyl-cyanamide

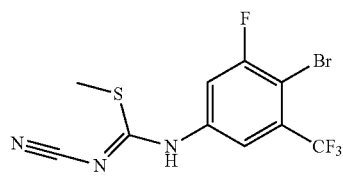 [SMILES: CS/C(=N\C#N)Nc1cc(F)c(Br)c(C(F)(F)F)c1]

2-bromo-1-fluoro-5-isothiocyanato-3-trifluoromethyl-benzene (4.71 g, 15.7 mmol, Eq: 1.00) was dissolved in anhydrous methanol (30 ml). Sodium hydrogencyanamide (1.00 g, 15.7 mmol, Eq: 1) was added and the reaction was stirred for 1 hr at ambient temperature. Methyl iodide (4.46 g, 1.96 ml, 31.4 mmol, Eq: 2) was added dropwise and the reaction was stirred overnight at ambient temperature. The light brown suspension was filtered to afford 1.91 g (34%) of the desired product as a pink solid.

MS +m/z: 357.7. (M+1)
$^1$H NMR (300 MHz, DMSO-d$_6$) δ ppm 2.78 (s, 3H) 7.87 (s, 1H) 7.97 (dd, J=1.00 Hz, 1H) 10.38 (br. s, 1H)

Prepared of N$^5$-(4-bromo-3-fluoro-5-trifluoromethylphenyl)-1H-[1,2,4]-triazole-3,5-diamine (Intermediate 3)

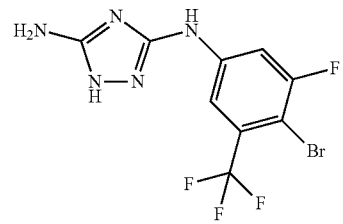 [SMILES: Nc1nc(Nc2cc(F)c(Br)c(C(F)(F)F)c2)n[nH]1]

Hydrazine (1.71 g, 53.4 mmol, Eq: 10) was added to a stirred suspension of (4-Bromo-3-fluoro-5-trifluoromethyl-phenylamino)-(methyl-λ$^4$sulfanylidene)-methyl-cyanamide (1.9 g, 5.34 mmol, Eq: 1.00) in ethanol (30 ml). The mixture was heated to 70° C. for 1 hr. The reaction mixture was concentrated to a reduced volume (~5 ml) and water (~10 ml) was added dropwise while stirring. The suspension was stirred for 30 min. The precipitate was filtered and washed with water (~50 ml), then dried under high vacuum at 70° C. for two hours to filtered to afford 1.73 g (95%) of the desired product as a light pink solid.

MS +m/z: 339.9. (M+1)
$^1$H NMR (400 MHz, DMSO-d$_6$) δ ppm 6.03 (s, 2H) 7.81 (s, 1H) 7.86 (d, J=12.13 Hz, 1H) 9.52 (s, 1H) 11.40 (s, 1H)

Intermediate 4

Procedure 1

N*5*-(4-Bromo-3,5-difluoro-phenyl)-1H-[1,2,4]triazole-3,5-diamine (Intermediate 4)

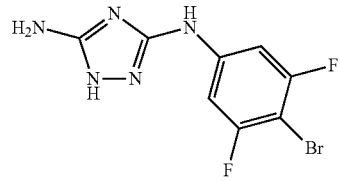 [SMILES: Nc1nc(Nc2cc(F)c(Br)c(F)c2)n[nH]1]

2-bromo-1,3-difluoro-5-isothiocyanatobenzene

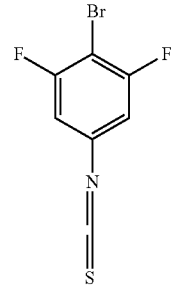 [SMILES: Fc1cc(N=CC=S)cc(F)c1Br]

4-bromo-3,5-difluoroaniline (5 g, 24.0 mmol, Eq: 1.00) and calcium carbonate (5.05 g, 1.72 ml, 50.5 mmol, Eq: 2.1) were suspended in a 50% aqueous dichlormethane (24 ml) mixture. The thick suspension was stirred vigorously at 0° C. Thiophosgene (3.04 g, 2.03 ml, 26.4 mmol, Eq: 1.1) was added slowly dropwise to the mixture. After the addition the mixture was stirred at 0° C. for 1 hr, then stirred overnight at room temperature. The precipitate was filtered and the filter cake was washed with dichloromethane. The phases were separated and the aqueous was extracted with dichloromethane. The combined organic phases were washed with water and brine, dried over sodium sulfate and concentrated in vacuo to afford 5.18 g (86%) of the desired product as an off-white solid which was used without further purification.

(4-Bromo-3,5-difluoro-phenylamino)-(methyl-λ$^4$-sulfanylidene)-methyl-cyanamide

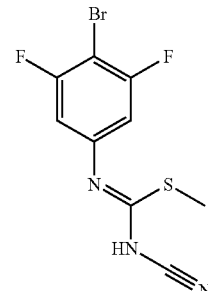

2-bromo-1,3-difluoro-5-isothiocyanatobenzene (5.18 g, 20.7 mmol, Eq: 1.00) was dissolved in anhydrous methanol (30.0 ml) and dichloromethane (10 ml). Sodium hydrogencyanamide (1.33 g, 20.7 mmol, Eq: 1) was added slowly and the reaction was stirred for 1 hr at room temperature. The reaction was cooled to 0° C. and methyl iodide (5.88 g, 2.59 ml, 41.4 mmol, Eq: 2) was added dropwise. The reaction was stirred overnight at room temperature. The white suspension was filtered and the filter cake was washed with methanol and dried under high vacuum to afford 4.62 g (73%) of the desired product as a white solid.

MS +m/z: 307. (M+1)

$^1$H NMR (300 MHz, DMSO-$d_6$) δ ppm 2.74 (s, 3H) 7.47 (d, J=8.69 Hz, 2H) 10.35 (s, 1H)

$N^5$-(4-bromo-3,5-difluorophenyl)-1H-[1,2,4]-triazole-3,5-diamine (Intermediate 4)

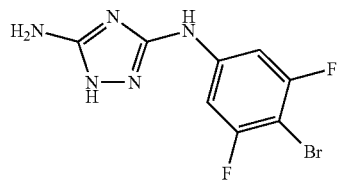 [SMILES: Nc1nc(Nc2cc(F)c(Br)c(F)c2)n[nH]1]

Hydrazine (4.84 g, 151 mmol, Eq: 10) was added to a stirred suspension of (4-Bromo-3,5-difluoro-phenylamino)-(methyl-$\lambda^4$-sulfanylidene)-methyl-cyanamide (4.62 g, 15.1 mmol, Eq: 1.00) in ethanol (78.9 ml). During the addition of hydrazine the reaction went into solution. The mixture was heated to 70° C. for 45 minutes. The reaction mixture was concentrated (~10 ml). Water (~80 ml) was added dropwise and the suspension was stirred for 30 min. The precipitate was filtered, washed with water (~100 ml) and dried under high vacuum at 70° C. to afford 4.28 g (97%) of the desired product as a white solid.

MS +m/z: 291.9. (M+1)

$^1$H NMR (300 MHz, DMSO-$d_6$) δ ppm 6.00 (br. s., 2H) 7.36 (d, J=10.58 Hz, 2H) 9.37 (s, 1H) 11.35 (br. s., 1H)

Intermediate 5

Procedure 1

N*3*-(4-Bromo-3-chloro-5-fluoro-phenyl)-1H-[1,2,4]triazole-3,5-diamine (Intermediate 5)

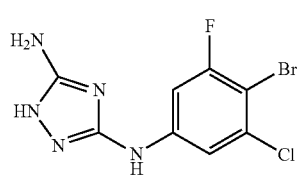 [SMILES: Nc1nc(Nc2cc(F)c(Br)c(Cl)c2)n[nH]1]

N-(3-chloro-5-fluorophenyl)acetamide

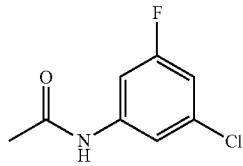

To a solution of 3-chloro-5-fluoroaniline (5.72 g, 39.3 mmol, Eq: 1.00) in EtOH (25 mL), was added Ac2O (4.87 g, 4.5 ml, 47.7 mmol, Eq: 1.21). The reaction was stirred at room temp overnight. The reaction mixture was concentrated to give 7.37 g (100%) of desired product as a white solid.

N-(4-bromo-3-chloro-5-fluorophenyl)acetamide

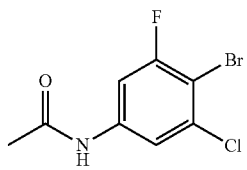

To a solution of N-(3-chloro-5-fluorophenyl)acetamide (5 g, 26.7 mmol, Eq: 1.00) in AcOH (50 mL) in a room temperature water bath, was added bromine (5.58 g, 1.8 ml, 34.9 mmol, Eq: 1.31) dropwise. The reaction was stirred overnight at room temperature. An additional 1.5 mL bromine was added. The reaction was carefully poured into ice water. The precipitate was filtered and washed with water. ~9 g crude was chromatographed (200 Silicycle, 10 to 30% ethyl acetate/hexane) to give 5.99 g (84%) of desired product as a white solid.

4-bromo-3-chloro-5-fluoroaniline

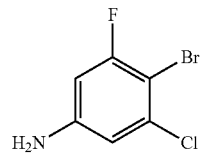

A solution of N-(4-bromo-3-chloro-5-fluorophenyl)acetamide (2.93 g, 11.0 mmol, Eq: 1.00) and HCl (44.4 g, 37 ml, 222 mmol, Eq: 20.2) in ethanol (35 ml) was heated at reflux o/n. The reaction mixture was concentrated, dissolved in ethyl acetate, washed with NaOH soln (8.8 g in 20 mL water) and dried over sodium sulfate to give 2.37 g (96%) of desired product as a pale yellow solid.

2-bromo-1-chloro-3-fluoro-5-isothiocyanatobenzene

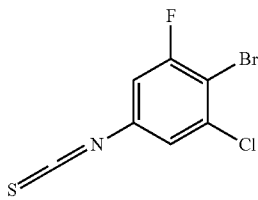 [SMILES: Fc1cc(N=CC=S)cc(Cl)c1Br]

To a suspension of calcium carbonate (2.64 g, 26.4 mmol, Eq: 2.5) and thiophosgene (1.46 g, 975 µl, 12.7 mmol, Eq: 1.2) in dichloromethane (10.0 ml)/water (10.0 ml) at 0, was added 4-bromo-3-chloro-5-fluoroaniline (2.37 g, 10.6 mmol, Eq: 1.00) The reaction was gradually warmed to room temperature and stirred overnight. Added 26 mL 1N HCl slowly. Separated organic layer and dried over sodium sulfate to give 2.46 g (87%) of desired product as a pale yellow solid.

N-((4-bromo-3-chloro-5-fluorophenylamino)(methylthio)methyl)cyanamide

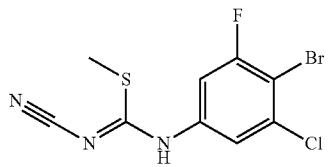 [SMILES: CS/C(=N\C#N)Nc1cc(F)c(Br)c(Cl)c1]

To a solution of 2-bromo-1-chloro-3-fluoro-5-isothiocyanatobenzene (2.46 g, 9.23 mmol, Eq: 1.00) in MeOH (20 mL) was added to sodium hydrogen cyanamide (627 mg, 9.79 mmol, Eq: 1.06). After 30 minutes, methyl iodide (2.62 g, 1.15 ml, 18.5 mmol, Eq: 2) was added and the reaction was stirred overnight at room temperature. The resulting suspension was filtered solid and dried with house vacuum to give 2.19 g (74%) of desired product as a white solid.

N*3*-(4-Bromo-3-chloro-5-fluoro-phenyl)-1H-[1,2,4]triazole-3,5-diamine (Intermediate 5)

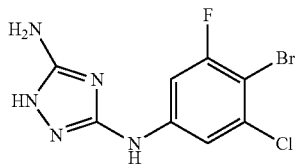 [SMILES: Nc1nc(Nc2cc(F)c(Br)c(Cl)c2)n[nH]1]

To a solution of N-((4-bromo-3-chloro-5-fluorophenylamino)(methylthio)methyl)cyanamide (2.19 g, 6.75 mmol, Eq: 1.00) in ethanol (30 mL) was added hydrazine (2.16 g, 2.12 ml, 67.5 mmol, Eq: 10). The reaction mixture was heated at 60 deg o/n. The reaction mixture was concentrated, suspended in Et2O and filtered to give 1.03 g of desired product as a white solid. The filtrate precipitated upon standing and was filtered to give 919 mg of desired product as a white solid. The solids were combined to give 1.95 g (94%) total product.
MS m/z 306, 308 [M+H]

Procedure 1, 7

4-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester (Compound 1)

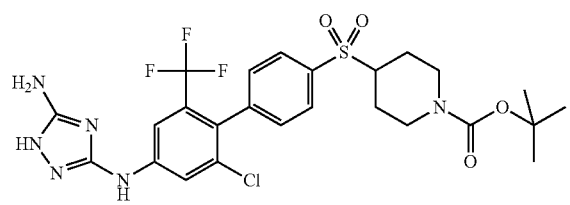 [SMILES: CC(C)(C)OC(=O)N1CCC(S(=O)(=O)c2ccc(-c3c(Cl)cc(Nc4n[nH]c(N)n4)cc3C(F)(F)F)cc2)CC1]

tert-butyl 4-(4-bromophenylthio)piperidine-1-carboxylate

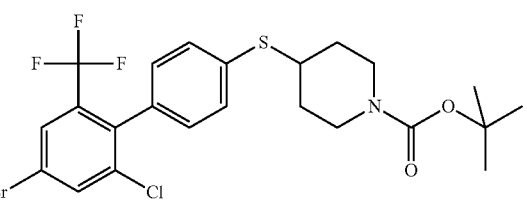

A suspension of tert-butyl 4-(methylsulfonyloxy)piperidine-1-carboxylate (1.58 g, 5.66 mmol, Eq: 1.07), 4-bromobenzenethiol (1 g, 5.29 mmol, Eq: 1.00), and potassium carbonate (1.57 g, 11.4 mmol, Eq: 2.15) in acetonitrile (50 mL) was heated at reflux overnight. The reaction mixture was cooled to room temperature and filtered. The filtrate was concentrated and the crude residue was chromatographed (80 g Redisep, 5 to 10% ethyl acetate/hexane) to give 1.35 g (69%) colorless oil.

tert-butyl 4-(4-bromophenylsulfonyl)piperidine-1-carboxylate

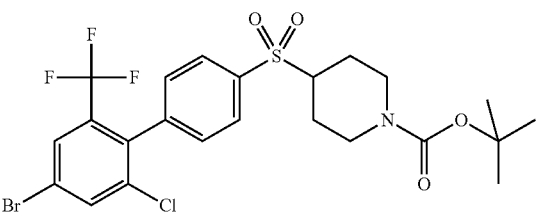 [SMILES: CC(C)(C)OC(=O)N1CCC(S(=O)(=O)c2ccc(-c3c(Cl)cc(Br)cc3C(F)(F)F)cc2)CC1]

To a suspension of tert-butyl 4-(4-bromophenylthio)piperidine-1-carboxylate (1.35 g, 3.63 mmol, Eq: 1.00) in dichloromethane (20 mL), was added mCPBA (2.27 g, 10.1 mmol, Eq: 2.79). The suspension was stirred at rt o/n. The reaction was quenched with Na2S2O3, diluted with dichloromethane and washed with saturated sodium carbonate 3×. The organic extract was dried over sodium sulfate and chromatographed (40 g Redisep, 10 to 30% ethyl acetate/hexane) to give 1.157 g (79%) colorless oil.

149 tert-butyl 4-(4-(4,4,5,5-tetramethyl-1,3,2-dioxaborolan-2-yl)phenylsulfonyl)piperidine-1-carboxylate

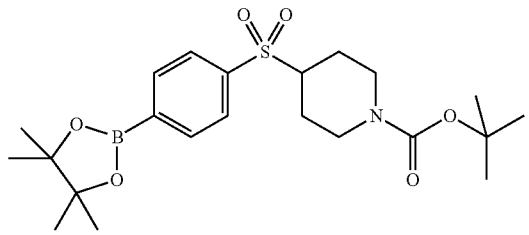 [SMILES: CC(C)(C)OC(=O)N1CCC(S(=O)(=O)c2ccc(B3OC(C)(C)C(C)(C)O3)cc2)CC1]

To a solution of tert-butyl 4-(4-bromophenylsulfonyl)piperidine-1-carboxylate (1.157 g, 2.86 mmol, Eq: 1.00), bis(pinacolato)diboron (1.82 g, 7.15 mmol, Eq: 2.5), and potassium acetate (1.26 g, 12.9 mmol, Eq: 4.5) in dioxane (15 mL), was added PdCl2(DPPF)-CH2Cl2 adduct (249 mg, 340 μmol, Eq: 0.119) The reaction was heated at 85 deg overnight with an Ar balloon. The reaction mixture was cooled to room temp, concentrated, diluted with ethyl acetate, washed with brine and dried over sodium sulfate. The crude residue was chromatographed (40 g Redisep, 30 to 50% ethyl acetate/hexane) to give 1.248 g pale yellow solid of desired product with ~50% of bis(pinacolato)diboron impurity.

tert-butyl 4-(4'-amino-2'-chloro-6'-(trifluoromethyl)biphenyl-4-ylsulfonyl)piperidine-1-carboxylate

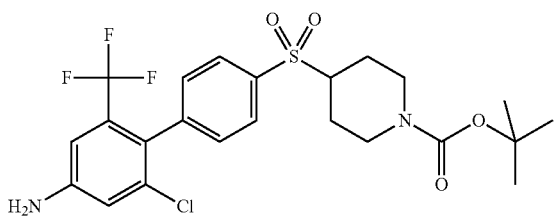 [SMILES: CC(C)(C)OC(=O)N1CCC(S(=O)(=O)c2ccc(-c3c(Cl)cc(N)cc3C(F)(F)F)cc2)CC1]

A microwave vial containing 4-bromo-3-chloro-5-(trifluoromethyl)aniline (400 mg, 1.46 mmol, Eq: 1.00), sodium carbonate (386 mg, 3.64 mmol, Eq: 2.5) and Pd(Ph3P)4 (249 mg, 215 μmol, Eq: 0.148) was degassed for 15 minutes with Ar. A solution of tert-butyl 4-(4-(4,4,5,5-tetramethyl-1,3,2-dioxaborolan-2-yl)phenylsulfonyl)piperidine-1-carboxylate (1.248 g, 1.38 mmol, Eq: 0.949) in dimethoxyethane (8 mL) was added, followed by water (2 mL). The suspension was degassed for 5 min with Argon with sonication, then heated at 125 deg for 2 hr in a microwave reactor. The reaction mixture was diluted with ethyl acetate, washed with brine. The organic extract was dried with sodium sulfate and the crude residue was chromatographed (40 g Redisep, 10% to 30% to 50% ethyl acetate/hexane) to give 450 mg (60%) pale yellow foam.

150 tert-butyl 4-(2'-chloro-4'-isothiocyanato-6'-(trifluoromethyl)biphenyl-4-ylsulfonyl)piperidine-1-carboxylate

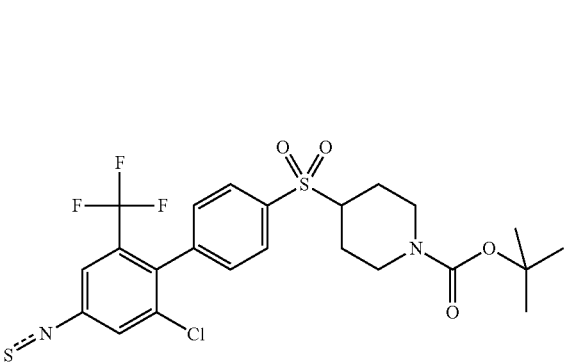

To a suspension of calcium carbonate (217 mg, 2.17 mmol, Eq: 2.5) and tert-butyl 4-(4'-amino-2'-chloro-6'-(trifluoromethyl)biphenyl-4-ylsulfonyl)piperidine-1-carboxylate (450 mg, 867 μmol, Eq: 1.00) in dichloromethane (13.2 g, 10.0 ml, 155 mmol, Eq: 25.3)/water (10.0 g, 10.0 ml, 555 mmol, Eq: 90.2) at 0, was added thiophosgene (135 mg, 90 μl, 1.17 mmol, Eq: 1.35) The reaction was gradually warmed to room temperature and stirred overnight. Added 2.5 mL 1N HCl slowly. Separated organic layer and dried over sodium sulfate. 460 mg crude chromatographed (24 g Redisep, 10 to 30% ethyl acetate/hexane) to give 351 mg (72%) of white foamy solid.

tert-butyl 4-(2'-chloro-4'-(cyanamido(methylthio)methylamino)-6'-(trifluoromethyl)biphenyl-4-ylsulfonyl)piperidine-1-carboxylate

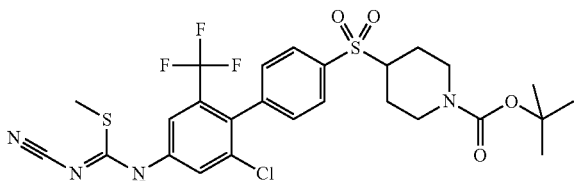

To a solution of tert-butyl 4-(2'-chloro-4'-isothiocyanato-6'-(trifluoromethyl)biphenyl-4-ylsulfonyl)piperidine-1-carboxylate (351 mg, 626 μmol, Eq: 1.00) in dimethoxyethane was added to sodium hydrogen cyanamide (48.1 mg, 751 μmol, Eq: 1.2) and methanol. After 30 minutes, methyl iodide (227 mg, 100 μl, 1.6 mmol, Eq: 2.56) was added and the reaction was stirred overnight at room temperature. The reaction was concentrated and chromatographed (12 g Redisep, 50 to 80% ethyl acetate/hexane) to give 304 mg (79%) colorless oil.

151

4-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester (Compound 1)

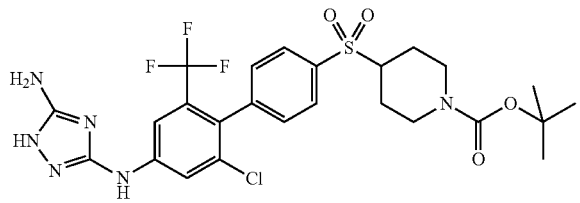 [SMILES: CC(C)(C)OC(=O)N1CCC(S(=O)(=O)c2ccc(-c3c(Cl)cc(Nc4n[nH]c(N)n4)cc3C(F)(F)F)cc2)CC1]

To a solution of tert-butyl 4-(2'-chloro-4'-(cyanamido(methylthio)methylamino)-6'-(trifluoromethyl)biphenyl-4-ylsulfonyl)piperidine-1-carboxylate (304 mg, 491 μmol, Eq: 1.00) in ethanol (10 mL) was added hydrazine (153 mg, 150 μl, 4.78 mmol, Eq: 9.73). The reaction mixture was heated at 65 deg o/n. The reaction mixture was concentrated and chromatographed (Redisep Gold 24 g, 1 to 10% methanol/dichloromethane) to give 255 mg (86%) of white solid.

MS m/z: 599 [M−H]

Procedure 1, 7

4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester (Compound 2)

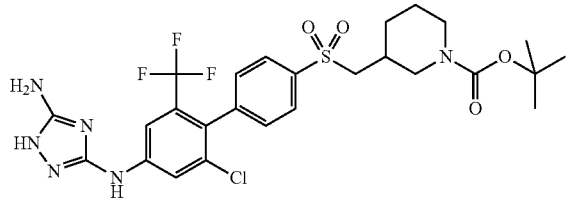 [SMILES: CC(C)(C)OC(=O)N1CCCC(CS(=O)(=O)c2ccc(-c3c(Cl)cc(Nc4n[nH]c(N)n4)cc3C(F)(F)F)cc2)C1]

tert-butyl 3-((4-bromophenylthio)methyl)piperidine-1-carboxylate

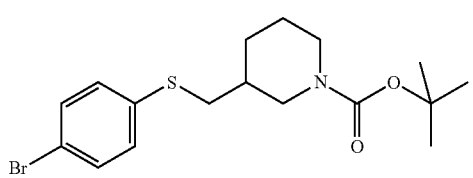 [SMILES: CC(C)(C)OC(=O)N1CCCC(CSc2ccc(Br)cc2)C1]

A suspension of tert-butyl 3-(bromomethyl)piperidine-1-carboxylate (1.51 g, 5.41 mmol, Eq: 1.29), 4-bromobenzenethiol (791 mg, 4.18 mmol, Eq: 1.00), and Cesium carbonate (3.41 g, 10.5 mmol, Eq: 2.5) in acetone (40 mL) was heated at reflux overnight. The reaction mixture was cooled to room temp and filtered. The filtrate was concentrated and 2.13 g crude was chromatographed (80 g Redisep, 5 to 10% ethyl acetatex/hexane) to give 1.94 g colorless oil of desired product with some piperidine-carboxylate sm impurity.

152 tert-butyl 3-((4-bromophenylsulfonyl)methyl)piperidine-1-carboxylate

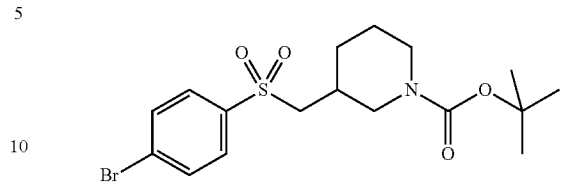

To a suspension of tert-butyl 3-((4-bromophenylthio)methyl)piperidine-1-carboxylate (1.62 g, 4.19 mmol, Eq: 1.00) in dichloromethane (25 mL), was added mCPBA (2.82 g, 12.6 mmol, Eq: 3). The suspension was stirred at rt o/n. The reaction was quenched with Na2S2O3 soln, diluted with dichloromethane and washed with saturated sodium carbonate 3×. The organic extract was dried over sodium sulfate and the crude residue was chromatographed (40 g Redisep, 10 to 30% ethyl acetate/hexane) to give 1.18 g (67%) white solid.

tert-butyl 3-((4-(4,4,5,5-tetramethyl-1,3,2-dioxaborolan-2-yl)phenylsulfonyl)methyl)piperidine-1-carboxylate

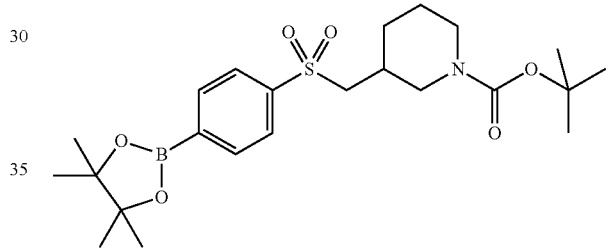

To a solution of tert-butyl 3-((4-bromophenylsulfonyl)methyl)piperidine-1-carboxylate (1.18 g, 2.82 mmol, Eq: 1.00), bis(pinacolato)diboron (1.79 g, 7.05 mmol, Eq: 2.5), and potassium acetate (1.25 g, 12.7 mmol, Eq: 4.5) in dioxane (10 mL), was added PdCl2(DPPF)-CH2Cl2 adduct (253 mg, 346 μmol, Eq: 0.123) The reaction was heated at 85 deg overnight with an Ar balloon. The reaction mixture was cooled to room temp, concentrated, diluted with ethyl acetate, washed with brine and dried over sodium sulfate. The crude residue was chromatographed (40 g Redisep, 30 to 50% ethyl acetate/hexane) to give 450 mg (34%) pale yellow oil, with pinacol diboron impurity (~20%)

tert-butyl 3-((4'-amino-2'-chloro-6'-(trifluoromethyl)biphenyl-4-ylsulfonyl)methyl)piperidine-1-carboxylate

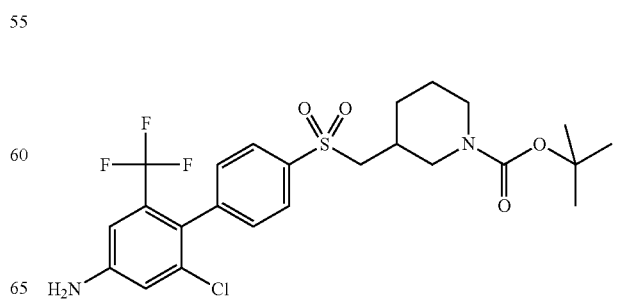

A microwave vial containing 4-bromo-3-chloro-5-(trifluoromethyl)aniline (450 mg, 1.64 mmol, Eq: 1.00), sodium carbonate (434 mg, 4.1 mmol, Eq: 2.5) and Pd(Ph3P)4 (284 mg, 246 µmol, Eq: 0.15) was degassed for 15 minutes with Ar. A solution of tert-butyl 3-((4-(4,4,5,5-tetramethyl-1,3,2-dioxaborolan-2-yl)phenylsulfonyl)methyl)piperidine-1-carboxylate (1.6 g, 1.72 mmol, Eq: 1.05) in dimethoxyethane (6 mL) was added, followed by water (1.5 mL). The suspension was degassed for 5 min with Ar with sonication, then heated at 125 deg for 2 hr with microwave. The reaction mixture was diluted with ethyl acetate and washed with brine. The organic extract was dried with sodium sulfate. 2 g crude chromatographed (40 g Redisep, 10% to 30% to 50% ethyl acetate/hexane) to give 170 mg (20%) pale yellow oil tert-butyl 3-((2'-chloro-4'-isothiocyanato-6'-(trifluoromethyl)biphenyl-4-ylsulfonyl)methyl)piperidine-1-carboxylate

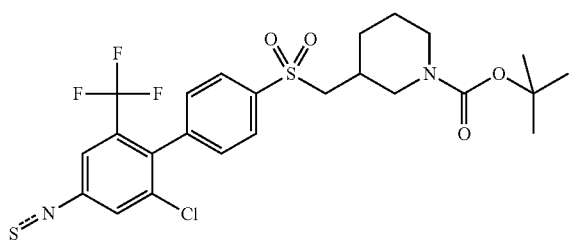

To a suspension of calcium carbonate (89 mg, 889 µmol, Eq: 2.79) and tert-butyl 3-((4'-amino-2'-chloro-6'-(trifluoromethyl)biphenyl-4-ylsulfonyl)methyl)piperidine-1-carboxylate (170 mg, 319 µmol, Eq: 1.00) in dichloromethane (10.0 ml)/water (10.0 ml) at 0, was added thiophosgene (52.5 mg, 35 µl, 457 µmol, Eq: 1.43) The reaction was gradually warmed to room temperature and stirred overnight. Added 1.5 mL 1N HCl slowly. Separated organic layer and extracted aq once more with dichloromethane. Dried over sodium sulfate. Chromatographed (12 g Redisep, 10 to 25% ethyl acetate/hexane) to give 134 mg (73%) colorless oil.

tert-butyl 3-((2'-chloro-4'-(cyanamido(methylthio)methylamino)-6'-(trifluoromethyl)biphenyl-4-ylsulfonyl)methyl)piperidine-1-carboxylate

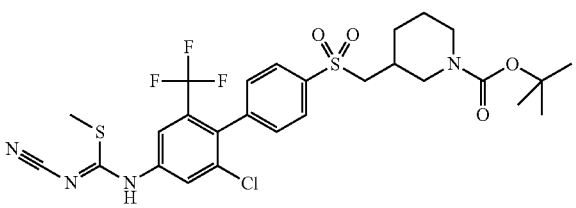 [SMILES: CS/C(=N\C#N)Nc1cc(Cl)c(-c2ccc(S(=O)(=O)CC3CCCN(C(=O)OC(C)(C)C)C3)cc2)c(C(F)(F)F)c1]

To a solution of tert-butyl 3-((2'-chloro-4'-isothiocyanato-6'-(trifluoromethyl)biphenyl-4-ylsulfonyl)methyl)piperidine-1-carboxylate (134 mg, 233 µmol, Eq: 1.00) in dimethoxyethane (5 mL) was added to sodium hydrogen cyanamide (19 mg, 297 µmol, Eq: 1.27) and methanol (0.5 mL). After 30 minutes, methyl iodide (82.7 mg, 36.4 µl, 583 µmol, Eq: 2.5) was added and the reaction was stirred overnight at room temperature. The reaction mixture was concentrated and chromatographed (12 g Redisep, 50 to 65% ethyl acetate/hexane) to give 95 mg (65%) colorless oil.

4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester (Compound 2)

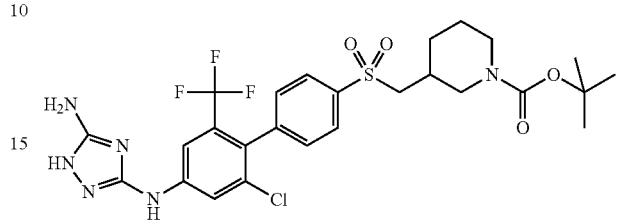

To a solution of tert-butyl 3-((2'-chloro-4'-(cyanamido(methylthio)methylamino)-6'-(trifluoromethyl)biphenyl-4-ylsulfonyl)methyl)piperidine-1-carboxylate (95 mg, 150 µmol, Eq: 1.00) in ethanol (5 mL) was added hydrazine (51.1 mg, 50 µl, 1.59 mmol, Eq: 10.6). The reaction mixture was heated at 65 deg overnight. The reaction mixture was concentrated and chromatographed (Supelco 11 g, 1 to 10% methanol/dichloromethane) to give 77 mg (83%) of white solid
MS m/z 613 [M–H]

Procedure 1, 7

(S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid tert-butyl ester (Compound 3)

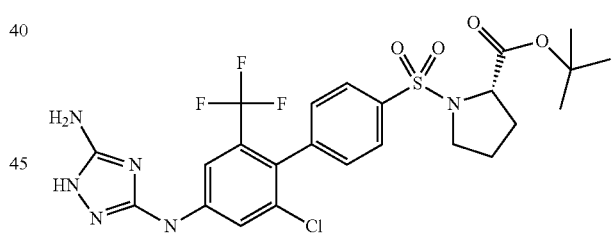

(S)-tert-butyl 1-(4-bromophenylsulfonyl)pyrrolidine-2-carboxylate

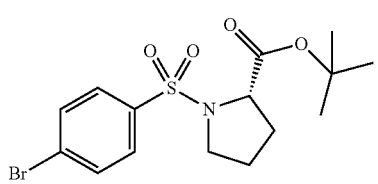 [SMILES: CC(C)(C)OC(=O)[C@@H]1CCCN1S(=O)(=O)c1ccc(Br)cc1]

To a solution of (S)-3,3-dimethyl-1-(pyrrolidin-2-yl)butan-1-one (500 mg, 2.95 mmol, Eq: 1.00) and Et3N (598 mg, 823 µl, 5.91 mmol, Eq: 2) in dichloromethane (10 mL) at 0 deg, was added 4-bromobenzene-1-sulfonyl chloride (793 mg, 3.1 mmol, Eq: 1.05). The solution was gradually warmed to room temp and stirred overnight. Diluted with dichloromethane, washed with 1N HCl, brine, and dried with sodium sulfate. 1.21 g crude chromatographed (40 g Analogix, 10 to 30% ethyl acetate/hexane) to give 982 mg (85%) of desired compounds as a white solid.

(S)-tert-butyl 1-(4-(4,4,5,5-tetramethyl-1,3,2-dioxaborolan-2-yl)phenylsulfonyl)pyrrolidine-2-carboxylate

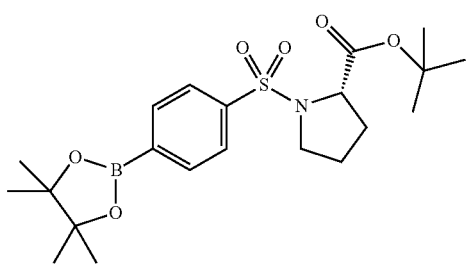 [SMILES: CC(C)(C)OC(=O)[C@@H]1CCCN1S(=O)(=O)c1ccc(B2OC(C)(C)C(C)(C)O2)cc1]

To a solution of (S)-tert-butyl 1-(4-bromophenylsulfonyl)pyrrolidine-2-carboxylate (982 mg, 2.52 mmol, Eq: 1.00), bis(pinacolato)diboron (1.6 g, 6.29 mmol, Eq: 2.5), and potassium acetate (1.11 g, 11.3 mmol, Eq: 4.5) in Dioxane (15 mL), was added PdCl2(DPPF)-CH2Cl2 adduct (220 mg, 301 µmol, Eq: 0.119) The reaction was heated at 85 deg overnight with an Ar balloon. The reaction mixture was cooled to room temp, concentrated, diluted with ethyl acetate, washed with brine and dried over sodium sulfate. 1.43 g crude chromatographed (40 g Redisep, 20 to 40% ethyl acetate/hexane) to give 880 mg (80%) of desired product as a pale yellow oil, with pinacol diboron imp (~50%)

(S)-tert-butyl 1-(4'-amino-2'-chloro-6'-(trifluoromethyl)biphenyl-4-ylsulfonyl)pyrrolidine-2-carboxylate

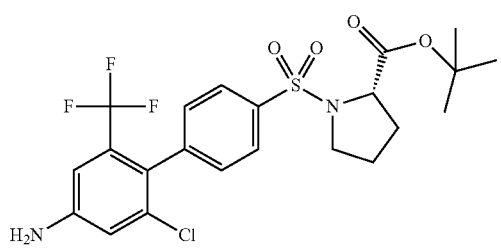 [SMILES: CC(C)(C)OC(=O)[C@@H]1CCCN1S(=O)(=O)c1ccc(-c2c(Cl)cc(N)cc2C(F)(F)F)cc1]

A microwave vial containing 4-bromo-3-chloro-5-(trifluoromethyl)aniline (400 mg, 1.46 mmol, Eq: 1.00), sodium carbonate (386 mg, 3.64 mmol, Eq: 2.5) and Pd(Ph3P)4 (269 mg, 233 µmol, Eq: 0.160) was degassed for 15 minutes with Ar. A solution of (S)-tert-butyl 1-(4-(4,4,5,5-tetramethyl-1,3,2-dioxaborolan-2-yl)phenylsulfonyl)pyrrolidine-2-carboxylate (880 mg, 2.01 mmol, Eq: 1.38) in dimethoxyethane (8 mL) was added, followed by water (2 mL). The suspension was degassed for 5 min with Ar with sonication, then heated at 125 deg for 2 hr with microwave. Diluted with ethyl acetate and washed with brine. Dried org extract with sodium sulfate. 1.59 g crude chromatographed (40 g Redisep, 10% to 30% to 50% ethyl acetate/hexane) to give 255 mg (35%) of desired product as a pale yellow oil.

(S)-tert-butyl 1-(2'-chloro-4'-isothiocyanato-6'-(trifluoromethyl)biphenyl-4-ylsulfonyl)pyrrolidine-2-carboxylate

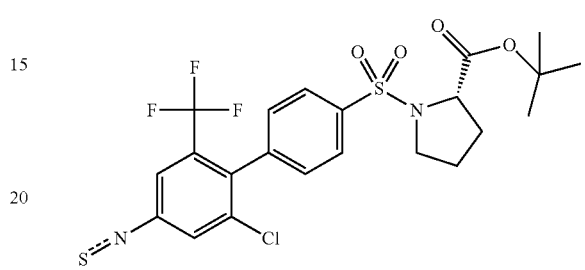

To a suspension of calcium carbonate (126 mg, 1.26 mmol, Eq: 2.5) and (S)-tert-butyl 1-(4'-amino-2'-chloro-6'-(trifluoromethyl)biphenyl-4-ylsulfonyl)pyrrolidine-2-carboxylate (255 mg, 505 µmol, Eq: 1.00) in dichloromethane (13.2 g, 10.0 ml, 155 mmol, Eq: 25.3)/water (10.0 g, 10.0 ml, 555 mmol, Eq: 90.2) at 0, was added thiophosgene (75.0 mg, 50 µl, 652 µmol, Eq: 1.29) The reaction was gradually warmed to room temperature and stirred overnight. Added 1.5 mL 1N HCl slowly. Separated organic layer and extracted aqueous once more with dichloromethane. Combined organic extracts were dried over sodium sulfate. 140 mg (51%) of desired product as a pale yellow oil, nmr ok with slight impurity.

(2S)-tert-butyl 1-(2'-chloro-4'-(cyanamido(methylthio)methylamino)-6'-(trifluoromethyl)biphenyl-4-ylsulfonyl)pyrrolidine-2-carboxylate

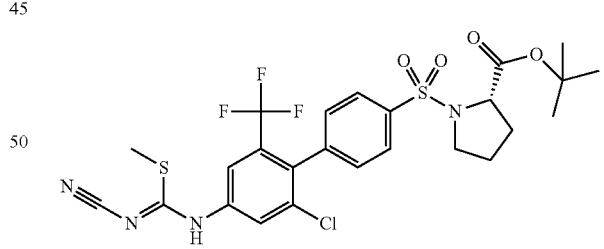

To a solution of (S)-tert-butyl 1-(2'-chloro-4'-isothiocyanato-6'-(trifluoromethyl)biphenyl-4-ylsulfonyl)pyrrolidine-2-carboxylate (140 mg, 256 µmol, Eq: 1.00) in dimethoxyethane (4 mL) was added to sodium hydrogen cyanamide (19.7 mg, 307 µmol, Eq: 1.2) and methanol (0.5 mL). After 30 minutes, methyl iodide (90.8 mg, 40 µl, 640 µmol, Eq: 2.5) was added and the reaction was stirred overnight at room temperature. The reaction mixture was concentrated and chromatographed (12 g Redisep, 50 to 75% ethyl acetate/hexane) to give 64 mg (42%) of desired product as a pale yellow oil.

(S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid tert-butyl ester (Compound 3)

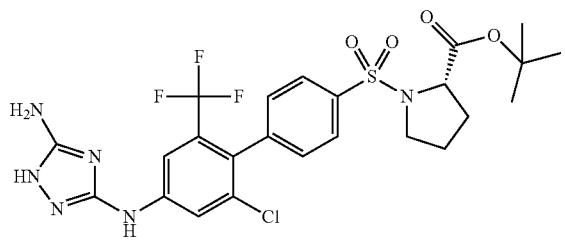 [SMILES: CC(C)(C)OC(=O)[C@@H]1CCCN1S(=O)(=O)c1ccc(-c2c(Cl)cc(Nc3n[nH]c(N)n3)cc2C(F)(F)F)cc1]

To a solution of (2S)-tert-butyl 1-(2'-chloro-4'-(cyanamido(methylthio)methylamino)-6'-(trifluoromethyl)biphenyl-4-ylsulfonyl)pyrrolidine-2-carboxylate (64 mg, 106 μmol, Eq: 1.00) in ethanol (5 mL) was added hydrazine (35.7 mg, 35 μl, 1.12 mmol, Eq: 10.5). The reaction mixture was heated at 65 deg overnight. The reaction mixture was concentrated and chromatographed (Supelco 11 g, 1 to 10% methanol/dichloromethane) to give 34 mg (55%) of desired product as a white solid.

MS m/z 587 [M+H]

Procedure 1, 7

N*3*-{2-Chloro-6-trifluoromethyl-4'-[1-(3,3,3-trifluoro-propyl)-piperidine-4-sulfonyl]-biphenyl-4-yl}-1H-[1,2,4]triazole-3,5-diamine; hydrochloride (Compound 4)

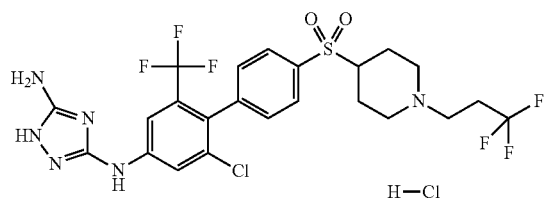 [SMILES: Nc1nc(Nc2cc(Cl)c(-c3ccc(S(=O)(=O)C4CCN(CCC(F)(F)F)CC4)cc3)c(C(F)(F)F)c2)n[nH]1 ; Cl]

To a suspension of N3-(2-chloro-4'-(piperidin-4-ylsulfonyl)-6-(trifluoromethyl)biphenyl-4-yl)-1H-1,2,4-triazole-3,5-diamine hydrochloride (91 mg, 169 μmol, Eq: 1.00) in methanol (10 mL), was added 3,3,3-trifluoropropanal (22 mg, 196 μmol, Eq: 1.16), followed by sodium cyanoborohydride (21 mg, 334 μmol, Eq: 1.97). The reaction was stirred at room temperature overnight. The reaction was diluted with ethyl acetate, basified with sodium carbonate aqueous solution, and extracted 3 times with EtAOc. The combined organic extracts were dried over sodium sulfate. Chromatography (12 g Redisep Gold, 1 to 10% methanol/dichloromethane) to give 48 mg of white solid as the free amine.

To a solution of 48 mg of amine in 2 mL methanol, was added a freshly prepared 2 mL solution of HCl (prepared from 0.2 mL of AcCl added to 2 mL methanol at rt, then cooled to 0 deg for 5 min). Stirred for 6 hr. The reaction mixture was concentrated to dryness, dissolved in 1 mL methanol, and triturated with ether to give white solid. Filtered off solid and rinsed with ether. Dried overnight at 70 deg with high vacuum to give 46 mg (43%) off-white solid.

MS m/z 597 [M+H]

Procedure 1, 7

N*3*-{2-Chloro-4'-[1-(3,3-dimethyl-butyl)-piperidine-4-sulfonyl]-6-trifluoromethyl-biphenyl-4-yl}-1H-[1,2,4]triazole-3,5-diamine; hydrochloride (Compound 5)

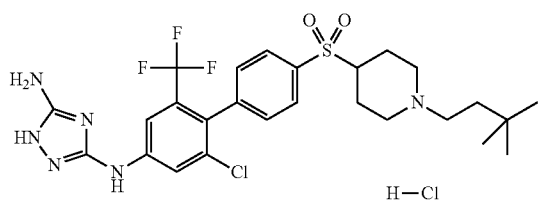 [SMILES: CC(C)(C)CCN1CCC(S(=O)(=O)c2ccc(-c3c(Cl)cc(Nc4n[nH]c(N)n4)cc3C(F)(F)F)cc2)CC1 ; Cl]

To a suspension of N3-(2-chloro-4'-(piperidin-4-ylsulfonyl)-6-(trifluoromethyl)biphenyl-4-yl)-1H-1,2,4-triazole-3,5-diamine hydrochloride (80 mg, 149 μmol, Eq: 1.00) in methanol (8 mL), was added 3,3-dimethylbutanal (23.9 mg, 30.0 μl, 239 μmol, Eq: 1.61), followed by sodium cyanoborohydride (19.4 mg, 309 μmol, Eq: 2.07). The reaction was stirred overnight at room temperature. The crude reaction was concentrated, diluted with ethyl acetate. And basified with sodium carbonate aqueous solution. The aqueous was extracted 3 times with ethyl acetate and dried over sodium sulfate. Chromatography (12 g Redisep, 1 to 10% methanol/dichloromethane) gave 60 mg white solid as the free amine.

To a solution of 60 mg of amine in 2 mL methanol, was added a freshly prepared 3 mL solution of HCl (prepared from 0.3 mL of AcCl added to 3 mL methanol at rt, then cooled to 0 deg for 5 min). White precipitate forms immediately. Stirred for 6 hr. Filtered off solid and rinsed with ether. Dried overnight at 70 deg with high vacuum to give 60 mg (65%) of white solid.

MS m/z 585 [M+H]

Procedure 1, 7

3-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester (Compound 6)

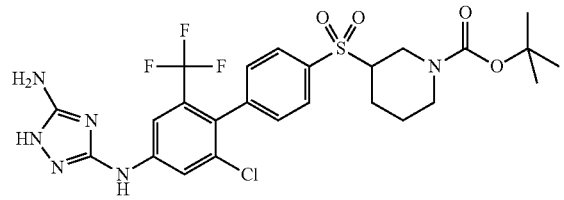 [SMILES: CC(C)(C)OC(=O)N1CCCC(S(=O)(=O)c2ccc(-c3c(Cl)cc(Nc4n[nH]c(N)n4)cc3C(F)(F)F)cc2)C1]

tert-butyl 3-(tosyloxy)piperidine-1-carboxylate

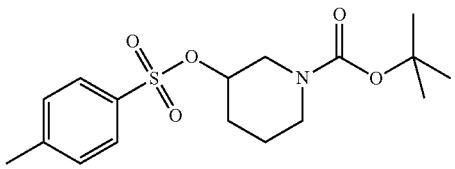 [SMILES: Cc1ccc(S(=O)(=O)OC2CCCN(C(=O)OC(C)(C)C)C2)cc1]

To a solution of tert-butyl 3-hydroxypiperidine-1-carboxylate (2 g, 9.94 mmol, Eq: 1.00) and pyridine (5.87 g, 6.00 ml, 74.2 mmol, Eq: 7.47) in dichloromethane (25 mL) at 0 deg, was added 4-methylbenzene-1-sulfonyl chloride (2.37 g, 12.4 mmol, Eq: 1.25). The solution was gradually warmed to room temp and stirred over the weekend. The reaction mixture was diluted with dichloromethane, washed with CuSO4 soln, 1N HCl, sodium carbonate, brine, dried with sodium sulfate. 3.3 g crude chromatographed (80 g Redisep, 10 to 35% ethyl acetate/hexane) to give 3.17 g (90%) of desired product as a colorless oil.

tert-butyl 3-(4-bromophenylthio)piperidine-1-carboxylate

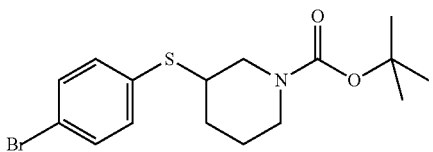

To a suspension of NaH (498 mg, 12.5 mmol, Eq: 1.4) in THF (15 mL) at 0 deg, was added 4-bromobenzenethiol (2.02 g, 10.7 mmol, Eq: 1.2). The suspension was stirred for 5 min, then a solution of tert-butyl 3-(tosyloxy)piperidine-1-carboxylate (3.17 g, 8.92 mmol, Eq: 1.00) in THF (15 mL) was added. The resulting solution was heated at reflux overnight. The reaction was cooled to rt and quenched with water (10 mL), extracted 3× with dichloromethane, dried with sodium sulfate. 4 g crude chromatographed (80 g Redisep, 0 to 10 to 15% ethyl acetate/hexane) to give 900 mg (27%) of desired product as a colorless oil.

tert-butyl 3-(4-bromophenylsulfonyl)piperidine-1-carboxylate

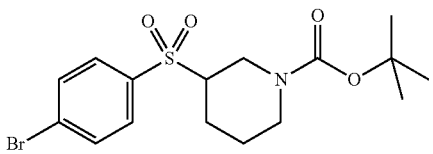 [SMILES: CC(C)(C)OC(=O)N1CCCC(S(=O)(=O)c2ccc(Br)cc2)C1]

To a suspension of tert-butyl 3-(4-bromophenylthio)piperidine-1-carboxylate (900 mg, 2.42 mmol, Eq: 1.00) in dichloromethane (15 mL), was added mCPBA (1.63 g, 7.25 mmol, Eq: 3). The suspension was stirred at rt o/n. The reaction was quenched with Na2S2O3 soln, diluted with dichloromethane and washed with saturated sodium carbonate 3×. Dried over sodium sulfate. 1.3 g crude chromatographed (40 g Redisep, 10 to 30% ethyl acetate/hexane) to give 908 mg (93%) of desired product as a colorless oil.

tert-butyl 3-(4-(4,4,5,5-tetramethyl-1,3,2-dioxaborolan-2-yl)phenylsulfonyl)piperidine-1-carboxylate

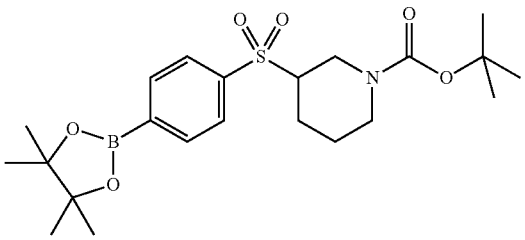 [SMILES: CC(C)(C)OC(=O)N1CCCC(S(=O)(=O)c2ccc(B3OC(C)(C)C(C)(C)O3)cc2)C1]

To a solution of tert-butyl 3-(4-bromophenylsulfonyl)piperidine-1-carboxylate (908 mg, 2.25 mmol, Eq: 1.00), bis(pinacolato)diboron (1.43 g, 5.61 mmol, Eq: 2.5), and potassium acetate (992 mg, 10.1 mmol, Eq: 4.5) in dioxane (10 mL), was added PdCl2(DPPF)-CH2Cl2 adduct (195 mg, 267 µmol, Eq: 0.119) The reaction was heated at 85 deg overnight with an Ar balloon. The reaction mixture was cooled to room temp, concentrated, diluted with ethyl acetate, washed with brine and dried over sodium sulfate. 2.19 g crude chromatographed (40 g Redisep, 30 to 50% ethyl acetate/hexane) to give 535 mg (53%) of desired product as a white oily solid, (contains ~20% pinacol diboron impurity)

tert-butyl 3-(4'-amino-2'-chloro-6'-(trifluoromethyl)biphenyl-4-ylsulfonyl)piperidine-1-carboxylate

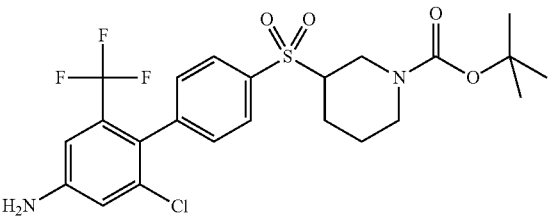 [SMILES: CC(C)(C)OC(=O)N1CCCC(S(=O)(=O)c2ccc(-c3c(Cl)cc(N)cc3C(F)(F)F)cc2)C1]

A microwave vial containing 4-bromo-3-chloro-5-(trifluoromethyl)aniline (303 mg, 1.1 mmol, Eq: 1.00), sodium carbonate (292 mg, 2.76 mmol, Eq: 2.5) and Pd(Ph3P)4 (238 mg, 206 µmol, Eq: 0.187) was degassed for 15 minutes with Ar. A solution of tert-butyl 3-(4-(4,4,5,5-tetramethyl-1,3,2-dioxaborolan-2-yl)phenylsulfonyl)piperidine-1-carboxylate (535 mg, 1.19 mmol, Eq: 1.07) in dimethoxyethane (6 mL) was added, followed by water (1.5 mL). The suspension was degassed for 5 min with Ar with sonication, then heated at 110 deg overnight in an oil bath. The reaction was diluted with ethyl acetate, washed with brine and dried with sodium sulfate. 1 g crude chromatographed (40 g Redisep, 10% to 30% to 50% ethyl acetate/hexane) to give 399 mg (70%) of desired product as a yellow solid.

tert-butyl 3-(2'-chloro-4'-isothiocyanato-6'-(trifluoromethyl)biphenyl-4-ylsulfonyl)piperidine-1-carboxylate

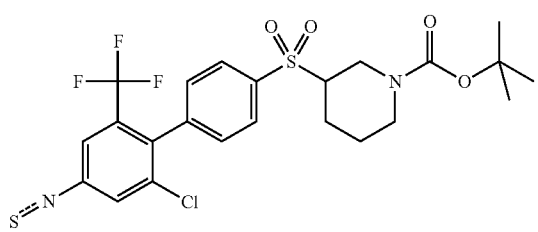

To a suspension of calcium carbonate (207 mg, 2.07 mmol, Eq: 2.69) and tert-butyl 3-(4'-amino-2'-chloro-6'-(trifluoromethyl)biphenyl-4-ylsulfonyl)piperidine-1-carboxylate (399 mg, 769 μmol, Eq: 1.00) in dichloromethane (13.2 g, 10.0 ml, 155 mmol, Eq: 25.3)/water (10.0 g, 10.0 ml, 555 mmol, Eq: 90.2) at 0, was added thiophosgene (112 mg, 75 μl, 978 μmol, Eq: 1.27) The reaction was gradually warmed to room temperature and stirred overnight. Added 2 mL 1N HCl slowly. Separated organic layer and extracted aq once more with dichloromethane. Dried over sodium sulfate. 500 mg crude chromatographed (24 g Redisep, 10 to 15% ethyl acetate/hexane) to give 339 mg (79%) of desired product as a colorless oil.

tert-butyl 3-(2'-chloro-4'-(cyanamido(methylthio)methylamino)-6'-(trifluoromethyl)biphenyl-4-ylsulfonyl)piperidine-1-carboxylate

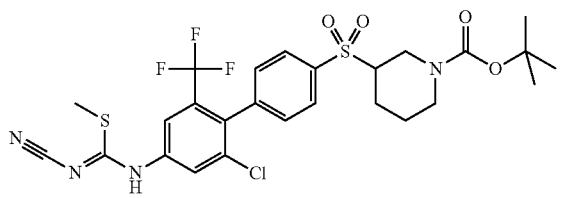 [SMILES: CS/C(=N\C#N)Nc1cc(Cl)c(-c2ccc(S(=O)(=O)C3CCCN(C(=O)OC(C)(C)C)C3)cc2)c(C(F)(F)F)c1]

To a solution of tert-butyl 3-(2'-chloro-4'-isothiocyanato-6'-(trifluoromethyl)biphenyl-4-ylsulfonyl)piperidine-1-carboxylate (339 mg, 604 μmol, Eq: 1.00) in dimethoxyethane (10 mL) was added to sodium hydrogen cyanamide (52 mg, 812 μmol, Eq: 1.34) and methanol (1 mL). After 30 minutes, methyl iodide (227 mg, 100 μl, 1.6 mmol, Eq: 2.65) was added and the reaction was stirred overnight at room temperature. The reaction mixture was concentrated and chromatographed (24 g Redisep, 50 to 75% ethyl acetate/hexane) to give 292 mg (78%) of desired product as a pale yellow oil.

3-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester (Compound 6)

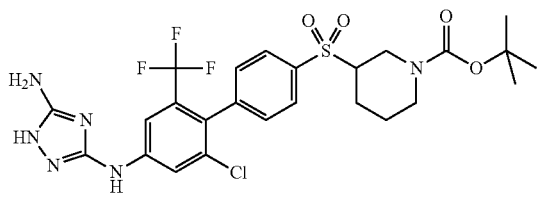 [SMILES: CC(C)(C)OC(=O)N1CCCC(S(=O)(=O)c2ccc(-c3c(Cl)cc(Nc4n[nH]c(N)n4)cc3C(F)(F)F)cc2)C1]

To a solution of tert-butyl 3-(2'-chloro-4'-(cyanamido(methylthio)methylamino)-6'-(trifluoromethyl)biphenyl-4-ylsulfonyl)piperidine-1-carboxylate (292 mg, 472 μmol, Eq: 1.00) in ethanol (10 mL) was added hydrazine (153 mg, 150 μl, 4.78 mmol, Eq: 10.1). The reaction mixture was heated at 65 deg overnight. The reaction mixture was concentrated and chromatographed (Redisep 24 g, 1 to 10% methanol/dichloromethane) to give 266 mg (94%) white solid.

MS m/z 545 [M+H]

Procedure 1, 7

4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester (Compound 7)

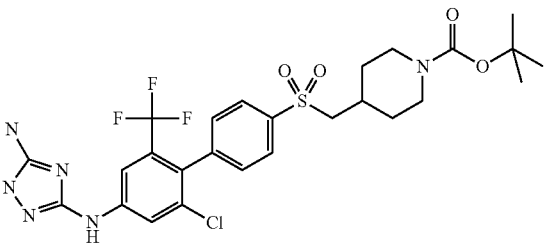 [SMILES: CC(C)(C)OC(=O)N1CCC(CS(=O)(=O)c2ccc(-c3c(Cl)cc(Nc4n[nH]c(N)n4)cc3C(F)(F)F)cc2)CC1]

tert-butyl 4-((4-bromophenylthio)methyl)piperidine-1-carboxylate

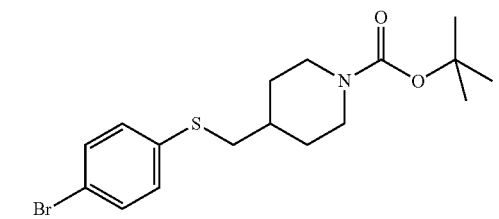 [SMILES: CC(C)(C)OC(=O)N1CCC(CSc2ccc(Br)cc2)CC1]

A suspension of tert-butyl 4-(bromomethyl)piperidine-1-carboxylate (1.506 g, 5.41 mmol, Eq: 1.29), 4-bromobenzenethiol (791 mg, 4.18 mmol, Eq: 1.00), and Cesium carbonate (3.41 g, 10.5 mmol, Eq: 2.5) in acetone (40 mL) was heated at reflux overnight. The reaction mixture was cooled to room temp and filtered. The filtrate was concentert-butyl 4-((4-bromophenylsulfonyl)methyl)piperidine-1-carboxylate

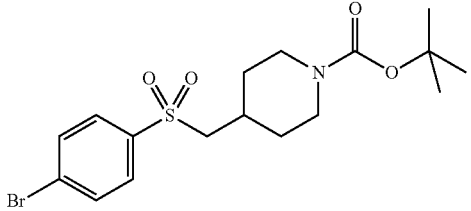 [SMILES: CC(C)(C)OC(=O)N1CCC(CS(=O)(=O)c2ccc(Br)cc2)CC1]

To a suspension of tert-butyl 4-((4-bromophenylthio)methyl)piperidine-1-carboxylate (900 mg, 2.33 mmol, Eq: 1.00) in dichloromethane (15 mL), was added mCPBA (1.31 g, 5.82 mmol, Eq: 2.5). The suspension was stirred at rt o/n. The reaction was quenched with Na2S2O3 soln, and washed 3× with saturated sodium carbonate. The organic extract was dried over sodium sulfate. 0.9 g crude chromatographed (40 g Redisep, 10 to 35% ethyl acetate/hexane) to give 684 mg (70%) of desired product as a colorless oil.

tert-butyl 4-((4-(4,4,5,5-tetramethyl-1,3,2-dioxaborolan-2-yl)phenylsulfonyl)methyl)piperidine-1-carboxylate

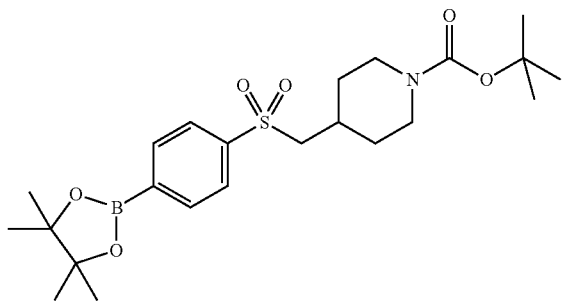 [SMILES: CC(C)(C)OC(=O)N1CCC(CS(=O)(=O)c2ccc(B3OC(C)(C)C(C)(C)O3)cc2)CC1]

To a solution of tert-butyl 4-((4-bromophenylsulfonyl)methyl)piperidine-1-carboxylate (684 mg, 1.64 mmol, Eq: 1.00), bis(pinacolato)diboron (1.04 g, 4.09 mmol, Eq: 2.5), and potassium acetate (722 mg, 7.36 mmol, Eq: 4.5) in dioxane (10 mL), was added PdCl2(DPPF)-CH2Cl2 adduct (143 mg, 195 μmol, Eq: 0.120) The reaction was heated at 85 deg overnight with an Ar balloon. The reaction mixture was cooled to room temp, concentrated, diluted with ethyl acetate, washed with brine and dried over sodium sulfate. 1 g crude chromatographed (40 g Redisep, 10 to 50% ethyl acetate/hexane) to give 616 mg white waxy solid, with ~50% pinacol diboron impurity.

tert-butyl 4-((4'-amino-2'-chloro-6'-(trifluoromethyl)biphenyl-4-ylsulfonyl)methyl)piperidine-1-carboxylate

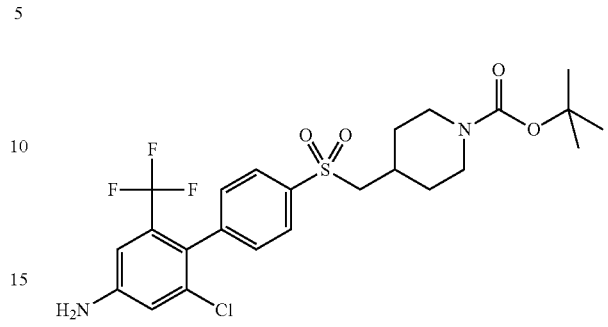

A microwave vial containing 4-bromo-3-chloro-5-(trifluoromethyl)aniline (215 mg, 783 μmol, Eq: 1.00), sodium carbonate (193 mg, 1.82 mmol, Eq: 2.32) and Pd(Ph3P)4 (139 mg, 120 μmol, Eq: 0.154) was degassed for 15 minutes with Ar. A solution of tert-butyl 4-((4-(4,4,5,5-tetramethyl-1,3,2-dioxaborolan-2-yl)phenylsulfonyl)methyl)piperidine-1-carboxylate (616 mg, 794 μmol, Eq: 1.01) in dimethoxyethane (6 mL) was added, followed by water (1.5 mL). The suspension was degassed for 5 min with Ar with sonication, then heated at 125 deg for 1.5 hr with microwave. The reaction mixture was diluted with ethyl acetate, washed with brine. Dried org extract with sodium sulfate. 1 g crude chromatographed (40 g Redisep, 10% to 10% to 20% to 40% ethyl acetate/hexane) to give 191 mg (46%) of desired product as a pale yellow solid.

tert-butyl 4-((2'-chloro-4'-isothiocyanato-6'-(trifluoromethyl)biphenyl-4-ylsulfonyl)methyl)piperidine-1-carboxylate

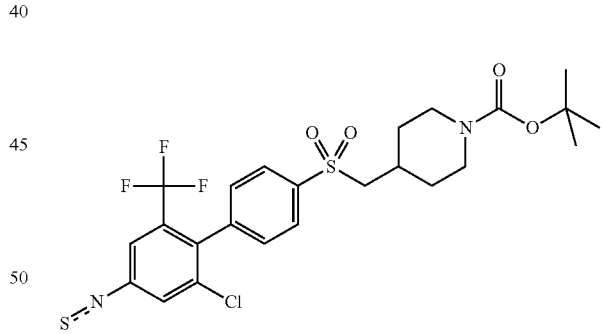

To a suspension of calcium carbonate (100 mg, 1.00 mmol, Eq: 2.8) and tert-butyl 4-((4'-amino-2'-chloro-6'-(trifluoromethyl)biphenyl-4-ylsulfonyl)methyl)piperidine-1-carboxylate (191 mg, 358 μmol, Eq: 1.00) in dichloromethane (13.2 g, 10.0 ml, 155 mmol, Eq: 25.3)/water (10.0 g, 10.0 ml, 555 mmol, Eq: 90.2) at 0, was added thiophosgene (60.0 mg, 40 μl, 522 μmol, Eq: 1.46) The reaction was gradually warmed to room temperature and stirred overnight. Added 1 mL 1N HCl slowly. Separated organic layer. Extracted aq once more with dichloromethane. Organic extracts dried over sodium sulfate. 180 mg crude chromatographed (24 g Redisep, 10 to 30% ethyl acetate/hexane) to give 168 mg (82%) of desired product as a white solid.

tert-butyl 4-((2'-chloro-4'-(cyanamido(methylthio) methylamino)-6'-(trifluoromethyl)biphenyl-4-ylsulfonyl)methyl)piperidine-1-carboxylate

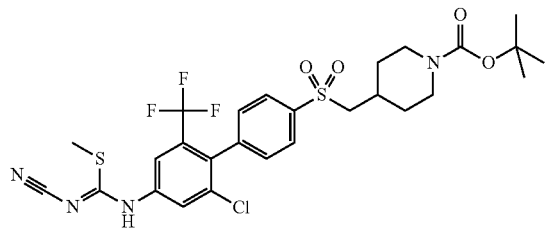 [SMILES: CS/C(=N\C#N)Nc1cc(Cl)c(-c2ccc(S(=O)(=O)CC3CCN(C(=O)OC(C)(C)C)CC3)cc2)c(C(F)(F)F)c1]

To a solution of tert-butyl 4-((2'-chloro-4'-isothiocyanato-6'-(trifluoromethyl)biphenyl-4-ylsulfonyl)methyl)piperidine-1-carboxylate (168 mg, 292 µmol, Eq: 1.00) in dimethoxyethane (5 mL) was added to sodium hydrogen cyanamide (22.4 mg, 351 µmol, Eq: 1.2) and methanol (1 mL). After 30 minutes, methyl iodide (114 mg, 50 µl, 800 µmol, Eq: 2.74) was added and the reaction was stirred overnight at room temperature. The reaction mixture was concentrated and chromatographed (12 g Redisep, 40 to 75% ethyl acetate/hexane) to give 133 mg (72%) of desired product as a white solid.

4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester (Compound 7)

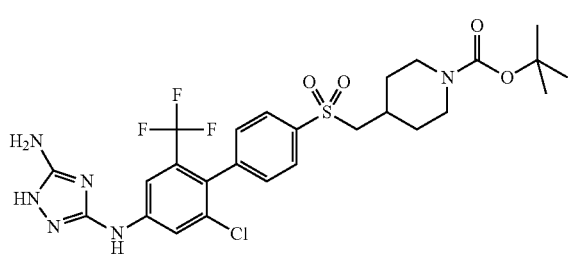 [SMILES: CC(C)(C)OC(=O)N1CCC(CS(=O)(=O)c2ccc(-c3c(Cl)cc(Nc4n[nH]c(N)n4)cc3C(F)(F)F)cc2)CC1]

To a solution of tert-butyl 4-((2'-chloro-4'-(cyanamido(methylthio)methylamino)-6'-(trifluoromethyl)biphenyl-4-ylsulfonyl)methyl)piperidine-1-carboxylate (133 mg, 210 µmol, Eq: 1.00) in ethanol (5 mL) was added hydrazine (66.4 mg, 65 µl, 2.07 mmol, Eq: 9.86). The reaction mixture was heated at 65 deg o/n. The reaction mixture was concentrated and chromatographed (Supelco 11 g, 1 to 10% methanol/dichloromethane) to give 114 mg (88%) of desired product as a white solid.

MS m/z 613 [M−H]

Procedure 6

4'-(5-Amino-1H-[1,2,4]triazol-3-ylamino)-2',6'-dichloro-biphenyl-4-carboxylic acid tert-butylamide (Compound 8)

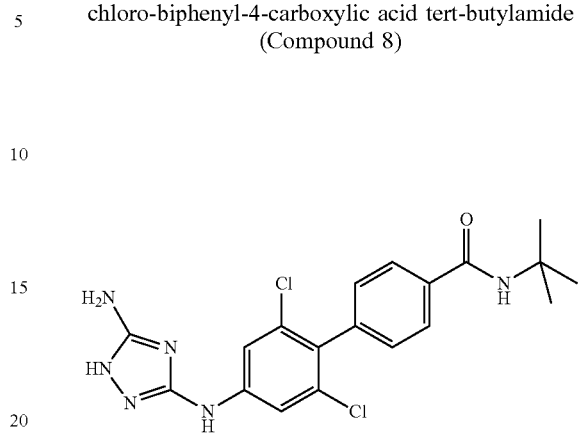

A microwave vial containing N3-(4-bromo-3,5-dichlorophenyl)-1H-1,2,4-triazole-3,5-diamine Intermediate 1 (100 mg, 310 µmol, Eq: 1.00), N3-(4-bromo-3,5-dichlorophenyl)-1H-1,2,4-triazole-3,5-diamine (100 mg, 310 µmol, Eq: 1.00), 4-(tert-butylcarbamoyl)phenylboronic acid (103 mg, 464 µmol, Eq: 1.5), sodium carbonate (82.0 mg, 774 µmol, Eq: 2.5) and tetrakis(triphenylphosphine)palladium (0) (38 mg, 32.9 µmol, Eq: 0.106) was degassed for 15 minutes with Argon. Dioxane (2 mL) was added, followed by water (0.5 mL), and the suspension was degassed for 5 minutes with sonication, and the reaction was heated at 125o for 1 hr with microwave. The reaction mixture was diluted with ethyl acetate, washed with brine, and dried with sodium sulfate. 300 mg crude chromatographed (24 g Redisep Gold, 1 to 10% methanol/dichloromethane) to give 120 mg of desired product and sm impurities. Preparative plate chromatography (10% methanol/dichloromethane) gave white solid, which contained impurities. The solid was suspended in dichloromethane, filtered and rinsed with dichloromethane. 35 mg (27%) of desired product as a white solid.

MS m/z 419 [M+H]

Procedure 6

Pentanoic acid [4'-(5-amino-1H-[1,2,4]triazol-3-ylamino)-2',6'-dichloro-biphenyl-4-yl]-amide (Compound 9)

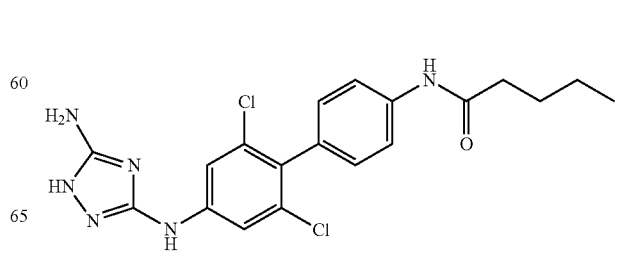

167

N-(4-(4,4,5,5-tetramethyl-1,3,2-dioxaborolan-2-yl)phenyl)pentanamide

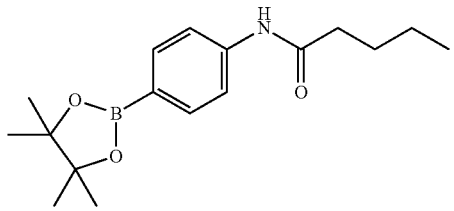 [SMILES: CCCCC(=O)Nc1ccc(B2OC(C)(C)C(C)(C)O2)cc1]

To a solution of 4-(4,4,5,5-tetramethyl-1,3,2-dioxaborolan-2-yl)aniline (500 mg, 2.28 mmol, Eq: 1.00) and Et3N (345 mg, 475 µl, 3.41 mmol, Eq: 1.49) in THF (10 mL) at 0 deg, was added pentanoyl chloride (328 g, 330 ml, 2.72 mol, Eq: 1190). The solution was gradually warmed to room temp and stirred overnight. The reaction mixture was diluted with ethyl acetate, washed with brine, and dried with sodium sulfate. The crude residue was chromatographed (40 g Redisep, 10 to 30% EtAOc/hexane) to give 521 mg (75%) of desired product as a white solid.

Pentanoic acid [4'-(5-amino-1H-[1,2,4]triazol-3-ylamino)-2',6'-dichloro-biphenyl-4-yl]-amide (Compound 9)

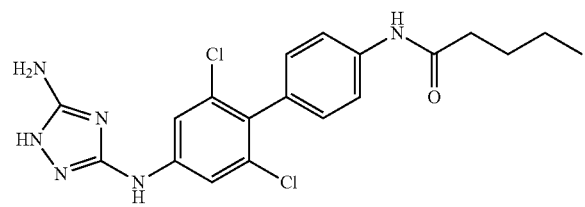 [SMILES: CCCCC(=O)Nc1ccc(-c2c(Cl)cc(Nc3n[nH]c(N)n3)cc2Cl)cc1]

A microwave vial containing N3-(4-bromo-3,5-dichlorophenyl)-1H-1,2,4-triazole-3,5-diamine Intermediate 2 (100 mg, 310 µmol, Eq: 1.00), N-(4-(4,4,5,5-tetramethyl-1,3,2-dioxaborolan-2-yl)phenyl)pentanamide (138 mg, 455 µmol, Eq: 1.47), sodium carbonate (82.0 mg, 774 µmol, Eq: 2.5) and 1,1'-bis(di-tert-butylphosphino)ferrocene palladium dichloride was degassed for 15 minutes with Argon. Dioxane (2 mL) and water (0.5 mL) was added, and the suspension was degassed for 5 minutes with sonication, and the reaction was heated at 125o for 1 hr with microwave. The reaction mixture was diluted with ethyl acetate, washed with brine, and dried with sodium sulfate. 262 mg crude was chromatographed (24 g Redisep Gold, 0 to 10% methanol/dichloromethane) to give 100 mg brown oil containing desired product, with impurities. The compound was purified twice by preparative plate chromatography (10% methanol/dichloromethane) to give 42 mg (32%) of desired product as a white solid.

MS m/z 419 [M+H]

168

Procedure 1, 7

N*3*-[4-(2-tert-Butyl-1,1-dioxo-2,3-dihydro-1H-1lambda*6*-benzo[d]isothiazol-6-yl)-3-chloro-5-trifluoromethyl-phenyl]-1H-[1,2,4]triazole-3,5-diamine (Compound 10)

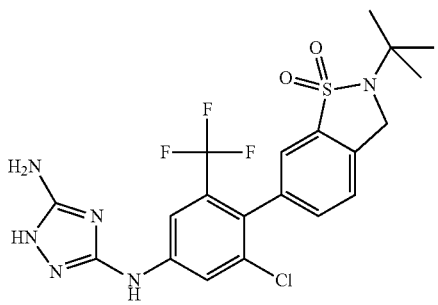 [SMILES: CC(C)(C)N1Cc2ccc(-c3c(Cl)cc(Nc4n[nH]c(N)n4)cc3C(F)(F)F)cc2S1(=O)=O]

5-bromo-N-tert-butyl-2-methylbenzenesulfonamide

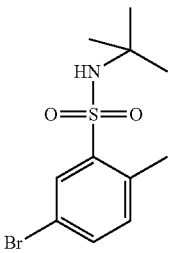

To a solution of 2-methylpropan-2-amine (905 mg, 1.3 ml, 12.4 mmol, Eq: 1.33) and Et3N (1.89 g, 2.6 ml, 18.7 mmol, Eq: 2.01) in dichloromethane (10 mL) at 0 deg, was added 5-bromo-2-methylbenzene-1-sulfonyl chloride (2.5 g, 9.27 mmol, Eq: 1.00). The solution immediately turned to a white suspension. The reaction mixture was gradually warmed to room temp and stirred overnight at rt. Diluted with dichloromethane, washed with 1N HCl, brine, dried with sodium sulfate. 2.6 g crude chromatographed (80 g Analogix, 10 to 25% ethyl acetate/hexane) to give 2.18 g (77%) of desired product as a white solid.

5-bromo-2-(bromomethyl)-N-tert-butylbenzenesulfonamide

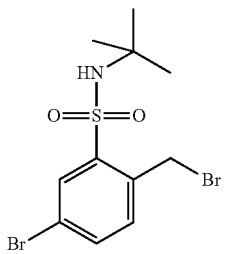 [SMILES: CC(C)(C)NS(=O)(=O)c1cc(Br)ccc1CBr]

To a solution of 5-bromo-N-tert-butyl-2-methylbenzenesulfonamide (1.46 g, 4.77 mmol, Eq: 1.00) in CCl4 (25 mL), was added benzoyl peroxide (120 mg, 495 μmol, Eq: 0.104) and NBS (852 mg, 4.79 mmol, Eq: 1.00). The reaction mixture was heated at reflux o/n. The reaction was concentrated and chromatographed (80 g Redisep, 0 to 10% ethyl acetate/hexane) to give 1.26 g (69%) of desired product as a white solid.

6-Bromo-2-tert-butyl-2,3-dihydro-benzo[d]isothiazole 1,1-dioxide

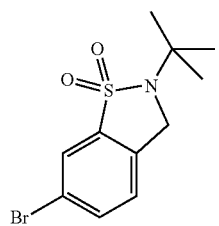 [SMILES: CC(C)(C)N1Cc2ccc(Br)cc2S1(=O)=O]

NaH (140 mg, 3.51 mmol, Eq: 1.3) was added to a solution of 5-bromo-2-(bromomethyl)-N-tert-butylbenzenesulfonamide (1.04 g, 2.7 mmol, Eq: 1.00) in DMF (10 mL) at 0 deg. The reaction mixture was gradually warmed to rt o/n. Diluted with ethyl acetate, washed with brine 3×. Dried over sodium sulfate and chromatographed (40 g Redisep, 10 to 25% ethyl acetate/hexane) to give 552 mg (67%) of desired product as a white solid.

2-tert-Butyl-6-(4,4,5,5-tetramethyl-[1,3,2]dioxaborolan-2-yl)-2,3-dihydro-benzo[d]isothiazole1,1-dioxide

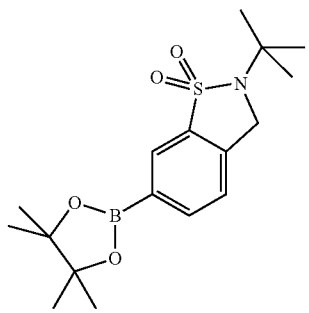 [SMILES: CC(C)(C)N1Cc2ccc(B3OC(C)(C)C(C)(C)O3)cc2S1(=O)=O]

In a 100 mL round bottom flask containing Reactant 1 (552 mg, 1.81 mmol, Eq: 1.00), bis(pinacolato)diboron (1.15 g, 4.54 mmol, Eq: 2.5), potassium acetate (801 mg, 8.17 mmol, Eq: 4.5) and PdCl2(DPPF)-CH2Cl2 adduct (133 mg, 181 μmol, Eq: 0.1) was degassed for 5 minutes with Argon. Dioxane (15 mL) was added and the reaction was heated at 85 deg overnight with an Ar balloon. The reaction mixture was cooled to room temp, concentrated, diluted with ethyl acetate, washed with brine and dried over sodium sulfate. 2 g crude chromatographed (24 g Redisep 20 to 50 EtOA/hexane) to give 874 mg off-white solid, containing desired product and pinacol diboron impurity.

4-(2-tert-Butyl-1,1-dioxo-2,3-dihydro-1H-1lambda*6*-benzo[d]isothiazol-6-yl)-3-chloro-5-trifluoromethyl-phenylamine

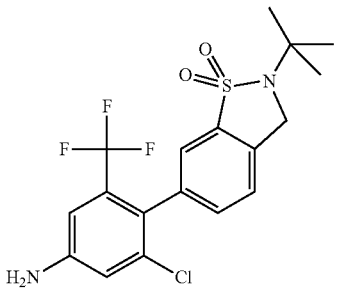 [SMILES: CC(C)(C)N1Cc2ccc(-c3c(Cl)cc(N)cc3C(F)(F)F)cc2S1(=O)=O]

A microwave vial containing 4-bromo-3-chloro-5-(trifluoromethyl)aniline (400 mg, 1.46 mmol, Eq: 1.00), sodium carbonate (386 mg, 3.64 mmol, Eq: 2.5) and Pd(Ph3P)4 (168 mg, 146 μmol, Eq: 0.1) was degassed for 15 minutes with Ar. A solution of Reactant 2 (637 mg, 1.81 mmol, Eq: 1.24) in dioxane (6 ml) was added, followed by water (1.5 mL). The suspension was degassed for 5 min with Ar with sonication, then capped and heated at 125 in microwave for 2 hr. Diluted with ethyl acetate, washed with brine. Dried org extract with sodium sulfate. 1 g crude chromatographed (40 g Redisep, 20% to 30% EOAc/hexane) to give 195 mg (32%) of desired product as a pale yellow oil.

2-tert-Butyl-6-(2-chloro-4-isothiocyanato-6-trifluoromethyl-phenyl)-2,3-dihydro-benzo[d]isothiazole 1,1-dioxide

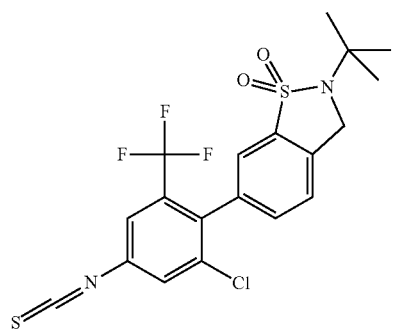 [SMILES: CC(C)(C)N1Cc2ccc(-c3c(Cl)cc(N=C=S)cc3C(F)(F)F)cc2S1(=O)=O]

To a suspension of calcium carbonate (121 mg, 1.21 mmol, Eq: 2.61) and [Reactants] in dichloromethane (13.2 g, 10.0 ml, 155 mmol, Eq: 25.3)/water (10.0 g, 10.0 ml, 555 mmol, Eq: 90.2) at 0, was added thiophosgene (75.0 mg, 50 μl, 652 μmol, Eq: 1.41) The reaction was gradually warmed to room temperature and stirred overnight. Added 1.5 mL 1N HCl slowly. Separated organic layer and extracted aq twice more with dichloromethane. Dried over sodium sulfate and chromatographed (24 g Redisep 0 to 10% ethyl acetate/hexane) to give 136 mg (64%) of desired product as a white solid.

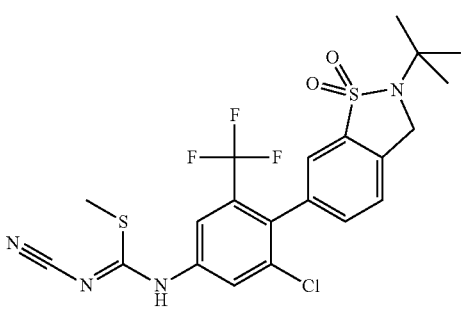 [SMILES: CS/C(=N\C#N)Nc1cc(Cl)c(-c2ccc3c(c2)S(=O)(=O)N(C(C)(C)C)C3)c(C(F)(F)F)c1]

To a solution of Reactant 1 (136 mg, 295 μmol, Eq: 1.00) in dimethoxyethane (5 mL) was added to sodium hydrogen cyanamide (29 mg, 453 μmol, Eq: 1.54) and methanol (0.5 mL). After 30 minutes, MEthyl iodide (136 mg, 60 μl, 960 μmol, Eq: 3.25) was added and the reaction was stirred at room temperature over the weekend. The reaction mixture was concentrated and chromatographed (12 g Redisep, 30 to 50% ethyl acetate/hexane) to give 85 mg (56%) of desired product as a white solid.

N*3*-[4-(2-tert-Butyl-1,1-dioxo-2,3-dihydro-1H-1lambda*6*-benzo[d]isothiazol-6-yl)-3-chloro-5-trifluoromethyl-phenyl]-1H-[1,2,4]triazole-3,5-diamine (Compound 10)

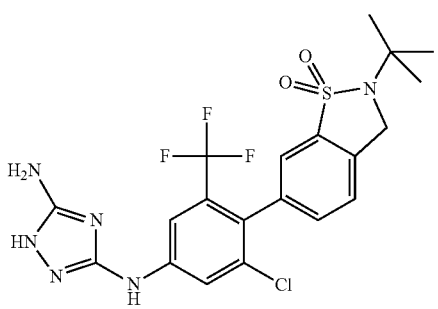 [SMILES: CC(C)(C)N1Cc2ccc(-c3c(Cl)cc(Nc4n[nH]c(N)n4)cc3C(F)(F)F)cc2S1(=O)=O]

To a solution of Reactant 1 (85 mg, 164 μmol, Eq: 1.00) in ethanol (8 mL) was added hydrazine (51.1 mg, 50 μl, 1.59 mmol, Eq: 9.73). The reaction mixture was heated at 65 deg o/n. The reaction mixture was concentrated and chromatographed (Redisep 12 g, 1 to 10% methanol/dichloromethane) to give 67 mg (83%) of desired product as a white solid.
MS m/z 501 [M+H]

Procedure 1, 7

N*3*-{2-Chloro-6-trifluoromethyl-4'-[1-(3,3,3-trifluoro-propyl)-piperidine-3-sulfonyl]-biphenyl-4-yl}-1H-[1,2,4]triazole-3,5-diamine; hydrochloride (Compound 11)

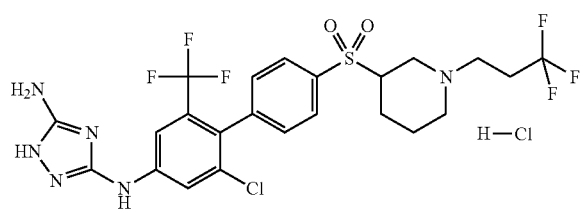

To a suspension of N3-(2-chloro-4'-(piperidin-3-ylsulfonyl)-6-(trifluoromethyl)biphenyl-4-yl)-1H-1,2,4-triazole-3,5-diamine hydrochloride (136 mg, 253 μmol, Eq: 1.00) in methanol (10 mL), was added 3,3,3-trifluoropropanal (35 mg, 312 μmol, Eq: 1.23), followed by sodium cyanoborohydride (31.8 mg, 506 μmol, Eq: 2). The white slurry was stirred overnight at room temperature. The resulting cloudy solution was concentrated, and then diluted with ethyl acetate and partitioned with sodium carbonate aqueous solution. The aqueous was extracted twice more with EtAOc. The combined organic extracts were dried over sodium sulfate and the crude residue was chromatographed (12 g Redisep Gold, 1 to 10% methanol/dichloromethane) to give 82 mg white solid as the free amine.

To a solution of 82 mg of amine in 2 mL methanol, was added a freshly prepared 2 mL solution of HCl (prepared from 0.4 mL of AcCl added to 4 mL methanol at rt, then cooled to 0 deg for 5 min). The solution was stirred for 6 hours. The reaction was concentrated, dissolved in 1 mL methanol, triturated with ether to give white precipitate, which was filtered, rinsed with ether, and dried overnight at 70 deg with high vacuum to give 68 mg (42%) of desired product as a white solid,
MS m/z 597 [M+H]

Procedure 6

N-[4'-(5-Amino-1H-[1,2,4]triazol-3-ylamino)-2',6'-dichloro-biphenyl-4-ylmethyl]-methanesulfonamide (Compound 12)

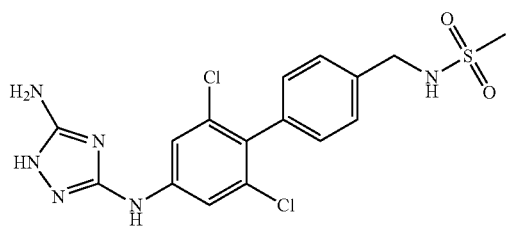 [SMILES: CS(=O)(=O)NCc1ccc(-c2c(Cl)cc(Nc3n[nH]c(N)n3)cc2Cl)cc1]

A microwave vial containing N3-(4-bromo-3,5-dichlorophenyl)-1H-1,2,4-triazole-3,5-diamine Intermediate 2 (100 mg, 310 μmol, Eq: 1.00), 4-(methylsulfonamidomethyl)phenylboronic acid (108 mg, 471 μmol, Eq: 1.52), sodium carbonate (84 mg, 793 μmol, Eq: 2.56) and Pd(Ph3P)4 (43 mg, 37.2 μmol, Eq: 0.120) was degassed for 15 minutes with Argon. Dioxane (2 mL) and water (0.5 mL) was added, and the suspension was degassed for 5 minutes with sonication, and the reaction was heated at 125o for 1 hr with microwave. The reaction mixture was concentrated, diluted with ethyl acetate, washed with brine, and dried with sodium sulfate. 300 mg crude was chromatographed (24 g Supelco, 100% dichloromethane to 10% methanol/dichloromethane) to give 140 mg orange oil, containing desired product and impurities. Further purification by preparative plate chromatography (10% methanol/dichloromethane) gave 60 mg (45%) of desired product as a yellow solid.
MS m/z 427 [M+H]

Procedure 1, 7

N—{(S)-1-[4'-(5-Amino-1H-[1,2,4]triazol-3-ylamino)-2'-chloro-6'-trifluoromethyl-biphenyl-4-yl]-ethyl}-methanesulfonamide (Compound 13)

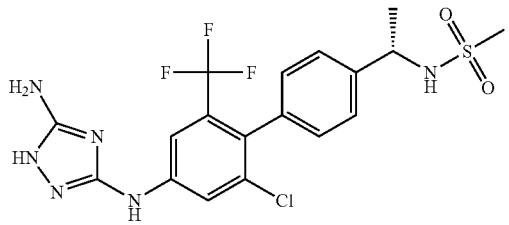 [SMILES: C[C@H](NS(C)(=O)=O)c1ccc(-c2c(Cl)cc(Nc3n[nH]c(N)n3)cc2C(F)(F)F)cc1]

(S)—N-(1-(4-bromophenyl)ethyl)methanesulfonamide

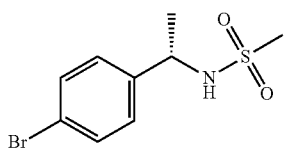

To a solution of (S)-1-(4-bromophenyl)ethanamine (1 g, 5.00 mmol, Eq: 1.00) and pyridine (1.37 g, 1.4 ml, 17.3 mmol, Eq: 3.46) in dichloromethane (15 mL) at 0 deg, was added Ms-Cl (1.43 g, 975 µl, 12.5 mmol, Eq: 2.5). The solution was gradually warmed to room temp and stirred overnight. Diluted with dichloromethane, washed with 1N HCl, brine, and dried with sodium sulfate. 1.91 g crude chromatographed (80 g Redisep 0 to 20 to 40% ethyl acetate/hexane) to give 1.008 g (73%) of desired product as a yellow solid.

(S)—N-(1-(4-(4,4,5,5-tetramethyl-1,3,2-dioxaborolan-2-yl)phenyl)ethyl)methanesulfonamide

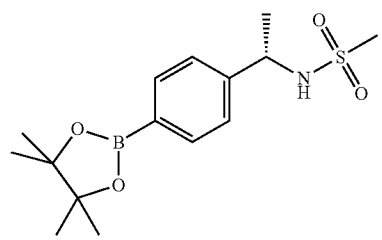

To a solution of (S)—N-(1-(4-bromophenyl)ethyl)methanesulfonamide (1.008 g, 3.62 mmol, Eq: 1.00), bis(pinacolato)diboron (2.3 g, 9.06 mmol, Eq: 2.5), and potassium acetate (1.8 g, 18.3 mmol, Eq: 5.06) in dioxane (10 mL), was added PdCl2(DPPF)-CH2Cl2 adduct (269 mg, 368 µmol, Eq: 0.102) The reaction was heated at 85 deg overnight with an N2 balloon. The reaction mixture was cooled to room temp, concentrated, diluted with ether, washed with brine and dried over sodium sulfate. 1.4 g crude chromatographed (80 g Redisep, 20 to 50% ethyl acetate/hexane) to give 473 mg (40%) of desired product as a white solid, containing some pinacol diboron impurity.

(S)—N-(1-(4'-amino-2'-chloro-6'-(trifluoromethyl)biphenyl-4-yl)ethyl)methanesulfonamide

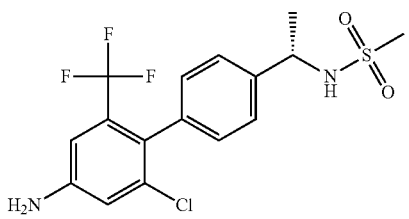 [SMILES: C[C@H](NS(C)(=O)=O)c1ccc(-c2c(Cl)cc(N)cc2C(F)(F)F)cc1]

A microwave vial containing 4-bromo-3-chloro-5-(trifluoromethyl)aniline (200 mg, 729 µmol, Eq: 1.00), (S)—N-(1-(4-(4,4,5,5-tetramethyl-1,3,2-dioxaborolan-2-yl)phenyl)ethyl)methanesulfonamide (473 mg, 727 µmol, Eq: 0.998), sodium carbonate (193 mg, 1.82 mmol, Eq: 2.5) and bis(triphenylphosphine)palladium (II) chloride (58 mg, 82.6 µmol, Eq: 0.113) in dimethoxyethane (4 mL)/water (1 mL) was heated for overnight at 110 with conventional heating. The reaction mixture was concentrated. Diluted with ethyl acetate, washed with brine. Dried org extract with sodium sulfate. 500 mg crude Chromatographed (40 g Redisep, 10% to 25% to 40% ethyl acetate/hexane) to give 75 mg (26%) of desired product as a white solid.

(S)—N-(1-(2'-chloro-4'-isothiocyanato-6'-(trifluoromethyl)biphenyl-4-yl)ethyl)methanesulfonamide

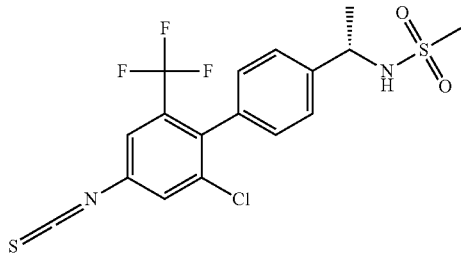 [SMILES: C[C@H](NS(C)(=O)=O)c1ccc(-c2c(Cl)cc(N=CC=S)cc2C(F)(F)F)cc1]

To a suspension of calcium carbonate (117 mg, 1.17 mmol, Eq: 3.06) and (S)—N-(1-(4'-amino-2'-chloro-6'-(trifluoromethyl)biphenyl-4-yl)ethyl)methanesulfonamide (150 mg, 382 µmol, Eq: 1.00) in dichloromethane (13.2 g, 10.0 ml, 155 mmol, Eq: 25.3)/water (10.0 g, 10.0 ml, 555 mmol, Eq: 90.2) at 0, was added thiophosgene (52.7 mg, 35.1 µl, 458 µmol, Eq: 1.2) The reaction was gradually warmed to room temperature and stirred overnight. Added 1.5 mL 1N HCl slowly. Separated organic layer, dried over sodium sulfate, and concentrated to give 120 mg (72%) of desired product as an off-white solid.

N-((1S)-1-(2'-chloro-4'-(cyanamido(methylthio)methylamino)-6'-(trifluoromethyl)biphenyl-4-yl)ethyl)methanesulfonamide

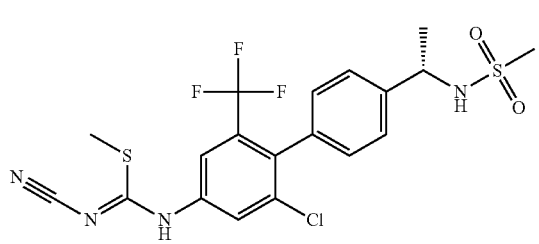 [SMILES: CS/C(=N\C#N)Nc1cc(Cl)c(-c2ccc([C@H](C)NS(C)(=O)=O)cc2)c(C(F)(F)F)c1]

To a solution of (S)—N-(1-(2'-chloro-4'-isothiocyanato-6'-(trifluoromethyl)biphenyl-4-yl)ethyl)methanesulfonamide (120 mg, 276 µmol, Eq: 1.00) in methanol (5 mL) was added to sodium hydrogen cyanamide (20 mg, 312 µmol, Eq: 1.13). After 30 minutes, methyl iodide (90.8 mg, 40 µl, 640 µmol, Eq: 2.32) was added and the reaction was stirred overnight at room temperature. The reaction mixture was concentrated and chromatographed (24 g Redisep, 25% to 75% ethyl acetate/hexane) to give 56 mg (41%) of desired product as a yellow solid.

N—{(S)-1-[4'-(5-Amino-1H-[1,2,4]triazol-3-ylamino)-2'-chloro-6'-trifluoromethyl-biphenyl-4-yl]-ethyl}-methanesulfonamide (Compound 13)

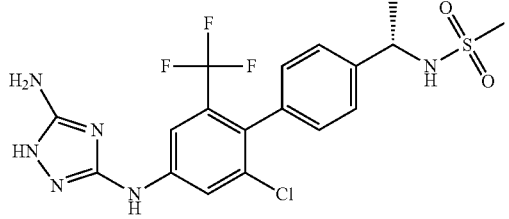 [SMILES: C[C@H](NS(C)(=O)=O)c1ccc(-c2c(Cl)cc(Nc3n[nH]c(N)n3)cc2C(F)(F)F)cc1]

To a solution of N-((1S)-1-(2'-chloro-4'-(cyanamido(methylthio)methylamino)-6'-(trifluoromethyl)biphenyl-4-yl)ethyl)methanesulfonamide (56 mg, 114 µmol, Eq: 1.00) in ethanol (5 mL) was added hydrazine (45.9 mg, 45 µl, 1.43 mmol, Eq: 12.6). The reaction mixture was heated at 60 deg o/n. Cooled to rt. No precipitate. Concentrated and chromatographed (11 g Supelco, 1 to 10% methanol/dichloromethane) to give 42 mg (76%) of desired product as a white solid.
MS m/z 475 [M+H]

Procedure 6

N*3*-(2,6-Dichloro-4'-methanesulfonyl-3'-trifluoromethyl-biphenyl-4-yl)-1H-[1,2,4]triazole-3,5-diamine (Compound 14)

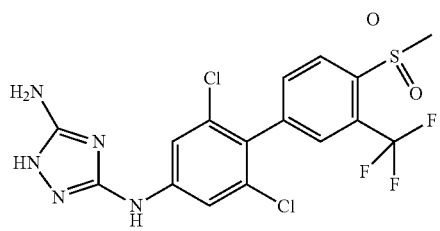

4,4,5,5-tetramethyl-2-(4-(methylsulfonyl)-3-(trifluoromethyl)phenyl)-1,3,2-dioxaborolane

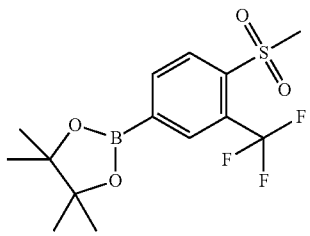

To a solution of 4-bromo-1-(methylsulfonyl)-2-(trifluoromethyl)benzene (498 mg, 1.64 mmol, Eq: 1.00), bis(pinacolato)diboron (1.04 g, 4.11 mmol, Eq: 2.5), and potassium acetate (760 mg, 7.74 mmol, Eq: 4.71) in dioxane (10 mL), was added PdCl2(DPPF)-CH2Cl2 adduct (126 mg, 172 µmol, Eq: 0.105) The reaction was heated at 85 deg overnight. The reaction mixture was cooled to room temp, diluted with ether, washed with brine and dried over sodium sulfate. 1.4 g crude chromatographed (80 g Redisep, 0 to 10% methanol/dichloromethane) to give 627 mg of desired product as a brown solid, containing some pinacol diboron impurity.

N*3*-(2,6-Dichloro-4'-methanesulfonyl-3'-trifluoromethyl-biphenyl-4-yl)-1H-[1,2,4]triazole-3,5-diamine (Compound 14)

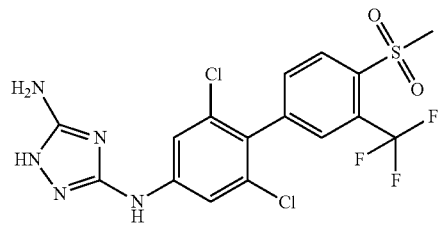 [SMILES: CS(=O)(=O)c1ccc(-c2c(Cl)cc(Nc3n[nH]c(N)n3)cc2Cl)cc1C(F)(F)F]

A microwave vial containing N3-(4-bromo-3,5-dichlorophenyl)-1H-1,2,4-triazole-3,5-diamine Intermediate 2 (100 mg, 310 µmol, Eq: 1.00), 4,4,5,5-tetramethyl-2-(4-(methylsulfonyl)-3-(trifluoromethyl)phenyl)-1,3,2-dioxaborolane (163 mg, 464 µmol, Eq: 1.5), sodium carbonate (92 mg, 868 µmol, Eq: 2.8) and bis(di-t-Bu-phosiphino)ferrocenyl PdCl2 (39 mg, 0.060 mmol, Eq: 0.193) was degassed for 15 minutes with Argon. Dioxane (2 mL) and water (0.5 mL) was added, and the suspension was degassed for 5 minutes with sonication, and the reaction was heated at 125o for 1 hr with microwave. Diluted with ethyl acetate, washed with brine, and dried with sodium sulfate. Chromatographed (24 g Redisep Gold, 0 to 10% methanol/dichloromethane) to give 43 mg. NMR shows prod+des-Br impurity.

Combined with 8237-68 (17 mg) and submitted for HPLC purification: 22.5 mg (16%) of desired product as an off-white solid.

MS m/z 466 [M+H]

Procedure 1, 7

N*3*-[3,5-Dichloro-4-(1-methanesulfonyl-1H-indol-4-yl)-phenyl]-1H-[1,2,4]triazole-3,5-diamine (Compound 15)

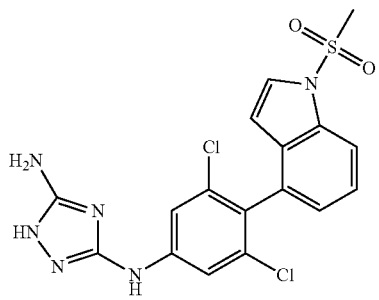 [SMILES: CS(=O)(=O)n1ccc2c(-c3c(Cl)cc(Nc4n[nH]c(N)n4)cc3Cl)cccc21]

4-bromo-1-(methylsulfonyl)-1H-indole

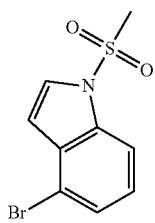

To a solution of 4-bromo-1H-indole (506 mg, 2.58 mmol, Eq: 1.00) in 5 mL THF at 0 deg, was added NaH (60%, 250 mg, 6.25 mmol, Eq: 2.42). The ice bath was removed. After 30 minutes, the reaction was cooled to 0 deg, and Ms-Cl (588 mg, 400 µl, 5.13 mmol, Eq: 1.99) was added. Gradually warmed to room temperature overnight. Diluted with ethyl acetate, washed with brine, dried over sodium sulfate. 720 mg crude chromatographed (40 g Redisep, 100% hexane to 15% ethyl acetate/hexane) gave 428 mg (62%) of desired product as a pale yellow oil, containing ~8% indole impurity.

1-(methylsulfonyl)-4-(4,4,5,5-tetramethyl-1,3,2-dioxaborolan-2-yl)-1H-indole

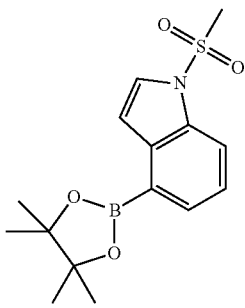 [SMILES: CC1(C)OB(c2cccc3c2ccn3S(C)(=O)=O)OC1(C)C]

To a solution of 4-bromo-1-(methylsulfonyl)-1H-indole (428 mg, 1.56 mmol, Eq: 1.00), bis(pinacolato)diboron (992 mg, 3.91 mmol, Eq: 2.5), and potassium acetate (644 mg, 6.56 mmol, Eq: 4.2) in Dioxane (15 mL), was added PdCl2(DPPF)-CH2Cl2 adduct (114 mg, 156 µmol, Eq: 0.1) The reaction was heated at 85 deg overnight. The reaction mixture was cooled to room temp, diluted with ether, washed with brine and dried over sodium sulfate. Chromatography (80 g Redisep, 10 to 20% ethyl acetate/hexane) to give 432 mg (86%) of desired product as a colorless oil, with a slight indole impurity.

N*3*-[3,5-Dichloro-4-(1-methanesulfonyl-1H-indol-4-yl)-phenyl]-1H-[1,2,4]triazole-3,5-diamine (Compound 15)

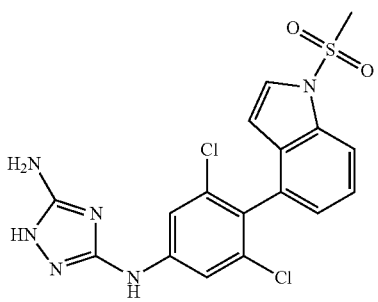 [SMILES: CS(=O)(=O)n1ccc2c(-c3c(Cl)cc(Nc4n[nH]c(N)n4)cc3Cl)cccc21]

A microwave vial containing N3-(4-bromo-3,5-dichlorophenyl)-1H-1,2,4-triazole-3,5-diamine Intermediate 2 (100 mg, 310 µmol, Eq: 1.00), 1-(methylsulfonyl)-4-(4,4,5,5-tetramethyl-1,3,2-dioxaborolan-2-yl)-1H-indole (149 mg, 464 µmol, Eq: 1.5), sodium carbonate (82.0 mg, 774 µmol, Eq: 2.5) and Pd(Ph3P)4 (38.0 mg, 32.9 µmol, Eq: 0.106) was degassed for 15 minutes with Argon. Dioxane (2 mL) and water (0.5 mL) was added, and the suspension was degassed for 5 minutes with sonication, and the reaction was heated at 125o for 1 hr with microwave. Diluted with ethyl acetate, washed with brine, and dried over sodium sulfate. Chromatographed (23 g Supelco, 0 to 10% methanol/dichloromethane) to give 91 mg of desired product and impurities. Further purification by preparative plate chromatography (10% methanol/dichloromethane) gave 62 mg of impure product. SFC purification gave 19 mg (14%) of desired product as an off-white solid.

MS m/z 437 [M+H]

Procedure 1, 7

4-[4'-(5-Amino-1H-[1,2,4]triazol-3-ylamino)-2'-chloro-6'-trifluoromethyl-biphenyl-4-sulfonyl]-piperazine-1-carboxylic acid tert-butyl ester (Compound 16)

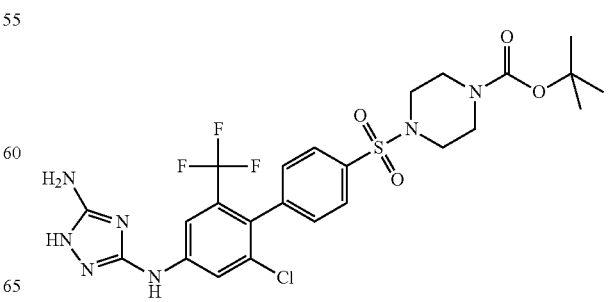

tert-butyl 4-(4-(4,4,5,5-tetramethyl-1,3,2-dioxaborolan-2-yl)phenylsulfonyl)piperazine-1-carboxylate

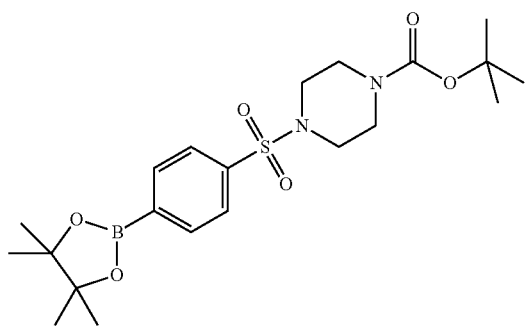 [SMILES: CC(C)(C)OC(=O)N1CCN(S(=O)(=O)c2ccc(B3OC(C)(C)C(C)(C)O3)cc2)CC1]

To a solution of tert-butyl 4-(4-bromophenylsulfonyl)piperazine-1-carboxylate (1 g, 2.47 mmol, Eq: 1.00), bis(pinacolato)diboron (1.58 g, 6.22 mmol, Eq: 2.52), and potassium acetate (1.09 g, 11.1 mmol, Eq: 4.5) in dioxane (15 mL), was added PdCl2(DPPF)-CH2Cl2 adduct (286 mg, 391 μmol, Eq: 0.158) The reaction was heated at 85 deg overnight with an N2 balloon. The reaction mixture was cooled to room temp, concentrated, diluted with ether, washed with brine and dried over sodium sulfate. 1.4 g crude chromatographed (80 g Redisep, 20 to 50% ethyl acetate/hexane) to give 742 mg (67%) of desired product as an off-white solid.

tert-butyl 4-(4'-amino-2'-chloro-6'-(trifluoromethyl)biphenyl-4-ylsulfonyl)piperazine-1-carboxylate

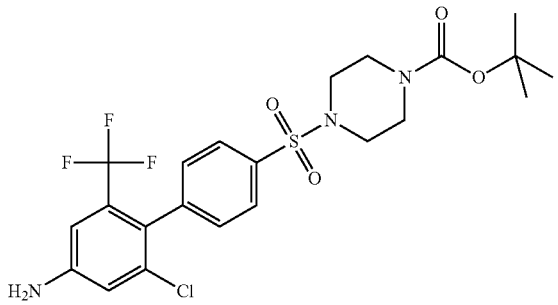 [SMILES: CC(C)(C)OC(=O)N1CCN(S(=O)(=O)c2ccc(-c3c(Cl)cc(N)cc3C(F)(F)F)cc2)CC1]

A microwave vial containing 4-bromo-3-chloro-5-(trifluoromethyl)aniline (375 mg, 1.37 mmol, Eq: 1.00), sodium carbonate (367 mg, 3.46 mmol, Eq: 2.53) and Pd(Ph3P)4 (158 mg, 137 μmol, Eq: 0.1) was degassed for 15 minutes with Ar. A solution of tert-butyl 4-(4-(4,4,5,5-tetramethyl-1,3,2-dioxaborolan-2-yl)phenylsulfonyl)piperazine-1-carboxylate (742 mg, 1.64 mmol, Eq: 1.2) in dimethoxyethane (8 mL) was added, followed by water (2 mL). The suspension was degassed for 5 min with Arwith sonication, then heated at 110 deg for 1 hr with microwave. Diluted with ethyl acetate, washed with brine, and dried organic extract with sodium sulfate. 1.5 g crude chromatographed (40 g Redisep, 15% to 30% ethyl acetate/hexane) to give 503 mg (71%) of desired product as an orange oil.

tert-butyl 4-(2'-chloro-4'-isothiocyanato-6'-(trifluoromethyl)biphenyl-4-ylsulfonyl)piperazine-1-carboxylate

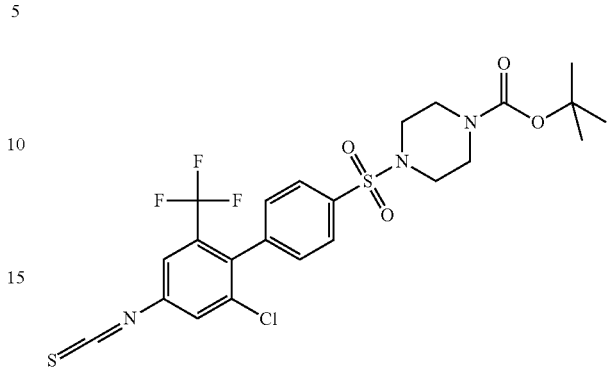

To a suspension of calcium carbonate (242 mg, 2.42 mmol, Eq: 2.5) and tert-butyl 4-(4'-amino-2'-chloro-6'-(trifluoromethyl)biphenyl-4-ylsulfonyl)piperazine-1-carboxylate (503 mg, 967 μmol, Eq: 1.00) in dichloromethane (13.2 g, 10.0 ml, 155 mmol, Eq: 25.3)/water (10.0 g, 10.0 ml, 555 mmol, Eq: 90.2) at 0, was added thiophosgene (133 mg, 89.0 μl, 1.16 mmol, Eq: 1.2) The reaction was gradually warmed to room temperature and stirred overnight. Added 2.5 mL 1N HCl slowly. Separated organic layer and dried over sodium sulfate. 381 mg (70%) of desired product as an orange oil.

tert-butyl 4-(2'-chloro-4'-(cyanamido(methylthio)methylamino)-6'-(trifluoromethyl)biphenyl-4-ylsulfonyl)piperazine-1-carboxylate

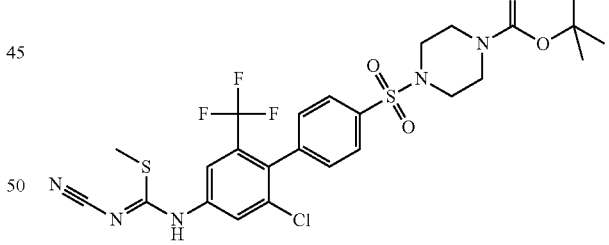

To a solution of tert-butyl 4-(2'-chloro-4'-isothiocyanato-6'-(trifluoromethyl)biphenyl-4-ylsulfonyl)piperazine-1-carboxylate (381 mg, 678 μmol, Eq: 1.00) in methanol (10 mL) was added to sodium hydrogen cyanamide (52 mg, 812 μmol, Eq: 1.2). After 30 minutes, methyl iodide (250 mg, 110 μl, 1.76 mmol, Eq: 2.6) was added and the reaction was stirred overnight at room temperature. The reaction mixture was concentrated and chromatographed (24 g Redisep, 10 to 50% ethyl acetate/hexane) to give 188 mg (45%) of desired product as a yellow solid.

181

4-[4'-(5-Amino-1H-[1,2,4]triazol-3-ylamino)-2'-chloro-6'-trifluoromethyl-biphenyl-4-sulfonyl]-piperazine-1-carboxylic acid tert-butyl ester (Compound 16)

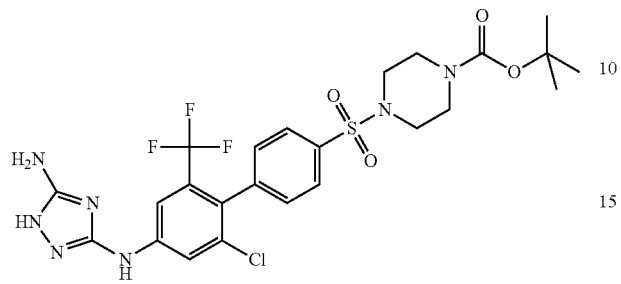

To a solution of tert-butyl 4-(2'-chloro-4'-(cyanamido(methylthio)methylamino)-6'-(trifluoromethyl)biphenyl-4-ylsulfonyl)piperazine-1-carboxylate (188 mg, 303 μmol, Eq: 1.00) in ethanol (5 mL) was added hydrazine (102 mg, 100 μl, 3.19 mmol, Eq: 10.5). The reaction mixture was heated at 60 deg o/n. Cooled to room temp and filtered suspension to give 57 mg white solid, containing desired product. The filtrate was concentrated and chromatographed (11 g Supelco, 1 to 10% methanol/dichloromethane) to give an additional 93 mg of desired product white solid, resulting in 150 mg (82%) total product.

MS m/z 600 [M–H]

Procedure 1, 7

N*3*-{2-Chloro-4'-[1-(3,3-dimethyl-butyl)-piperidine-3-sulfonyl]-6-trifluoromethyl-biphenyl-4-yl}-1H-[1,2,4]triazole-3,5-diamine; hydrochloride (Compound 17)

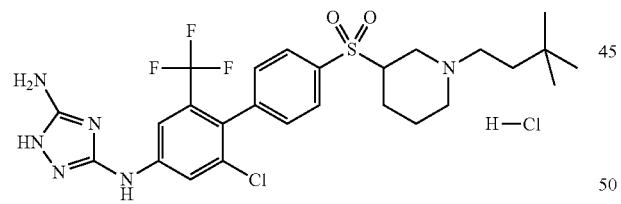

To a suspension of N3-(2-chloro-4'-(piperidin-3-ylsulfonyl)-6-(trifluoromethyl)biphenyl-4-yl)-1H-1,2,4-triazole-3,5-diamine hydrochloride Example 30 (40 mg, 74.4 μmol, Eq: 1.00) in methanol (5 mL), was added 3,3-dimethylbutanal (12.0 mg, 15 μl, 120 μmol, Eq: 1.61), followed by sodium cyanoborohydride (9.7 mg, 154 μmol, Eq: 2.07). Diluted with ethyl acetate and basified with sodium carbonate aq solution and separated org extract. Extracted aq twice more with EtAOc. Combined org extracts were dried over sodium sulfate and chromatographed (12 g Redisep, 1 to 10% methanol/dichloromethane) to give 27 mg white solid, as the free amine product.

To a solution of 27 mg of amine in 2 mL methanol, was added a freshly prepared 2 mL solution of HCl (prepared from 0.2 mL of AcCl added to 2 mL methanol at rt, then cooled to 0 deg for 5 min). Stirred for 6 hr. Filtered off suspension to give white solid, which was rinsed with ether. Dried over weekend at 65 deg with house vacuum to give 26 mg (56%) of desired product as a white solid.

MS m/z 585 [M+H]

Procedure 1, 7

4'-(5-Amino-1H-[1,2,4]triazol-3-ylamino)-2'-chloro-4-methyl-6'-trifluoromethyl-biphenyl-3-sulfonic acid tert-butylamide (Compound 18)

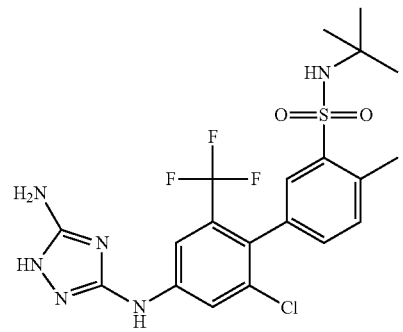 [SMILES: Cc1ccc(-c2c(Cl)cc(Nc3n[nH]c(N)n3)cc2C(F)(F)F)cc1S(=O)(=O)NC(C)(C)C]

5-bromo-N-tert-butyl-2-methylbenzenesulfonamide

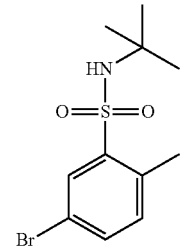 [SMILES: Cc1ccc(Br)cc1S(=O)(=O)NC(C)(C)C]

To a solution of 2-methylpropan-2-amine (905 mg, 1.3 ml, 12.4 mmol, Eq: 1.33) and Et3N (1.89 g, 2.6 ml, 18.7 mmol, Eq: 2.01) in dichloromethane (10 mL) at 0 deg, was added 5-bromo-2-methylbenzene-1-sulfonyl chloride (2.5 g, 9.27 mmol, Eq: 1.00). The solution immediately turned to a white suspension. The reaction mixture was gradually warmed to room temp and stirred overnight at rt. The reaction was diluted with dichloromethane, washed with 1N HCl, brine, dried with sodium sulfate. 2.6 g crude chromatographed (80 g Analogix, 10 to 25% ethyl acetate/hexane) to give 2.18 g (77%) of desired product as a white solid.

183
N-tert-butyl-2-methyl-5-(4,4,5,5-tetramethyl-1,3,2-dioxaborolan-2-yl)benzenesulfonamide

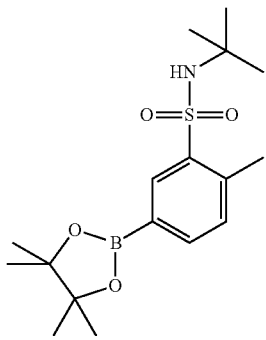 [SMILES: Cc1ccc(B2OC(C)(C)C(C)(C)O2)cc1S(=O)(=O)NC(C)(C)C]

In a 100 mL round bottom flask containing 5-bromo-N-tert-butyl-2-methylbenzenesulfonamide (750 mg, 2.45 mmol, Eq: 1.00), bis(pinacolato)diboron (1.55 g, 6.12 mmol, Eq: 2.5), potassium acetate (1.08 g, 11.0 mmol, Eq: 4.5) and PdCl2(DPPF)-CH2Cl2 adduct (90 mg, 123 µmol, Eq: 0.0502) was degassed for 5 minutes with Argon. Dioxane (10 mL) was added and the reaction was heated at 85 deg overnight with an Ar balloon. The reaction mixture was cooled to room temp, concentrated, diluted with ethyl acetate, washed with brine and dried over sodium sulfate. 2 g crude chromatographed (40 g Redisep 10 to 25% EtOA/hexane) to give 540 mg (62%) of desired product as a white solid.

4'-amino-N-tert-butyl-2'-chloro-4-methyl-6'-(trifluoromethyl)biphenyl-3-sulfonamide

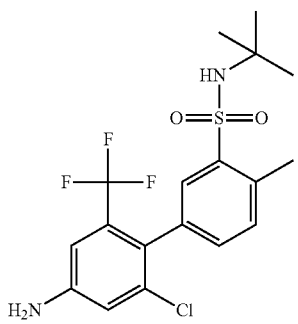 [SMILES: Cc1ccc(-c2c(Cl)cc(N)cc2C(F)(F)F)cc1S(=O)(=O)NC(C)(C)C]

A microwave vial containing 4-bromo-3-chloro-5-(trifluoromethyl)aniline (352 mg, 1.28 mmol, Eq: 1.00), sodium carbonate (340 mg, 3.21 mmol, Eq: 2.5) and Pd(Ph3P)4 (142 mg, 123 µmol, Eq: 0.0958) was degassed for 15 minutes with Ar. A solution of N-tert-butyl-2-methyl-5-(4,4,5,5-tetramethyl-1,3,2-dioxaborolan-2-yl)benzenesulfonamide (540 mg, 1.53 mmol, Eq: 1.19) in Dioxane (4 mL) was added, followed by water (1 mL). The suspension was degassed for 5 min with Ar with sonication, then capped and heated at 125 in microwave for 2 hr. The reaction mixture was diluted with ethyl acetate, washed with brine. Dried org extract with sodium sulfate. 1 g crude chromatographed (40 g Redisep, 20% to 30% EOAc/hexane) to give 458 mg (85%) of desired product as a colorless oil.

184
N-tert-butyl-2'-chloro-4'-isothiocyanato-4-methyl-6'-(trifluoromethyl)biphenyl-3-sulfonamide

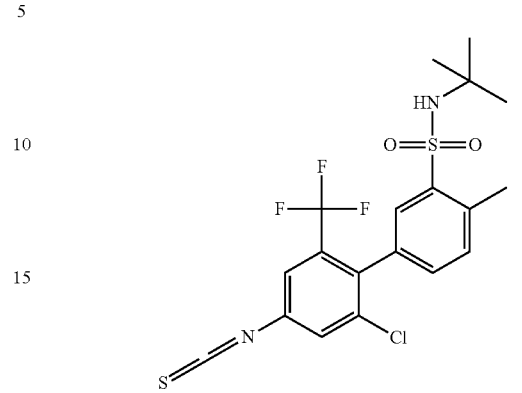

To a suspension of calcium carbonate (313 mg, 3.13 mmol, Eq: 2.87) and 4'-amino-N-tert-butyl-2'-chloro-4-methyl-6'-(trifluoromethyl)biphenyl-3-sulfonamide in dichloromethane (13.2 g, 10.0 ml, 155 mmol, Eq: 25.3)/water (10.0 g, 10.0 ml, 555 mmol, Eq: 90.2) at 0, was added thiophosgene (163 mg, 108 µl, 1.41 mmol, Eq: 1.3) The reaction was gradually warmed to room temperature and stirred overnight.

September 20 9 am TLC ok. Added 3 mL 1N HCl slowly. Separated organic layer and extracted aq twice more with dichloromethane. Dried over sodium sulfate and chromatographed (24 g Redisep 10 to 25% ethyl acetate/hexane) to give 425 mg (84%) of desired product as a white foamy solid.

N-tert-butyl-2'-chloro-4'-(cyanamido(methylthio)methylamino)-4-methyl-6'-(trifluoromethyl)biphenyl-3-sulfonamide

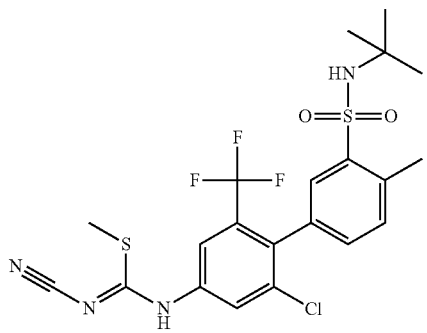 [SMILES: CS/C(=N\C#N)Nc1cc(Cl)c(-c2ccc(C)c(S(=O)(=O)NC(C)(C)C)c2)c(C(F)(F)F)c1]

To a solution of N-tert-butyl-2'-chloro-4'-isothiocyanato-4-methyl-6'-(trifluoromethyl)biphenyl-3-sulfonamide in dimethoxyethane (10 mL) was added to sodium hydrogen cyanamide (79 mg, 1.23 mmol, Eq: 1.34) and methanol (1 mL). After 30 minutes, methyl iodide (340 mg, 150 µL, 2.4 mmol, Eq: 2.61) was added and the reaction was stirred overnight at room temperature. The reaction was concentrated and chromatographed (24 g Redisep, 20 to 40% ethyl acetate/hexane) to give 375 mg (79%) white solid.

4'-(5-Amino-1H-[1,2,4]triazol-3-ylamino)-2'-chloro-4-methyl-6'-trifluoromethyl-biphenyl-3-sulfonic acid tert-butylamide (Compound 18)

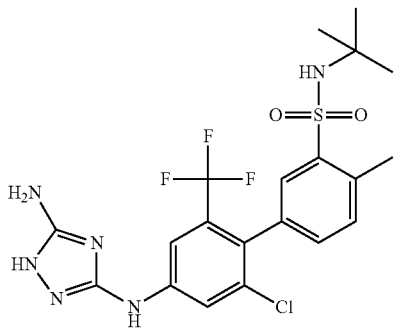 [SMILES: Cc1ccc(-c2c(Cl)cc(Nc3n[nH]c(N)n3)cc2C(F)(F)F)cc1S(=O)(=O)NC(C)(C)C]

To a solution of N-tert-butyl-2'-chloro-4'-(cyanamido(methylthio)methylamino)-4-methyl-6'-(trifluoromethyl)biphenyl-3-sulfonamide (375 mg, 720 μmol, Eq: 1.00) in ethanol (10 mL) was added hydrazine (204 mg, 200 μl, 6.37 mmol, Eq: 8.85). The reaction mixture was heated at 65 deg o/n. The reaction mixture was concentrated and chromatographed (Redisep 24 g, 1 to 10% methanol/dichloromethane) to give 333 mg (92%) of desired product as a white.
MS m/z 503 [M+H]

Procedure 6

N*3*-[2-Chloro-4'-methoxy-3'-(propane-2-sulfonyl)-6-trifluoromethyl-biphenyl-4-yl]-1H-[1,2,4]triazole-3,5-diamine (Compound 19)

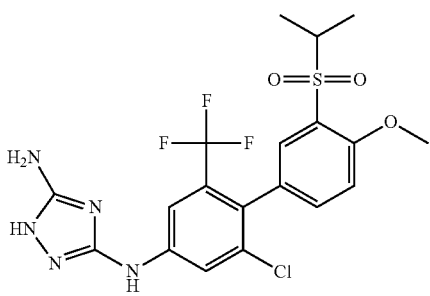

4-bromo-2-(isopropylsulfonyl)-1-methoxybenzene

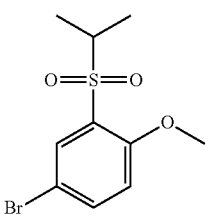

A solution of 5-bromo-2-methoxybenzene-1-sulfonyl chloride (1 g, 3.5 mmol, Eq: 1.00), sodium sulfite (817 mg, 6.48 mmol, Eq: 1.85), and sodium bicarbonate (588 mg, 7.00 mmol, Eq: 2) in water (10 mL) was heated at 95 deg for 1 hr. The reaction was cooled to room temp, and tetrabutylammonium bromide (126 mg, 391 μmol, Eq: 0.112) and 2-iodopropane (3.4 g, 2 mL, 20.0 mmol, Eq: 5.71) was added and the reaction was heated at 70 deg for 6 hr, then stirred at room temp over the weekend. Diluted with water, extracted 3× with dichloromethane and dried over sodium sulfate. 1.2 g crude chromatographed (40 g Redisep, 10 to 35% ethyl acetate/hec) to give 670 mg (65%) of desired product as a white solid.

2-(3-(isopropylsulfonyl)-4-methoxyphenyl)-4,4,5,5-tetramethyl-1,3,2-dioxaborolane

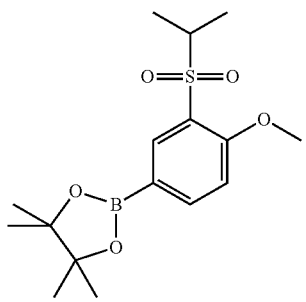

To a solution of 4-bromo-2-(isopropylsulfonyl)-1-methoxybenzene (670 mg, 2.29 mmol, Eq: 1.00), bis(pinacolato)diboron (1.45 g, 5.71 mmol, Eq: 2.5), and potassium acetate (897 mg, 9.14 mmol, Eq: 4) in Dioxane (10 mL), was added PdCl2(DPPF)-CH2Cl2 adduct (171 mg, 234 μmol, Eq: 0.102) The reaction was heated at 85 deg overnight with an Ar balloon. The reaction mixture was cooled to room temp, concentrated, diluted with ethyl acetate, washed with brine and dried over sodium sulfate. 1.8 g crude chromatographed (40 g Redisep, 30 to 50% ethyl acetate/hexane) to give 726 mg (93%) of desired product as a colorless oil, containing some pinacol diboron impurity.

N*3*-[2-Chloro-4'-methoxy-3'-(propane-2-sulfonyl)-6-trifluoromethyl-biphenyl-4-yl]-1H-[1,2,4]triazole-3,5-diamine (Compound 19)

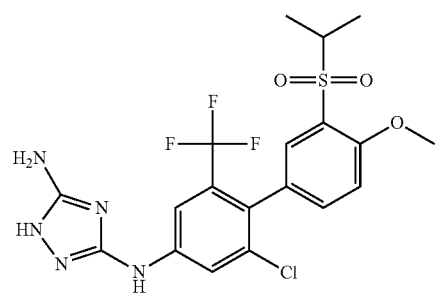 [SMILES: COc1ccc(-c2c(Cl)cc(Nc3n[nH]c(N)n3)cc2C(F)(F)F)cc1S(=O)(=O)C(C)C]

A microwave vial containing N3-(4-bromo-3-chloro-5-(trifluoromethyl)phenyl)-1H-1,2,4-triazole-3,5-diamine Intermediate 1 (250 mg, 701 μmol, Eq: 1.00), sodium carbonate (186 mg, 1.75 mmol, Eq: 2.5) and Pd(Ph3P)4 (120 mg, 104 μmol, Eq: 0.148) was degassed for 15 minutes with Ar. A solution of 2-(3-(isopropylsulfonyl)-4-methoxyphenyl)-4,4,5,5-tetramethyl-1,3,2-dioxaborolane (726 mg, 1.07 mmol, Eq: 1.52) in dioxane (6 mL) was added, followed by water (1.5 mL). The suspension was degassed for 5 min with Ar with sonication, then capped and heated at 110 deg overnight in an oil bath. The reaction was diluted with ethyl acetate, washed with brine. Dried org extract with sodium sulfate. 1 g crude chromatographed (24 g Redisep Gold, 1% to 10% methanol/dichloromethane) to give 195 mg yellow solid, containing desired product and other impurities. Further purification by SFC gave 18 mg (4%) of desired product was a light brown solid.

MS m/z 490 [M+H]

Procedure 1, 7

N3-(2-chloro-4'-(piperidin-4-ylsulfonyl)-6-(trifluoromethyl)biphenyl-4-yl)-1H-1,2,4-triazole-3,5-diamine hydrochloride (Compound 20)

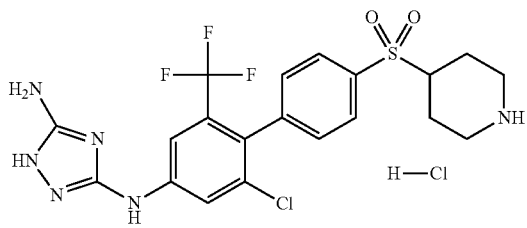

AcCl (1.1 g, 1 ml, 14.1 mmol, Eq: 33.1) was slowly added to 10 of methanol (exotherm), and cooled to room temperature. The solution was added to a solution of tert-butyl 4-(4'-(5-amino-1H-1,2,4-triazol-3-ylamino)-2'-chloro-6'-(trifluoromethyl)biphenyl-4-ylsulfonyl)piperidine-1-carboxylate Compound 1 (255 mg, 424 μmol, Eq: 1.00) in methanol (5 mL) and stirred at room temp for 5 hr. The reaction mixture was concentrated to dryness. Dissolved crude oil in 0.5 mL methanol, triturated with Et2O, and filtered the suspension to give 213 mg (93%) of desired product as a white solid.

MS m/z 501 [M+H]

Procedure 1, 7

4-[4'-(5-Amino-1H-[1,2,4]triazol-3-ylamino)-2'-chloro-6'-trifluoromethyl-biphenyl-3-yloxy]-piperidine-1-carboxylic acid tert-butyl ester (Compound 21)

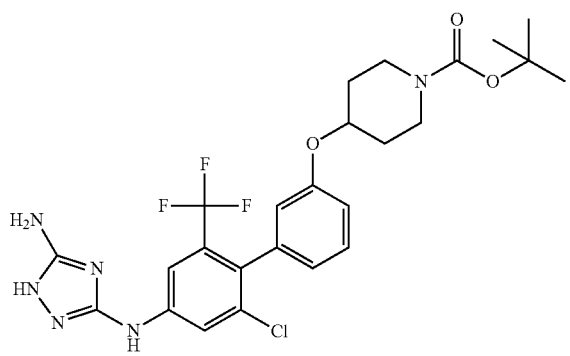 [SMILES: CC(C)(C)OC(=O)N1CCC(Oc2cccc(-c3c(Cl)cc(Nc4n[nH]c(N)n4)cc3C(F)(F)F)c2)CC1]

tert-butyl 4-(3-(4,4,5,5-tetramethyl-1,3,2-dioxaborolan-2-yl)phenoxy)piperidine-1-carboxylate

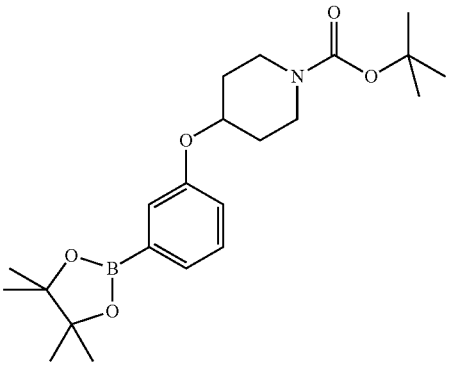 [SMILES: CC(C)(C)OC(=O)N1CCC(Oc2cccc(B3OC(C)(C)C(C)(C)O3)c2)CC1]

To a solution of 3-(4,4,5,5-tetramethyl-1,3,2-dioxaborolan-2-yl)phenol (999 mg, 4.54 mmol, Eq: 1.00), tert-butyl 4-hydroxypiperidine-1-carboxylate (914 mg, 4.54 mmol, Eq: 1.00), and triphenylphosphine (1.25 g, 4.77 mmol, Eq: 1.05) in THF (15 mL) at 0 deg, was added a solution of (E)-diazene-1,2-diylbis(piperidin-1-ylmethanone) (1.2 g, 4.77 mmol, Eq: 1.05) in THF (10 mL) dropwise. The reaction was gradually warmed to room temp and stirred overnight. The reaction mixture was concentrated, diluted with EtAOc, washed with brine, dried over sodium sulfate and chromatographed (80 g Redisep, 5 to 15% ethyl acetate-.hexane) to give 560 mg (31%) of desired product as a colorless oil.

tert-butyl 4-(4'-amino-2'-chloro-6'-(trifluoromethyl)biphenyl-3-yloxy)piperidine-1-carboxylate

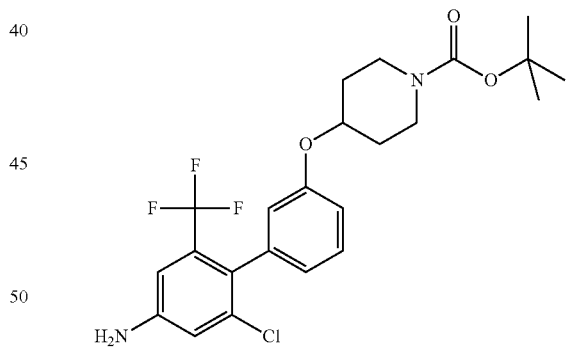

A microwave vial containing 4-bromo-3-chloro-5-(trifluoromethyl)aniline (330 mg, 1.2 mmol, Eq: 1.00), sodium carbonate (340 mg, 3.21 mmol, Eq: 2.67) and Pd(Ph3P)4 (208 mg, 180 μmol, Eq: 0.15) was degassed for 15 minutes with Ar. A solution of tert-butyl 4-(3-(4,4,5,5-tetramethyl-1,3,2-dioxaborolan-2-yl)phenoxy)piperidine-1-carboxylate (560 mg, 1.39 mmol, Eq: 1.15) in dioxane (4 mL) was added, followed by water (1 mL). The suspension was degassed for 5 min with Ar with sonication, then capped and heated at 125 in microwave for 2 hr The reaction mixture was diluted with ethyl acetate, washed with brine. Dried org extract with sodium sulfate. 1 g crude chromatographed (40 g Redisep, 20% to 30% EOAc/hexane) to give 250 mg (44%) of desired product as a colorless oil.

189 tert-butyl 4-(2'-chloro-4'-isothiocyanato-6'-(trifluoromethyl)biphenyl-3-yloxy)piperidine-1-carboxylate

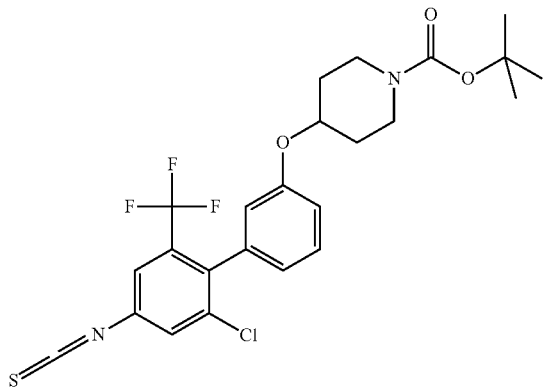 [SMILES: CC(C)(C)OC(=O)N1CCC(Oc2cccc(-c3c(Cl)cc(N=CC=S)cc3C(F)(F)F)c2)CC1]

To a suspension of calcium carbonate (153 mg, 1.53 mmol, Eq: 2.88) and tert-butyl 4-(4'-amino-2'-chloro-6'-(trifluoromethyl)biphenyl-3-yloxy)piperidine-1-carboxylate (250 mg, 531 μmol, Eq: 1.00) in dichloromethane (13.2 g, 10.0 ml, 155 mmol, Eq: 25.3)/WATER (10.0 g, 10.0 ml, 555 mmol, Eq: 90.2) at 0, was added thiophosgene (90.0 mg, 60 μl, 783 μmol, Eq: 1.47) The reaction was gradually warmed to room temperature and stirred overnight. Added 1.5 mL 1N HCl slowly. Separated organic layer and extracted aq twice more with dichloromethane. Dried over sodium sulfate and chromatographed (24 g Redisep 0 to 15% ethyl acetate/hexane) to give 175 mg (64%) of desired product as a colorless oil.

tert-butyl 4-(2'-chloro-4'-(cyanamido(methylthio)methylamino)-6'-(trifluoromethyl)biphenyl-3-yloxy)piperidine-1-carboxylate

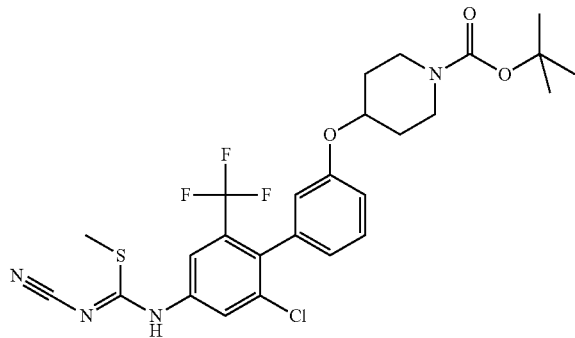 [SMILES: CS/C(=N\C#N)Nc1cc(Cl)c(-c2cccc(OC3CCN(C(=O)OC(C)(C)C)CC3)c2)c(C(F)(F)F)c1]

To a solution of tert-butyl 4-(2'-chloro-4'-isothiocyanato-6'-(trifluoromethyl)biphenyl-3-yloxy)piperidine-1-carboxylate (175 mg, 341 μmol, Eq: 1.00) in dimethoxyethane (10 mL) was added to sodium hydrogen cyanamide (33.2 mg, 519 μmol, Eq: 1.52) and methanol (1 mL). After 30 minutes, methyl iodide (145 mg, 64.0 μL, 1.02 mmol, Eq: 3) was added and the reaction was stirred overnight at room temperature. The reaction mixture was concentrated and chromatographed (24 g Redisep, 30 to 50% ethyl acetate/hexane) to give 135 mg (70%) of desired product as a colorless oil.

190

4-[4'-(5-Amino-1H-[1,2,4]triazol-3-ylamino)-2'-chloro-6'-trifluoromethyl-biphenyl-3-yloxy]-piperidine-1-carboxylic acid tert-butyl ester (Compound 21)

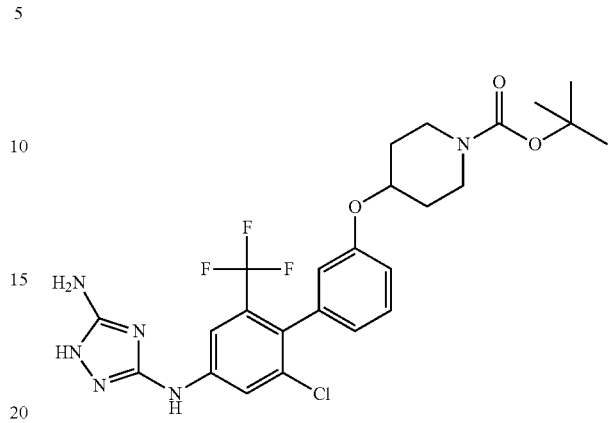

To a solution of tert-butyl 4-(2'-chloro-4'-(cyanamido(methylthio)methylamino)-6'-(trifluoromethyl)biphenyl-3-yloxy)piperidine-1-carboxylate (135 mg, 236 μmol, Eq: 1.00) in ethanol (5 mL) was added hydrazine (81.7 mg, 80 μl, 2.55 mmol, Eq: 10.8). The reaction mixture was heated at 65 deg o/n. The reaction mixture was concentrated and chromatographed (Redisep 12 g, 1 to 8% methanol/dichloromethane) to give 116 mg (89%) of desired product as a white solid.

MS m/z 497 [M+H-t-Bu]

Procedure 1, 7

N*3*-[2-Chloro-4'-(4-methyl-piperazine-1-sulfonyl)-6-trifluoromethyl-biphenyl-4-yl]-1H-[1,2,4]triazole-3,5-diamine (Compound 22)

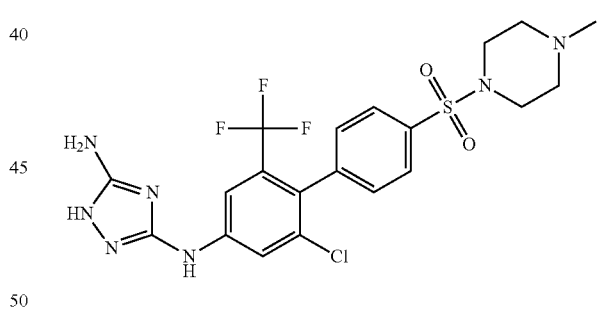

2-chloro-4'-(4-methylpiperazin-1-ylsulfonyl)-6-(trifluoromethyl)biphenyl-4-amine

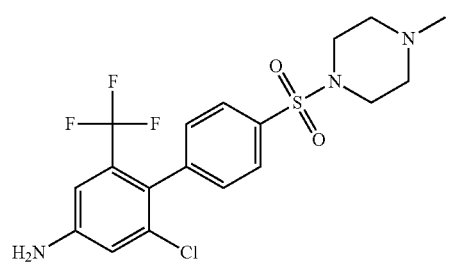 [SMILES: CN1CCN(S(=O)(=O)c2ccc(-c3c(Cl)cc(N)cc3C(F)(F)F)cc2)CC1]

A microwave vial containing 4-bromo-3-chloro-5-(trifluoromethyl)aniline (250 mg, 911 µmol, Eq: 1.00), 1-methyl-4-(4-(4,4,5,5-tetramethyl-1,3,2-dioxaborolan-2-yl)phenylsulfonyl)piperazine (412 mg, 1.12 mmol, Eq: 1.23), sodium carbonate (248 mg, 2.34 mmol, Eq: 2.57) and bis(triphenylphosphine)palladium (II) chloride (63.9 mg, 91.1 µmol, Eq: 0.1) in dimethoxyethane (4 mL)/water (1 ml) was heated overnight at 110 deg. The reaction mixture was diluted with ethyl acetate, washed with brine. Dried org extract with sodium sulfate. 500 mg crude chromatographed (40 g Redisep, 50 to 75% ethyl acetate/hexane) to give 162 mg (41%) of desired product as a colorless oil.

1-(2'-chloro-4'-isothiocyanato-6'-(trifluoromethyl)biphenyl-4-ylsulfonyl)-4-methylpiperazine

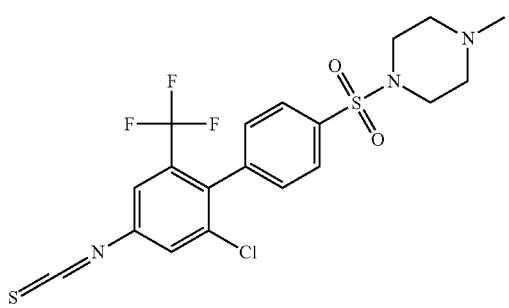 [SMILES: CN1CCN(S(=O)(=O)c2ccc(-c3c(Cl)cc(N=CC=S)cc3C(F)(F)F)cc2)CC1]

To a suspension of calcium carbonate (126 mg, 1.26 mmol, Eq: 3.37) and thiophosgene (75.0 mg, 50 µl, 652 µmol, Eq: 1.75) in dichloromethane (13.2 g, 10.0 ml, 155 mmol, Eq: 25.3)/water (10.0 g, 10.0 ml, 555 mmol, Eq: 90.2) at 0, was added 2-chloro-4'-(4-methylpiperazin-1-ylsulfonyl)-6-(trifluoromethyl)biphenyl-4-amine (162 mg, 373 µmol, Eq: 1.00) The reaction was gradually warmed to room temperature and stirred overnight. Added 1 mL 1N HCl slowly. Separated organic layer and dried over sodium sulfate. 123 mg (69%) of desired product as a yellow oil.

N-((2-chloro-4'-(4-methylpiperazin-1-ylsulfonyl)-6-(trifluoromethyl)biphenyl-4-ylamino)(methylthio)methyl)cyanamide

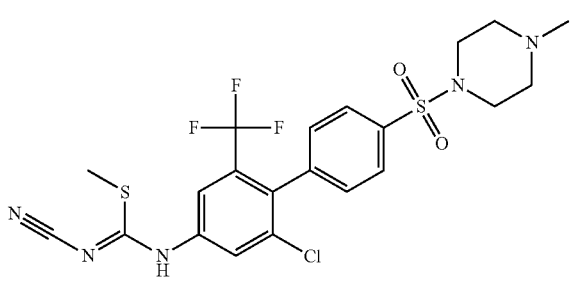 [SMILES: CS/C(=N\C#N)Nc1cc(Cl)c(-c2ccc(S(=O)(=O)N3CCN(C)CC3)cc2)c(C(F)(F)F)c1]

To a solution of 1-(2'-chloro-4'-isothiocyanato-6'-(trifluoromethyl)biphenyl-4-ylsulfonyl)-4-methylpiperazine (123 mg, 258 µmol, Eq: 1.00) in methanol (5 mL) was added to sodium hydrogen cyanamide (21.6 mg, 337 µmol, Eq: 1.31). After 30 minutes, methyl iodide (90.8 mg, 640 µmol, Eq: 2.48) was added and the reaction was stirred overnight at room temperature. The reaction mixture was concenrated and chromatographed (12 g Redisep, 10% methanol/dichloromethane) to give 51 mg (37%) of desired product as a pale yellow oil, N*3*-[2-Chloro-4'-(4-methyl-piperazine-1-sulfonyl)-6-trifluoromethyl-biphenyl-4-yl]-1H-[1,2,4]triazole-3,5-diamine (Compound 22)

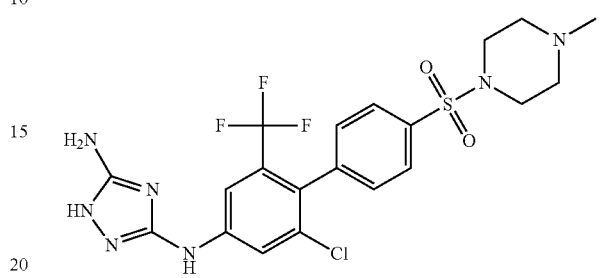

To a solution of N-((2-chloro-4'-(4-methylpiperazin-1-ylsulfonyl)-6-(trifluoromethyl)biphenyl-4-ylamino)(methylthio)methyl)cyanamide (51 mg, 95.5 µmol, Eq: 1.00) in ethanol (3 mL) was added hydrazine (30.6 mg, 30.0 µl, 955 µmol, Eq: 10). The reaction mixture was heated at 60 deg o/n. The reaction mixture was concentrated and purified by preparative plate chromatography (10% methanol/dichloromethane) to give 16 mg (33%) of desired product as a white solid.

MS m/z 517 [M+H]

Procedure 1, 7

N*3*-[2-Chloro-6-fluoro-4'-(propane-2-sulfonyl)-biphenyl-4-yl]-1H-[1,2,4]triazole-3,5-diamine (Compound 23)

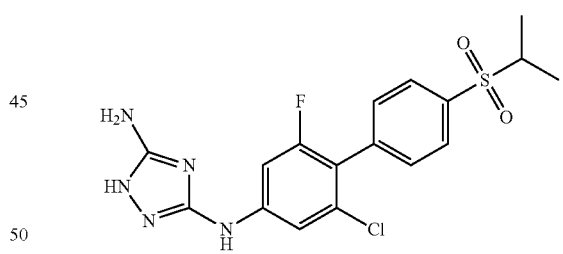

A solution N3-(4-bromo-3-chloro-5-fluorophenyl)-1H-1,2,4-triazole-3,5-diamine Intermediate 5 (100 mg, 326 µmol, Eq: 1.00), 4-(isopropylsulfonyl)phenylboronic acid (112 mg, 489 µmol, Eq: 1.5), sodium carbonate (86.4 mg, 816 µmol, Eq: 2.5) and Pd(Ph3P)4 in dioxane (2 mL)/water (0.5 mL) was heated at 95 o/n. LCMS indicated incomplete conversion. Added 2.5 mL dioxane and heated at 100 deg with microwave for 30 minutes. The reaction mixture was concentrated, diluted with ethyl acetate, washed with brine, and dried with sodium sulfate. Chromatographed (24 g Supelco, 100% dichloromethane to 10% methanol/dichloromethane) to give mixture of sm and product. Further SFC purification gave 22 mg (17%) of desired product as a light brown solid.

MS m/z 410 [M+H]

Procedure 1, 7

N—{(R)-1-[4'-(5-Amino-1H-[1,2,4]triazol-3-ylamino)-2'-chloro-6'-trifluoromethyl-biphenyl-4-yl]-ethyl}-methanesulfonamide (Compound 24)

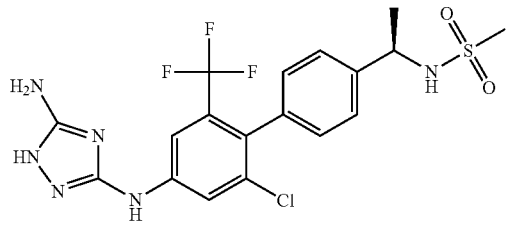 [SMILES: C[C@@H](NS(C)(=O)=O)c1ccc(-c2c(Cl)cc(Nc3n[nH]c(N)n3)cc2C(F)(F)F)cc1]

(R)—N-(1-(4-bromophenyl)ethyl)methanesulfonamide

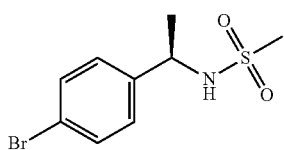

To a solution of (R)-1-(4-bromophenyl)ethanamine (1 g, 5.00 mmol, Eq: 1.00) and pyridine (587 mg, 600 µl, 7.42 mmol, Eq: 1.48) in dichloromethane (10 mL) at 0 deg, was added Ms-Cl (676 mg, 460 µl, 5.9 mmol, Eq: 1.18). The solution was gradually warmed to room temp and stirred overnight. The reaction mixture was diluted with ethyl acetate, washed with 1N HCl, brine, dried with sodium sulfate. 1.04 g crude chromatographed (40 g Redisep 0 to 50% ethyl acetate/hexane) to give 656 mg (47%) of desired product as an off-white solid.

(R)—N-(1-(4-(4,4,5,5-tetramethyl-1,3,2-dioxaborolan-2-yl)phenyl)ethyl)methanesulfonamide

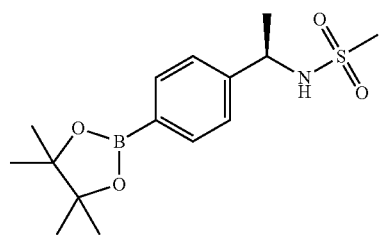

To a solution of (R)—N-(1-(4-bromophenyl)ethyl)methanesulfonamide (656 mg, 2.36 mmol, Eq: 1.00), bis(pinacolato)diboron (1.853 g, 7.3 mmol, Eq: 3.09), and potassium acetate (1.06 g, 10.8 mmol, Eq: 4.58) in Dioxane (10 mL), was added PdCl2(DPPF)-CH2Cl2 adduct (185 mg, 253 µmol, Eq: 0.107) The reaction was heated at 85 deg overnight with an Ar balloon. The reaction mixture was cooled to room temp, diluted with ether, washed with brine and dried over sodium sulfate. 1.5 g crude chromatographed (40 g Redisep, 20 to 50% ethyl acetate/hexane) to give 917 mg white solid, containing desired product and pinacol diboron impurity.

(R)—N-(1-(4'-amino-2'-chloro-6'-(trifluoromethyl)biphenyl-4-yl)ethyl)methanesulfonamide

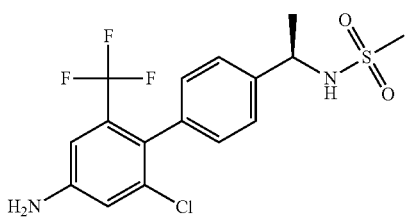 [SMILES: C[C@@H](NS(C)(=O)=O)c1ccc(-c2c(Cl)cc(N)cc2C(F)(F)F)cc1]

A microwave vial containing 4-bromo-3-chloro-5-(trifluoromethyl)aniline (304 mg, 1.11 mmol, Eq: 1.00), sodium carbonate (292 mg, 2.76 mmol, Eq: 2.49) and Pd(Ph3P)4 (211 mg, 183 µmol, Eq: 0.165) was degassed for 15 min with argon. A solution of (R)—N-(1-(4-(4,4,5,5-tetramethyl-1,3,2-dioxaborolan-2-yl)phenyl)ethyl)methanesulfonamide (917 mg, 1.13 mmol, Eq: 1.02) in dimethoxyethane (6 mL) was added, followed by water (1.5 mL). The suspension was degassed for 5 minutes with sonication, then heated at 110 deg for 1 hr with the microwave. The reaction mixture was diluted with ethyl acetate, washed with brine. Dried org extract with sodium sulfate. 1.3 g crude Chromatographed (40 g Redisep, 10% to 25% to 40% ethyl acetate/hexane) to give 140 mg (32%) of desired product as a light yellow solid.

(R)—N-(1-(2'-chloro-4'-isothiocyanato-6'-(trifluoromethyl)biphenyl-4-yl)ethyl)methanesulfonamide

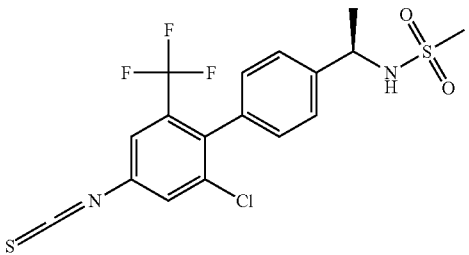 [SMILES: C[C@@H](NS(C)(=O)=O)c1ccc(-c2c(Cl)cc(N=CC=S)cc2C(F)(F)F)cc1]

To a suspension of calcium carbonate (179 mg, 1.78 mmol, Eq: 3.06) and (R)—N-(1-(4'-amino-2'-chloro-6'-(trifluoromethyl)biphenyl-4-yl)ethyl)methanesulfonamide (229 mg, 583 µmol, Eq: 1.00) in dichloromethane (10.0 ml)/water (10.0 ml) at 0, was added thiophosgene (90.0 mg, 60 µl, 783 µmol, Eq: 1.34) The reaction was gradually warmed to room temperature and stirred overnight. Added 2 mL 1N HCl slowly. Separated organic layer, dried over sodium sulfate, and concentrated to give 220 mg (87%) of desired product as a yellow solid.

N-((1R)-1-(2'-chloro-4'-(cyanamido(methylthio)
methylamino)-6'-(trifluoromethyl)biphenyl-4-yl)
ethyl)methanesulfonamide

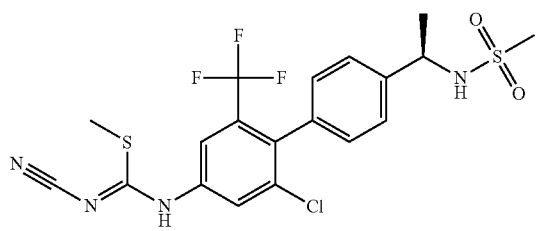 [SMILES: CS/C(=N\C#N)Nc1cc(Cl)c(-c2ccc([C@@H](C)NS(C)(=O)=O)cc2)c(C(F)(F)F)c1]

To a solution of (R)—N-(1-(2'-chloro-4'-isothiocyanato-6'-(trifluoromethyl)biphenyl-4-yl)ethyl)methanesulfonamide (220 mg, 506 µmol, Eq: 1.00) in methanol (5 mL) was added to sodium hydrogen cyanamide (44 mg, 687 µmol, Eq: 1.36). After 30 minutes, methyl iodide (182 mg, 80 µl, 1.28 mmol, Eq: 2.53) was added and the reaction was stirred overnight at room temperature. The reaction mixture was concentrated and chromatographed (24 g Redisep, 10 to 50% ethyl acetate/hexane) to give 144 mg (58%) of desired product as a yellow solid.

N—{(R)-1-[4'-(5-Amino-1H-[1,2,4]triazol-3-ylamino)-2'-chloro-6'-trifluoromethyl-biphenyl-4-yl]-ethyl}-methanesulfonamide (Compound 24)

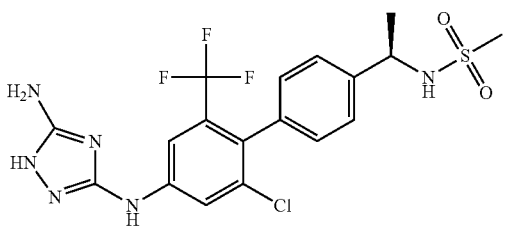 [SMILES: C[C@@H](NS(C)(=O)=O)c1ccc(-c2c(Cl)cc(Nc3n[nH]c(N)n3)cc2C(F)(F)F)cc1]

To a solution of N-((1R)-1-(2'-chloro-4'-(cyanamido(methylthio)methylamino)-6'-(trifluoromethyl)biphenyl-4-yl)ethyl)methanesulfonamide (115 mg, 233 µmol, Eq: 1.00) in ethanol (5 mL) was added hydrazine (81.7 mg, 80 µl, 2.55 mmol, Eq: 10.9). The reaction mixture was heated at 60 deg o/n. The reaction mixture was concentrated and chromatographed (11 g Supelco, 1 to 10% methanol/dichloromethane) to give 68 mg (61%) of desired product as an off-white solid
MS m/z 475 [M+H]

Procedure 1, 7

N*3*-[2-Chloro-4'-(piperidin-3-ylmethanesulfonyl)-6-trifluoromethyl-biphenyl-4-yl]-1H-[1,2,4]triazole-3,5-diamine; hydrochloride (Compound 25)

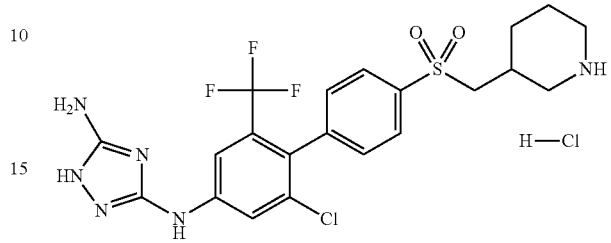

AcCl (552 mg, 500 µl, 7.03 mmol, Eq: 67.6) was slowly added to 5 mL of methanol (exotherm), and cooled to room temperature. The solution was added to a solution of tert-butyl 3-((4'-(5-amino-1H-1,2,4-triazol-3-ylamino)-2'-chloro-6'-(trifluoromethyl)biphenyl-4-ylsulfonyl)methyl)piperidine-1-carboxylate Compound 2 (64 mg, 104 µmol, Eq: 1.00) in methanol (3 mL) and stirred at room temp for 5 hr. The resulting suspension was filtered to give 55 mg (96%) of desired product as a white solid.
MS mix 515 [M+H]

Procedure 1, 7

4-[4'-(5-Amino-1H-[1,2,4]triazol-3-ylamino)-2',6'-dichloro-biphenyl-4-yloxy]-butyronitrile (Compound 26)

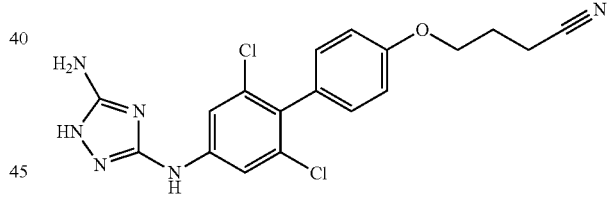

4-(2',6'-dichloro-4'-nitrobiphenyl-4-yloxy)butanenitrile

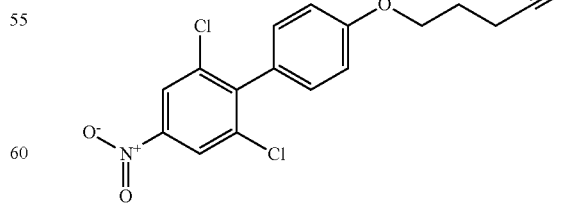

A solution of 2',6'-dichloro-4'-nitrobiphenyl-4-ol (175 mg, 616 µmol, Eq: 1.00), potassium carbonate (183 mg, 1.32 mmol, Eq: 2.15), and 4-bromobutanenitrile (186 mg, 125 µL, 1.26 mmol, Eq: 2.04) in DMF (5 mL) was stirred at room temp overnight. Diluted with ethyl acetate and washed with 1N HCl and brine. Dried over sodium sulfate. 0.4 g crude chromatographed (24 g Redisep, 5 to 15% ethyl acetate/hexane) to give 150 mg (69%) of desired product as an off-white solid.

4-(4'-amino-2',6'-dichlorobiphenyl-4-yloxy)butanenitrile

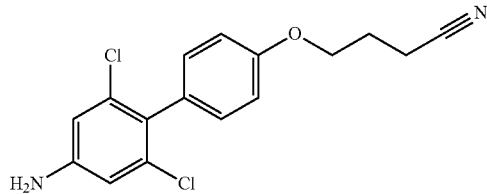 [SMILES: N#CCCCOc1ccc(-c2c(Cl)cc(N)cc2Cl)cc1]

A solution of 4-(2',6'-dichloro-4'-nitrobiphenyl-4-yloxy)butanenitrile (1.19 g, 3.39 mmol, Eq: 1.00), iron (977 mg, 17.5 mmol, Eq: 5.16) and ammonium chloride (1.85 g, 34.6 mmol, Eq: 10.2) in methanol (20 mL)/water (10 mL) was heated at 60° o/n. Filtered over Celite. Washed with methanol/ethyl acetate. Concentrated off methanol. Diluted with ethyl acetate, separated organic. Washed org extract with water and dried over sodium sulfate. 1.1 crude chromatographed (80 g Analogix, 20 to 40% ethyl acetate/hexane) to give 618 mg (57%) of desired product as a pale yellow solid.

4-(2',6'-dichloro-4'-isothiocyanatobiphenyl-4-yloxy)butanenitrile

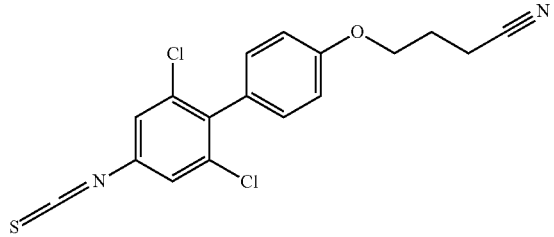 [SMILES: N#CCCCOc1ccc(-c2c(Cl)cc(N=CC=S)cc2Cl)cc1]

To a suspension of calcium carbonate (543 mg, 5.42 mmol, Eq: 2.5) and thiophosgene (315 mg, 210 µl, 2.74 mmol, Eq: 1.26) in dichloromethane (10.0 ml)/water (10.0 ml) at 0, was added 4-(4'-amino-2',6'-dichlorobiphenyl-4-yloxy)butanenitrile (697 mg, 2.17 mmol, Eq: 1.00) The reaction was gradually warmed to room temperature and stirred overnight. Added 6 mL 1N HCl slowly. Separated organic layer and dried over sodium sulfate. 0.8 g crude chromatographed (40 g Analogix, 100% hexane to 25% EtOA/hexane) to give 724 mg (92%) of desired product as a colorless oil.

(Z)-methyl N'-cyano-N-(2,6-dichloro-4'-(3-cyanopropoxy)biphenyl-4-yl)carbamimidothioate

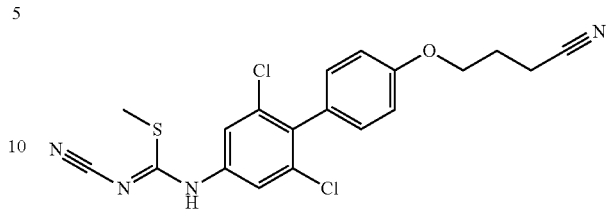

To a solution of 4-(2',6'-dichloro-4'-isothiocyanatobiphenyl-4-yloxy)butanenitrile (724 mg, 1.99 mmol, Eq: 1.00) in methanol (10 mL) was added to sodium hydrogen cyanamide (138 mg, 2.16 mmol, Eq: 1.08). After 30 minutes, methyl iodide (624 mg, 275 µl, 4.4 mmol, Eq: 2.21) was added and the reaction was stirred overnight at room temperature. The resulting suspension was filtered to give 556 mg (67%) of desired product as a white solid.

4-[4'-(5-Amino-1H-[1,2,4]triazol-3-ylamino)-2',6'-dichloro-biphenyl-4-yloxy]-butyronitrile (Compound 26)

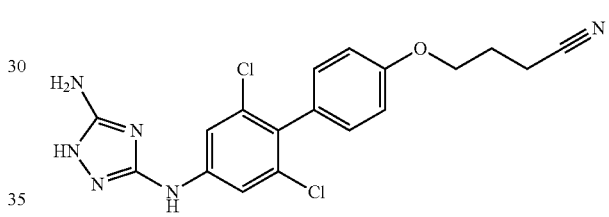

To a solution of (Z)-methyl N'-cyano-N-(2,6-dichloro-4'-(3-cyanopropoxy)biphenyl-4-yl)carbamimidothioate (556 mg, 1.33 mmol, Eq: 1.00) in methanol (10 mL) was added hydrazine (459 mg, 450 µl, 14.3 mmol, Eq: 10.8). The reaction mixture was heated at 60 deg o/n. The reaction mixture was concentrated and chromatographed (50 g Supelco 100% dichloromethane to 10% methanol/dichloromethane) to give 340 mg (64%) of desired product as a white solid.
MS m/z 403 [M+H]

Procedure 1, 7

4'-(5-Amino-1H-[1,2,4]triazol-3-ylamino)-2'-chloro-6'-trifluoromethyl-biphenyl-4-sulfonic acid ((S)-1-pyrrolidin-2-ylmethyl)-amide; hydrochloride (Compound 27)

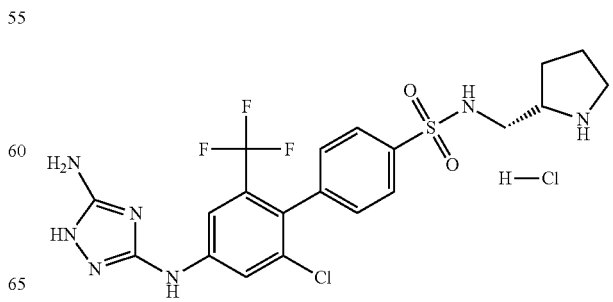

199

(S)-tert-butyl 2-((4-bromophenylsulfonamido)methyl)pyrrolidine-1-carboxylate

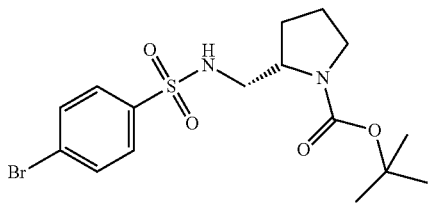

To a solution of (S)-tert-butyl 2-(aminomethyl)pyrrolidine-1-carboxylate (403 mg, 2.01 mmol, Eq: 1.00) and Et3N (436 mg, 600 µl, 4.3 mmol, Eq: 2.14) in dichloromethane (10 mL) at 0 deg, was added 4-bromobenzene-1-sulfonyl chloride (540 mg, 2.11 mmol, Eq: 1.05). The solution was gradually warmed to room temp and stirred overnight. The reaction was diluted with dichloromethane, washed with 1N HCl, brine, dried with sodium sulfate. 900 mg crude chromatographed (40 g Analogix, 10 to 35% ethyl acetate/hexane) to give 639 mg (76%) of desired product as a colorless oil.

(S)-tert-butyl 2-((4-(4,4,5,5-tetramethyl-1,3,2-dioxaborolan-2-yl)phenylsulfonamido)methyl)pyrrolidine-1-carboxylate

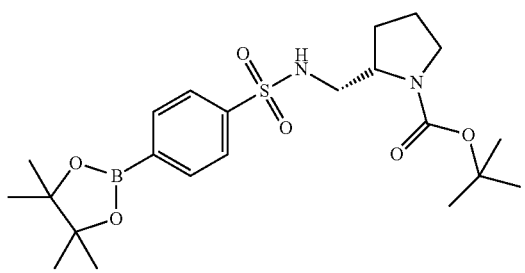

To a solution of (S)-tert-butyl 2-((4-bromophenylsulfonamido)methyl)pyrrolidine-1-carboxylate (639 mg, 1.52 mmol, Eq: 1.00), bis(pinacolato)diboron (967 mg, 3.81 mmol, Eq: 2.5), and potassium acetate (673 mg, 6.86 mmol, Eq: 4.5) in Dioxane (10 mL), was added PdCl2(DPPF)-CH2Cl2 adduct (112 mg, 152 µmol, Eq: 0.1) The reaction was heated at 85 deg overnight with an Ar balloon. The reaction mixture was cooled to room temp, concentrated, diluted with ether, washed with brine and dried over sodium sulfate. 1.4 g crude was chromatographed (40 g Redisep, 10 to 50% ethyl acetate/hexane) to give 880 mg pale yellow oil, containing desired product with pinacol diboron impurity.

200

(S)-tert-butyl 2-((4'-amino-2'-chloro-6'-(trifluoromethyl)biphenyl-4-ylsulfonamido)methyl)pyrrolidine-1-carboxylate

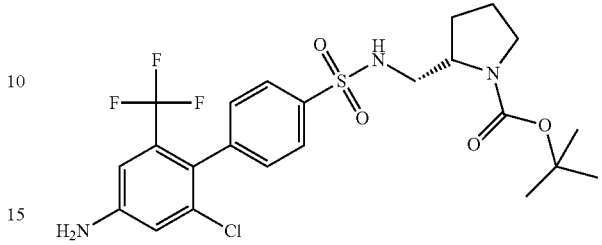

A microwave vial containing 4-bromo-3-chloro-5-(trifluoromethyl)aniline (308 mg, 1.12 mmol, Eq: 1.00), sodium carbonate (297 mg, 2.81 mmol, Eq: 2.5) and Pd(Ph3P)4 (195 mg, 168 µmol, Eq: 0.15) was degassed for 15 minutes with Ar. A solution of (S)-tert-butyl 2-((4-(4,4,5,5-tetramethyl-1,3,2-dioxaborolan-2-yl)phenylsulfonamido)methyl)pyrrolidine-1-carboxylate (880 mg, 1.13 mmol, Eq: 1.01) in dimethoxyethane (6 mL) was added, followed by water (1.5 mL). The suspension was degassed for 5 min with Ar with sonication, then heated at 125 deg for 1.5 hr with microwave. The reaction mixture was diluted with ethyl acetate, washed with brine. Dried org extract with sodium sulfate. 1.59 g crude chromatographed (80 g Redisep, 10% to 30% ethyl acetate/hexane) to give 158 mg (26%) of desired product as a pale yellow oil.

(S)-tert-butyl 2-((2'-chloro-4'-isothiocyanato-6'-(trifluoromethyl)biphenyl-4-ylsulfonamido)methyl)pyrrolidine-1-carboxylate

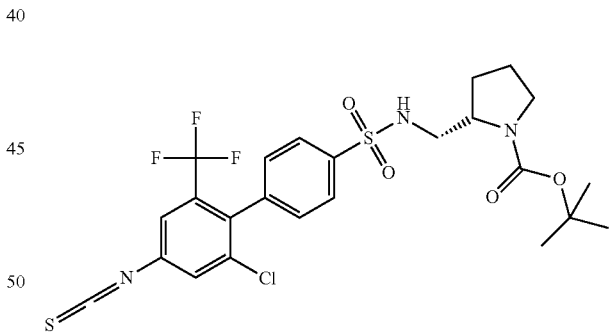

To a suspension of calcium carbonate (82.9 mg, 828 µmol, Eq: 2.8) and (S)-tert-butyl 2-((4'-amino-2'-chloro-6'-(trifluoromethyl)biphenyl-4-ylsulfonamido)methyl)pyrrolidine-1-carboxylate (158 mg, 296 µmol, Eq: 1.00) in dichloromethane (10.0 ml)/water (10.0 ml) at 0, was added thiophosgene (45.0 mg, 30 µl, 391 µmol, Eq: 1.32) The reaction was gradually warmed to room temperature and stirred overnight. Added 1 mL 1N HCl slowly. Separated organic layer. Extracted aq once more with dichloromethane. Organic extracts dried over sodium sulfate. 180 mg crude chromatographed (24 g Redisep, 10 to 30% ethyl acetate/hexane) to give 137 mg (90%) of desired product as a colorless oil.

(2S)-tert-butyl 2-((2'-chloro-4'-(cyanamido(methyl-thio)methylamino)-6'-(trifluoromethyl)biphenyl-4-ylsulfonamido)methyl)pyrrolidine-1-carboxylate

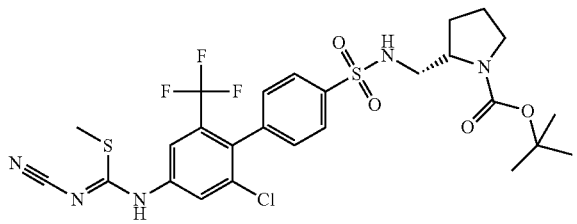

To a solution of (S)-tert-butyl 2-((2'-chloro-4'-isothiocyanato-6'-(trifluoromethyl)biphenyl-4-ylsulfonamido)methyl)pyrrolidine-1-carboxylate (154 mg, 267 µmol, Eq: 1.00) in dimethoxyethane (5 mL) was added to sodium hydrogen cyanamide (20.5 mg, 321 µmol, Eq: 1.2) and methanol (1 mL). After 30 minutes, methyl iodide (90.8 mg, 40 µl, 640 µmol, Eq: 2.39) was added and the reaction was stirred overnight at room temperature. The reaction mixture was concentrated and chromatographed (12 g Redisep, 40 to 75% ethyl acetate/hexane) to give 81 mg (48%) colorless oil.

(S)-tert-butyl 2-((4'-(5-amino-1H-1,2,4-triazol-3-ylamino)-2'-chloro-6'-(trifluoromethyl)biphenyl-4-ylsulfonamido)methyl)pyrrolidine-1-carboxylate

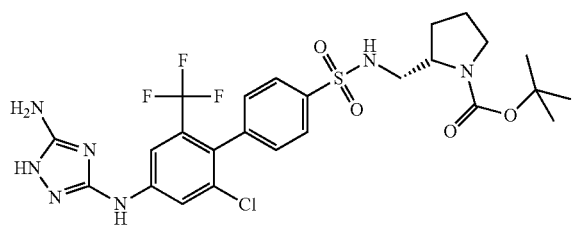

To a solution of (2S)-tert-butyl 2-((2'-chloro-4'-(cyanamido(methylthio)methylamino)-6'-(trifluoromethyl)biphenyl-4-ylsulfonamido)methyl)pyrrolidine-1-carboxylate (81 mg, 128 µmol, Eq: 1.00) in ethanol (5 mL) was added hydrazine (40.8 mg, 40 µl, 1.27 mmol, Eq: 9.98). The reaction mixture was heated at 65 deg o/n. The reaction mixture was concentrated and chromatographed (Supelco 11 g, 1 to 10% methanol/dichloromethane) to give 62 mg (79%) of desired product as a white solid.

4'-(5-Amino-1H-[1,2,4]triazol-3-ylamino)-2'-chloro-6'-trifluoromethyl-biphenyl-4-sulfonic acid ((S)-1-pyrrolidin-2-ylmethyl)-amide; hydrochloride (Compound 27)

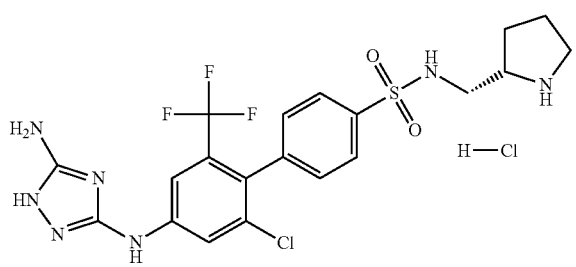

AcCl (552 mg, 0.5 mL, 7.03 mmol, Eq: 69.9) was added to 10 mL of methanol. The solution was added to a solution of (S)-tert-butyl 2-((4'-(5-amino-1H-1,2,4-triazol-3-ylamino)-2'-chloro-6'-(trifluoromethyl)biphenyl-4-ylsulfonamido)methyl)pyrrolidine-1-carboxylate (62 mg, 101 µmol, Eq: 1.00) in methanol (3 mL) and stirred at room temp for 5 hr. The reaction was concentrated to dryness. triturated with Et2O, and filtered to give 52 mg (94%) of desired product as a white solid.

MS m/z 516 [M+H]

Procedure 6

N-[4'-(5-Amino-1H-[1,2,4]triazol-3-ylamino)-2',6'-dichloro-2-fluoro-biphenyl-4-yl]-methanesulfonamide (Compound 28)

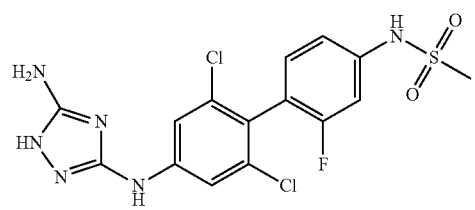 [SMILES: CS(=O)(=O)Nc1ccc(-c2c(Cl)cc(Nc3n[nH]c(N)n3)cc2Cl)c(F)c1]

N-(3-fluoro-4-(4,4,5,5-tetramethyl-1,3,2-dioxaborolan-2-yl)phenyl)methanesulfonamide

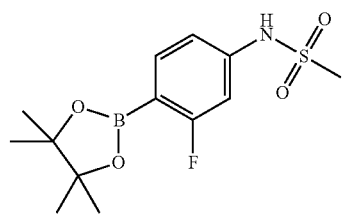

To a solution of 3-fluoro-4-(4,4,5,5-tetramethyl-1,3,2-dioxaborolan-2-yl)aniline (300 mg, 1.27 mmol, Eq: 1.00) and pyridine (0.350 mmol, 4.33 mmol, Eq: 3.42) in dichloromethane (10 mL) at 0 deg, was added Ms-Cl (368 mg, 250 µl, 3.21 mmol, Eq: 2.54). The solution was gradually warmed to room temp and stirred overnight. Diluted with dichloromethane, washed with 1N HCl, brine, dried with sodium sulfate. 600 mg crude chromatographed (40 g Redisep 15 to 30% ethyl acetate/hexane) to give 213 mg (53%) of desired product as a white solid.

N-[4'-(5-Amino-1H-[1,2,4]triazol-3-ylamino)-2',6'-dichloro-2-fluoro-biphenyl-4-yl]-methanesulfonamide (Compound 28)

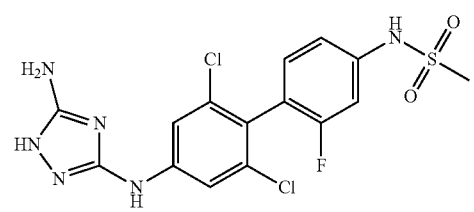 [SMILES: CS(=O)(=O)Nc1ccc(-c2c(Cl)cc(Nc3n[nH]c(N)n3)cc2Cl)c(F)c1]

A microwave vial containing N3-(4-bromo-3,5-dichlorophenyl)-1H-1,2,4-triazole-3,5-diamine Intermediate 2 (100 mg, 310 μmol, Eq: 1.00), N3-(4-bromo-3,5-dichlorophenyl)-1H-1,2,4-triazole-3,5-diamine (100 mg, 310 μmol, Eq: 1.00), sodium carbonate (82.0 mg, 774 μmol, Eq: 2.5) and bis(di-t-Bu-phosiphino)ferrocenyl PdCl2 (30.3 mg, 46.4 μmol, Eq: 0.15) was degassed for 15 minutes with Argon. A solution of N-(3-fluoro-4-(4,4,5,5-tetramethyl-1,3,2-dioxaborolan-2-yl)phenyl)methanesulfonamide (213 mg, 676 μmol, Eq: 2.18) in Dioxane (2 mL) was added, followed by water (0.5 mL), and the suspension was degassed for 5 minutes with sonication, and the reaction was heated at 125o for 1 hr with microwave. The reaction mixture was diluted with ethyl acetate, washed with brine, and dried with sodium sulfate. Chromatographed (40 g Redisep Gold, 0 to 10% methanol/dichloromethane) gave 63 mg light brown solid, containing desired product and impurity. Triturated with dichloromethane/methanol and filtered to give 40 mg (30%) of desired product as a light brown solid.

MS m/z 433 [M+H]

Procedure 1, 7

N*3*-[2-Chloro-4'-(piperidine-3-sulfonyl)-6-trifluoromethyl-biphenyl-4-yl]-1H-[1,2,4]triazole-3,5-diamine; hydrochloride (Compound 29)

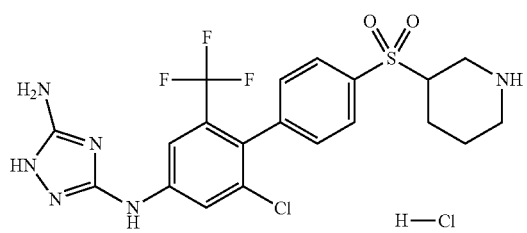 [SMILES: Nc1nc(Nc2cc(Cl)c(-c3ccc(S(=O)(=O)C4CCCNC4)cc3)c(C(F)(F)F)c2)n[nH]1 ; Cl]

AcCl (1.1 g, 1 mL, 14.1 mmol, Eq: 33.4) was slowly added to 10 of methanol (exotherm), and cooled to room temperature. The solution was added to a solution of tert-butyl 3-(4'-(5-amino-1H-1,2,4-triazol-3-ylamino)-2'-chloro-6'-(trifluoromethyl)biphenyl-4-ylsulfonyl)piperidine-1-carboxylate Compound 6 (253 mg, 421 μmol, Eq: 1.00) in methanol (5 mL) and stirred at room temp for 5 hr. TLC ok, no sm. White precipitate forms. Filtered off solid and dried at 45 deg over weekend w. house vac to give 208 mg (92%) of desired product as a white solid.

MS m/z 501 [M+H]

Procedure 1, 7

N*3*-(2-Chloro-6-fluoro-4'-methanesulfonyl-biphenyl-4-yl)-1H-[1,2,4]triazole-3,5-diamine (Compound 30)

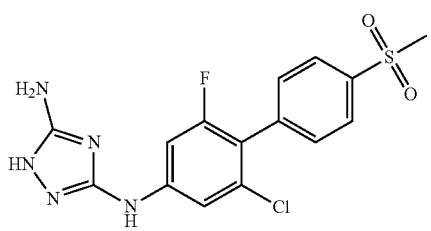 [SMILES: CS(=O)(=O)c1ccc(-c2c(F)cc(Nc3n[nH]c(N)n3)cc2Cl)cc1]

N-(2-chloro-6-fluoro-4'-(methylsulfonyl)biphenyl-4-yl)acetamide

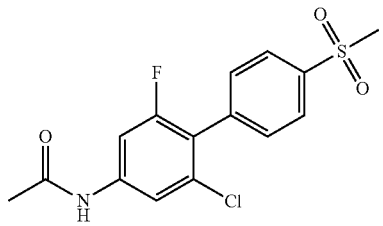 [SMILES: CC(=O)Nc1cc(F)c(-c2ccc(S(C)(=O)=O)cc2)c(Cl)c1]

A solution N-(4-bromo-3-chloro-5-fluorophenyl)acetamide (500 mg, 1.88 mmol, Eq: 1.00), 4-(methylsulfonyl)phenylboronic acid (450 mg, 2.25 mmol, Eq: 1.2), sodium carbonate (497 mg, 4.69 mmol, Eq: 2.5) and bis(triphenylphosphine)palladium (II) chloride (135 mg, 192 μmol, Eq: 0.103) in dimethoxyethane (10 mL)/water (2.5 mL) was heated overnight at 95° C. The reaction was concentrated, diluted with ethyl acetate, washed with brine and dried over sodium sulfate. 0.6 g crude was chromatographed (80 g Analogix, 10% to 20% ethyl acetate/hexane) to give 528 mg (82%) of desired product as a white solid.

2-chloro-6-fluoro-4'-(methylsulfonyl)biphenyl-4-amine

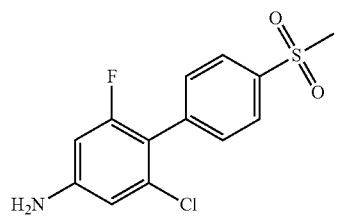 [SMILES: CS(=O)(=O)c1ccc(-c2c(F)cc(N)cc2Cl)cc1]

A solution of N-(2-chloro-6-fluoro-4'-(methylsulfonyl)biphenyl-4-yl)acetamide (616 mg, 1.8 mmol, Eq: 1.00) and HCl (7.2 g, 6 mL, 36.0 mmol, Eq: 20.0) in ethanol (5 mL) was heated at reflux for 2 hr. The reaction mixture was concentrated, dissolved in ethyl acetate, washed with 36 mL 1N NaOH and dried over sodium sulfate. 0.6 g crude was chromatographed (40 g Analogix, 100% hexane to 50% ethyl acetate/hexane) to give 429 mg (79%) of desired product as a white solid.

2-chloro-6-fluoro-4-isothiocyanato-4'-(methylsulfonyl)biphenyl

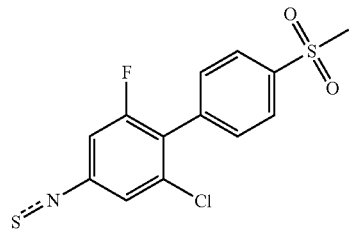

To a suspension of calcium carbonate (358 mg, 3.58 mmol, Eq: 2.5) and thiophosgene (188 mg, 125 μl, 1.63 mmol, Eq: 1.14) in dichloromethane (10.0 ml)/water (10.0 ml) at 0, was added 2-chloro-6-fluoro-4'-(methylsulfonyl) biphenyl-4-amine (429 mg, 1.43 mmol, Eq: 1.00) The reaction was gradually warmed to room temperature and stirred overnight. Added 4 mL 1N HCl slowly. Separated organic layer and dried over sodium sulfate. 396 mg (81%) of desired product as a white solid.

N-((2-chloro-6-fluoro-4'-(methylsulfonyl)biphenyl-4-ylamino)(methylthio)methyl)cyanamide

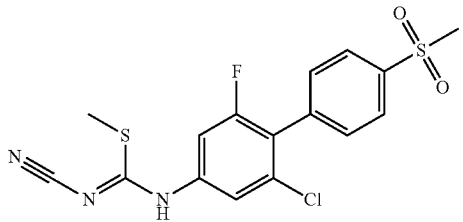 [SMILES: CS/C(=N\C#N)Nc1cc(F)c(-c2ccc(S(C)(=O)=O)cc2)c(Cl)c1]

To a solution of 2-chloro-6-fluoro-4-isothiocyanato-4'-(methylsulfonyl)biphenyl (396 mg, 1.16 mmol, Eq: 1.00) in methanol (5 mL) was added to sodium hydrogen cyanamide (77.9 mg, 1.22 mmol, Eq: 1.05). After 30 minutes, methyl iodide (340 mg, 150 μl, 2.4 mmol, Eq: 2.07) was added and the reaction was stirred overnight at room temperature. The resulting suspension was filtered to give 263 mg (57%) of desired product as a white solid.

N*3*-(2-Chloro-6-fluoro-4'-methanesulfonyl-biphenyl-4-yl)-1H-[1,2,4]triazole-3,5-diamine (Compound 30)

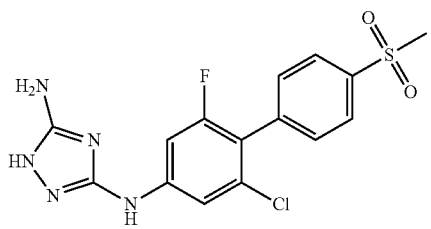 [SMILES: CS(=O)(=O)c1ccc(-c2c(F)cc(Nc3n[nH]c(N)n3)cc2Cl)cc1]

To a solution of N-((2-chloro-6-fluoro-4'-(methylsulfonyl)biphenyl-4-ylamino)(methylthio)methyl)cyanamide (264 mg, 660 μmol, Eq: 1.00) in ethanol (5 mL) was added hydrazine (245 mg, 240 μl, 7.65 mmol, Eq: 11.6). The reaction mixture was heated at 60 deg o/n. The resulting suspension was filtered to give 190 mg (75%) of desired product as a white solid.

MS m/z 382 [M+H]

Procedure 6

N*3*-(2,6-Dichloro-4'-methanesulfonylmethyl-biphenyl-4-yl)-1H-[1,2,4]triazole-3,5-diamine (Compound 31)

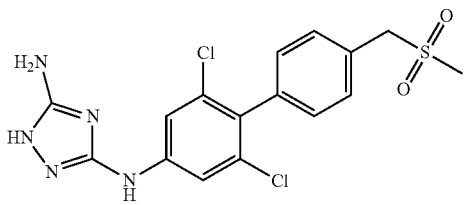 [SMILES: CS(=O)(=O)Cc1ccc(-c2c(Cl)cc(Nc3n[nH]c(N)n3)cc2Cl)cc1]

4,4,5,5-tetramethyl-2-(4-(methylsulfonylmethyl) phenyl)-1,3,2-dioxaborolane

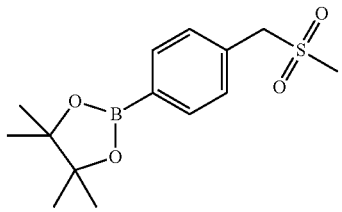

To a solution of 1-bromo-4-(methylsulfonylmethyl)benzene (500 mg, 2.01 mmol, Eq: 1.00), bis(pinacolato)diboron (1.27 g, 5.02 mmol, Eq: 2.5), and potassium acetate (940 mg, 9.58 mmol, Eq: 4.77) in dioxane (10 mL), was added PdCl2(DPPF)-CH2Cl2 adduct (147 mg, 201 μmol, Eq: 0.1) The reaction was heated at 85 deg overnight. The reaction mixture was cooled to room temp, concentrated, diluted with ether, washed with brine and dried over sodium sulfate. 1.71 g crude chromatographed (80 g Redisep, 10 to 20% ethyl acetate/hexane) to give 1.17 g brown oil, containing desired product and pinacol diboron impurity (~50%).

N*3*-(2,6-Dichloro-4'-methanesulfonylmethyl-biphenyl-4-yl)-1H-[1,2,4]triazole-3,5-diamine (Compound 31)

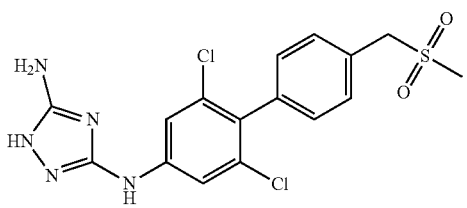 [SMILES: CS(=O)(=O)Cc1ccc(-c2c(Cl)cc(Nc3n[nH]c(N)n3)cc2Cl)cc1]

A microwave vial containing N3-(4-bromo-3,5-dichlorophenyl)-1H-1,2,4-triazole-3,5-diamine Intermediate 2 (101 mg, 313 μmol, Eq: 1.00), sodium carbonate (85.0 mg, 802 μmol, Eq: 2.56) and bis(di-t-Bu-phosiphino)ferrocenyl PdCl2 (33.0 mg, 50.6 μmol, Eq: 0.162) was degassed for 15 minutes with Argon. A solution of 4,4,5,5-tetramethyl-2-(4-(methylsulfonylmethyl)phenyl)-1,3,2-dioxaborolane (300 mg, 1.01 mmol, Eq: 3.24) in Dioxane (2 mL) was added, followed by water (0.5 mL), and the suspension was degassed for 5 minutes with sonication, and the reaction was heated at 125o for 1 hr with microwave. The reaction mixture as diluted with ethyl acetate, washed with brine, and dried with sodium sulfate. 190 mg crude chromatographed (24 g Redisep Gold, 0 to 10% methanol/dichloromethane) to give 50 mg of desired product with impurities. Further purification (SFC) gave 38 mg (30%) of desired product as a white solid.

MS m/z 412 [M+H]

Compound 32

Procedure 1, 7

N*3*-[4'-(Azetidin-3-ylmethoxy)-2,6-dichloro-biphenyl-4-yl]-1H-[1,2,4]triazole-3,5-diamine; hydrochloride (Compound 32)

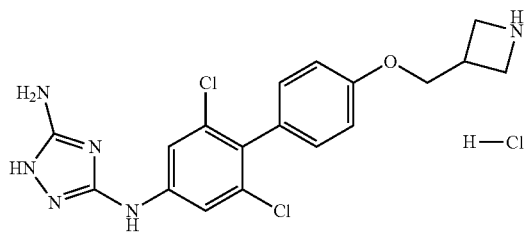 [SMILES: Nc1nc(Nc2cc(Cl)c(-c3ccc(OCC4CNC4)cc3)c(Cl)c2)n[nH]1 ; Cl]

3-[4-(4,4,5,5-Tetramethyl-[1,3,2]dioxaborolan-2-yl)-phenoxymethyl]-azetidine-1-carboxylic acid tert-butyl ester

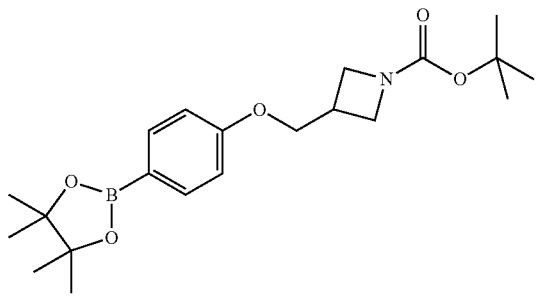 [SMILES: CC(C)(C)OC(=O)N1CC(COc2ccc(B3OC(C)(C)C(C)(C)O3)cc2)C1]

In a 100 mL round-bottomed flask, triphenylphosphine (1.25 g, 4.77 mmol, Eq: 1.05), tert-butyl 3-(hydroxymethyl)azetidine-1-carboxylate (851 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.85 g (48.1%) oil. MH+ 390.0

3-(4'-Amino-2',6'-dichloro-biphenyl-4-yloxymethyl)-azetidine-1-carboxylic acid tert-butyl ester

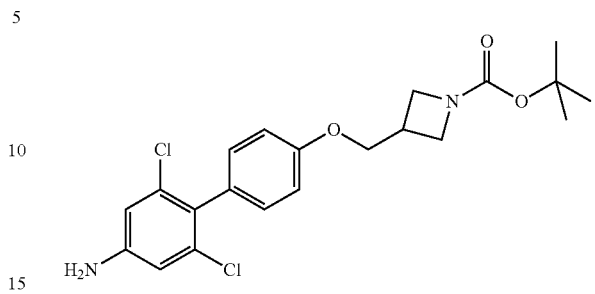

A microwave vial containing 4-bromo-3,5-dichloroaniline (303 mg, 1.26 mmol, Eq: 1.00), sodium carbonate (333 mg, 3.14 mmol, Eq: 2.5), tert-butyl 3-((4-(4,4,5,5-tetramethyl-1,3,2-dioxaborolan-2-yl)phenoxy)methyl)azetidine-1-carboxylate (558 mg, 1.43 mmol, Eq: 1.14) and Pd(Ph3P)4 (124 mg, 107 µmol, Eq: 0.0853) was degassed for 15 minutes with Ar. Dioxane was added, followed by water. The suspension was degassed for 5 min with Ar with sonication, then capped and heated at 125 in microwave for 2 hr. Diluted with ethyl acetate, washed with brine, and dried org extract with sodium sulfate. 1 g crude chromatographed (40 g Redisep, 10% to 25% EOAc/hex) to give 282 mg (53%) of desired product as a pale yellow oil.

3-(2',6'-Dichloro-4'-isothiocyanato-biphenyl-4-yloxymethyl)-azetidine-1-carboxylic acid tert-butyl ester

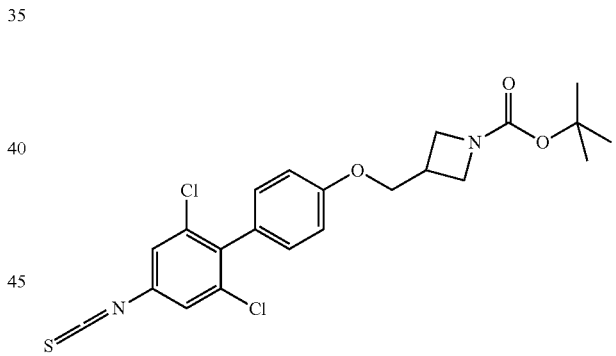

To a suspension of calcium carbonate (62 mg, 619 µmol, Eq: 2.72) tert-butyl 3-((4'-amino-2'-chloro-6'-(trifluoromethyl)biphenyl-4-yloxy)methyl)azetidine-1-carboxylate in dichloromethane (10.0 ml)/water (10.0 ml) at 0, was added thiophosgene (37.5 mg, 25 µl, 326 µmol, Eq: 1.43) The reaction was gradually warmed to room temperature and stirred overnight. Added 1 mL 1N HCl slowly. Separated organic layer and extracted aq twice more with dichloromethane. Dried over sodium sulfate to give 92 mg (81%) of desired product as a pale yellow oil.

To a suspension of calcium carbonate (187 mg, 1.87 mmol, Eq: 2.8) and 3-(4'-Amino-2',6'-dichloro-biphenyl-4-yloxymethyl)-azetidine-1-carboxylic acid tert-butyl ester (282 mg, 666 µmol, Eq: 1.00) in dichloromethane (10.0 ml)/water (10.0 ml) at 0, was added thiophosgene (105 mg, 70 µl, 913 µmol, Eq: 1.37) The reaction was gradually warmed to room temperature and stirred overnight. Added 2 mL 1N HCl slowly. Separated organic layer and extracted aq twice more with DCM. Dried over sodium sulfate and concentrated to give 222 mg (72%) of desired product as a pale yellow oil.

3-(2',6'-Dichloro-4'-(cyanamido(methylthio)methyl-amino)-azetidine-1-carboxylic acid tert-butyl ester

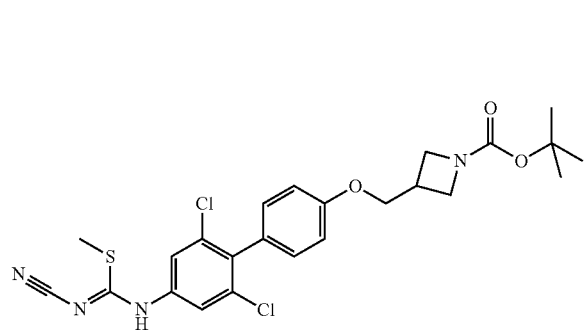 [SMILES: CS/C(=N\C#N)Nc1cc(Cl)c(-c2ccc(OCC3CN(C(=O)OC(C)(C)C)C3)cc2)c(Cl)c1]

To a solution of tert-butyl 3-42',6'-dichloro-4'-isothiocyanatobiphenyl-4-yloxy)methyl)azetidine-1-carboxylate (222 mg, 477 µmol, Eq: 1.00) in dimethoxethane (10 mL) was added to sodium hydrogen cyanamide (46 mg, 719 µmol, Eq: 1.51) and methanol (1 mL). After 30 minutes, methyl iodide (204 mg, 90 µl, 1.44 mmol, Eq: 3.02) was added and the reaction was stirred overnight at room temperature. The reaction mixture was concentrated and chromatographed (12 g Redisep, 50 to 75% EtOAc/hex) to give 149 mg (60%) of desired product as a white solid.

3-[4'-(5-Amino-1H-[1,2,4]triazol-3-ylamino)-2',6'-dichloro-biphenyl-4-yloxymethyl]-azetidine-1-carboxylic acid tert-butyl ester

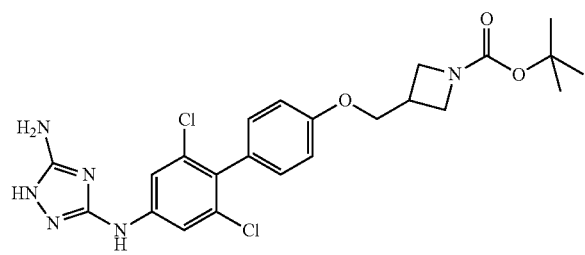 [SMILES: CC(C)(C)OC(=O)N1CC(COc2ccc(-c3c(Cl)cc(Nc4n[nH]c(N)n4)cc3Cl)cc2)C1]

To a solution of tert-butyl 3-((2',6'-dichloro-4'-(cyanamido(methylthio)methylamino)biphenyl-4-yloxy)methyl) azetidine-1-carboxylate (149 mg, 285 µmol, Eq: 1.00) in ethanol (5 mL) was added hydrazine (102 mg, 100 µl, 3.19 mmol, Eq: 11.2). The reaction mixture was heated at 65 deg o/n. The suspension was filtered to give 90 mg of desired product as a white solid. The filtrate was concentrated and chromatographed (Redisep 12 g, 1 to 10% MeOH/DCM) to give an additional 52 mg of desired product as a white solid. Total product 142 mg (99%).

N*3*-[4'-(Azetidin-3-ylmethoxy)-2,6-dichloro-biphenyl-4-yl]-1H-[1,2,4]triazole-3,5-diamine; hydrochloride (Compound 32)

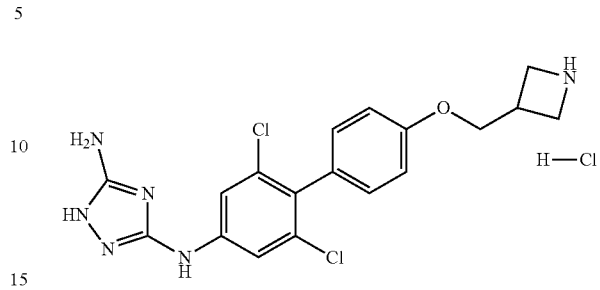

AcCl (552 mg, 500 µl, 7.03 mmol, Eq: 88.1) was slowly added to 10 mL of methanol (exotherm), and cooled to room temperature. The solution was added to a solution of tert-butyl 3-((4'-(5-amino-1H-1,2,4-triazol-3-ylamino)-2'-chloro-6'-(trifluoromethyl)biphenyl-4-yloxy)methyl)azetidine-1-carboxylate (43 mg, 79.8 µmol, Eq: 1.00) in methanol (2 mL) and stirred at room temp for 5 hr. The reaction mixture was concentrated, dissolved in 1 mL methanol, triturated with ether, and filtered to give 32 mg (84%) of desired product as a white solid.

MS m/z 439 [M+H]

AcCl (1.1 g, 1 ml, 14.1 mmol, Eq: 50.1) was slowly added to 10 of methanol (exotherm), and cooled to room temperature. The solution was added to a solution of tert-butyl 3-((4'-(5-amino-1H-1,2,4-triazol-3-ylamino)-2',6'-dichloro-biphenyl-4-yloxy)methyl)azetidine-1-carboxylate (142 mg, 281 µmol, Eq: 1.00) in methanol (5 mL) and stirred at room temp for 5 hr. The resulting suspension was filtered and rinsed with ether to give 109 mg (88%) of desired product as a white solid.

MS m/z 405, 441 [M+H]

Procedure 1, 7

N*3*-[2-Chloro-4'-(piperazine-1-sulfonyl)-6-trifluoromethyl-biphenyl-4-yl]-1H-[1,2,4]triazole-3,5-diamine (Compound 33)

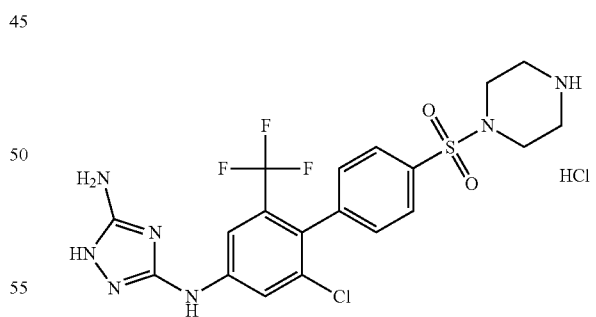

AcCl (1.1 g, 1 mL, 14.1 mmol, Eq: 62.3) was added to 10 mL of methanol. The solution was added to a solution of tert-butyl 4-(4'-(5-amino-1H-1,2,4-triazol-3-ylamino)-2'-chloro-6'-(trifluoromethyl)biphenyl-4-ylsulfonyl)piperazine-1-carboxylate compound 16 (136 mg, 226 µmol, Eq: 1.00) in methanol (5 mL) and stirred at room temp for 3 hr. The reaction mixture was concentrated to dryness, triturated with Et2O, and filtered to give 106 mg (87%) of desired product as a white solid.

MS m/z 502 [M+H]

Procedure 6

4'-(5-Amino-1H-[1,2,4]triazol-3-ylamino)-2'-chloro-6'-fluoro-biphenyl-4-sulfonic acid dimethylamide (Compound 34)

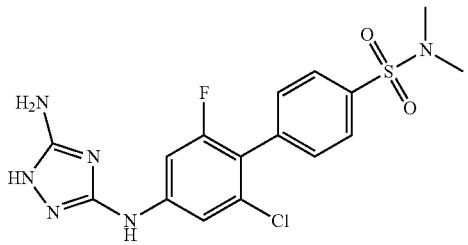 [SMILES: CN(C)S(=O)(=O)c1ccc(-c2c(F)cc(Nc3n[nH]c(N)n3)cc2Cl)cc1]

A microwave vial containing N3-(4-bromo-3-chloro-5-fluorophenyl)-1H-1,2,4-triazole-3,5-diamine, Intermediate 5 (100 mg, 326 μmol, Eq: 1.00), N,N-dimethyl-4-(4,4,5,5-tetramethyl-1,3,2-dioxaborolan-2-yl)benzenesulfonamide (153 mg, 492 μmol, Eq: 1.51), sodium carbonate (89 mg, 840 μmol, Eq: 2.57) and Pd(Ph3P)4 (37.7 mg, 32.6 μmol, Eq: 0.1) was degassed for 15 minutes with Argon. Dioxane (2 mL) and water (0.5 mL) was added and the reaction was heated at 125o for 30 min with microwave. The reaction mixture was concentrated, diluted with ethyl acetate, washed with brine, and dried with sodium sulfate. 250 mg crude was chromatographed (24 g Supelco, 100% dichloromethane to 5% methanol/dichloromethane) to give 55 mg of desired product and impurities. Further purification (SFC) gave 29 mg (22%) of desired product as an off-white solid.
MS m/z 411 [M+H]

Procedure 1, 7

N*3*-[2-Chloro-4'-((S)-1-pyrrolidin-2-ylmethanesulfonyl)-6-trifluoromethyl-biphenyl-4-yl]-1H-[1,2,4]triazole-3,5-diamine; hydrochloride (Compound 35)

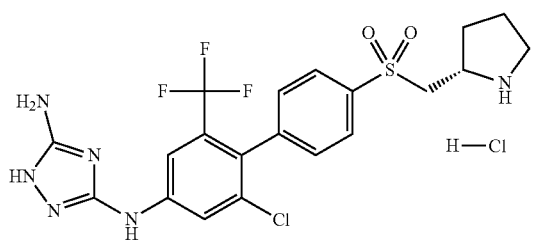 [SMILES: Nc1nc(Nc2cc(Cl)c(-c3ccc(S(=O)(=O)C[C@@H]4CCCN4)cc3)c(C(F)(F)F)c2)n[nH]1 ; Cl]

(S)-tert-butyl 2-(tosyloxymethyl)pyrrolidine-1-carboxylate

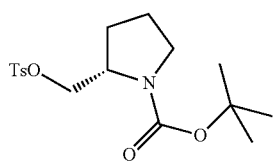 [SMILES: Cc1ccc(S(=O)(=O)OC[C@@H]2CCCN2C(=O)OC(C)(C)C)cc1]

To a solution of (S)-tert-butyl 2-(hydroxymethyl)pyrrolidine-1-carboxylate (2.5 g, 12.4 mmol, Eq: 1.00) and pyridine (7.34 g, 7.5 mL, 92.7 mmol, Eq: 7.47) in dichloromethane (25 mL) at 0 deg, was added 4-methylbenzene-1-sulfonyl chloride (2.96 g, 15.5 mmol, Eq: 1.25). The solution was gradually warmed to room temp and stirred overnight. The reaction mixture was diluted with dichloromethane, washed with water, 1N HCl, sodium carbonate, brine, dried with sodium sulfate. 4 g crude chromatographed (120 g Analogix, 10 to 20% ethyl acetate/hexane) to give 3.86 g (87%) of desired product as a colorless oil.

(S)-tert-butyl 2-((4-bromophenylthio)methyl)pyrrolidine-1-carboxylate

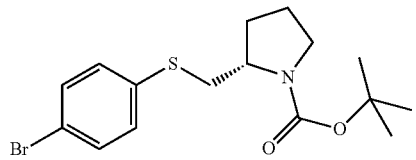 [SMILES: CC(C)(C)OC(=O)N1CCC[C@H]1CSc1ccc(Br)cc1]

To a suspension of NaH (263 mg, 6.58 mmol, Eq: 1.3) in THF (7 mL) at 0 deg, was added 4-bromobenzenethiol (1.15 g, 6.08 mmol, Eq: 1.2). The suspension was stirred for 5 min, then a solution of (S)-tert-butyl 2-(tosyloxymethyl)pyrrolidine-1-carboxylate (1.8 g, 5.06 mmol, Eq: 1.00) in THF (10 mL) was added. The resulting solution was heated at reflux for 5 hr. The reaction was quenched at 0 deg with water (10 mL), extracted 3× with dichloromethane, dried with sodium sulfate. 2.45 g crude chromatographed (80 g Redisep, 0 to 7% ethyl acetate/hexane) to give 1.295 g (69%) of desired product as a colorless oil.

(S)-tert-butyl 2-((4-bromophenylsulfonyl)methyl)pyrrolidine-1-carboxylate

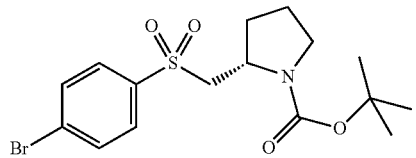 [SMILES: CC(C)(C)OC(=O)N1CCC[C@H]1CS(=O)(=O)c1ccc(Br)cc1]

To a suspension of (S)-tert-butyl 2-((4-bromophenylthio)methyl)pyrrolidine-1-carboxylate (1.295 g, 3.48 mmol, Eq: 1.00) in dichloromethane (15 mL), was added mCPBA (1.8 g, 8.03 mmol, Eq: 2.31). The suspension was stirred at rt o/n. The reaction was quenched with Na2S2O3 and saturated sodium carbonate and extracted with dichloromethane. Dried over sodium sulfate and chromatographed (40 g Redisep, 10 to 25% ethyl acetate/hexane) to give 1.302 g (93%) of desired product as a colorless oil.

(S)-tert-butyl 2-((4-(4,4,5,5-tetramethyl-1,3,2-dioxaborolan-2-yl)phenylsulfonyl)methyl)pyrrolidine-1-carboxylate

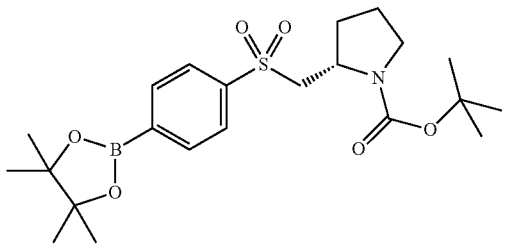 [SMILES: CC(C)(C)OC(=O)N1CCC[C@H]1CS(=O)(=O)c1ccc(B2OC(C)(C)C(C)(C)O2)cc1]

To a solution of (S)-tert-butyl 2-((4-bromophenylsulfonyl)methyl)pyrrolidine-1-carboxylate (1.302 g, 3.22 mmol, Eq: 1.00), bis(pinacolato)diboron (2.05 g, 8.07 mmol, Eq: 2.51), and potassium acetate (1.42 g, 14.5 mmol, Eq: 4.5) in dioxane (20 mL), was added PdCl2(DPPF)-CH2Cl2 adduct (250 mg, 342 µmol, Eq: 0.106) The reaction was heated at 85 deg overnight with an Ar balloon. The reaction mixture was cooled to room temp, concentrated, diluted with ethyl acetate, washed with brine and dried over sodium sulfate. 2.9 g crude chromatographed (80 g Redisep, 0 to 25% ethyl acetate/hexane) to give 1.33 g (92%) of desired product as a pale yellow oil

(S)-tert-butyl 2-((4'-amino-2'-chloro-6'-(trifluoromethyl)biphenyl-4-ylsulfonyl)methyl)pyrrolidine-1-carboxylate

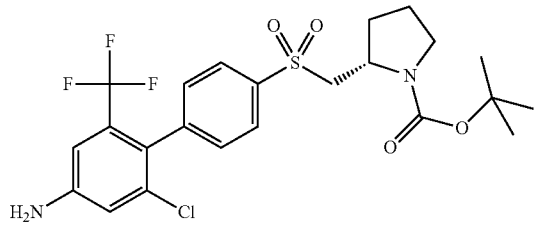 [SMILES: CC(C)(C)OC(=O)N1CCC[C@H]1CS(=O)(=O)c1ccc(-c2c(Cl)cc(N)cc2C(F)(F)F)cc1]

A microwave vial containing 4-bromo-3-chloro-5-(trifluoromethyl)aniline (501 mg, 1.83 mmol, Eq: 1.00), sodium carbonate (484 mg, 4.56 mmol, Eq: 2.5) and Pd(Ph3P)4 (316 mg, 274 µmol, Eq: 0.15) was degassed for 15 minutes with Ar. A solution of (S)-tert-butyl 2-((4-(4,4,5,5-tetramethyl-1,3,2-dioxaborolan-2-yl)phenylsulfonyl)methyl)pyrrolidine-1-carboxylate (900 mg, 1.99 mmol, Eq: 1.09) in dimethoxyethane (8 mL) was added, followed by water (2 mL). The suspension was degassed for 5 min with Ar with sonication, then heated at 110 deg for 1 hr with microwave. The reaction mixture was diluted with ethyl acetate, washed with brine. Dried org extract with sodium sulfate. 1.59 g crude chromatographed (80 g Redisep, 10% to 25% to 40% ethyl acetate/hexane) to give 208 mg (22%) of desired product as a yellow solid.

(S)-tert-butyl 2-((2'-chloro-4'-isothiocyanato-6'-(trifluoromethyl)biphenyl-4-ylsulfonyl)methyl)pyrrolidine-1-carboxylate

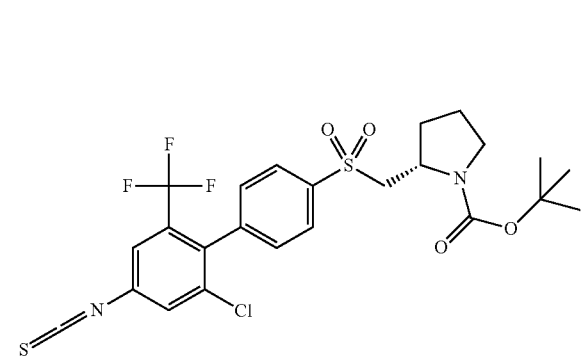 [SMILES: CC(C)(C)OC(=O)N1CCC[C@H]1CS(=O)(=O)c1ccc(-c2c(Cl)cc(N=CC=S)cc2C(F)(F)F)cc1]

To a suspension of calcium carbonate (110 mg, 1.1 mmol, Eq: 2.74) and (S)-tert-butyl 2-((4'-amino-2'-chloro-6'-(trifluoromethyl)biphenyl-4-ylsulfonyl)methyl)pyrrolidine-1-carboxylate (208 mg, 401 µmol, Eq: 1.00) in dichloromethane (10.0 ml)/water (10.0 ml) at 0, was added thiophosgene (60.0 mg, 40 µl, 522 µmol, Eq: 1.3) The reaction was gradually warmed to room temperature and stirred overnight. Added 1.5 mL 1N HCl slowly. Separated organic layer and dried over sodium sulfate. 180 mg crude chromatographed (24 g Redisep, 10 to 25% ethyl acetate/hexane) to give 140 mg (62%) of desired product as a colorless oil.

(2S)-tert-butyl 2-((2'-chloro-4'-(cyanamido(methylthio)methylamino)-6'-(trifluoromethyl)biphenyl-4-ylsulfonyl)methyl)pyrrolidine-1-carboxylate

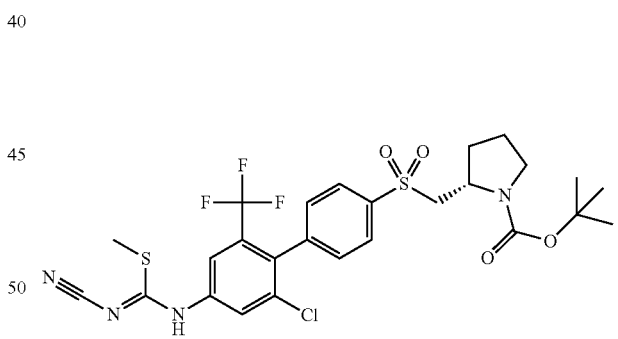

To a solution of (S)-tert-butyl 2-((2'-chloro-4'-isothiocyanato-6'-(trifluoromethyl)biphenyl-4-ylsulfonyl)methyl)pyrrolidine-1-carboxylate (140 mg, 250 µmol, Eq: 1.00) in methanol (5 mL) was added to sodium hydrogen cyanamide (26 mg, 406 µmol, Eq: 1.63). After 30 minutes, methyl iodide (90.8 mg, 40 µl, 640 µmol, Eq: 2.56) was added and the reaction was stirred overnight at room temperature. The reaction mixture was concentrated and chromatographed (12 g Redisep, 10 to 50% ethyl acetate/hexane) to give 53 mg (34%) of desired product as a yellow solid.

215

(S)-tert-butyl 2-((4'-(5-amino-1H-1,2,4-triazol-3-ylamino)-2'-chloro-6'-(trifluoromethyl)biphenyl-4-ylsulfonyl)methyl)pyrrolidine-1-carboxylate

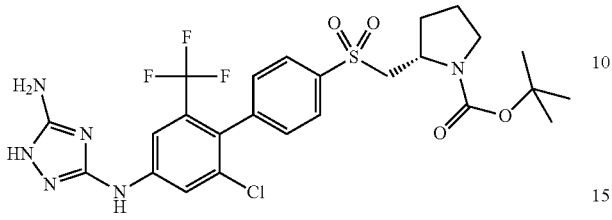

To a solution of (2S)-tert-butyl 2-((2'-chloro-4'-(cyanamido(methylthio)methylamino)-6'-(trifluoromethyl)biphenyl-4-ylsulfonyl)methyl)pyrrolidine-1-carboxylate (53 mg, 85.6 µmol, Eq: 1.00) in ethanol (3 mL) was added hydrazine (30.6 mg, 30 µl, 956 µmol, Eq: 11.2). The reaction mixture was heated at 60 deg for 6 hr. TLC shows new spot, no sm present. The reaction mixture was concentrated and chromatographed (Supelco, 1 to 10% methanol/dichloromethane) to give 46.6 mg (91%) of desired product as a white solid, N*3*-[2-Chloro-4'-((S)-1-pyrrolidin-2-ylmethanesulfonyl)-6-trifluoromethyl-biphenyl-4-yl]-1H-[1,2,4]triazole-3,5-diamine; hydrochloride (Compound 35)

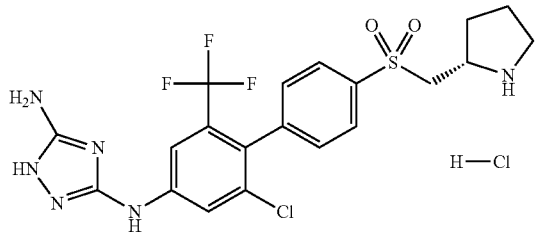 [SMILES: Nc1nc(Nc2cc(Cl)c(-c3ccc(S(=O)(=O)C[C@@H]4CCCN4)cc3)c(C(F)(F)F)c2)n[nH]1 ; Cl]

AcCl (552 mg, 0.5 ml, 7.03 mmol, Eq: 90.7) was slowly added to 5 of methanol (exotherm), and cooled to room temperature. The solution was added to a solution of (S)-tert-butyl 2-((4'-(5-amino-1H-1,2,4-triazol-3-ylamino)-2'-chloro-6'-(trifluoromethyl)biphenyl-4-ylsulfonyl)methyl)pyrrolidine-1-carboxylate (46.6 mg, 77.5 µmol, Eq: 1.00) in methanol (2 mL) and stirred at room temp for 5 hr. The reaction mixture was concentrated to dryness, triturated with Et2O, and filtered to give 37 mg (89%) of desired product as an off-white solid.

MS m/z 501 [M+H]

216

Procedure 1, 7

N*3*-[2-Chloro-4'-(morpholine-4-sulfonyl)-6-trifluoromethyl-biphenyl-4-yl]-1H-[1,2,4]triazole-3,5-diamine (Compound 36)

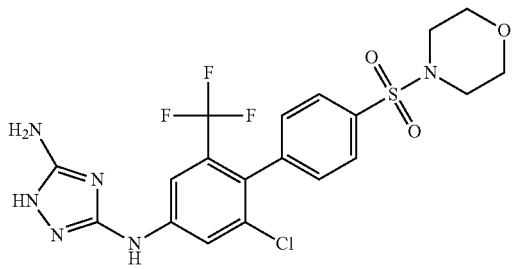 [SMILES: Nc1nc(Nc2cc(Cl)c(-c3ccc(S(=O)(=O)N4CCOCC4)cc3)c(C(F)(F)F)c2)n[nH]1]

2-chloro-4'-(morpholinosulfonyl)-6-(trifluoromethyl)biphenyl-4-amine

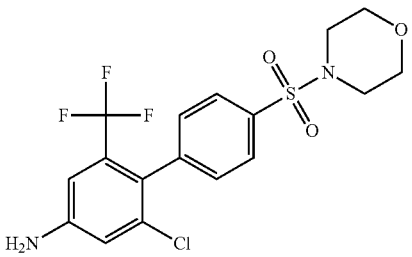 [SMILES: Nc1cc(Cl)c(-c2ccc(S(=O)(=O)N3CCOCC3)cc2)c(C(F)(F)F)c1]

A microwave vial containing 4-bromo-3-chloro-5-(trifluoromethyl)aniline (250 mg, 911 µmol, Eq: 1.00), 4-(morpholinosulfonyl)phenylboronic acid, (472 mg, 1.74 mmol, Eq: 1.91) sodium carbonate (237 mg, 2.24 mmol, Eq: 2.45) and bis(triphenylphosphine)palladium (II) chloride (72 mg, 103 µmol, Eq: 0.113) in dimethoxyethane (3 mL)/water (1 mL) was heated overnight at 110 deg. The reaction mixture was diluted with ethyl acetate, washed with brine, and dried with sodium sulfate. 500 mg crude was chromatographed (40 g Redisep, 20% to 40% ethyl acetate/hexane) to give 261 mg (68%) of desired product as a colorless oil.

4-(2'-chloro-4'-isothiocyanato-6'-(trifluoromethyl)biphenyl-4-ylsulfonyl)morpholine

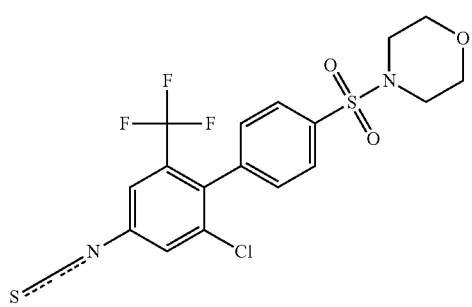

To a suspension of calcium carbonate (177 mg, 1.77 mmol, Eq: 2.85) and thiophosgene (90.0 mg, 60 μl, 783 μmol, Eq: 1.26) in dichloromethane (10.0 ml)/water (10.0 ml) at 0, was added 2-chloro-4'-(morpholinosulfonyl)-6-(trifluoromethyl)biphenyl-4-amine (261 mg, 620 μmol, Eq: 1.00) The reaction was gradually warmed to room temperature and stirred overnight. Added 2 mL 1N HCl slowly. Separated organic layer and dried over sodium sulfate to give 229 mg (80%) of desired product as a pale yellow solid.

N-((2-chloro-4'-(morpholinosulfonyl)-6-(trifluoromethyl)biphenyl-4-amino)(methylthio)methyl)cyanamide

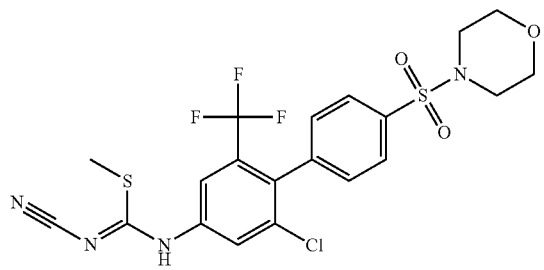 [SMILES: CS/C(=N\C#N)Nc1cc(Cl)c(-c2ccc(S(=O)(=O)N3CCOCC3)cc2)c(C(F)(F)F)c1]

To a solution of 4-(2'-chloro-4'-isothiocyanato-6'-(trifluoromethyl)biphenyl-4-ylsulfonyl)morpholine (229 mg, 495 μmol, Eq: 1.00) in methanol (5 mL) was added to sodium hydrogen cyanamide (34.8 mg, 544 μmol, Eq: 1.1). After 30 minutes, methyl iodide (170 mg, 75 μl, 1.2 mmol, Eq: 2.42) was added and the reaction was stirred overnight at room temperature. The reaction mixture was concentrated and chromatographed (24 g Redisep 25 to 75% ethyl acetate/hexane) to give 146 mg (57%) of desired product as a yellow solid.

N*3*-[2-Chloro-4'-(morpholine-4-sulfonyl)-6-trifluoromethyl-biphenyl-4-yl]-1H-[1,2,4]triazole-3,5-diamine (Compound 36)

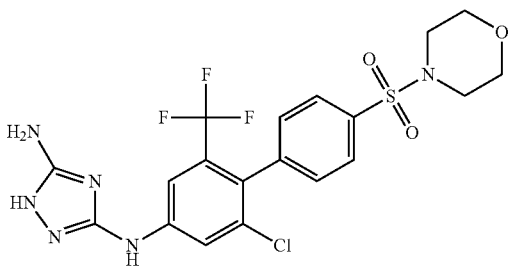 [SMILES: Nc1nc(Nc2cc(Cl)c(-c3ccc(S(=O)(=O)N4CCOCC4)cc3)c(C(F)(F)F)c2)n[nH]1]

To a solution of N-((2-chloro-4'-(morpholinosulfonyl)-6-(trifluoromethyl)biphenyl-4-ylamino)(methylthio)methyl)cyanamide (146 mg, 280 μmol, Eq: 1.00) in ethanol (5 mL) was added hydrazine (102 mg, 100 μl, 3.19 mmol, Eq: 11.4). The reaction mixture was heated at 60 deg o/n. The resulting suspension was cooled to rt and filtered to give 78 mg (55%) of desired product as a white solid.

MS m/z 503 [M+H]

Procedure 1, 7

N*3*-[4'-(Azetidin-3-ylmethoxy)-2-chloro-6-trifluoromethyl-biphenyl-4-yl]-1H-[1,2,4]triazole-3,5-diamine; hydrochloride (Compound 37)

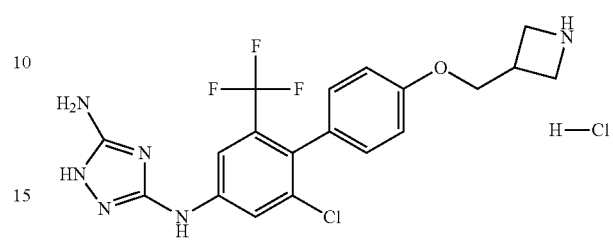

tert-butyl 3-((4'-amino-2'-chloro-6'-(trifluoromethyl)biphenyl-4-yloxy)methyl)azetidine-1-carboxylate

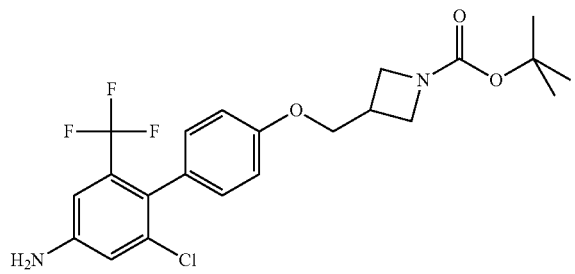 [SMILES: CC(C)(C)OC(=O)N1CC(COc2ccc(-c3c(Cl)cc(N)cc3C(F)(F)F)cc2)C1]

A microwave vial containing 4-bromo-3-chloro-5-(trifluoromethyl)aniline (500 mg, 1.82 mmol, Eq: 1.00), sodium carbonate (483 mg, 4.55 mmol, Eq: 2.5) and Pd(Ph3P)4 (211 mg, 182 Eq: 0.1) was degassed for 15 minutes with Ar. A solution of tert-butyl 3-((4-(4,4,5,5-tetramethyl-1,3,2-dioxaborolan-2-yl)phenoxy)methyl)azetidine-1-carboxylate (993 mg, 2.55 mmol, Eq: 1.4) in dimethoxyethane (6 mL) was added, followed by water (1.5 mL). The suspension was degassed for 5 min with Ar with sonication, then capped and heated at 125 in microwave for 2 hr. Diluted with ethyl acetate, washed with brine. Dried org extract with sodium sulfate. 1 g crude chromatographed (40 g Redisep, 20% to 30% EOAc/hexane) to give 104 mg (13%) of desired product as a pale yellow oil.

tert-butyl 3-((2'-chloro-4'-isothiocyanato-6'-(trifluoromethyl)biphenyl-4-yloxy)methyl)azetidine-1-carboxylate

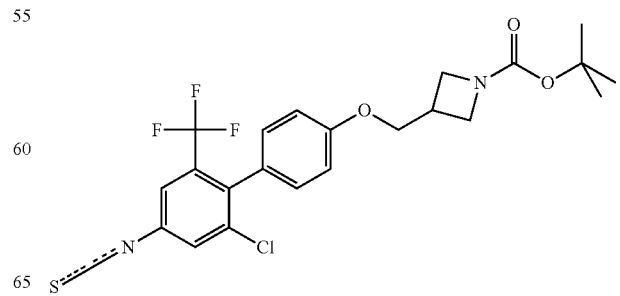

To a suspension of calcium carbonate (62 mg, 619 µmol, Eq: 2.72) tert-butyl chloro-6'-(trifluoromethyl)biphenyl-4-yloxy)methyl)azetidine-1-carboxylate in dichloromethane (10.0 ml)/water (10.0 ml) at 0, was added thiophosgene (37.5 mg, 25 µl, 326 µmol, Eq: 1.43) The reaction was gradually warmed to room temperature and stirred overnight. Added 1 mL 1N HCl slowly. Separated organic layer and extracted aq twice more with dichloromethane. Dried over sodium sulfate to give 92 mg (81%) of desired product as a pale yellow oil.

tert-butyl 3-((2'-chloro-4'-(cyanamido(methylthio) methylamino)-6'-(trifluoromethyl)biphenyl-4-yloxy) methyl)azetidine-1-carboxylate

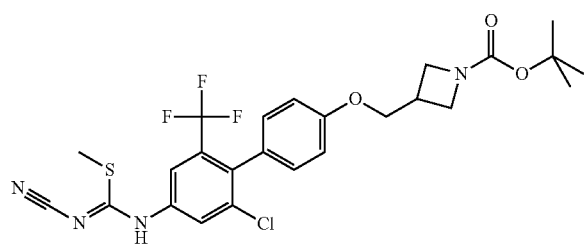 [SMILES: CS/C(=N\C#N)Nc1cc(Cl)c(-c2ccc(OCC3CN(C(=O)OC(C)(C)C)C3)cc2)c(C(F)(F)F)c1]

To a solution of tert-butyl 3-((2'-chloro-4'-isothiocyanato-6'-(trifluoromethyl)biphenyl-4-yloxy)methyl)azetidine-1-carboxylate (104 mg, 208 µmol, Eq: 1.00) in dimethoxyethane (5 mL) was added to sodium hydrogen cyanamide (23 mg, 359 µmol, Eq: 1.72) and methanol (0.5 mL). After 30 minutes, methyl iodide (102 mg, 45 µl, 720 µmol, Eq: 3.45) was added and the reaction was stirred at room temperature over the weekend. The reaction mixture was concentrated and chromatographed (12 g Redisep, 10 to 40% ethyl acetate/hexane) to give 56 mg (48%) of desired product as a white solid.

tert-butyl 3-((4'-(5-amino-1H-1,2,4-triazol-3-ylamino)-2'-chloro-6'-(trifluoromethyl)biphenyl-4-yloxy)methyl)azetidine-1-carboxylate

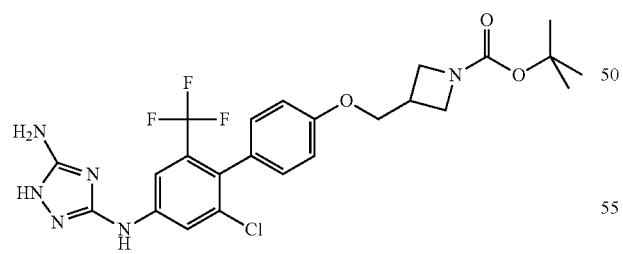

To a solution of tert-butyl 3-((2'-chloro-4'-(cyanamido (methylthio)methylamino)-6'-(trifluoromethyl)biphenyl-4-yloxy)methyl)azetidine-1-carboxylate (56 mg, 101 µmol, Eq: 1.00) in ethanol (5 mL) was added hydrazine (40.8 mg, 40 µl, 1.27 mmol, Eq: 12.7). The reaction mixture was heated at 65 deg o/n. The solution was concentrated and chromatographed (Redisep 12 g, 1 to 10% methanol/dichloromethane) to give 54 mg (43%) of desired product as a white solid.

N*3*-[4'-(Azetidin-3-ylmethoxy)-2-chloro-6-trifluoromethyl-biphenyl-4-yl]-1H-[1,2,4]triazole-3,5-diamine hydrochloride (Compound 37)

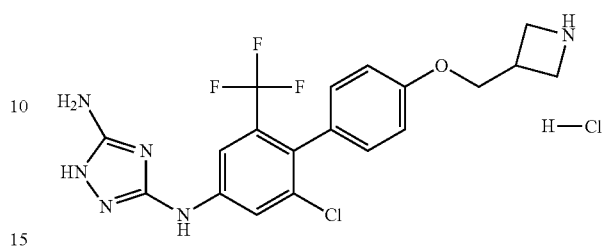

AcCl (552 mg, 500 µl, 7.03 mmol, Eq: 88.1) was slowly added to 10 of methanol (exotherm), and cooled to room temperature. The solution was added to a solution of tert-butyl 3-((4'-(5-amino-1H-1,2,4-triazol-3-ylamino)-2'-chloro-6'-(trifluoromethyl)biphenyl-4-yloxy)methyl)azetidine-1-carboxylate (43 mg, 79.8 µmol, Eq: 1.00) in methanol (2 mL) and stirred at room temp for 5 hr. The reaction mixture was concentrated, dissolved in 1 mL methanol, triturated with ether, and filtered to give 32 mg (84%) of desired product as a white solid.

MS m/z 439 [M+H]

Procedure 1, 7

N-{2-[4'-(5-Amino-1H-[1,2,4]triazol-3-ylamino)-2'-chloro-6'-trifluoromethyl-biphenyl-4-yl]-ethyl}-methanesulfonamide (Compound 38)

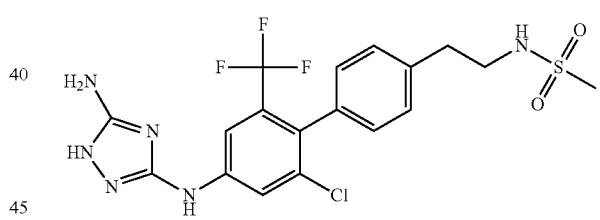

N-(4-bromophenethyl)methanesulfonamide

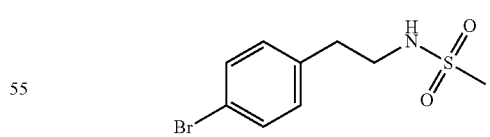

To a solution of 2-(4-bromophenyl)ethanamine (1 g, 5.00 mmol, Eq: 1.00) and pyridine (597 mg, 610 µl, 7.54 mmol, Eq: 1.51) in dichloromethane (10 mL) at 0 deg, was added methanesulfonyl chloride (685 mg, 465 µl, 5.98 mmol, Eq: 1.2). The solution was gradually warmed to room temp and stirred overnight. Diluted with ethyl acetate, washed with 1N HCl, brine, dried with sodium sulfate, and chromatographed (40 g Redisep 0 to 50% ethyl acetate/hexane) to give 480 mg (35%) of desired product as a white solid.

221

N-(4-(4,4,5,5-tetramethyl-1,3,2-dioxaborolan-2-yl)phenethyl)methanesulfonamide

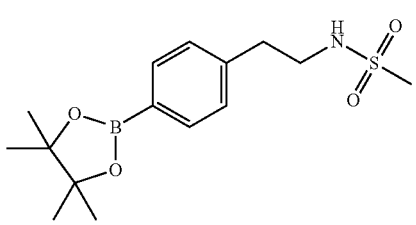

To a solution of N-(4-bromophenethyl)methanesulfonamide (480 mg, 1.73 mmol, Eq: 1.00), bis(pinacolato)diboron (1.1 g, 4.31 mmol, Eq: 2.5), and potassium acetate (762 mg, 7.77 mmol, Eq: 4.5) in dioxane (8 mL), was added PdCl2 (DPPF)-CH2Cl2 adduct (128 mg, 175 μmol, Eq: 0.102) The reaction was heated at 85 deg overnight with an N2 balloon. The reaction mixture was cooled to room temp, concentrated, diluted with ether, washed with brine and dried over sodium sulfate. 1.64 g crude chromatographed (40 g Redisep, 20 to 50% ethyl acetate/hexane) to give 433 mg (77%) of desired product as a white solid, containing a slight amount of picacol diboron impurity,

N-(2-(4'-amino-2'-chloro-6'-(trifluoromethyl)biphenyl-4-yl)ethyl)methanesulfonamide

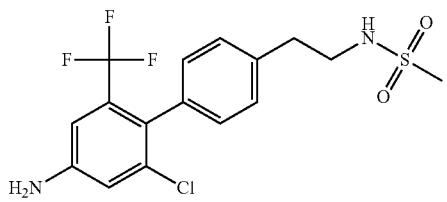 [SMILES: CS(=O)(=O)NCCc1ccc(-c2c(Cl)cc(N)cc2C(F)(F)F)cc1]

A microwave vial containing 4-bromo-3-chloro-5-(trifluoromethyl)aniline (250 mg, 911 μmol, Eq: 1.00), N-(4-(4,4,5,5-tetramethyl-1,3,2-dioxaborolan-2-yl)phenethyl)methanesulfonamide (433 mg, 1.33 mmol, Eq: 1.46), sodium carbonate (243 mg, 2.29 mmol, Eq: 2.52) and bis(triphenylphosphine)palladium (II) chloride (63.9 mg, 91.1 μmol, Eq: 0.1) in dimethoxyethane (2.5 mL)/water (0.5 mL) was heated for 30 min with the microwave at 115 deg. LCMS shows incomplete reaction, added more Pd (87 mg) and heated for 1 hr at 125. LCMS still shows sm. Heated overnight at 110 with conventional heating. The reaction mixture was concentrated, diluted with ethyl acetate, washed with brine, dried org extract with sodium sulfate, and chromatographed (40 g Redisep, 10% to 20 to 40% ethyl acetate/hexane) to give 156 mg (44%) of desired product as a white solid.

222

N-(2-(2'-chloro-4'-isothiocyanato-6'-(trifluoromethyl)biphenyl-4-yl)ethyl)methanesulfonamide

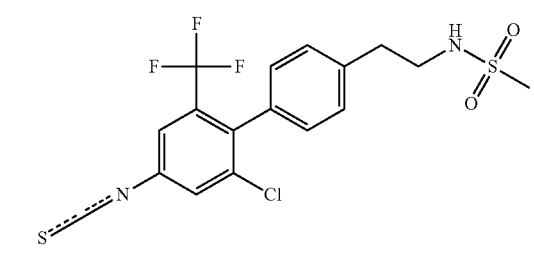

A suspension of N-(2-(4'-amino-2'-chloro-6'-(trifluoromethyl)biphenyl-4-yl)ethyl)methanesulfonamide (156 mg, 397 μmol, Eq: 1.00), thiophosgene (188 mg, 125 μl, 1.63 mmol, Eq: 4.11), triethylamine (182 mg, 250 μl, 1.79 mmol, Eq: 4.52) in benzene (10.0 ml) was heated at reflux overnight. The brown reaction mixture was concentrated, diluted with dichloromethane, washed with 1N HCl (5 mL) and brine, dried over sodium sulfate. 0.5 g crude was chromatographed (24 g Redesip, 10 to 35 ethyl acetate/hexaneane) to give 177 mg orange oil of desired product.

N-(2-(2'-chloro-4'-(cyanamido(methylthio)methylamino)-6'-(trifluoromethyl)biphenyl-4-yl)ethyl)methanesulfonamide

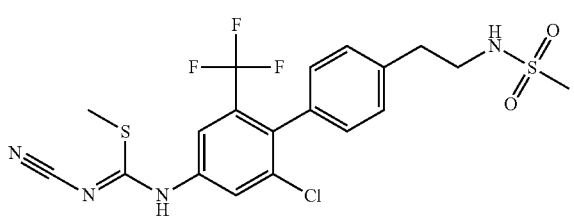 [SMILES: CS/C(=N\C#N)Nc1cc(Cl)c(-c2ccc(CCNS(C)(=O)=O)cc2)c(C(F)(F)F)c1]

To a solution of N-(2-(2'-chloro-4'-isothiocyanato-6'-(trifluoromethyl)biphenyl-4-yl)ethyl)methanesulfonamide (173 mg, 398 μmol, Eq: 1.00) in methanol (4 mL) was added to sodium hydrogen cyanamide (32 mg, 500 μmol, Eq: 1.26). After 30 minutes, methyl iodide (125 mg, 55 μl, 880 μmol, Eq: 2.21) was added and the reaction was stirred overnight at room temperature. The reaction mixture was concentrated and chromatographed (24 g Redisep, 25% to 75% ethyl acetate/hexane) to give 67 mg (34%) of desired product as a yellow solid.

N-{2-[4'-(5-Amino-1H-[1,2,4]triazol-3-ylamino)-2'-chloro-6'-trifluoromethyl-biphenyl-4-yl]-ethyl}-methanesulfonamide (Compound 38)

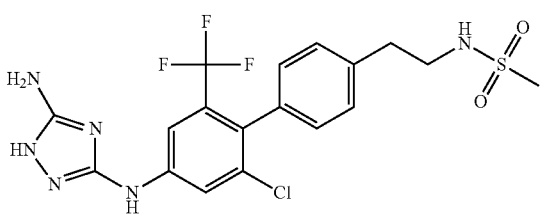 [SMILES: CS(=O)(=O)NCCc1ccc(-c2c(Cl)cc(Nc3n[nH]c(N)n3)cc2C(F)(F)F)cc1]

To a solution of N-(2-(2'-chloro-4'-(cyanamido(methylthio)methylamino)-6'-(trifluoromethyl)biphenyl-4-yl)ethyl)methanesulfonamide (67 mg, 136 µmol, Eq: 1.00) in ethanol (5 mL) was added hydrazine (51.1 mg, 50 µl, 1.59 mmol, Eq: 11.7). The reaction mixture was heated at 60 deg o/n. The reaction was cooled to rt concentrated, and chromatographed (11 g Supelco, 1 to 10% methanol/dichloromethane) to give 50 mg (78%) of desired product as a white solid.

MS m/z 475 [M+H]

Procedure 6

5-((3aS,4S,6aR)-2-Oxo-hexaneahydro-thieno[3,4-d]imidazol-4-yl)-pentanoic acid [4'-(5-amino-1H-[1,2,4]triazol-3-ylamino)-2',6'-dichloro-biphenyl-4-yl]-amide (Compound 39)

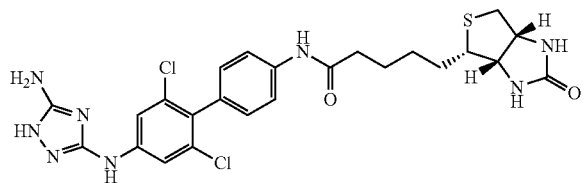 [SMILES: Nc1nc(Nc2cc(Cl)c(-c3ccc(NC(=O)CCCC[C@@H]4SC[C@@H]5NC(=O)N[C@@H]54)cc3)c(Cl)c2)n[nH]1]

5-((3aS,4S,6aR)-2-oxohexaneahydro-1H-thieno[3,4-d]imidazol-4-yl)-N-(4-(4,4,5,5-tetramethyl-1,3,2-dioxaborolan-2-yl)phenyl)pentanamide

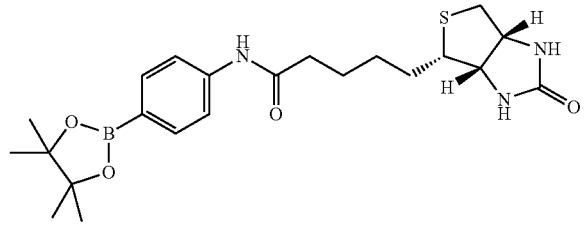 [SMILES: CC1(C)OB(c2ccc(NC(=O)CCCC[C@@H]3SC[C@@H]4NC(=O)N[C@@H]43)cc2)OC1(C)C]

A solution of 5-((3aS,4S,6aR)-2-oxohexaneahydro-1H-thieno[3,4-d]imidazol-4-yl)pentanoic acid (505 mg, 2.07 mmol, Eq: 1.00) and thionyl chloride (16.3 g, 10 ml, 137 mmol, Eq: 66.3) was stirred at room temperature for 30 minutes, then concentrated to dryness. Added chloroform and concentrated once more to dryness.

To a solution of 5-((3aS,4S,6aR)-2-oxohexaneahydro-1H-thieno[3,4-d]imidazol-4-yl)pentanoyl chloride (539 mg, 2.05 mmol, Eq: 1.00) in acetonitrile (10 mL), was added a solution of 4-(4,4,5,5-tetramethyl-1,3,2-dioxaborolan-2-yl)aniline (449 mg, 2.05 mmol, Eq: 1.00) in acetonitrile (10 mL). The reaction was stirred overnight at room temperature, then concentrated, diluted with ethyl acetate, washed with brine, dried over sodium sulfate, and chromatographed (40 g Redisep, 100% dichloromethane to 5% methanol/dichloromethane) to give 205 mg (23%) of desired product as a brown solid.

5-((3aS,4S,6aR)-2-Oxo-hexaneahydro-thieno[3,4-d]imidazol-4-yl)-pentanoic acid [4'-(5-amino-1H-[1,2,4]triazol-3-ylamino)-2',6'-dichloro-biphenyl-4-yl]-amide (Compound 39)

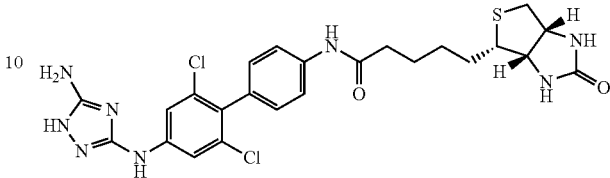

A microwave vial containing N3-(4-bromo-3,5-dichlorophenyl)-1H-1,2,4-triazole-3,5-diamine Intermediate 2 (100 mg, 310 µmol, Eq: 1.00), 5-((3aS,4S,6aR)-2-oxohexaneahydro-1H-thieno[3,4-d]imidazol-4-yl)-N-(4-(4,4,5,5-tetramethyl-1,3,2-dioxaborolan-2-yl)phenyl)pentanamide (175 mg, 393 µmol, Eq: 1.27), sodium carbonate (88.0 mg, 830 µmol, Eq: 2.68) and bis(di-t-Butylphosphino)ferrocenyl PdCl2 (32 mg, 49.1 µmol, Eq: 0.159) was degassed with argon for 15 minutes. Dioxane (2 mL)/water (0.5 mL) was added and the suspension was degassed for an additional 5 minutes with sonication. The reaction was heated at 125 for 1 hr with the microwave. The reaction mixture was concentrated and purified by preparative plate chromatography (15% methanol/dichloromethane) to give 22 mg (13%) of desired product as a light brown solid.

MS ok m/z 561 [M–H]

Procedure 1, 7

N*3*-[2-Chloro-4'-(piperidin-4-ylmethanesulfonyl)-6-trifluoromethyl-biphenyl-4-yl]-1H-[1,2,4]triazole-3,5-diamine; hydrochloride (Compound 40)

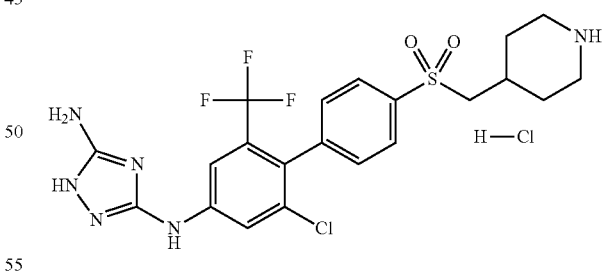

AcCl (1.1 g, 1 ml, 14.1 mmol, Eq: 86.5) was slowly added to 5 of methanol (exotherm), and cooled to room temperature. The solution was added to a solution of tert-butyl 4-((4'-(5-amino-1H-1,2,4-triazol-3-ylamino)-2'-chloro-6'-(trifluoromethyl)biphenyl-4-ylsulfonyl)methyl)piperidine-1-carboxylate Compound 7 in methanol (5 mL) and stirred at room temp for 5 hr. The reaction was concentrated to dryness, triturated with Et2O, and filtered to give 67 mg (75%) of desired product as an off-white solid.

MS m/z 515 [M+H]

Procedure 1, 7

N*3*-[2-Chloro-3'-(piperidin-4-yloxy)-6-trifluoromethyl-biphenyl-4-yl]-1H-[1,2,4]triazole-3,5-diamine; hydrochloride (Compound 41)

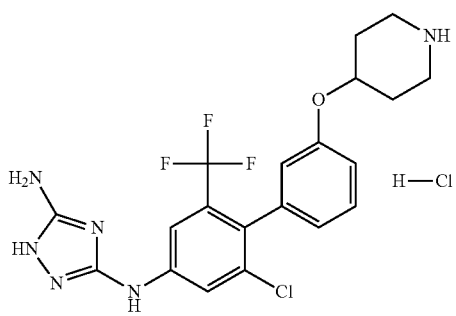

AcCl (552 mg, 0.5 ml, 7.03 mmol, Eq: 40.5) was slowly added to 10 of methanol (exotherm), and cooled to room temperature. The solution was added to a solution of tert-butyl 4-(4'-(5-amino-1H-1,2,4-triazol-3-ylamino)-2'-chloro-6'-(trifluoromethyl)biphenyl-3-yloxy)piperidine-1-carboxylate Compound 21 (96 mg, 174 μmol, Eq: 1.00) in methanol (2 mL) and stirred at room temp for 5 hr. The reaction was concentrated, dissolved in 1 mL methanol, triturated with ether, and filtered to give 77 mg (91%) of desired product as a white solid.
MS m/z 453 [M−HCl]

Procedure 1, 7

N*3*-[3,5-Dichloro-4-(1-methanesulfonyl-1H-indol-5-yl)-phenyl]-1H-[1,2,4]triazole-3,5-diamine (Compound 42)

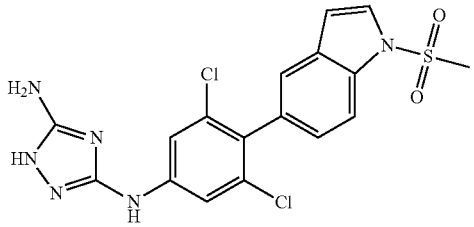 [SMILES: CS(=O)(=O)n1ccc2cc(-c3c(Cl)cc(Nc4n[nH]c(N)n4)cc3Cl)ccc21]

5-bromo-1-(methylsulfonyl)-1H-indole

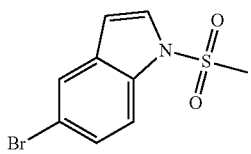

To a solution of 5-bromo-1H-indole (502 mg, 2.56 mmol, Eq: 1.00) in THF (5 mL) at 0 deg, was added NaH (60%, 285 mg, 7.13 mmol, Eq: 2.78). The ice bath was removed. After 30 minutes, the reaction was cooled to 0 deg, and Ms-Cl (588 mg, 400 μl, 5.13 mmol, Eq: 2.00) was added. Gradually warmed to room temperature overnight. The reaction mixture was diluted with ethyl acetate, washed with brine, dried over sodium sulfate, and chromatographed (40 g Redisep, 100% hexane to 15% ethyl acetate/hexane) gave 411 mg (59%) of desired product as a white solid, containing ~15% indole impurity.

1-(methylsulfonyl)-5-(4,4,5,5-tetramethyl-1,3,2-dioxaborolan-2-yl)-1H-indole

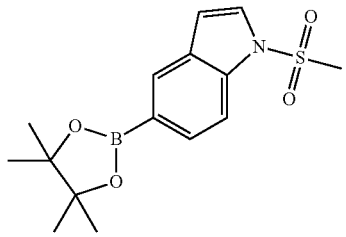

To a solution of 5-bromo-1-(methylsulfonyl)-1H-indole (411 mg, 1.5 mmol, Eq: 1.00), bis(pinacolato)diboron (953 mg, 3.75 mmol, Eq: 2.5), and potassium acetate (629 mg, 6.41 mmol, Eq: 4.27) in dioxane (10 mL), was added PdCl2(DPPF)-CH2Cl2 adduct (113 mg, 154 μmol, Eq: 0.103) The reaction was heated at 85 deg overnight. The reaction mixture was cooled to room temp, diluted with ether, washed with brine and dried over sodium sulfate. The crude residue was chromatographed (80 g Redisep, 10 to 20% ethyl acetate/hexane) to give 319 mg (66%) of desired product as a colorless oil, containing ~15% indole impurity.

N*3*-[3,5-Dichloro-4-(1-methanesulfonyl-1H-indol-5-yl)-phenyl]-1H-[1,2,4]triazole-3,5-diamine (Compound 42)

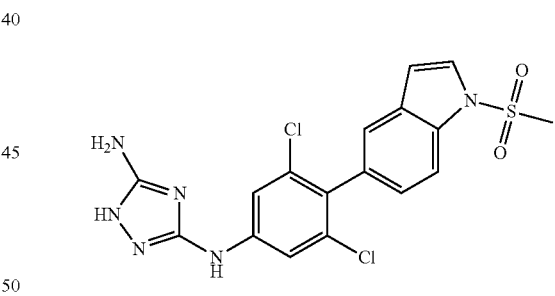

A microwave vial containing N3-(4-bromo-3,5-dichlorophenyl)-1H-1,2,4-triazole-3,5-diamine Intermediate 2 (100 mg, 310 μmol, Eq: 1.00), sodium carbonate (82.0 mg, 774 μmol, Eq: 2.5) and Pd(PPh3)4 (58 mg, 50.2 μmol, Eq: 0.162) was degassed for 15 minutes with Argon. A solution of 1-(methylsulfonyl)-5-(4,4,5,5-tetramethyl-1,3,2-dioxaborolan-2-yl)-1H-indole (181 mg, 564 μmol, Eq: 1.82) in dioxane (2 mL) was added, followed by water (0.5 mL), and the suspension was degassed for 5 minutes with sonication, and the reaction was heated at 125o for 1 hr with microwave. The reaction was diluted with ethyl acetate, washed with brine, dried with sodium sulfate, and chromatographed (40 g Redsiep Gold, 0 to 10% methanol/dichloromethane) to give 86 mg brown solid, containing desired product and impurities. Further purification (SFC) gave 56 mg (21%) of desired product as a white solid.
MS m/z 437 [M−H]

Procedure 6

1-[4'-(5-Amino-1H-[1,2,4]triazol-3-ylamino)-2',6'-dichloro-biphenyl-4-yl]-pyrrolidin-2-one (Compound 43)

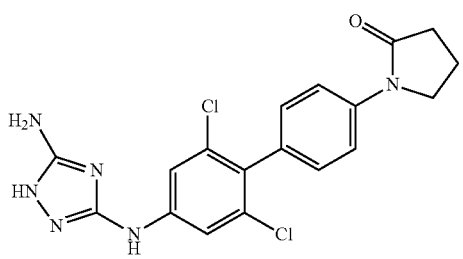

1-(4-(4,4,5,5-tetramethyl-1,3,2-dioxaborolan-2-yl)phenyl)pyrrolidin-2-one

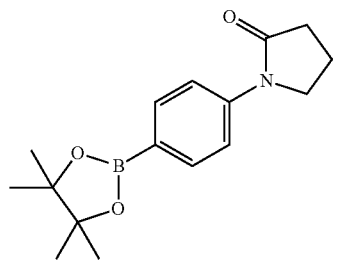 [SMILES: CC1(C)OB(c2ccc(N3CCCC3=O)cc2)OC1(C)C]

To a solution of 4-(4,4,5,5-tetramethyl-1,3,2-dioxaborolan-2-yl)aniline (500 mg, 2.28 mmol, Eq: 1.00) and Et3N (272 mg, 375 µl, 2.69 mmol, Eq: 1.18) in dichloromethane (15 mL) at 0 deg, was added 4-bromobutanoyl chloride (423 mg, 325 µl, 2.28 mmol, Eq: 1.00). The reaction mixture was gradually warmed to room temperature. After 4 hr, the reaction was quenched with water. The organic layer was separated, washed with sodium carbonate and brine, and dried over sodium sulfate.

To a solution of 4-bromo-N-(4-(4,4,5,5-tetramethyl-1,3,2-dioxaborolan-2-yl)phenyl)butanamide (839 mg, 2.28 mmol, Eq: 1.00) in DMF (20 mL) at 0 deg, was added NaH (120 mg, 3.00 mmol, Eq: 1.32). The reaction mixture was gradually warmed to room temperature. The reaction was diluted with ethyl acetate and washed with brine 3x. Dried org extract over sodium sulfate and chromatographed (1.5 g crude, 80 Redisep, 10 to 25 to 50% ethyl acetate/hexane) to give 145 mg (22%) of desired product as a white solid.

1-[4'-(5-Amino-1H-[1,2,4]triazol-3-ylamino)-2',6'-dichloro-biphenyl-4-yl]-pyrrolidin-2-one (Compound 43)

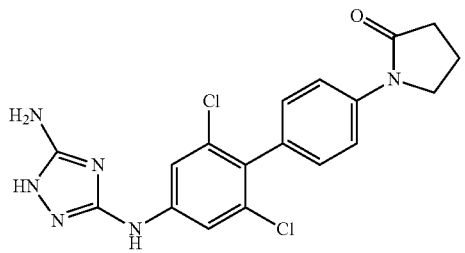 [SMILES: Nc1nc(Nc2cc(Cl)c(-c3ccc(N4CCCC4=O)cc3)c(Cl)c2)n[nH]1]

A microwave vial containing N3-(4-bromo-3,5-dichlorophenyl)-1H-1,2,4-triazole-3,5-diamine Intermediate 2 (110 mg, 341 µmol, Eq: 1.00), sodium carbonate (90.2 mg, 851 µmol, Eq: 2.5) and Pd(Ph3P)4 (38.0 mg, 32.9 µmol, Eq: 0.0966) was degassed for 15 minutes with Argon. A solution of 1-(4-(4,4,5,5-tetramethyl-1,3,2-dioxaborolan-2-yl)phenyl)pyrrolidin-2-one (149 mg, 519 µmol, Eq: 1.52) in dioxane (2 mL) was added to the reaction. Water (0.5 mL) was added and the suspension was degassed for 5 minutes with sonication, and the reaction was heated at 125o for 1 hr with microwave. The reaction mixture was diluted with ethyl acetate, washed with brine, dried over sodium sulfate, and chromatographed (23 g Supelco, 0 to 10% methanol/dichloromethane) to give 46 mg (34%) of desired product as a yellow solid.

MS m/z 403 [M+H]

Procedure 1, 7

N*3*-[3-Chloro-4-(4-methanesulfonyl-3,4-dihydro-2H-benzo[1,4]oxazin-6-yl)-5-trifluoromethyl-phenyl]-1H-[1,2,4]triazole-3,5-diamine (Compound 44)

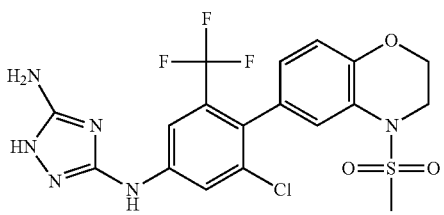 [SMILES: CS(=O)(=O)N1CCOc2ccc(-c3c(Cl)cc(Nc4n[nH]c(N)n4)cc3C(F)(F)F)cc21]

6-bromo-3,4-dihydro-2H-benzo[b][1,4]oxazine

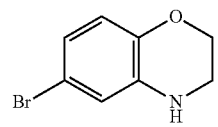

To a solution of 6-bromo-2H-benzo[b][1,4]oxazin-3(4H)-one (2 g, 8.77 mmol, Eq: 1.00) in THF (20 mL) at 0 deg, was added LAH (2.0M in THF, 5.2 ml, 10.4 mmol, Eq: 1.19). The reaction was gradually warmed to room temp and stirred o/n. The reaction was cooled to 0 deg and quenched with water and 1N NaOH. Evaporated off THF, suspended in ethyl acetate/water and filtered off solid. Filtrate was partitioned and the org extract dried over sodium sulfate to give 1 g crude. Chromatographed (40 g Redisep, 5 to 10% ethyl acetate/hexane) to give 1.59 g (85%) of desired product as a brown oil.

6-(4,4,5,5-tetramethyl-1,3,2-dioxaborolan-2-yl)-3,4-dihydro-2H-benzo[b][1,4]oxazine

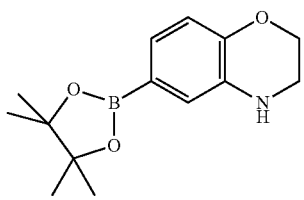 [SMILES: CC1(C)OB(c2ccc3c(c2)NCCO3)OC1(C)C]

To a solution of 6-bromo-3,4-dihydro-2H-benzo[b][1,4]oxazine (1.59 g, 7.43 mmol, Eq: 1.00), bis(pinacolato)diboron (4.72 g, 18.6 mmol, Eq: 2.5), and potassium acetate (3.28 g, 33.4 mmol, Eq: 4.5) in dioxane (20 mL), was added PdCl2(DPPF)-CH2Cl2 adduct (543 mg, 742 µmol, Eq: 0.0999) The reaction was heated at 85 deg overnight with an Ar balloon. The reaction mixture was cooled to room temp, concentrated, diluted with ethyl acetate, washed with brine and dried over sodium sulfate. 2 g crude chromatographed (40 g Redisep, 30 to 50% ethyl acetate/hexane) to give 892 mg (46%) of desired product as a light brown oil, containing ~20% pinacol diboron impurity.

4-(methylsulfonyl)-6-(4,4,5,5-tetramethyl-1,3,2-dioxaborolan-2-yl)-3,4-dihydro-2H-benzo[b][1,4]oxazine

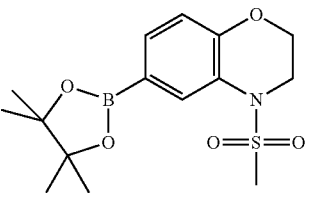 [SMILES: CC1(C)OB(c2ccc3c(c2)N(S(C)(=O)=O)CCO3)OC1(C)C]

To a solution of 6-(4,4,5,5-tetramethyl-1,3,2-dioxaborolan-2-yl)-3,4-dihydro-2H-benzo[b][1,4]oxazine (892 mg, 3.42 mmol, Eq: 1.00) and pyridine (538 mg, 550 µl, 6.8 mmol, Eq: 1.99) in dichloromethane (15 mL) at 0 deg, was added Ms-Cl (735 mg, 500 µl, 6.42 mmol, Eq: 1.88). The reaction was gradually warmed to room temp and stirred o/n. The reaction was diluted with dichloromethane, washed with 1N HCl and brine. Dried with sodium sulfate and chromatographed (40 g Redisep, 10 to 30% ethyl acetate/hexane) to give 523 mg (45%) of desired product as a pale yellow oil.

3-chloro-4-(4-(methylsulfonyl)-3,4-dihydro-2H-benzo[b][1,4]oxazin-6-yl)-5-(trifluoromethyl)aniline

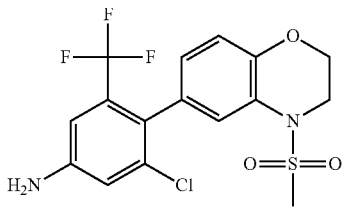 [SMILES: CS(=O)(=O)N1CCOc2ccc(-c3c(Cl)cc(N)cc3C(F)(F)F)cc21]

A microwave vial containing 4-bromo-3-chloro-5-(trifluoromethyl)aniline (350 mg, 1.28 mmol, Eq: 1.00), sodium carbonate (340 mg, 3.21 mmol, Eq: 2.52) and Pd(Ph3P)4 (120 mg, 104 µmol Eq: 0.0814) was degassed for 15 minutes with Ar. A solution of 4-(methylsulfonyl)-6-(4,4,5,5-tetramethyl-1,3,2-dioxaborolan-2-yl)-3,4-dihydro-2H-benzo[b][1,4]oxazine (523 mg, 1.54 mmol, Eq: 1.21) in dioxane (4 mL) was added, followed by water (1 mL). The suspension was degassed for 5 min with Ar with sonication, then capped and heated at 125 in microwave for 2 hr. The reaction was diluted with ethyl acetate, washed with brine. Dried org extract with sodium sulfate. 1 g crude chromatographed (40 g Redisep, 10% to 25% EOAc/hexane) to give 354 mg (68%) of desired product as a colorless oil.

6-(2-chloro-4-isothiocyanato-6-(trifluoromethyl)phenyl)-4-(methylsulfonyl)-3,4-dihydro-2H-benzo[b][1,4]oxazine

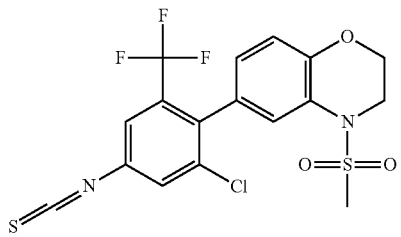 [SMILES: CS(=O)(=O)N1CCOc2ccc(-c3c(Cl)cc(N=CC=S)cc3C(F)(F)F)cc21]

To a suspension of calcium carbonate (244 mg, 2.44 mmol, Eq: 2.8) and 3-chloro-4-(4-(methylsulfonyl)-3,4-dihydro-2H-benzo[b][1,4]oxazin-6-yl)-5-(trifluoromethyl)aniline (354 mg, 870 µmol, Eq: 1.00) in dichloromethane (10.0 ml)/water (10.0 ml) at 0 deg, was added thiophosgene (150 mg, 100 µl, 1.3 mmol, Eq: 1.5) The reaction was gradually warmed to room temperature and stirred overnight. Added 2.5 mL 1N HCl slowly. Separated organic layer and extracted aq once more with dichloromethane. Dried over sodium sulfate and chromatographed (40 g Redisep, 10 to 25% ethyl acetate/hexane) to give 245 mg (63%) of desired product as a white solid.

N-((3-chloro-4-(4-(methylsulfonyl)-3,4-dihydro-2H-benzo[b][1,4]oxazin-6-yl)-5-(trifluoromethyl)phenylamino)(methylthio)methyl)cyanamide

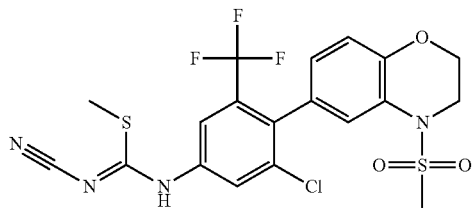 [SMILES: CS/C(=N\C#N)Nc1cc(Cl)c(-c2ccc3c(c2)N(S(C)(=O)=O)CCO3)c(C(F)(F)F)c1]

To a solution of 6-(2-chloro-4-isothiocyanato-6-(trifluoromethyl)phenyl)-4-(methylsulfonyl)-3,4-dihydro-2H-benzo[b][1,4]oxazine (245 mg, 546 µmol, Eq: 1.00) in dimethoxyethane (10 mL) was added to sodium hydrogen cyanamide (45.4 mg, 710 µmol, Eq: 1.3) and methanol (1 mL). After 30 minutes, methyl iodide (227 mg, 100 µl, 1.6 mmol, Eq: 2.93) was added and the reaction was stirred overnight at room temperature. The reaction was concentrated and chromatographed (24 g Redisep, 10 to 40% ethyl acetate/hexane) to give 238 mg (86%) of desired product as an off-white solid.

N*3*-[3-Chloro-4-(4-methanesulfonyl-3,4-dihydro-2H-benzo[1,4]oxazin-6-yl)-5-trifluoromethyl-phenyl]-1H-[1,2,4]triazole-3,5-diamine (Compound 44)

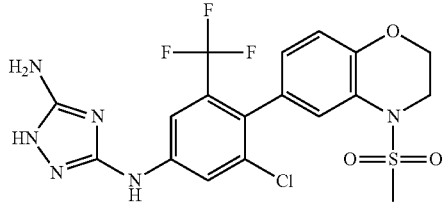 [SMILES: CS(=O)(=O)N1CCOc2ccc(-c3c(Cl)cc(Nc4n[nH]c(N)n4)cc3C(F)(F)F)cc21]

To a solution of N-((3-chloro-4-(4-(methylsulfonyl)-3,4-dihydro-2H-benzo[b][1,4]oxazin-6-yl)-5-(trifluoromethyl)phenylamino)(methylthio)methyl)cyanamide (238 mg, 469 µmol, Eq: 1.00) in ethanol (10 mL) was added hydrazine (153 mg, 150 µl, 4.78 mmol, Eq: 10.2). The reaction mixture was heated at 65 deg o/n. The reaction mixture was concentrated and chromatographed (Redisep 12 g, 1 to 10% methanol/dichloromethane) to give 170 mg (74%) of desired product as a white solid.

MS m/z 489 [M+H]

Procedure 1, 7

N*3*-[2-Chloro-4'-(1,1-dioxo-1lambda*6*-thiomorpholine-4-sulfonyl)-6-trifluoromethyl-biphenyl-4-yl]-1H-[1,2,4]triazole-3,5-diamine (Compound 45)

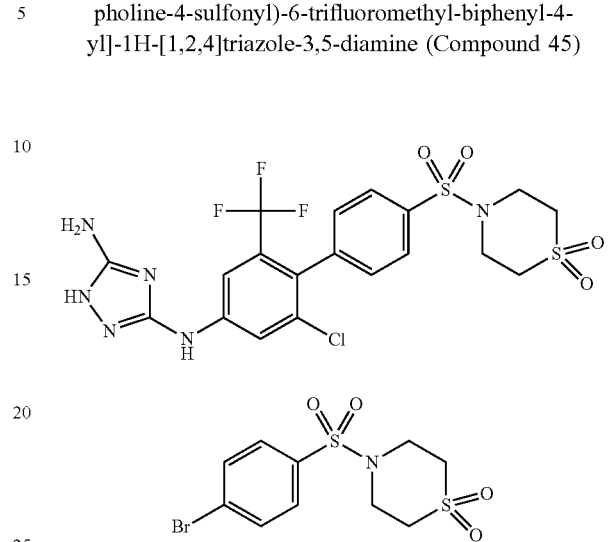

To a solution of thiomorpholine 1,1-dioxide2 (635 mg, 4.7 mmol, Eq: 1.2) and Et3N (799 mg, 1.1 ml, 7.89 mmol, Eq: 2.02) in dichloromethane (10 mL) at 0 deg, was added 4-bromobenzene-1-sulfonyl chloride (1 g, 3.91 mmol, Eq: 1.00). The solution was gradually warmed to room temp and stirred over the weekend at rt. The reaction was diluted with dichloromethane, washed with 1N HCl, brine, dried with sodium sulfate to give 948 mg (68%) of desired product as a white solid.

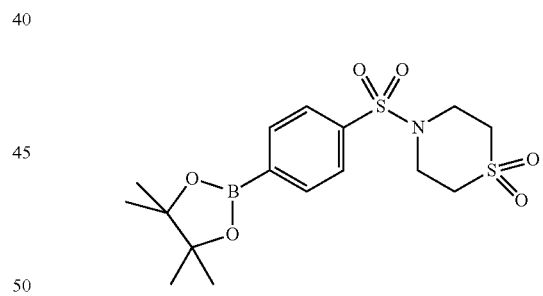

In a 100 mL round bottom flask containing N-(4-bromobenzene-1-sulfonyl)thiomorpholine 1,1 dioxide (948 mg, 2.68 mmol, Eq: 1.00), bis(pinacolato)diboron (1.7 g, 6.69 mmol, Eq: 2.5), potassium acetate (1.18 g, 12.0 mmol, Eq: 4.5) and PdCl2(DPPF)-CH2Cl2 adduct (196 mg, 268 µmol, Eq: 0.1) was degassed for 5 minutes with Argon. Dioxane (20 mL) was added and the reaction was heated at 85 deg overnight with an Ar balloon. The reaction mixture was cooled to room temp, concentrated, diluted with ethyl acetate, washed with brine and dried over sodium sulfate. 2 g crude chromatographed (40 g Redisep 30 to 50 EtOA/hexane) to give 850 mg (79%) of desired product as a pale yellow solid.

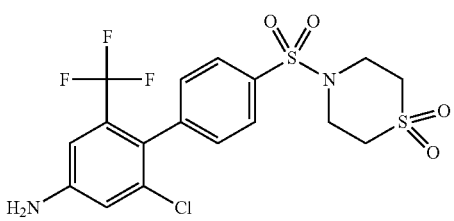 [SMILES: Nc1cc(Cl)c(-c2ccc(S(=O)(=O)N3CCS(=O)(=O)CC3)cc2)c(C(F)(F)F)c1]

A microwave vial containing 4-bromo-3-chloro-5-(trifluoromethyl)aniline (255 mg, 929 μmol, Eq: 1.00), sodium carbonate (247 mg, 2.33 mmol, Eq: 2.51) and Pd(Ph3P)4 (182 mg, 157 μmol, Eq: 0.170) was degassed for 15 minutes with Ar. A solution of N-4-(4,4,5,5-tetramethyl-1,3,2-dioxaboralan-2-yl)benzene-1-sulfonyl thiomorpholine 1,1 dioxide (850 mg, 1.06 mmol, Eq: 1.14) in Dioxane (6 mL) was added, followed by water (1.5 mL). The suspension was degassed for 5 min with Ar with sonication, then capped and heated at 125 in microwave for 2 hr. The reaction was diluted with ethyl acetate, washed with brine, dried with sodium sulfate, and chromatographed (40 g Redisep, 20% to 40% EOAc/hexane) to give 290 mg (67%) of desired product as an off-white solid.

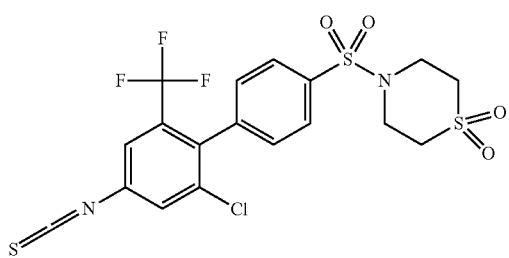 [SMILES: O=S1(=O)CCN(S(=O)(=O)c2ccc(-c3c(Cl)cc(N=CC=S)cc3C(F)(F)F)cc2)CC1]

To a suspension of calcium carbonate (161 mg, 1.61 mmol, Eq: 2.6) and N*3*-[2-Chloro-4'-(1,1-dioxo-1lambda*6*-thiomorpholine-4-sulfonyl)-6-trifluoromethyl-biphenylamine in dichloromethane (10.0 ml)/water (10.0 ml) at 0, was added thiophosgene (105 mg, 70 μl, 913 μmol, Eq: 1.48) The reaction was gradually warmed to room temperature and stirred overnight. Added 2 mL 1N HCl slowly. Separated organic layer and extracted aq twice more with dichloromethane. Dried over sodium sulfate and 350 mg crude was chromatographed (24 g Redisep 10 to 30% ethyl acetate/hexane) to give 257 mg (81%) of desired product as a white solid.

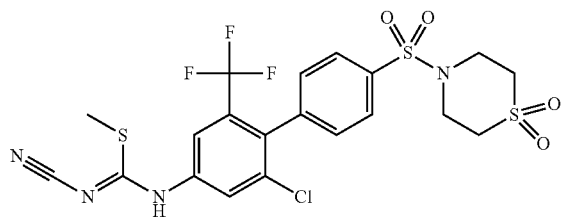 [SMILES: CS/C(=N\C#N)Nc1cc(Cl)c(-c2ccc(S(=O)(=O)N3CCS(=O)(=O)CC3)cc2)c(C(F)(F)F)c1]

To a solution of N*3*-[2-Chloro-4'-(1,1-dioxo-1lambda*6*-thiomorpholine-4-sulfonyl)-6-trifluoromethyl-biphenylisothiocyanate in dimethoxyethane (10 mL) was added to sodium hydrogen cyanamide (50 mg, 781 μmol, Eq: 1.55) and methanol (1 mL). After 30 minutes, methyl iodide (227 mg, 100 μl, 1.6 mmol, Eq: 3.18) was added and the reaction was stirred overnight at room temperature. The reaction mixture was concentrated and chromatographed (24 g Redisep, 40 to 60% ethyl acetate/hexane) to give 185 mg (65%) of desired product as a white solid.

N*3*-[2-Chloro-4'-(1,1-dioxo-1lambda*6*-thiomorpholine-4-sulfonyl)-6-trifluoromethyl-biphenyl-4-yl]-1H-[1,2,4]triazole-3,5-diamine (Compound 45)

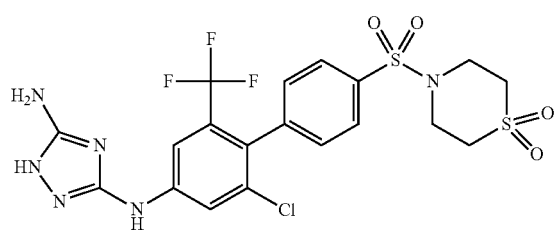 [SMILES: Nc1nc(Nc2cc(Cl)c(-c3ccc(S(=O)(=O)N4CCS(=O)(=O)CC4)cc3)c(C(F)(F)F)c2)n[nH]1]

To a solution of N*3*-[2-Chloro-4'-(1,1-dioxo-1lambda*6*-thiomorpholine-4-sulfonyl)-6-trifluoromethyl-phenylamino(methylthiocyanamide) (185 mg, 325 μmol, Eq: 1.00) in ethanol (10 mL) was added hydrazine (102 mg, 100 μl, 3.19 mmol, Eq: 9.8). The reaction mixture was heated at 65 deg o/n. The reaction mixture was cooled to rt, and the white solid was filtered and dried o/n at 80 deg with high vac to give 166 mg (93%) of desired product as a white solid.

MS m/z 551 [M+H]

Procedure 6

N-(2-fluoro-4-(4,4,5,5-tetramethyl-1,3,2-dioxaborolan-2-yl)phenyl)methanesulfonamide (Compound 46)

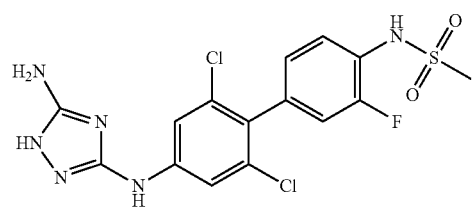

N-[2-Fluoro-4-(4,4,5,5-tetramethyl-[1,3,2]dioxaborolan-2-yl)-phenyl]-methanesulfonamide

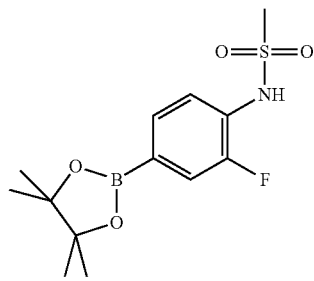 [SMILES: CC1(C)OB(c2ccc(NS(C)(=O)=O)c(F)c2)OC1(C)C]

To a solution of 2-fluoro-4-(4,4,5,5-tetramethyl-1,3,2-dioxaborolan-2-yl)aniline (300 mg, 1.27 mmol, Eq: 1.00) in pyridine (10 mL) at 0 deg, was added Ms-Cl (184 mg, 125 µL, 1.6 mmol, Eq: 1.27). The solution was gradually warmed to room temp and stirred overnight. TLC shows incomplete reaction. Added 125 µL MsCl and stirred for 6 hr. The reaction was diluted with ethyl acetate, washed with brine 3×, washed with 1N HCl, dried with sodium sulfate, and chromatographed (40 g Redisep, 15 to 30% ethyl acetate/hexane) to give 171 mg (43%) of desired product as a colorless waxy solid.

N-(2-fluoro-4-(4,4,5,5-tetramethyl-1,3,2-dioxaborolan-2-yl)phenyl)methanesulfonamide (Compound 46)

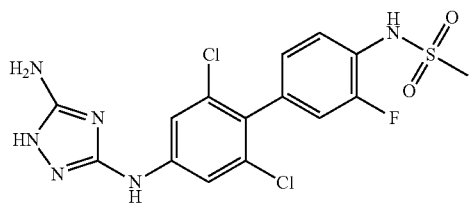 [SMILES: CS(=O)(=O)Nc1ccc(-c2c(Cl)cc(Nc3n[nH]c(N)n3)cc2Cl)cc1F]

A microwave vial containing N3-(4-bromo-3,5-dichlorophenyl)-1H-1,2,4-triazole-3,5-diamine Intermediate 2 (100 mg, 310 µmol, Eq: 1.00), sodium carbonate (82.0 mg, 774 µmol, Eq: 2.5) and bis(di-t-Bu-phosphino)ferrocenyl PdCl2 (29.6 mg, 45.4 µmol, Eq: 0.147) was degassed for 15 minutes with Argon. A solution of N-(2-fluoro-4-(4,4,5,5-tetramethyl-1,3,2-dioxaborolan-2-yl)phenyl)methanesulfonamide (171 mg, 543 µmol, Eq: 1.75) in dioxane (2.5 mL) was added, followed by water (0.5 mL), and the suspension was degassed for 5 minutes with sonication, and the reaction was heated at 125o for 1 hr with microwave. The reaction was diluted with ethyl acetate, washed with brine, dried with sodium sulfate, and chromatographed (24 g Redisep Gold, 0 to 10% methanol/dichloromethane) to give 69 mg brown solid, containing desired product and impurities. The compound was triturated with dichloromethane/methanol to give 54 mg (40%) of desired product as a brown solid.

MS m/z 431 [M+H]

Procedure 1, 7

6-[4-(5-Amino-1H-[1,2,4]triazol-3-ylamino)-2-chloro-6-trifluoromethyl-phenyl]-4H-benzo[1,4]oxazin-3-one (Compound 47)

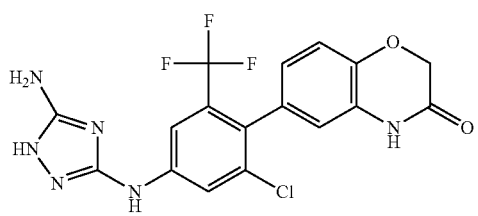 [SMILES: Nc1nc(Nc2cc(Cl)c(-c3ccc4c(c3)NC(=O)CO4)c(C(F)(F)F)c2)n[nH]1]

6-(4,4,5,5-tetramethyl-1,3,2-dioxaborolan-2-yl)-2H-benzo[b][1,4]oxazin-3(4H)-one

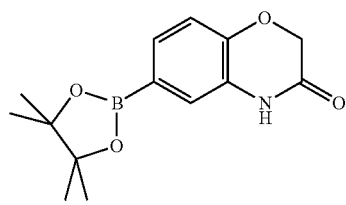 [SMILES: CC1(C)OB(c2ccc3c(c2)NC(=O)CO3)OC1(C)C]

To a solution of 6-bromo-2H-benzo[b][1,4]oxazin-3(4H)-one (1 g, 4.39 mmol, Eq: 1.00), bis(pinacolato)diboron (2.78 g, 11.0 mmol, Eq: 2.5), and potassium acetate (1.94 g, 19.7 mmol, Eq: 4.5) in dioxane (15 mL), was added PdCl2(DPPF)-CH2Cl2 adduct (241 mg, 329 µmol, Eq: 0.0751) The reaction was heated at 85 deg overnight with an Ar balloon. The reaction mixture was cooled to room temp, concentrated, diluted with ethyl acetate, washed with brine and dried over sodium sulfate. 2 g crude chromatographed (40 g Redisep, 10 to 40% ethyl acetate/hexane) to give 1.66 g mg white solid, containing desired product and ~50% of pinacol diboron impurity.

6-(4-amino-2-chloro-6-(trifluoromethyl)phenyl)-2H-benzo[b][1,4]oxazin-3(4H)-one

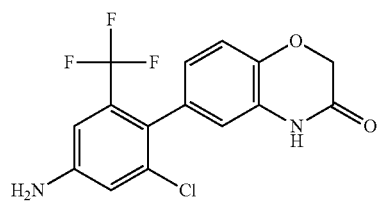 [SMILES: Nc1cc(Cl)c(-c2ccc3c(c2)NC(=O)CO3)c(C(F)(F)F)c1]

A microwave vial containing 4-bromo-3-chloro-5-(trifluoromethyl)aniline (400 mg, 1.46 mmol, Eq: 1.00), sodium carbonate (386 mg, 3.64 mmol, Eq: 2.5) and Pd(Ph3P)4 (141 mg, 122 µmol, Eq: 0.0837) was degassed for 15 minutes with Ar. A solution of 6-(4,4,5,5-tetramethyl-1,3,2-dioxaborolan-2-yl)-2H-benzo[b][1,4]oxazin-3(4H)-one (1 g, 1.82 mmol, Eq: 1.25) in dioxane (6 mL) was added, followed by water (1.5 mL). The suspension was degassed for 5 min with Ar with sonication, then capped and heated at 125 in microwave for 2 hr. The reaction mixture was diluted with ethyl acetate, washed with brine, dried with sodium sulfate, and crude chromatographed (40 g Redisep, 10% to 30% ethyl acetate/hexane) to give 108 mg (22%) of desired product as an off-white solid.

6-(2-chloro-4-isothiocyanato-6-(trifluoromethyl)phenyl)-2H-benzo[b][1,4]oxazin-3(4H)-one

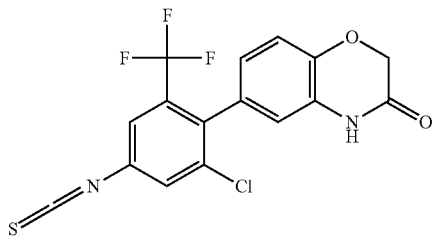 [SMILES: O=C1COc2ccc(-c3c(Cl)cc(N=CC=S)cc3C(F)(F)F)cc2N1]

To a suspension of calcium carbonate (88.3 mg, 882 µmol, Eq: 2.8) and 6-(4-amino-2-chloro-6-(trifluoromethyl)phenyl)-2H-benzo[b][1,4]oxazin-3(4H)-one (108 mg, 315 µmol, Eq: 1.00) in dichloromethane (10.0 ml)/water (10.0 ml) at 0, was added thiophosgene (75.0 mg, 50 µl, 652 µmol, Eq: 2.07) The reaction was gradually warmed to room temperature and stirred overnight. Added 1 mL 1N HCl slowly. Separated organic layer and extracted aq twice more with dichloromethane. Dried over sodium sulfate and concentrated to give 92 mg (76%) of desired product as an off-white solid.

N-((3-chloro-4-(3-oxo-3,4-dihydro-2H-benzo[b][1,4]oxazin-6-yl)-5-(trifluoromethyl)phenylamino)(methylthio)methyl)cyanamide

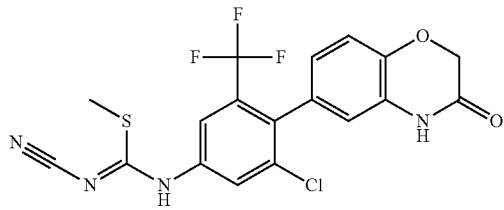 [SMILES: CS/C(=N\C#N)Nc1cc(Cl)c(-c2ccc3c(c2)NC(=O)CO3)c(C(F)(F)F)c1]

To a solution of 6-(2-chloro-4-isothiocyanato-6-(trifluoromethyl)phenyl)-2H-benzo[b][1,4]oxazin-3(4H)-one (92 mg, 239 µmol, Eq: 1.00) in dimethoxyethane (5 mL) was added to sodium hydrogen cyanamide (19.9 mg, 311 µmol, Eq: 1.3) and methanol (0.5 mL). After 30 minutes, METHYL IODIDE (90.8 mg, 40 µl, 640 µmol, Eq: 2.68) was added and the reaction was stirred overnight at room temperature. The reaction mixture was concentrated and chromatographed (24 g Redisep, 50 to 75% ethyl acetate/hexane) to give 71 mg (67%) of desired product as a white solid.

6-[4-(5-Amino-1H-[1,2,4]triazol-3-ylamino)-2-chloro-6-trifluoromethyl-phenyl]-4H-benzo[1,4]oxazin-3-one (Compound 47)

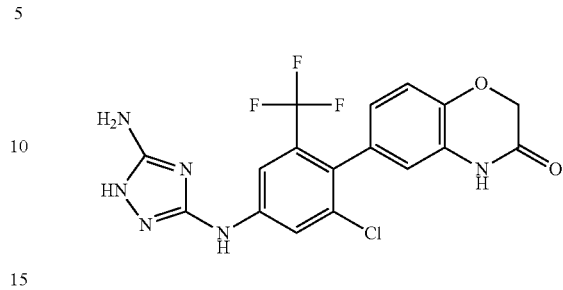

To a solution of N-((3-chloro-4-(3-oxo-3,4-dihydro-2H-benzo[b][1,4]oxazin-6-yl)-5-(trifluoromethyl)phenylamino)(methylthio)methyl)cyanamide (71 mg, 160 µmol, Eq: 1.00) in ethanol (5 mL) was added hydrazine (51.4 mg, 50.3 µl, 1.6 mmol, Eq: 10). The reaction mixture was heated at 65 deg o/n. The reaction mixture was concentrated and chromatographed (Redisep 12 g, 1 to 10% methanol/dichloromethane) to give 48 mg (71%) of desired product as a white solid.

MS m/z 425 [M+H]

Procedure 1, 7

N*3*-(2,6-Dichloro-biphenyl-4-yl)-1H-[1,2,4]triazole-3,5-diamine (Compound 48)

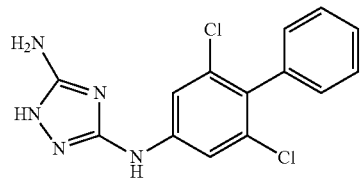 [SMILES: Nc1nc(Nc2cc(Cl)c(-c3ccccc3)c(Cl)c2)n[nH]1]

2,6-dichloro-4-nitrobiphenyl

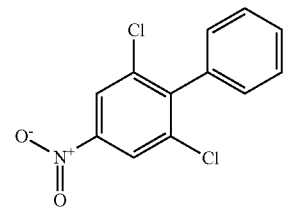 [SMILES: O=[N+]([O-])c1cc(Cl)c(-c2ccccc2)c(Cl)c1]

A solution of 1,3-dichloro-2-iodo-5-nitrobenzene (1 g, 3.15 mmol, Eq: 1.00), phenylboronic acid (583 mg, 4.78 mmol, Eq: 1.52), sodium carbonate (834 mg, 7.86 mmol, Eq: 2.5) and bis(triphenylphosphine)palladium (II) chloride (221 mg, 315 µmol, Eq: 0.1) in methanol (4 mL)/dichloromethane (1 mL) were placed in a microwave vial and heated 110 for 30 min. The reaction was concentrated and chromatographed (120 g Analogix, 100% hexane to 3% ethyl acetate/hexane) to give 718 mg (85%) of desired product as a light yellow oil.

239

2,6-dichlorobiphenyl-4-amine

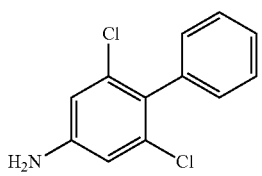 [SMILES: Nc1cc(Cl)c(-c2ccccc2)c(Cl)c1]

A solution of 2,6-dichloro-4-nitrobiphenyl (718 mg, 2.68 mmol, Eq: 1.00), iron (745 mg, 13.3 mmol, Eq: 4.98) and ammonium chloride (1.41 g, 26.4 mmol, Eq: 9.84) in methanol (10 mL)/water (5 mL) was heated at 60° o/n. Filtered over Celite and concentrated off methanol. Diluted with ethyl acetate, separated organic extract, washed with water and dried over sodium sulfate to give 615 mg (96%) of desired product as a yellow solid.

2,6-dichloro-4-isothiocyanatobiphenyl

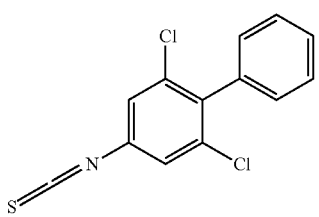 [SMILES: S=CC=Nc1cc(Cl)c(-c2ccccc2)c(Cl)c1]

To a suspension of calcium carbonate (650 mg, 6.49 mmol, Eq: 2.51) and thiophosgene (375 mg, 250 µl, 3.26 mmol, Eq: 1.26) in dichloromethane (10.0 ml)/water (10.0 ml) at 0, was added 2,6-dichlorobiphenyl-4-amine (615 mg, 2.58 mmol, Eq: 1.00) The reaction was gradually warmed to room temperature and stirred overnight. Added 7 mL 1N HCl. Separated organic layer and dried over sodium sulfate to give 619 mg (86%) of desired product as a brown oil.

(Z)-methyl N'-cyano-N-(2,6-dichlorobiphenyl-4-yl)carbamimidothioate

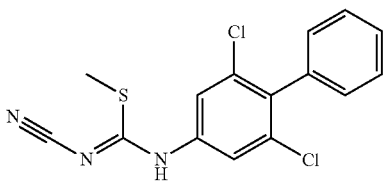 [SMILES: CS/C(=N\C#N)Nc1cc(Cl)c(-c2ccccc2)c(Cl)c1]

Sodium methoxide (0.5M in methanol) (2.6 ml, 1.3 mmol, Eq: 1.21) was added to cyanamide (50 mg, 1.19 mmol, Eq: 1.11). After 15 minutes, a solution of 2,6-dichloro-4-isothiocyanatobiphenyl (300 mg, 1.07 mmol, Eq: 1.00) in methanol (5 mL) was added. After 1 hr, methyl iodide (318 mg, 140 µl, 2.24 mmol, Eq: 2.09) was added and the reaction was stirred overnight at room temperature. The reaction mixture concentrated and chromatographed (40 g Analogix, 25% ethyl acetate/hexane to 40% ethyl acetate/hexane) to give 136 mg (38%) of desired product as a pale yellow solid.

240

N*3*-(2,6-Dichloro-biphenyl-4-yl)-1H-[1,2,4]triazole-3,5-diamine (Compound 48)

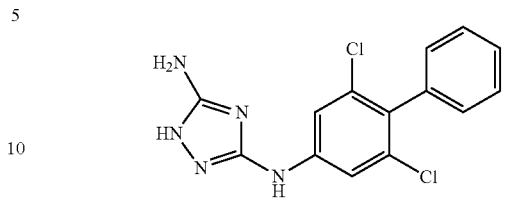

A solution of (Z)-methyl N'-cyano-N-(2,6-dichlorobiphenyl-4-yl)carbamimidothioate (136 mg, 404 µmol, Eq: 1.00) and hydrazine (128 mg, 125 µl, 3.98 mmol, Eq: 9.85) in ethanol (5 mL) was heated at 70 deg o/n. The reaction mixture was concentrated and chromatographed (11 g Supelco, 100% dichloromethane to 10% methanol/dichloromethane) to give 89 mg (69%) of desired product as an off-white solid.
MS m/z 320, 322 [M+H]

Procedure 1, 7

N*3*-[4'-(4-Amino-butoxy)-2,6-dichloro-biphenyl-4-yl]-1H-[1,2,4]triazole-3,5-diamine; trifluoro-acetate (Compound 49)

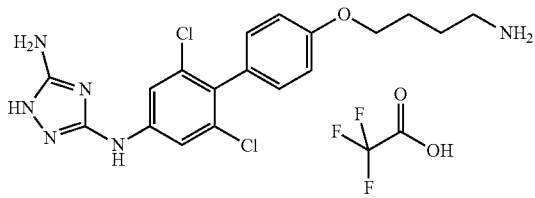 [SMILES: NCCCCOc1ccc(-c2c(Cl)cc(Nc3n[nH]c(N)n3)cc2Cl)cc1 ; O=C(O)C(F)(F)F]

To a solution of 4-(4'-(5-amino-1H-1,2,4-triazol-3-ylamino)-2',6'-dichlorobiphenyl-4-yloxy)butanenitrile Compound 26 (196 mg, 486 µmol, Eq: 1.00) in THF (8 mL) at 0° C., was added LiAlH4 (2M in THF, 1.5 ml, 3.00 mmol, Eq: 6.17). After 3 hr, the reaction was quenched with 1N HCl 5 mL, stirred for 30 min. neutralized with 1N NaOH 5 mL, and extracted with ethyl acetate. The organic extract was dried over sodium sulfate and purified by preparative plate chromatography to give 53 mg pale yellow oil, containing desired product and impurities. Further purification by SFC gave 16 mg (6%) of desired product as a white solid.
MS m/z 407 [M+H-TFA]

Procedure 6

N*3*-(4'-Amino-2,6-dichloro-biphenyl-4-yl)-1H-[1,2,4]triazole-3,5-diamine (Compound 50)

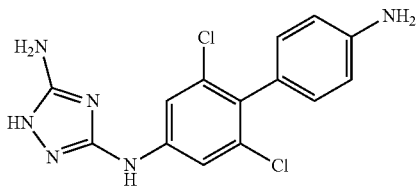 [SMILES: Nc1ccc(-c2c(Cl)cc(Nc3n[nH]c(N)n3)cc2Cl)cc1]

A microwave vial containing N3-(4-bromo-3,5-dichlorophenyl)-1H-1,2,4-triazole-3,5-diamine Intermediate 2 (100 mg, 310 µmol, Eq: 1.00), 4-(4,4,5,5-tetramethyl-1,3,2-dioxaborolan-2-yl)aniline (103 mg, 470 µmol, Eq: 1.52), sodium carbonate (85 mg, 802 µmol, Eq: 2.59) and Pd(Ph3P)4 (38.0 mg, 32.9 µmol, Eq: 0.106) was degassed for 15 minutes with Argon. Dioxane (2 mL) and water (0.5 mL) was added, and the suspension was degassed for 5 minutes with sonication, and the reaction was heated at 125o for 1.5 hr with microwave, The reaction was concentrated, diluted with ethyl acetate, washed with brine, dried with sodium sulfate, and chromatographed (24 g Redisep, 0 to 10% methanol/dichloromethane) to give 67 mg yellow solid, containing desired product and impurities. The compound was suspended in methanol and dichloromethane and filtered to give 16 mg (15%) of desired product as an off-white solid.

MS m/z 333 [M–H]

Procedure 1, 7

(S)-1-[4'-(5-Amino-1H-[1,2,4]triazol-3-ylamino)-2'-chloro-6'-trifluoromethyl-biphenyl-4-sulfonyl]-pyrrolidine-2-carboxylic acid (Compound 51)

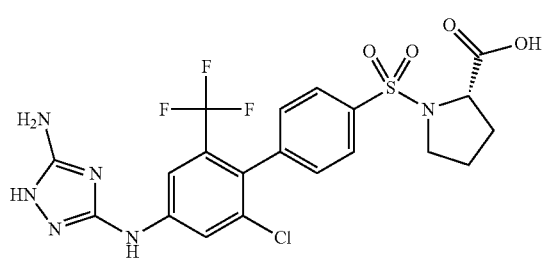 [SMILES: Nc1nc(Nc2cc(Cl)c(-c3ccc(S(=O)(=O)N4CCC[C@H]4C(=O)O)cc3)c(C(F)(F)F)c2)n[nH]1]

A solution of (S)-tert-butyl 1-(4'-(5-amino-1H-1,2,4-triazol-3-ylamino)-2'-chloro-6'-(trifluoromethyl)biphenyl-4-ylsulfonyl)pyrrolidine-2-carboxylate Compound 3 (24 mg, 40.9 µmol, Eq: 1.00) in hexaneafluoroisopropanol (5 mL) was heated at 110 deg for 6 hr with microwave. The reaction was concentrated and dried under vacuum to give 19 mg (88%) of desired product as a light brown solid.

MS m/z 531

N*3*-[3,5-Dichloro-4-(2,2-dimethyl-4,4-dioxo-3,4-dihydro-2H-4lambda*6*-benzo[1,4]oxathiin-6-yl)-phenyl]-1H-[1,2,4]triazole-3,5-diamine (Compound 52)

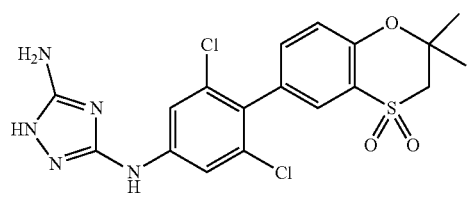 [SMILES: CC1(C)CS(=O)(=O)c2cc(-c3c(Cl)cc(Nc4n[nH]c(N)n4)cc3Cl)ccc2O1]

6-bromo-2,2-dimethyl-2,3-dihydrobenzo[b][1,4]oxathiine

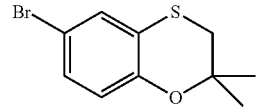

To a suspension of sodium hydride (dispersion in oil, 506 mg, 11.6 mmol, Eq: 1.5) in dry dimethylformamide (20 mL) was added a solution of 4-bromo-2-fluorobenzenethiol (1.6 g, 7.73 mmol, Eq: 1.00) in dimethylformamide (5 mL).

The reaction mixture was stirred 15 min then 2,2-dimethyloxirane (1.11 g, 1.38 mL, 15.5 mmol, Eq: 2) was slowly added. The flash was sealed and stirred at 50° C. for 16 h.

The reaction mixture was partitioned between water and ethyl acetate then HCl 1 N (12 mL) was added to adjust the pH to ca. 5.

Organic layer was washed with water then brine then adsorbed unto silica (2 g), concentrated and purified on silica gel (silica 40 g, Hexane/ethyl acetate 95:5 to 65:35). One fraction was isolated and dried in vacuo to afford 171 mg (8%) of the desired product as colorless oil.

6-Bromo-2,2-dimethyl-2,3-dihydro-benzo[1,4]oxathiine 4,4-dioxide

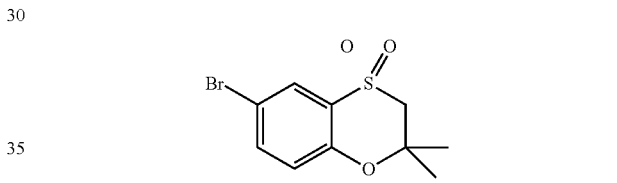

To a solution of 6-bromo-2,2-dimethyl-2,3-dihydrobenzo[b][1,4]oxathiine (138 mg, 532 µmol, Eq: 1.00) in dry dichloromethane (10 ml) was successively added sodium hydrogencarbonate (340 mg, 4.05 mmol, Eq: 7.6) and 3-chlorobenzoperoxoic acid (453 mg, 2.02 mmol, Eq: 3.8). The reaction mixture was allowed to warm up to room temperature then stirred 14 h. The reaction mixture was washed with sat. aqueous solution of sodium sulfite, sat. aqueous solution of sodium hydrogenocarbonate then brine.

The organic layer was adsorbed unto silica (1.5 g), concentrated and purified on silica gel (silica 24 g, Hexanes/ethyl acetate 98:2 to 60:40). One fraction was isolated and dried in vacuo to afford 128 mg (83%) of the desired product as a white solid.

2,2-Dimethyl-6-(4,4,5,5-tetramethyl-[1,3,2]dioxaborolan-2-yl)-2,3-dihydro-benzo[1,4]oxathiine 4,4-dioxide

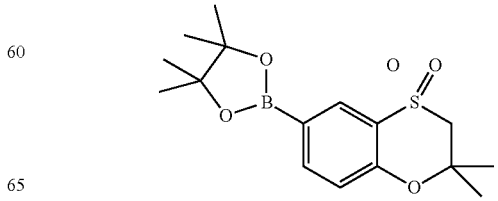

A mixture of 6-Bromo-2,2-dimethyl-2,3-dihydro-benzo[1,4]oxathiine 4,4-dioxide (125 mg, 429 μmol, Eq: 1.00), 4,4,4',4',5,5,5',5'-octamethyl-2,2'-bi(1,3,2-dioxaborolane) (273 mg, 1.07 mmol, Eq: 2.5), potassium acetate (190 mg, 1.93 mmol, Eq: 4.5) and dichloro[1,1'-bis(diphenylphosphino)ferrocene]palladium (II) (31.4 mg, 42.9 μmol, Eq: 0.1) was degassed (vacuum/nitrogen cycles) then degassed (nitrogen bubbling with sonication)dioxane dry (8 ml) was added. The mixture was stirred at 80° C. for 18 h in the sealed vial.

The reaction mixture was adsorbed unto silica (1 g), concentrated and purified on silica gel (silica 24 g, Hexane/ethyl acetate 95:5 to 55:45 within 30 min). One fraction was isolated and dried in vacuo to afford 105 mg (72%) of the desired product as a white solid.

N*3*-[3,5-Dichloro-4-(2,2-dimethyl-4,4-dioxo-3,4-dihydro-2H-4lambda*6*-benzo[1,4]oxathiin-6-yl)-phenyl]-1H-[1,2,4]triazole (Compound 52)

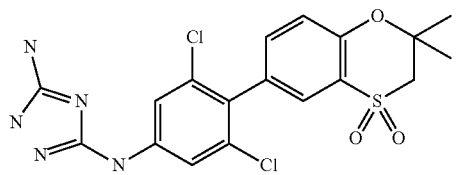 [SMILES: CC1(C)CS(=O)(=O)c2cc(-c3c(Cl)cc(NC(=N)N=C(N)N)cc3Cl)ccc2O1]

A mixture of N3-(4-bromo-3,5-dichlorophenyl)-1H-1,2,4-triazole-3,5-diamine Intermediate 2 (100 mg, 310 μmol, Eq: 1.05), 2,2-dimethyl-6-(4,4,5,5-tetramethyl-[1,3,2]dioxaborolan-2-yl)-2,3-dihydro-benzo[1,4]oxathiine 4,4-dioxide (100 mg, 296 μmol, Eq: 1.00) and tetrakis(triphenylphosphine)palladium (0) (34.1 mg, 29.6 μmol, Eq: 0.1) was degassed (vacuum/nitrogen cycles) then degassed (nitrogen bubbling with sonication) dry dioxane (1.06 ml) and a degassed (nitrogen bubbling with sonication) 2M solution of sodium carbonate in water (316 μl, 633 μmol, Eq: 2.14) were added and the reaction mixture was sealed and stirred at 100° C. for 18 h in a sealed vial.

The reaction mixture was adsorbed unto silica (1 g), concentrated and purified on silica gel (column 24 g, dichloromethane/methanol 97:3 to 65:35). One fraction was isolated and dried in vacuo to afford 74 mg of a yellow solid. This solid was further purified by reverse phase HLPC to afford 13 mg of the desired product as an off white solid.

SFC purification gave 13 mg of desired product as an off-white solid.

MS m/z 454 [M+H]

Procedure 1

Pentanoic acid [4'-(5-amino-1H-[1,2,4]triazol-3-ylamino)-biphenyl-4-yl]-amide (Compound 53)

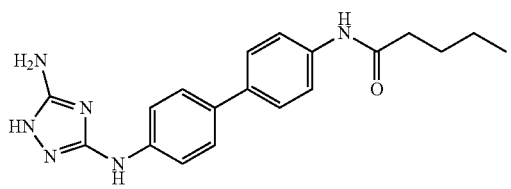 [SMILES: CCCCC(=O)Nc1ccc(-c2ccc(Nc3n[nH]c(N)n3)cc2)cc1]

N-(4'-nitrobiphenyl-4-yl)butyramide

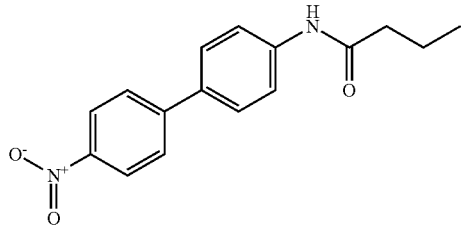 [SMILES: CCCC(=O)Nc1ccc(-c2ccc([N+](=O)[O-])cc2)cc1]

To a solution of 4'-nitrobiphenyl-4-amine (1 g, 4.67 mmol, Eq: 1.00) and Et3N (726 mg, 1 mL, 7.17 mmol, Eq: 1.54) in THF (10 mL) at 0 deg, was added pentanoyl chloride (696 mg, 700 μL, 5.78 mmol, Eq: 1.24). The solution was gradually warmed to room temp and stirred overnight. TLC still shows trace of sm. Added 350 μL pentanoyl chloride and stirred at rt for 6 hr. The reaction mixture was diluted with ethyl acetate, washed with brine, dried with sodium sulfate, and chromatographed (40 g Redisep, 10 to 30 to 50% EtAOc/hexane) to give 1.304 g (94%) of desired product as a yellow solid.

N-(4'-aminobiphenyl-4-yl)pentanamide

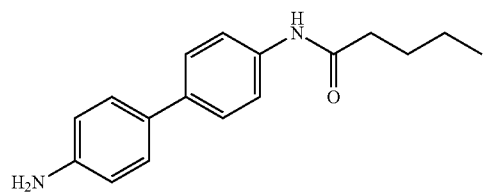 [SMILES: CCCCC(=O)Nc1ccc(-c2ccc(N)cc2)cc1]

A solution of N-(4'-nitrobiphenyl-4-yl)butyramide (700 mg, 2.46 mmol, Eq: 1.00), iron (687 mg, 12.3 mmol, Eq: 5) and ammonium chloride (1.32 g, 24.6 mmol, Eq: 10) in methanol (40 mL)/water (20 mL) was heated at 60° o/n. Filtered over Celite and washed with methanol/ethyl acetate. Concentrated off methanol, diluted with ethyl acetate, washed with brine, and concentrated to give 338 mg (54%) of desired product as a pale yellow solid.

N-(4'-isothiocyanatobiphenyl-4-yl)pentanamide

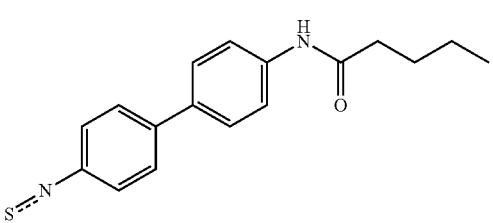

A suspension of N-(4'-aminobiphenyl-4-yl)pentanamide (338 mg, 1.26 mmol, Eq: 1.00), thiophosgene (563 mg, 375 μL, 4.89 mmol, Eq: 3.88), triethylamine (545 mg, 750 μL, 5.38 mmol, Eq: 4.27) in benzene (15 mL) was heated at reflux overnight. The brown reaction mixture was concentrated, diluted with dichloromethane, washed with 1N HCl (5 mL) and brine, and dried over sodium sulfate. 0.5 g crude was chromatographed (24 g Redesip, 10% to 35% ethyl acetate/hexaneane) to give 266 mg (68%) of desired product as a yellow solid.

N-(4'-(cyanamido(methylthio)methylamino)biphenyl-4-yl)pentanamide

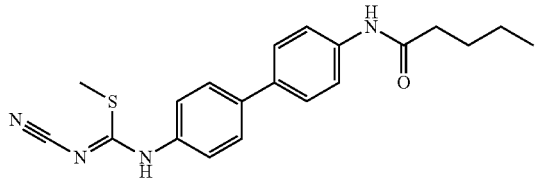 [SMILES: CCCCC(=O)Nc1ccc(-c2ccc(N/C(=N/C#N)SC)cc2)cc1]

To a solution of N-(4'-isothiocyanatobiphenyl-4-yl)pentanamide (266 mg, 857 µmol, Eq: 1.00) in dimethoxyethane (6 mL) was added to sodium hydrogen cyanamide (69 mg, 1.08 mmol, Eq: 1.26) and methanol (1.5 mL). After 30 minutes, methyl iodide (318 mg, 140 µL, 2.24 mmol, Eq: 2.61) was added and the reaction was stirred overnight at room temperature. The resulting suspension was filtered and rinsed with methanol, to give 188 mg (60%) of desired product as an off-white solid.

Pentanoic acid [4'-(5-amino-1H-[1,2,4]triazol-3-ylamino)-biphenyl-4-yl]-amide (Compound 53)

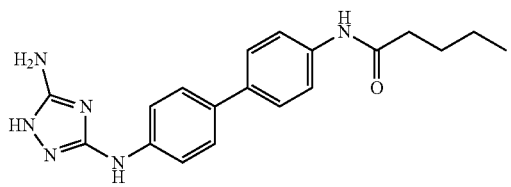 [SMILES: CCCCC(=O)Nc1ccc(-c2ccc(Nc3n[nH]c(N)n3)cc2)cc1]

To a solution of N-(4'-(cyanamido(methylthio)methylamino)biphenyl-4-yl)pentanamide (188 mg, 510 µmol, Eq: 1.00) in ethanol (8 mL) was added hydrazine (179 mg, 175 µl, 5.58 mmol, Eq: 10.9). The reaction mixture was heated at 65 deg o/n. The resulting suspension was filtered to give 139 mg (78%) of desired product as a white solid.
MS m/z 351 [M+H]

Procedure 6

5-((3aS,4S,6aR)-2-Oxo-hexaneahydro-thieno[3,4-d]imidazol-4-yl)-pentanoic acid [4'-(5-amino-1H-[1,2,4]triazol-3-ylamino)-biphenyl-4-yl]-amide (Compound 54)

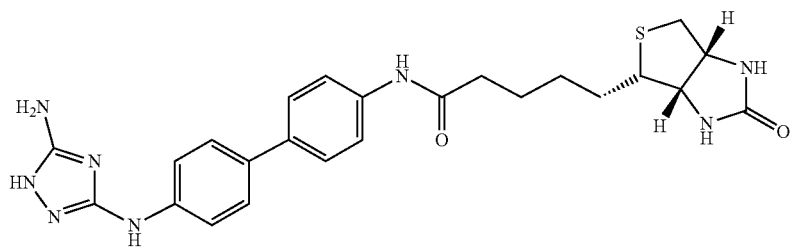

N-((4-iodophenylamino)(methylthio)methyl)cyanamide

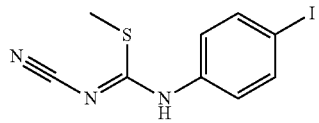

To a solution of 1-iodo-4-isothiocyanatobenzene (2.066 g, 7.91 mmol, Eq: 1.00) in methanol (20 mL) was added to sodium hydrogen cyanamide (563 mg, 8.79 mmol, Eq: 1.11). After 30 minutes, methyl iodide (2.27 g, 1 mL, 16.0 mmol, Eq: 2.02) was added and the reaction was stirred overnight at room temperature. The resulting gray suspension was filtered to give 1.713 g (68%) of desired product as a grey solid.

N3-(4-iodophenyl)-1H-1,2,4-triazole-3,5-diamine

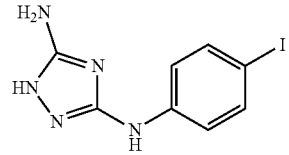 [SMILES: Nc1nc(Nc2ccc(I)cc2)n[nH]1]

To a solution of N-((4-iodophenylamino)(methylthio)methyl)cyanamide (500 mg, 1.57 mmol, Eq: 1.00) in ethanol (15 mL) was added hydrazine (502 mg, 492 µl, 15.7 mmol, Eq: 10). The reaction mixture was heated at 60 deg o/n. The reaction was concentrated and chromatographed (40 g Redisep, 0 to 10% methanol/dichloromethane) to give 473 mg (100%) of desired product as a white solid.
MS m/z 302 [M+H]

5-((3aS,4S,6aR)-2-Oxo-hexaneahydro-thieno[3,4-d]imidazol-4-yl)-pentanoic acid [4'-(5-amino-1H-[1,2,4]triazol-3-ylamino)-biphenyl-4-yl]-amide (Compound 54)

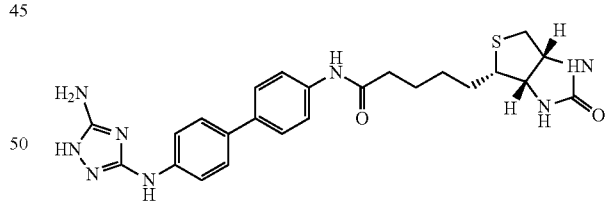

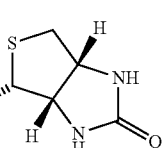

A microwave vial containing N3-(4-iodophenyl)-1H-1,2,4-triazole-3,5-diamine (50 mg, 166 µmol, Eq: 1.00), 5-((3aS,4S,6aR)-2-oxohexaneahydro-1H-thieno[3,4-d]imidazol-4-yl)-N-(4-(4,4,5,5-tetramethyl-1,3,2-dioxaborolan-2-yl)phenyl)pentanamide (88.8 mg, 199 µmol, Eq: 1.2), sodium carbonate (44.0 mg, 415 µmol, Eq: 2.5) and bis(di-t-Butylphosphino)ferrocenyl PdCl2 (10.8 mg, 16.6 µmol, Eq: 0.1) was degassed with argon for 15 minutes. Dioxane (2 mL)/water (0.5 mL) was added and the suspension was degassed for an additional 5 minutes with argon, while sonicated. The reaction was heated at 125 for 1 hr with the microwave. The reaction was diluted with ethyl acetate, washed with brine. Filtered off insoluble precipitate (insoluble in both org and aq layer) to give brown solid containing desired product and impurities. Purification by SFC gave 16 mg (20%) of desired product as a white solid.

MS m/z 493 [M+H]

Procedure 2

N*3*-Biphenyl-4-yl-1H-[1,2,4]triazole-3,5-diamine (Compound 55)

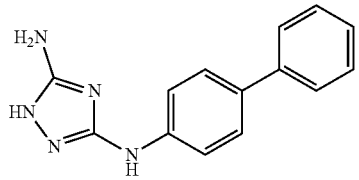 [SMILES: Nc1nc(Nc2ccc(-c3ccccc3)cc2)n[nH]1]

(Z)-phenyl N-biphenyl-4-yl-N'-cyanocarbamimidate

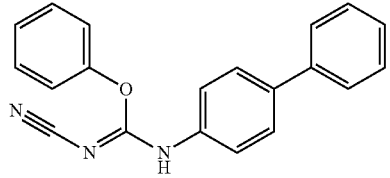 [SMILES: N#C/N=C(/Nc1ccc(-c2ccccc2)cc1)Oc1ccccc1]

A solution of biphenyl-4-amine (153 mg, 904 µmol, Eq: 1.00) and diphenyl cyanocarbonimidate (258 mg, 1.08 mmol, Eq: 1.2) in acetonitrile (5 mL) was heated at 50 overnight. Filtered off white solid and rinsed with hexaneane to give 123 mg (43%) of desired product as an off-white solid.

N*3*-Biphenyl-4-yl-1H-[1,2,4]triazole-3,5-diamine (Compound 55)

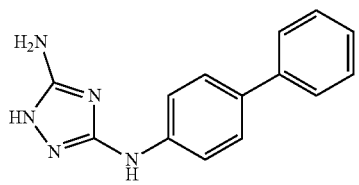 [SMILES: Nc1nc(Nc2ccc(-c3ccccc3)cc2)n[nH]1]

To a solution of (Z)-phenyl N-biphenyl-4-yl-N'-cyanocarbamimidate (123 mg, 393 µmol, Eq: 1.00) in methanol (5 mL) was added hydrazine (128 mg, 125 µl, 3.98 mmol, Eq: 10.1). The reaction mixture was heated at 60 deg for 4 hrs, then stirred at room temperature over the weekend. The reaction mixture was concentrated and chromatographed (11 g Supelco, 0 to 10% methanol/dichloromethane) to give desired product and impurities. Suspended solid in dichloromethane and filtered to give 98 mg (99%) of desired product as an off white solid.

MS m/z 252 [M+H]

Procedure 1, 7

N*3*-{2-Chloro-4'-[1-(3,3-dimethyl-butyl)-piperidin-3-ylmethanesulfonyl]-6-trifluoromethyl-biphenyl-4-yl}-1H-[1,2,4]triazole-3,5-diamine; hydrochloride (Compound 56)

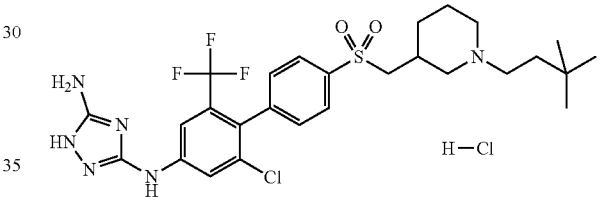

To a suspension of N3-(2-chloro-4'-((1-(3,3-dimethylbutyl)piperidin-3-yl)methylsulfonyl)-6-(trifluoromethyl)biphenyl-4-yl)-1H-1,2,4-triazole-3,5-diamine hydrochloride Compound 25 (30 mg, 47.2 µmol, Eq: 1.00) in methanol (4 mL), was added 3,3-dimethylbutanal (7.98 mg, 10 µl, 79.7 µmol, Eq: 1.69), followed by sodium cyanoborohydride (6 mg, 95.5 µmol, Eq: 2.02). The white slurry was stirred o/n.

The colorless soln was concd, diluted with ethyl acetate, basified with sodium carbonate aq solution and the organic layer was separated. Extracted aqueous twice more with EtAOc. Combined org extracts and dried over sodium sulfate and chromatographed (12 g Redisep, 1 to 10% methanol/dichloromethane) to give 17 mg white solid of free amine.

To a solution of 17 mg of amine in 2 mL methanol, was added a freshly prepared 2 mL solution of HCl (prepared from 0.2 mL of AcCl added to 2 mL methanol at rt, then cooled to 0 deg for 5 min). Stirred for 6 hr and concentrated to dryness. Dissolved in 0.5 mL methanol, triturated with ether, and decant off filtrate to give 13.5 mg (47%) of desired product as an off-white solid.

MS m/z 599 [M+H−HCl]

Procedure 1, 7

N*3*-{2-Chloro-4'-[1-(3,3-dimethyl-butyl)-piperidin-4-ylmethanesulfonyl]-6-trifluoromethyl-biphenyl-4-yl}-1H-[1,2,4]triazole-3,5-diamine; hydrochloride (Compound 57)

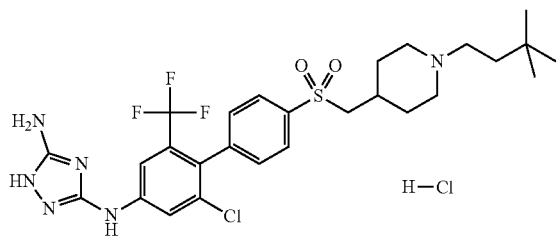 [SMILES: CC(C)(C)CCN1CCC(CS(=O)(=O)c2ccc(-c3c(Cl)cc(Nc4n[nH]c(N)n4)cc3C(F)(F)F)cc2)CC1 ; Cl]

To a suspension of N3-(2-chloro-4'-((1-(3,3-dimethylbutyl)piperidin-4-yl)methylsulfonyl)-6-(trifluoromethyl)biphenyl-4-yl)-1H-1,2,4-triazole-3,5-diamine hydrochloride Compound 40 (50 mg, 78.7 µmol, Eq: 1.00) in methanol (6 mL), was added 3,3-dimethylbutanal (12.8 mg, 16 µl, 127 µmol, Eq: 1.62), followed by sodium cyanoborohydride (10 mg, 159 µmol, Eq: 2.02). The yellow soln was stirred overnight. The reaction was concentrated, diluted with ethyl acetate, basified with sodium carbonate aq solution and the organic layer was separated. Extracted aqueous twice more with EtAOc. Combined org extracts, dried over sodium sulfate, and chromatographed (12 g Redisep, 1 to 10% methanol/dichloromethane) to give 27 mg white solid of free amine.

To a solution of 27 mg of amine in 2 mL methanol, was added a freshly prepared 2 mL solution of HCl (prepared from 0.2 mL of AcCl added to 2 mL methanol at rt, then cooled to 0 deg for 5 min). Stirred for 4 hr. Filtered off solid and rinsed with ether to give 26 mg (52%) of desired product as a white solid.

MS m/z 599 [M+H−HCl]

Procedure 6

N*3*-[4'-(tert-Butylamino-methyl)-2-chloro-6-trifluoromethyl-biphenyl-4-yl]-1H-[1,2,4]triazole-3,5-diamine; hydrochloride (Compound 58)

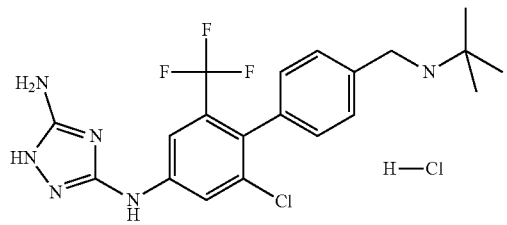 [SMILES: CC(C)(C)NCc1ccc(-c2c(Cl)cc(Nc3n[nH]c(N)n3)cc2C(F)(F)F)cc1 ; Cl]

A microwave vial containing N3-(4-bromo-3-chloro-5-(trifluoromethyl)phenyl)-1H-1,2,4-triazole-3,5-diamine Intermediate 1 (150 mg, 421 µmol, Eq: 1.00), sodium carbonate (111 mg, 1.05 mmol, Eq: 2.5) and Pd(Ph3P)4 (72.9 mg, 63.1 µmol, Eq: 0.15) was degassed for 15 minutes with Ar. A solution of 2-methyl-N-(4-(4,4,5,5-tetramethyl-1,3,2-dioxaborolan-2-yl)benzyl)propan-2-amine (183 mg, 631 µmol, Eq: 1.5) in dioxane (1.5 mL)/dimethoxyethane (1.5 mL) was added, followed by water (1 mL). The suspension was degassed for 5 min with Ar with sonication, then capped and heated at 125 deg for 3 hr. The reaction mixture was diluted with ethyl acetate, washed with brine, dried with sodium sulfate, and chromatographed (24 g Redisep Gold, 1% to 10% methanol/dichloromethane w/1% NH4OH in methanol) to give 57 mg white solid as the free amine.

Dissolved in 2 mL methanol and added 5 mL freshly prepared HCl soln (from 5 mL methanol and 0.5 mL AcCl added at rt, then cooled to 0 deg for 5 min). After 4 hr, the reaction was concentrated, dissolved in 1 mL methanol/1 mL dichloromethane, triturated with hexaneane, and filtered to give 49 mg (25%) of desired product as an off-white solid.

MS m/z 438 [M+H−HCl]

Procedure 6

3-[4'-(5-Amino-1H-[1,2,4]triazol-3-ylamino)-6'-chloro-2'-trifluoromethyl-biphenyl-4-sulfonyl]-azetidine-1-carboxylic acid tert-butyl ester (Compound 59)

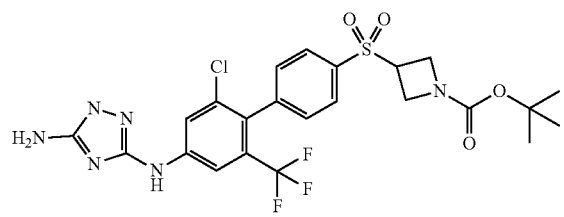 [SMILES: CC(C)(C)OC(=O)N1CC(S(=O)(=O)c2ccc(-c3c(Cl)cc(Nc4n[nH]c(N)n4)cc3C(F)(F)F)cc2)C1]

3-[4-(4,4,5,5-Tetramethyl-[1,3,2]dioxaborolan-2-yl)-benzenesulfonyl]-azetidine-1-carboxylic acid tert-butyl ester

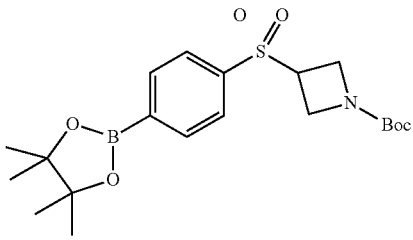

In a pressure tube, Potassium acetate (751 mg, 7.65 mmol), tert-butyl 3-(4-bromophenylsulfonyl)azetidine-1-carboxylate (purchased from Beta Pharma, 576 mg, 1.53 mmol), bis(pinacolato)diboron (1.17 g, 4.60 mmol) were combined with 1,4-dioxane (anhydrous, 8 ml). The reaction mixture was bubbled with Argon stream for 4 min. Then PdCl2(DPPF) (112 mg, 0.153 mmol) was added to the reaction mixture. The reaction mixture was bubbled with Argon stream for 4 min before the sealed tube was capped. The sealed tube was then heated with an oil bath at 90° C. for overnight. The crude mixture was filtered through a Celite bed and washed with DCM. The resulting filtration was diluted with DCM/Water. The aqueous phase was extracted with DCM (2×). The combined DCM phases were dried over Na2SO4 and concentrated. The residue was purified by flash silica gel column separation (EtOAc/Hexane 0-30% gradient, then 30%) to obtain 634 mg (94% yield) desired product as waxy solid to use for next reaction without further purification.

MS +m/z: 324.0 (M−100+H)+.

3-[4'-(5-Amino-1H-[1,2,4]triazol-3-ylamino)-6'-chloro-2'-trifluoromethyl-biphenyl-4-sulfonyl]-azetidine-1-carboxylic acid tert-butyl ester (Compound 59)

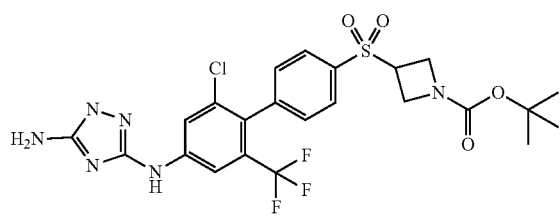 [SMILES: CC(C)(C)OC(=O)N1CC(S(=O)(=O)c2ccc(-c3c(Cl)cc(Nc4n[nH]c(N)n4)cc3C(F)(F)F)cc2)C1]

In a microwave vial, the mixture of (N3-(4-bromo-3-chloro-5-(trifluoromethyl)phenyl)-1H-1,2,4-triazole-3,5-diamine Intermediate 1 (300 mg, 0.84 mmol), tert-butyl 3-(4-(4,4,5,5-tetramethyl-1,3,2-dioxaborolan-2-yl)phenylsulfonyl)azetidine-1-carboxylate (386 mg, 1.09 mmol), K₂CO₃ (580 mg, 4.2 mmol) was added DME (1.5 ml) and Dioxane (1.5 ml) and Water (0.5 ml). The mixture was degassed by two careful vacuum/Argon Bubbling cycles in 4 min. Then Pd(PPh₃)₄ (243 mg, 0.21 mmol) was added to the mixture. The mixture was degassed by another two careful vacuum/Argon cycles in 4 min. The resulting mixture was capped and then was heated in Microwave at 130° C. for 3 h. The crude mixture was filtered through a Celite bed and washed with DCM. The resulting filtration was diluted with DCM/Water. The resulting aqueous phase was extracted with DCM (2×). The combined DCM phases were dried over Na₂SO₄ and concentrated. The residue was separated by flash silica gel column (MeOH/EtOAc 0 to 2% gradient, then 2%). The fractions which contained the desired product were concentrated and were further separated by Prep-HPLC (JSPhere column 3×10 cm, NH4Ac/ACN 30-85%, 30 ml/min) to obtain 11 mg (2% yield) desired product as white powder.

MS +m/z: 516.9 (M−56+H)+.

Procedure 6

4'-(5-Amino-1H-[1,2,4]triazol-3-ylamino)-6'-chloro-2'-trifluoromethyl-biphenyl-4-sulfonic acid (3-methyl-oxetan-3-yl)-amide (Compound 60)

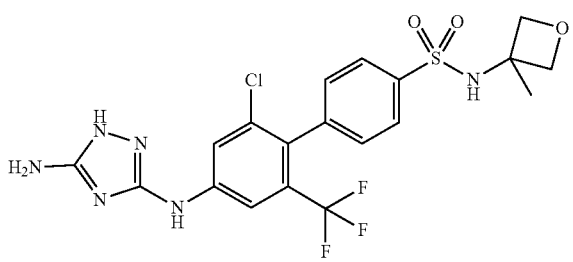 [SMILES: CC1(NS(=O)(=O)c2ccc(-c3c(Cl)cc(Nc4n[nH]c(N)n4)cc3C(F)(F)F)cc2)COC1]

4-Bromo-N-(3-methyl-oxetan-3-yl)-benzenesulfonamide

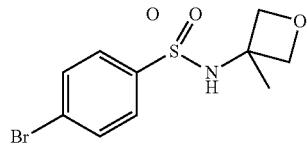

To the mixture of 4-bromobenzene-1-sulfonyl chloride (500 mg, 1.96 mmol) and 3-methyloxetan-3-amine (170 mg, 1.96 mmol) in DCM (9 ml) at 0° C. in ice-water bath, DIPEA (1.02 ml, 5.88 mmol) was added slowly. The reaction mixture was stirred at 0° C. for 20 min and then at RT for 2 h. The reaction mixture was added HCl (1N) to neutral and then diluted with DCM. The DCM phase was separated and the aqueous phase was extracted with DCM (2×). The combined DCM phases were evaporated. The residue was purified by flash silica gel column separation (EtOAc/Hexane 0-30% gradient, and then 30%) to obtain 471 mg (78% yield) desired product as waxy solid.

MS +m/z: 305.9 (M+H)+.

N-(3-Methyl-oxetan-3-yl)-4-(4,4,5,5-tetramethyl-[1,3,2]dioxaborolan-2-yl)-benzenesulfonamide

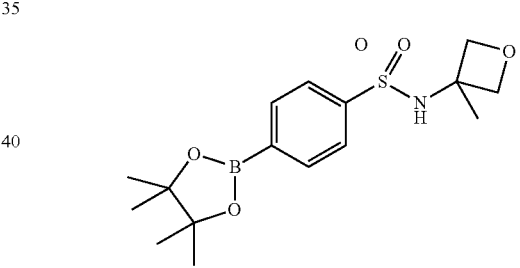

In a pressure tube, Potassium acetate (751 mg, 7.65 mmol), 4-bromo-N-(3-methyloxetan-3-yl)benzenesulfonamide (469 mg, 1.53 mmol), bis(pinacolato)diboron (1.17 g, 4.60 mmol) were combined with 1,4-dioxane (anhydrous, 8 ml). The reaction mixture was bubbled with Argon stream for 4 min. Then PdCl₂(DPPF) (112 mg, 0.153 mmol) was added to the reaction mixture. The reaction mixture was bubbled with Argon stream for 4 min before the sealed tube was capped. The sealed tube was then heated with an oil bath at 90° C. for overnight. The crude mixture was filtered through a Celite bed and washed with DCM. The resulting filtration was diluted with DCM/Water. The resulting aqueous phase was extracted with DCM (2×). The combined DCM phases were dried over Na₂SO₄ and concentrated. The residue was purified by flash silica gel column separation (EtOAc/Hexane 0-40% gradient, then 40%) to obtain 501 mg (93% yield) desired product as waxy solid.

MS +m/z: 354.0 (M+H)+.

4'-(5-Amino-1H-[1,2,4]triazol-3-ylamino)-6'-chloro-2'-trifluoromethyl-biphenyl-4-sulfonic acid (3-methyl-oxetan-3-yl)-amide (Compound 60)

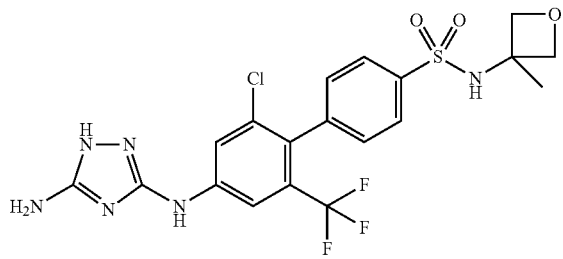 [SMILES: CC1(NS(=O)(=O)c2ccc(-c3c(Cl)cc(Nc4n[nH]c(N)n4)cc3C(F)(F)F)cc2)COC1]

In a microwave vial, the mixture of N3-(4-bromo-3-chloro-5-(trifluoromethyl)phenyl)-1H-1,2,4-triazole-3,5-diamine Intermediate 1 (300 mg, 0.84 mmol), N-(3-methyl-oxetan-3-yl)-4-(4,4,5,5-tetramethyl-1,3,2-dioxaborolan-2-yl)benzenesulfonamide (386 mg, 1.09 mmol), $K_2CO_3$ (580 mg, 4.2 mmol) was added DME (1.5 ml) and Dioxane (1.5 ml) and Water (0.5 ml). The mixture was degassed by two careful vacuum/Argon Bubbling cycles in 4 min. Then $Pd(PPh_3)_4$ (243 mg, 0.21 mmol) was added to the mixture. The mixture was degassed by another two careful vacuum/Argon cycles in 4 min. The resulting mixture was capped and then was heated in Microwave at 130° C. for 3 h.

The crude mixture was filtered through a Celite bed and washed with DCM. The resulting filtration was diluted with DCM/Water. The resulting aqueous phase was extracted with DCM (2×). The combined DCM phases were dried over $Na_2SO_4$ and concentrated. The residue was separated by flash silica gel column (MeOH/EtOAc 0 to 2% gradient, then 2%). The fractions which contained the desired product were concentrated and were further separated by SFC with 35% MeOH/$CO_2$ at 70 ml/min on YMC Diol column to provide desired product 64 mg (15% yield) as light-yellow solid.

MS +m/z: 502.1 (M+H)$^+$.

Procedure 6

N*3*-[6-Chloro-4'-(3-methyl-butane-1-sulfonyl)-2-trifluoromethyl-biphenyl-4-yl]-1H-1,2,4-triazole-3,5-diamine (Compound 61)

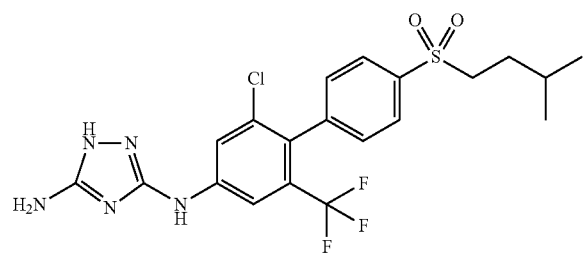 [SMILES: CC(C)CCS(=O)(=O)c1ccc(-c2c(Cl)cc(Nc3n[nH]c(N)n3)cc2C(F)(F)F)cc1]

In a microwave vial, the mixture of N3-(4-bromo-3-chloro-5-(trifluoromethyl)phenyl)-1H-1,2,4-triazole-3,5-diamine Intermediate 1 (N3-(4-bromo-3-chloro-5-(trifluoromethyl)phenyl)-1H-1,2,4-triazole-3,5-diamine (300 mg, 0.84 mmol), 4-(isopentylsulfonyl)phenylboronic acid (430 mg, 1.09 mmol), $K_2CO_3$ (580 mg, 4.2 mmol) was added DME (1.5 ml) and Dioxane (1.5 ml) and Water (0.5 ml). The mixture was degassed by two careful vacuum/Argon Bubbling cycles in 4 min. Then $Pd(PPh_3)_4$ (243 mg, 0.21 mmol) was added to the mixture. The mixture was degassed by another two careful vacuum/Argon cycles in 4 min. The resulting mixture was capped and then was heated in Microwave at 130° C. for 3 h. The crude mixture was filtered through a Celite bed and washed with DCM. The resulting filtration was diluted with DCM/Water. The resulting aqueous phase was extracted with DCM (2×). The combined DCM phases were dried over $Na_2SO_4$ and concentrated. The residue was separated by flash silica gel column (MeOH/EtOAc 0% to 2% gradient, then 2%). The fractions which contained the desired product were concentrated and were further separated by SFC with 30% MeOH/$CO_2$ at 70 ml/min on Cyano column (3*25 cm) to provide desired product 60 mg (15% yield) as light-yellow solid.

MS +m/z: 488.0 (M+H)$^+$.

Procedure 6

N*3*-[6-Chloro-4'-(3,3-difluoro-pyrrolidine-1-sulfonyl)-2-trifluoromethyl-biphenyl-4-yl]-1H-[1,2,4]triazole-3,5-diamine (Compound 62)

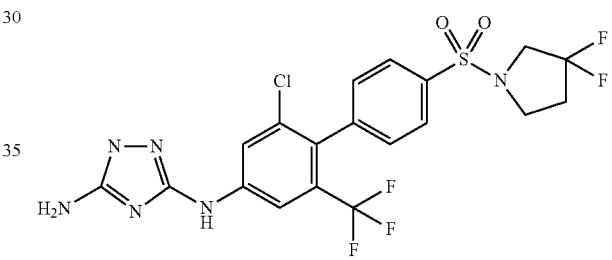

1-(4-Bromo-benzenesulfonyl)-3,3-difluoro-pyrrolidine

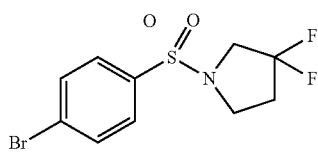

To the mixture of 4-bromobenzene-1-sulfonyl chloride (600 mg, 2.35 mmol) and (3,3-difluoropyrrolidine hydrochloride (337 mg, 2.35 mmol) in DCM (9 ml) at 0° C. in ice-water bath, DIPEA (2.05 ml, 11.75 mmol) was added slowly. The reaction mixture was stirred at 0° C. for 20 min and then at RT for 2 h. The reaction mixture was added HCl (1N) to neutral and then diluted with DCM. The DCM phase was separated and the aqueous phase was extracted with DCM (2×). The combined DCM phases were evaporated. The residue was purified by flash silica gel column separation (EtOAc/Hexane 0-30% gradient, then 30%) to obtain 639 mg (83% yield) desired product as solid.

MS +m/z: 326.0 (M+H)$^+$.

3,3-Difluoro-1-[4-(4,4,5,5-tetramethyl-[1,3,2]dioxaborolan-2-yl)-benzenesulfonyl]-pyrrolidine

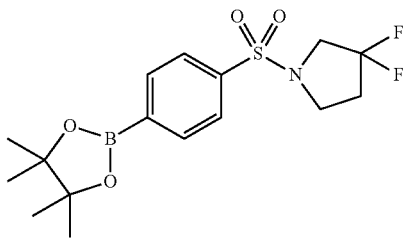 [SMILES: CC1(C)OB(c2ccc(S(=O)(=O)N3CCC(F)(F)C3)cc2)OC1(C)C]

In a pressure tube, Potassium acetate (751 mg, 7.65 mmol), 1-(4-bromophenylsulfonyl)-3,3-difluoropyrrolidine (499 mg, 1.53 mmol), (bis(pinacolato)diboron (1.17 g, 4.60 mmol) were combined with 1,4-dioxane (anhydrous, 8 ml). The reaction mixture was bubbled with Argon stream for 4 min. Then PdCl$_2$(DPPF) (112 mg, 0.153 mmol) was added to the reaction mixture. The reaction mixture was bubbled with Argon stream for 4 min before the sealed tube was capped. The sealed tube was then heated with an oil bath at 90° C. for overnight. The crude mixture was filtered through Celite and washed with DCM. The resulting filtration was diluted with DCM/Water. The aqueous phase was extracted with DCM (2×). The combined DCM phases were dried over Na$_2$SO$_4$ and concentrated. The residue was purified by flash silica gel column separation (EtOAc/Hexane 0-30% gradient, then 30%) to obtain 560 mg (98% yield) desired product as waxy solid to use for next reaction without further purification.

MS +m/z: 374.0 (M+H)$^+$

N*3*-[6-Chloro-4'-(3,3-difluoro-pyrrolidine-1-sulfonyl)-2-trifluoromethyl-biphenyl-4-yl]-1H-[1,2,4]triazole-3,5-diamine (Compound 62)

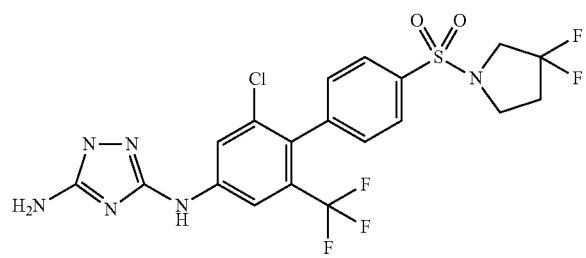 [SMILES: Nc1nc(Nc2cc(Cl)c(-c3ccc(S(=O)(=O)N4CCC(F)(F)C4)cc3)c(C(F)(F)F)c2)n[nH]1]

In a microwave vial, the mixture of N3-(4-bromo-3-chloro-5-(trifluoromethyl)phenyl)-1H-1,2,4-triazole-3,5-diamine Intermediate 1 (300 mg, 0.84 mmol), 3,3-difluoro-1-(4-(4,4,5,5-tetramethyl-1,3,2-dioxaborolan-2-yl)phenylsulfonyl)pyrrolidine (407 mg, 1.09 mmol), K$_2$CO$_3$ (580 mg, 4.2 mmol) was added DME (1.5 ml) and Dioxane (1.5 ml) and Water (0.5 ml). The mixture was degassed by two careful vacuum/Argon Bubbling cycles in 4 min. Then Pd(PPh$_3$)$_4$ (243 mg, 0.21 mmol) was added to the mixture. The mixture was degassed by another two careful vacuum/Argon cycles in 4 min. The resulting mixture was capped and then was heated in Microwave at 130° C. for 3 h.

The crude mixture was filtered through Celite and washed with DCM. The resulting filtration was diluted with DCM/Water. The aqueous phase was extracted with DCM (2×). The combined DCM phases were dried over Na$_2$SO$_4$ and concentrated. The residue was separated by flash silica gel column (MeOH/EtOAc 0 to 2% gradient, then 2%). The fractions which contained the desired product were concentrated and were further separated by SFC with 30% MeOH/CO$_2$ at 70 ml/min on YMC Diol column to provide desired product 38 mg (9% yield) as solid.

MS +m/z: 523.0 (M+H)$^+$.

Procedure 6

1-[4'-(5-Amino-1H-[1,2,4]triazol-3-ylamino)-6'-chloro-2'-trifluoromethyl-biphenyl-4-sulfonyl]-3-methyl-azetidin-3-ol (Compound 66)

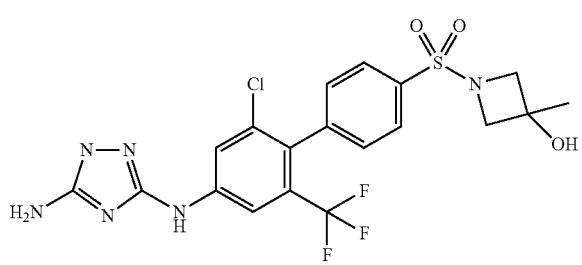 [SMILES: CC1(O)CN(S(=O)(=O)c2ccc(-c3c(Cl)cc(Nc4n[nH]c(N)n4)cc3C(F)(F)F)cc2)C1]

1-(4-Bromo-benzenesulfonyl)-3-methyl-azetidin-3-ol

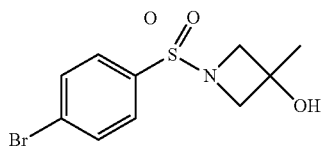

To the mixture of 4-bromobenzene-1-sulfonyl chloride (600 mg, 2.35 mmol) and 3-methylazetidin-3-ol hydrochloride (290 mg, 2.35 mmol) in DCM (9 ml) at 0° C. (in ice-water bath), DIPEA (2.05 ml, 11.75 mmol) was added slowly. The reaction mixture was stirred at 0° C. for 20 min and then at RT for 2 h. The reaction mixture was added HCl (1N) to neutral and then diluted with DCM. The DCM phase was separated and the aqueous phase was extracted with DCM (2×). The combined DCM phases were evaporated. The residue was purified by flash silica gel column separation (EtOAc/Hexane 0 to 30% gradient, then 30%) to obtain 524 mg (73% yield) desired product as solid.

MS +m/z: 307 (M+H)$^+$.

3-Methyl-1-[4-(4,4,5,5-tetramethyl-[1,3,2]dioxaborolan-2-yl)-benzenesulfonyl]-azetidin-3-ol

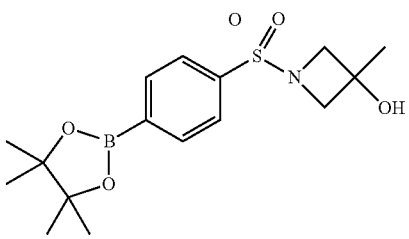

In a pressure tube, Potassium acetate (751 mg, 7.65 mmol), 1-(4-bromophenylsulfonyl)-3-methylazetidin-3-ol (468 mg, 1.53 mmol), bis(pinacolato)diboron (1.17 g, 4.60 mmol) were combined with 1,4-dioxane (anhydrous, 8 ml). The reaction mixture was bubbled with Argon stream for 4 min. Then PdCl$_2$(DPPF) (112 mg, 0.153 mmol, 10% eq) was added to the reaction mixture. The reaction mixture was bubbled with Argon stream for 4 min before the sealed tube was capped. The sealed tube was then heated with an oil bath at 90° C. for 4 h. The crude mixture was filtered through Celite and washed with DCM. The resulting filtration was diluted with DCM/Water. The aqueous phase was extracted with DCM (2×). The combined DCM phases were dried over Na$_2$SO$_4$ and concentrated. The residue was purified by flash silica gel column separation (EtOAc/Hexane 0-50% gradient, then 50%) to obtain 490 mg (88% yield) desired product as waxy solid to use for next reaction without further purification.

MS +m/z: 354.1 (M+H)$^+$

1-[4'-(5-Amino-1H-[1,2,4]triazol-3-ylamino)-6'-chloro-2'-trifluoromethyl-biphenyl-4-sulfonyl]-3-methyl-azetidin-3-ol (Compound 63)

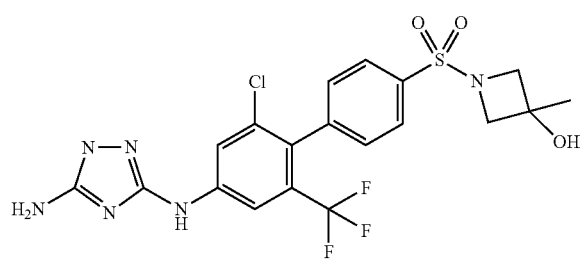 [SMILES: CC1(O)CN(S(=O)(=O)c2ccc(-c3c(Cl)cc(Nc4n[nH]c(N)n4)cc3C(F)(F)F)cc2)C1]

In a microwave vial, the mixture of N3-(4-bromo-3-chloro-5-(trifluoromethyl)phenyl)-1H-1,2,4-triazole-3,5-diamine Intermediate 1 (450 mg, 1.26 mmol), 3-methyl-1-(4-(4,4,5,5-tetramethyl-1,3,2-dioxaborolan-2-yl)phenylsulfonyl)azetidin-3-ol (580 mg, 1.64 mmol), K$_2$CO$_3$ (872 mg, 6.31 mmol) was added DME (2 ml) and Dioxane (2 ml) and Water (0.5 ml). The mixture was degassed by two careful vacuum/Argon Bubbling cycles in 4 min. Then Pd(PPh$_3$)$_4$ (365 mg, 0.25 mmol) was added to the mixture. The mixture was degassed by another two careful vacuum/Argon cycles in 4 min.

The resulting mixture was capped and then was heated in Microwave at 130° C. for 3 h. The crude mixture was filtered through Celite and washed with DCM. The resulting filtration was diluted with DCM/Water. The aqueous phase was extracted with DCM (2×). The combined DCM phases were dried over Na$_2$SO$_4$ and concentrated. The residue was separated by flash silica gel column, MeOH/EtOAc 0 to 1% gradient, then 1%). The fractions which contained the desired product were concentrated and were further separated by SFC with 25% MeOH/CO$_2$ at 70 ml/min on Kromasil Silica column to provide desired product 127 mg (20% yield) as solid.

MS +m/z: 503.0 (M+H)$^+$

Procedure 6

N*3*-(6-Chloro-4'-cyclopropylmethanesulfonyl-2-trifluoromethyl-biphenyl-4-yl)-1H-1,2,4-triazole-3,5-diamine (Compound 64)

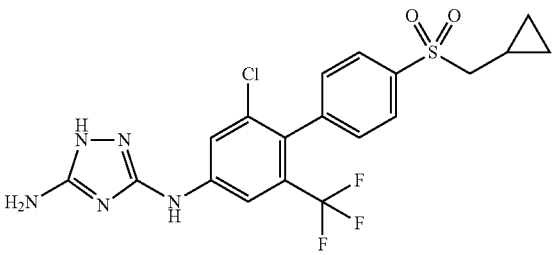 [SMILES: Nc1nc(Nc2cc(Cl)c(-c3ccc(S(=O)(=O)CC4CC4)cc3)c(C(F)(F)F)c2)n[nH]1]

In a microwave vial, the mixture of N3-(4-bromo-3-chloro-5-(trifluoromethyl)phenyl)-1H-1,2,4-triazole-3,5-diamine Intermediate 1, N3-(4-bromo-3-chloro-5-(trifluoromethyl)phenyl)-1H-1,2,4-triazole-3,5-diamine, 300 mg, 0.84 mmol), 4-(cyclopropylmethylsulfonyl)phenylboronic acid, 403 mg, 1.09 mmol), K$_2$CO$_3$ (580 mg, 4.2 mmol) was added DME (1.5 ml) and Dioxane (1.5 ml) and Water (0.5 ml). The mixture was degassed by two careful vacuum/Argon Bubbling cycles in 4 min. Then Pd(PPh$_3$)$_4$ (243 mg, 0.21 mmol) was added to the mixture. The mixture was degassed by another two careful vacuum/Argon cycles in 4 min. The resulting mixture was capped and then was heated in Microwave at 130° C. for 3 h. The crude mixture was filtered through a Celite bed and washed with DCM. The resulting filtration was diluted with DCM/Water. The resulting aqueous phase was extracted with DCM (2×). The combined DCM phases were dried over Na$_2$SO$_4$ and concentrated. The residue was separated by flash silica gel column (MeOH/EtOAc 0 to 2% gradient, then 2%). The fractions which contained the desired product were concentrated and were further separated by SFC with 305 MeOH/CO$_2$ at 70 ml/min on Cyano column (3*25 cm) to provide desired product 75 mg (19% yield) as off-white solid.

MS +m/z: 471.1 (M+H)$^+$.

Procedure 6

N*3*-[6-Chloro-4'-(2-methyl-propane-1-sulfonyl)-2-trifluoromethyl-biphenyl-4-yl]-1H-[1,2,4]triazole-3,5-diamine (Compound 65)

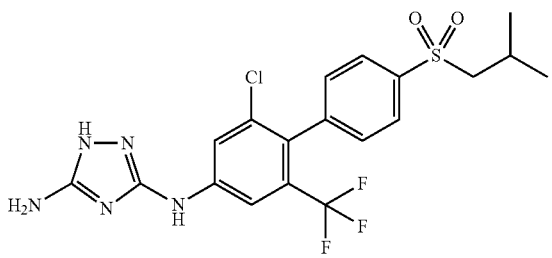 [SMILES: CC(C)CS(=O)(=O)c1ccc(-c2c(Cl)cc(Nc3n[nH]c(N)n3)cc2C(F)(F)F)cc1]

In a microwave vial, the mixture of N3-(4-bromo-3-chloro-5-(trifluoromethyl)phenyl)-1H-1,2,4-triazole-3,5-diamine Intermediate 1, N3-(4-bromo-3-chloro-5-(trifluoromethyl)phenyl)-1H-1,2,4-triazole-3,5-diamine (300 mg, 0.84 mmol), 4-(isobutylsulfonyl)phenylboronic acid (430 mg, 1.09 mmol), K$_2$CO$_3$ (580 mg, 4.2 mmol) was added DME (1.5 ml) and Dioxane (1.5 ml) and Water (0.5 ml). The mixture was degassed by two careful vacuum/Argon Bubbling cycles in 4 min. Then Pd(PPh$_3$)$_4$ (243 mg, 0.21 mmol) was added to the mixture. The mixture was degassed by another two careful vacuum/Argon cycles in 4 min. The resulting mixture was capped and then was heated in Microwave at 130° C. for 3 h. The crude mixture was filtered through a Celite bed and washed with DCM. The resulting filtration was diluted with DCM/Water. The resulting aqueous phase was extracted with DCM (2×). The combined DCM phases were dried over Na$_2$SO$_4$ and concentrated. The residue was separated by flash silica gel column (MeOH/EtOAc 0 to 2% gradient, then 2%). The fractions which contained the desired product were concentrated and were further separated by SFC with 25% MeOH/CO$_2$+0.1% TEA at 70 ml/min on Cyano column to provide desired product 90 mg (23% yield) as solid.

MS +m/z: 473.1 (M+H)$^+$.

Procedure 6

1-[4'-(5-Amino-1H-[1,2,4]triazol-3-ylamino)-6'-chloro-2'-trifluoromethyl-biphenyl-4-sulfonyl]-4-methyl-piperidin-4-ol (Compound 66)

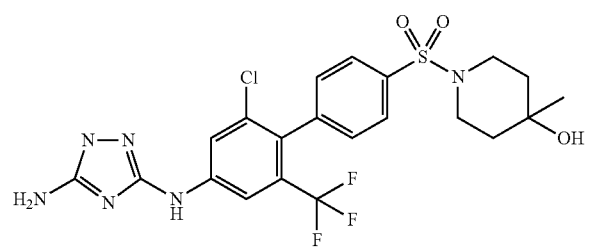 [SMILES: CC1(O)CCN(S(=O)(=O)c2ccc(-c3c(Cl)cc(Nc4n[nH]c(N)n4)cc3C(F)(F)F)cc2)CC1]

1-(4-Bromo-benzenesulfonyl)-4-methyl-piperidin-4-ol

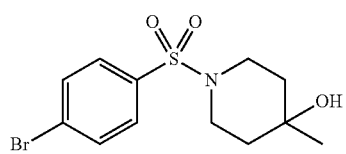 [SMILES: CC1(O)CCN(S(=O)(=O)c2ccc(Br)cc2)CC1]

To the mixture of 4-bromobenzene-1-sulfonyl chloride (1 g, 3.91 mmol) and 4-methylpiperidin-4-ol (451 mg, 3.91 mmol) in DCM (15 ml) at 0° C. in ice-water bath, DIPEA (3.41 ml, 19.55 mmol) was added slowly. The reaction mixture was stirred at 0° C. for 20 min and then at RT for 4 h. The reaction mixture was added HCl (1N) to neutral and then diluted with DCM. The DCM phase was separated and the aqueous phase was extracted with DCM (2×). The combined DCM phases were evaporated. The residue was purified by flash silica gel column separation (EtOAc/Hexane 0-50% gradient, then 50%) to obtain 900 mg (69% yield) desired product as solid.

MS +m/z: 335 (M+H)$^+$.

4-Methyl-1-[4-(4,4,5,5-tetramethyl-[1,3,2]dioxaborolan-2-yl)-benzenesulfonyl]-piperidin-4-ol

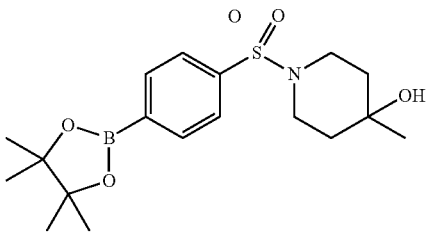

In a pressure tube, Potassium acetate (1.32 g, 13.45 mmol), 1-(4-bromophenylsulfonyl)-4-methylpiperidin-4-ol (900 mg, 1.53 mmol), bis(pinacolato)diboron (2.05 g, 8.08 mmol) were combined with 1,4-dioxane (anhydrous, 10 ml). The reaction mixture was bubbled with Argon stream for 4 min. Then PdCl$_2$(DPPF) (197 mg, 0.269 mmol) was added to the reaction mixture. The reaction mixture was bubbled with Argon stream for 4 min before the sealed tube was capped. The sealed tube was then heated with an oil bath at 90° C. for 4 h. The crude mixture was filtered through a celite bed and washed with DCM. The resulting filtration was diluted with DCM/Water. The aqueous phase was extracted with DCM (2×). The combined DCM phases were dried over Na$_2$SO$_4$ and concentrated. The residue was purified by flash silica gel column separation (EtOAc/Hexane 0-40% gradient, then 40%) to obtain 964 mg (93% yield) desired product as waxy solid to use for next reaction without further purification.

MS +m/z: 382.0 (M+H)$^+$.

1-[4'-(5-Amino-1H-[1,2,4]triazol-3-ylamino)-6'-chloro-2'-trifluoromethyl-biphenyl-4-sulfonyl]-4-methyl-piperidin-4-ol (Compound 66)

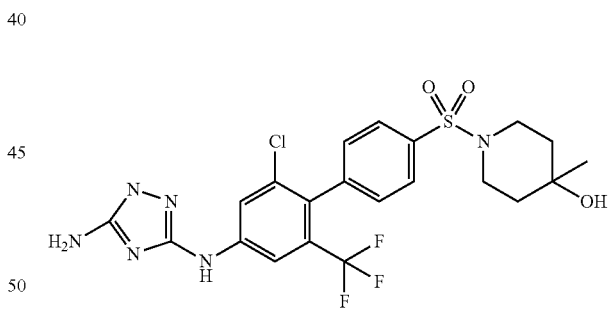

In a microwave vial, the mixture of N3-(4-bromo-3-chloro-5-(trifluoromethyl)phenyl)-1H-1,2,4-triazole-3,5-diamine Intermediate 1 (300 mg, 0.84 mmol), 4-methyl-1-(4-(4,4,5,5-tetramethyl-1,3,2-dioxaborolan-2-yl)phenylsulfonyl)piperidin-4-ol (385 mg, 1.09 mmol), K$_2$CO$_3$ (580 mg, 4.2 mmol) was added DME (1.5 ml) and Dioxane (1.5 ml) and Water (0.5 ml). The mixture was degassed by two careful vacuum/Argon Bubbling cycles in 4 min. Then Pd(PPh$_3$)$_4$ (243 mg, 0.21 mmol) was added to the mixture. The mixture was degassed by another two careful vacuum/Argon cycles in 4 min. The resulting mixture was capped and then was heated in Microwave at 130° C. for 3 h. The crude mixture was filtered through Celite and washed with DCM. The resulting filtration was diluted with DCM/Water. The aqueous phase was extracted with DCM (2×). The combined DCM phases were dried over Na₂SO₄ and concentrated. The residue was separated by flash silica gel column (MeOH/DCM 0 to 5% gradient, 5%, 5-10% gradient, then 10%) to obtain 65 mg (15% yield) desired product as off-white solid.

MS +m/z: 531.1 (M+H)⁺.

Procedure 6

N*3*-[4'-(Azetidine-3-sulfonyl)-6-chloro-2-trifluoromethyl-biphenyl-4-yl]-1H-[1,2,4]triazole-3,5-diamine hydrochloride (Compound 67)

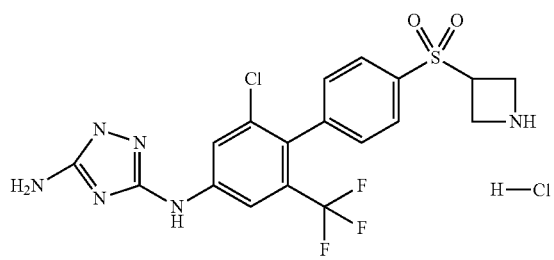 [SMILES: Nc1nc(Nc2cc(Cl)c(-c3ccc(S(=O)(=O)C4CNC4)cc3)c(C(F)(F)F)c2)n[nH]1 ; Cl]

To the solution of Compound 59 tert-butyl 3-(4'-(5-amino-1H-1,2,4-triazol-3-ylamino)-2'-chloro-6'-(trifluoromethyl)biphenyl-4-ylsulfonyl)azetidine-1-carboxylate (80 mg, 0.140 mmol) in DCM (2 ml), HCl (4M in dioxane, 0.698 ml, 2.79 mmol) was added. The reaction mixture was stirred at RT for 1 h. The mixture was evaporated under vacuum to remove solvent and HCl. The resulting solid was further dried under high vacuum overnight to obtain 70 mg (98% yield) desired product as solid.

MS +m/z: 472.9 (M+H)⁺.

Procedure 6

1-[4'-(5-Amino-1H-[1,2,4]triazol-3-ylamino)-6'-chloro-2'-trifluoromethyl-biphenyl-4-sulfonyl]-3-methyl-pyrrolidin-3-ol (Compound 68)

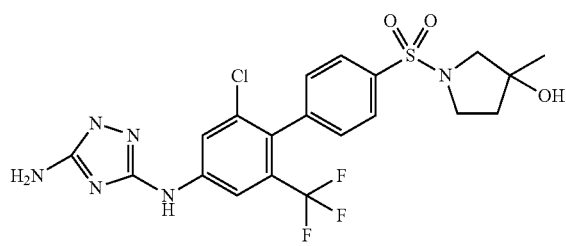 [SMILES: CC1(O)CCN(S(=O)(=O)c2ccc(-c3c(Cl)cc(Nc4n[nH]c(N)n4)cc3C(F)(F)F)cc2)C1]

1-(4-Bromo-benzenesulfonyl)-3-methyl-pyrrolidin-3-ol

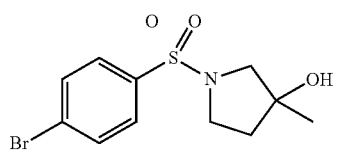

To the mixture of 4-bromobenzene-1-sulfonyl chloride (1 g, 3.91 mmol) and 3-methylpyrrolidin-3-ol hydrochloride (538 mg, 3.91 mmol) in DCM (15 ml) at 0° C. in ice-water bath, DIPEA (3.41 ml, 19.6 mmol) was added slowly. The reaction mixture was stirred at 0° C. for 20 min and then at RT for 4 h. The reaction mixture was added HCl(1N) to neutral and then diluted with DCM. The DCM phase was separated and the aqueous phase was extracted with DCM (2×). The combined. DCM phases were evaporated. The residue was purified by flash silica gel column separation (EtOAc/Hexane 0-50% gradient, then 50%) to obtain 949 mg (76% yield) desired product as solid.

MS +m/z: 321 (M+H)⁺

3-Methyl-1-[4-(4,4,5,5-tetramethyl-[1,3,2]dioxaborolan-2-yl)-benzenesulfonyl]-pyrrolidin-3-ol

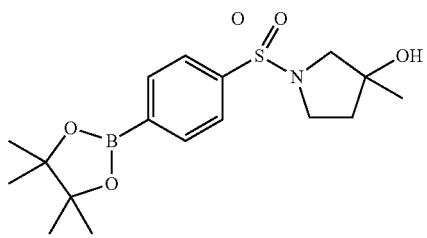

In a pressure tube, potassium acetate (1.32 g, 13.45 mmol), (1-(4-bromophenylsulfonyl)-3-methylpyrrolidin-3-ol, 861 mg, 2.69 mmol), (bis(pinacolato)diboron, 2.05 g, 8.08 mmol) were combined with 1,4-dioxane (anhydrous, 10 ml). The reaction mixture was bubbled with Argon stream for 4 min. Then PdCl₂(DPPF) (197 mg, 0.269 mmol) was added to the reaction mixture. The reaction mixture was bubbled with Argon stream for 4 min before the sealed tube was capped. The sealed tube was then heated with an oil bath at 90° C. for 4 h. The crude mixture was filtered through Celite and washed with DCM. The resulting filtration was diluted with DCM/Water. The resulting aqueous phase was extracted with DCM 2×. The combined DCM phases were dried over Na₂SO₄ and concentrated. The residue was purified by flash silica gel column separation (40 g cartridge, EtOAc/Hexane 0-50% in 6 CV, and then 50% in 15 CV) to obtain 890 mg (90% yield) desired product as waxy solid to use for next reaction without further purification.

MS +m/z: 368.1 (M+H)⁺

1-[4'-(5-Amino-1H-[1,2,4]triazol-3-ylamino)-6'-chloro-2'-trifluoromethyl-biphenyl-4-sulfonyl]-3-methyl-pyrrolidin-3-ol (Compound 68)

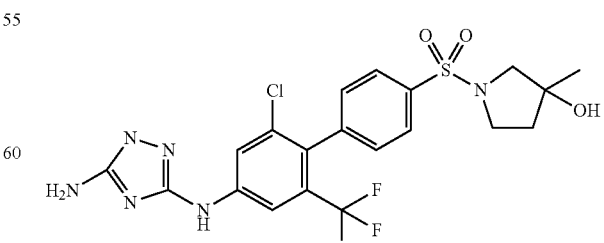

In a microwave vial, the mixture of N3-(4-bromo-3-chloro-5-(trifluoromethyl)phenyl)-1H-1,2,4-triazole-3,5-diamine Intermediate 1 (400 mg, 1.12 mmol), 3-methyl-1-(4-(4,4,5,5-tetramethyl-1,3,2-dioxaborolan-2-yl)phenylsulfonyl)pyrrolidin-3-ol (536 mg, 1.46 mmol), $K_2CO_3$ (775 mg, 5.61 mmol) was added DME (1.5 ml) and Dioxane (1.5 ml) and Water (0.5 ml). The mixture was degassed by two careful vacuum/Argon Bubbling cycles in 4 min. Then $Pd(PPh_3)_4$ (324 mg, 0.28 mmol) was added to the mixture. The mixture was degassed by another two careful vacuum/Argon cycles in 4 min. The resulting mixture was capped and then was heated in Microwave at 130° C. for 3 h.

The crude mixture was filtered through Celite and washed with DCM. The resulting filtration was diluted with DCM/Water. The aqueous phase was extracted with DCM (2×). The combined DCM phases were dried over $Na_2SO_4$ and concentrated. The combined DCM phases were dried over $Na_2SO_4$ and concentrated. The residue was separated by flash silica gel column (MeOH/DCM 0 to 5% gradient, 5%, 5-10% gradient, then 10%) to obtain 165 mg (28% yield) desired product as off-white solid.

MS +m/z: 517.0 (M+H)$^+$

Procedure 6

N*3*-[6-Chloro-4'-(2-oxa-6-aza-spiro[3.3]heptane-6-sulfonyl)-2-trifluoromethyl-biphenyl-4-yl]-1H-[1,2,4]triazole-3,5-diamine (Compound 69)

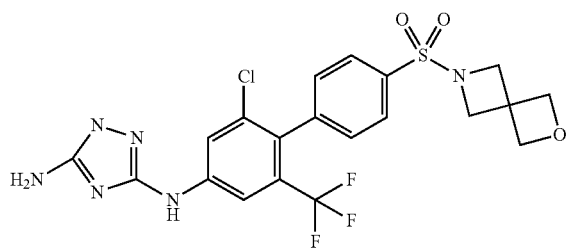 [SMILES: Nc1nc(Nc2cc(Cl)c(-c3ccc(S(=O)(=O)N4CC5(COC5)C4)cc3)c(C(F)(F)F)c2)n[nH]1]

6-(4-Bromo-benzenesulfonyl)-2-oxa-6-aza-spiro[3.3]heptane

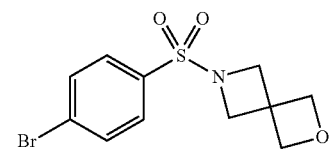 [SMILES: O=S(=O)(c1ccc(Br)cc1)N1CC2(COC2)C1]

To the mixture of 4-bromobenzene-1-sulfonyl chloride (1 g, 3.91 mmol) and 2-oxa-6-azaspiro[3.3]heptane hemioxalate (565 mg, 1.96 mmol) in DCM (15 ml) at 0° C. in ice-water bath, DIPEA (3.41 ml, 19.6 mmol) was added slowly. The reaction mixture was stirred at 0° C. for 20 min and then at RT for 4 h. The reaction mixture was added HCl (1N) to neutral and then diluted with DCM. The DCM phase was separated and the aqueous phase was extracted with DCM (2×). The combined DCM phases were evaporated. The residue was purified by flash silica gel column separation (EtOAc/Hexane 0-50% gradient, then 50%) to obtain 503 mg (40% yield) desired product as solid.

MS +m/z: 318.9 (M+H)$^+$

6-[4-(4,4,5,5-Tetramethyl-[1,3,2]dioxaborolan-2-yl)-benzenesulfonyl]-2-oxa-6-aza-spiro[3.3]heptane

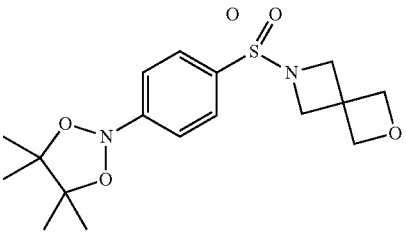

In a pressure tube, potassium acetate (770 mg, 7.85 mmol), 6-(4-bromophenylsulfonyl)-2-oxa-6-azaspiro[3.3]heptane (500 mg, 1.57 mmol), bis(pinacolato)diboron (1.2 g, 4.71 mmol) were combined with 1,4-dioxane (anhydrous, 8 ml). The reaction mixture was bubbled with Argon stream for 4 min. Then $PdCl_2(DPPF)$ (197 mg, 0.269 mmol) was added to the reaction mixture. The reaction mixture was bubbled with Argon stream for 4 min before the sealed tube was capped. The sealed tube was then heated with an oil bath at 90° C. for 4 h. The crude mixture was filtered through Celite and washed with DCM. The resulting filtration was diluted with DCM/Water. The resulting aqueous phase was extracted with DCM (2×). The combined DCM phases were dried over $Na_2SO_4$ and concentrated. The residue was purified by flash silica gel column separation (EtOAc/Hexane 0-60% gradient, then 60%) to obtain 508 mg (88% yield) desired product as waxy solid to use for next reaction without further purification.

MS +m/z: 366.0 (M+H)$^+$

N*3*-[6-Chloro-4'-(2-oxa-6-aza-spiro[3.3]heptane-6-sulfonyl)-2-trifluoromethyl-biphenyl-4-yl]-1H-[1,2,4]triazole-3,5-diamine (Compound 69)

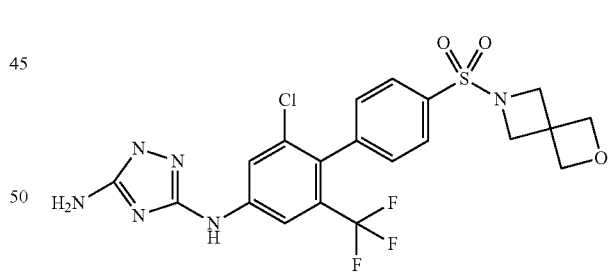

In a microwave vial, the mixture of N3-(4-bromo-3-chloro-5-(trifluoromethyl)phenyl)-1H-1,2,4-triazole-3,5-diamine Intermediate 1 (300 mg, 0.84 mmol), 6-(4-(4,4,5,5-tetramethyl-1,3,2-dioxaborolan-2-yl)phenylsulfonyl)-2-oxa-6-azaspiro[3.3]heptane (400 mg, 1.09 mmol), $K_2CO_3$ (581 mg, 4.21 mmol) was added DME (1.5 ml) and Dioxane (1.5 ml) and Water (0.5 ml). The mixture was degassed by two careful vacuum/Argon Bubbling cycles in 4 min. Then $Pd(PPh_3)_4$ (243 mg, 0.21 mmol) was added to the mixture. The mixture was degassed by another two careful vacuum/Argon cycles in 4 min. The resulting mixture was capped and then was heated in Microwave at 130° C. for 3 h. The crude mixture was filtered through Celite and washed with DCM. The resulting filtration was diluted with DCM/Water. The resulting aqueous phase was extracted with DCM (2×). The combined. DCM phases were dried over $Na_2SO_4$ and concentrated. The residue was separated by flash silica gel column (MeOH/DCM 0 to 5% gradient, then 5%, then 5-10% gradient, then, 10%). The fractions which contained the desired product were concentrated and were further separated by SFC with 35% MeOH/$CO_2$ plus 0.1% TEA at 70 ml/min on YMC Diol column to provide desired product 45 mg (10% yield) as off-white solid.

MS +m/z: 515.0 (M+H)$^+$

Procedure 6

$N^5$-(2-Fluoro-4'-(methylsulfonyl)-6-trifluoromethyl-biphenyl-4-yl)-1H-[1,2,4]-triazole-3,5-diamine (Compound 70)

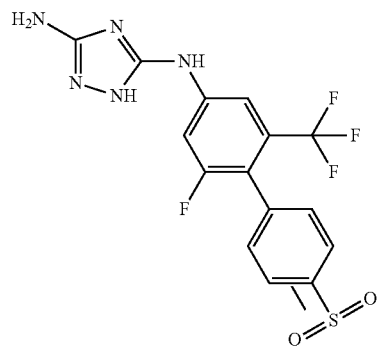

Intermediate 3 (94 mg, 276 µmol, Eq: 1.00), 4,4,5,5-tetramethyl-2-(4-(methylsulfonyl)phenyl)-1,3,2-dioxaborolane (117 mg, 415 µmol, Eq: 1.5) and cesium carbonate (225 mg, 691 µmol, Eq: 2.5) were dissolved in 20% aqueous n-butanol (2.4 ml). $PdCl_2$(DPPF)-$CH_2Cl_2$ adduct (12.1 mg, 16.6 µmol, Eq: 0.06) was added under an argon atmosphere. The reaction mixture was heated at 135° C. for 30 min in the microwave. After 30 minutes, $PdCl_2$(DPPF)-CH2Cl2 adduct (12.1 mg, 16.6 µmol, Eq: 0.06) was added again and the reaction was heated at 100° C. for 16 hr. The reaction mixture was filtered over a plug of silica gel and washed with dichloromethane. The filtrate was concentrated in vacuo to give a brown solid. The solid was triturated with methanol (2 ml) and filtered. The filtrate was concentrated to give a light brown solid. The crude product was purified by preparative HPLC 0.1% TFA in water/0.1% TFA in AcCN) 95% to 10% over 16 mins to afford 24 mg (21%) of the desired material as a light yellow solid.

MS +m/z: 416.0. (M+1)

$^1$H NMR (400 MHz, MeOD) δ ppm 3.21 (s, 3H) 7.56 (d, J=8.08 Hz, 2H) 7.68 (s, 1H) 7.73 (d, J=12.13 Hz, 1H) 8.03 (d, J=8.34 Hz, 2H)

Procedure 6

$N^5$-[6-Fluoro-4'-(propane-2-sulfonyl)-2-trifluoromethyl-biphenyl-4-yl]-1H-[1,2,4]-triazole-3,5-diamine (Compound 71)

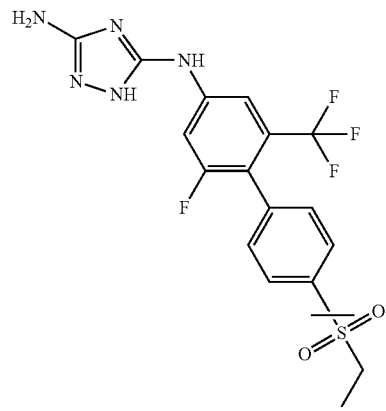

Prepared by a similar procedure to Compound 70, except substituted 4-(isopropylsulfonyl)phenylboronic acid for 4,4,5,5-tetramethyl-2-(4-(methylsulfonyl)phenyl)-1,3,2-dioxaborolane in step 1 to afford 15 mg (16%) of the desired material as a yellow solid.

MS +m/z: 444.0. (M+1)

$^1$H NMR (300 MHz, MeOD) δ ppm 1.30 (d, J=6.80 Hz, 6H) 3.36-3.46 (m, 1H) 7.58 (d, J=8.31 Hz, 2H) 7.65-7.78 (m, 2H) 7.95 (d, J=8.31 Hz, 2H)

Procedure 6

4'-(5-Amino-2H-[1,2,4]-triazol-3-ylamino)-6'-fluoro-2'-trifluoromethyl-biphenyl-4-sulfonic acid methylamide (Compound 72)

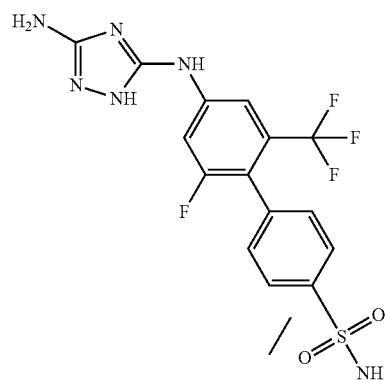

Prepared by a similar procedure to Compound 70, except substituted 4-(N-methylsulfamoyl)phenylboronic acid for 4,4,5,5-tetramethyl-2-(4-(methylsulfonyl)phenyl)-1,3,2-dioxaborolane for in step 1 to afford 9 mg (10%) of the desired material as a yellow solid.

MS +m/z: 431.0. (M+1)

$^1$H NMR (300 MHz, MeOD) δ ppm 2.60 (s, 3H) 7.51 (d, J=8.31 Hz, 2H) 7.65-7.78 (m, 2H) 7.90 (d, J=8.31 Hz, 2H)

Procedure 6

N-(4'-(5-amino-1H-[1,2,4]triazol-3-ylamino)-2',6'-dichlorobiphenyl-4-yl)-2-methoxyacetamide (Compound 73)

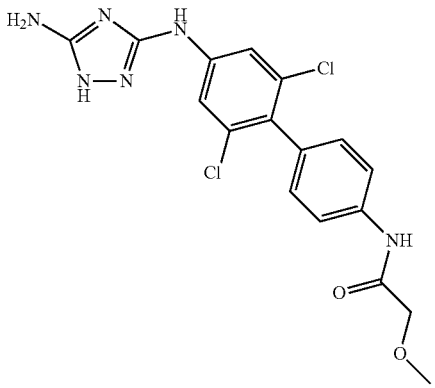 [SMILES: COCC(=O)Nc1ccc(-c2c(Cl)cc(Nc3n[nH]c(N)n3)cc2Cl)cc1]

(4'-(5-amino-1H-[1,2,4]triazol-3-ylamino)-2',6'-dichlorobiphenyl-4-yl)-carbamic acid tert-butyl ester

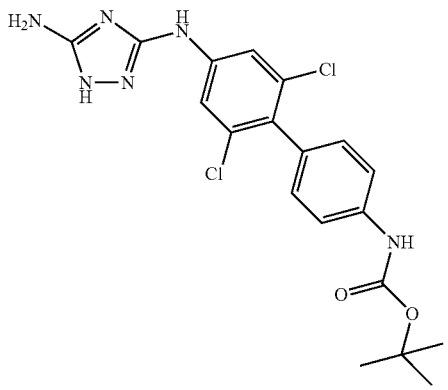 [SMILES: CC(C)(C)OC(=O)Nc1ccc(-c2c(Cl)cc(Nc3n[nH]c(N)n3)cc2Cl)cc1]

Intermediate 2 (0.200 g, 619 μmol, Eq: 1.00), 4-(tert-butoxycarbonylamino)phenylboronic acid (220 mg, 929 μmol, Eq: 1.5) and cesium carbonate (504 mg, 1.55 mmol, Eq: 2.5) were dissolved in dioxane (2 ml) and Water (400 μl). PdCl$_2$(DPPF)-CH2Cl$_2$ (45.3 mg, 61.9 μmol, Eq: 0.1) was added. The reaction mixture was heated under an argon atmosphere to 135° C. for 45 min in the microwave.

Reaction mixture was loaded into a silica gel column (40 g) and purified (0-10% MeOH in ethyl acetate 1:1 n-hexane for 15 min) to afford a light yellow gum (230 mg). The gum was dissolved in ethyl acetate (4 ml) and Hexane (10 ml) was added. The precipitate was filtered off and the filtrate was concentrated to give a light yellow solid. The solid was triturated with dichloromethane (5 ml), filtered and combined with the previously filtered solid to afford 142 mg (53%) of the product as a light yellow solid.

MS +m/z: 435.0 (M+1)

$^1$H NMR (400 MHz, DMSO-d$_6$) δ ppm 1.50 (s, 9H) 7.11 (d, J=8.34 Hz, 2H) 7.45-7.60 (m, 3H) 7.70 (s, 2H) 9.16-9.24 (m, 1H) 9.45 (s, 1H) 11.30 (s, 1H)

N3-(4'-(4'-Amino-2,6-dichlorobiphenyl-4-yl)-1H-[1,2,4]triazole-3,5-diamine

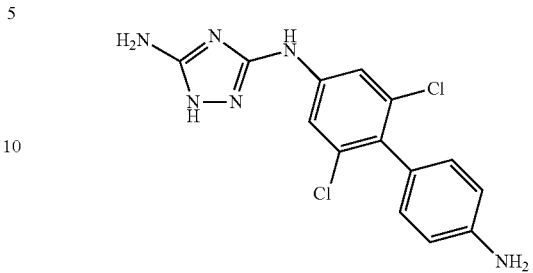

To a 2 mL microwave vial was added tert-butyl 4'-(3-amino-1H-1,2,4-triazol-5-ylamino)-2',6'-dichlorobiphenyl-4-ylcarbamate (142 mg, 326 μmol, Eq: 1.00) in 1,1,1,3,3,3-Hexaluoro-2-propanol (54.8 mg, 326 μmol, Eq: 1.00). The vial was capped and heated in the microwave at 140° C. for 10 min. The crude reaction mixture was concentrated in vacuo to give a light brown solid (139 mg) and used without further purification.

MS +m/z: 335.0 (M+1)

N-(4'-(5-amino-1H-[1,2,4]triazol-3-ylamino)-2',6'-dichlorobiphenyl-4-yl)-2-methoxyacetamide (Compound 73)

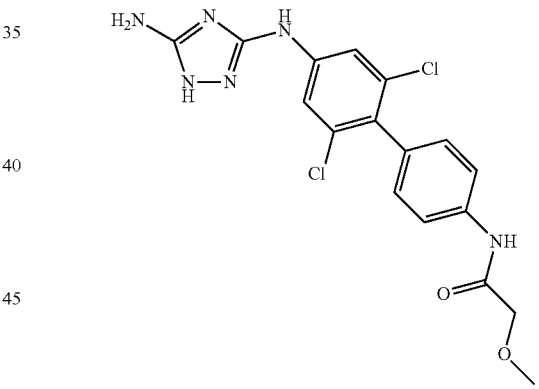

N3-(4'-amino-2,6-dichlorobiphenyl-4-yl)-1H-1,2,4-triazole-3,5-diamine (70 mg, 146 μmol, Eq: 1.00), 2-methoxy-acetic acid (20 mg, 222 μmol, Eq: 1.52), DIEA (37.8 mg, 51.1 μl, 292 μmol, Eq: 2) and HATU (61.1 mg, 161 μmol, Eq: 1.1) were dissolved in DMF (1.22 ml). The reaction mixture was stirred overnight at room temperature. Water (10 ml) was added and a dark brown solid was precipitated. The reaction mixture was filtered and the filter solid was purified by 16 g reversed phase chromatography with a gradient of 0-10% MeOH (0.1% TFA) in water (0.1% TFA) to afford 14 mg (24%) of the desired product as a white solid.

MS +m/z: 407.0 (M+1)

$^1$H NMR (400 MHz, MeOD) δ ppm 3.52 (s, 3H) 4.08 (s, 2H) 7.21 (d, J=8.59 Hz, 2H) 7.64 (s, 2H) 7.71 (d, J=8.34 Hz, 2H)

Procedure 6

N$^5$-(2-Fluoro-3'-(methylsulfonyl)-6-trifluoromethyl-biphenyl-4-yl)-1H-[1,2,4]-triazole-3,5-diamine (Compound 74)

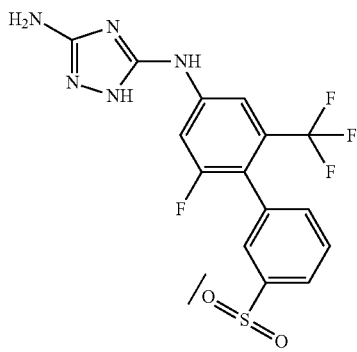

Prepared by a similar procedure to Compound 70, except substituted 3-(methylsulfonyl)phenylboronic acid for 4,4,5,5-tetramethyl-2-(4-(methylsulfonyl)phenyl)-1,3,2-dioxaborolane in step 1 to afford 8 mg (11%) of the desired material as a yellow solid.

MS +m/z: 416.0. (M+1)

$^1$H NMR (400 MHz, MeOD) δ ppm 3.16 (s, 3H) 7.35-7.41 (m, 1H) 7.63-7.78 (m, 4H) 7.88 (s, 1H) 8.03 (d, J=7.83 Hz, 1H)

Procedure 6

4'-(5-Amino-2H-[1,2,4]-triazol-3-ylamino)-6'-fluoro-2'-trifluoromethyl-biphenyl-4-sulfonic acid dimethylamide (Compound 75)

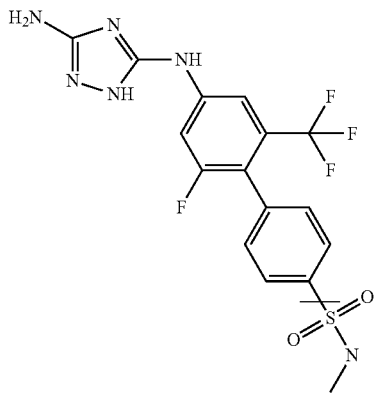 [SMILES: CNS(=O)(=O)c1ccc(-c2c(F)cc(Nc3nc(N)n[nH]3)cc2C(F)(F)F)cc1]

Prepared by a similar procedure to Compound 70, except substituted 4-(N,N-dimethylsulfamoyl)phenylboronic acid for 4,4,5,5-tetramethyl-2-(4-(methylsulfonyl)phenyl)-1,3,2-dioxaborolane in step 1 to afford 4 mg (4%) of the desired material as a light yellow solid.

MS +m/z: 444.9. (M+1)

$^1$H NMR (300 MHz, MeOD) δ ppm 2.74 (s, 6H) 7.48-7.92 (m, 6H) Procedure 6

N$^5$-(2,6-difluoro-4'-(methylsulfonyl)biphenyl-4-yl)-1H-[1,2,4]-triazole-3,5-diamine (Compound 76)

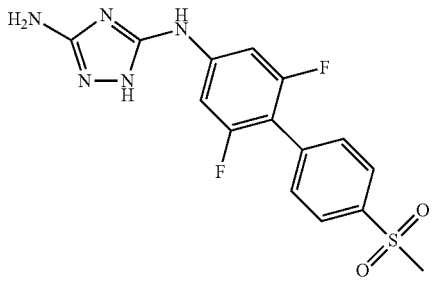 [SMILES: CS(=O)(=O)c1ccc(-c2c(F)cc(Nc3nc(N)n[nH]3)cc2F)cc1]

2-bromo-1,3-difluoro-5-isothiocyanatobenzene

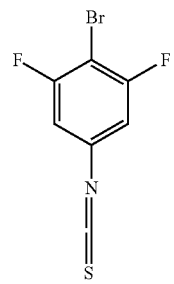

4-bromo-3,5-difluoroaniline (5 g, 24.0 mmol, Eq: 1.00) and calcium carbonate (5.05 g, 1.72 ml, 50.5 mmol, Eq: 2.1) were suspended in a 50% aqueous dichlormethane (24 ml) mixture. The thick suspension was stirred vigorously at 0° C. Thiophosgene (3.04 g, 2.03 ml, 26.4 mmol, Eq: 1.1) was added slowly dropwise to the mixture. After the addition the mixture was stirred at 0° C. for 1 hr, then stirred overnight at room temperature. The precipitate was filtered and the filter cake was washed with dichloromethane. The phases were separated and the aqueous was extracted with dichloromethane. The combined organic phases were washed with water and brine, dried over sodium sulfate and concentrated in vacuo to afford 5.18 g (86%) of the desired product as an off-white solid which was used without further purification.

(4-Bromo-3,5-difluoro-phenylamino)-(methyl-λ$^4$-sulfanylidene)-methyl-cyanamide

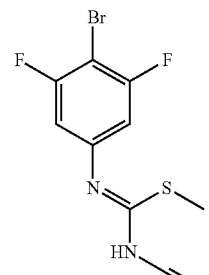

2-bromo-1,3-difluoro-5-isothiocyanatobenzene (5.18 g, 20.7 mmol, Eq: 1.00) was dissolved in anhydrous methanol (30.0 ml) and dichloromethane (10 ml). Sodium hydrogencyanamide (1.33 g, 20.7 mmol, Eq: 1) was added slowly and the reaction was stirred for 1 hr at room temperature. The reaction was cooled to 0° C. and methyl iodide (5.88 g, 2.59 ml, 41.4 mmol, Eq: 2) was added dropwise. The reaction was stirred overnight at room temperature. The white suspension was filtered and the filter cake was washed with methanol and dried under high vacuum to afford 4.62 g (73%) of the desired product as a white solid.

MS +m/z: 307. (M+1)

$^1$H NMR (300 MHz, DMSO-$d_6$) δ ppm 2.74 (s, 3H) 7.47 (d, J=8.69 Hz, 2H) 10.35 (s, 1H)

N$^5$-(4-bromo-3,5-difluorophenyl)-1H-[1,2,4]-triazole-3,5-diamine (Intermediate 4)

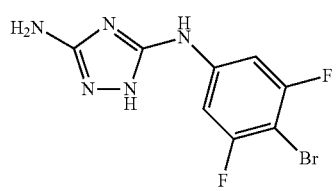 [SMILES: Nc1n[nH]c(Nc2cc(F)c(Br)c(F)c2)n1]

Hydrazine (4.84 g, 151 mmol, Eq: 10) was added to a stirred suspension of (4-Bromo-3,5-difluoro-phenylamino)-(methyl-λ$^4$-sulfanylidene)-methyl-cyanamide (4.62 g, 15.1 mmol, Eq: 1.00) in ethanol (78.9 ml). During the addition of hydrazine the reaction went into solution. The mixture was heated to 70° C. for 45 minutes. The reaction mixture was concentrated (~10 ml). Water (~80 ml) was added dropwise and the suspension was stirred for 30 min. The precipitate was filtered, washed with water (~100 ml) and dried under high vacuum at 70° C. to afford 4.28 g (97%) of the desired product as a white solid.

MS +m/z: 291.9. (M+1)

$^1$H NMR (300 MHz, DMSO-$d_6$) δ ppm 6.00 (br. s., 2H) 7.36 (d, J=10.58 Hz, 2H) 9.37 (s, 1H) 11.35 (br. s., 1H)

N$^5$-(2,6-difluoro-4'-(methylsulfonyl)biphenyl-4-yl)-1H-[1,2,4]-triazole-3,5-diamine (Compound 76)

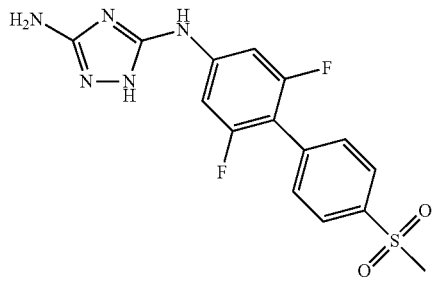 [SMILES: CS(=O)(=O)c1ccc(-c2c(F)cc(Nc3nc(N)n[nH]3)cc2F)cc1]

Intermediate 4 (80 mg, 276 µmol, Eq: 1.00), 4,4,5,5-tetramethyl-2-(4-(methylsulfonyl)phenyl)-1,3,2-dioxaborolane (117 mg, 414 µmol, Eq: 1.5) and Cs$_2$CO$_3$ (225 mg, 689 µmol, Eq: 2.5) were dissolved in 20% aq. n-butanol (2.4 ml). PdCl$_2$(DPPF)-CH2Cl$_2$ adduct (20.2 mg, 27.6 µmol, Eq: 0.1) was added under an argon atmosphere and the reaction mixture was heated to 135° C. for 40 min in a microwave. The reaction mixture was filtered over a plug of silica gel and washed with dioxane. The filtrate was concentrated and the crude material was purified by preparative HPLC (0.1% TFA in water/0.1% TFA in AcCN) 95% to 10% TFA water over 16 minutes to afford 42 mg (32%) of the desired product as a white solid.

MS +m/z: 366.0. (M+1)

$^1$H NMR (+D2O) (300 MHz, DMSO-$d_6$) δ ppm 3.25 (s, 3H) 7.34 (d, J=11.33 Hz, 2H) 7.68 (d, J=8.31 Hz, 2H) 7.87-8.07 (d, 2H)

Procedure 6

N$^5$-(2,6-difluoro-4'-(morpholine-4-sulfonyl)biphenyl-4-yl)-1H-[1,2,4]-triazole-3,5-diamine (Compound 77)

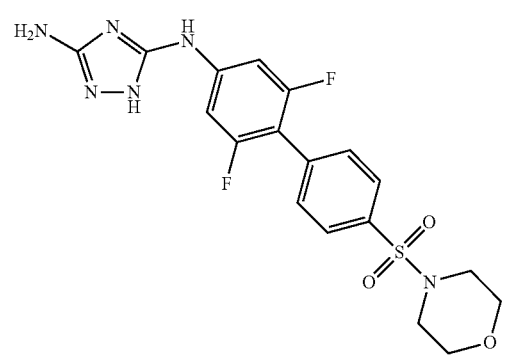 [SMILES: Nc1n[nH]c(Nc2cc(F)c(-c3ccc(S(=O)(=O)N4CCOCC4)cc3)c(F)c2)n1]

Prepared by a similar procedure to Compound 76, except substituted 4-(morpholinosulfonyl)phenylboronic acid for 4,4,5,5-tetramethyl-2-(4-(methylsulfonyl)phenyl)-1,3,2-dioxaborolane in step 4 to afford 72 mg (47%) of the desired material as a white foam.

MS +m/z: 437.0. (M+1)

Procedure 6

N$^5$-[6-Fluoro-4'-(morpholine-4-sulfonyl)-2-trifluoromethylbiphenyl-4-yl]-1H-[1,2,4]-triazole-3,5-diamine (Compound 78)

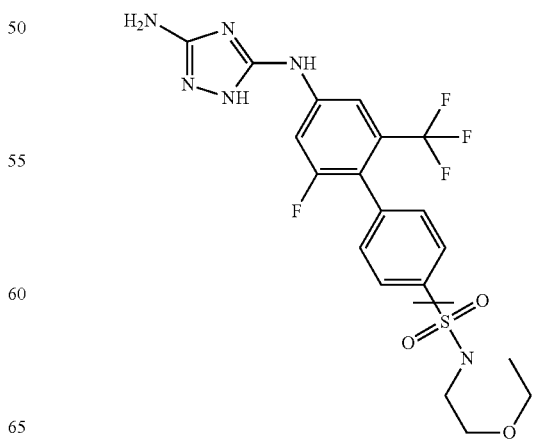

Prepared by a similar procedure to Compound 70, except substituted 4-(morpholinosulfonyl)phenylboronic acid for 4,4,5,5-tetramethyl-2-(4-(methylsulfonyl)phenyl)-1,3,2-dioxaborolane in step 1 to afford 8 mg (8%) of the desired material as a white foam.

MS +m/z: 486.9. (M+1)

Procedure 6

4'-(5-Amino-2H-[1,2,4]-triazol-3-ylamino)-6'-fluoro-2'-trifluoromethyl-biphenyl-4-carbonitrile (Compound 79)

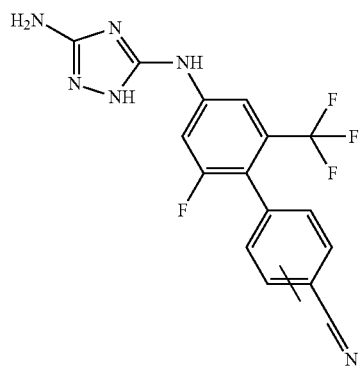 [SMILES: N=Cc1ccc(-c2c(F)cc(Nc3nc(N)n[nH]3)cc2C(F)(F)F)cc1]

Prepared by a similar procedure to Compound 70, except substituted 4-cyanophenylboronic acid for 4,4,5,5-tetramethyl-2-(4-(methylsulfonyl)phenyl)-1,3,2-dioxaborolane in step 1 to afford 10 mg (13%) of the desired material as a white solid.

MS +m/z: 363.0. (M+1)

$^1$H NMR (400 MHz, MeOD) δ ppm 7.48 (d, J=8.08 Hz, 2H) 7.67 (s, 1H) 7.73 (dd, J=12.13, 1.77 Hz, 1H) 7.80 (d, J=8.08 Hz, 2H)

Procedure 6

$N^5$-(2,6-difluoro-3'-(methylsulfonyl)biphenyl-4-yl)-1H-[1,2,4]-triazole-3,5-diamine (Compound 80)

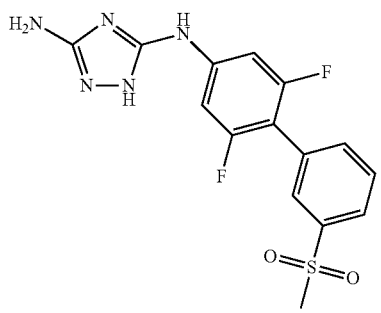 [SMILES: CS(=O)(=O)c1cccc(-c2c(F)cc(Nc3nc(N)n[nH]3)cc2F)c1]

Prepared by a similar procedure to Compound 76, except substituted 3-(methylsulfonyl)phenylboronic acid for 4,4,5,5-tetramethyl-2-(4-(methylsulfonyl)phenyl)-1,3,2-dioxaborolane in step 4 to afford 46 mg (35%) of the desired material as a white solid.

MS +m/z: 366.0. (M+1)

Procedure 6

4'-(5-Amino-2H-[1,2,4]-triazol-3-ylamino)-6'-fluoro-2'-trifluoromethyl-biphenyl-3-sulfonic acid methylamide (Compound 81)

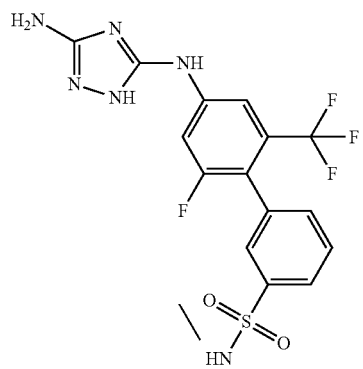 [SMILES: Nc1n[nH]c(Nc2cc(F)c(-c3cccc(S(N)(=O)=O)c3)c(C(F)(F)F)c2)n1]

Prepared by a similar procedure to Compound 70, except substituted 3-(N-methylsulfamoyl)phenylboronic acid for 4,4,5,5-tetramethyl-2-(4-(methylsulfonyl)phenyl)-1,3,2-dioxaborolane in step 1 to afford 10 mg (11%) of the desired material as a light yellow solid.

MS +m/z: 431.0. (M+1)

$^1$H NMR (300 MHz, MeOD) δ ppm 2.55 (d, J=2.27 Hz, 3H) 7.49-7.96 (m, 6H)

Procedure 6

Tetrahydropyran-4-carboxylic acid-(4'-(5-amino-1H-[1,2,4]triazol-3-ylamino)-2',6'-dichlorobiphenyl-4-yl)-amide (Compound 82)

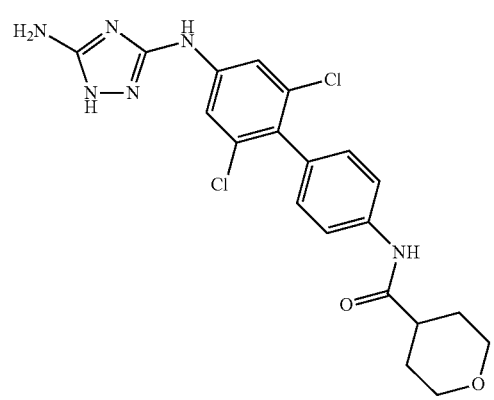 [SMILES: Nc1nc(Nc2cc(Cl)c(-c3ccc(NC(=O)C4CCOCC4)cc3)c(Cl)c2)n[nH]1]

Prepared as described for compound 73 except substituting tetrahydro-2H-pyran-4-carboxylic acid for methoxyacetic acid in step 3 to afford 10 mg (4%) of the desired product as a white solid.

MS +m/z: 447.0 (M+1)

$^1$H NMR (400 MHz, DMSO-$d_6$) δ ppm 1.60-1.75 (m, 2H) 1.94 (d, J=12.88 Hz, 2H) 3.43-3.50 (m, 2H) 3.96 (d, J=9.60 Hz, 2H) 6.83 (br. s., 1H) 7.01 (d, J=8.08 Hz, 2H) 7.72 (br. s., 1H) 7.76 (s, 2H) 9.77 (s, 1H)

Procedure 6

N³-2',6'-Dichloro-4-nitrobiphenyl-4-yl)-1H-[1,2,4]triazole-3,5-diamine (Compound 83)

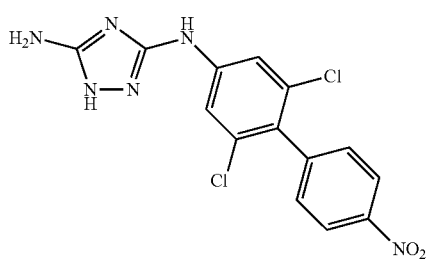 [SMILES: Nc1nc(Nc2cc(Cl)c(-c3ccc([N+](=O)[O-])cc3)c(Cl)c2)n[nH]1]

N³-2',6'-Dichloro-4-nitrobiphenyl-4-yl)-1H-[1,2,4]triazole-3,5-diamine

Intermediate 2 (422 mg, 1.31 mmol, Eq: 1.00), 4-nitrophenylboronic acid (327 mg, 1.96 mmol, Eq: 1.5) and cesium carbonate (1.06 g, 3.27 mmol, Eq: 2.5) were suspended in 20% aq. dioxane solution (5 ml). PdCl$_2$(DPPF) (95.6 mg, 131 μmol, Eq: 0.1) was added and the reaction was heated to 135° C. for 30 min in the microwave. The reaction mixture was filtered over celite, washed with dioxane and concentrated to give a black amorphous solid. The crude material was purified by silica gel chromatography (40 g, dichloromethane/methanol 9:1) to give 280 mg of a yellow gum. 80 mg of the impure gum was repurified by preparative HPLC (0.1% TFA in water/0.1% TFA in AcCN) 95% to 10% TFA water over 25 mins to afford 33 mg (5%) of the desired product as an off white solid.

MS +m/z: 365/367 (M+1)
$^1$H NMR (400 MHz, MeOD) δ ppm 7.53 (d, J=8.59 Hz, 2H) 7.69 (s, 2H) 8.34 (d, J=8.84 Hz, 2H).

Procedure 6

4'-(5-Amino-2H-[1,2,4]-triazol-3-ylamino)-6'-fluoro-2'-trifluoromethyl-biphenyl-3-sulfonic acid dimethylamide (Compound 84)

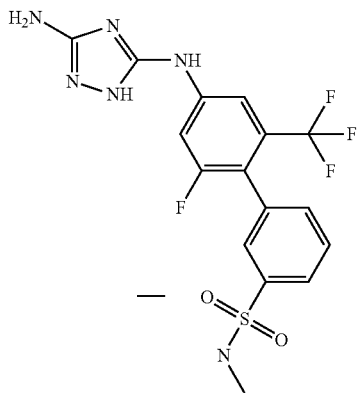 [SMILES: CNS(=O)(=O)c1cccc(-c2c(F)cc(Nc3nc(N)n[nH]3)cc2C(F)(F)F)c1]

Prepared by a similar procedure to Compound 70, except substituted 3-(N,N-dimethylsulfamoyl)phenylboronic acid for 4,4,5,5-tetramethyl-2-(4-(methylsulfonyl)phenyl)-1,3,2-dioxaborolane in step 1 to afford 6 mg (7%) of the desired material as an off-white solid.

MS +m/z: 444.9. (M+1)
$^1$H NMR (300 MHz, MeOD) δ ppm 2.70 (s, 6H) 7.55-7.91 (m, 6H)

Procedure 6

4'-(5-Amino-2H-[1,2,4]-triazol-3-ylamino)-6'-fluoro-2'-trifluoromethyl-biphenyl-4-carboxylic acid dimethylamide (Compound 85)

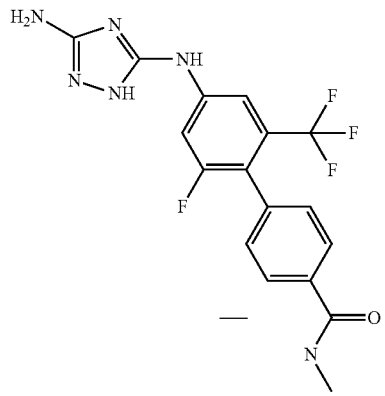 [SMILES: CNC(=O)c1ccc(-c2c(F)cc(Nc3nc(N)n[nH]3)cc2C(F)(F)F)cc1]

Prepared by a similar procedure to Compound 70, except substituted 4-(dimethylcarbamoyl)phenylboronic acid for 4,4,5,5-tetramethyl-2-(4-(methylsulfonyl)phenyl)-1,3,2-dioxaborolane in step 1 to afford 7 mg (8%) of the desired material as a light yellow solid.

MS +m/z: 409.0. (M+1)
$^1$H NMR (300 MHz, MeOD) δ ppm 3.11 (br. d, J=1.00 Hz, 6H) 7.38 (d, J=7.18 Hz, 2H) 7.46-7.54 (m, 2H) 7.60-7.75 (m, 2H)

Procedure 6

N⁵-[6-Fluoro-4'-methoxy-2-trifluoromethylbiphenyl-4-yl]-1H-[1,2,4]-triazole-3,5-diamine (Compound 86)

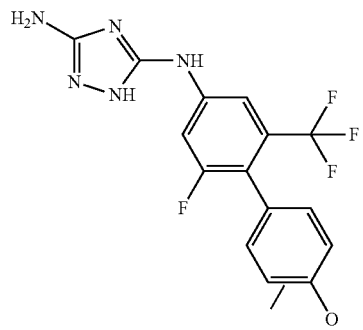 [SMILES: Nc1n[nH]c(Nc2cc(F)c(-c3ccc(O)cc3)c(C(F)(F)F)c2)n1]

Prepared by a similar procedure to Compound 70, except substituted 4-methoxyphenylboronic acid for 4,4,5,5-tetramethyl-2-(4-(methylsulfonyl)phenyl)-1,3,2-dioxaborolane in step 1 to afford 17 mg (22%) of the desired material as a white solid.

MS +m/z: 367.9. (M+1)

$^1$H NMR (300 MHz, MeOD) δ ppm 3.11 (br. d, J=1.00 Hz, 6H) 7.38 (d, J=7.18 Hz, 2H) 7.46-7.54 (m, 2H) 7.60-7.75 (m, 2H)

Procedure 6

[4'-(5-amino-1H-[1,2,4]triazol-3-ylamino)-2',6'-difluorobiphenyl-4-carbonitrile (Compound 87)

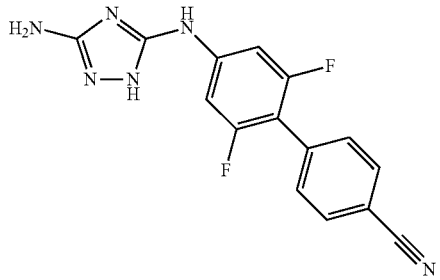 [SMILES: N#Cc1ccc(-c2c(F)cc(Nc3nc(N)n[nH]3)cc2F)cc1]

Prepared by a similar procedure to Compound 76, except substituted 4-cyanophenylboronic acid for 4,4,5,5-tetramethyl-2-(4-(methylsulfonyl)phenyl)-1,3,2-dioxaborolane in step 4 to afford 34 mg (29%) of the desired material as a white solid.

MS +m/z: 313.0. (M+1)

$^1$H NMR (300 MHz, DMSO-d$_6$) δ ppm 6.52 (br. s, 2H) 7.33 (d, J=11.33 Hz, 2H) 7.61 (d, J=7.93 Hz, 2H) 7.85-7.97 (m, 2H) 9.62 (s, 1H)

Procedure 6

N$^5$-[6-Fluoro-4'-trifluoromethanesulfonyl-2-trifluoromethylbiphenyl-4-yl]-1H-[1,2,4]-triazole-3,5-diamine (Compound 88)

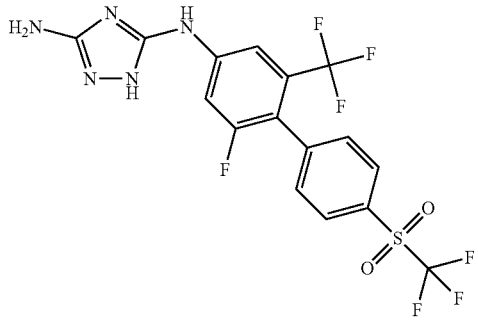 [SMILES: Nc1n[nH]c(Nc2cc(F)c(-c3ccc(S(=O)(=O)C(F)(F)F)cc3)c(C(F)(F)F)c2)n1]

Prepared by a similar procedure to Compound 70, except substituted 4,4,5,5-tetramethyl-2-(4-(trifluoromethylsulfonyl)phenyl)-1,3,2-dioxaborolane for 4,4,5,5-tetramethyl-2-(4-(methylsulfonyl)phenyl)-1,3,2-dioxaborolane in step 1 to afford 45 mg (26%) of the desired material as a white solid.

MS +m/z: 469.9. (M+1)

$^1$H NMR (400 MHz, DMSO-d$_6$) δ ppm 7.77-7.89 (m, 4H) 8.23 (d, J=8.34 Hz, 2H) 9.74 (s, 1H)

Procedure 6

4'-(5-Amino-2H-[1,2,4]-triazol-3-ylamino)-6'-fluoro-2'-trifluoromethyl-biphenyl-3-carbonitrile (Compound 89)

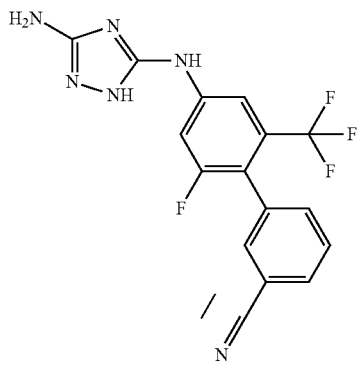 [SMILES: N=Cc1cccc(-c2c(F)cc(Nc3nc(N)n[nH]3)cc2C(F)(F)F)c1]

Prepared by a similar procedure to Compound 70, except substituted 3-cyanophenylboronic acid for 4,4,5,5-tetramethyl-2-(4-(methylsulfonyl)phenyl)-1,3,2-dioxaborolane in step 1 to afford 5 mg (7%) of the desired material as a light brown solid.

MS +m/z: 363.0. (M+1)

Procedure 7

N3-(4'-(methylsulfonyl)-2-(trifluoromethyl)biphenyl-4-yl)-1H-1,2,4-triazole-3,5-diamine (Compound 90)

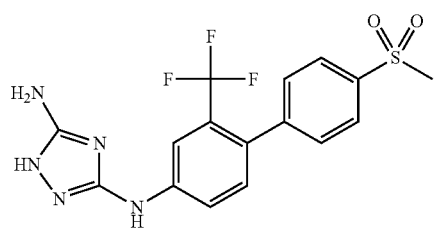 [SMILES: CS(=O)(=O)c1ccc(-c2ccc(Nc3n[nH]c(N)n3)cc2C(F)(F)F)cc1]

4'-Methanesulfonyl-2-trifluoromethyl-biphenyl-4-ylamine

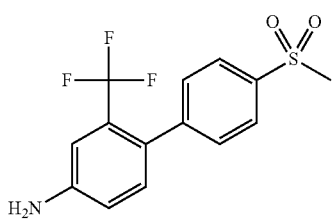 [SMILES: CS(=O)(=O)c1ccc(-c2ccc(N)cc2C(F)(F)F)cc1]

In a 250 mL round-bottomed flask, 4-(methylsulfonyl)phenylboronic acid (1.0 g, 5.00 mmol, Eq: 1.00), 4-bromo-3-(trifluoromethyl)aniline (1.2 g, 5.00 mmol, Eq: 1.00) and tetrakis(triphenylphosphine)-palladium (578 mg, 500 µmol, Eq: 0.1) were combined with toluene (27 mL) to give a yellow suspension. A 4.0 M solution of aqueous sodium carbonate (5.00 mL, 20.0 mmol, Eq: 4.00) was added, followed by ethanol. The reaction mixture was heated at 110° C. for 6 hours. The heating bath was removed, and the reaction mixture was stirred overnight at room temperature. In the morning, the mixture was partitioned between ethyl acetate and brine. The organic phase was dried over MgSO₄, filtered, and concentrated over silica gel. The silica-supported crude product was loaded onto a 120 gram SiliCycle column. Flash chromatography was used to purify the product (40%-80% ethyl acetate in hexanes). 4'-Methanesulfonyl-2-trifluoromethyl-biphenyl-4-ylamine (1.29 g, 82%) was obtained as a yellow liquid.

4-isothiocyanato-4'-methanesulfonyl-2-trifluoromethyl-biphenyl

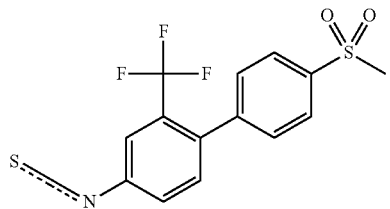

In a 1 L round-bottomed flask, 4'-(methylsulfonyl)-2-(trifluoromethyl)biphenyl-4-amine (1.28 g, 4.06 mmol, Eq: 1.00) and di(1H-imidazol-1-yl)methanethione (800 mg, 4.49 mmol, Eq: 1.11) were combined with methylene chloride (27 ml) to give a brown solution. The reaction mixture was stirred at room temperature over the weekend. After this time, the reaction mixture was concentrated over silica gel. The silica gel supported crude product was loaded onto a 120 gram ISCO column. Flash chromatography (35% ethyl acetate-hexanes) afforded 4-isothiocyanato-4'-methanesulfonyl-2-trifluoromethyl-biphenyl (1.18 g, 81%) as a white solid.

(Z)-methyl N'-cyano-N-(4'-(methylsulfonyl)-2-(trifluoromethyl)biphenyl-4-yl)carbamimidothioate

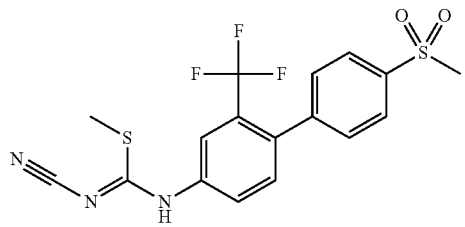 [SMILES: CS/C(=N\C#N)Nc1ccc(-c2ccc(S(C)(=O)=O)cc2)c(C(F)(F)F)c1]

In a 50 mL pear-shaped flask, cyanamide (416 mg, 9.91 mmol, Eq: 3.0) and sodium methoxide (9.90 ml, 4.95 mmol, Eq: 1.5) were combined to give a colorless solution. This reaction mixture was stirred at room temperature for 15 minutes. After this time, the cyanamide and sodium methoxide mixture was added dropwise to a mixture of 4-isothiocyanato-4'-(methylsulfonyl)-2-(trifluoromethyl)biphenyl (1.18 g, 3.3 mmol, Eq: 1.00) in methanol (10 mL). The resulting solution was stirred at room temperature for 1 hour. Methyl iodide (707 mg, 310 µl, 4.98 mmol, Eq: 1.51) was added. The reaction mixture was stirred at room temperature overnight. In the morning, a white solid had precipitated. This product was collected via vacuum filtration to provide (Z)-methyl N'-cyano-N-(4'-(methylsulfonyl)-2-(trifluoromethyl)biphenyl-4-yl)carbamimidothioate (505 mg, 99%) as an off-white solid.

N3-(4'-(methylsulfonyl)-2-(trifluoromethyl)biphenyl-4-yl)-1H-1,2,4-triazole-3,5-diamine (Compound 90)

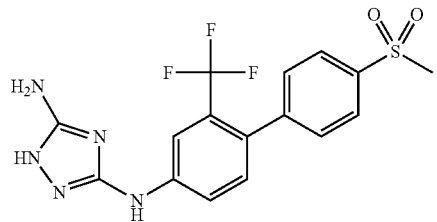 [SMILES: CS(=O)(=O)c1ccc(-c2ccc(Nc3n[nH]c(N)n3)cc2C(F)(F)F)cc1]

In a 250 mL round-bottomed flask, (Z)-methyl N'-cyano-N-(4'-(methylsulfonyl)-2-(trifluoromethyl)-biphenyl-4-yl)carbamimidothioate (530 mg, 1.28 mmol, Eq: 1.00) and hydrazine (408 mg, 400 µl, 12.7 mmol, Eq: 9.94) were combined with ethanol (8 ml) to give a colorless solution. The mixture was heated at 85° C. for five hours. The reaction mixture was cooled to room temperature. Solvent was evaporated using the rotary evaporator, giving a slightly yellow oil. This crude product was further dried in the vacuum oven to give N3-(4'-(methylsulfonyl)-2-(trifluoromethyl)biphenyl-4-yl)-1H-1,2,4-triazole-3,5-diamine as an off-white solid cald. for $C_{16}H_{15}F_3N_5O_2S$ [(M+H)]: 398.0, obsd. 398.1.

Procedure 1, 6

N-3-(2,6-Dichloro-4'-trifluoromethyoxy-biphenyl-4-yl)-1H[1,2,4]triazole-3,5-diamine (Compound 91)

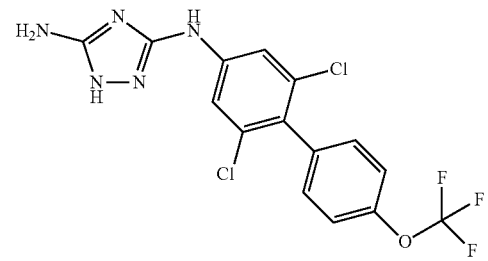 [SMILES: Nc1nc(Nc2cc(Cl)c(-c3ccc(OC(F)(F)F)cc3)c(Cl)c2)n[nH]1]

To a solution of N-3-(4-bromo-3,5-dichlorophenyl)-1H-1,2,4-triazole-3,5-diamine Intermediate 2 (64.6 mg, 0.2 mmol, Eq: 1.00) in dioxane (1 ml) was added tetrakis (triphenylphosphine)palladium(0) (18.5 mg, 16 µmol, Eq: 0.08), potassium carbonate (133 µl, 3M, Eq: 2), and 4-trifluoromethyoxyboronic acid (82.5 mg, 0.4 mmol, Eq: 2). The mixture was degassed twice under Nitrogen, then was heated at 100° C. for 16 hours. After being cooled to room temperature, the solvent was removed in vacuo. To the crude product was added a few drops of acetic acid, followed by addition of mixture of MeOH/CH3CN/H2O (45%/45%/10%)(2 ml). The resulting suspension was centrifuged, and the solution was separated to be purified by reverse phase HPLC (0.1% HOAc in acetonitrile and water). Product fractions were collected and lyophilized to afford N-3-(2,6-Dichloro-4'-trifluoromethyoxy-biphenyl-4-yl)-1H[1,2,4]triazole-3,5-diamine (23.8 mg, 29.4%) as a white solid. MS m/z: 405 (M+H)+.

The following compounds were all prepared in an analogous manner to example 91:

N3-(2,3',6-Trichlorobiphenyl-4-yl)-1H-1,2,4-triazole-3,5-diamine (Compound 92)

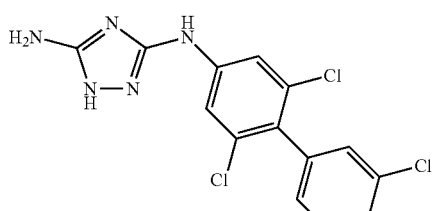

Starting from 3-Chlorophenylboronic acid, yield=38%, MS m/z 356 (M+H)

4'-(5-Amino-1H-1,2,4-triazol-3-ylamino)-2',6'-dichlorobiphenyl-4-carbonitrile (Compound 93)

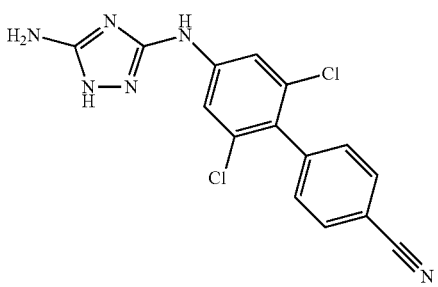 [SMILES: N#Cc1ccc(-c2c(Cl)cc(Nc3n[nH]c(N)n3)cc2Cl)cc1]

Starting from 4-Cyanophenylboronic acid, yield—18%, MS m/z 346 (M+H)

N3-(2,6-Dichloro-4'-(methylsulfonyl)biphenyl-4-yl)-1H-1,2,4-triazole-3,5-diamine (Compound 94)

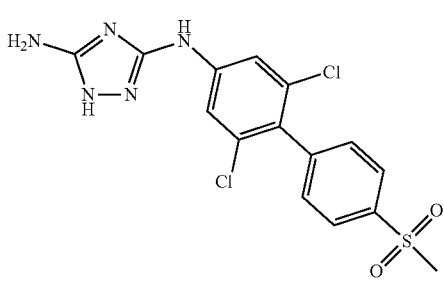 [SMILES: CS(=O)(=O)c1ccc(-c2c(Cl)cc(Nc3n[nH]c(N)n3)cc2Cl)cc1]

Starting from 4-(Methylsulfonyl)phenylboronic acid, yield=31%, MS m/z 399 (M+H)

N-3-(3,5-Dichloro-4-naphthalen-1-yl-phenyl)-1H-[1,2,4]triazole-3,5-diamine (Compound 95)

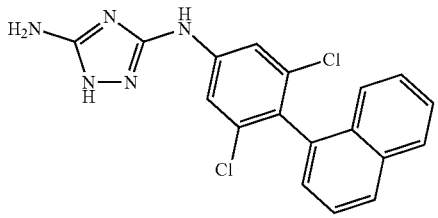 [SMILES: Nc1nc(Nc2cc(Cl)c(-c3cccc4ccccc34)c(Cl)c2)n[nH]1]

Starting from 1-Naphthaleneboronic acid, yield—1%, MS m/z 371 (M+H)

N-3-(2,6,4'-Trichloro-biphenyl-4-yl)-1H-[1,2,4]triazole-3,5-diamine (Compound 96)

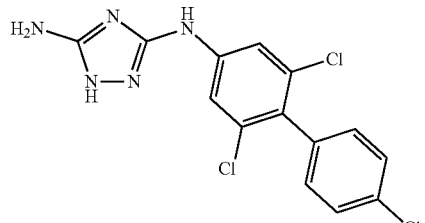

Starting from 4-Chlorophenylboronic acid, yield=54%, MS m/z 356 (M+H)

N-3-(2,6-Dichloro-4'-methyl-biphenyl-4-yl)-1H-[1,2,4]triazole-3,5-diamine (Compound 97)

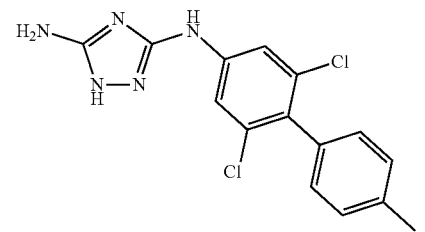 [SMILES: Cc1ccc(-c2c(Cl)cc(Nc3n[nH]c(N)n3)cc2Cl)cc1]

Starting from 4-Methylphenylboronic acid, yield=66%, MS m/z 335 (M+H)

N-3-(2,6-Dichloro-4'-methoxy-biphenyl-4-yl)-1H-[1,2,4]triazole-3,5-diamine (Compound 98)

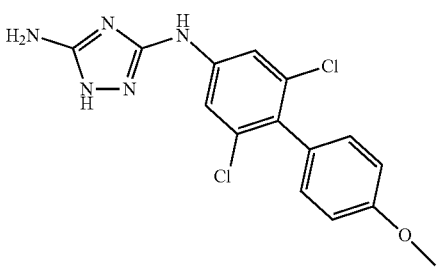 [SMILES: COc1ccc(-c2c(Cl)cc(Nc3n[nH]c(N)n3)cc2Cl)cc1]

Starting from 4-Methoxyphenylboronic acid, yield=60%, MS m/z 351 (M+H)

283

N-3-(2,6-Dichloro-4'-trifluoromethyl-biphenyl-4-yl)-1H-[1,2,4]triazole-3,5-diamine (Compound 99)

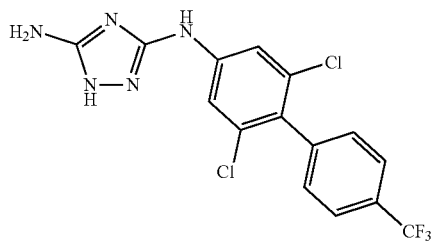 [SMILES: Nc1nc(Nc2cc(Cl)c(-c3ccc(C(F)(F)F)cc3)c(Cl)c2)n[nH]1]

Starting from 4-(Trifluoromethyl)phenylboronic acid, yield=42%, MS m/z 389 (M+H)

N-3-(2,6-Dichloro-3'-methoxy-biphenyl-4-yl)-1H-[1,2,4]triazole-3,5-diamine (Compound 100)

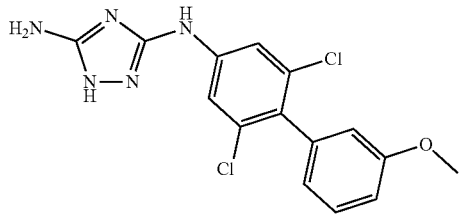 [SMILES: COc1cccc(-c2c(Cl)cc(Nc3n[nH]c(N)n3)cc2Cl)c1]

Starting from 3-Methoxyphenylboronic acid, yield=78%, MS m/z 351 (M+H)

N-3-(2,6,2'-Trichloro-biphenyl-4-yl)-1H-[1,2,4]triazole-3,5-diamine (Compound 101)

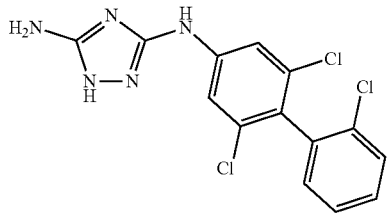 [SMILES: Nc1nc(Nc2cc(Cl)c(-c3ccccc3Cl)c(Cl)c2)n[nH]1]

Starting from 2-Chlorophenylboronic acid, yield=2%, MS m/z 356 (M+H)

N-3-(2,6,3',4'-Tetrachloro-biphenyl-4-yl)-1H-[1,2,4]triazole-3,5-diamine (Compound 102)

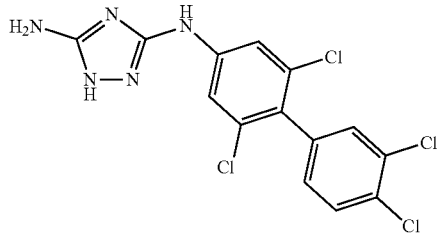 [SMILES: Nc1nc(Nc2cc(Cl)c(-c3ccc(Cl)c(Cl)c3)c(Cl)c2)n[nH]1]

Starting from 3,4-Dichlorophenylboronic acid, yield=32%, MS m/z 390 (M+H)

284

4'-(5-Amino-1H-[1,2,4]triazol-3-ylamino)-2',6'-dichloro-biphenyl-3-carbonitrile (Compound 103)

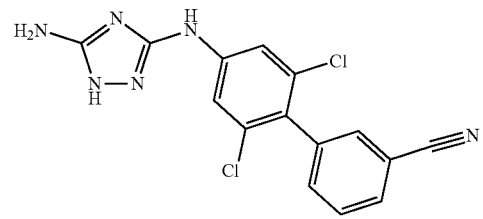 [SMILES: N#Cc1cccc(-c2c(Cl)cc(Nc3n[nH]c(N)n3)cc2Cl)c1]

Starting from 3-Cyanophenylboronic acid, yield=42%, MS m/z 346 (M+H)

4'-(5-Amino-1H-[1,2,4]triazol-3-ylamino)-2',6'-dichloro-biphenyl-2-carbonitrile (Compound 104)

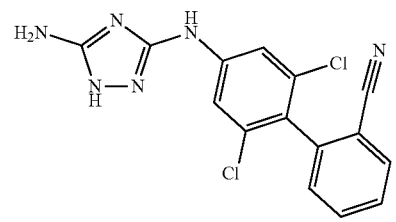 [SMILES: N#Cc1ccccc1-c1c(Cl)cc(Nc2n[nH]c(N)n2)cc1Cl]

Starting from 2-Cyanophenylboronic acid, yield=3%, MS m/z 346 (M+H)

4'-(5-Amino-1H-[1,2,4]triazol-3-ylamino)-4,2',6'-trichloro-biphenyl-3-carbonitrile (Compound 105)

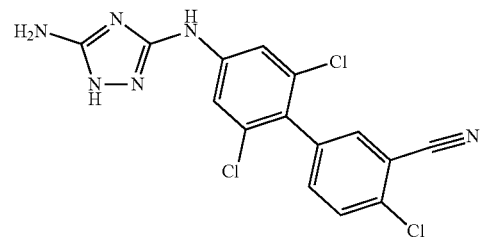 [SMILES: N#Cc1cc(-c2c(Cl)cc(Nc3n[nH]c(N)n3)cc2Cl)ccc1Cl]

Starting from 4-Chloro-3-cyanophenylboronic acid, yield=16%, MS m/z 381 (M+H)

4'-(5-Amino-1H-[1,2,4]triazol-3-ylamino)-2',6'-dichloro-biphenyl-3-carboxylic acid (Compound 106)

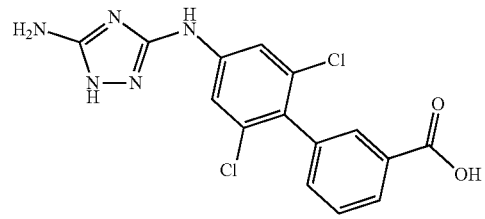 [SMILES: Nc1nc(Nc2cc(Cl)c(-c3cccc(C(=O)O)c3)c(Cl)c2)n[nH]1]

Starting from 3-Carboxyphenylboronic acid, yield=6%, MS m/z 365 (M+H)

285

1-[4'-(5-Amino-1H-[1,2,4]triazol-3-ylamino)-2',6'-dichloro-biphenyl-4-yl]-ethanone (Compound 107)

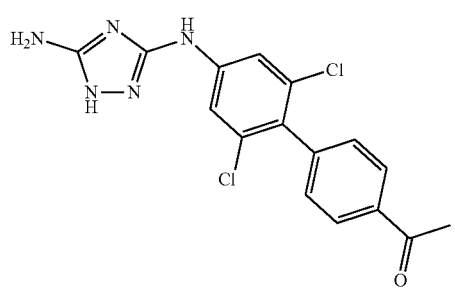 [SMILES: CC(=O)c1ccc(-c2c(Cl)cc(Nc3n[nH]c(N)n3)cc2Cl)cc1]

Starting from 4-Acetylphenylboronic acid, yield=19%, MS m/z 363 (M+H)

N-3-(2,6-Dichloro-3'-trifluoromethyl-biphenyl-4-yl)-1H-[1,2,4]triazole-3,5-diamine (Compound 108)

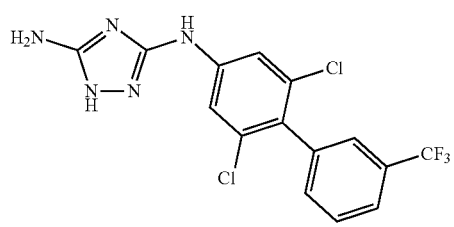 [SMILES: Nc1nc(Nc2cc(Cl)c(-c3cccc(C(F)(F)F)c3)c(Cl)c2)n[nH]1]

Starting from 3-(Trifluoromethyl)phenylboronic acid, yield=48%, MS m/z 389 (M+H)

N-3-(2,6,2',3'-Tetrachloro-biphenyl-4-yl)-1H-[1,2,4]triazole-3,5-diamine (Compound 109)

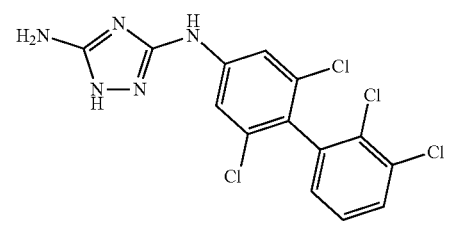 [SMILES: Nc1nc(Nc2cc(Cl)c(-c3cccc(Cl)c3Cl)c(Cl)c2)n[nH]1]

Starting from 2,3-Dichlorophenylboronic acid, yield=2%, MS m/z 390 (M+H)

4'-(5-Amino-1H-[1,2,4]triazol-3-ylamino)-2',6'-dichloro-biphenyl-4-carboxylic acid methyl ester (Compound 110)

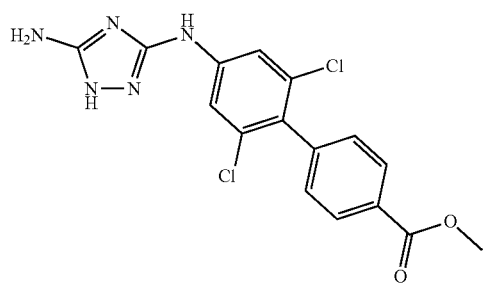 [SMILES: COC(=O)c1ccc(-c2c(Cl)cc(Nc3n[nH]c(N)n3)cc2Cl)cc1]

Starting from 4-Methoxycarbonylphenylboronic acid, yield=26%, MS m/z 379 (M+H)

286

N-[4'-(5-Amino-1H-[1,2,4]triazol-3-ylamino)-2',6'-dichloro-biphenyl-4-yl]-methanesulfonamide (Compound 111)

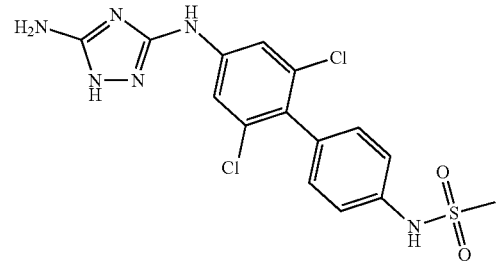 [SMILES: CS(=O)(=O)Nc1ccc(-c2c(Cl)cc(Nc3n[nH]c(N)n3)cc2Cl)cc1]

Starting from 4-(Methanesulfonylamino)phenylboronic acid, yield=27%, MS m/z 414 (M+H)

N-[4'-(5-Amino-1H-[1,2,4]triazol-3-ylamino)-2',6'-dichloro-biphenyl-3-yl]-methanesulfonamide (Compound 112)

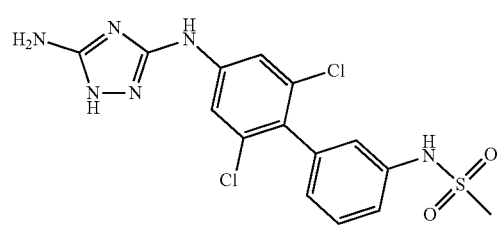 [SMILES: CS(=O)(=O)Nc1cccc(-c2c(Cl)cc(Nc3n[nH]c(N)n3)cc2Cl)c1]

Starting from 3-(Methylsulfonylamino)phenylboronic acid, yield=57%, MS m/z 414 (M+H)

4'-(5-Amino-1H-[1,2,4]triazol-3-ylamino)-2',6'-dichloro-biphenyl-4-carboxylic acid dimethylamide (Compound 113)

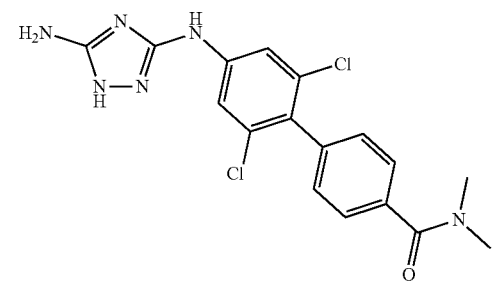 [SMILES: CN(C)C(=O)c1ccc(-c2c(Cl)cc(Nc3n[nH]c(N)n3)cc2Cl)cc1]

Starting from 4-(N,N-Dimethylaminocarbonyl)phenylboronic acid, yield=36%, MS m/z 392 (M+H)

287

N-3-(2,6-Dichloro-3'-methanesulfonyl-biphenyl-4-yl)-1H-[1,2,4]triazole-3,5-diamine (Compound 114)

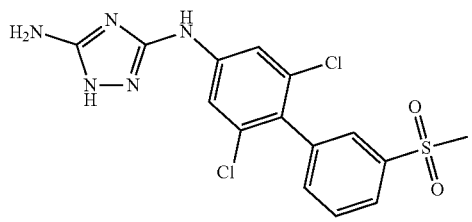 [SMILES: CS(=O)(=O)c1cccc(-c2c(Cl)cc(Nc3n[nH]c(N)n3)cc2Cl)c1]

Starting from 3-(Methylsulfonyl)phenylboronic acid, yield=63%, MS m/z 399 (M+H)

4'-(5-Amino-1H-[1,2,4]triazol-3-ylamino)-2',6'-dichloro-biphenyl-3-carboxylic acid dimethylamide (Compound 115)

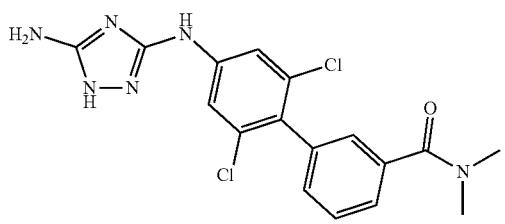 [SMILES: CN(C)C(=O)c1cccc(-c2c(Cl)cc(Nc3n[nH]c(N)n3)cc2Cl)c1]

Starting from 3-(Dimethylcarbamoyl)phenylboronic acid, yield=54%, MS m/z 392 (M+H)

4'-(5-Amino-1H-[1,2,4]triazol-3-ylamino)-2',6'-dichloro-biphenyl-4-carboxylic acid methylamide (Compound 116)

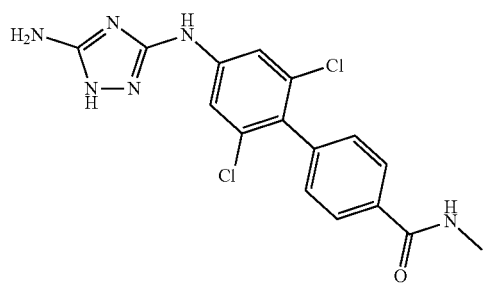 [SMILES: CNC(=O)c1ccc(-c2c(Cl)cc(Nc3n[nH]c(N)n3)cc2Cl)cc1]

Starting from 4-(N-Methylaminocarbonyl)phenylboronic acid, yield=66%, MS m/z 378 (M+H)

288

4'-(5-Amino-1H-[1,2,4]triazol-3-ylamino)-2',6'-dichloro-biphenyl-3-carboxylic acid methylamide (Compound 117)

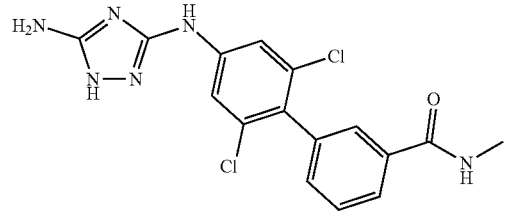 [SMILES: CNC(=O)c1cccc(-c2c(Cl)cc(Nc3n[nH]c(N)n3)cc2Cl)c1]

Starting from 3-(N-Methylaminocarbonyl)phenylboronic acid, yield=52%, MS m/z 378 (M+H)

4'-(5-Amino-1H-[1,2,4]triazol-3-ylamino)-2',6'-dichloro-biphenyl-4-sulfonic acid methylamide (Compound 118)

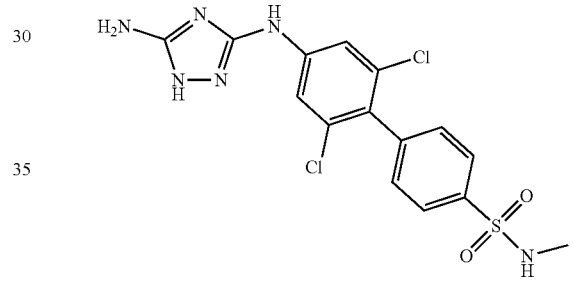

Starting from Methyl 4-boronobenzenesulfonamide, yield=57%, MS m/z 414 (M+H)

4'-(5-Amino-1H-[1,2,4]triazol-3-ylamino)-2',6'-dichloro-biphenyl-3-sulfonic acid methylamide (Compound 119)

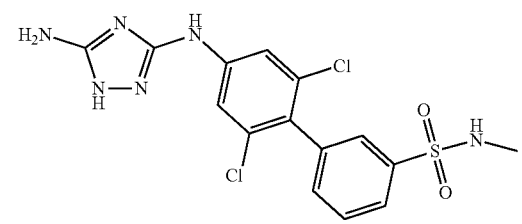 [SMILES: CNS(=O)(=O)c1cccc(-c2c(Cl)cc(Nc3n[nH]c(N)n3)cc2Cl)c1]

Starting from 3-Methylsulfamoylphenylboronic acid, yield=59%, MS m/z 414 (M+H)

289

N-3-(2,6-Dichloro-2'-methoxy-biphenyl-4-yl)-1H-[1,2,4]triazole-3,5-diamine (Compound 120)

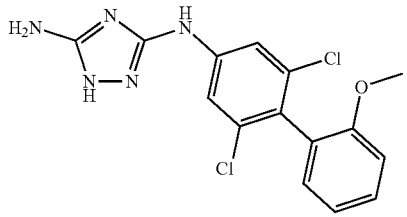 [SMILES: COc1ccccc1-c1c(Cl)cc(Nc2n[nH]c(N)n2)cc1Cl]

Starting from 2-Methoxyphenylboronic acid, yield=17%, MS m/z 351 (M+H)

N-3-(2,6-Dichloro-3'-fluoro-4'-methanesulfonyl-biphenyl-4-yl)-1H-[1,2,4]triazole-3,5-diamine (Compound 121)

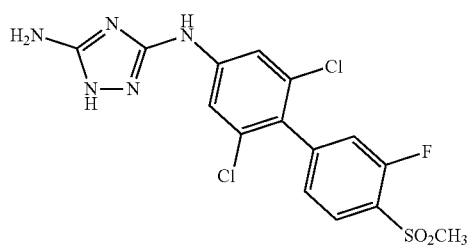 [SMILES: CS(=O)(=O)c1ccc(-c2c(Cl)cc(Nc3n[nH]c(N)n3)cc2Cl)cc1F]

Starting from 3-Fluoro-4-(methylsulfonyl)phenylboronic acid, yield=57%, MS m/z 417 (M+H)

N-3-[2,6-Dichloro-4'-(propane-2-sulfonyl)-biphenyl-4-yl]-1H-[1,2,4]triazole-3,5-diamine (Compound 122)

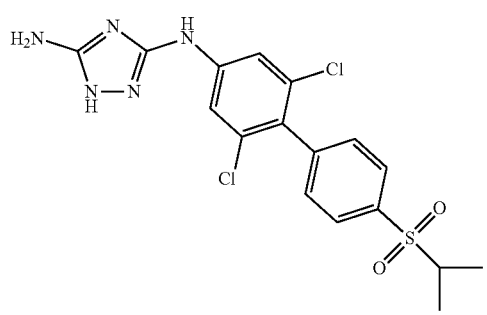 [SMILES: CC(C)S(=O)(=O)c1ccc(-c2c(Cl)cc(Nc3n[nH]c(N)n3)cc2Cl)cc1]

Starting from 4-(Isopropylsulfonylphenyl)boronic acid, yield=39%, MS m/z 427 (M+H)

290

4'-(5-Amino-1H-[1,2,4]triazol-3-ylamino)-2',6'-dichloro-biphenyl-4-sulfonic acid dimethylamide (Compound 123)

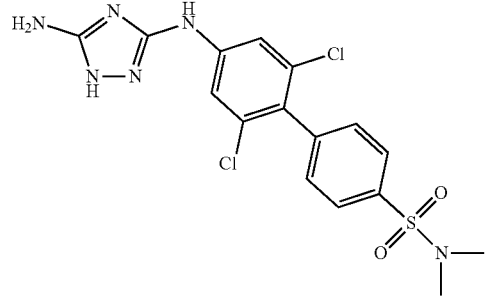 [SMILES: CN(C)S(=O)(=O)c1ccc(-c2c(Cl)cc(Nc3n[nH]c(N)n3)cc2Cl)cc1]

Starting from 4-(N,N-Dimethylsulfamoyl)phenylboronic acid, yield=47%, MS m/z 428 (M+H)

N-3-(2,6,2',4'-Tetrachloro-biphenyl-4-yl)-1H-[1,2,4]triazole-3,5-diamine (Compound 124)

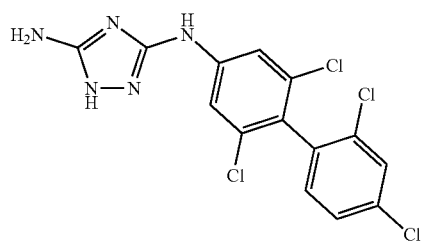 [SMILES: Nc1nc(Nc2cc(Cl)c(-c3ccc(Cl)cc3Cl)c(Cl)c2)n[nH]1]

Starting from 2,4-Dichlorophenylboronic acid, yield=4%, MS m/z 390 (M+H)

Procedure 6

{2-[4'-(5-Amino-1H-[1,2,4]triazol-3-ylamino)-6'-chloro-2'-trifluoromethyl-biphenyl-4-yloxy]-ethyl}-methyl-carbamic acid tert-butyl ester (Compound 125)

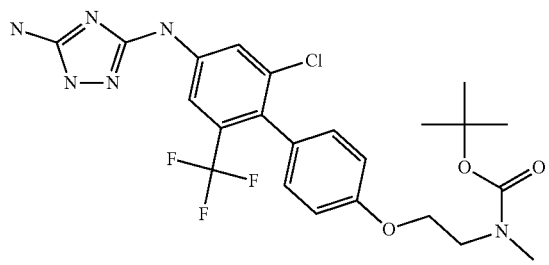 [SMILES: CN(CCOc1ccc(-c2c(Cl)cc(Nc3n[nH]c(N)n3)cc2C(F)(F)F)cc1)C(=O)OC(C)(C)C]

Methyl-{2-[4-(4,4,5,5-tetramethyl-[1,3,2]dioxaborolan-2-yl)-phenoxy]-ethyl}-carbamic acid tert-butyl ester

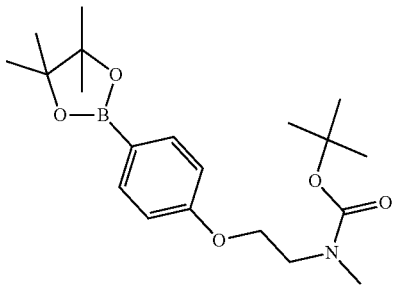

To a solution of 4-(4,4,5,5-tetramethyl-1,3,2-dioxaborolan-2-yl) phenol (1.3 g, 5.91 mmol, Eq: 1.00) in tetrahydrofuran (25 ml) were added triphenylphosphine (1.63 g, 6.2 mmol, Eq: 1.05) and tert-butyl 2-hydroxyethyl(methyl) carbamate (1.04 g, 5.91 mmol, Eq: 1.00). The reaction mixture was cooled to 0° C., a solution of (E)-diazene-1,2-diylbis (piperidin-1-ylmethanone) (1.56 g, 6.2 mmol, Eq: 1.05) in tetrahydrofuran (5 mL) was added dropwise. After the addition, the reaction mixture was slowly warmed up to room temperature and stirred at room temperature overnight. The reaction mixture was concentrated in vacuo. The residue was purified by flash chromatography (silica gel, hexane/ethyl acetate=70/30) to afford 1.0 g (45%) of the desired product as a white solid.

{2-[4'-(5-Amino-1H-[1,2,4]triazol-3-ylamino)-6'-chloro-2'-trifluoromethyl-biphenyl-4-yloxy]-ethyl}-methyl-carbamic acid tert-butyl ester (Compound 125)

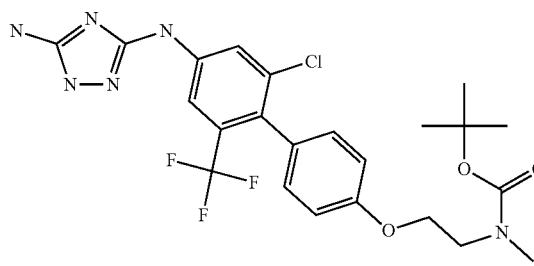

In a microwave vial, N3-(4-bromo-3-chloro-5-(trifluoromethyl)phenyl)-1H-1,2,4-triazole-3,5-diamine Intermediate 1 (0.18 g, 505 μmol, Eq: 1.00), tert-butyl methyl(2-(4-(4,4,5,5-tetramethyl-1,3,2-dioxaborolan-2-yl)phenoxy)ethyl)carbamate (0.31 g, 808 μmol, Eq: 1.6) and 3M of K₂CO₃ (337 μl, 1.01 mmol, Eq: 2 solution were combined with 1,4-dioxane (1 mL) and dimethoxyethane (1 mL) to give a solution. The reaction mixture was degassed with argon for 5 minutes. Tetrakis(triphenylphosphine)palladium (0) (89.8 mg, 77.7 μmol, Eq: 0.154) was added. The reaction mixture was heated in microwave at 128° C. for 3 h. The reaction mixture was partitioned between water/ethyl acetate=15 mL/40 mL. The organic layer was collected and the aqueous layer was extracted with ethyl acetate (3×10 mL). The combined organic layers were washed with brine, dried over MgSO₄ and concentrated in vacuo. The residue was purified by flash chromatography (silica gel, 40 g, 0% to 8% methanol in dichloromethane). The fractions which contained the desired product were concentrated and further purified with SFC to afford 96 mg (36%) of the desired product as a white solid.

MS +m/z: 527.1 (M+H)$^+$

N*3*-[6-Chloro-4'-(2-methylamino-ethoxy)-2-trifluoromethyl-biphenyl-4-yl]-1H-[1,2,4]triazole-3,5-diamine hydrochloride (Compound 126)

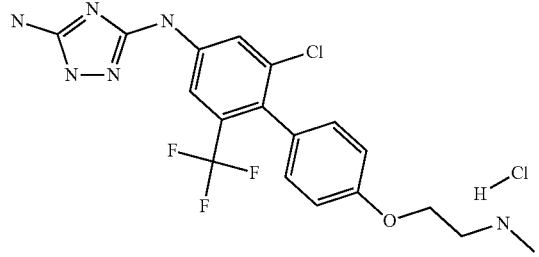

To a solution of compound 125, tert-butyl 2-(4'-(5-amino-1H-1,2,4-triazol-3-ylamino)-2'-chloro-6'-(trifluoromethyl) biphenyl-4-yloxy)ethyl(methyl)carbamate (90 mg, 171 μmol, Eq: 1.00) solution in dichloromethane (5 mL) was added a freshly made 0.5 mL of HCl solution (prepared from 1 mL of acetyl chloride added to 10 mL of methanol). The reaction mixture was stirred at room temperature for overnight. The precipitate was filtered and washed with ethanol, dried to afford 52 mg (66%) of the desired product as a white solid.

MS +m/z: 427.0 (M+H)$^+$

Procedure 6

N*3*-[6-Chloro-4'-(1,2,2,6,6-pentamethyl-piperidin-4-ylsulfanyl)-2-trifluoromethyl-biphenyl-4-yl]-1H-[1,2,4]triazole-3,5-diamine (Compound 127)

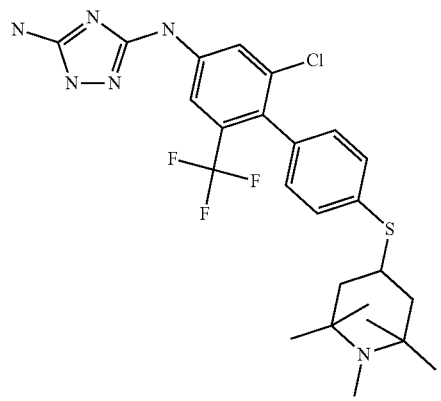

Methanesulfonic acid
1,2,2,6,6-pentamethyl-piperidin-4-yl ester

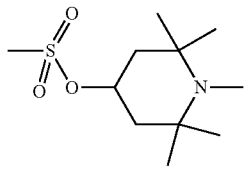

To a mixture of 1,2,2,6,6-pentamethylpiperidin-4-ol (5 g, 29.2 mmol, Eq: 1.00) and triethylamine (5.91 g, 8.14 ml, 58.4 mmol, Eq: 2) in dichloromethane (83.3 mL) at 0° C. was added methanesulfonyl chloride (4.01 g, 2.73 ml, 35.0 mmol, Eq: 1.2) dropwise. The reaction mixture was warmed up to room temperature and stirred for 1 h. The reaction mixture was diluted with dichloromethane (100 mL), washed with sat. NaHCO$_3$, water, brine, dried over MgSO$_4$ and concentrated to afford 6.8 g (93%) of the product as yellow oil which was used for the next step without further purification.

4-(4-Bromo-phenylsulfanyl)-1,2,2,6,6-pentamethyl-piperidine

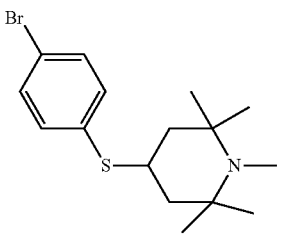 [SMILES: CN1C(C)(C)CC(Sc2ccc(Br)cc2)CC1(C)C]

To a solution of 4-bromobenzenethiol (3.2 g, 16.9 mmol, Eq: 1.00) in DMF (50 ml) were added 1,2,2,6,6-pentamethylpiperidin-4-yl methanesulfonate (6.33 g, 25.4 mmol, Eq: 1.5) and cesium carbonate (16.5 g, 50.8 mmol, Eq: 3). The reaction mixture was bubbled with argon for 5 minutes, and then heated at 70° C. for 16 h. The reaction mixture was cooled down to room temperature, then partitioned between water (150 mL) and ethyl acetate (150 mL). The organic layer was collected and the aqueous layer was extracted with ethyl acetate (3×100 mL). The combined organic layers were washed with water (3×100 mL), brine (100 mL), dried over MgSO$_4$, filtered and concentrated in vacuo. The residue was purified by flash chromatography (silica gel, 80 g, 0% to 10% methanol in dichloromethane) to afford 1.6 g (28%) of the desired product as yellow oil.

1,2,2,6,6-Pentamethyl-4-[4-(4,4,5,5-tetramethyl-[1,3,2]dioxaborolan-2-yl)-phenylsulfanyl]-piperidine

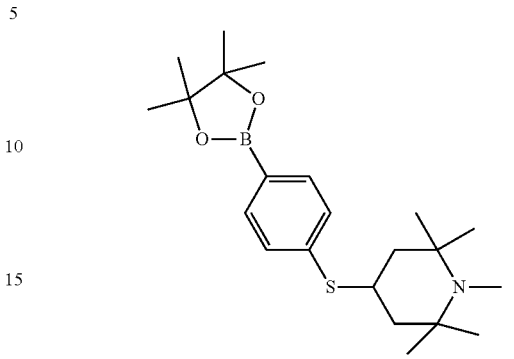

In a sealed tube, 4-(4-bromophenylthio)-1,2,2,6,6-pentamethylpiperidine (0.2 g, 584 µmol, Eq: 1.00), 4,4,4',4',5,5,5',5'-octamethyl-2,2'-bi(1,3,2-dioxaborolane) (445 mg, 1.75 mmol, Eq: 3) and potassium acetate (287 mg, 2.92 mmol, Eq: 5) were combined with 1,4-dioxane (5 ml) to give a colorless solution. The reaction mixture was bubbled with argon for 5 minutes. 1,1'-Bis(diphenylphosphino)ferrocene-palladium(II)dichloride dichloromethane complex (42.7 mg, 58.4 µmol, Eq: 0.10) was added, sealed heating at 85° C. for 20 h. The reaction mixture was cooled to room temperature, filtered through the celite bed, washed with dichloromethane and concentrated in vacuo. The residue was purified by flash chromatography (silica gel, 24 g, 0% to 15% methanol in dichloromethane) to afford 0.13 g (57%) of the desired product as brownish oil.

N*3*-[6-Chloro-4'-(1,2,2,6,6-pentamethyl-piperidin-4-ylsulfanyl)-2-trifluoromethyl-biphenyl-4-yl]-1H-[1,2,4]triazole-3,5-diamine (Compound 127)

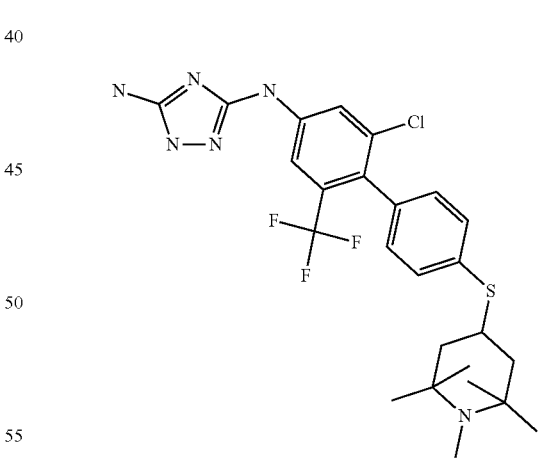

In a microwave vial, N3-(4-bromo-3-chloro-5-(trifluoromethyl)phenyl)-1H-1,2,4-triazole-3,5-diamine Intermediate 1 (75 mg, 210 µmol, Eq: 1.00), 1,2,2,6,6-pentamethyl-4-(4-(4,4,5,5-tetramethyl-1,3,2-dioxaborolan-2-yl)phenylthio)piperidine (131 mg, 337 µmol, Eq: 1.6) and 3 M of K$_2$CO$_3$ (140 µl, 421 µmol, Eq: 2) were combined with 1,4-dioxane (0.5 mL) and dimethoxyethane (0.5 mL) to give a solution. This was degassed with argon for 5 minutes. Tetrakis(triphenylphosphine)palladium(0) (37.4 mg, 32.4 µmol, Eq: 0.154) was added. The reaction mixture was heated in microwave at 128° C. for 3 h. The reaction mixture was concentrated in vacuo. The residue was purified by prep-HPLC. The fractions which contained the desired product were concentrated. The residue was partitioned between ethyl acetate and sat. NaHCO₃. The organic layer was separated, washed with water, brine, dried over MgSO₄ and concentrated. The residue was purified by flash chromatography (silica gel, 4 g, 10% methanol/1% of NH3 solution/dichloromethane) to afford the desired product 7 mg (6.2%) as a white solid.

MS +m/z: 539.1 (M+H)⁺

Procedure 6

{2-[4'-(5-Amino-1H-[1,2,4]triazol-3-ylamino)-6'-chloro-2'-trifluoromethyl-biphenyl-4-yloxy]-1,1-dimethyl-ethyl}-methyl-carbamic acid tert-butyl ester (Compound 128)

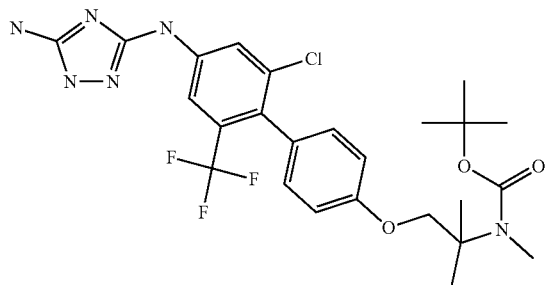 [SMILES: CN(C(=O)OC(C)(C)C)C(C)(C)COc1ccc(-c2c(Cl)cc(Nc3n[nH]c(N)n3)cc2C(F)(F)F)cc1]

Methanesulfonic acid 2-methyl-2-nitro-propyl ester

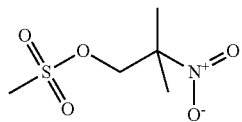

To a mixture of 2-methyl-2-nitropropan-1-ol (10 g, 83.9 mmol, Eq: 1.00) and triethylamine (10.2 g, 13.0 ml, 101 mmol, Eq: 1.2) in dichloromethane (200 ml) at 0° C. was added methanesulfonyl chloride (11.5 g, 7.85 ml, 101 mmol, Eq: 1.2) dropwise. The reaction mixture was then allowed to warm to room temperature and stirred for 1 h. The reaction mixture was diluted with dichloromethane and washed with water, sat. NaHCO₃, brine, dried over MgSO₄ and concentrated to afford 16 g (97%) of the desired product as light yellow oil which was used for the next step without further purification.

1-Bromo-4-(2-methyl-2-nitro-propoxy)-benzene

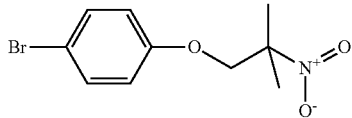

To a solution of 4-bromophenol (11 g, 63.6 mmol, Eq: 1.00) in DMF (100 ml) were added 2-methyl-2-nitropropyl methanesulfonate (16 g, 81.1 mmol, Eq: 1.28) and cesium carbonate (41.7 g, 127 mmol, Eq: 2). The reaction mixture was then stirred at 60° C. for 68 h. The reaction mixture was diluted with ethyl acetate (200 mL) and washed with 1N of NaOH solution (100 mL), water (3×100 mL), brine (1×100 mL), dried over MgSO₄ and concentrated to afford 16 g (92%) of the desired product as light yellow oil which was used for the next step without further purification.

2-(4-Bromo-phenoxy)-1,1-dimethyl-ethylamine

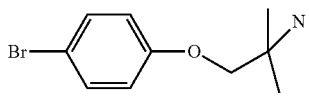

To a solution of 1-bromo-4-(2-methyl-2-nitropropoxy)benzene (9.5 g, 34.7 mmol, Eq: 1.00) in methanol (50 ml) were added ammonium chloride (14.8 g, 277 mmol, Eq: 8) solution in water (150 mL) and zinc (13.6 g, 208 mmol, Eq: 6). The reaction mixture was stirred at room temperature for 30 minutes. The reaction mixture was filtered through the celite bed and concentrated. The residue was partitioned between dichloromethane (200 mL) and water (100 mL). The organic layer was collected and washed with sat. NaHCO₃ (1×100 mL), brine (1×100 mL), dried over MgSO₄ and concentrated to afford 6 g (71%) of the desired product as yellow oil which was used for the next step without further purification.

[2-(4-Bromo-phenoxy)-1,1-dimethyl-ethyl]-carbamic acid tert-butyl ester

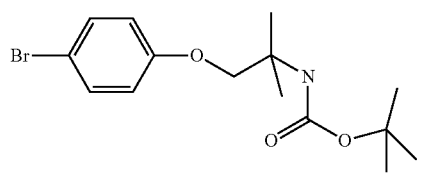 [SMILES: CC(C)(COc1ccc(Br)cc1)NC(=O)OC(C)(C)C]

To a solution of 1-(4-bromophenoxy)-2-methylpropan-2-amine (6 g, 24.6 mmol, Eq: 1.00) in dichloromethane (100 mL) was added di-tert-butyl dicarbonate (9.66 g, 44.2 mmol, Eq: 1.8). The reaction mixture was stirred at room temperature for 30 minutes. The reaction mixture was concentrated in vacuo. The residue was purified by flash chromatography (silica gel, 80 g, 5% to 50% ethyl acetate in hexanes) to afford 3.6 g (43%) of the desired product as colorless oil.

[2-(4-Bromo-phenoxy)-1,1-dimethyl-ethyl]-methyl-carbamic acid tert-butyl ester

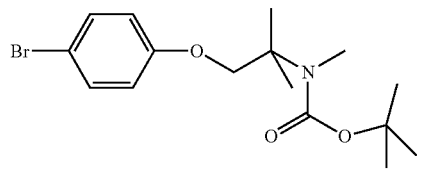 [SMILES: CN(C(=O)OC(C)(C)C)C(C)(C)COc1ccc(Br)cc1]

To a solution of tert-butyl 1-(4-bromophenoxy)-2-methylpropan-2-ylcarbamate (3.5 g, 10.2 mmol, Eq: 1.00) in DMF (20 ml) at 0° C. was added sodium hydride (529 mg, 13.2 mmol, Eq: 1.3). The reaction mixture was allowed to warm to room temperature and stirred for 30 minutes. Iodomethane (1.73 g, 761 µl, 12.2 mmol, Eq: 1.2) was added and the reaction mixture was stirred at room temperature for 1 h. The reaction mixture was then heated to 60° C. and stirred for 1 hr. The reaction mixture was partitioned between ethyl acetate (100 mL) and water (50 mL). The organic layer was collected and washed with water, brine and dried over MgSO$_4$ and concentrated in vacuo. The residue was purified by flash chromatography (silica gel, 40 g, 0% to 35% ethyl acetate in hexanes) to afford 1.4 g (38%) of the desired product as colorless oil.

{1,1-Dimethyl-2-[4-(4,4,5,5-tetramethyl-[1,3,2]dioxaborolan-2-yl)-phenoxy]-ethyl}-methyl-amine

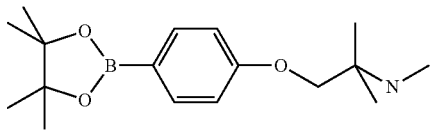

In a sealed tube, tert-butyl 1-(4-bromophenoxy)-2-methylpropan-2-yl(methyl)carbamate (0.5 g, 1.4 mmol, Eq: 1.00), 4,4,4',4',5,5,5'-heptamethyl-2,2'-bi(1,3,2-dioxaborolane) (1.00 g, 4.19 mmol, Eq: 3) and potassium acetate (685 mg, 6.98 mmol, Eq: 5) were combined with 1,4-dioxane (6 ml) to give a colorless solution. The reaction mixture was bubbled with argon for 5 minutes. 1,1'-Bis(diphenylphosphino)ferrocene-palladium(II)dichloride dichloromethane complex (102 mg, 140 µmol, Eq: 0.10) was added, sealed heating at 80° C. for 16 hr. The reaction mixture was cooled to room temperature, filtered through the celite bed and concentrated in vacuo. The residue was purified by flash chromatography (silica gel, 24 g, 12% methanol/dichloromethane) to afford 0.18 g (42%) of the desired product as a brownish solid.

{1,1-Dimethyl-2-[4-(4,4,5,5-tetramethyl-[1,3,2]dioxaborolan-2-yl)-phenoxy]-ethyl}-methyl-carbamic acid tert-butyl ester

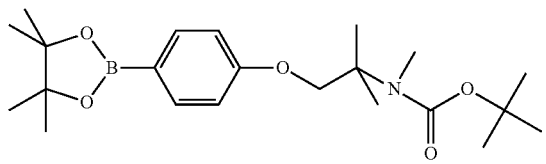 [SMILES: CN(C(=O)OC(C)(C)C)C(C)(C)COc1ccc(B2OC(C)(C)C(C)(C)O2)cc1]

To a solution of N,2-dimethyl-1-(4-(4,4,5,5-tetramethyl-1,3,2-dioxaborolan-2-yl)phenoxy)propan-2-amine (0.18 g, 590 µmol, Eq: 1.00) in dichloromethane (5 mL) was added di-tert-butyl dicarbonate (515 mg, 2.36 mmol, Eq: 4). The reaction mixture was stirred at room temperature for 1 h, then concentrated in vacuo. The residue was purified by flash chromatography (silica gel, 40 g, 5% to 30% ethyl acetate/hexane) to give 0.17 g (71%) of the product as colorless oil.

{2-[4'-(5-Amino-1H-[1,2,4]triazol-3-ylamino)-6'-chloro-2'-trifluoromethyl-biphenyl-4-yloxy]-1,1-dimethyl-ethyl}-methyl-carbamic acid tert-butyl ester (Compound 128)

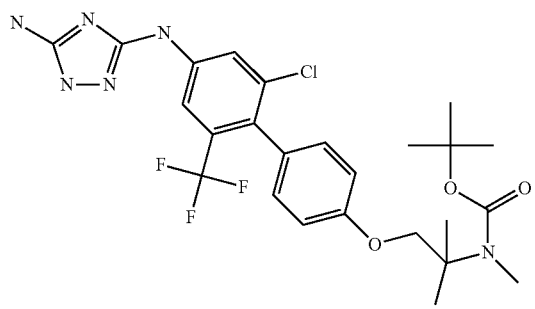 [SMILES: CN(C(=O)OC(C)(C)C)C(C)(C)COc1ccc(-c2c(Cl)cc(Nc3n[nH]c(N)n3)cc2C(F)(F)F)cc1]

In a microwave vial, N3-(4-bromo-3-chloro-5-(trifluoromethyl)phenyl)-1H-1,2,4-triazole-3,5-diamine Intermediate 1 (90 mg, 252 µmol, Eq: 1.00), tert-butyl methyl(2-methyl-1-(4-(4,4,5,5-tetramethyl-1,3,2-dioxaborolan-2-yl)phenoxy)propan-2-yl)carbamate (164 mg, 404 µmol, Eq: 1.6) and 3 M of K$_2$CO$_3$ (168 µL, 505 µmol, Eq: 2) solution were combined with 1,4-dioxane (0.5 mL) and dimethoxyethane (0.5 mL) to give a solution. This was degassed with argon for 5 minutes and tetrakis(triphenylphosphine)palladium(0) (44.9 mg, 38.9 µmol, Eq: 0.154) was added. The reaction mixture was heated in microwave at 128° C. for 3 h. The reaction mixture was partitioned with water/ethyl acetate=15 mL/40 mL. The organic layer was collected and the aqueous layer was extracted with ethyl acetate (3×10 mL). The combined organic layers were washed with brine, dried over MgSO$_4$ and concentrated in vacuo. The residue was purified by SFC and then prep-HPLC to afford 8 mg (5.7%) of the desired product as an off-white solid.

MS +m/z: 555.2 (M+H)$^+$

Procedure 7

3-[4'-(5-Amino-1H-[1,2,4]triazol-3-ylamino)-6'-chloro-2'-trifluoromethyl-biphenyl-4-yloxy]-piperidine-1-carboxylic acid tert-butyl ester (Compound 129)

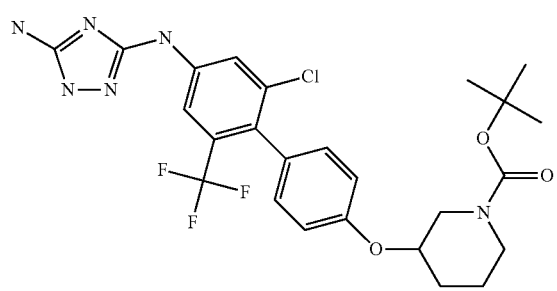 [SMILES: CC(C)(C)OC(=O)N1CCCC(Oc2ccc(-c3c(Cl)cc(Nc4n[nH]c(N)n4)cc3C(F)(F)F)cc2)C1]

3-[4-(4,4,5,5-Tetramethyl-[1,3,2]dioxaborolan-2-yl)-phenoxyl]-piperidine-1-carboxylic acid tert-butyl ester

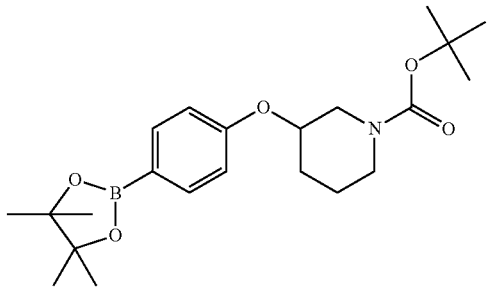

To a solution of 4-(4,4,5,5-tetramethyl-1,3,2-dioxaborolan-2-yl)phenol (4 g, 18.2 mmol, Eq: 1.00) in tetrahydrofuran (60 ml) were added triphenylphosphine (5.01 g, 19.1 mmol, Eq: 1.05) and tert-butyl 3-hydroxypiperidine-1-carboxylate (4.39 g, 21.8 mmol, Eq: 1.2). The reaction mixture was cooled to 0° C., a solution of (E)-diazene-1,2-diylbis(piperidin-1-ylmethanone) (4.82 g, 19.1 mmol, Eq: 1.05) in tetrahydrofuran (20 mL) was added dropwise. After the addition, the reaction mixture was slowly warmed up to room temperature and stirred for 72 h. The reaction mixture was filtered through the celite bed and the filtrate was concentrated in vacuo. The residue was diluted with dichloromethane (100 mL), washed with 1N of NaOH solution, saturated $NaHCO_3$, brine, dried over $MgSO_4$ and concentrated in vacuo. The residue was purified by flash chromatography (silica gel, hexane/ethyl acetate=70/30) to afford 1.4 g (19%) of desired product as a white solid.

3-(4'-Amino-6'-chloro-2'-trifluoromethyl-biphenyl-4-yloxy)-piperidine-1-carboxylic acid tert-butyl ester

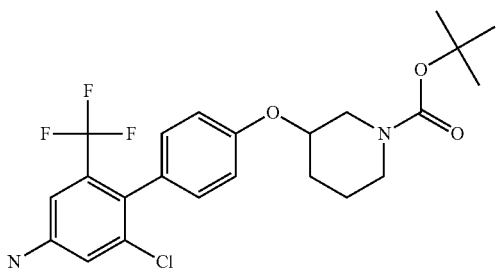 [SMILES: CC(C)(C)OC(=O)N1CCCC(Oc2ccc(-c3c(Cl)cc(N)cc3C(F)(F)F)cc2)C1]

In a sealed tube, 4-bromo-3-chloro-5-(trifluoromethyl)aniline (823 mg, 3.00 mmol, Eq: 1.1), tert-butyl 3-(4-(4,4,5,5-tetramethyl-1,3,2-dioxaborolan-2-yl)phenoxy)piperidine-1-carboxylate (1.1 g, 2.73 mmol, Eq: 1.00) and 2 M of $Na_2CO_3$ (3.14 ml, 6.27 mmol, Eq: 2.3) were combined with dioxane (15.00 mL) to give a suspension and degassed with argon for 5 minutes. Tetrakis(triphenylphosphine)palladium (0) (485 mg, 420 µmol, Eq: 0.154) was added. It was sealed heating at 100° C. for 20 h. The reaction mixture was partitioned between water and ethyl acetate. The organic layer was collected and the aqueous layer was extracted with ethyl acetate (3×50 mL). The combined organic layers were washed with water, brine, dried over $MgSO_4$ and concentrated in vacuo. The residue was purified by flash chromatography (silica gel, 80 g, 0% to 40% of ethyl acetate/hexane) to afford 0.7 g (54%) of the desired product as light-yellow oil.

3-(6'-Chloro-4'-isothipcyanato-2'-trifluoromethyl-biphenyl-4-yloxy)-piperidine-1-carboxylic acid tert-butyl ester

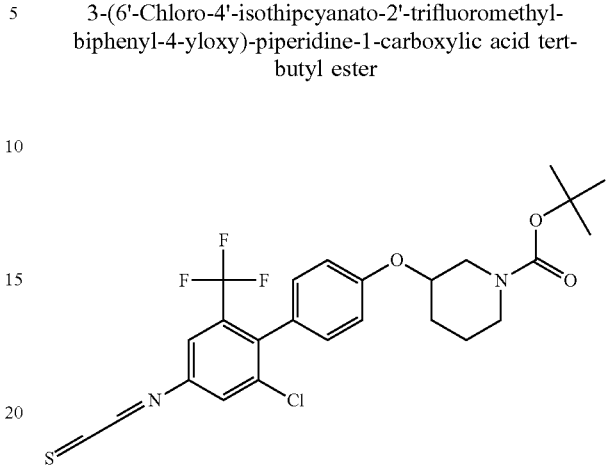

To a solution of tert-butyl 3-(4'-amino-2'-chloro-6'-(trifluoromethyl)biphenyl-4-yloxy)piperidine-1-carboxylate (0.7 g, 1.49 mmol, Eq: 1.00) in dichloromethane (6 mL) at 0° C. was added di(1H-imidazol-1-yl)methanethione (795 mg, 4.46 mmol, Eq: 3). The reaction mixture was stirred at 0° C. for 30 minutes, then allowed to warm to room temperature and stirred for 5 h. The reaction mixture was concentrated in vacuo. The residue was purified by flash chromatography (silica gel, 80 g, 0% to 45% ethyl acetate in hexanes) to afford 0.58 g (76%) of the desired product as white form.

(Z)-tert-butyl 3-(2'-chloro-4'-((cyanoimino)(methylthio)methylamino)-6'-(trifluoromethyl)biphenyl-4-yloxy)piperidine-1-carboxylate

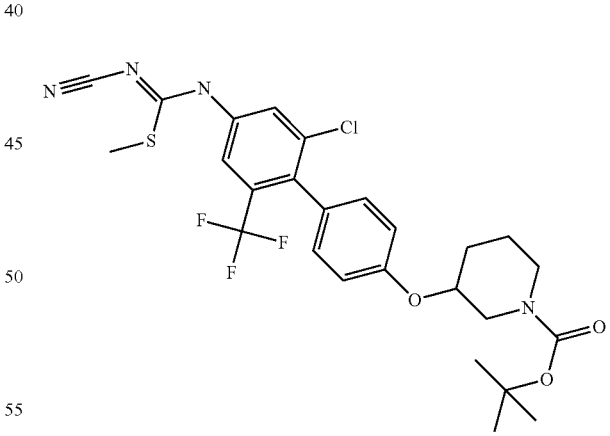

To a solution of tert-butyl 3-(2'-chloro-4'-isothiocyanato-6'-(trifluoromethyl)biphenyl-4-yloxy) piperidine-1-carboxylate (0.58 g, 1.13 mmol, Eq: 1.00) in dimethoxyethane (15 ml) were added sodium hydrogen cyanamide (86.9 mg, 1.36 mmol, Eq: 1.2) and methanol (3 mL). The reaction mixture was stirred at room temperature for 30 minutes, then iodomethane (411 mg, 181 µl, 2.89 mmol, Eq: 2.56) was added and the reaction mixture was stirred at room temperature for 4 h. The reaction mixture was concentrated in vacuo. The residue was purified by flash chromatography (silica gel, 40 g, 20% to 80% ethyl acetate in hexanes) to afford 0.54 g (84%) of the desired product as a white solid.

3-[4'-(5-Amino-1H-[1,2,4]triazol-3-ylamino)-6'-chloro-2'-trifluoromethyl-biphenyl-4-yloxy]-piperidine-1-carboxylic acid tert-butyl ester (Compound 129)

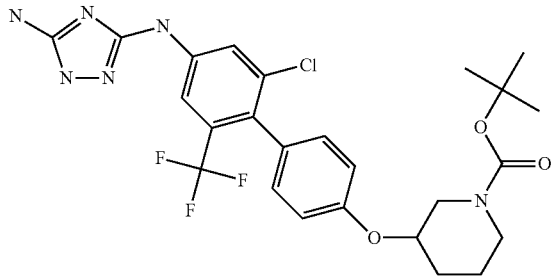 [SMILES: CC(C)(C)OC(=O)N1CCCC(Oc2ccc(-c3c(Cl)cc(Nc4n[nH]c(N)n4)cc3C(F)(F)F)cc2)C1]

A mixture of (Z)-tert-butyl 3-(2'-chloro-4'-((cyanoimino)(methylthio)methylamino)-6'-(trifluoromethyl)biphenyl-4-yloxy)piperidine-1-carboxylate (0.54 g, 949 µmol, Eq: 1.00) and hydrazine (304 mg, 298 µl, 9.49 mmol, Eq: 10) in dry ethanol (10 ml) was stirred overnight at 65° C. The reaction mixture was concentrated in vacuo. The residue was purified by flash chromatography (silica gel, 24 g, 1% to 10% methanol in dichloromethane) to afford 0.49 g (94%) of the desired product as a white solid.

MS +m/z: 553.1 (M+H)$^+$

N*3*-[6-Chloro-4'-(piperidin-3-yloxy)-2-trifluoromethyl-biphenyl-4-yl]-1H-[1,2,4]triazole-3,5-diamine hydrochloride (Compound 130)

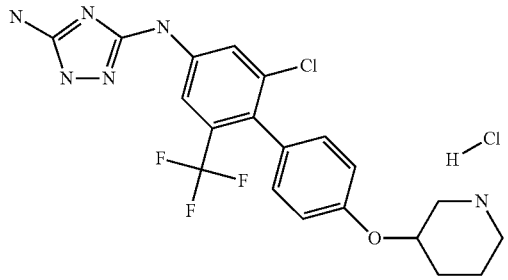

To a solution of compound 129 tert-butyl 3-(4'-(5-amino-1H-1,2,4-triazol-3-ylamino)-2'-chloro-6'-(trifluoromethyl)biphenyl-4-yloxy)piperidine-1-carboxylate (0.49 g, 886 µmol, Eq: 1.00) solution in methanol (5 mL) was added a freshly made HCl solution (prepared from 1.5 mL acetyl chloride added to 15 mL of methanol). The reaction mixture was stirred at room temperature for 5 h, and then concentrated in vacuo. The residue was triturated with methanol/ether. The solid was collected and washed with ether, dried to afford 0.38 g (88%) of the desired product as a white solid.

MS +m/z: 453.0 (M+H)$^+$

N*3*-{6-Chloro-4'-[1-(3,3-dimethyl-butyl)-piperidin-3-yloxy]-2-trifluoromethyl-biphenyl-4-yl}-1H-[1,2,4]triazole-3,5-diamine hydrochloride (Compound 131)

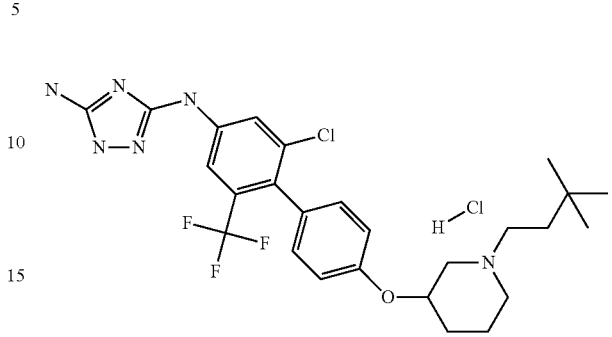

To a solution of compound 130, N3-(2-chloro-4'-(piperidin-3-yloxy)-6-(trifluoromethyl)biphenyl-4-yl)-1H-1,2,4-triazole-3,5-diamine hydrochloride (56 mg, 114 µmol, Eq: 1.00) in methanol (4 mL) were added 3,3-dimethylbutanal (34.4 mg, 343 µmol, Eq: 3) and sodium cyanoborohydride (36.0 mg, 572 µmol, Eq: 5). The reaction mixture was stirred at room temperature for 3 h. Ethyl acetate (50 mL) was added, then sat. NaHCO$_3$ was added to adjust pH>7. The organic layer was collected and the aqueous layer was extracted with ethyl acetate (2×25 mL). The combined organic layers were washed with water, brine, dried over MgSO$_4$, filtered and concentrated. The residue was purified by flash chromatography (silica gel, 12 g, 2% to 10% methanol in dichloromethane) to give free amine as a white solid. To the solution of free amine in dichloromethane (2 mL) was added a freshly made HCl solution (prepared from 0.3 mL of acetyl chloride added to 3 mL of methanol). The reaction mixture was stirred at room temperature for 2 h, and then concentrated in vacuo. The residue was triturated with methanol/methyl tert-butyl ether. The resulting solid was collected and washed with methyl tert-butyl ether, dried to afford 28 mg (43%) of the desired product as a white solid.

MS +m/z: 537.1 (M+H)$^+$

N*3*-[6-Chloro-4'-(1-methyl-piperidin-3-yloxy)-2-trifluoromethyl-biphenyl-4-yl]-1H-[1,2,4]triazole-3,5-diamine hydrochloride (Compound 132)

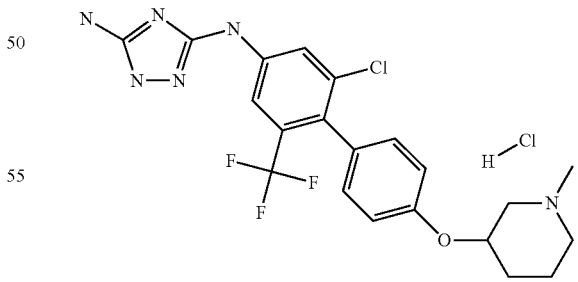

To a solution of compound 130, N3-(2-chloro-4'-(piperidin-3-yloxy)-6-(trifluoromethyl)biphenyl-4-yl)-1H-1,2,4-triazole-3,5-diamine hydrochloride (70 mg, 143 µmol, Eq: 1.00) in methanol (5 mL) were added formaldehyde (37% aqueous solution) (34.8 mg, 32.0 µl, 429 µmol, Eq: 3) and sodium cyanoborohydride (44.9 mg, 715 µmol, Eq: 5). The reaction mixture was stirred at room temperature for 30 minutes. Ethyl acetate (50 mL) was added, and then sat. NaHCO₃ was added to adjust the pH>7. The organic layer was collected and the aqueous layer was extracted with ethyl acetate (2×25 mL). The combined organic layers were washed with water, brine, dried over MgSO₄ and concentrated in vacuo. The residue was purified by flash chromatography (silica gel, 12 g, 2% to 12% 7N NH₃ in methanol/dichloromethane) to give free amine as a white solid. To the solution of free amine in dichloromethane (1 mL) was added a freshly made 0.5 mL of HCl solution (prepared from 0.3 mL of acetyl chloride added to 3 mL of methanol). The reaction mixture was stirred at room temperature for 2 h. The precipitate formed was collected and washed with methyl tert-butyl ether, dried to afford 11 mg (15%) the desired product as a white solid.

MS +m/z: 467.0 (M+H)⁺

Example 10

N*3*-{6-Chloro-2-trifluoromethyl-4'-[1-(3,3,3-trifluoro-propyl)-piperidin-3-yloxy]-biphenyl-4-yl}-1H-[1,2,4]triazole-3,5-diamine hydrochloride (Compound 133)

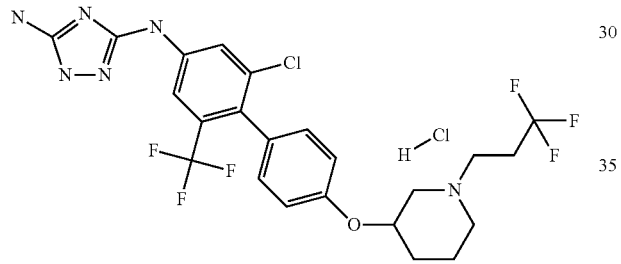

To a solution of compound 130, N3-(2-chloro-4'-(piperidin-3-yloxy)-6-(trifluoromethyl)biphenyl-4-yl)-1H-1,2,4-triazole-3,5-diamine hydrochloride (80 mg, 163 μmol, Eq: 1.00) in methanol (5 ml) were added 3,3,3-trifluoropropionaldehydel (45.8 mg, 409 μmol, Eq: 2.5) and sodium cyanoborohydride (51.4 mg, 817 μmol, Eq: 5). The reaction mixture was stirred at room temperature for 3 h. Ethyl acetate (50 mL) was added, and then sat. NaHCO₃ was added to adjust the pH>7. The organic layer was collected and the aqueous layer was extracted with ethyl acetate (2×25 mL). The combined organic layers were washed with water, brine, dried over MgSO₄ and concentrated in vacuo. The residue was purified by flash chromatography (silica gel, 12 g, 2% to 10% methanol in chloromethane) to give free amine as a white solid. To the solution of free amine in dichloromethane (2 mL) was added a freshly made 1 mL of HCl solution (prepared from 0.3 mL of acetyl chloride added to 3 mL of methanol). The reaction mixture was stirred at room temperature for 2 h, and then concentrated in vacuo. The residue was triturated with methanol/methyl tert-butyl ether. The resulting solid was collected and washed with methyl tert-butyl ether, dried to afford 52 mg (54%) of the desired product as a white solid.

MS +m/z: 549.0 (M+H)⁺

Procedure 6

{2-[4'-(5-Amino-1H-[1,2,4]triazol-3-ylamino)-6'-chloro-2'-trifluoromethyl-biphenyl-4-yloxy]-ethyl}-carbamic acid tert-butyl ester (Compound 134)

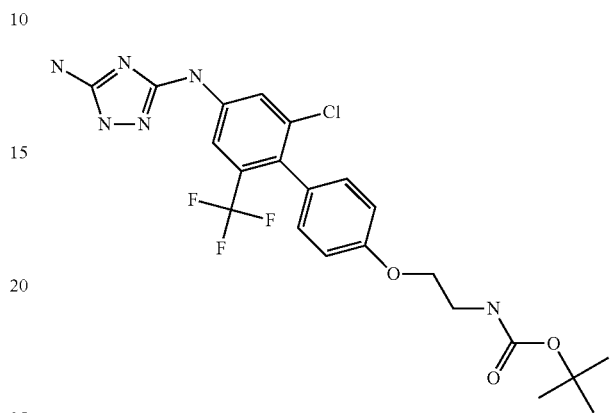

{2-[4-(4,4,5,5-Tetramethyl-[1,3,2]dioxaborolan-2-yl)-phenoxy]-ethyl}-carbamic acid tert-butyl ester

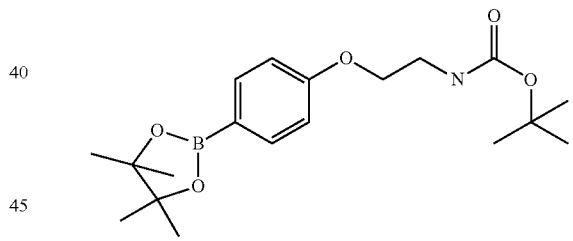

To a solution of 4-(4,4,5,5-tetramethyl-1,3,2-dioxaborolan-2-yl)phenol (1.5 g, 6.82 mmol, Eq: 1.00) in tetrahydrofuran (20 ml) to were added triphenylphosphine (1.88 g, 7.16 mmol, Eq: 1.05) and tert-butyl 2-hydroxyethylcarbamate (1.1 g, 6.82 mmol, Eq: 1.00). The reaction mixture was cooled to 0° C. The solution of (E)-diazene-1,2-diylbis(piperidin-1-ylmethanone) (1.81 g, 7.16 mmol, Eq: 1.05) in tetrahydrofuran (6 mL) was added dropwise. After the addition, the reaction mixture was slowly warmed up to room temperature and stirred for 60 h. The reaction mixture was filtered through the celite bed. The filtrate was diluted with ethyl acetate (50 mL) and washed with 1N of NaOH solution (20 mL), water (20 mL), brine (20 mL), dried over MgSO₄ and concentrated in vacuo. The residue was purified by flash chromatography (silica gel, 40 g, hexane/ethyl acetate=60/40) to afford 1.0 g (40%) of the desired product as a white solid.

{2-[4'-(5-Amino-1H-[1,2,4]triazol-3-ylamino)-6'-chloro-2'-trifluoromethyl-biphenyl-4-yloxy]-ethyl}-carbamic acid tert-butyl ester (Compound 134)

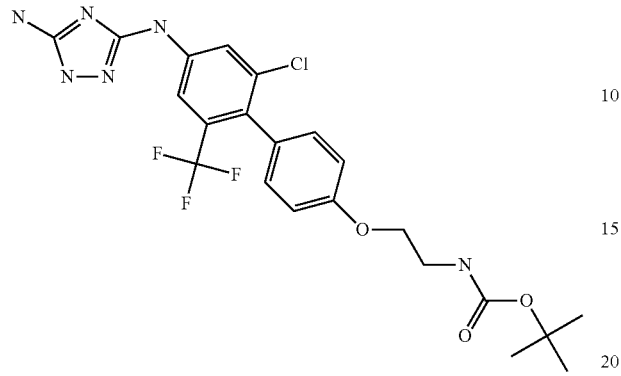

In a microwave vial, N3-(4-bromo-3-chloro-5-(trifluoromethyl)phenyl)-1H-1,2,4-triazole-3,5-diamine Intermediate 1 (0.36 g, 1.01 mmol, Eq: 1.00), tert-butyl 2-(4-(4,4,5,5-tetramethyl-1,3,2-dioxaborolan-2-yl)phenoxy)ethylcarbamate (587 mg, 1.62 mmol, Eq: 1.6) and 3 M of $K_2CO_3$ (673 µl, 2.02 mmol, Eq: 2) were combined with 1,4-dioxane (2.00 mL) and dimethoxyethane (2 mL) to give a solution. This was degassed with argon for 5 minutes and tetrakis(triphenylphosphine)palladium(0) (180 mg, 155 µmol, Eq: 0.154) was added. The reaction mixture was heated in microwave at 128° C. for 3 h. The reaction mixture was partitioned with water/ethyl acetate=15 mL/40 mL. The organic layer was collected and the aqueous layer was extracted with ethyl acetate (3×10 mL). The combined organic layers were washed with brine, dried over $MgSO_4$ and concentrated in vacuo. The residue was purified by flash chromatography (silica gel, 40 g, 0% to 8% methanol in dichloromethane). The fractions which contained the desired product were concentrated and further purified with SFC to afford 0.15 mg (29%) of the desired product as a yellow solid.

MS +m/z: 513.1 $(M+H)^+$

N*3*-[4'-(2-Amino-ethoxy)-6-chloro-2-trifluoromethyl-biphenyl-4-yl]-1H-[1,2,4]-triazole-3,5-diamine hydrochloride (Compound 135)

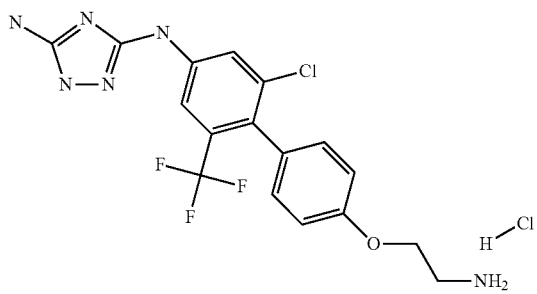

To a solution of compound 134, tert-butyl 2-(4'-(5-amino-1H-1,2,4-triazol-3-ylamino)-2'-chloro-6'-(trifluoromethyl)biphenyl-4-yloxy)ethylcarbamate (0.14 g, 273 µmol, Eq: 1.00) in methanol (2 mL) was added a freshly made HCl solution (prepared from 0.5 mL acetyl chloride added to 5 mL methanol) at room temperature. The reaction mixture was stirred at room temperature for 20 h, and then concentrated in vacuo. The residue was triturated in methanol/methyl tert-butyl ether to afford 0.115 g (94%) of the desired product as a white solid.

MS +m/z: 413.0 $(M+H)^+$

N*3*-{6-Chloro-4'-[2-(3,3-dimethyl-butylamino)-ethoxy]-2-trifluoromethyl-biphenyl-4-yl}-1H-[1,2,4]triazole-3,5-diamine hydrochloride (Compound 136)

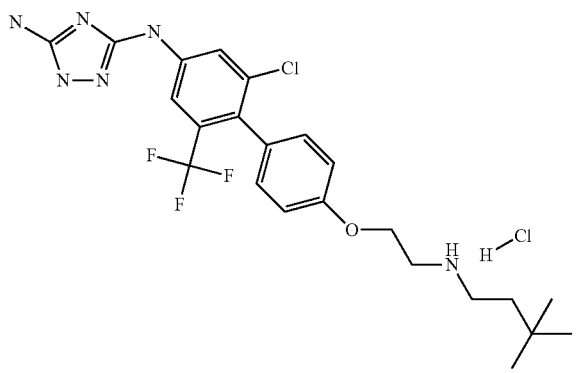

To a solution of compound 135, N3-(4'-(2-aminoethoxy)-2-chloro-6-(trifluoromethyl)biphenyl-4-yl)-1H-1,2,4-triazole-3,5-diamine hydrochloride (45 mg, 100 µmol, Eq: 1.00) in methanol (3 mL) were added 3,3-dimethylbutanal (20.1 mg, 200 µmol, Eq: 2) and sodium cyanoborohydride (18.9 mg, 300 µmol, Eq: 3). The reaction mixture was stirred at room temperature for 3 h. Ethyl acetate (50 mL) was added, and then sat. $NaHCO_3$ to adjust pH>7. The organic layer was collected and the aqueous layer was extracted with ethyl acetate (2×25 mL). The combined organic layers were washed with water, brine, dried over $MgSO_4$ and concentrated in vacuo. The residue was purified by flash chromatography (silica gel, 12 g, 2% to 10% 7 N of methanol/dichloromethane) to give free amine as a white solid. To the solution of free amine in dichloromethane (0.5 mL) was added a freshly made HCl solution (prepared from 0.1 mL of acetyl chloride added to 1 mL of methanol). The reaction mixture was stirred at room temperature for 2 h and then concentrated in vacuo. The residue was triturated with methanol/methyl tert-butyl ether. The resulting solid was collected, washed with methyl tert-butyl ether and dried to afford 12 mg of the desired product as a white solid.

MS +m/z: 497.1 $(M+H)^+$

307

N\*3\*-(4'-{2-[Bis-(3,3-dimethyl-butyl-amino)-ethoxy}-6-chloro-2-trifluoromethyl-biphenyl-4-yl]-1H-[1,2,4]triazole-3,5-diamine (Compound 137)

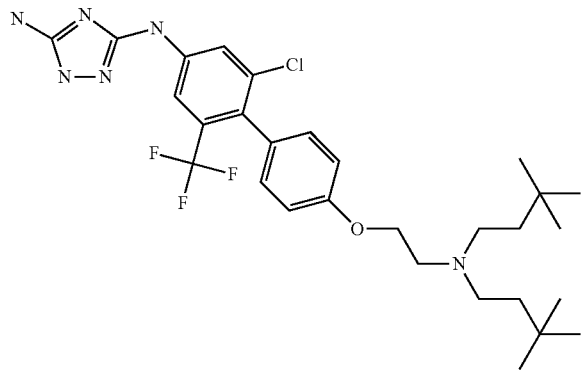 [SMILES: CC(C)(C)CCN(CCOc1ccc(-c2c(Cl)cc(Nc3n[nH]c(N)n3)cc2C(F)(F)F)cc1)CCC(C)(C)C]

To a solution of compound 135, N3-(4'-(2-aminoethoxy)-2-chloro-6-(trifluoromethyl)biphenyl-4-yl)-1H-1,2,4-triazole-3,5-diamine hydrochloride (45 mg, 100 µmol, Eq: 1.00) in methanol (3 mL) were added 3,3-dimethylbutanal (20.1 mg, 200 µmol, Eq: 2) and sodium cyanoborohydride (18.9 mg, 300 µmol, Eq: 3). The reaction mixture was stirred at room temperature for 3 h. Ethyl acetate (50 mL) was added, and then sat. NaHCO₃ to adjust pH>7. The organic layer was collected and the aqueous layer was extracted with ethyl acetate (2×25 mL). The combined organic layers were washed with water, brine, dried over MgSO₄ and concentrated in vacuo. The residue was purified by flash chromatography (silica gel, 12 g, 2% to 10% 7 N of methanol/dichloromethane) to afford 15 mg (26%) of the desired product as a white solid.

MS +m/z: 581.2 (M+H)⁺

Procedure 7

4-[4'-(5-Amino-1H-[1,2,4]triazol-3-ylamino)-6'-chloro-2'-trifluoromethyl-biphenyl-4-yloxy]-piperidine-1-carboxylic acid tert-butyl ester (Compound 138)

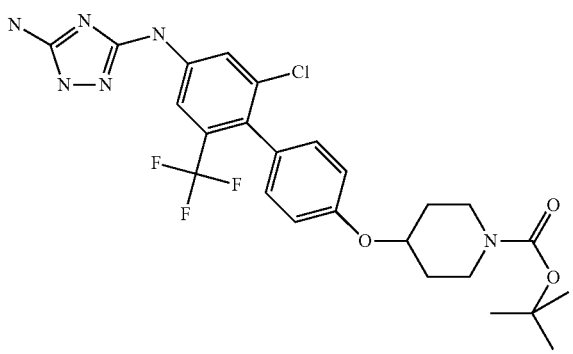 [SMILES: CC(C)(C)OC(=O)N1CCC(Oc2ccc(-c3c(Cl)cc(Nc4n[nH]c(N)n4)cc3C(F)(F)F)cc2)CC1]

308

4-[4-(4,4,5,5-Tetramethyl-[1,3,2]dioxaborolan-2-yl)-phenoxyl]-piperidine-1-carboxylic acid tert-butyl ester

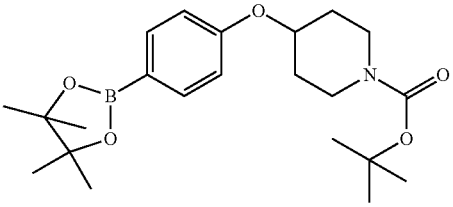

To a solution of 4-(4,4,5,5-tetramethyl-1,3,2-dioxaborolan-2-yl)phenol (3 g, 13.6 mmol, Eq: 1.00) in tetrahydrofuran (45.0 ml) were added triphenylphosphine (3.75 g, 14.3 mmol, Eq: 1.05) and tert-butyl 4-hydroxypiperidine-1-carboxylate (4.12 g, 20.4 mmol, Eq: 1.5). The reaction mixture was cooled to 0° C., a solution of (E)-diazene-1,2-diylbis(piperidin-1-ylmethanone) (3.61 g, 14.3 mmol, Eq: 1.05) in tetrahydrofuran (20 mL) was added dropwise. After the addition, the reaction mixture was slowly warmed up to room temperature and stirred at room temperature for 20 h. The reaction mixture was filtered through the celite bed and the filtrate was concentrated in vacuo. The residue was then diluted with dichloromethane (100 mL), washed with 1N of NaOH solution, sat. NaHCO₃ solution, brine, dried over MgSO₄ and concentrated in vacuo. The residue was purified by flash chromatography (silica gel, hexane/ethyl acetate=70/30) to afford 3.0 g (55%) of the desired product as a white solid.

4-(4'-Amino-6'-chloro-2'-trifluoromethyl-biphenyl-4-yloxy)-piperidine-1-carboxylic acid tert-butyl ester

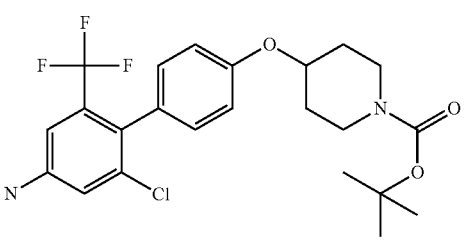 [SMILES: CC(C)(C)OC(=O)N1CCC(Oc2ccc(-c3c(Cl)cc(N)cc3C(F)(F)F)cc2)CC1]

In a sealed tube, 4-bromo-3-chloro-5-(trifluoromethyl)aniline (1 g, 3.64 mmol, Eq: 1.00), tert-butyl 4-(4-(4,4,5,5-tetramethyl-1,3,2-dioxaborolan-2-yl)phenoxy)piperidine-1-carboxylate (1.91 g, 4.74 mmol, Eq: 1.3) and 2 M of Na₂CO₃ (3.64 ml, 7.29 mmol, Eq: 2) were combined with 1,4-dioxane (15.00 mL) to give a suspension. This was degassed with argon for 5 minutes and then tetrakis(triphenylphosphine)palladium(0) (505 mg, 437 µmol, Eq: 0.12) was added. The reaction mixture was stirred at 100° C. for 20 h, then cooled to room temperature. The reaction mixture was diluted with water/ethyl acetate=50 mL/200 mL. The organic layer was collected and the aqueous layer was extracted with ethyl acetate (3×50 mL). The combined organic layers were washed with water, brine, dried over MgSO₄ and concentrated in vacuo. The residue was purified by flash chromatography (silica gel, 80 g, 0% to 40% ethyl acetate/hexane) to afford 0.7 g (41%) of the desired product as light-yellow oil.

4-(6-Chloro-4'-isothipcyanato-2'-trifluoromethyl-biphenyl-4-yloxy)-piperidine-1-carboxylic acid tert-butyl ester

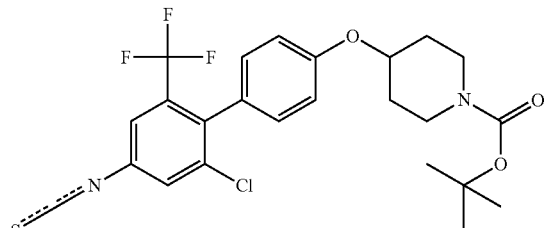

To a solution of tert-butyl 4-(4'-amino-2'-chloro-6'-(trifluoromethyl)biphenyl-4-yloxy)piperidine-1-carboxylate (0.7 g, 1.49 mmol, Eq: 1.00) in dichloromethane (6 mL) at 0° C. was added di(1H-imidazol-1-yl)methanethione (795 mg, 4.46 mmol, Eq: 3). The reaction was stirred at 0° C. for 30 minutes, then allowed to warm to room temperature and stirred at room temperature for 5 h. The reaction mixture was concentrated in vacuo. The residue was purified by flash chromatography (silica gel, 80 g, 0% to 45% ethyl acetate in hexanes) to afford 0.35 g (46%) of the desired product as white form.

(Z)-tert-butyl 4-(2'-chloro-4'-((cyanoimino)(methylthio)methylamino)-6'-(trifluoromethyl)biphenyl-4-yloxy)piperidine-1-carboxylate

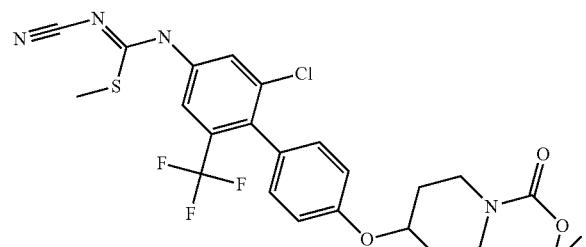

To a solution of tert-butyl 4-(2'-chloro-4'-isothiocyanato-6'-(trifluoromethyl)biphenyl-4-yloxy)piperidine-1-carboxylate (0.85 g, 1.66 mmol, Eq: 1.00) in dimethoxyethane (22.0 ml) were added sodium hydrogen cyanamide (127 mg, 1.99 mmol, Eq: 1.2) and methanol (3 mL). The reaction mixture was stirred at room temperature for 30 minutes, then iodomethane (602 mg, 265 µl, 4.24 mmol, Eq: 2.56) was added and the reaction mixture was stirred at room temperature for 4 h. The reaction mixture was concentrated in vacuo. The residue was purified by flash chromatography (silica gel, 40 g, 20% to 80% ethyl acetate in hexanes) to afford 0.73 g (77%) of the desired product as a white solid.

4-[4'-(5-Amino-1H-[1,2,4]triazol-3-ylamino)-6'-chloro-2'-trifluoromethyl-biphenyl-4-yloxy]-piperidine-1-carboxylic acid tert-butyl ester (Compound 138)

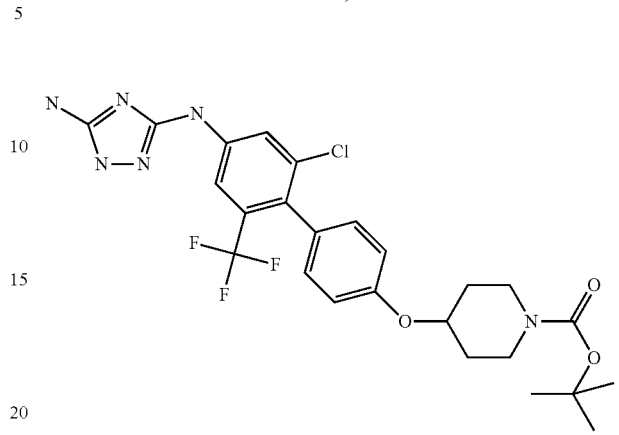

A mixture of (Z)-tert-butyl 4-(2'-chloro-4'-((cyanoimino)(methylthio)methylamino)-6'-(trifluoromethyl)biphenyl-4-yloxy)piperidine-1-carboxylate (0.73 g, 1.28 mmol, Eq: 1.00) and hydrazine (411 mg, 403 µl, 12.8 mmol, Eq: 10) in ethanol (15 ml) was stirred at 65° C. for overnight. The reaction mixture was concentrated in vacuo. The residue was purified by flash chromatography (silica gel, 24 g, 1% to 10% methanol in dichloromethane) to afford 0.64 g (90%) of the desired product as a white solid.

MS +m/z: 553.1 (M+H)$^+$

N*3*-[6-Chloro-4'-(piperidin-4-yloxy)-2-trifluoromethyl-biphenyl-4-yl]-1H-[1,2,4]triazole-3,5-diamine hydrochloride (Compound 139)

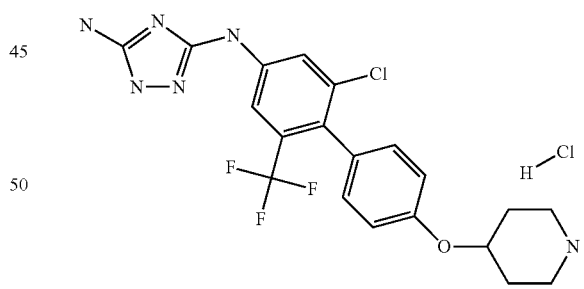

To a solution of compound 138, tert-butyl 4-(4'-(5-amino-1H-1,2,4-triazol-3-ylamino)-2'-chloro-6'-(trifluoromethyl)biphenyl-4-yloxy)piperidine-1-carboxylate (0.64 g, 1.16 mmol, Eq: 1.00) in dichloromethane (5 mL) was added a freshly made HCl solution (prepared from 1 mL acetyl chloride added to 10 mL methanol). The reaction mixture was stirred at room temperature for 5 h, and then concentrated in vacuo. The residue was triturated with methanol/dichloromethane to afford 0.5 g (88%) of the desired product as a white solid.

MS +m/z: 453.0 (M+H)$^+$

311

N*3*-{6-Chloro-2-trifluoromethyl-4'-[1-(3,3,3-trifluoro-propyl)-piperidin-4-yloxy]-biphenyl-4-yl}-1H-[1,2,4]triazole-3,5-diamine hydrochloride (Compound 140)

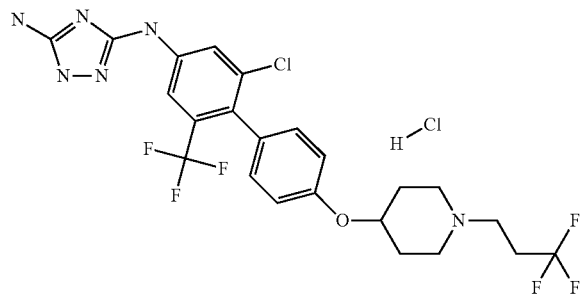

To a solution of compound 139, N3-(2-chloro-4'-(piperidin-4-yloxy)-6-(trifluoromethyl)biphenyl-4-yl)-1H-1,2,4-triazole-3,5-diamine hydrochloride (80 mg, 163 µmol, Eq: 1.00) in methanol (5 mL) were added 3,3,3-trifluoropropanal (45.8 mg, 409 µmol, Eq: 2.5) and sodium cyanoborohydride (51.4 mg, 817 µmol, Eq: 5). The reaction mixture was stirred at room temperature for 3 h. Ethyl acetate (50 mL) was added, then sat. NaHCO₃ solution to adjust pH>7. The organic layer was collected and the aqueous layer was extracted with ethyl acetate (2×25 mL). The combined organic layers were washed with water, brine, dried over MgSO₄ and concentrated in vacuo. The residue was purified by flash chromatography (silica gel, 12 g, 2% to 10% methanol in dichloromethane) to give free amine as a white solid. To the solution of free amine in methanol (2 mL) was added a freshly made 1 mL of HCl solution (prepared from 0.3 mL of acetyl chloride added to 3 mL of methanol). The reaction mixture was stirred at room temperature for 2 h, and then concentrated in vacuo. The residue was triturated with methanol/methyl tert-butyl ether. The resulting solid was collected, washed with methyl tert-butyl ether, dried to give 53 mg (55%) of the desired product as a white solid.

MS +m/z: 549.0 (M+H)⁺

N*3*-{6-Chloro-4'-[1-(2-methanesulfonyl-ethyl)-piperidin-4-yloxy]-2-trifluoromethyl-biphenyl-4-yl}-1H-[1,2,4]triazole-3,5-diamine hydrochloride (Compound 141)

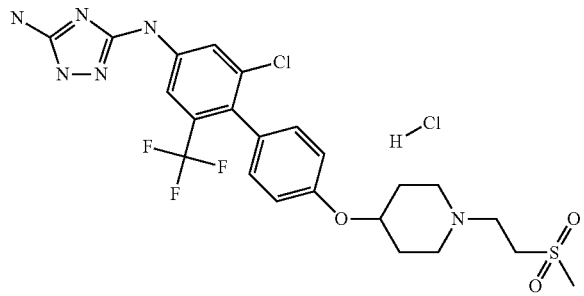

312

Methanesulfonic acid 2-methanesulfonyl-ethyl ester

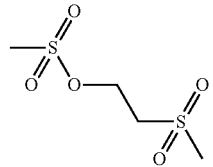

To a mixture of 2-(methylsulfonyl)ethanol (2 g, 16.1 mmol, Eq: 1.00) and triethylamine (2.45 g, 3.37 ml, 24.2 mmol, Eq: 1.5) in dichloromethane (30 ml) at 0° C. was added methanesulfonyl chloride (2.21 g, 1.51 ml, 19.3 mmol, Eq: 1.2) dropwise. The reaction mixture was then allowed to warm to room temperature and stirred for 3 h. The reaction mixture was diluted with dichloromethane (100 mL), and then washed with sat. NaHCO₃ solution, water, brine, dried over MgSO₄ and concentrated in vacuo. The residue was purified by flash chromatography (silica gel, 40 g, 0% to 100% ethyl acetate in hexanes) to afford 0.7 g (21%) of the desired product as colorless oil.

N*3*-{6-Chloro-4'-[1-(2-methanesulfonyl-ethyl)-piperidin-4-yloxy]-2-trifluoromethyl-biphenyl-4-yl}-1H-[1,2,4]triazole-3,5-diamine hydrochloride (Compound 141)

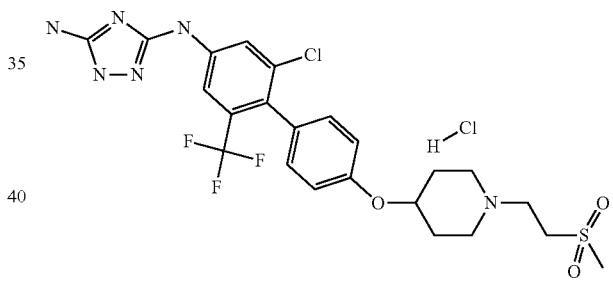

To a suspension of compound 139, N3-(2-chloro-4'-(piperidin-4-yloxy)-6-(trifluoromethyl)biphenyl-4-yl)-1H-1,2,4-triazole-3,5-diamine hydrochloride (80 mg, 163 µmol, Eq: 1.00) in dichloromethane (3 mL) were added 2-(methylsulfonyl)ethyl methanesulfonate (99.2 mg, 490 µmol, Eq: 3) and N-ethyl-N-isopropylpropan-2-amine (106 mg, 142 µl, 817 µmol, Eq: 5). The reaction mixture was stirred at room temperature for 20 h. The reaction mixture was diluted with dichloromethane (50 mL), then washed with water (2×20 mL), brine (10 mL), dried over MgSO₄ and concentrated in vacuo. The residue was purified by flash chromatography (silica gel, 12 g, 2% to 13% methanol in dichloromethane) to give a white solid as free amine. To the solution of free amine in dichloromethane (2 mL) was added a freshly made 1 mL of HCl solution (prepared from 0.3 mL of acetyl chloride added to 3 mL of methanol). The reaction mixture was stirred at room temperature for 2 h, and then concentrated in vacuo. The residue was triturated with methanol/methyl tert-butyl ether. The resulting solid was filtered and washed with methyl tert-butyl ether, dried to afford 23 mg (24%) of the desired product as an off-white solid.

MS +m/z: 559.0 (M+H)⁺

N*3*-{6-Chloro-4'-[1-(3-methanesulfonyl-propyl)-piperidin-4-yloxy]-2-trifluoromethyl-biphenyl-4-yl}-1H-[1,2,4]triazole-3,5-diamine hydrochloride (Compound 142)

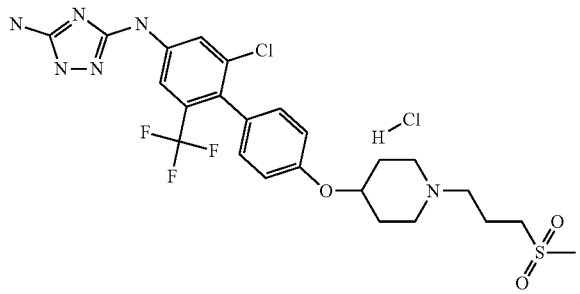

Methanesulfonic acid 3-methanesulfonyl-propyl ester

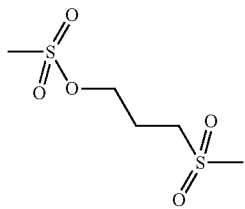

To a mixture of 3-(methylsulfonyl)propan-1-ol (0.25 g, 1.81 mmol, Eq: 1.00) and triethylamine (275 mg, 378 μl, 2.71 mmol, Eq: 1.5) in dichloromethane (3.00 ml) at 0° C. was added methanesulfonyl chloride (249 mg, 169 μl, 2.17 mmol, Eq: 1.2) dropwise. The reaction mixture was then allowed to warm to room temperature and stirred for 1 h. The reaction mixture was diluted with dichloromethane (100 mL), and then washed with sat. NaHCO$_3$, water, brine, dried over MgSO$_4$ and concentrated in vacuo. The residue was purified by flash chromatography (silica gel, 40 g, 0% to 100% ethyl acetate in hexanes) to afford 0.25 g (64%) of the desired product as colorless oil.

N*3*-{6-Chloro-4'-[1-(3-methanesulfonyl-propyl)-piperidin-4-yloxy]-2-trifluoromethyl-biphenyl-4-yl}-1H-[1,2,4]triazole-3,5-diamine hydrochloride (Compound 142)

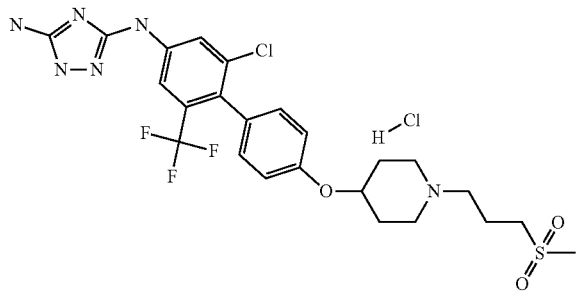

To a suspension of compound 139, N3-(2-chloro-4'-(piperidin-4-yloxy)-6-(trifluoromethyl)biphenyl-4-yl)-1H-1,2,4-triazole-3,5-diamine hydrochloride (80 mg, 163 μmol, Eq: 1.00) in dichloromethane (3.00 ml) were added 3-(methylsulfonyl)propyl methanesulfonate (106 mg, 490 μmol, Eq: 3) and N-ethyl-N-isopropylpropan-2-amine (106 mg, 142 μl, 817 μmol, Eq: 5). The reaction mixture was stirred at room temperature for 20 h. DMF (3 mL) was added. The reaction mixture was heated at 80° C. for 5 h. It was diluted with dichloromethane (50 mL), washed with water (2×20 mL), brine (10 mL), dried over MgSO$_4$ and concentrated. The residue was purified by flash chromatography (silica gel, 12 g, 2% to 13% methanol in dichloromethane) to give free amine as a white solid. To the solution of free amine in dichloromethane (2 mL) was added a freshly made 1 mL of HCl (prepared from 0.3 mL of acetyl chloride added to 3 mL of methanol). The reaction mixture was stirred at room temperature for 2 h, and then concentrated in vacuo. The residue was triturated with methanol/methyl tert-butyl ether. The resulting solid was filtered, washed with methyl tert-butyl ether and dried to afford 17 mg (17%) of the desired product as an off-white solid.

MS +m/z: 573.0 (M+H)$^+$

N*3*-{6-Chloro-4'-[1-(2-methoxy-ethyl)-piperidin-4-yloxy]-2-trifluoromethyl-biphenyl-4-yl}-1H-[1,2,4]triazole-3,5-diamine hydrochloride (Compound 143)

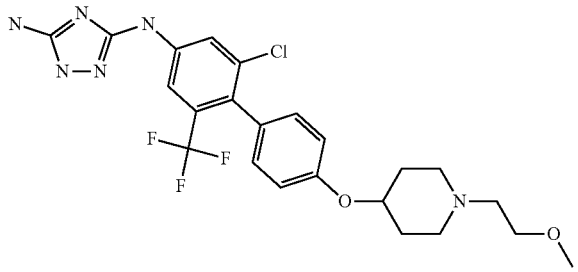 [SMILES: COCCN1CCC(Oc2ccc(-c3c(Cl)cc(Nc4n[nH]c(N)n4)cc3C(F)(F)F)cc2)CC1]

Methanesulfonic acid 2-methoxy-ethyl ester

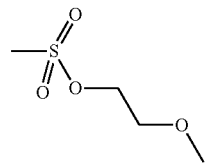

To a mixture of 2-methoxyethanol (2.5 g, 32.9 mmol, Eq: 1.00) and triethylamine (4.99 g, 6.87 ml, 49.3 mmol, Eq: 1.5) in dichloromethane (30 mL) at 0° C. was added methanesulfonyl chloride (4.52 g, 3.07 ml, 39.4 mmol, Eq: 1.2) dropwise. The reaction mixture was allowed to warm to room temperature and stirred for 1 h. The reaction mixture was diluted with DCM (100 mL), and then washed with sat. NaHCO$_3$, brine, dried over MgSO$_4$ and concentrated in vacuo. The residue was purified by flash chromatography (silica gel, 40 g, 0% to 100% ethyl acetate in hexanes) to afford 3 g (59%) of the desired product as colorless liquid.

N*3*-{6-Chloro-4'-[1-(2-methoxyl-ethyl)-piperidin-4-yloxy]-2-trifluoromethyl-biphenyl-4-yl}-1H-[1,2,4]triazole-3,5-diamine (Compound 143)

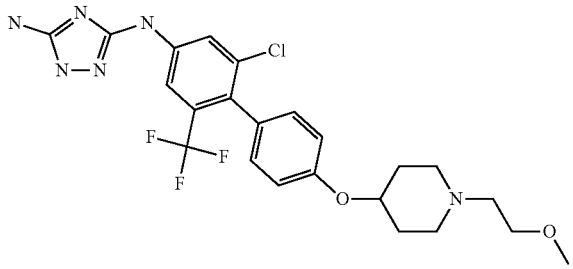 [SMILES: COCCN1CCC(Oc2ccc(-c3c(Cl)cc(Nc4n[nH]c(N)n4)cc3C(F)(F)F)cc2)CC1]

To a suspension compound 139, N3-(2-chloro-4'-(piperidin-4-yloxy)-6-(trifluoromethyl)biphenyl-4-yl)-1H-1,2,4-triazole-3,5-diamine hydrochloride (60 mg, 123 µmol, Eq: 1.00) in dichloromethane (2 mL) was added 2-methoxyethyl methanesulfonate (56.7 mg, 368 µmol, Eq: 3) and N-ethyl-N-isopropylpropan-2-amine (79.2 mg, 107 µl, 613 µmol, Eq: 5). The reaction mixture was stirred at room temperature for 20 h.

DMF (3 mL) was added. The reaction mixture was heated at 80° C. for 5 h. It was diluted with dichloromethane (50 mL), washed with water (2×20 mL), brine (10 mL), dried over MgSO$_4$ and concentrated in vacuo. The residue was purified by flash chromatography (silica gel, 12 g, 2% to 13% methanol in dichloromethane) to afford 9 mg (14%) of the desired product as a white solid.

MS +m/z: 511.1 (M+H)$^+$

Procedure 1

N*3*-(2-Chloro-biphenyl-4-yl)-1H-[1,2,4]triazole-3,5-diamine (Compound 144)

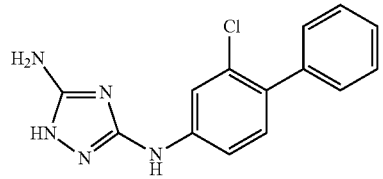 [SMILES: Nc1nc(Nc2ccc(-c3ccccc3)c(Cl)c2)n[nH]1]

2-chloro-4-nitrobiphenyl

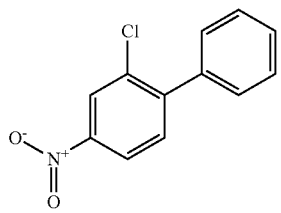 [SMILES: O=[N+]([O-])c1ccc(-c2ccccc2)c(Cl)c1]

Purged a 3-neck, 250-mL round-bottom flask with argon. Meanwhile, charged 2-chloro-1-iodo-4-nitrobenzene (1.00 g, 3.53 mmol, Eq: 1.00), phenylboronic acid (4646.3 mg, 38.1 mmol, Eq: 10.8), and tetrakis(triphenylphosphine)palladium (0) (412 mg, 357 µmol, Eq: 0.101) while still purging with argon. Added toluene (30 mL), ethanol (6.0 mL), and 2 M sodium carbonate solution (7.06 mL, 14.1 mmol, Eq: 4.0) all via syringes. Refluxed the mixture (~95° C.) for 18 h; at which time HPLC determined the reaction was complete. Diluted the mixture with ethyl acetate and washed with 1 N hydrochloric acid and saturated sodium chloride solution. Dried over magnesium sulfate, filtered, and concentrated onto Celite. Purified using a 120 g column on an Intelliflash 280; collected peaks only in 28 mL fractions at 76 mL/min; equilibrated with hexanes; dry loaded; eluted 2 min with hexanes; increased from 0-15% dichloromethane/hexanes over 30 min; held for 5.5 min. Obtained 780 mg (94.6%) of 2-chloro-4-nitrobiphenyl as a light yellow solid.

2-chlorobiphenyl-4-amine

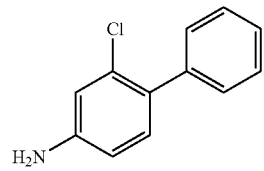

Purged the 250-mL round-bottomed flask containing 2-chloro-4-nitrobiphenyl (780 mg, 3.34 mmol, Eq: 1.00) with argon. Charged iron (930.4 mg, 16.7 mmol, Eq: 4.99) and ammonium chloride (1.79 g, 33.4 mmol, Eq: 10) to the reaction vessel. Added methanol (30 mL) and water (15 mL), then fitted a condenser to the flask. Heated the mixture to reflux (~85° C.). After 5 h, HPLC confirmed all the starting material had been consumed. Cooled to room temperature overnight. Filtered the reaction mixture through a bed of Celite rinsing with copious amounts of methanol. Concentrated the filtrate. The solid were then treated with ethyl acetate and filtered. The filtrate was concentrated. Obtained 660 mg (97% yield) of 2-chlorobiphenyl-4-amine as a brown oil.

2-chloro-4-isothiocyanatobiphenyl

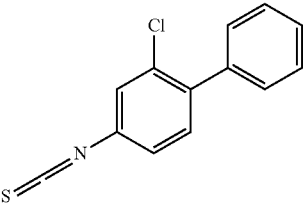

Purged the 100-mL round-bottomed flask containing 2-chlorobiphenyl-4-amine (660 mg, 3.24 mmol, Eq: 1.00) with argon. Added dichloromethane (15 mL) and 1,1'-thiocarbonyldiimidazole (866 mg, 4.86 mmol, Eq: 1.5) then stirred at room temperature. After 1.5 h took a HPLC: the reaction was complete. Diluted with dichloromethane and concentrated onto Celite. Purified using a 40 g silica gel column on an Intelliflash 280; collected peaks only in 28 mL fractions at 53 mL/min; equilibrated with hexanes; dry loaded on Celite; eluted 2 min with hexanes; increased from 0-15% dichloromethane/hexanes over 10 min. Obtained 690 mg (87%) of 2-chloro-4-isothiocyanatobiphenyl as a clear, colorless oil.

(Z)-methyl N-2-chlorobiphenyl-4-yl-N'-cyanocarbamimidothioate

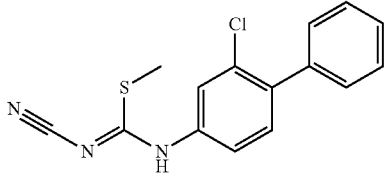 [SMILES: CS/C(=N\C#N)Nc1ccc(-c2ccccc2)c(Cl)c1]

Purged a 50-mL round-bottomed flask with argon. Charged cyanamide (87.6 mg, 2.08 mmol, Eq: 2.06) to the flask followed by 0.5 M sodium methoxide in methanol (3.04 mL, 1.52 mmol, Eq: 1.5). Stirred for several minutes at room temperature, then diluted with methanol (10 mL). After ~15 min of stirring, added 2-chloro-4-isothiocyanatobiphenyl (248.8 mg, 1.01 mmol, Eq: 1.00). After ~45 min, no starting material remained by HPLC. Added iodomethane (159 mg, 0.07 mL, 1.12 mmol, Eq: 1.11) and stirred over for 3 days at room temperature. Solids crashed out. Placed the reaction vessel in the freezer for ~45 min, then filtered off the solids. Air dried for ~45 min and isolated 69 mg (23%) of (Z)-methyl N-2-chlorobiphenyl-4-yl-N'-cyanocarbamimidothioate as a white solid.

N*3*-(2-Chloro-biphenyl-4-yl)-1H-[1,2,4]triazole-3,5-diamine (Compound 144)

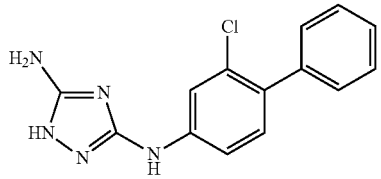 [SMILES: Nc1nc(Nc2ccc(-c3ccccc3)c(Cl)c2)n[nH]1]

Charged (Z)-methyl N-2-chlorobiphenyl-4-yl-N'-cyanocarbamimidothioate (69 mg, 229 µmol, Eq: 1.00) into a 50-mL round-bottomed flask and purged with argon. Added ethanol (10 mL) and hydrazine (102 mg, 0.10 mL, 3.19 mmol, Eq: 13.9). Refluxed for ~1.5 h, then removed an aliquot and took a HPLC: no starting material remained. Cooled to room temperature overnight. Diluted the mixture with ethanol and concentrated onto Celite. Purified using a 12 g silica gel column on an Intelliflash 280; collected peaks only in 9 mL fractions at 32 mL/min (0.5 min/CV); equilibrated with 2% methanol/dichloromethane with 1% ammonium hydroxide; dry loaded; eluted 1 min with 2% methanol/dichloromethane with 1% ammonium hydroxide; increased from 2-8% methanol/dichloromethane with 1% ammonium hydroxide over 10 min; held at 8% for 1 min. Obtained 59 mg (90%) of N*3*-(2-Chloro-biphenyl-4-yl)-1H-[1,2,4]triazole-3,5-diamine as a white solid. The product contained a minor methanol impurity. MS calcd. for C14H12ClN5 [(M+H)+] 286.1, obsd. 286.0.

Procedure 1

N*3*-(2-Chloro-4'-fluoro-biphenyl-4-yl)-1H-[1,2,4]triazole-3,5-diamine (Compound 145)

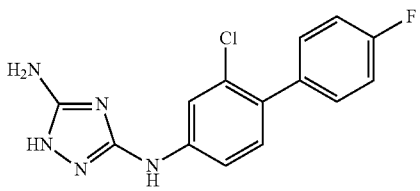 [SMILES: Nc1nc(Nc2ccc(-c3ccc(F)cc3)c(Cl)c2)n[nH]1]

2-chloro-4'-fluoro-4-nitrobiphenyl

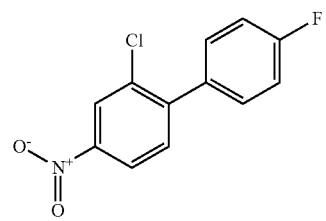 [SMILES: O=[N+]([O-])c1ccc(-c2ccc(F)cc2)c(Cl)c1]

Purged a 3-neck, 250-mL round-bottomed flask with argon. Charged 2-chloro-1-iodo-4-nitrobenzene (1.0 g, 3.53 mmol, Eq: 1.00), 4-fluorophenylboronic acid (739 mg, 5.28 mmol, Eq: 1.5), and tetrakis(triphenylphosphine)palladium (0) (409.5 mg, 354 µmol, Eq: 0.100) while purging with argon. Added toluene (30 mL), ethanol (6 mL), and 2.0 M sodium carbonate solution (7.06 mL, 14.1 mmol, Eq: 4.0) via syringes. Heated the mixture to reflux (~95° C.). After 6 h, HPLC confirmed all the starting material had been consumed. Cooled to room temperature. Diluted the reaction mixture with ethyl acetate and treated with 1 N hydrochloric acid and saturated sodium chloride solution. Dried over magnesium sulfate, filtered, and concentrated on Celite. Purified using a 120 g silica gel column on an Intelliflash 280; collected peaks only in 28 mL fractions at 40 mL/min; equilibrated with hexanes; dry loaded; eluted 4 min with hexanes; increased from 0-15% dichloromethane/hexanes over 60 min. Obtained 827 mg (93%) of 2-chloro-4'-fluoro-4-nitrobiphenyl as an light yellow solid.

2-chloro-4'-fluorobiphenyl-4-amine

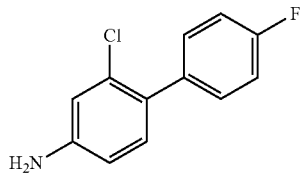 [SMILES: Nc1ccc(-c2ccc(F)cc2)c(Cl)c1]

Purged the 250-mL round-bottomed flask containing 2-chloro-4'-fluoro-4-nitrobiphenyl (827 mg, 3.29 mmol, Eq: 1.00) with argon. Charged iron (934.6 mg, 16.7 mmol, Eq: 5.09), ammonium chloride (1.76 g, 32.9 mmol, Eq: 10.0), methanol (30 mL), and water (15 mL) to the reaction flask.

Equipped the flask with a condenser and heated to reflux. After 1.5 h, the reaction was complete according to HPLC. Cooled the mixture to room temperature overnight. Filtered the reaction mixture through a bed of Celite, rinsing with copious amounts of methanol. Concentrated the filtrate. The concentrate contained ammonium chloride; washed and filtered with ethyl acetate. Concentrated the filtrate to obtain 705 mg (89%) of 2-chloro-4'-fluorobiphenyl-4-amine as a brown oil.

2-chloro-4'-fluoro-4-isothiocyanatobiphenyl

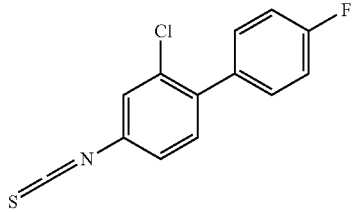

Purged the 250-mL round-bottomed flask containing 2-chloro-4'-fluorobiphenyl-4-amine (703 mg, 3.17 mmol, Eq: 1.00) with argon, then added dichloromethane (15 mL) followed by 1,1'-thiocarbonyldiimidazole (848 mg, 4.76 mmol, Eq: 1.5). After 45 min, HPLC confirmed that the starting material had been consumed. Stirred over weekend at room temperature. Diluted the reaction mixture with dichloromethane, then concentrated onto Celite. Purified using a 40 g silica gel column on an Intelliflash 280; collected peaks only in 28 mL fractions at 53 mL/min; equilibrated with hexanes; dry loaded on Celite; eluted 2 min with hexanes; increased from 0-15% dichloromethane/hexanes over 10 min. Obtained 738 mg (88%) of 2-chloro-4'-fluoro-4-isothiocyanatobiphenyl as a white solid.

(Z)-methyl N-2-chloro-4'-fluorobiphenyl-4-yl-N'-cyanocarbamimidothioate

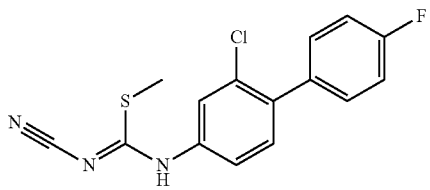 [SMILES: CS/C(=N\C#N)Nc1ccc(-c2ccc(F)cc2)c(Cl)c1]

Purged a 5-mL round-bottomed flask with argon. Charged cyanamide (79.7 mg, 1.9 mmol, Eq: 2.0) into the flask while purging with argon. Added 0.5 M sodium methoxide in methanol (2.9 mL, 1.45 mmol, Eq: 1.53) and stirred at room temperature for ~15 min. Meanwhile, purged a 50-mL round-bottomed flask with argon. Charged 2-chloro-4'-fluoro-4-isothiocyanatobiphenyl (249.9 mg, 948 µmol, Eq: 1.00) into the 50-mL round-bottomed flask while puring with argon. Added methanol (7 mL) and began to stir. Transferred the cyanamide mixture to the isothiocyanate mixture via syringe. Stirred at room temperature for ~1 h. HPLC confirmed the consumption of starting material. Added iodomethane (227 mg, 0.10 mL, 1.6 mmol, Eq: 1.69) and stirred overnight at room temperature. Observed that solids crashed out overnight. Placed the reaction mixture in the freezer for 30 min, then filtered off the solids. Obtained 93.1 mg (31%) of (Z)-methyl N-2-chloro-4'-fluorobiphenyl-4-yl-N'-cyanocarbamimidothioate as a white solid.

N*3*-(2-Chloro-4'-fluoro-biphenyl-4-yl)-1H-[1,2,4]triazole-3,5-diamine (Compound 145)

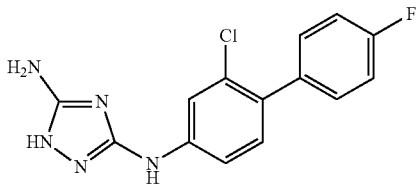 [SMILES: Nc1nc(Nc2ccc(-c3ccc(F)cc3)c(Cl)c2)n[nH]1]

Charged (Z)-methyl N-2-chloro-4'-fluorobiphenyl-4-yl-N'-cyanocarbamimidothioate (93 mg, 291 µmol, Eq: 1.00) into a 50-mL round-bottomed flask and purged with argon. Added ethanol (10 mL) and hydrazine (123 mg, 0.12 mL, 3.82 mmol, Eq: 13.1). Refluxed for ~1 h, then removed an aliquot and took a HPLC: no starting material remained. Cooled to room temperature, then diluted the mixture with ethanol and concentrated onto Celite. Purified using a 12 g silica gel column on an Intelliflash 280; collected peaks only in 9 mL fractions at 32 mL/min (0.5 min/CV); equilibrated with 2% methanol/dichloromethane with 1% ammonium hydroxide; dry loaded; eluted 1 min with 2% methanol/dichloromethane with 1% ammonium hydroxide; increased from 2-10% methanol/dichloromethane with 1% ammonium hydroxide over 14.5 min; obtained 86.3 mg (98%) of N*3*-(2-Chloro-4'-fluoro-biphenyl-4-yl)-1H-[1,2,4]triazole-3,5-diamine as a white solid. MS calcd. for C14H11ClFN5 [(M+H)+] 304.1, obsd. 303.9.

Procedure 1

N*3*-(2-Chloro-2'-fluoro-biphenyl-4-yl)-1H-[1,2,4]triazole-3,5-diamine (Compound 146)

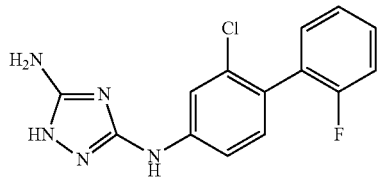 [SMILES: Nc1nc(Nc2ccc(-c3ccccc3F)c(Cl)c2)n[nH]1]

2-chloro-2'-fluoro-4-nitrobiphenyl

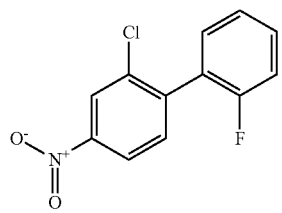 [SMILES: O=[N+]([O-])c1ccc(-c2ccccc2F)c(Cl)c1]

While purging a 3-neck, 250-mL round-bottomed flask with argon, charged 2-chloro-1-iodo-4-nitrobenzene (1.0 g, 3.53 mmol, Eq: 1.00), 2-fluorophenylboronic acid (801.5 mg, 5.73 mmol, Eq: 1.62), tetrakis(triphenylphosphine)palladium (0) (410 mg, 355 μmol, Eq: 0.101), toluene (30 mL), ethanol (6 mL), and 2.0 M sodium carbonate (7.06 mL, 14.1 mmol, Eq: 4.0). Refluxed the mixture overnight. After 18 h, HPLC showed all the starting material had been consumed. Cooled the mixture to room temperature. Diluted with ethyl acetate and washed with 1 N hydrochloric acid and saturated sodium chloride solution. Dried over magnesium sulfate, filtered, and concentrated onto Celite. Purified using a 120 g silica gel column on an Intelliflash 280; collected peaks only in 28 mL fractions at 40 mL/min; equilibrated with hexanes; dry loaded; eluted 4 min with hexanes; increased from 0-15% dichloromethane/hexanes over 60 min; held at 15% for 4 min. Obtained 802 mg (93%) of 2-chloro-2'-fluoro-4-nitrobiphenyl as an light yellow solid.

2-chloro-2'-fluorobiphenyl-4-amine

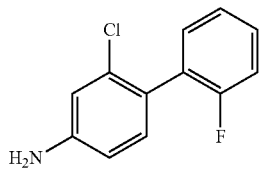 [SMILES: Nc1ccc(-c2ccccc2F)c(Cl)c1]

Purged the 100-mL round-bottomed flask containing 2-chloro-2'-fluoro-4-nitrobiphenyl (788 mg, 3.13 mmol, Eq: 1.00) with argon. Charged iron (881.7 mg, 15.8 mmol, Eq: 5.04) and ammonium chloride (1.68 g, 31.3 mmol, Eq: 10) followed by methanol (30 mL) and water (15 mL). Heated to reflux. After 4 h the reaction appeared complete according to HPLC. Cooled the mixture to room temperature, then filtered the mixture through a bed of Celite rinsing with large amounts of methanol. Concentrated the filtrate, but the residue contained ammonium chloride. Washed the solids with ethyl acetate, then filtered. Concentrated the filtrate and obtained 715 mg (82% yield at est. 80% purity) of 2-chloro-2'-fluorobiphenyl-4-amine as an oil.

2-chloro-2'-fluoro-4-isothiocyanatobiphenyl

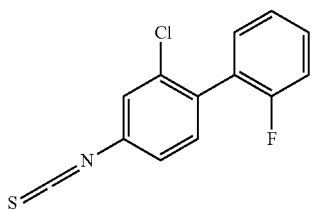

Purged the 100-mL round-bottomed flask containing 2-chloro-2'-fluorobiphenyl-4-amine (700 mg, 3.16 mmol, Eq: 1.00) with argon. Added dichloromethane (20 mL) and 1,1'-thiocarbonyldiimidazole (851.5 mg, 4.78 mmol, Eq: 1.51) and stirred at room temperature. After 6 h, removed an aliquot and took an HPLC: no starting material remained. Diluted the mixture with dichloromethane and concentrated onto Celite. Purified using a 40 g silica gel column on an Intelliflash 280; collected peaks only in 28 mL fractions at 53 mL/min; equilibrated with hexanes; dry loaded on Celite; eluted 2 min with hexanes; increased from 0-15% dichloromethane/hexanes over 10 min. Obtained 685 mg (82%) of 2-chloro-2'-fluoro-4-isothiocyanatobiphenyl as a clear, colorless oil.

(Z)-methyl N-2-chloro-2'-fluorobiphenyl-4-yl-N'-cyanocarbamimidothioate

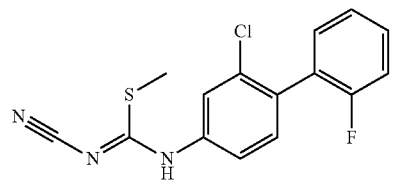 [SMILES: CS/C(=N\C#N)Nc1ccc(-c2ccccc2F)c(Cl)c1]

Purged a 25-mL round-bottomed flask with argon. Charged cyanamide (334.1 mg, 7.95 mmol, Eq: 3.06) to the flask, then added 0.5 M sodium methoxide in methanol (7.79 mL, 3.9 mmol, Eq: 1.5). Stirred at room temperature for 15 min. Meanwhile, added methanol (20 mL) to the 100 mL round-bottomed flask containing 2-chloro-2'-fluoro-4-isothiocyanatobiphenyl (685 mg, 2.6 mmol, Eq: 1.00) while purging argon. Added the cyanamide mixture to the isothiocyanate mixture via syringe. Stirred at room temperature for 1 h. HPLC at this time showed all the starting material consumed. Added Iodomethane (738 mg, 0.325 mL, 5.2 mmol, Eq: 2.00) and stirred overnight at room temperature. In the morning, observed that white solids had precipitated. Filtered off the solids and concentrated the filtrate onto Celite. The solids were pure product according to HPLC; obtained 385 mg (46%) of (Z)-methyl N-2-chloro-2'-fluorobiphenyl-4-yl-N'-cyanocarbamimidothioate as a white solid. The filtrate was purified using a 60 g silica gel column on an Intelliflash 280; collected peaks only in 28 mL fractions at 40 mL/min; equilibrated with 10% ethyl acetate/hexanes; dry loaded on Celite; eluted 2 min with 10% ethyl acetate/hexanes; increased to 60% ethyl acetate/hexanes over 20 min; held at 60% for 7.25 min. Obtained another 203 mg (25%) of (Z)-methyl N-2-chloro-2'-fluorobiphenyl-4-yl-N'-cyanocarbamimidothioate as a white solid. Combined the solids to obtain 587 mg (71% yield) of (Z)-methyl N-2-chloro-2'-fluorobiphenyl-4-yl-N'-cyanocarbamimidothioate as a white solid.

N*3*-(2-Chloro-2'-fluoro-biphenyl-4-yl)-1H-[1,2,4]triazole-3,5-diamine (Compound 146)

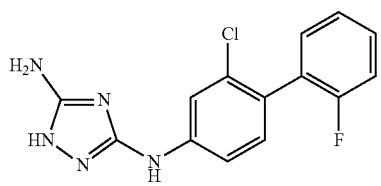 [SMILES: Nc1nc(Nc2ccc(-c3ccccc3F)c(Cl)c2)n[nH]1]

Added ethanol (20 mL) and hydrazine (581 mg, 0.569 mL, 18.1 mmol, Eq: 10.0) to the 100-mL round-bottomed flask containing (Z)-methyl N-2-chloro-2'-fluorobiphenyl-4-yl-N'-cyanocarbamimidothioate (580 mg, 1.81 mmol, Eq: 1.00). Refluxed the mixture for ~2 h. HPLC showed the reaction was complete. Cooled the mixture to room temperature. Transferred to a larger flask and concentrated onto Celite. Purified using a 40 g silica gel column on an Intelliflash 280; collected peaks only in 28 mL fractions at 16 mL/min; equilibrated with 1% methanol/dichloromethane with 1% ammonium hydroxide; dry loaded on Celite; immediately after loading the compound it crashed out on the column and caused very large back pressure; stepped to 5% methanol/dichloromethane with 1% ammonium hydroxide and let solvent sit on column to dissolve the compound; eluted from 5-10% methanol/dichloromethane with 1% ammonium hydroxide over 22 min. Obtained 414 mg (75.2%) of N*3*-(2-Chloro-2'-fluoro-biphenyl-4-yl)-1H-[1,2,4]triazole-3,5-diamine as an off-white solid after removing all the methanol in a 70° C. drying pistol overnight. MS calcd. for C14H11ClFN5 [(M+H)+] 304.1, obsd. 303.9.

N*3*-(2-Chloro-3',4'-difluoro-biphenyl-4-yl)-1H-[1,2,4]triazole-3,5-diamine (Compound 147)

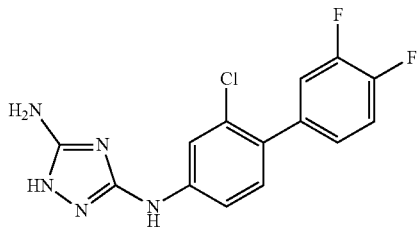 [SMILES: Nc1nc(Nc2ccc(-c3ccc(F)c(F)c3)c(Cl)c2)n[nH]1]

Purged a 15-mL seal tube with argon. Added N3-(4-bromo-3-chlorophenyl)-1H-1,2,4-triazole-3,5-diamine (100.5 mg, 348 µmol, Eq: 1.00), 3,4-difluorophenylboronic acid (110.0 mg, 697 µmol, Eq: 2.00), potassium carbonate (195.1 mg, 1.41 mmol, Eq: 4.05), tetrakis(triphenylphosphine)palladium (0) (80.5 mg, 69.7 µmol, Eq: 0.200), and dioxane (4 mL) while purging with argon. Sealed under argon and heated to 120° C. After 23 h, cooled the mixture to room temperature. The HPLC showed most of the starting material consumed. Diluted the reaction with ethyl acetate and washed with water and saturated sodium chloride solution. Dried over Sodium sulfate, filtered, and concentrated onto Celite. Pre-purified using flash chromatography; purified using prep-HPLC. Obtained 27.4 mg (24%) of N*3*-(2-Chloro-3',4'-difluoro-biphenyl-4-yl)-1H-[1,2,4]triazole-3,5-diamine after lyophilizing off the acetate salt as an off-white solid. MS calcd. for C14H10ClF2N5 [(M+H)+] 322.1, obsd. 321.9.

N*3*-(2-Chloro-3'-fluoro-biphenyl-4-yl)-1H-[1,2,4]triazole-3,5-diamine (Compound 148)

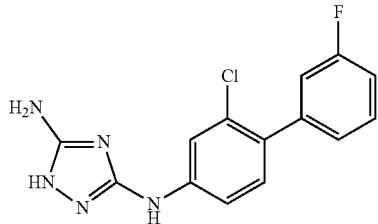 [SMILES: Nc1nc(Nc2ccc(-c3cccc(F)c3)c(Cl)c2)n[nH]1]

Purged a 15-mL seal tube with argon. Added N3-(4-bromo-3-chlorophenyl)-1H-1,2,4-triazole-3,5-diamine (100.3 mg, 348 µmol, Eq: 1.00; 3-fluorophenylboronic acid (91.9 mg, 657 µmol, Eq: 1.89), potassium carbonate (198.8 mg, 1.44 mmol, Eq: 4.14), tetrakis(triphenylphosphine)palladium (0) (80.5 mg, 69.7 µmol, Eq: 0.200), and dioxane (4 mL) while purging with argon. Sealed under argon and heated to 120° C. After 23 h, cooled the mixture to room temperature. The HPLC showed most of the starting material consumed. Diluted the reaction with ethyl acetate and washed with water and saturated sodium chloride solution. Dried over Sodium sulfate, filtered, and concentrated onto Celite. Pre-purified using flash chromatography before purifying via prep-HPLC purification. Obtained 34.8 mg (24%) of N*3*-(2-Chloro-3'-fluoro-biphenyl-4-yl)-1H-[1,2,4]triazole-3,5-diamine after lyophilizing off the acetate salt as an off-white solid. MS calcd. for C14H11ClFN5 [(M+H)+] 304.1, obsd. 303.9.

N*3*-(2-Trifluoromethyl-biphenyl-4-yl)-1H-[1,2,4]triazole-3,5-diamine (Compound 149)

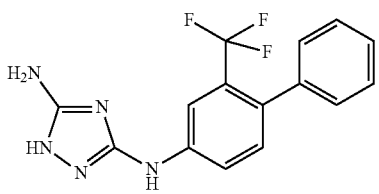 [SMILES: Nc1nc(Nc2ccc(-c3ccccc3)c(C(F)(F)F)c2)n[nH]1]

While purging a 15-mL seal tube with argon, charged N3-(4-bromo-3-(trifluoromethyl)phenyl)-1H-1,2,4-triazole-3,5-diamine (100.8 mg, 313 µmol, Eq: 1.00; phenylboronic acid (75.6 mg, 620 µmol, Eq: 1.98), potassium carbonate (214 mg, 1.55 mmol, Eq: 4.95), tetrakis(triphenylphosphine) palladium (0) (74.0 mg, 64.0 µmol, Eq: 0.205), and dioxane (2.0 mL). Heated to 120° C. and stirred for 18 h. Cooled to room temperature, removed an aliquot, and took HPLC and LC/MS: no starting material remained and product mass found as major peak. Diluted the reaction mixture with ethyl acetate and washed with water and saturated sodium chloride solution. Dried over magnesium sulfate, filtered, and concentrated onto Celite. Prepurified the crude material by flash column chromatography (5-10% methanol/dichloromethane with 1% ammonium hydroxide), then purified by prep-HPLC. The material obtained was transferred to a vial with a barcode and treated with ammonium hydroxide because it was the acetate salt. Lyophilized. Obtained 22.5 mg (22%) of N*3*-(2-Trifluoromethyl-biphenyl-4-yl)-1H-[1,2,4]triazole-3,5-diamine as an off-white solid. MS calcd. for C15H12F3N5 [(M+H)+] 320.1, obsd. 320.0.

N*3*-(2'-Fluoro-2-trifluoromethyl-biphenyl-4-yl)-1H-[1,2,4]triazole-3,5-diamine (Compound 150)

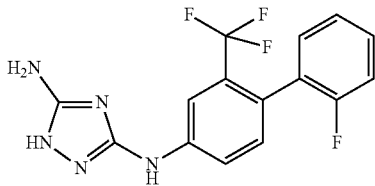

While purging a 15-mL seal tube with argon, charged into the reaction vessel N3-(4-bromo-3-(trifluoromethyl)phenyl)-1H-1,2,4-triazole-3,5-diamine (100.4 mg, 312 µmol, Eq: 1.00; 2-fluorophenylboronic acid (88.8 mg, 635 µmol, Eq: 2.04), potassium carbonate (213.9 mg, 1.55 mmol, Eq: 4.97), tetrakis(triphenylphosphine)-palladium (0) (74.7 mg, 64.6 µmol, Eq: 0.207), and dioxane (2 mL). Heated at 120° C. for 18 h. Cooled to room temperature, removed an aliquot, and took HPLC and LC/MS: no starting material remained and product mass found as major peak. Diluted the reaction mixture with ethyl acetate and washed with water and saturated sodium chloride solution. Dried over magnesium sulfate, filtered, and concentrated onto Celite. Prepurified the crude material by flash column chromatography (5-10% methanol/dichloromethane with 1% ammonium hydroxide), then purified by prep-HPLC. The material obtained was transferred to a vial with a barcode and treated with ammonium hydroxide because it was the acetate salt. Lyophilized. Obtained 22.4 mg (21%) of N*3*-(2'-Fluoro-2-trifluoromethyl-biphenyl-4-yl)-1H-[1,2,4]triazole-3,5-diamine as an off-white solid. MS calcd. for C15H11F4N5 [(M+H)+] 338.1, obsd. 307.9.

N*3*-(4'-Fluoro-2-trifluoromethyl-biphenyl-4-yl)-1H-[1,2,4]triazole-3,5-diamine (Compound 151)

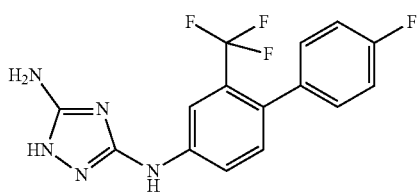 [SMILES: Nc1nc(Nc2ccc(-c3ccc(F)cc3)c(C(F)(F)F)c2)n[nH]1]

While purging a 15 mL seal tube with argon, charged into the reaction vessel N3-(4-bromo-3-(trifluoromethyl)phenyl)-1H-1,2,4-triazole-3,5-diamine (101.0 mg, 314 µmol, Eq: 1.00, 4-fluorophenylboronic acid (88.3 mg, 631 µmol, Eq: 2.01), potassium carbonate (214.7 mg, 1.55 mmol, Eq: 4.95), tetrakis(triphenylphosphine)-palladium (0) (78.0 mg, 67.5 µmol, Eq: 0.215), and dioxane (2 mL). Heated at 120° C. for 18 h. Cooled to room temperature, removed an aliquot, and took HPLC and LC/MS: no starting material remained and product mass found as major peak. Diluted the reaction mixture with ethyl acetate and washed with water and saturated sodium chloride. Dried over magnesium sulfate, filtered, and concentrated onto Celite. Prepurified the crude material by flash column chromatography (5-10% methanol/dichloromethane with 1% ammonium hydroxide), then purified by prep-HPLC. The material obtained was transferred to a vial with a barcode and treated with ammonium hydroxide because it was the acetate salt. Lyophilized. Obtained 30.7 mg (29%) of N*3*-(4'-Fluoro-2-trifluoromethyl-biphenyl-4-yl)-1H-[1,2,4]triazole-3,5-diamine as an off-white solid. MS calcd. for C15H11F4N5 [(M+H)+] 338.1, obsd. 307.9.

N*3*-(3',4'-Difluoro-2-trifluoromethyl-biphenyl-4-yl)-1H-[1,2,4]triazole-3,5-diamine (Compound 152)

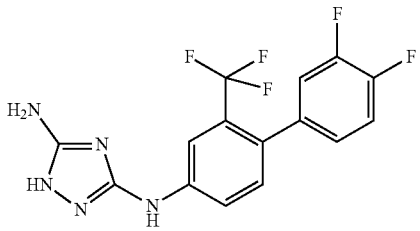 [SMILES: Nc1nc(Nc2ccc(-c3ccc(F)c(F)c3)c(C(F)(F)F)c2)n[nH]1]

While purging a 15-mL seal tube with argon, charged into the reaction vessel N3-(4-bromo-3-(trifluoromethyl)phenyl)-1H-1,2,4-triazole-3,5-diamine (100.3 mg, 311 µmol, Eq: 1.00), 3,4-difluorophenylboronic acid (98.1 mg, 621 µmol, Eq: 1.99), potassium carbonate (216.5 mg, 1.57 mmol, Eq: 5.03), tetrakis-(triphenylphosphine)palladium (0) (74.8 mg, 64.7 µmol, Eq: 0.208), and dioxane (2 mL). Heated at 120° C. for 18 h. Cooled to room temperature, removed an aliquot, and took HPLC and LC/MS: no starting material remained and product mass found as major peak. Diluted the reaction mixture with ethyl acetate and washed with water and saturated sodium chloride. Dried over magnesium sulfate, filtered, and concentrated onto Celite. Prepurified the crude material by flash column chromatography (5-10% methanol/dichloromethane with 1% ammonium hydroxide), then purified by prep-HPLC. The material obtained was transferred to a vial with a barcode and treated with ammonium hydroxide because it was the acetate salt. Lyophilized. Obtained 24.4 mg (22%) of N*3*-(3',4'-Difluoro-2-trifluoromethyl-biphenyl-4-yl)-1H-[1,2,4]triazole-3,5-diamine as an off-white solid. MS calcd. for C15H10F5N5 [(M+H)+] 356.1, obsd. 305.9.

N*3*-(2'-Chloro-2-trifluoromethyl-biphenyl-4-yl)-1H-[1,2,4]triazole-3,5-diamine (Compound 153)

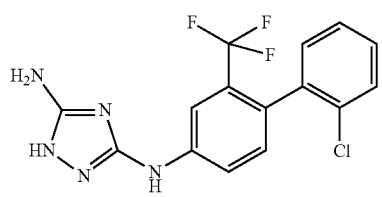

While purging with argon, charged N3-(4-bromo-3-(trifluoromethyl)phenyl)-1H-1,2,4-triazole-3,5-diamine (151.4 mg, 470 µmol, Eq: 1.00), 2-chlorophenylboronic acid (146.7 mg, 938 µmol, Eq: 2.00), potassium carbonate (265.0 mg, 1.92 mmol, Eq: 4.08), tetrakis(triphenylphosphine)palladium (0) (111.7 mg, 96.7 µmol, Eq: 0.206), and dioxane (3 mL) into a 15-mL seal tube. Sealed the reaction vessel and heated at 123° C. overnight. After 18 h the reaction was complete according to HPLC. Diluted the reaction mixture with ethyl acetate and washed with water and saturated sodium chloride. Dried over sodium sulfate, filtered, and concentrated onto Celite. Purified using a 50 g spherical silica gel column on an Intelliflash 280; collected peaks only in 9 mL fractions at 40 mL/min; equilibrated with 1% methanol/dichloromethane with 1% ammonium hydroxide;

dry loaded; eluted 4 min with 1% methanol/dichloromethane with 1% ammonium hydroxide; increased from 1-6% methanol/dichloromethane with 1% ammonium hydroxide over 38 min; held at 6% methanol/dichloromethane with 1% ammonium hydroxide for 18 min. Obtained 57.2 mg (33.3%) of N*3*-(2'-Chloro-2-trifluoromethyl-biphenyl-4-yl)-1H-[1,2,4]triazole-3,5-diamine as light yellow solid. MS calcd. for C15H11ClF3N5 [(M+H)+] 354.1, obsd. 353.9.

N*3*-(2-Chloro-4'-methanesulfonyl-biphenyl-4-yl)-1H-[1,2,4]triazole-3,5-diamine (Compound 154)

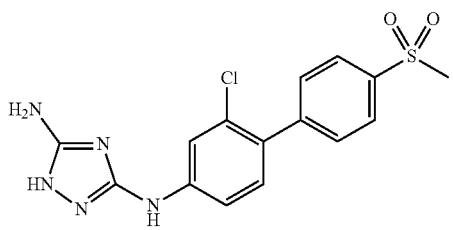 [SMILES: CS(=O)(=O)c1ccc(-c2ccc(Nc3n[nH]c(N)n3)cc2Cl)cc1]

2-chloro-4'-(methylsulfonyl)biphenyl-4-amine

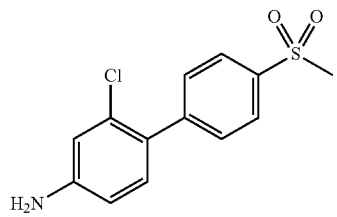 [SMILES: CS(=O)(=O)c1ccc(-c2ccc(N)cc2Cl)cc1]

Purged a 2-neck, 10-mL round-bottomed flask, fitted with a condenser and rubber septum, with argon. Charged 4-bromo-3-chloroaniline (1.0 g, 4.84 mmol, Eq: 1.00; from Oakwood), 4-(methylsulfonyl)phenylboronic acid (1.16 g, 5.81 mmol, Eq: 1.2), tetrakis(triphenylphosphine)palladium (0) (567 mg, 491 µmol, Eq: 0.101), toluene (20 mL), 2 M sodium carbonate (9.7 mL, 19.4 mmol, Eq: 4.01), and ethanol (4 mL) into the reaction vessel while purging with argon. Heated at 110° C. overnight. HPLC in the morning showed most of the starting material consumed. Diluted the reaction mixture with ~200 mL ethyl acetate and washed with water and saturated sodium chloride solution (note: slow layer separation); dried over Sodium sulfate, filtered, and concentrated on Celite. Purified using an 80 g silica gel column; collected peaks only in 28 mL fractions at 53 mL/min; equilibrated with 10% ethyl acetate/hexanes; dry loaded; eluted 4 min with 10% ethyl acetate/hexanes; increased from 10-40% over 24 min; held at 40% for 2 min; increased from 40-60% ethyl acetate/hexanes over 12 min. Obtained 1.10 g (78%) of 2-chloro-4'-(methylsulfonyl)biphenyl-4-amine as an orange solid. The $^1$H NMR showed an unknown impurity in the aromatic region as low broad peaks.

2-chloro-4-isothiocyanato-4'-(methylsulfonyl)biphenyl

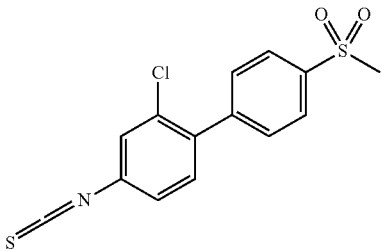

Purged the 250-mL round-bottomed flask containing 2-chloro-4'-(methylsulfonyl)biphenyl-4-amine (1.10 g, 3.9 mmol, Eq: 1.00), with argon. Dissolved the starting material in dichloromethane (45 mL), then added 1,1'-thiocarbonyldiimidazole (1.0 g, 5.61 mmol, Eq: 1.44). Stirred at room temperature for ~2 h; HPLC showed no more starting material. Diluted with dichloromethane and concentrated on Celite. Purified using an 80 g silica gel column on an Intelliflash 280; collected peaks only in 28 mL fractions at 53 mL/min; equilibrated with hexanes; dry loaded; eluted 2 min with hexanes; increased from 0-40% ethyl acetate/hexanes over 33 min; held at 40% for 7 min. Obtained 1.02 g (81%) of 2-chloro-4-isothiocyanato-4'-(methylsulfonyl) biphenyl as white solid.

(Z)-methyl N-2-chloro-4'-(methylsulfonyl)biphenyl-4-yl-N'-cyanocarbamimidothioate

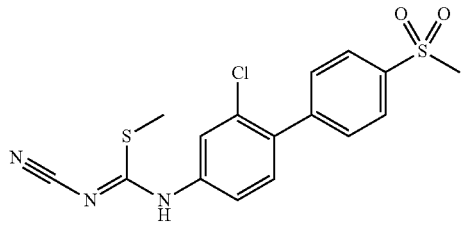 [SMILES: CS/C(=N\C#N)Nc1ccc(-c2ccc(S(C)(=O)=O)cc2)c(Cl)c1]

Purged a 100 mL round-bottomed flask with argon, then charged cyanamide (265 mg, 6.3 mmol, Eq: 2.0) into the flask. Added 0.5 M sodium methoxide in methanol (7.56 mL, 3.78 mmol, Eq: 1.2) at room temperature in one portion. Stirred for 15 min. Meanwhile, charged methanol (30 mL) and toluene (10 mL) to the 250 mL round-bottomed flask containing the starting material, 2-chloro-4-isothiocyanato-4'-(methylsulfonyl)biphenyl (1.02 g, 3.15 mmol, Eq: 1.00). Transferred the cyanamide mixture to the isothiocyanate mixture via syringe. Stirred at room temperature for 1.5 h, then added iodomethane (447 mg, 197 µL, 3.15 mmol, Eq: 1.00) and stirred overnight at room temperature. HPLC and LC/MS showed that the reaction was complete. Placed in the freezer for 2 h, then filtered rinsing with cold methanol. Air dried the solid for 2 h. Obtained 813 mg (68%) of (Z)-methyl N-2-chloro-4'-(methylsulfonyl)biphenyl-4-yl-N'-cyanocarbamimidothioate as an off-white solid.

N*3*-(2-Chloro-4'-methanesulfonyl-biphenyl-4-yl)-1H-[1,2,4]triazole-3,5-diamine (Compound 154)

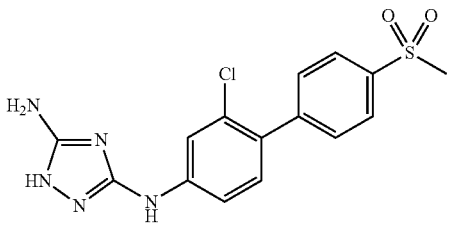 [SMILES: CS(=O)(=O)c1ccc(-c2ccc(Nc3n[nH]c(N)n3)cc2Cl)cc1]

Added ethanol (20 mL) to the 100-mL round-bottomed flask containing (Z)-methyl N-2-chloro-4'-(methylsulfonyl) biphenyl-4-yl-N'-cyanocarbamimidothioate (813 mg, 2.14 mmol, Eq: 1.00). Added hydrazine (408 mg, 0.4 mL, 12.7 mmol, Eq: 5.96) and heated to 95° C. After 4 h, the HPLC showed no starting material remaining. Cool to room temperature. Removed the solvent in vacuo. Obtained 778 mg (98%) of N*3*-(2-Chloro-4'-methanesulfonyl-biphenyl-4-yl)-1H-[1,2,4]triazole-3,5-diamine as a white solid. MS calcd. for C15H14ClN5O2S [(M+H)+] 364.1, obsd. 363.9.

N*3*-(2,2'-Dichloro-biphenyl-4-yl)-1H-[1,2,4]triazole-3,5-diamine (Compound 155)

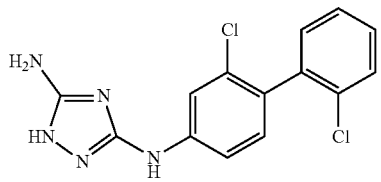 [SMILES: Nc1nc(Nc2ccc(-c3ccccc3Cl)c(Cl)c2)n[nH]1]

2,2'-dichlorobiphenyl-4-amine

Purged a 3-neck, 100-mL round-bottomed flask, fitted with a condenser, glass stopper, and rubber septum, with argon. Charged 4-bromo-3-chloroaniline (1.0 g, 4.84 mmol, Eq: 1.00; from Oakwood), 2-chlorophenylboronic acid (914 mg, 5.84 mmol, Eq: 1.21), tetrakis(triphenylphosphine)palladium (0) (563.6 mg, 488 µmol, Eq: 0.101), toluene (20 mL), ethanol (4 mL), and 2 M sodium carbonate (10 mL, 20.0 mmol, Eq: 4.13) into the reaction vessel while purging with argon. Heated at 110° C. overnight. HPLC after 18 h showed that some starting material remained. Cooled the reaction mixture to room temperature and added more 2-chlorophenylboronic acid (450 mg, 2.88 mmol, Eq: 0.594) and tetrakis(triphenylphosphine)palladium (0) (280 mg, 0.242 mmol, Eq: 0.050). Heated the mixture to 110° C. After 6 h, the reaction was complete according to HPLC. Cooled to room temperature. Diluted with ethyl acetate and washed with water and saturated sodium chloride solution. Dried over Sodium sulfate, filtered, and concentrated onto Celite. Purified using an 80 g silica gel column on an Intelliflash 280; collected peaks only in 28 mL fractions at 53 mL/min; equilibrated with hexanes; dry loaded; eluted 2 min with hexanes; increased from 0-25% ethyl acetate/hexanes over 20 min; held at 25% for 12 min. Obtained 1.09 g (91%) of 2,2'-dichlorobiphenyl-4-amine as a yellow oil that slowly crystallized into a dark yellow solid.

2,2'-dichloro-4-isothiocyanatobiphenyl

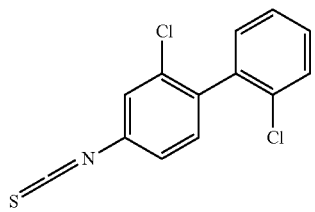

Purged the 250-mL round-bottomed flask containing 2,2'-dichlorobiphenyl-4-amine (1.09 g, 4.58 mmol, Eq: 1.00) with argon. Added dichloromethane (40 mL) and 1,1'-thiocarbonyldiimidazole (1.14 g, 6.41 mmol, Eq: 1.4) in one portion at room temperature. Stirred over the weekend. TLC in 1:1 ethyl acetate/hexanes confirmed the starting material had been consumed. Diluted the reaction mixture with dichloromethane, then concentrated onto Celite. Purified using an 80 g silica gel column on an Intelliflash 280; collected peaks only in 28 mL fractions at 53 mL/min; equilibrated with hexanes; dry loaded; eluted 2 min with 100% hexanes; increased from 0-10% ethyl acetate, hexanes over 20 min. Obtained 956 mg (74%) of 2,2'-dichloro-4-isothiocyanatobiphenyl as a clear, colorless oil.

(Z)-methyl N'-cyano-N-(2,2'-dichlorobiphenyl-4-yl)carbamimidothioate

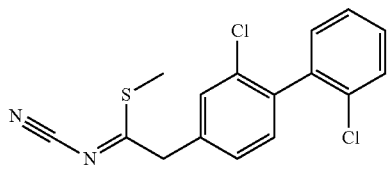 [SMILES: CS/C(Cc1ccc(-c2ccccc2Cl)c(Cl)c1)=N\C#N]

Charged cyanamide (295 mg, 7.02 mmol, Eq: 2.06) into a 25-mL round-bottomed flask while purging with argon. Added 0.5 M sodium methoxide in methanol (8.19 mL, 4.09 mmol, Eq: 1.2) and stirred for 15 min. Meanwhile, added methanol (20 mL) to the 100-mL round-bottomed flask containing 2,2'-dichloro-4-isothiocyanatobiphenyl (956 mg, 3.41 mmol, Eq: 1.00). Transferred the cyanamide mixture to the starting material mixture via syringe. Stirred at room temperature for 1 h, then added iodomethane (969 mg, 0.427 mL, 6.83 mmol, Eq: 2.00) and stirred overnight at room temperature. HPLC and LC/MS showed that the reaction was complete. Placed in the freezer for 2 h, then filtered rinsing with cold methanol. Air dried the solid for 2 h. Obtained 675 mg (59%) of (Z)-methyl N'-cyano-N-(2,2'-dichlorobiphenyl-4-yl)carbamimidothioate as a white solid.

N*3*-(2,2'-Dichloro-biphenyl-4-yl)-1H-[1,2,4]triazole-3,5-diamine (Compound 155)

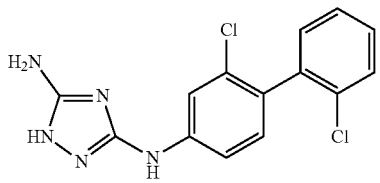 [SMILES: Nc1nc(Nc2ccc(-c3ccccc3Cl)c(Cl)c2)n[nH]1]

Added ethanol (20 mL) to the 100-mL round-bottomed flask that contained (Z)-methyl N'-cyano-N-(2,2'-dichlorobiphenyl-4-yl)carbamimidothioate (675 mg, 2.01 mmol, Eq: 1.00). Added hydrazine (322 mg, 0.315 mL, 10.0 mmol, Eq: 5.00) and heated at reflux (95° C.). After 3 h, HPLC showed all the starting material had been consumed. Removed the solvent in vacuo. Dried in a drying pistol under high vacuum at 50° C. overnight. Obtained 622.6 mg (97%) of N*3*-(2,2'-Dichloro-biphenyl-4-yl)-1H-[1,2,4]triazole-3,5-diamine as a white solid. MS calcd. for C14H11Cl2N5 [(M+H)+] 320.0, obsd. 319.9.

N*3*-(2-Chloro-2'-fluoro-4'-methylsulfanyl-biphenyl-4-yl)-1H-[1,2,4]triazole-3,5-diamine (Compound 156)

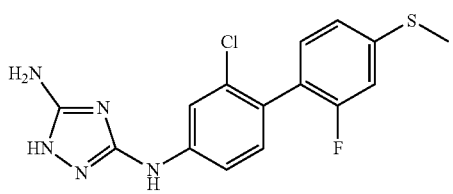 [SMILES: CSc1ccc(-c2ccc(Nc3n[nH]c(N)n3)cc2Cl)c(F)c1]

2-chloro-2'-fluoro-4'-(methylthio)biphenyl-4-amine

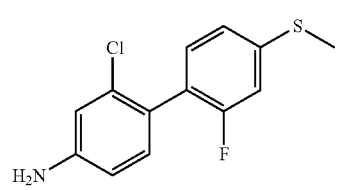

Purged a 2-neck, 100-mL round-bottomed flask (fitted with a condenser) with argon. While purging with argon charged 4-bromo-3-chloroaniline (500.6 mg, 2.42 mmol, Eq: 1.00), 2-fluoro-4-(methylthio)phenylboronic acid (728.8 mg, 3.92 mmol, Eq: 1.62), tetrakis(triphenylphosphine)palladium (0) (561.2 mg, 486 µmol, Eq: 0.200), toluene (12 mL), ethanol (2.4 mL), and 2 M sodium carbonate (6.0 mL, 12.0 mmol, Eq: 4.95) into the round-bottomed flask. Heated at 95° C. overnight. After ~19 h of heating, HPLC showed most of the starting material consumed. Heated for another 5 h, but the HPLC looked about the same. Cooled to room temperature. Diluted with ethyl acetate, and washed with water and saturated sodium chloride solution. Dried over sodium sulfate overnight. Filtered and concentrated onto Celite. Purified using an 80 g silica gel column on an Intelliflash 280; collected peaks only in 28 mL fractions at 53 mL/min; equilibrated with hexanes; dry loaded; eluted 2 min with hexanes; increased from 0-25% ethyl acetate/hexanes over 26 min; held at 25% for 7 min. Obtained 514 mg (79%) of 2-chloro-2'-fluoro-4'-(methylthio)biphenyl-4-amine as a yellow oil.

(2'-chloro-2-fluoro-4'-isothiocyanatobiphenyl-4-yl)(methyl)sulfane

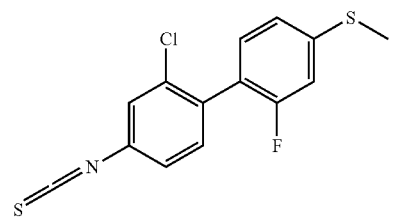

Added dichloromethane (10 mL) to the 50-mL round-bottomed flask containing 2-chloro-2'-fluoro-4'-(methylthio)biphenyl-4-amine (510 mg, 1.9 mmol, Eq: 1.00), and began stirring. Charged 1,1'-thiocarbonyldiimidazole (511 mg, 2.87 mmol, Eq: 1.51) into the mixture in one portion at room temperature. Stirred for 1.5 h and took an HPLC and the starting material had been consumed. Diluted with dichloromethane and concentrated onto Celite. Purified using a 60 g silica gel column on an Intelliflash 280; collected peaks only in 28 mL fractions at 40 mL/min; equilibrated with hexanes; dry loaded; eluted 2 min with hexanes; increased from 0-15% ethyl acetate/hexanes over 20 min. The run was stopped after 10 min because the product had eluted at 6% ethyl acetate/hexanes. Obtained 317 mg (51% yield) of (2'-chloro-2-fluoro-4'-isothiocyanatobiphenyl-4-yl)(methyl)sulfane as colorless oil.

methyl N-2-chloro-2'-fluoro-4'-(methylthio)biphenyl-4-yl-N'-cyanocarbamimidothioate

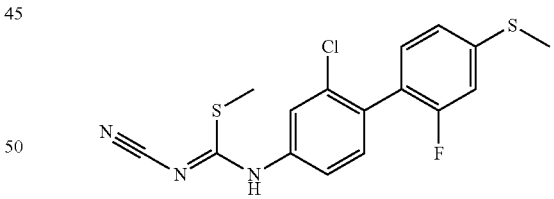

To a 10-mL round-bottomed flask, charged cyanamide (76.2 mg, 1.81 mmol, Eq: 1.8) while purging with argon. Added 0.5 M sodium methoxide in methanol (2.11 mL, 1.06 mmol, Eq: 1.05) to the round-bottomed flask and stirred at room temperature for ~15 min. Meanwhile, added methanol (10 mL) and toluene (5.00 mL) to the 100-mL round-bottomed flask containing (2'-chloro-2-fluoro-4'-isothiocyanatobiphenyl-4-yl)(methyl)sulfane (312 mg, 1.01 mmol, Eq: 1.00) while purging with argon. Combined the cyanamide mixture with the starting material mixture via syringe transfer. Stirred at room temperature for ~50 min, then added iodomethane (286 mg, 126 µL, 2.01 mmol, Eq: 2.0) and stirred at room temperature. After about 1 h solids began to crash out. After another 20 min it appeared the solids stopped crashing out. Filtered off the solids and washed with cold methanol. Air dried for about 20 min. Obtained 139 mg (36% yield) of desired product as a white solid. The filtrate was place in the freezer for 6 days. Filtered off the resulting solids and obtained 78.8 mg of desired product as a white solid. Obtained a total of 217.8 mg (59.2%) of methyl N-2-chloro-2'-fluoro-4'-(methylthio)biphenyl-4-yl-N'-cyanocarbamimidothioate as a white solid.

N*3*-(2-Chloro-2'-fluoro-4'-methylsulfanyl-biphenyl-4-yl)-1H-[1,2,4]triazole-3,5-diamine (Compound 156)

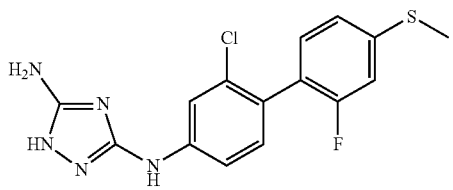 [SMILES: CSc1ccc(-c2ccc(Nc3n[nH]c(N)n3)cc2Cl)c(F)c1]

Added ethanol (10 mL) and hydrazine (60.9 mg, 59.6 µL, 1.9 mmol, Eq: 5.00) to the 50-mL round-bottomed flask containing methyl N-2-chloro-2'-fluoro-4'-(methylthio)biphenyl-4-yl-N'-cyanocarbamimidothioate (139 mg, 380 µmol, Eq: 1.00). Heated at reflux for 2 h. HPLC confirmed that all the starting material had been consumed. Cooled room temperature. Concentrated and obtained a white foam that was redissolved in methanol and reconcentrated in a tared flask. Obtained 130 mg (93%) of N*3*-(2-Chloro-2'-fluoro-4'-methylsulfanyl-biphenyl-4-yl)-1H-[1,2,4]triazole-3,5-diamine as a white solid. MS calcd. for C15H13ClFN5S [(M+H)+] 350.1, obsd. 349.9.

N3-(2-chloro-2'-fluoro-4'-(methylsulfonyl)biphenyl-4-yl)-1H-1,2,4-triazole-3,5-diamine (Compound 157)

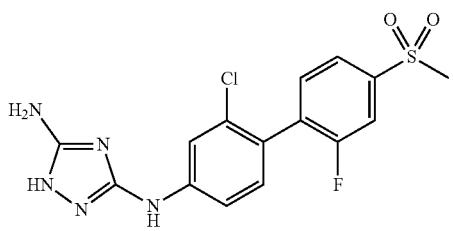 [SMILES: CS(=O)(=O)c1ccc(-c2ccc(Nc3n[nH]c(N)n3)cc2Cl)c(F)c1]

Charged N3-(2-chloro-2'-fluoro-4'-(methylthio)biphenyl-4-yl)-1H-1,2,4-triazole-3,5-diamine (120 mg, 343 µmol, Eq: 1.00; compound 156) and methanol (5 mL) into a 50-mL round-bottomed flask. Heated the mixture at 60° C. for 20 h; HPLC and LC/MS showed sulfone product only. Cooled to room temperature. Diluted with ethyl acetate and filtered off the solids. Washed the filtrate with water and saturated sodium chloride. Dried over sodium sulfate, filtered and concentrated. Purified by prep-HPLC. Obtained 17.1 mg (13%) of N3-(2-chloro-2'-fluoro-4'-(methylsulfonyl)biphenyl-4-yl)-1H-1,2,4-triazole-3,5-diamine as a light yellow solid. MS calcd. for C15H13ClFN5O2S [(M+H)+] 382.0, obsd. 381.9.

4'-(5-amino-1H-1,2,4-triazol-3-ylamino)-2',6'-dichlorobiphenyl-3-carboxamide (Compound 158)

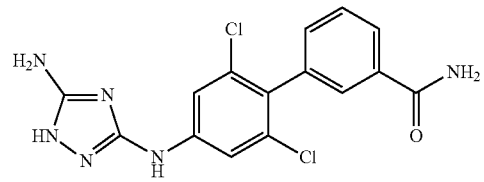 [SMILES: NC(=O)c1cccc(-c2c(Cl)cc(Nc3n[nH]c(N)n3)cc2Cl)c1]

While purging with argon, charged N3-(4-bromo-3,5-dichlorophenyl)-1H-1,2,4-triazole-3,5-diamine Intermediate 2 (202.9 mg, 628 µmol, Eq: 1.00), 3-carbamoylphenylboronic acid (163.3 mg, 990 µmol, Eq: 1.58), potassium carbonate (349.7 mg, 2.53 mmol, Eq: 4.03), tetrakis(triphenylphosphine)palladium (0) (110.0 mg, 95.2 µmol, Eq: 0.152), and dioxane (3.0 mL) into a 15-mL seal tube. Sealed the reaction vessel and heated for 20 h at 120° C. Cooled the mixture to room temperature, removed an aliquot (while purging with argon), and took a HPLC: the reaction was not complete. Added water (0.83 mL) while purging with argon, re-sealed, and heated at 120° C. for 20 h. HPLC showed all the starting material was consumed. Diluted the reaction with water and extracted with ethyl acetate (2×). Combined organics and washed with saturated sodium chloride. Dried over sodium sulfate, filtered, and concentrated onto Celite. Purified using a 23 g spherical silica gel column on an Intelliflash 280; collected peaks only in 9 mL fractions at 32 mL/min; equilibrated with 4% methanol/dichloromethane with 1% ammonium hydroxide; dry loaded; eluted 2 min with 4% methanol/dichloromethane with 1% ammonium hydroxide; increased from 4-10% methanol/dichloromethane with 1% ammonium hydroxide over 15 min; held at 10% methanol/dichloromethane with 1% ammonium hydroxide for 13 min. Obtained 92.6 mg (41%) of 4'-(5-amino-1H-1,2,4-triazol-3-ylamino)-2',6'-dichlorobiphenyl-3-carboxamide as a yellow solid. MS calcd. for C15H12Cl2N6O [(M+H)+] 363.0, obsd. 362.9.

4'-(5-amino-1H-1,2,4-triazol-3-ylamino)-2',6'-dichlorobiphenyl-4-carboxamide (Compound 159)

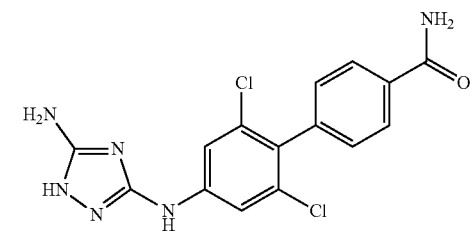 [SMILES: NC(=O)c1ccc(-c2c(Cl)cc(Nc3n[nH]c(N)n3)cc2Cl)cc1]

While purging with argon, charged N3-(4-bromo-3,5-dichlorophenyl)-1H-1,2,4-triazole-3,5-diamine Intermediate 2 (201.1 mg, 623 µmol, Eq: 1.00), 4-carbamoylphenylboronic acid (205 mg, 1.25 mmol, Eq: 2.0), potassium carbonate (348.3 mg, 2.52 mmol, Eq: 4.05), tetrakis(triphenylphosphine)palladium (0) (112 mg, 96.9 µmol, Eq: 0.156), and dioxane (3 mL) into a 15-mL seal tube. Sealed the reaction vessel and heated for 20 h at 120° C. Cooled the mixture to room temperature, removed an aliquot (while purging with argon), and took a HPLC: the reaction was not complete.

Added water (0.83 mL) while purging with argon, re-sealed, and heated at 120° C. for 20 h. HPLC showed no starting material remaining. Diluted the reaction with water and extracted with ethyl acetate (2×). Combined organics and washed with saturated sodium chloride. Dried over sodium sulfate, filtered, and concentrated onto Celite. Purified using a 23 g spherical silica gel column on an Intelliflash 280; collected peaks only in 9 mL fractions at 32 mL/min; equilibrated with 4% methanol/dichloromethane with 1% ammonium hydroxide; dry loaded; eluted 2 min with 4% methanol/dichloromethane with 1% ammonium hydroxide; increased from 4-10% methanol/dichloromethane with 1% ammonium hydroxide over 15 min; held at 10% methanol/dichloromethane with 1% ammonium hydroxide for 9 min. Obtained 39.1 mg (47%) of 4'-(5-amino-1H-1,2,4-triazol-3-ylamino)-2',6'-dichlorobiphenyl-4-carboxamide as a yellow solid. MS calcd. for C15H12Cl2N6O [(M+H)+] 363.0, obsd. 362.9.

4'-(5-Amino-1H-[1,2,4]triazol-3-ylamino)-2',6'-dichloro-biphenyl-4-sulfonic acid (2-hydroxy-ethyl)-amide (Compound 160)

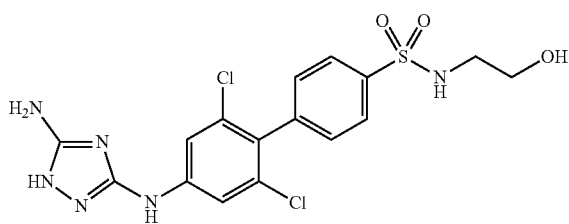 [SMILES: Nc1nc(Nc2cc(Cl)c(-c3ccc(S(=O)(=O)NCCO)cc3)c(Cl)c2)n[nH]1]

While purging a 15-mL seal tube with argon, added N3-(4-bromo-3,5-dichlorophenyl)-1H-1,2,4-triazole-3,5-diamine Intermediate 2 (250 mg, 774 μmol, Eq: 1.00), 4-(N-(2-hydroxyethyl)sulfamoyl)phenylboronic acid (379 mg, 1.55 mmol, Eq: 2.0), potassium carbonate (535 mg, 3.87 mmol, Eq: 5.0), and tetrakis(triphenylphosphine)palladium (0) (179 mg, 155 μmol, Eq: 0.2) to the reaction vessel. Evacuated the seal tube, then back-filled with argon (2×). Added dioxane (5 mL) and water (0.5 mL), then sealed the reaction mixture under argon. Heated at 120° C. for 5 h: TLC in 10% methanol/dichloromethane with 1% ammonium hydroxide showed mostly starting material. Heated at 120° C. for 3 days. TLC appeared to show starting material, but LC/MS showed major spot to be product. Transferred the reaction mixture to a 250-mL round-bottomed flask and removed the solvent in vacuo. Added ethyl acetate, water, and saturated ammonium chloride solution. Transferred to a separatory funnel, shook, and filtered (because of a large amount of insoluble material). Split layers and washed the organics with saturated sodium chloride. Dried over magnesium sulfate, filtered, and concentrated onto Celite. Purified using a 40 g small particle size (15-40 μm) silica gel column on an Intelliflash 280; collected peaks only in 9 mL fractions at 35 mL/min; equilibrated with 4% methanol/dichloromethane with 1% ammonium hydroxide; dry loaded; eluted 3 min with 4% methanol/dichloromethane with 1% ammonium hydroxide; increased from 4-10% methanol/dichloromethane with 1% ammonium hydroxide over 21 min; held at 10% for 21 min. Obtained 70 mg (20%) of 4'-(5-Amino-1H-[1,2,4]triazol-3-ylamino)-2',6'-dichloro-biphenyl-4-sulfonic acid (2-hydroxy-ethyl)-amide as a light brown solid. MS calcd. for C16H16Cl2N6O3S [(M+H)+] 443.0, obsd. 442.9.

4'-(5-Amino-1H-[1,2,4]triazol-3-ylamino)-2'-chloro-6'-trifluoromethyl-biphenyl-4-sulfonic acid (2-hydroxy-ethyl)-amide (Compound 161)

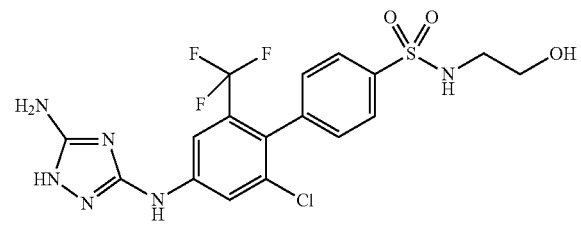 [SMILES: Nc1nc(Nc2cc(Cl)c(-c3ccc(S(=O)(=O)NCCO)cc3)c(C(F)(F)F)c2)n[nH]1]

Purged a 15-mL seal tube with argon and added N3-(4-bromo-3-chloro-5-(trifluoromethyl)phenyl)-1H-1,2,4-triazole-3,5-diamine Intermediate 1 (300 mg, 841 μmol, Eq: 1.00), 4-(N-(2-hydroxyethyl)sulfamoyl)-phenylboronic acid (311 mg, 1.27 mmol, Eq: 1.51), and tetrakis(triphenylphosphine)palladium (0) (167 mg, 145 μmol, Eq: 0.172). Evacuated the tube and back-filled with argon (3×). Added dioxane (2.5 mL), 1,2-dimethoxyethane (2.5 mL), and 3 M potassium carbonate solution (1.20 mL, 3.6 mmol, Eq: 4.28), then pulled vacuum for ~15 sec and back-filled with argon (2×). Heated the mixture at 130° C. for 18 h. Cooled to room temperature, removed an aliquot, and took a TLC in 10% methanol/dichloromethane with 1% ammonium hydroxide. The TLC looked like starting material only; LC/MS showed that no starting material remained and the major peak was the product. Diluted the reaction mixture with ethyl acetate and washed with water. Split layers and extracted the aqueous layer with ethyl acetate. Combined organics and washed with 50% saturated sodium chloride solution. Split layers and dried the organics over sodium sulfate, filtered, and concentrated onto Celite. Purified using a 24 g silica gel column on an Intelliflash 280; collected peaks only in 9 mL fractions at 35 mL/min (~1.5 min/CV); equilibrated with 2% methanol/ethyl acetate with 1% ammonium hydroxide; dry loaded; eluted 3 min with 2% methanol/ethyl acetate with 1% ammonium hydroxide; increased from 2-10% methanol/ethyl acetate with 1% ammonium hydroxide over 24 min; held at 10% methanol/ethyl acetate with 1% ammonium hydroxide for 11 min. Obtained 106 mg (25%) of 4'-(5-Amino-1H-[1,2,4]triazol-3-ylamino)-2'-chloro-6'-trifluoromethyl-biphenyl-4-sulfonic acid (2-hydroxy-ethyl)-amide as a yellow solid. MS calcd. for C17H16ClF3N6O3S [(M+H)+] 477.1, obsd. 476.9.

2-[4'-(5-Amino-1H-[1,2,4]triazol-3-ylamino)-2'-chloro-6'-trifluoromethyl-biphenyl-4-sulfonyl]-ethanol (Compound 162)

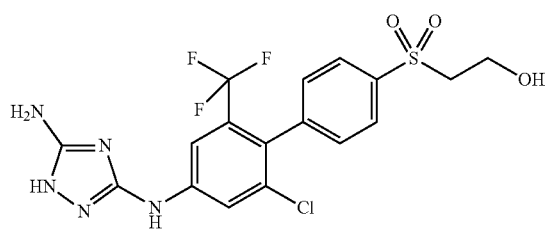 [SMILES: Nc1nc(Nc2cc(Cl)c(-c3ccc(S(=O)(=O)CCO)cc3)c(C(F)(F)F)c2)n[nH]1]

Purged a 15-mL seal tube with argon and added N3-(4-bromo-3-chloro-5-(trifluoromethyl)phenyl)-1H-1,2,4-triazole-3,5-diamine Intermediate 1 (211.7 mg, 594 µmol, Eq: 1.00), 2-(4-(4,4,5,5-tetramethyl-1,3,2-dioxaborolan-2-yl)phenylsulfonyl)ethanol (270 mg, 865 µmol, Eq: 1.46), and tetrakis(triphenylphosphine)palladium (0) (135.7 mg, 117 µmol, Eq: 0.198). Evacuated the tube and back-filled with argon (2×). Added dioxane (2.0 mL), 1,2-dimethoxyethane (2.00 mL), and 3 M potassium carbonate solution (0.8 mL, 2.4 mmol, Eq: 4.04). Bubbled argon through the reaction mixture for several minutes, then heated the mixture at 130° C. for 18 h. Cooled to room temperature, removed an aliquot, and took a TLC in 10% methanol/dichloromethane with 1% ammonium hydroxide. The TLC looked like starting material remained; LC/MS showed that no starting material remained and two major peaks were des-bromo starting material and product. Diluted the reaction mixture with ethyl acetate and washed with 50% saturated ammonium chloride, then with 50% saturated sodium chloride. Dried the organic layer over sodium sulfate, filtered, and concentrated onto Celite. Pre-purified using flash chromatography (4-10% methanol/ethyl acetate with 1% ammonium hydroxide) Obtained 36 mg which was further purified by prep-HPLC. Obtained 15 mg (5.5%) of 2-[4'-(5-Amino-1H-[1,2,4]triazol-3-ylamino)-2'-chloro-6'-trifluoromethyl-biphenyl-4-sulfonyl]-ethanol as an off-white solid. 1H NMR (DMSO-d6) Shift: 11.41 (br. s., 1H), 9.49 (br. s., 1H), 8.08 (s, 1H), 7.87-8.03 (m, 3H), 7.50 (d, J=8.1 Hz, 2H), 6.05 (br. s., 2H), 4.94 (br. s., 1H), 3.69 (d, J=5.3 Hz, 2H), 3.46-3.60 (m, 2H). No MS data.

Procedure 6 tert-butyl 4-(4'-(5-amino-1H-1,2,4-triazol-3-ylamino)-2'-chloro-3-methoxy-6'-(trifluoromethyl)biphenyl-4-ylsulfonamido)piperidine-1-carboxylate (Compound 163)

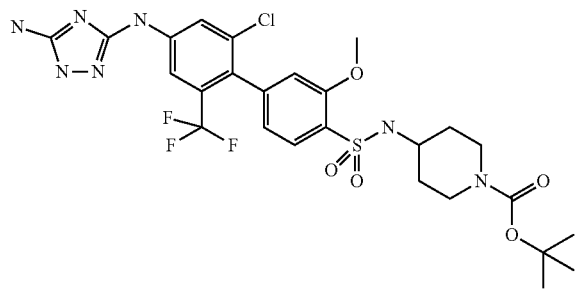 [SMILES: COc1cc(-c2c(Cl)cc(Nc3n[nH]c(N)n3)cc2C(F)(F)F)ccc1S(=O)(=O)NC1CCN(C(=O)OC(C)(C)C)CC1]

4-bromo-2-methoxy-benzenesulfonyl chloride

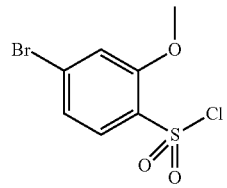

To chlorosulfonic acid (34.9 g, 300 mmol) at 0° C. was slowly added 3-bromoanisole (18.7 g, 100 mmol) maintaining the low temperature. The mixture was stirred at 0° C. for 1 hour and then added dropwisely to crushed ice (800 ml) to give a suspension. This was filtered to give a white solid which was purified by flash chromatography (silica gel, 80 g, 4% EtOAc in hexanes) to give a 1:2 mixture of desired product and an isomer 2-Bromo-4-methoxy-benzenesulfonyl chloride (2.5 g, 9% yield). The filtrate was extracted with EtOAc (3×150 ml). The combined organic solution was washed with water and brine, dried and concentrated to give a white solid as a mixture of 1:3 of desired product and an isomer 2-Bromo-4-methoxy-benzenesulfonyl chloride (6.06 g, 21% yield).

4-4-bromo-2-methoxy-benzenesulfonylamino)-piperidine-1-carboxylic acid tert-butyl ester

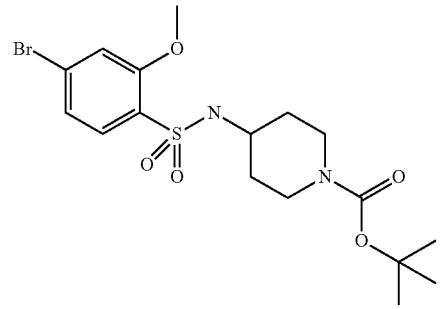 [SMILES: COc1cc(Br)ccc1S(=O)(=O)NC1CCN(C(=O)OC(C)(C)C)CC1]

To a 1:3 mixture of 2-bromo-4-methoxybenzene-1-sulfonyl chloride and 4-bromo-2-methoxybenzene-1-sulfonyl chloride (1.5 g, 5.25 mmol) and Et3N (1.46 ml, 10.5 mmol) in THF (20.0 ml) was added 4-amino-1-Boc-piperidine (2.81 g 14.0 mmol). The reaction was stirred at room temperature overnight. The reaction mixture was washed with 0.5 N HCl solution (2×40 ml), water (20 ml) and brine (25 ml), dried and concentrated to give a white solid as a 1:3 mixture of desired product and the isomer.

4-[2-methoxy-4-(4,4,5,5-tetramethyl-[1,3,2]dioxaborolan-2-yl)-benzenesulfonylamino]-piperidine-1-carboxylic acid tert-butyl ester

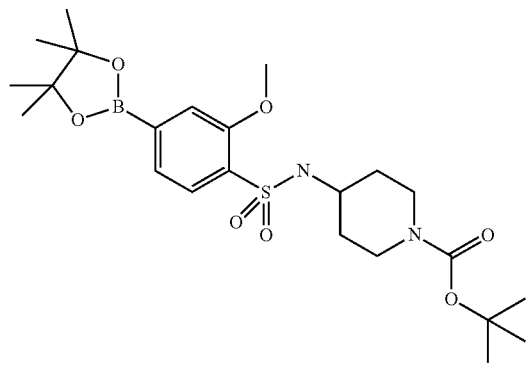 [SMILES: COc1cc(B2OC(C)(C)C(C)(C)O2)ccc1S(=O)(=O)NC1CCN(C(=O)OC(C)(C)C)CC1]

A 1:3 mixture of tert-butyl 4-(4-bromo-2-methoxyphenylsulfonamido)piperidine-1-carboxylate and an isomer (2.98 g, 6.63 mmol), bis(pinacolato)diboron (3.37 g, 13.3 mmol), and potassium acetate (1.95 g, 19.9 mmol) in dioxane (30 ml) was degased with argon and then [1,1-bis(diphenylphosphino)ferrocene]dichloropalladium(II) (291 mg, 398 μmol) was added. The reaction was heated at 105° C. for 18 hours. The reaction mixture was partitioned between EtOAc (35 ml) and 10% NaHCO3 (20 ml) and the layers were separated. The aqueous layer was extracted with EtOAc (2×25 ml). The combined organic solution was dried over Na2SO4, filtered, and concentrated in vacuo. The residue was purified by flash chromatography (silica gel, 80 g, 20% to 40% EtOAc in hexanes) and was triturated with hexanes (2×10 ml) to give a yellow gum as a mixture of desired product and impurity (1 g, ~1:2 ratio).

tert-butyl 4-(4'-(5-amino-1H-1,2,4-triazol-3-ylamino)-2'-chloro-3-methoxy-6'-(trifluoromethyl)biphenyl-4-ylsulfonamido)piperidine-1-carboxylate (Compound 163)

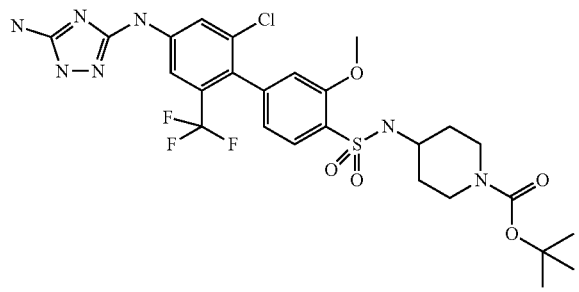 [SMILES: COc1cc(-c2c(Cl)cc(Nc3n[nH]c(N)n3)cc2C(F)(F)F)ccc1S(=O)(=O)NC1CCN(C(=O)OC(C)(C)C)CC1]

A mixture of N3-(4-bromo-3-chloro-5-(trifluoromethyl)phenyl)-1H-1,2,4-triazole-3,5-diamine Intermediate 1 (200 mg, 561 μmol), tert-butyl 4-(2-methoxy-4-(4,4,5,5-tetramethyl-1,3,2-dioxaborolan-2-yl)phenylsulfonamido)piperidine-1-carboxylate (995 mg, 841 μmol) and 3M K2CO3 (374 μl, 1.12 mmol) in dioxane (2.6 ml) and DME (2.6 ml) was degased with argon and then tetrakis(triphenylphosphine)palladium(0) (130 mg, 112 μmol) was added. The reaction was heated in a microwave at 128° C. for 3 hours. The reaction mixture was partitioned between water and EtOAc (3 ml/8 ml), layers separated and the aqueous layer was extracted with EtOAc (3×5 ml). The combined organic solution was dried with Na2SO4, concentrated to give a residue which was purified by flash chromatography (silica gel, 40 g, 3% to 7% MeOH in DCM). Further purification by super fluid chromatography gave a white solid as desired product (73 mg, 20% yield). MS +m/z: 546 (M+H−100)+

4'-(5-amino-1H-1,2,4-triazol-3-ylamino)-N-tert-butyl-2',6'-dichlorobiphenyl-4-sulfonamide (Compound 164)

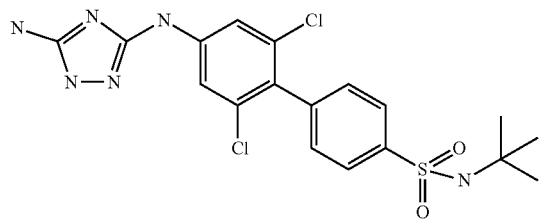 [SMILES: CC(C)(C)NS(=O)(=O)c1ccc(-c2c(Cl)cc(Nc3n[nH]c(N)n3)cc2Cl)cc1]

A mixture of N3-(4-bromo-3,5-dichlorophenyl)-1H-1,2,4-triazole-3,5-diamine Intermediate 2 (200 mg, 619 μmol, intermediate 1), 4-(tert-butylaminosulphonyl)benzeneboronic acid (318 mg, 1.24 mmol, Combi-blocks) and 3M K2CO3 (454 μl, 1.36 mmol) in DME (1.33 ml) and dioxane (1.33 ml) was degased with argon and tetrakis(triphenylphosphine)palladium(0) (71.6 mg, 61.9 μmol) was added. This was heated in the microwave oven at 125° C. for 2 hours. The reaction mixture was diluted with MeOH/EtOAc (1/5), dried over Na2SO4, filtered and concentrated in vacuo. The residue was purified by flash chromatography (silica gel, 24 g, 3% to 7% MeOH in DCM). Further purification by super fluid chromatography gave a white solid as desired product (92 mg, 33% yield). MS +m/z: 455 (M+H)+

Procedure 6

4'-(5-amino-1H-1,2,4-triazol-3-ylamino)-2'-chloro-N-(1,1,1-trifluoro-2-methylpropan-2-yl)-6'-(trifluoromethyl)biphenyl-4-sulfonamide (Compound 165)

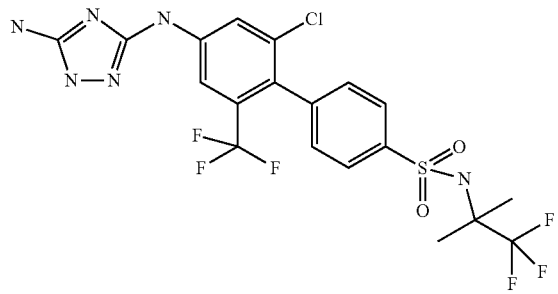 [SMILES: CC(C)(NS(=O)(=O)c1ccc(-c2c(Cl)cc(Nc3n[nH]c(N)n3)cc2C(F)(F)F)cc1)C(F)(F)F]

4-bromo-N-(1,1,1-trifluoro-2-methylpropan-2-yl)benzenesulfonamide

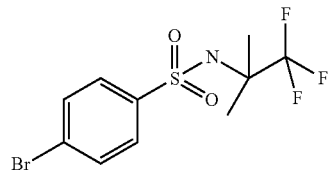 [SMILES: CC(C)(NS(=O)(=O)c1ccc(Br)cc1)C(F)(F)F]

To a solution of 2,2,2-TRIFLUORO-1,1-DIMETHYL-ETHYLAMINE (1.04 g, 8.22 mmol, Oakwood) and DIPEA (1.26 g, 1.71 ml, 9.78 mmol) in CH2Cl2 (20.0 ml) was added 4-bromobenzenesulfonyl chloride (2 g, 7.83 mmol). The reaction was stirred at RT for 4 days, washed with 1N HCl solution (1×25 ml), water (20 ml) and brine (20 ml), dried and concentrated to give a white solid as desired product (245 mg, 9% yield).

4-(4,4,5,5-tetramethyl-1,3,2-dioxaborolan-2-yl)-N-(1,1,1-trifluoro-2-methylpropan-2-yl)benzenesulfonamide

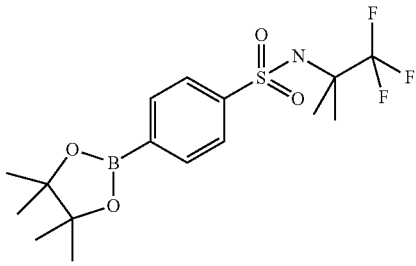 [SMILES: CC(C)(NS(=O)(=O)c1ccc(B2OC(C)(C)C(C)(C)O2)cc1)C(F)(F)F]

A mixture of 4-bromo-N-(1,1,1-trifluoro-2-methylpropan-2-yl)benzenesulfonamide (240 mg, 693 μmol), bis(pinacolato)diboron (352 mg, 1.39 mmol) and potassium acetate (204 mg, 2.08 mmol) in dioxane (4.00 ml) was degased with argon and then [1,1'-bis(diphenylphosphino)ferrocene]dichloropalladium(II) (50.7 mg, 69.3 μmol) was added. The reaction mixture was heated at 105° C. for 18 hours, partitioned between EtOAc (15 ml) and water (5 ml), and the layers separated. The aqueous layer was extracted with EtOAc (2×10 ml). The combined organic solution was washed with dilute NaHCO3 (2×10 ml), dried over Na2SO4, concentrated to give a residue. The crude material was purified by flash chromatography (silica gel, 24 g, 10% to 30% EtOAc in hexanes) and was triturated with hexanes (1×) to give a white solid as desired product (212 mg, 78% yield).

4'-(5-amino-1H-1,2,4-triazol-3-ylamino)-2'-chloro-N-(1,1,1-trifluoro-2-methylpropan-2-yl)-6'-(trifluoromethyl)biphenyl-4-sulfonamide (Compound 165)

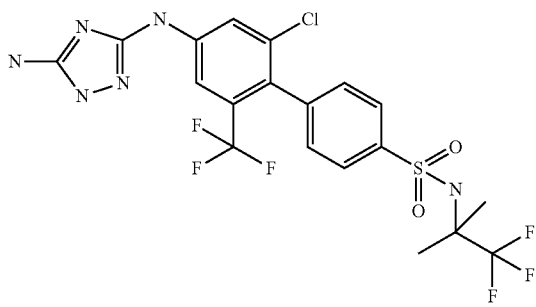 [SMILES: CC(C)(NS(=O)(=O)c1ccc(-c2c(Cl)cc(Nc3n[nH]c(N)n3)cc2C(F)(F)F)cc1)C(F)(F)F]

A mixture of N3-(4-bromo-3-chloro-5-(trifluoromethyl)phenyl)-1H-1,2,4-triazole-3,5-diamine Intermediate 1 (150 mg, 421 μmol), 4-(4,4,5,5-tetramethyl-1,3,2-dioxaborolan-2-yl)-N-(1,1,1-trifluoro-2-methylpropan-2-yl)benzenesulfonamide (220 mg, 559 μmol) and 3M K2CO3 (280 μl, 841 μmol) in DME (1 ml) and dioxane (1 ml) was degased with argon and then tetrakis(triphenylphosphine)palladium(0) (78 mg, 67.5 μmol) was added. This was heated in the microwave at 128° C. for 3 hours. The reaction mixture was partitioned between water and EtOAc (3 ml/8 ml) and the layers were separated. The aqueous layer was extracted with EtOAc (3×5 ml). The combined organic solution was dried over Na2SO4, concentrated to give a residue which was purified by flash chromatography (silica gel, 24 g, 4% to 10% MeOH in DCM). Further purification by super fluid chromatography and freeze drying gave a white foam as desired product (62.1 mg, 27% yield). MS +m/z: 543 (M+H)+

Procedure 6 tert-butyl 4-(4'-(5-amino-1H-1,2,4-triazol-3-ylamino)-2'-chloro-4-methoxy-6'-(trifluoromethyl)biphenyl-3-ylsulfonyl)piperazine-1-carboxylate (Compound 166)

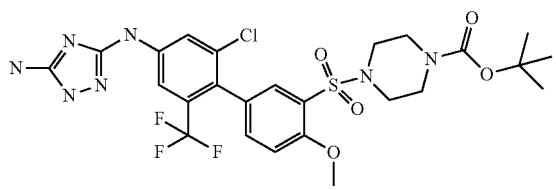 [SMILES: COc1ccc(-c2c(Cl)cc(Nc3n[nH]c(N)n3)cc2C(F)(F)F)cc1S(=O)(=O)N1CCN(C(=O)OC(C)(C)C)CC1]

tert-butyl 4-(5-bromo-2-methoxyphenylsulfonyl)piperazine-1-carboxylate

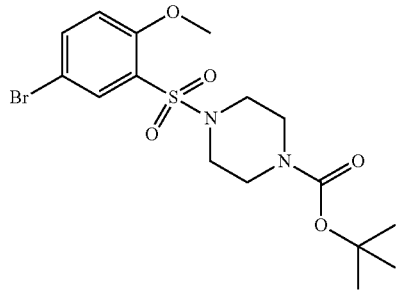 [SMILES: COc1ccc(Br)cc1S(=O)(=O)N1CCN(C(=O)OC(C)(C)C)CC1]

To a mixture of 1-Boc-piperazine (342 mg, 1.84 mmol, Aldrich) and 5-bromo-2-methoxybenzenesulfonyl chloride (500 mg, 1.75 mmol, Combi-Blocks) in CH2Cl2 (20.0 ml) was added DIPEA (566 mg, 765 μl, 4.38 mmol). The reaction was stirred at room temperature overnight, and washed with 0.5 N HCl (2×10 ml), water (10 ml) and brine (10 ml). This was dried over Na2SO4, filtered and concentrated in vacuo to give a white solid as desired product (720 mg, 94% yield).

tert-butyl 4-(2-methoxy-5-(4,4,5,5-tetramethyl-1,3,2-dioxaborolan-2-yl)phenylsulfonyl)piperazine-1-carboxylate

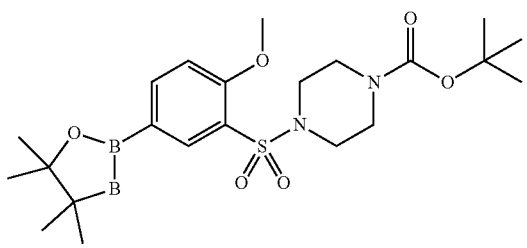

A mixture of tert-butyl 4-(5-bromo-2-methoxyphenylsulfonyl)piperazine-1-carboxylate (710 mg, 1.63 mmol), bis(pinacolato)diboron (828 mg, 3.26 mmol) and potassium acetate (480 mg, 4.89 mmol) in dioxane (4 ml) was degased with argon and then [1,1'-bis(diphenylphosphino)ferrocene]dichloropalladium(II) (70 mg, 95.7 μmol) was added. The reaction was heated at 105° C. for 18 hours, partitioned between EtOAc (25 ml) and 10% NaHCO3 (15 ml), and the layers were separated. The aqueous layer was extracted with EtOAc (2×10 ml). The combined organic solution was dried over Na2SO4, concentrated to give a residue. The crude material was purified by flash chromatography (silica gel, 40 g, 10% to 30% EtOAc in hexanes) to give a white solid as desired product (596 mg, 68% yield).

tert-butyl 4-(4'-(5-amino-1H-1,2,4-triazol-3-ylamino)-2'-chloro-4-methoxy-6'-(trifluoromethyl)biphenyl-3-ylsulfonyl)piperazine-1-carboxylate (Compound 166)

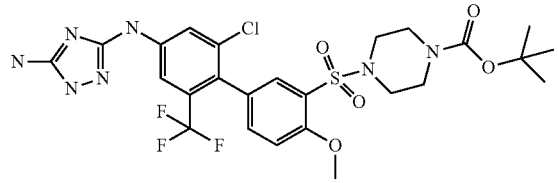 [SMILES: COc1ccc(-c2c(Cl)cc(Nc3n[nH]c(N)n3)cc2C(F)(F)F)cc1S(=O)(=O)N1CCN(C(=O)OC(C)(C)C)CC1]

A mixture of N3-(4-bromo-3-chloro-5-(trifluoromethyl)phenyl)-1H-1,2,4-triazole-3,5-diamine Intermediate 1 (240 mg, 673 μmol), tert-butyl 4-(2-methoxy-5-(4,4,5,5-tetramethyl-1,3,2-dioxaborolan-2-yl)phenylsulfonyl)piperazine-1-carboxylate (585 mg, 1.21 mmol) and 3M K2CO3 (449 μl, 1.35 mmol) in DME (1.3 ml) and dioxane (1.3 ml) was degased with argon and then tetrakis(triphenylphosphine)palladium(0) (124 mg, 108 μmol) was added. The reaction was heated in microwave at 128° C. for 3 hours. The reaction mixture was partitioned between water and EtOAc (3 ml/8 ml), layers separated and the aqueous layer was extracted with EtOAc (3×5 ml). The combined organic solution was dried with Na2SO4, concentrated to give a residue which was purified by flash chromatography (silica gel, 24 g, 3% to 7% MeOH in DCM). Further purification by super fluid chromatography and freeze drying gave a white foam as desired product (130.6 mg, 31% yield). MS +m/z: 632 (M+H)+

4'-(5-amino-1H-1,2,4-triazol-3-ylamino)-2'-chloro-N-(trans-4-hydroxycyclohexyl)-3-methoxy-6'-(trifluoromethyl)biphenyl-4-sulfonamide (Compound 167)

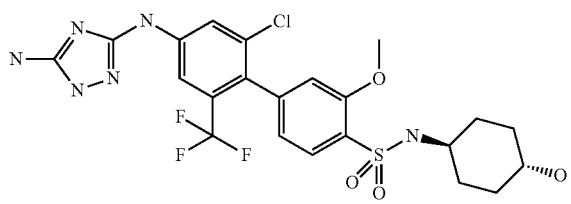 [SMILES: COc1cc(-c2c(Cl)cc(Nc3n[nH]c(N)n3)cc2C(F)(F)F)ccc1S(=O)(=O)N[C@H]1CC[C@H](O)CC1]

4-Bromo-N-(trans-4-hydroxy-cyclohexyl)-2-methoxy-benzenesulfonamide

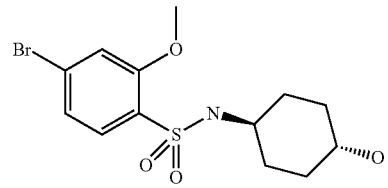 [SMILES: COc1cc(Br)ccc1S(=O)(=O)N[C@H]1CC[C@H](O)CC1]

A 1:2 mixture of 4-bromo-2-methoxybenzene-1-sulfonyl chloride and an isomer 2-bromo-4-methoxybenzene-1-sulfonyl chloride (800 mg, 2.8 mmol) and Et3N (709 mg, 976 μl, 7.00 mmol) were combined with THF (12.0 ml). Trans-4-aminocyclohexanol (565 mg, 4.9 mmol) was added. The reaction was stirred at room temperature for overnight. The reaction mixture was washed with 0.5 N HCl solution (20 ml), water (20 ml) and brine (25 ml), dried, concentrated and was triturated with hexanes (1×) to give a white solid as a mixture of the desired product and the isomer (1.5 g, 98% yield).

N-(trans-4-Hydroxy-cyclohexyl)-2-methoxy-4-(4,4,5,5-tetramethyl-[1,3,2]dioxaborolan-2-yl)-benzenesulfonamide

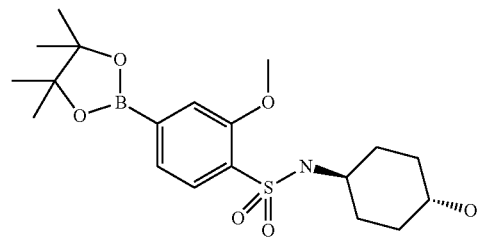 [SMILES: COc1cc(B2OC(C)(C)C(C)(C)O2)ccc1S(=O)(=O)N[C@H]1CC[C@H](O)CC1]

A 1:2 mixture of 4-bromo-N-(trans-4-hydroxycyclohexyl)-2-methoxybenzenesulfonamide and the isomer (1.5 g, 4.12 mmol), bis(pinacolato)diboron (2.09 g, 8.24 mmol), and potassium acetate (1.21 g, 12.4 mmol) in dioxane (21.4 ml) was degased with argon and then [1,1'-bis(diphenylphosphino)ferrocene]dichloropalladium(II) (181 mg, 247 μmol) was added. The reaction was heated at 105° C. for 18 hours. The reaction was diluted with EtOAc (35 ml) and washed with 10% NaHCO3 (2×20 ml). The organic solution was dried over Na2SO4, filtered and concentrated to give a residue. The residue was purified by flash chromatography (silica gel, 80 g, 2% to 7% MeOH in DCM) and then was triturated with hexanes (2×10 ml) to give a light brown solid as a mixture of desired product and the isomer byproduct (335 mg, about 1:3 ratio).

4'-(5-amino-1H-1,2,4-triazol-3-ylamino)-2'-chloro-N-(trans-4-hydroxycyclohexyl)-3-methoxy-6'-(trifluoromethyl)biphenyl-4-sulfonamide (Compound 167)

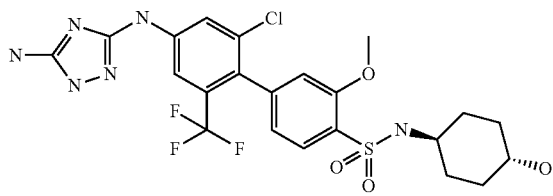 [SMILES: COc1cc(-c2c(Cl)cc(Nc3n[nH]c(N)n3)cc2C(F)(F)F)ccc1S(=O)(=O)N[C@H]1CC[C@H](O)CC1]

A mixture of N3-(4-bromo-3-chloro-5-(trifluoromethyl)phenyl)-1H-1,2,4-triazole-3,5-diamine Intermediate 1 (180 mg, 505 µmol), N-(trans-4-hydroxycyclohexyl)-2-methoxy-4-(4,4,5,5-tetramethyl-1,3,2-dioxaborolan-2-yl)benzenesulfonamide (332 mg, 808 µmol) and 3M K2CO3 (337 µl, 1.01 mmol) in dioxane (1 ml) and DME (1 ml) was degased with argon and then tetrakis(triphenylphosphine)palladium(0) (87.5 mg, 75.7 µmol) was added. The reaction was heated in a microwave at 128° C. for 3 hours. The reaction was partitioned between water and EtOAc (3 ml/8 ml) and the layers were separated. The aqueous layer was extracted with EtOAc (3×5 ml). The combined organic solution was dried with Na2SO4, concentrated to give a residue which was purified by flash chromatography (silica gel, 24 g, 4% to 10% MeOH in DCM). Further purification by super fluid chromatography and freeze drying afforded a white foam as desired product (16.9 mg, 6% yield). MS +m/z: 561 (M+H)+

4'-(5-amino-1H-1,2,4-triazol-3-ylamino)-2'-chloro-4-methoxy-N-(tetrahydro-2H-pyran-4-yl)-6'-(trifluoromethyl)biphenyl-3-sulfonamide (Compound 168)

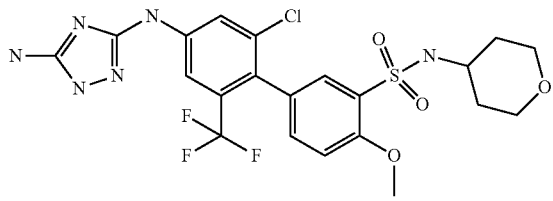 [SMILES: COc1ccc(-c2c(Cl)cc(Nc3n[nH]c(N)n3)cc2C(F)(F)F)cc1S(=O)(=O)NC1CCOCC1]

5-bromo-2-methoxy-N-(tetrahydro-2H-pyran-4-yl)benzenesulfonamide

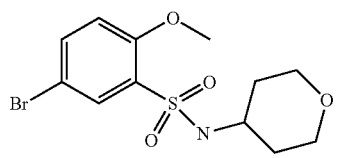 [SMILES: COc1ccc(Br)cc1S(=O)(=O)NC1CCOCC1]

To a solution of 5-bromo-2-methoxybenzenesulfonyl chloride (500 mg, 1.75 mmol) and Et3N (195 mg, 268 µl, 1.93 mmol) in THF (10 ml) was added 4-aminotetrahydropyran (266 mg, 2.63 mmol) and the reaction was stirred at RT overnight. The reaction mixture was washed with 0.5 N HCl solution (2×20 ml), water (20 ml) and brine (15 ml), dried and concentrated in vacuo. The crude material was triturated with hexanes (1×20 ml) to give a white solid as desired product (325 mg, 53% yield).

2-methoxy-N-(tetrahydro-2H-pyran-4-yl)-5-(4,4,5,5-tetramethyl-1,3,2-dioxaborolan-2-yl)benzenesulfonamide

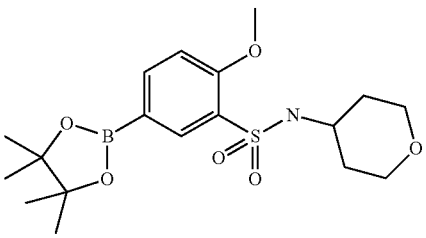 [SMILES: COc1ccc(B2OC(C)(C)C(C)(C)O2)cc1S(=O)(=O)NC1CCOCC1]

A mixture of bis(pinacolato)diboron (464 mg, 1.83 mmol), 5-bromo-2-methoxy-N-(tetrahydro-2H-pyran-4-yl)benzenesulfonamide (320 mg, 914 µmol) and potassium acetate (269 mg, 2.74 mmol) in dioxane (7 ml) was degased with argon and [1,1'-bis(diphenylphosphino)ferrocene]dichloropalladium(II) (50 mg, 68.3 µmol) was added. The reaction was heated at 105° C. for 18 hour, partitioned between EtOAc (15 ml) and 10% NaHCO3 (10 ml) and the layers were separated. The aqueous layer was extracted with EtOAc (2×10 ml). The combined organic solution was dried over Na2SO4, concentrated to give a residue, which was triturated with hexanes, then DCM/MeOH/Hexanes to give a brownish solid as desired product (208 mg, 57% yield).

The solution from trituration was concentrated and purified by flash chromatography (silica gel, 24 g, 20% to 70% EtOAc in Hexanes) to give a white solid as desired product (90 mg, 25% yield).

4'-(5-amino-1H-1,2,4-triazol-3-ylamino)-2'-chloro-4-methoxy-N-(tetrahydro-2H-pyran-4-yl)-6'-(trifluoromethyl)biphenyl-3-sulfonamide (Compound 168)

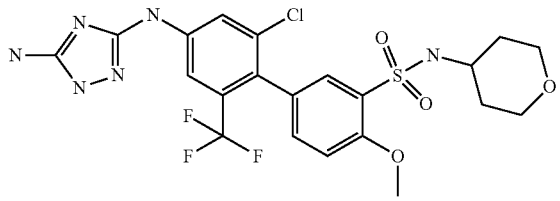 [SMILES: COc1ccc(-c2c(Cl)cc(Nc3n[nH]c(N)n3)cc2C(F)(F)F)cc1S(=O)(=O)NC1CCOCC1]

A mixture of N3-(4-bromo-3-chloro-5-(trifluoromethyl)phenyl)-1H-1,2,4-triazole-3,5-diamine Intermediate 1 (160 mg, 449 µmol), 2-methoxy-N-(tetrahydro-2H-pyran-4-yl)-5-(4,4,5,5-tetramethyl-1,3,2-dioxaborolan-2-yl)benzenesulfonamide (285 mg, 718 µmol) and 3M K2CO3 (299 µl, 898 µmol) in DME (1 ml) and dioxane (1 ml) was degased with argon and tetrakis(triphenylphosphine)palladium(0) (75.0 mg, 64.9 µmol) was added. This was heated in microwave at 128° C. for 3 hours. The reaction was partitioned between water and EtOAc (3 ml/8 ml) and the layers were separated. The aqueous layer was extracted with EtOAc (3×5 ml). The combined organic solution was dried over Na2SO4, concentrated to give a residue which was purified by flash chromatography (silica gel, 24 g, 4% to 10% MeOH in DCM). Further purification by super fluid chromatography gave a white solid as desired product (75 mg, 31% yield). MS +m/z: 547 (M+H)+

4'-(5-amino-1H-1,2,4-triazol-3-ylamino)-2'-chloro-N-cyclopropyl-6'-(trifluoromethyl)biphenyl-4-sulfonamide (Compound 169)

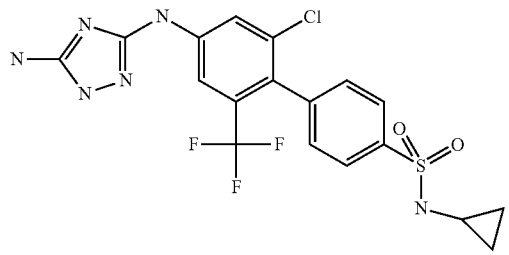 [SMILES: Nc1nc(Nc2cc(Cl)c(-c3ccc(S(=O)(=O)NC4CC4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), 4-(N-cyclopropylsulfamoyl)phenylboronic acid (162 mg, 673 µmol) and 3M K2CO3 (280 µl, 841 µmol) in DME (1 ml) and dioxane (1 ml) was degased with argon and tetrakis(triphenylphosphine)palladium(0) (80 mg, 69.2 µmol) was added. This was heated in microwave at 125° C. for 3 hours and then partitioned between water and EtOAc (3 ml/8 ml). The layers were separated and the aqueous was extracted with EtOAc (3×5 ml). The combined organic solution was dried over Na2SO4, concentrated to give a residue which was purified by flash chromatography (silica gel, 24 g, 3% to 8% MeOH in DCM). Further purification by super fluid chromatography and freeze drying gave a white foam as desired product (5.3 mg, 2.53% yield). MS +m/z: 473 (M+H)+

N3-(2-chloro-4'-(pyrrolidin-1-ylsulfonyl)-6-(trifluoromethyl)biphenyl-4-yl)-1H-1,2,4-triazole-3,5-diamine (Compound 170)

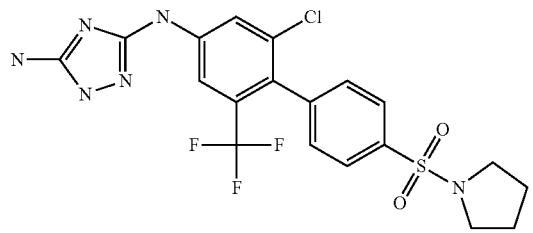 [SMILES: Nc1nc(Nc2cc(Cl)c(-c3ccc(S(=O)(=O)N4CCCC4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), (4-boronophenyl)(pyrrolidin-1-yl)sulfone (268 mg, 1.05 mmol) and 3M K2CO3 (351 µl, 1.05 mmol) in DME (1 ml) and dioxane (1 ml) was degased with argon and tetrakis(triphenylphosphine)palladium(0) (97.2 mg, 84.1 µmol) was added. This was heated in microwave at 125° C. for 3 hours. The reaction mixture was diluted with MeOH, filtered, and concentrated in vacuo. The residue was purified by flash chromatography (silica gel, 24 g, 3% to 7% MeOH in DCM). Further purification with super fluid chromatography gave an off white solid as desired product (56 mg, 27%). MS +m/z: 487 (M+H)+

4'-(5-amino-1H-1,2,4-triazol-3-ylamino)-2'-chloro-6'-(trifluoromethyl)biphenyl-4-sulfonamide (Compound 171)

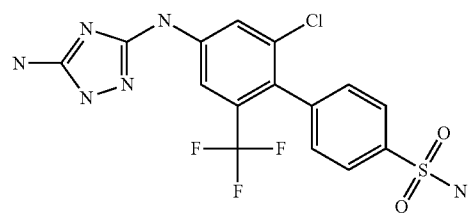 [SMILES: Nc1nc(Nc2cc(Cl)c(-c3ccc(S(N)(=O)=O)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), 4-(4,4,5,5-tetramethyl-1,3,2-dioxaborolan-2-yl)benzenesulfonamide (298 mg, 1.05 mmol) and 3M K2CO3 (351 µl, 1.05 mmol) in DME (1 ml) and dioxane (1 ml) was degased with argon and tetrakis(triphenylphosphine)palladium(0) (97.2 mg, 84.1 µmol) was added. This was heated in microwave at 125° C. for 2 hours, then another 2 hours. The reaction mixture was diluted with MeOH, filtered and concentrated in vacuo. The crude material was purified by flash chromatography (silica gel, 24 g, 4% to 10% MeOH in DCM). Further purification by reversed phase HPLC gave a white foam as TFA salt (5.5 mg). This was partitioned between EtOAc/5% Na2CO3 and the layers were separated. The aqueous layer was extracted with EtOAc (2×5 ml) and the combined organic solution was washed with brine, dried over MgSO4, filtered, concentrated and freeze dried to give a white foam as desired product (2.4 mg, 1.3% yield). MS +m/z: 433 (M+H)+

4'-(5-amino-1H-1,2,4-triazol-3-ylamino)-2'-chloro-N-(3-hydroxycyclobutyl)-6'-(trifluoromethyl)biphenyl-4-sulfonamide (Compound 172)

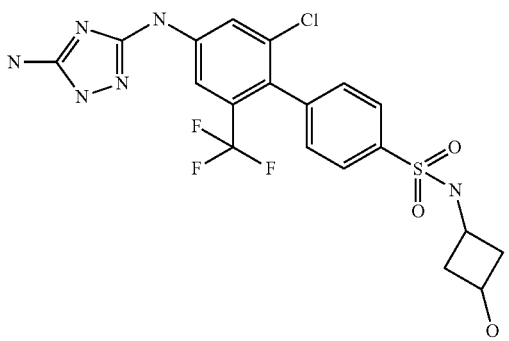 [SMILES: Nc1nc(Nc2cc(Cl)c(-c3ccc(S(=O)(=O)NC4CC(O)C4)cc3)c(C(F)(F)F)c2)n[nH]1]

4-bromo-N-(3-hydroxycyclobutyl)benzenesulfonamide

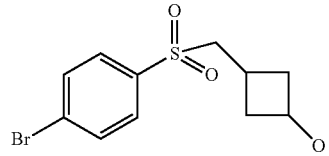 [SMILES: O=S(=O)(CC1CC(O)C1)c1ccc(Br)cc1]

To a solution of 3-aminocyclobutanol hydrochloride (120 mg, 971 µmol) and DIPEA (740 mg, 5.73 mmol) in CH2Cl2 (5 ml) was added 4-bromobenzenesulfonyl chloride (248 mg, 971 µmol, Fluka). The reaction was stirred at RT overnight, washed with 0.5 N HCl solution (2×5 ml), water (6 ml) and brine (5 ml), dried and concentrated to give a residue. The crude material was purified by flash chromatography (silica gel, 12 g, 2% to 5% MeOH in DCM) to give a clear gum as a mixture of cis and trans isomers. Further purification by super fluid afforded the desired product (107 mg, 36% yield).

N-(3-hydroxycyclobutyl)-4-(4,4,5,5-tetramethyl-1,3,2-dioxaborolan-2-yl)benzenesulfonamide

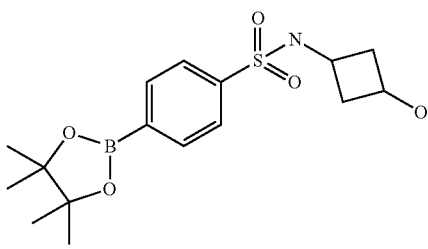 [SMILES: CC1(C)OB(c2ccc(S(=O)(=O)NC3CC(O)C3)cc2)OC1(C)C]

A mixture of 4-bromo-N-(3-hydroxycyclobutyl)benzenesulfonamide (103 mg, 336 µmol), bis(pinacolato)diboron (171 mg, 673 µmol) and potassium acetate (99.0 mg, 1.01 mmol) in dioxane (3 ml) was degased with argon and then [1,1'-bis(diphenylphosphino)ferrocene]dichloropalladium (II) (24.6 mg, 33.6 µmol) was added. The reaction was heated at 105° C. for 18, partitioned between EtOAc (7 ml) and water (5 ml), and the layers were separated. The aqueous layer was extracted with EtOAc (2×5 ml). The combined organic solution was dried over Na2SO4, concentrated to give a residue. The crude material was purified by flash chromatography (silica gel, 24 g, 2% to 5% MeOH in DCM) and was triturated with hexanes (2×) to give a white solid as a mixture of cis and trans isomers of desired product (88.5 mg, 90% pure, 67% yield).

4'-(5-amino-1H-1,2,4-triazol-3-ylamino)-2'-chloro-N-(3-hydroxycyclobutyl)-6'-(trifluoromethyl)biphenyl-4-sulfonamide (Compound 172)

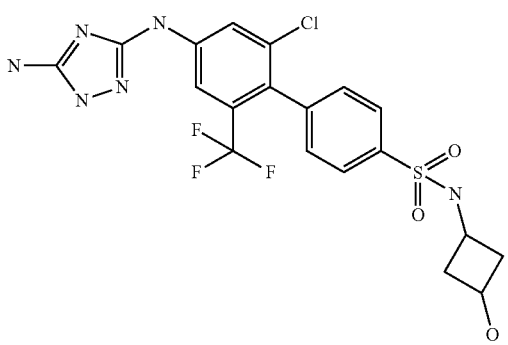 [SMILES: Nc1nc(Nc2cc(Cl)c(-c3ccc(S(=O)(=O)NC4CC(O)C4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (86.8 mg, 243 µmol), N-(3-hydroxycyclobutyl)-4-(4,4,5,5-tetramethyl-1,3,2-dioxaborolan-2-yl)benzenesulfonamide (86 mg, 243 µmol) and 3M K2CO3 (162 µl, 487 µmol) in DME (0.6 ml) and dioxane (0.6 ml) was degased with argon and tetrakis(triphenylphosphine)palladium(0) (45 mg, 38.9 µmol) was added. This was heated in microwave at 128° C. for 3 hours. The reaction mixture was partitioned between water and EtOAc (3 ml/8 ml). The layers were separated and the aqueous layer was extracted with EtOAc (3×5 ml). The combined organic solution was dried with Na2SO4, concentrated to give a residue which was purified by flash chromatography (silica gel, 24 g, 4% to 10% MeOH in DCM) to afford a light brown solid as the cis and trans mixture of the desired product (23 mg, 19% yield).

MS +m/z: 503 (M+H)$^+$

4'-(5-amino-1H-1,2,4-triazol-3-ylamino)-2'-chloro-N-(trans-3-hydroxycyclobutyl)-6'-(trifluoromethyl)biphenyl-4-sulfonamide (Compound 173)

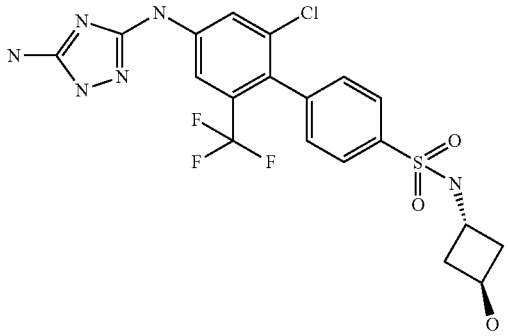 [SMILES: Nc1nc(Nc2cc(Cl)c(-c3ccc(S(=O)(=O)N[C@H]4C[C@H](O)C4)cc3)c(C(F)(F)F)c2)n[nH]1]

Reversed phase HPLC separation of compound 172 gave the title compound as a 78:22 mixture of trans:cis isomers. NMR NOE experiment confirmed the structure.

4'-(5-amino-1H-1,2,4-triazol-3-ylamino)-2'-chloro-N-(cis-3-hydroxycyclobutyl)-6'-(trifluoromethyl)biphenyl-4-sulfonamide (Compound 174)

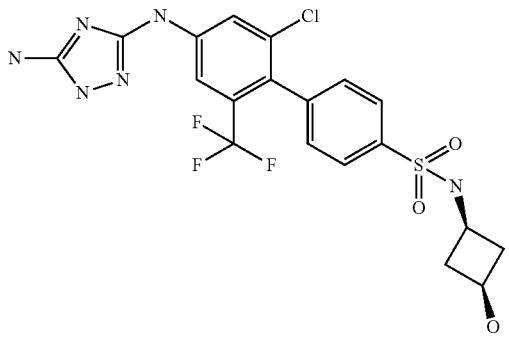 [SMILES: Nc1nc(Nc2cc(Cl)c(-c3ccc(S(=O)(=O)N[C@H]4C[C@@H](O)C4)cc3)c(C(F)(F)F)c2)n[nH]1]

HPLC separation of compound 172
MS +m/z: 537 (M+H)+

4'-(5-amino-1H-1,2,4-triazol-3-ylamino)-2'-chloro-N-(2-hydoxyethyl)-4-methoxy-6'-(trifluoromethyl)biphenyl-3-sulfonamide (Compound 175)

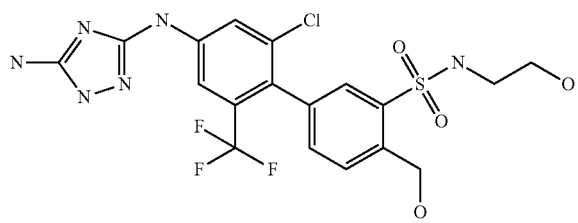 [SMILES: Nc1nc(Nc2cc(Cl)c(-c3ccc(CO)c(S(=O)(=O)NCCO)c3)c(C(F)(F)F)c2)n[nH]1]

N-(2-hydroxyethyl)-2-methoxy-5-(4,4,5,5-tetramethyl-1,3,2-dioxaborolan-2-yl)benzenesulfonamide

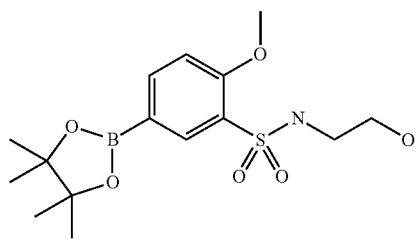 [SMILES: COc1ccc(B2OC(C)(C)C(C)(C)O2)cc1S(=O)(=O)NCCO]

A mixture of bis(pinacolato)diboron (819 mg, 3.22 mmol), 5-bromo-N-(2-hydroxyethyl)-2-methoxybenzenesulfonamide (500 mg, 1.61 mmol, Combi-Blocks) and potassium acetate (475 mg, 4.84 mmol) in dioxane (7 ml) was degased with argon and [1,1']BIS(DIPHENYLPHOSPHINO)FERROCENE]DICHLOROPALLADIUM(II) (80 mg, 109 μmol) was added. The reaction was heated at 105° C. for 18 hours. The reaction mixture was partitioned between EtOAc (15 ml) and 10% NaHCO3 (10 ml) and the layers were separated. The aqueous layer was extracted with EtOAc (2×10 ml). The combined organic solution was dried over Na2SO4, filtered and concentrated in vacuo. The residue was purified by flash chromatography (silica gel, 24 g, 20% to 60% EtOAc in Hexanes) and was triturated with hexanes (1×) to give a white solid as desired product (550 mg, 95% yield).

4'-(5-amino-1H-1,2,4-triazol-3-ylamino)-2'-chloro-N-(2-hydoxyethyl)-4-methoxy-6'-(trifluoromethyl)biphenyl-3-sulfonamide (Compound 175)

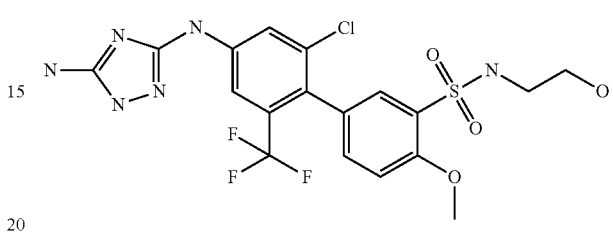

A mixture of N3-(4-bromo-3-chloro-5-(trifluoromethyl)phenyl)-1H-1,2,4-triazole-3,5-diamine Intermediate 1 (150 mg, 421 μmol), N-(2-hydroxyethyl)-2-methoxy-5-(4,4,5,5-tetramethyl-1,3,2-dioxaborolan-2-yl)benzenesulfonamide (271 mg, 757 μmol) and 3M K2CO3 (280 μL, 841 μmol) in DME (1 ml) and dioxane (1 ml) was degased with argon and tetrakis(triphenylphosphine)palladium(0) (75.0 mg, 64.9 μmol, Eq: 0.154) was added. The reaction mixture was heated in microwave at 128° C. for 3 hours, partitioned between water and EtOAc (3 ml/8 ml) and the layers were separated. The aqueous layer was extracted with EtOAc (3×5 ml). The combined organic solution was dried over Na2SO4 and concentrated in vacuo. The residue was purified by flash chromatography (silica gel, 24 g, 4% to 10% MeOH in DCM) to give a light brown foam as desired product (41.2 mg, 19% yield). MS +m/z: 507 (M+H)+

4'-(5-amino-1H-1,2,4-triazol-3-ylamino)-N-tert-butyl-2'-chloro-6'-(trifluoromethyl)biphenyl-3-sulfonamide (Compound 176)

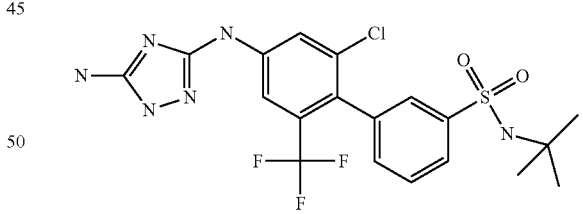

A mixture of N3-(4-bromo-3-chloro-5-(trifluoromethyl)phenyl)-1H-1,2,4-triazole-3,5-diamine Intermediate 1 (250 mg, 701 μmol), T-BUTYL 3-BORONOBENZENESULFONAMIDE (397 mg, 1.54 mmol, Combi-Blocks) and 3M K2CO3 (514 μl, 1.54 mmol) in DME (1.2 ml) and dioxane (1.2 ml) was degased with argon and tetrakis(triphenylphosphine)palladium(0) (162 mg, 140 μmol) was added. This was heated in microwave at 128° C. for 3 hours. The reaction mixture was diluted with MeOH, filtered and concentrated in vacuo. The residue was purified by flash chromatography (silica gel, 24 g, 3% to 7% MeOH in DCM). Recrystallization with MeOH gave a white solid as desired product (54 mg, 16% yield). MS +m/z: 489 (M+H)+

N3-(2-chloro-4'-methoxy-3'-(morpholinosulfonyl)-6-(trifluoromethyl)biphenyl-4-yl)-1H-1,2,4-triazole-3,5-diamine (Compound 177)

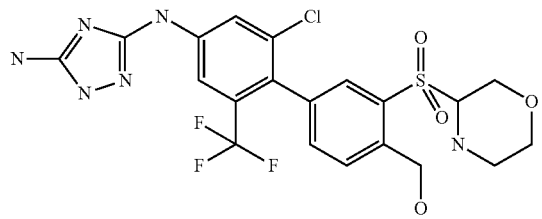 [SMILES: Nc1nc(Nc2cc(Cl)c(-c3ccc(CO)c(S(=O)(=O)C4COCCN4)c3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), 4-methoxy-3-(morpholin-4-yl-sulphonyl)benzeneboronic acid (203 mg, 673 µmol, Combi-Blocks) and 3M K2CO3 (280 µl, 841 µmol) in DME (1 ml) and dioxane (1 ml) was degased with argon and tetrakis(triphenylphosphine)palladium(0) (90.0 mg, 77.9 µmol) was added. The reaction was heated in microwave at 128° C. for 3 hours, and was partitioned between water and EtOAc (3 ml/8 ml) and the layers were separated. The aqueous layer was extracted with EtOAc (3×5 ml). The combined organic solution was dried over NaS2O4, filtered and concentrated to give a residue which was purified by flash chromatography (spherical silica gel, 24 g, 3.5% to 8% MeOH in DCM). Further purification by super fluid chromatography gave a white foam as desired product (37.4 mg, 16% yield). MS +m/z: 533 (M+H)$^+$

4'-(5-amino-1H-1,2,4-triazol-3-ylamino)-2'-chloro-3-methoxy-N-(piperidin-4-yl)-6'-(trifluoromethyl)biphenyl-4-sulfonamide hydrochloride (Compound 178)

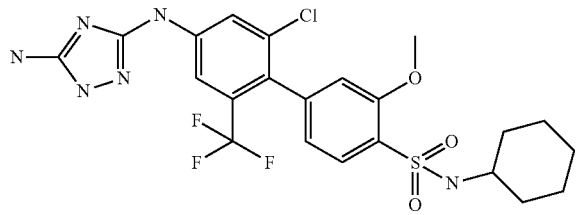 [SMILES: COc1cc(-c2c(Cl)cc(Nc3n[nH]c(N)n3)cc2C(F)(F)F)ccc1S(=O)(=O)NC1CCCCC1]

4-(4-Bromo-2-methoxy-benzenesulfonylamino)-piperidine-1-carboxylic acid tert-butyl ester

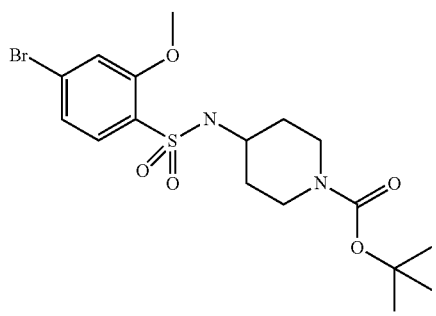 [SMILES: COc1cc(Br)ccc1S(=O)(=O)NC1CCN(C(=O)OC(C)(C)C)CC1]

To a solution of a 1:3 mixture of 2-bromo-4-methoxybenzene-1-sulfonyl chloride and 4-bromo-2-methoxybenzene-1-sulfonyl chloride (1.5 g, 5.25 mmol) and Et3N (1.06 g, 1.46 ml, 10.5 mmol) in THF (20.0 ml) was added 4-amino-1-Boc-piperidine (2.81 g, 14.0 mmol). The reaction was stirred at room temperature overnight. The reaction mixture was washed with 0.5 N HCl solution (2×40 ml), water (20 ml) and brine (25 ml), dried over Na2SO4 and concentrated to give a white solid as a 1:3 mixture of desired product and the isomer (2.98 g, 95% yield).

4-[2-Methoxy-4-(4,4,5,5-tetramethyl-[1,3]dioxolan-2-yl)-benzenesulfonylamino]-piperidine-1-carboxylic acid tert-butyl ester

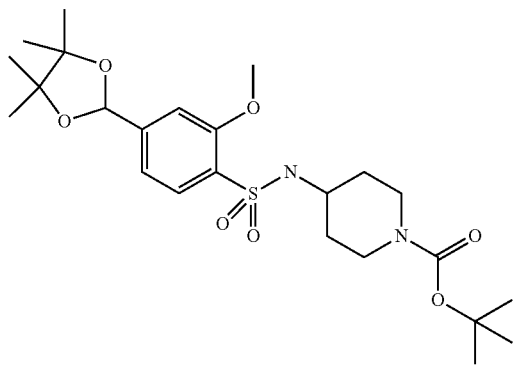 [SMILES: COc1cc(C2OC(C)(C)C(C)(C)O2)ccc1S(=O)(=O)NC1CCN(C(=O)OC(C)(C)C)CC1]

A 1:3 mixture of tert-butyl 4-(4-bromo-2-methoxyphenylsulfonamido)piperidine-1-carboxylate and the isomer (2.98 g, 6.63 mmol), bis(pinacolato)diboron (3.37 g, 13.3 mmol), and potassium acetate (1.95 g, 19.9 mmol) in dioxane (30 ml) was degased with argon and then [1,1'-bis(diphenylphosphino)ferrocene]dichloropalladium(II) (291 mg, 398 µmol) was added. The reaction was heated at 105° C. for 18 hours. The reaction was partitioned between EtOAc (35 ml) and 10% NaHCO3 (20 ml) and the layers were separated. The aqueous layer was extracted with EtOAc (2×25 ml). The combined organic solution was dried over Na2SO4, concentrated to give a residue.

The crude material was purified by flash chromatography (silica gel, 80 g, 20% to 40% EtOAc in hexanes), and was triturated with hexanes (2×10 ml) to give a yellow gum as a 1:2 mixture of desired product and byproduct (1 g).

tert-butyl 4-(4'-(5-amino-1H-1,2,4-triazol-3-ylamino)-2'-chloro-3-methoxy-6'-(trifluoromethyl)biphenyl-4-ylsulfonamido)piperidine-1-carboxylate

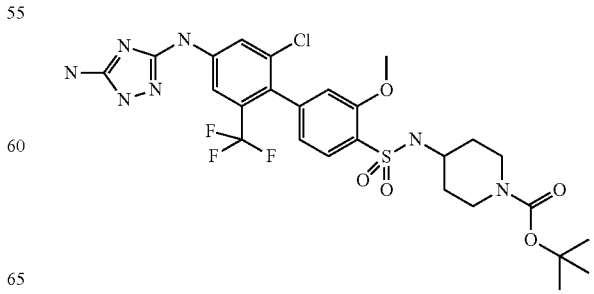

A mixture of N3-(4-bromo-3-chloro-5-(trifluoromethyl)phenyl)-1H-1,2,4-triazole-3,5-diamine Intermediate 1 (200 mg, 561 µmol), tert-butyl 4-(2-methoxy-4-(4,4,5,5-tetramethyl-1,3,2-dioxaborolan-2-yl)phenylsulfonamido)piperidine-1-carboxylate (995 mg, 841 µmol) and 3M K2CO3 (374 µl, 1.12 mmol) in dioxane (2.6 ml) and DME (2.6 ml) was degased with argon and then tetrakis(triphenylphosphine)palladium(0) (130 mg, 112 µmol) was added. The reaction was heated in the microwave at 128° C. for 3 hours. The reaction mixture was partitioned between water and EtOAc (3 ml/8 ml) and the layers were separated. The aqueous layer was extracted with EtOAc (3×5 ml). The combined organic solution was dried over Na2SO4, filtered and concentrated to give a residue which was purified by flash chromatography (silica gel, 40 g, 3% to 7% MeOH in DCM). Further purification by super fluid chromatography gave a solid as desired product (73 mg, 20% yield). MS +m/z: 546 (M+H−100)+

4'-(5-amino-1H-1,2,4-triazol-3-ylamino)-2'-chloro-3-methoxy-N-(piperidin-4-yl)-6'-(trifluoromethyl)biphenyl-4-sulfonamide hydrochloride (Compound 178)

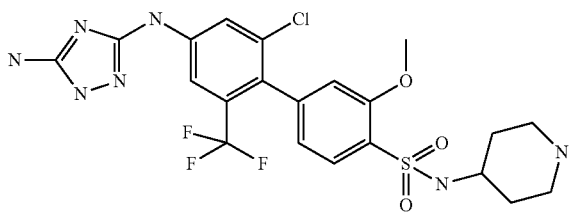 [SMILES: COc1cc(-c2c(Cl)cc(Nc3n[nH]c(N)n3)cc2C(F)(F)F)ccc1S(=O)(=O)NC1CCNCC1]

To anhydrous MeOH (5 ml) was quickly added acetyl chloride (552 mg, 0.5 ml, 7.03 mmol) to give a solution. The solution was cooled with ice bath and was added to a solution of tert-butyl 4-(4'-(5-amino-1H-1,2,4-triazol-3-ylamino)-2'-chloro-3-methoxy-6'-(trifluoromethyl)biphenyl-4-ylsulfonamido)piperidine-1-carboxylate (45 mg, 69.7 µmol) in MeOH (3 ml). The reaction was stirred at RT for 3 hours. The reaction mixture was concentrated to a residue and was triturated with diethyl ether (2×2 ml), and DCM (3×1 ml) to afford an off white solid as desired product (42 mg, quantative yield). MS +m/z: 546 (M+H)+

4'-(5-amino-1H-1,2,4-triazol-3-ylamino)-N-tert-butyl-2'-chloro-3-methoxy-6'-(trifluoromethyl)biphenyl-4-sulfonamide (Compound 179)

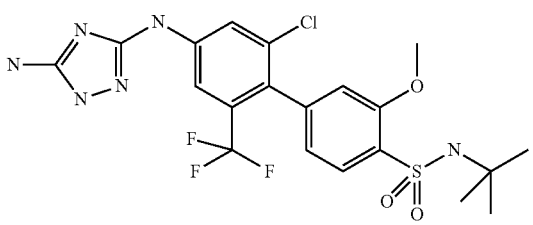 [SMILES: COc1cc(-c2c(Cl)cc(Nc3n[nH]c(N)n3)cc2C(F)(F)F)ccc1S(=O)(=O)NC(C)(C)C]

4-Bromo-N-tert-butyl-2-methoxy-benzenesulfonamide

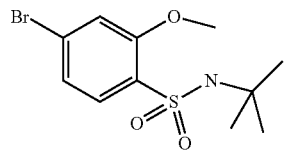 [SMILES: COc1cc(Br)ccc1S(=O)(=O)NC(C)(C)C]

A 1:3 mixture of 4-bromo-2-methoxybenzene-1-sulfonyl chloride and 2-bromo-4-methoxybenzene-1-sulfonyl chloride (2.0 g, 7.0 mmol) and Et3N (886 mg, 1.22 ml, 8.76 mmol) were combined with THF (40 ml) and tert-butylamine (1.02 g, 1.48 ml, 14.0 mmol) was added. The reaction was stirred at RT overnight. The reaction mixture was washed with 0.5 N HCl solution (2×40 ml), water (20 ml) and brine (25 ml), dried and concentrated to give a white solid as a 1:3 mixture of desired product and the isomer (1.85 g, 82% yield).

N-tert-butyl-2-methoxy-4-(4,4,5,5-tetramethyl-1,3,2-dioxaborolan-2-yl)benzenesulfonamide

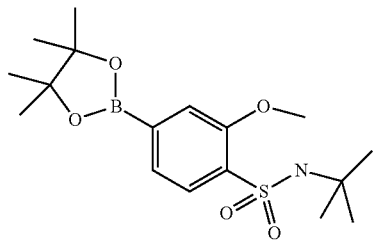 [SMILES: COc1cc(B2OC(C)(C)C(C)(C)O2)ccc1S(=O)(=O)NC(C)(C)C]

A 1:3 mixture of 4-bromo-N-tert-butyl-2-methoxybenzenesulfonamide and 2-bromo-N-tert-butyl-4-methoxybenzenesulfonamide (1.8 g, 5.6 mmol), bis(pinacolato)diboron (2.84 g, 11.2 mmol) and potassium acetate (1.35 g, 13.8 mmol) were combined with dioxane (25.7 ml) This was degased with argon and then [1,1'-bis(diphenylphosphino)ferrocene]dichloropalladium(II) (245 mg, 335 µmol) was added. The reaction was heated at 105° C. for 18 hours. The reaction was partitioned between EtOAc (35 ml) and 10% NaHCO3 (20 ml) and the layers were separated. The aqueous layer was extracted with EtOAc (2×25 ml). The combined organic solution was dried over Na2SO4, filtered, and concentrated to give a residue. The crude material was purified by flash chromatography (spherical silica gel, 80 g, 10% to 25% EtOAc in hexanes) and was triturated with hexanes (2×10 ml) to give a white solid as desired product (301 mg, 58% yield).

4'-(5-amino-1H-1,2,4-triazol-3-ylamino)-N-tert-butyl-2'-chloro-3-methoxy-6'-(trifluoromethyl)biphenyl-4-sulfonamide (Compound 179)

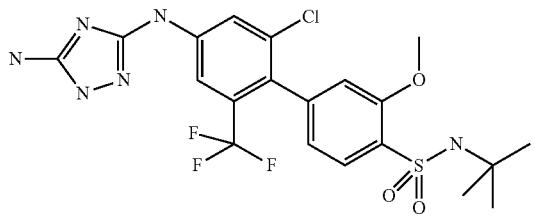 [SMILES: COc1cc(-c2c(Cl)cc(Nc3n[nH]c(N)n3)cc2C(F)(F)F)ccc1S(=O)(=O)NC(C)(C)C]

A mixture of N3-(4-bromo-3-chloro-5-(trifluoromethyl)phenyl)-1H-1,2,4-triazole-3,5-diamine Intermediate 1 (180 mg, 505 µmol), N-tert-butyl-2-methoxy-4-(4,4,5,5-tetramethyl-1,3,2-dioxaborolan-2-yl)benzenesulfonamide (298 mg, 808 µmol) and 3M K2CO3 (337 µl, 1.01 mmol) in dioxane (1 ml) and DME (1 ml) was degased with argon and then tetrakis(triphenylphosphine)palladium(0) (90 mg, 77.9 µmol) was added. The reaction was heated in a microwave at 128° C. for 3 hours. The reaction mixture was partitioned between water (3 ml/8 ml) and the layers were separated. The aqueous layer was extracted with EtOAc (3×5 ml). The combined organic solution was dried over Na2SO4, filtered and concentrated to give a residue. The residue was purified by flash chromatography (silica gel, 24 g, 4% to 7% MeOH in DCM). Further purification by super fluid chromatography afforded a white solid as desired product (88 mg, 95%). MS +m/z: 519 (M+H)+

4'-(5-amino-1H-1,2,4-triazol-3-ylamino)-2'-chloro-4-methoxy-6'-(trifluoromethyl)biphenyl-3-sulfonamide (Compound 180)

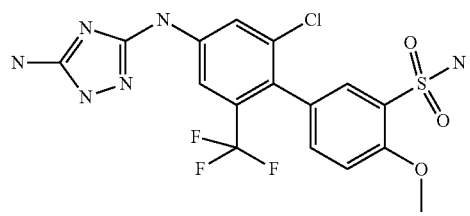 [SMILES: COc1ccc(-c2c(Cl)cc(Nc3n[nH]c(N)n3)cc2C(F)(F)F)cc1S(N)(=O)=O]

2-methoxy-5-(4,4,5,5-tetramethyl-1,3,2-dioxaborolan-2-yl)benzenesulfonamide

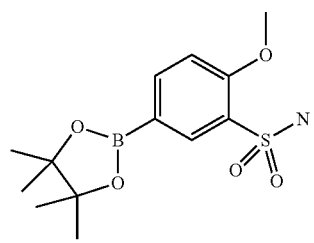 [SMILES: COc1ccc(B2OC(C)(C)C(C)(C)O2)cc1S(N)(=O)=O]

A mixture of bis(pinacolato)diboron (573 mg, 2.25 mmol), 5-bromo-2-methoxybenzenesulfonamide (300 mg, 1.13 mmol, Combi-Blocks) and potassium acetate (332 mg, 3.38 mmol) in dioxane (5 ml) was degased with argon and [1,1'-bis(diphenylphosphino)ferrocene]dichloropalladium (II) (49.5 mg, 67.6 µmol) was added. The reaction was heated at 105° C. for 18 hours, and was partitioned between EtOAc (15 ml) and 10% NaHCO3 (10 ml). The layers were separated and the aqueous layer was extracted with EtOAc (2×10 ml). The combined organic solution was dried over Na2SO4, filtered and concentrated to give a residue. The residue was purified by flash chromatography (silica gel, 24 g, 20% to 60% EtOAc in Hexanes) and was triturated with hexanes (1×) to give a white solid as desired product (294 mg, 80% yield).

4'-(5-amino-1H-1,2,4-triazol-3-ylamino)-2'-chloro-4-methoxy-6'-(trifluoromethyl)biphenyl-3-sulfonamide (Compound 180)

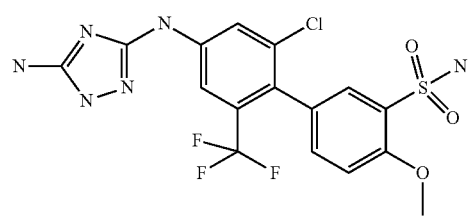 [SMILES: COc1ccc(-c2c(Cl)cc(Nc3n[nH]c(N)n3)cc2C(F)(F)F)cc1S(N)(=O)=O]

A mixture of N3-(4-bromo-3-chloro-5-(trifluoromethyl)phenyl)-1H-1,2,4-triazole-3,5-diamine Intermediate 1 (200 mg, 561 µmol), 2-methoxy-5-(4,4,5,5-tetramethyl-1,3,2-dioxaborolan-2-yl)benzenesulfonamide (281 mg, 898 µmol) and 3M K2CO3 (374 µl, 1.12 mmol) in DME (1 ml) and dioxane (1 ml) was degased with argon and tetrakis(triphenylphosphine)palladium(0) (100 mg, 86.5 µmol) was added. This was heated in microwave at 128° C. for 3 hours. The reaction mixture was partitioned between water and EtOAc (3 ml/8 ml) and the layers were separated. The aqueous layer was extracted with EtOAc (3×5 ml). The combined organic solution was dried over Na2SO4 and concentrated in vacuo. The residue was purified by flash chromatography (silica gel, 24 g, 4% to 10% MeOH in DCM) to give a light brown solid as desired product (66 mg, 25% yield). MS +m/z: 463 (M+H)+

N3-(2-chloro-4'-(isopropylsulfonyl)-6-(trifluoromethyl)biphenyl-4-yl)-1H-1,2,4-triazole-3,5-diamine (Compound 181)

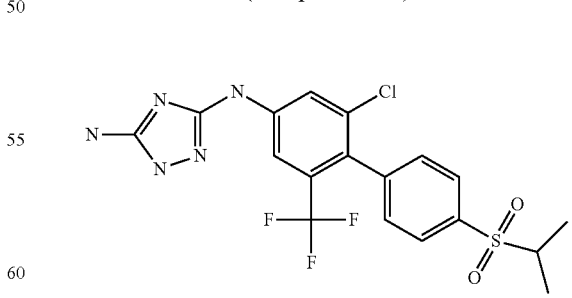

A mixture of N3-(4-bromo-3-chloro-5-(trifluoromethyl)phenyl)-1H-1,2,4-triazole-3,5-diamine Intermediate 1 (150 mg, 421 µmol), 4-(isopropylsulfonyl)phenylboronic acid (240 mg, 1.05 mmol, Combi-Blocks) and 3M K2CO3 (351 µl, 1.05 mmol) in DME (1 ml) and dioxane (1 ml) was degased with argon and tetrakis(triphenylphosphine)palladium(0) (97.2 mg, 84.1 μmol) was added. The reaction mixture was heated in microwave at 125° C. for 3 hours, diluted with MeOH, filtered, and concentrated in vacuo. The residue was purified by flash chromatography (silica gel, 24 g, 3% to 7% MeOH in DCM). Further purification by super fluid chromatography afforded a white foam (32 mg, 16% yield) as desired product. MS +m/z: 460 (M+H)⁺

N3-(2-chloro-4'-methoxy-3'-(piperazin-1-ylsulfonyl)-6-(trifluoromethyl)biphenyl-4-yl)-1H-1,2,4-triazole-3,5-diamine hydrochloride (Compound 182)

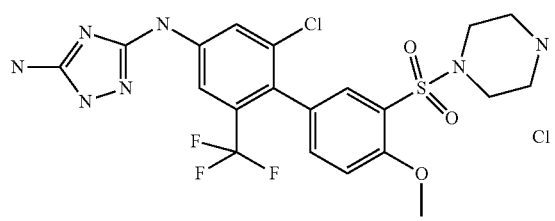 [SMILES: COc1ccc(-c2c(Cl)cc(Nc3n[nH]c(N)n3)cc2C(F)(F)F)cc1S(=O)(=O)N1CCNCC1 ; Cl]

To anhydrous MeOH (5 ml) was quickly added acetyl chloride (552 mg, 0.5 ml, 7.03 mmol) to give a solution. The solution was cooled with ice bath and to it was added a solution of tert-butyl 4-(4'-(5-amino-1H-1,2,4-triazol-3-ylamino)-2'-chloro-4-methoxy-6'-(trifluoromethyl)biphenyl-3-yl sulfonyl)piperazine-1-carboxylate (85 mg, 134 μmol, example 7) in MeOH (3 ml). The reaction was stirred at RT for 3 hours, concentrated to a residue and was triturated with diethyl ether (3×6 ml) to give a white solid as desired product (75 mg, 98% yield). MS +m/z: 532 (M+H)⁺

N3-(2-chloro-4'-(4,4-difluoropiperidin-1-ylsulfonyl)-6-(trifluoromethyl)biphenyl-4-yl)-1H-1,2,4-triazole-3,5-diamine (Compound 183)

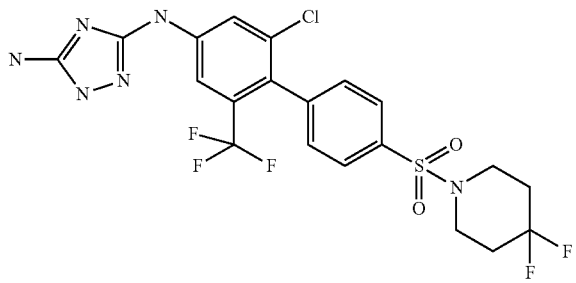 [SMILES: Nc1nc(Nc2cc(Cl)c(-c3ccc(S(=O)(=O)N4CCC(F)(F)CC4)cc3)c(C(F)(F)F)c2)n[nH]1]

1-(4-bromophenylsulfonyl)-4,4-difluoropiperidine

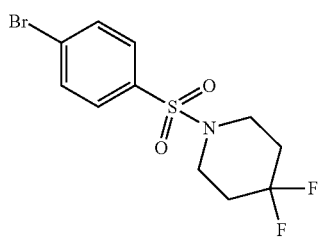 [SMILES: O=S(=O)(c1ccc(Br)cc1)N1CCC(F)(F)CC1]

To a solution of 4-bromobenzene-1-sulfonyl chloride (0.6 g, 2.35 mmol, Aldrich) in THF (10 ml) was added 4,4-difluoropiperidine hydrochloride (407 mg, 2.58 mmol, Aldrich) followed by Et3N (832 mg, 1.15 ml, 8.22 mmol). The reaction was stirred at RT overnight. The reaction mixture was washed with 0.5 N HCl solution (2×20 ml), water (20 ml) and brine (15 ml), dried and concentrated to give a white solid as desired product (717 mg, 89% yield).

4,4-difluoro-1-(4-(4,4,5,5-tetramethyl-1,3,2-dioxaborolan-2-yl)phenylsulfonyl)piperidine

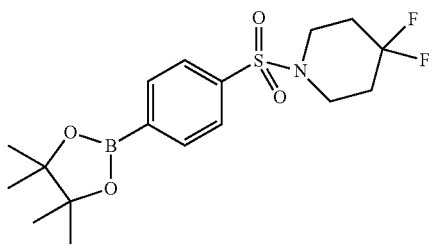 [SMILES: CC1(C)OB(c2ccc(S(=O)(=O)N3CCC(F)(F)CC3)cc2)OC1(C)C]

A mixture of bis(pinacolato)diboron (1.05 g, 4.12 mmol), 1-(4-bromophenylsulfonyl)-4,4-difluoropiperidine (700 mg, 2.06 mmol) and potassium acetate (606 mg, 6.17 mmol) in dioxane (20 ml) was degased with argon and then [1,1'-bis(diphenylphosphino)ferrocene]dichloropalladium(II) (75.3 mg, 103 μmol) was added. The reaction was heated at 105° C. for 18 hours, partitioned between EtOAc (35 ml) and 10% NaHCO3 (20 ml) and the layers separated. The aqueous layer was extracted with EtOAc (2×25 ml) and the combined organic solution was dried over Na2SO4, filtered and concentrated to give a residue. The crude material was purified by flash chromatography (silica gel, 40 g, 20% EtOAc in hexanes) and was triturated with hexanes (2×10 ml) to give a white solid as desired product (604 mg, 76% yield).

N3-(2-chloro-4'-(4,4-difluoropiperidin-1-ylsulfonyl)-6-(trifluoromethyl)biphenyl-4-yl)-1H-1,2,4-triazole-3,5-diamine (Compound 183)

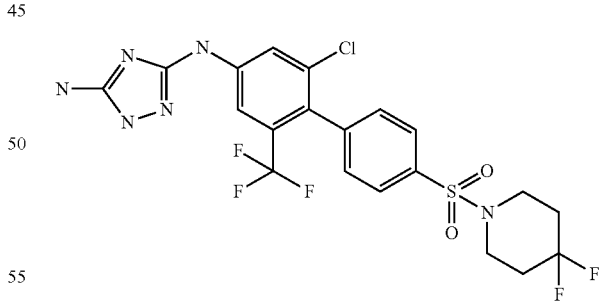

A mixture of N3-(4-bromo-3-chloro-5-(trifluoromethyl)phenyl)-1H-1,2,4-triazole-3,5-diamine Intermediate 1 (200 mg, 561 μmol), 4,4-difluoro-1-(4-(4,4,5,5-tetramethyl-1,3,2-dioxaborolan-2-yl)phenylsulfonyl)piperidine (348 mg, 898 μmol) and 3M K2CO3 (374 μl, 1.12 mmol) in dioxane (1 ml) and DME (1 ml) was degased with argon and then tetrakis(triphenylphosphine)palladium(0) (100 mg, 86.5 μmol) was added. The reaction was heated in a microwave at 125° C. for 3 hours, and then partitioned between water and EtOAc (5 ml/15 ml). The layers were separated and the aqueous layer was extracted with EtOAc (3×10 ml). The combined organic solution was dried over Na2SO4, filtered and concentrated to give a residue which was purified by flash chromatography (silica gel, 24 g, 3% to 7% MeOH in DCM). Further purification by super fluid chromatography gave a white solid as desired product (61 mg, 20% yield). MS +m/z: 537 (M+H)+

4'-(5-amino-1H-1,2,4-triazol-3-ylamino)-2'-chloro-N-(trans-4-hydroxycyclohexyl)-6'-(trifluoromethyl)biphenyl-4-sulfonamide (Compound 184)

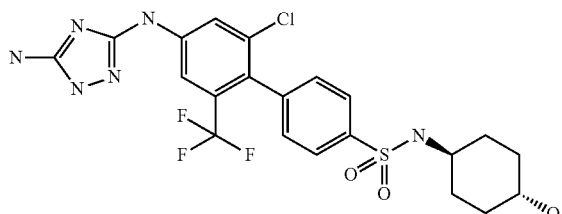

4-Bromo-N-(trans-4-hydroxy-cyclohexyl)-benzenesulfonamide

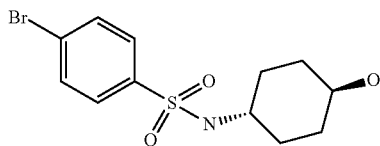 [SMILES: O=S(=O)(N[C@H]1CC[C@H](O)CC1)c1ccc(Br)cc1]

To a solution of 4-bromobenzene-1-sulfonyl chloride (1 g, 3.91 mmol, Aldrich) and Et3N (594 mg, 5.87 mmol) in THF (20 ml) was added trans-4-aminocyclohexanol (541 mg, 4.7 mmol, Combi-Blocks). The reaction was stirred at RT overnight. The reaction mixture was washed with 0.5 N HCl solution (2×40 ml), water (20 ml) and brine (25 ml), dried over Na2SO4 and concentrated to give a residue. The residue was triturated with hexanes (1×) to give a white solid as desired product (1.27 g, 97% yield).

N-(trans-4-hydroxycyclohexyl)-4-(4,4,5,5-tetramethyl-1,3,2-dioxaborolan-2-yl)benzenesulfonamide

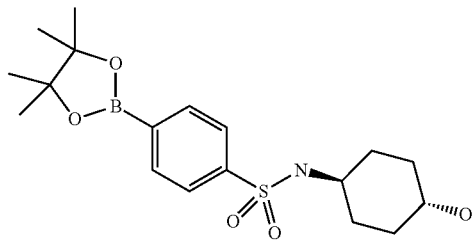 [SMILES: CC1(C)OB(c2ccc(S(=O)(=O)N[C@H]3CC[C@H](O)CC3)cc2)OC1(C)C]

A mixture of bis(pinacolato)diboron (1.06 g, 4.19 mmol), 4-bromo-N-trans-4-hydroxycyclohexyl)benzenesulfonamide (700 mg, 2.09 mmol) and potassium acetate (617 mg, 6.28 mmol) in dioxane (10 ml) was degased with argon and then [1,1'-bis(diphenylphosphino)ferrocene]dichloropalladium(II) (80 mg, 109 μmol) was added. The reaction was heated at 105° C. for 18 hours. The reaction mixture was partitioned between EtOAc (35 ml) and 10% NaHCO3 (20 ml) and the layers were separated. The aqueous layer was extracted with EtOAc (2×25 ml). The combined organic solution was dried over Na2SO4, concentrated to give a residue. The residue was purified by flash chromatography (silica gel, 24 g, 2% to 5% MeOH in DCM) to give a light brown solid as desired product (778 mg, 97% yield).

4'-(5-amino-1H-1,2,4-triazol-3-ylamino)-2'-chloro-N-(trans-4-hydroxycyclohexyl)-6'-(trifluoromethyl)biphenyl-4-sulfonamide (Compound 184)

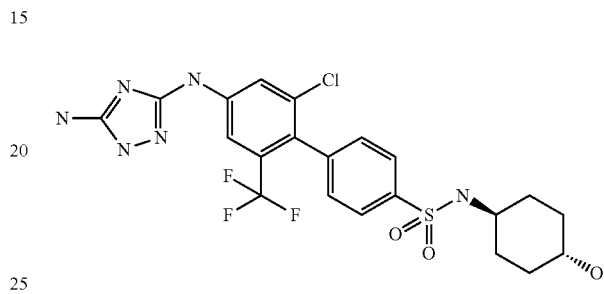

A mixture of N3-(4-bromo-3-chloro-5-(trifluoromethyl)phenyl)-1H-1,2,4-triazole-3,5-diamine Intermediate 1 (180 mg, 505 μmol), N-(trans-4-hydroxycyclohexyl)-4-(4,4,5,5-tetramethyl-1,3,2-dioxaborolan-2-yl)benzenesulfonamide (308 mg, 808 μmol) and 3M K2CO3 (337 μl, 1.01 mmol) in dioxane (1 ml) and DME (1 ml) was degased with argon and then tetrakis(triphenylphosphine)palladium(0) (87.5 mg, 75.7 μmol) was added. The reaction was heated in a microwave at 128° C. for 3 hours. The reaction was partitioned between water and EtOAc (3 ml/8 ml) and the layers were separated. The aqueous layer was extracted with EtOAc (3×5 ml). The combined organic solution was dried with Na2SO4, filtered and concentrated to give a residue which was purified by flash chromatography (silica gel, 24 g, 4% to 10% MeOH in DCM) to give a yellow solid as desired product (80 mg, 30% yield). MS +m/z: 531 (M+H)+

4'-(5-amino-1H-1,2,4-triazol-3-ylamino)-2'-chloro-N,N-dimethyl-6'-(trifluoromethyl)biphenyl-4-sulfonamide (Compound 185)

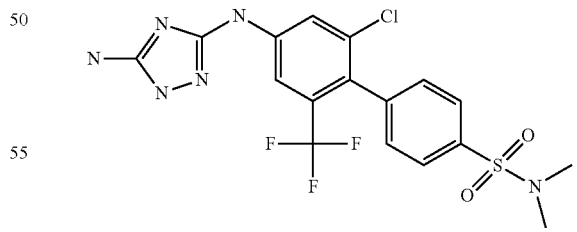

A mixture of N3-(4-bromo-3-chloro-5-(trifluoromethyl)phenyl)-1H-1,2,4-triazole-3,5-diamine Intermediate 1 (150 mg, 421 μmol), 4-(N,N-dimethylaminosulfonyl)phenylboronic acid pinacol ester (262 mg, 841 μmol) and 3M K2CO3 (351 μl, 1.05 mmol) in DME (1 ml) and dioxane (1 ml) was degased with argon and tetrakis(triphenylphosphine)palladium(0) (97.2 mg, 84.1 μmol) was added. This was heated in microwave at 125° C. for 1.5 hours. The reaction mixture was partitioned between EtOAc (10 ml) and water (5 ml) and the layers were separated. The aqueous layer was extracted with EtOAc (2×8 ml). The combined organic solution was washed with brine, dried over MgSO4, filtered and concentrated to give a residue. The crude material was purified by flash chromatography (silica gel, 23 g, 4% to 7% MeOH in DCM). Further purification by super fluid chromatography afforded a white powder as desired product (20.3 mg, 10% yield).
MS +m/z: 537 (M+H)+

N-((4'-(5-amino-1H-1,2,4-triazol-3-ylamino)-2'-chloro-6'-(trifluoromethyl)biphenyl-4-yl)methyl)methanesulfonamide (Compound 186)

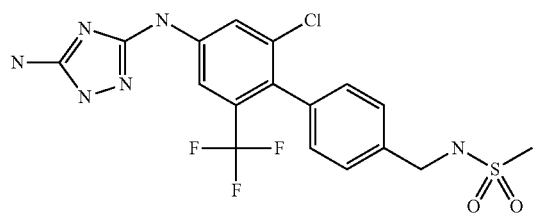 [SMILES: CS(=O)(=O)NCc1ccc(-c2c(Cl)cc(Nc3n[nH]c(N)n3)cc2C(F)(F)F)cc1]

A mixture of N3-(4-bromo-3-chloro-5-(trifluoromethyl)phenyl)-1H-1,2,4-triazole-3,5-diamine Intermediate 1 (150 mg, 421 µmol), 4-(methylsulfonamidomethyl)phenylboronic acid (200 mg, 873 µmol, Combi-Blocks) and 3M K2CO3 (309 µl, 926 µmol) in DME (1 ml) and dioxane (1.2 ml) was degased with argon and tetrakis(triphenylphosphine)palladium(0) (97.2 mg, 84.1 µmol) was added. This was heated in microwave at 128° C. for 3 hours. The reaction mixture was diluted with MeOH and EtOAc and filtered. The filtrate was dried over Na2SO4 and concentrated in vacuo. The residue was purified by flash chromatography (silica gel, 24 g, 3% to 7% MeOH in DCM). Further purification by super fluid chromatography gave a white foam as desired product (34.8 mg, 18% yield). MS +m/z: 461 (M+H)+

N3-(2-chloro-4'-(methylsulfonyl)-6-(trifluoromethyl)biphenyl-4-yl)-1H-1,2,4-triazole-3,5-diamine (Compound 187)

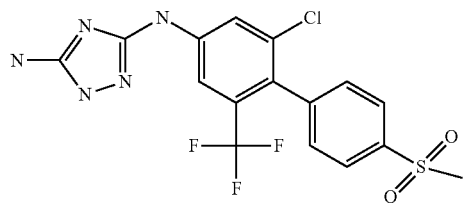 [SMILES: CS(=O)(=O)c1ccc(-c2c(Cl)cc(Nc3n[nH]c(N)n3)cc2C(F)(F)F)cc1]

A mixture of N3-(4-bromo-3-chloro-5-(trifluoromethyl)phenyl)-1H-1,2,4-triazole-3,5-diamine Intermediate 1 (300 mg, 841 µmol), 2-(4-methanesulfonylphenyl)-4,4,5,5-tetramethyl-1,3,2-dioxaborolane (475 mg, 1.68 mmol) and 3M K2CO3 (617 µl, 1.85 mmol) in DME (1.5 ml) and dioxane (1.5 ml) was degased with argon and tetrakis(triphenylphosphine)palladium(0) (194 mg, 168 µmol) was added. This was heated in microwave at 127° C. for 3 hours. The reaction mixture was partitioned between water and EtOAc (5 ml/8 ml) and the layers were separated. The aqueous layer was extracted with EtOAc (4×5 ml). The combined organic solution was dried over Na2SO4, concentrated to a residue which was purified by flash chromatography (silica gel, 24 g, 3% to 7% MeOH in DCM). Further purification by super fluid chromatography purification afforded a white solid as desired product (99.4 mg, 27% yield). MS +m/z: 432 (M+H)+

N3-(2-chloro-4'-(cyclopropylsulfonyl)-6-(trifluoromethyl)biphenyl-4-yl)-1H-1,2,4-triazole-3,5-diamine (Compound 188)

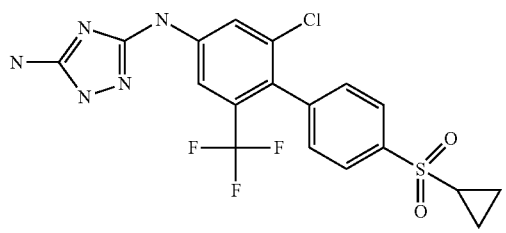 [SMILES: Nc1nc(Nc2cc(Cl)c(-c3ccc(S(=O)(=O)C4CC4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), 4-(cyclopropylsulfonyl)phenylboronic acid (128 mg, 568 µmol) and 3M K2CO3 (280 µl, 841 µmol) in DME (1 ml) and dioxane (1.2 ml) was degased with argon and tetrakis(triphenylphosphine)palladium(0) (97.2 mg, 84.1 µmol) was added. This was heated in microwave at 128° C. for 3 hours. The reaction mixture was partitioned between water and EtOAc (5 ml/8 ml) and the layers were separated. The aqueous layer was extracted with EtOAc (3×10 ml). The combined organic solution was dried and concentrated to give a residue which was purified by flash chromatography (silica gel, 24 g, 3% to 7% MeOH in DCM). Further purification by super fluid chromatography afforded a white foam as desired product (28.8 mg, 15% yield). MS +m/z: 458 (M+H)+

4'-(5-amino-1H-1,2,4-triazol-3-ylamino)-2'-chloro-N-methyl-6'-(trifluoromethyl)biphenyl-4-carboxamide (Compound 189)

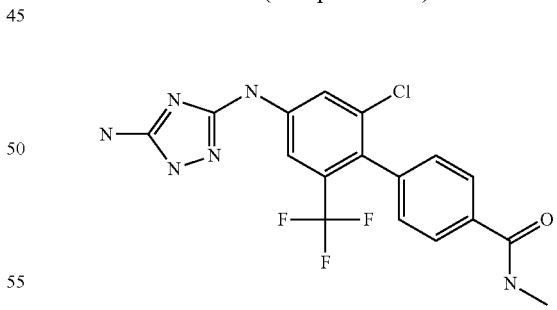

A mixture of N3-(4-bromo-3-chloro-5-(trifluoromethyl)phenyl)-1H-1,2,4-triazole-3,5-diamine Intermediate 1 (150 mg, 421 µmol), 4-(n-methylaminocarbonyl)phenylboronic acid (188 mg, 1.05 mmol) and 3M K2CO3 (351 µl, 1.05 mmol) in DME (1 ml) and dioxane (1 ml) was degased with argon and tetrakis(triphenylphosphine)palladium(0) (97.2 mg, 84.1 µmol) was added. This was heated in microwave at 125° C. for 3.5 h. The reaction was diluted with MeOH, filtered and the filtrated was concentrated in vacuo. Purification by super fluid chromatography and freeze drying afforded a yellow powder as desired product (60.8 mg, 35% yield). MS +m/z: 411 (M+H)+

4'-(5-amino-1H-1,2,4-triazol-3-ylamino)-2'-chloro-N-(trans-4-hydroxycyclohexyl)-4-methoxy-6'-(trifluoromethyl)biphenyl-3-sulfonamide (Compound 190)

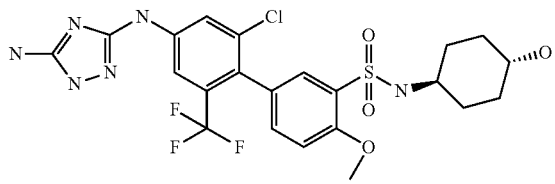 [SMILES: COc1ccc(-c2c(Cl)cc(Nc3n[nH]c(N)n3)cc2C(F)(F)F)cc1S(=O)(=O)N[C@H]1CC[C@H](O)CC1]

5-bromo-N-(trans-4-hydroxycyclohexyl)-2-methoxy-benzenesulfonamide

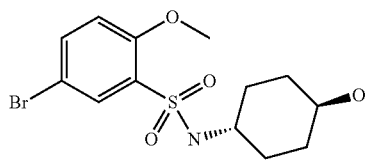 [SMILES: COc1ccc(Br)cc1S(=O)(=O)N[C@H]1CC[C@H](O)CC1]

To a solution of trans-4-aminocyclohexanol (424 mg, 3.68 mmol, Combi-Blocks) and DIPEA (1.13 g, 1.53 ml, 8.76 mmol) in CH2Cl2 (20 ml) was added 5-bromo-2-methoxy-benzenesulfonyl chloride (1.0 g, 3.5 mmol, Combi-Blocks). The reaction was stirred at RT overnight. The reaction mixture was washed with 0.5 N HCl solution (2×20 ml), water (20 ml) and brine (15 ml), The organic solution was dried over Na2SO4, filtered and concentrated and was triturated with hexanes (2×) to give a white solid as desired product (1.14 g, 89% yield).

4'-(5-amino-1H-1,2,4-triazol-3-ylamino)-2'-chloro-N-(trans-4-hydroxycyclohexyl)-4-methoxy-6'-(trifluoromethyl)biphenyl-3-sulfonamide (Compound 190)

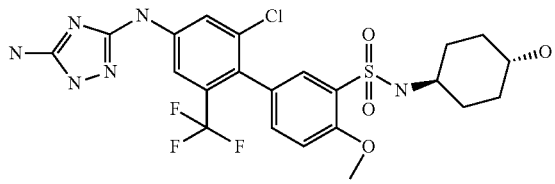 [SMILES: COc1ccc(-c2c(Cl)cc(Nc3n[nH]c(N)n3)cc2C(F)(F)F)cc1S(=O)(=O)N[C@H]1CC[C@H](O)CC1]

A mixture of bis(pinacolato)diboron (214 mg, 841 µmol), 5-bromo-N-(trans-4-hydroxycyclohexyl)-2-methoxybenzenesulfonamide (153 mg, 421 µmol), N3-(4-bromo-3-chloro-5-(trifluoromethyl)phenyl)-1H-1,2,4-triazole-3,5-diamine Intermediate 1 (150 mg, 421 µmol), potassium acetate (124 mg, 1.26 mmol) and 3M K2CO3 (280 µl, 841 µmol) in dioxane (2 ml) and DME (2 ml) was degased with argon and then tetrakis(triphenylphosphine)palladium(0) (72.9 mg, 63.1 µmol) and [1,1'-bis(diphenylphosphino)ferrocene]dichloropalladium(II) (30.8 mg, 42.1 µmol) were added. The reaction was heated in a microwave at 145° C. for 2 hours. The reaction mixture was partitioned between EtOAc (7 ml) and water (5 ml) and the layers were separated. The aqueous layer was extracted with EtOAc (2×5 ml). The combined organic solution was dried over Na2SO4, filtered and concentrated to give a residue. The crude material was purified by flash chromatography (silica gel, 24 g, 2% to 10% MeOH in DCM), and further purified by super fluid chromatography to give a white foam as desired product (26.1 mg, 95% pure, 11% yield). MS +m/z: 561 (M+H)+

1-(4'-(5-amino-1H-1,2,4-triazol-3-ylamino)-2'-chloro-6'-(trifluoromethyl)biphenyl-4-ylsulfonyl)azetidin-3-ol (Compound 191)

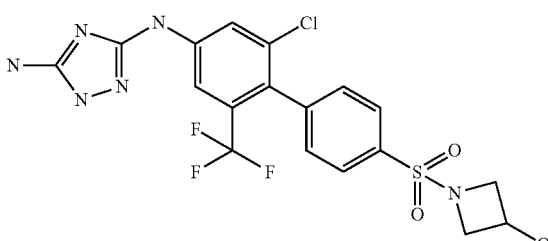

1-(4-bromophenylsulfonyl)azetidin-3-ol

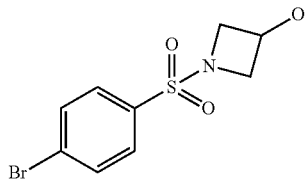

To a solution of 3-azetidinol (300 mg, 4.1 mmol) and DIPEA (632 mg, 4.89 mmol) in CH2Cl2 (15 ml) was added 4-bromobenzenesulfonyl chloride (1 g, 3.91 mmol, Fluka). The reaction was stirred at RT overnight. The reaction mixture was washed with 1N HCl solution (1×25 ml), water (40 ml) and brine (30 ml). It was dried over Na2SO4, filtered and concentrated to give a white solid. The crude material was purified by flash chromatography (silica gel, 40 g, 0% to 4% MeOH in DCM). Recrystallization from EtOAc/Hexanes gave a white solid as desired product (0.205 g, 18% yield).

1-(4-(4,4,5,5-tetramethyl-1,3,2-dioxaborolan-2-yl)phenylsulfonyl)azetidin-3-ol

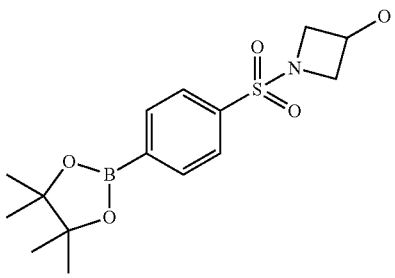 [SMILES: CC1(C)OB(c2ccc(S(=O)(=O)N3CC(O)C3)cc2)OC1(C)C]

A mixture of 1-(4-bromophenylsulfonyl)azetidin-3-ol (285 mg, 976 µmol), bis(pinacolato)diboron (495 mg, 1.95 mmol) and potassium acetate (287 mg, 2.93 mmol) in dioxane (4 ml) was degased with argon and then [1,1'-bis(diphenylphosphino)ferrocene]dichloropalladium(II) (71.4 mg, 97.6 µmol) was added. The reaction was heated at 105° C. for 18 hours. The reaction was partitioned between EtOAc (15 ml) and water (5 ml) and the layers were separated. The aqueous layer was extracted with EtOAc (2×10 ml). The combined organic solution was dried over Na2SO4, filtered and concentrated to give a residue. The crude material was purified by flash chromatography (silica gel, 40 g, 0% to 3% MeOH in DCM) and was triturated with hexanes (2×) to give a brownish oil as desired product (0.430 g, 75% pure, 97% yield).

1-(4'-(5-amino-1H-1,2,4-triazol-3-ylamino)-2'-chloro-6'-(trifluoromethyl)biphenyl-4-ylsulfonyl)azetidin-3-ol (Compound 191)

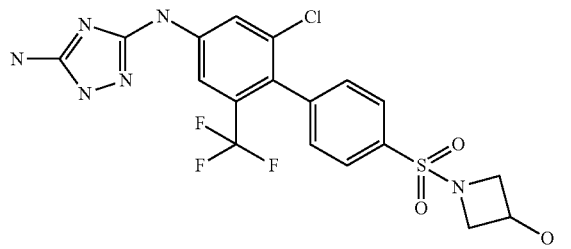 [SMILES: Nc1nc(Nc2cc(Cl)c(-c3ccc(S(=O)(=O)N4CC(O)C4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), 1-(4-(4,4,5,5-tetramethyl-1,3,2-dioxaborolan-2-yl)phenylsulfonyl)azetidin-3-ol (214 mg, 631 µmol) and 3M K2CO3 (280 µl, 841 µmol) in DME (1 ml) and dioxane (1 ml) was degased with argon and tetrakis(triphenylphosphine)palladium(0) (90.0 mg, 77.9 µmol) was added. This was heated in microwave at 128° C. for 3 hours. The reaction was partitioned between water and EtOAc (3 ml/8 ml) and the layers were separated. The aqueous solution was extracted with EtOAc (3×5 ml). The combined organic solution was dried with Na2SO4, filtered and concentrated to give a residue. The crude material was purified by flash chromatography (silica gel, 24 g, 4% to 10% MeOH in DCM) to afford a light brown solid as desired product (64 mg, 31% yield). MS +m/z: 489 (M+H)+

N3-(2-chloro-3'-(pyrrolidin-1-ylsulfonyl)-6-(trifluoromethyl)biphenyl-4-yl)-1H-1,2,4-triazole-3,5-diamine (Compound 192)

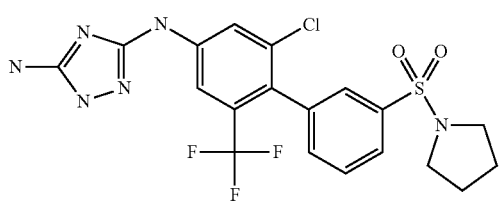 [SMILES: Nc1nc(Nc2cc(Cl)c(-c3cccc(S(=O)(=O)N4CCCC4)c3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 µmol), 3-(pyrrolidin-1-ylsulfonyl)phenylboronic acid (236 mg, 926 µmol, Combi-Blocks) and 3M K2CO3 (309 µl, 926 µmol) in DME (1 ml) and dioxane (1 ml) was degased with argon and tetrakis(triphenylphosphine)palladium(0) (97.2 mg, 84.1 µmol) was added. This was heated in microwave at 128° C. for 3 hours. The reaction mixture was diluted with MeOH, filtered, and the filtrate was concentrated in vacuo. The residue was purified by flash chromatography (silica gel, 24 g, 3% to 7% MeOH in DCM), and further purified by super fluid chromatography. Recrystallization from acetonitrile gave a white solid as desired product (44 mg, 22% yield). MS +m/z: 487 (M+H)+

4'-(5-amino-1H-1,2,4-triazol-3-ylamino)-N-tert-butyl-2'-chloro-4-(trifluoromethoxy)-6'-(trifluoromethyl)biphenyl-3-sulfonamide (Compound 193)

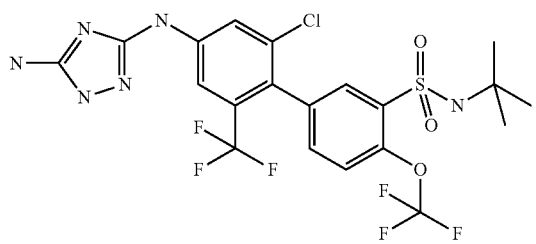 [SMILES: CC(C)(C)NS(=O)(=O)c1cc(-c2c(Cl)cc(Nc3n[nH]c(N)n3)cc2C(F)(F)F)ccc1OC(F)(F)F]

5-bromo-2-trifluoromethoxy-benzenesulfonyl chloride

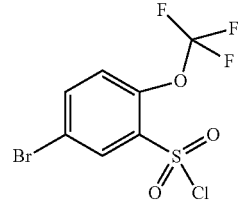 [SMILES: O=S(=O)(Cl)c1cc(Br)ccc1OC(F)(F)F]

To chlorosulfonic acid (48.3 g, 415 mmol, aldrich) was added 1-bromo-4-(trifluoromethoxy)benzene (10 g, 41.5 mmol, Oakwood) slowly. The reaction was stirred at RT for 30 min, then 2 h at 50° C. The reaction mixture was poured slowly to crushed ice (600 ml) and then extracted with ether (3×150 ml). The combined organic solution was washed with water (1×200 ml) and brine (1×100 ml), dried over Na2SO4 and concentrated to give a residue. The residue was suspended in DCM/chloroform (50/50 ml) and filtered. The filtrate was concentrated to give a light yellow oil as desired product (12.53 g, 88% yield)

5-bromo-N-tert-butyl-2-(trifluoromethoxy)benzenesulfonamide

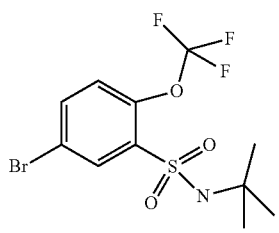 [SMILES: CC(C)(C)NS(=O)(=O)c1cc(Br)ccc1OC(F)(F)F]

To a solution of 5-bromo-2-(trifluoromethoxy)benzene-1-sulfonyl chloride (900 mg, 2.65 mmol) and Et3N (536 mg, 739 µl, 5.3 mmol) in THF (25 ml) was added tert-butylamine (291 mg, 3.98 mmol, Aldrich). The reaction was stirred at RT overnight. The reaction mixture was washed with 0.5 N HCl solution (2×40 ml), water (20 ml) and brine (25 ml). The organic solution was dried over Na2SO4, concentrated in vacuo and was triturated with hexanes (2×) to give a white solid as desired product (0.7 g, 70 yield).

N-tert-butyl-5-(4,4,5,5-tetramethyl-1,3,2-dioxaborolan-2-yl)-2-(trifluoromethoxy)benzenesulfonamide

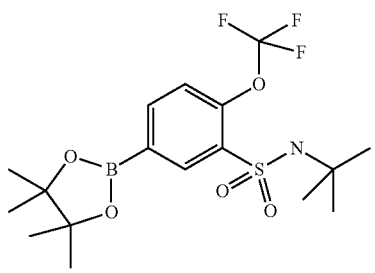 [SMILES: CC(C)(C)NS(=O)(=O)c1cc(B2OC(C)(C)C(C)(C)O2)ccc1OC(F)(F)F]

A mixture of bis(pinacolato)diboron (938 mg, 3.69 mmol), 5-bromo-N-tert-butyl-2-(trifluoromethoxy)benzenesulfonamide (695 mg, 1.85 mmol) and potassium acetate (544 mg, 5.54 mmol) in dioxane (5 ml) was degased with argon and then [1,1'-bis(diphenylphosphino)ferrocene]dichloropalladium(II) (100 mg, 137 µmol) was added. The reaction was heated at 105° C. for 18 hours. The reaction was partitioned between EtOAc (30 ml) and 10% NaHCO3 (10 ml) and layers were separated. The aqueous layer was extracted with EtOAc (2×10 ml). The combined organic solution was dried over Na2SO4 and concentrated to give a residue.

The crude material was purified by flash chromatography (silica gel, 24 g, 10% to 20% EtOAc in Hexanes) and was triturated with hexanes (1×) to give a white solid as desired product (0.27 mg, 34% yield).

N3-(2-chloro-3'-(pyrrolidin-1-ylsulfonyl)-6-(trifluoromethyl)biphenyl-4-yl)-1H-1,2,4-triazole-3,5-diamine (Compound 193)

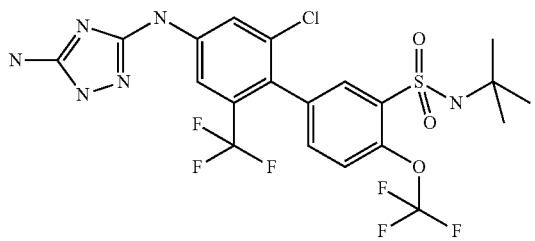 [SMILES: CC(C)(C)NS(=O)(=O)c1cc(-c2c(Cl)cc(Nc3n[nH]c(N)n3)cc2C(F)(F)F)ccc1OC(F)(F)F]

A mixture of N3-(4-bromo-3-chloro-5-(trifluoromethyl)phenyl)-1H-1,2,4-triazole-3,5-diamine Intermediate 1 (150 mg, 421 µmol), N-tert-butyl-5-(4,4,5,5-tetramethyl-1,3,2-dioxaborolan-2-yl)-2-(trifluoromethoxy)benzenesulfonamide (265 mg, 626 µmol) and K2CO3 (280 µl, 841 µmol) in dioxane (2.6 ml) and DME (2.6 ml) was degased with argon and then tetrakis(triphenylphosphine)palladium(0) (80 mg, 69.2 µmol) was added. The reaction was heated in a microwave at 128° C. for 3 hours. The reaction was partitioned between water and EtOAc (5 ml/15 ml), layers separated and the aqueous layer was extracted with EtOAc (3×10 ml) The combined organic solution was dried over Na2SO4, concentrated to give a residue which was purified by flash chromatography (silica gel, 24 g, 3% to 7% MeOH in DCM). Further purification by HPLC (with 0.075% TFA) and freeze drying afforded a white foam as desired product (42 mg, 20% yield). MS +m/z: 573 (M+H)+

1-(4'-(5-amino-1H-1,2,4-triazol-3-ylamino)-2'-chloro-6'-(trifluoromethyl)biphenyl-4-ylsulfonyl)piperidin-4-ol (Compound 194)

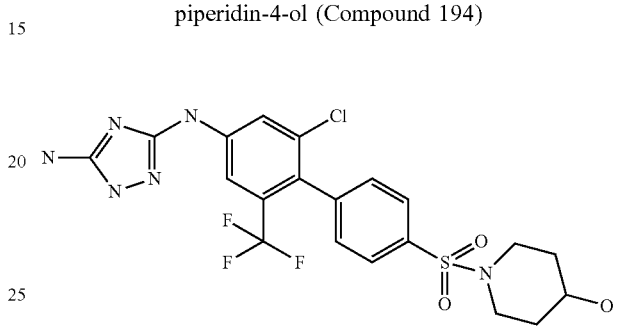

1-(4-bromo-benzenesulfonyl)-piperidin-4-ol

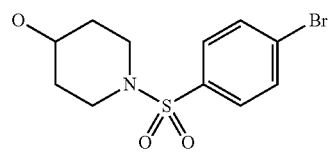 [SMILES: O=S(=O)(c1ccc(Br)cc1)N1CCC(O)CC1]

To a solution of piperidin-4-ol (1.09 g, 10.8 mmol, Aldrich) and DIPEA (2.14 ml, 12.2 mmol) in CH2Cl2 (50 ml) was added 4-bromobenzenesulfonyl chloride (2.5 g, 9.78 mmol, Fluka) and the reaction was stirred at RT overnight. The reaction mixture was washed with 1N HCl solution (1×25 ml), water (40 ml) and brine (30 ml), dried and concentrated to give a white solid as desired product (3.07 g, 98% yield)

1-(4-(4,4,5,5-tetramethyl-1,3,2-dioxaborolan-2-yl)phenylsulfonyl)piperidin-4-ol

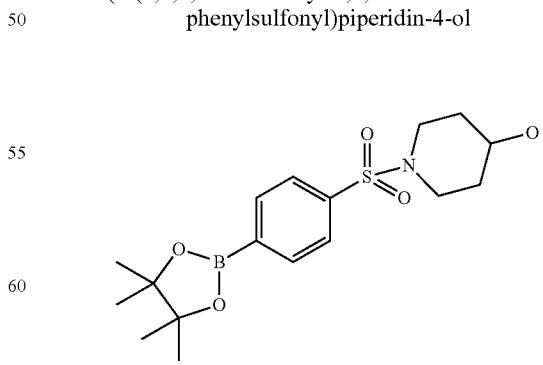

A mixture of 1-(4-bromophenylsulfonyl)piperidin-4-ol (400 mg, 1.25 mmol), bis(pinacolato)diboron (793 mg, 3.12 mmol) and potassium acetate (490 mg, 5.00 mmol) in dioxane (5 ml) was degased with argon and then [1,1'-bis(diphenylphosphino)ferrocene]dichloropalladium(II) (91.4 mg, 125 μmol) was added. The reaction was heated at 105° C. for 24 hours. The reaction was partitioned between EtOAc (15 ml) and water (5 ml) and the layers were separated. The aqueous layer was extracted with EtOAc (2×10 ml). The combined organic solution was dried over Na2SO4, concentrated to give a residue. The crude material was purified by flash chromatography (silica gel, 40 g, 0% to 3% MeOH in DCM) and was triturated with hexanes (2×) to give an off white solid as desired product (235 mg, 51% yield).

1-(4'-(5-amino-1H-1,2,4-triazol-3-ylamino)-2'-chloro-6'-(trifluoromethyl)biphenyl-4-ylsulfonyl)piperidin-4-ol (Compound 194)

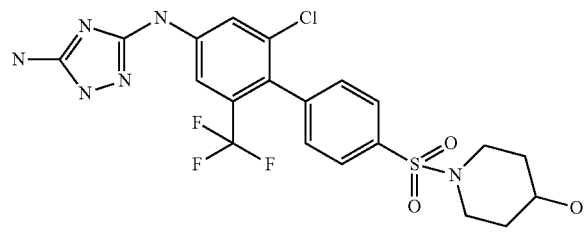 [SMILES: Nc1nc(Nc2cc(Cl)c(-c3ccc(S(=O)(=O)N4CCC(O)CC4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (150 mg, 421 μmol), 1-(4-(4,4,5,5-tetramethyl-1,3,2-dioxaborolan-2-yl)phenylsulfonyl)piperidin-4-ol (235 mg, 640 μmol) and 3M K2CO3 (280 μl, 841 μmol) in DME (1 ml) and dioxane (1 ml) was degased with argon and then tetrakis(triphenylphosphine)palladium(0) (90 mg, 77.9 μmol) was added. This was heated in microwave at 128° C. for 3 hours. The reaction mixture was partitioned between water and EtOAc (5 ml/8 ml) and the layers were separated. The aqueous layer was extracted with EtOAc (3×5 ml). The combined organic solution was dried over Na2SO4, concentrated to give a residue which was purified by flash chromatography (silica gel, 24 g, 3% to 10% MeOH in DCM). Recrystallization from acetonitrile afforded a light brown solid as desired product (64 mg, 29% yield). MS +m/z: 517 (M+H)+

N3-(2-chloro-3'-(methylsulfonyl)-6-(trifluoromethyl)biphenyl-4-yl)-1H-1,2,4-triazole-3,5-diamine (Compound 195)

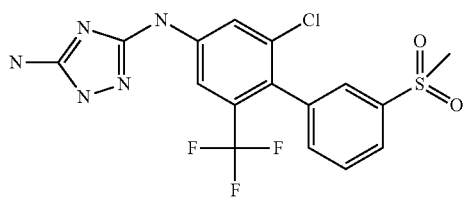 [SMILES: CS(=O)(=O)c1cccc(-c2c(Cl)cc(Nc3n[nH]c(N)n3)cc2C(F)(F)F)c1]

A mixture of N3-(4-bromo-3-chloro-5-(trifluoromethyl)phenyl)-1H-1,2,4-triazole-3,5-diamine Intermediate 1 (150 mg, 421 μmol), 3-(methylsulfonyl)phenylboronic acid (210 mg, 1.05 mmol) and 3M K2CO3 (351 μl, 1.05 mmol) in DME (1 ml) and dioxane (1 ml) was degased with argon and then tetrakis(triphenylphosphine)palladium(0) (97.2 mg, 84.1 μmol) was added. This was heated in microwave at 125° C. for 3 hours. The reaction was diluted with MeOH, filtered and the filtrate was concentrated and then purified by flash chromatography (silica gel, 24 g, 3% to 7% MeOH in DCM). Further purification by super fluid chromatography and freeze drying afforded a white powder as desired product (37.5 mg, 20.6% yield). MS +m/z: 432 (M+H)+

4'-(5-amino-1H-1,2,4-triazol-3-ylamino)-N-tert-butyl-2'-chloro-N-methyl-6'-(trifluoromethyl)biphenyl-3-sulfonamide (Compound 196)

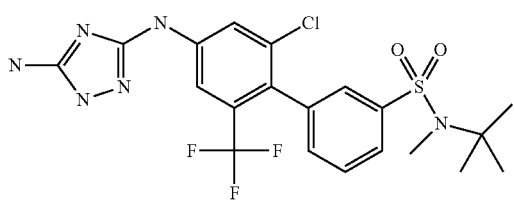 [SMILES: CN(C(C)(C)C)S(=O)(=O)c1cccc(-c2c(Cl)cc(Nc3n[nH]c(N)n3)cc2C(F)(F)F)c1]

A mixture of N3-(4-bromo-3-chloro-5-(trifluoromethyl)phenyl)-1H-1,2,4-triazole-3,5-diamine Intermediate 1 (150 mg, 421 μmol), 3-(N-tert-butyl-N-methylsulfamoyl)phenylboronic acid (251 mg, 926 μmol) and 3M K2CO3 (309 μL, 926 μmol) in DME (1 ml) and dioxane (1 ml) was degased with argon and then tetrakis(triphenylphosphine)palladium(0) (97.2 mg, 84.1 μmol) was added. This was heated in microwave at 128° C. for 3 hours. The reaction was diluted with MeOH, filtered and the filtrate was concentrated and then purified by flash chromatography (silica gel, 24 g, 3% to 7% MeOH in DCM). Further purification by super fluid chromatography afforded a white solid as desired product (46.5 mg, 22% yield). MS +m/z: 503 (M+H)+

4'-(5-amino-1H-1,2,4-triazol-3-ylamino)-2'-chloro-6'-(trifluoromethyl)biphenyl-3-sulfonamide 2,2,2-trifluoroacetate (Compound 197)

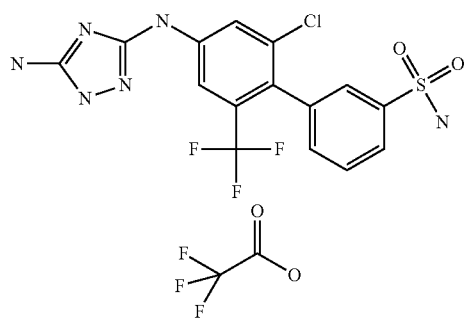

4'-(5-amino-1H-1,2,4-triazol-3-ylamino)-N-tert-butyl-2'-chloro-6'-(trifluoromethyl)biphenyl-3-sulfonamide

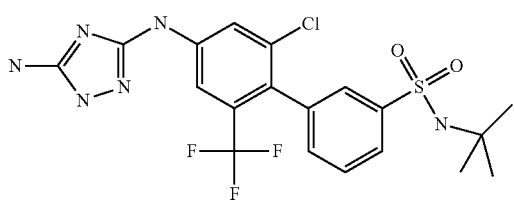 [SMILES: CC(C)(C)NS(=O)(=O)c1cccc(-c2c(Cl)cc(Nc3n[nH]c(N)n3)cc2C(F)(F)F)c1]

A mixture of N3-(4-bromo-3-chloro-5-(trifluoromethyl)phenyl)-1H-1,2,4-triazole-3,5-diamine Intermediate 1 (250 mg, 701 µmol), t-butyl 3-boronobenzenesulfonamide (397 mg, 1.54 mmol) and 3M K2CO3 (514 µl, 1.54 mmol) in DME (1.2 ml) and dioxane (1.2 ml) was degased with argon and then tetrakis(triphenylphosphine)palladium(0) (162 mg, 140 µmol) was added. This was heated in microwave at 128° C. for 3 hours. The reaction was diluted with MeOH, filtered and the filtrate was concentrated and then purified by flash chromatography (silica gel, 24 g, 3% to 7% MeOH in DCM). Recrystallization from Methanol gave a white solid as desired product (54 mg, 16% yield). MS +m/z: 489 (M+H)+

4'-(5-amino-1H-1,2,4-triazol-3-ylamino)-2'-chloro-6'-(trifluoromethyl)biphenyl-3-sulfonamide 2,2,2-trifluoroacetate (Compound 197)

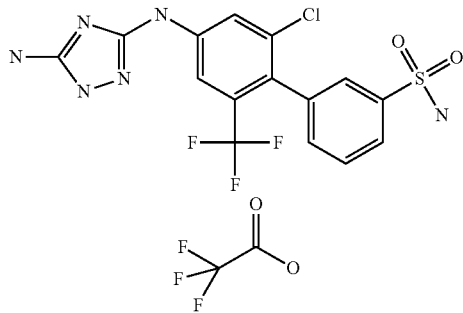

To a suspension of 4'-(5-amino-1H-1,2,4-triazol-3-ylamino)-N-tert-butyl-2'-chloro-6'-(trifluoromethyl)biphenyl-3-sulfonamide (23 mg, 47.0 µmol) in CH2Cl2 (1 ml) was added TFA (1.48 g, 1 ml, 13.0 mmol) and the reaction was stirred at RT for 3 days. The reaction mixture was concentrated in vacuo and the residue was tritruated with diethyl ether (2×3 ml) to give a white solid as desired product (21.2 mg, 82% yield). MS +m/z: 433 (M+H)+

4'-(5-amino-1H-1,2,4-triazol-3-ylamino)-2'-chloro-N,N-dimethyl-6'-(trifluoromethyl)biphenyl-3-sulfonamide (Compound 198)

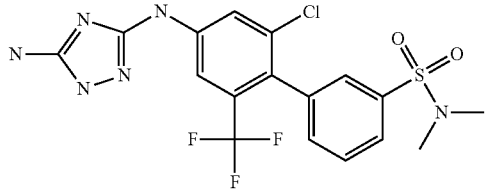 [SMILES: CN(C)S(=O)(=O)c1cccc(-c2c(Cl)cc(Nc3n[nH]c(N)n3)cc2C(F)(F)F)c1]

A mixture of N3-(4-bromo-3-chloro-5-(trifluoromethyl)phenyl)-1H-1,2,4-triazole-3,5-diamine Intermediate 1 (150 mg, 421 µmol), 3-(N,N-dimethylsulphonamido)benzeneboronic acid (241 mg, 1.05 mmol) and 3M K2CO3 (351 µl, 1.05 mmol) in DME (1 ml) and dioxane (1 ml) was degased with argon and then tetrakis(triphenylphosphine)palladium (0) (97.2 mg, 84.1 µmol) was added. This was heated in microwave at 125° C. for 3 hours. The reaction mixture was diluted with MeOH and filtered. The filtrate was concentrated and purified by flash chromatography (silica gel, 24 g, 3% to 7% MeOH in DCM). Further purification by super fluid chromatography and freeze dry afforded a white foam as desired product (43.1 mg, 22% yield). MS +m/z: 461 (M+H)+

N-((4'-(5-amino-1H-1,2,4-triazol-3-ylamino)-2'-chloro-6'-(trifluoromethyl)biphenyl-3-yl)methyl)methanesulfonamide (Compound 199)

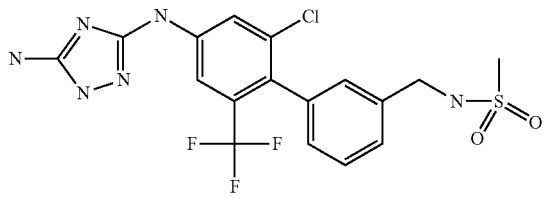 [SMILES: CS(=O)(=O)NCc1cccc(-c2c(Cl)cc(Nc3n[nH]c(N)n3)cc2C(F)(F)F)c1]

A mixture of N3-(4-bromo-3-chloro-5-(trifluoromethyl)phenyl)-1H-1,2,4-triazole-3,5-diamine Intermediate 1 (150 mg, 421 µmol), (3-methanesulfonylaminomethylphenyl)boronic acid (193 mg, 841 µmol) and 3M K2CO3 (309 µl, 926 µmol) in DME (1 ml) and dioxane (1 ml) was degased with argon and then tetrakis(triphenylphosphine)palladium(0) (97.2 mg, 84.1 µmol) was added. This was heated in microwave at 128° C. for 3 hours. The reaction mixture was partitioned between water and EtOAc (5 ml/8 ml) and the layers were separated. The aqueous layer was extracted with EtOAc (3×5 ml). The combined organic solution was dried over Na2SO4, filtered and concentrated in vacuo. The residue was purified by flash chromatography (silica gel, 24 g, 3% to 7% MeOH in DCM). Recrystallization from DCM/Hexanes afforded a light yellow solid as desired product (37.5 mg, 19.3% yield). MS +m/z: 461 (M+H)+

Procedure A tert-butyl 4'-(5-amino-1H-1,2,4-triazol-3-ylamino)-2'-chloro-6'-(trifluoromethyl)biphenyl-4-carboxylate (Compound 200)

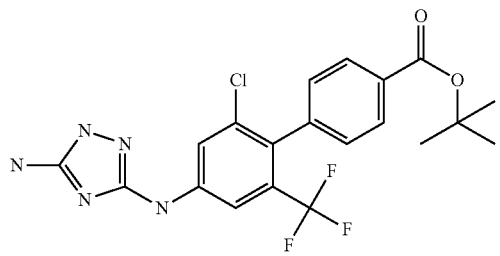 [SMILES: CC(C)(C)OC(=O)c1ccc(-c2c(Cl)cc(Nc3n[nH]c(N)n3)cc2C(F)(F)F)cc1]

4-amino-2-chloro-6-trifluoromethyl-benzoic acid tert-butyl ester

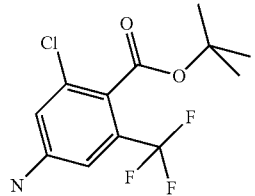 [SMILES: CC(C)(C)OC(=O)c1c(Cl)cc(N)cc1C(F)(F)F]

A mixture of 4-bromo-3-chloro-5-(trifluoromethyl)aniline (1.0 g, 3.64 mmol, APAC), 4-(tert-butoxycarbonyl)phenylboronic acid (1.05 g, 4.74 mmol, Combi-Blocks) and 2M Na2CO3 (3.64 ml, 7.29 mmol) in dioxane (15 ml) was degased with argon and tetrakis(triphenylphosphine)palladium(0) (421 mg, 364 µmol) was added. This was heated at 100° C. for 24 h. The reaction was partitioned between EtOAc (30 ml) and water (15 ml), layers separated and the aqueous layer was extracted with EtOAc (2×15 ml). The combined organic solution was dried over Na2SO4, concentrated to give a residue. The residue was purified by flash chromatography (silica gel, 24 g, 5% to 25% EtOAc/Hexanes) to give an orange oil as desired product. (1.7 g, 75% pure, 94% yield).

2-chloro-4-isothiocyanato-6-trifluoromethyl-benzoic acid tert-butyl ester

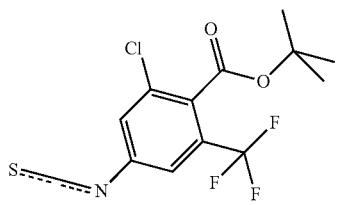

To a suspension of tert-butyl 4'-amino-2'-chloro-6'-(trifluoromethyl)biphenyl-4-carboxylate (1.35 g, 3.63 mmol) in CH2Cl2 (18.0 ml) at 0° C. was added 1,1'-thiocarbonyldiimidazole (777 mg, 4.36 mmol, Chem-Impex Intl, Inc.). The reaction was stirred at 0° C. for 30 minutes and then at RT overnight. The reaction was concentrated and the crude material was purified by flash chromatography (silica gel, 40 g, 2% to 10% DCM/Hexanes) to give a colorless oil as desired product (1.006 g, 67% yield).

(Z)-tert-butyl 2'-chloro-4'-((cyanoimino)(methylthio)methylamino)-6'-(trifluoromethyl)biphenyl-4-carboxylate

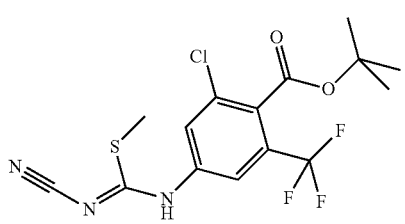 [SMILES: CS/C(=N\C#N)Nc1cc(Cl)c(C(=O)OC(C)(C)C)c(C(F)(F)F)c1]

To a solution of tert-butyl 2'-chloro-4'-isothiocyanato-6'-(trifluoromethyl)biphenyl-4-carboxylate (1.0 g, 2.42 mmol) in DME (12 ml) was added sodium hydrogencyanamide (232 mg, 3.62 mmol) followed by MeOH (2 ml). The reaction was stirred at RT for 1.5 hours and methyl iodide (686 mg, 4.83 mmol) was added. Continued stirring for another 2 hours and then the reaction mixture was partition between EtOAc and water (40 ml/30 ml) and the layers was separated. The aqueous layer was extracted with EtOAc (3×25 ml). The combined organic solution was washed with brine (1×20 ml), dried over MgSO4 and concentrated in vacuo to give a white foam as desired product (1.11 g, 85% pure, 83% yield).

tert-butyl 4'-(5-amino-1H-1,2,4-triazol-3-ylamino)-2'-chloro-6'-(trifluoromethyl)biphenyl-4-carboxylate (Compound 200)

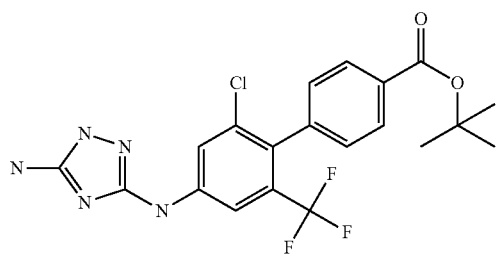 [SMILES: CC(C)(C)OC(=O)c1ccc(-c2c(Cl)cc(Nc3n[nH]c(N)n3)cc2C(F)(F)F)cc1]

To a suspension of (Z)-tert-butyl 2'-chloro-4'-((cyanoimino)(methylthio)methylamino)-6'-(trifluoromethyl)biphenyl-4-carboxylate (1.11 g, 2.01 mmol) in ethanol (15 ml) was added hydrazine (643 mg, 630 µl, 20.1 mmol) and the reaction was stirred at 70° C. for 2 h. The reaction mixture was cooled and concentrated in vacuo and was purified by flash chromatography (silica gel, 40 g column, 3% to 8% MeOH in DCM) to give a white solid as desired product (0.67 g, 73% yield). MS +m/z: 454 (M+H)+

N3-(2-chloro-6-(trifluoromethyl)biphenyl-4-yl)-1H-1,2,4-triazole-3,5-diamine 2,2,2-trifluoroacetate (Compound 201)

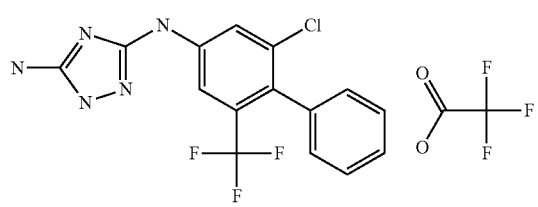

A mixture of phenylboronic acid (34.2 mg, 280 µmol), N3-(4-bromo-3-chloro-5-(trifluoromethyl)phenyl)-1H-1,2,4-triazole-3,5-diamine Intermediate 1 (50 mg, 140 µmol) and 3M potassium phosphate tribasic monohydrate (250 µl, 750 µmol) in acetonitrile (1 ml) was degased with argon and then 1,1-bis(diphenylphosphino)ferrocene]dichloropalladium(II) (22.9 mg, 28.0 µmol) was added. The mixture was heated to 110° C. for 20 minutes in microwave. The reaction mixture was partitioned between water and EtOAc (5 ml/5 ml) and the layers was separated. The aqueous layer was extracted with EtOAc (3×5 ml). The combined organic solution was dried over Na2SO4, filtered and concentrated in vacuo. The crude material was purified by preparative HPLC (0.75% TFA) to afford a brownish powder as desired product (6 mg, 9% yield). MS +m/z: 354 (M+H)+

4'-(5-amino-1H-1,2,4-triazol-3-ylamino)-2'-chloro-6'-(trifluoromethyl)biphenyl-4-carboxylic acid 2,2,2-trifluoroacetate (Compound 202)

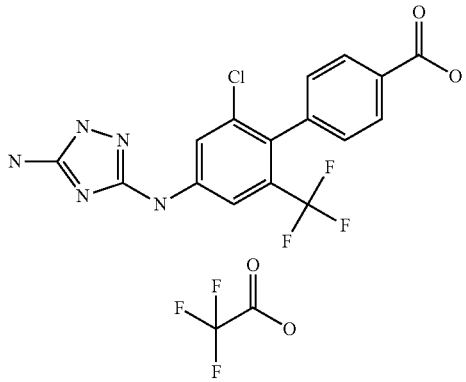

To a suspension of tert-butyl 4'-(5-amino-1H-1,2,4-triazol-3-ylamino)-2'-chloro-6'-(trifluoromethyl)biphenyl-4-carboxylate Compound 200 (150 mg, 331 µmol, Example 45) in DCM (4 ml) was added TFA (1.27 ml, 16.5 mmol) and the reaction was stirred at RT for overnight. The reaction mixture was concentrated in vacuo and was triturated with DCM (2×5 ml), Hexanes (2×5 ml) to give a white solid as desired product (155 mg, 91% yield). MS +m/z: 398 (M+H)+

N3-(2-chloro-4'-methoxy-3'-(pyrrolidin-1-ylsulfonyl)-6-(trifluoromethyl)biphenyl-4-yl)-1H-(Compound 203)

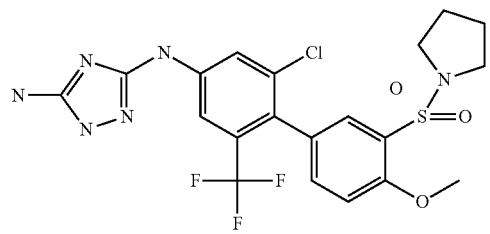

A mixture of N3-(4-bromo-3-chloro-5-(trifluoromethyl)phenyl)-1H-1,2,4-triazole-3,5-diamine Intermediate 1 (150 mg, 421 µmol), 4-methoxy-3-(pyrrolidin-1-ylsulfonyl)phenylboronic acid (264 mg, 926 µmol) and 3M K2CO3 (309 µl, 926 µmol) in DME (1 ml) and dioxane (1.2 ml) was degased with argon and then tetrakis(triphenylphosphine)palladium(0) (97.2 mg, 84.1 µmol) was added. This was heated in microwave at 128° C. for 3 hours. The reaction mixture was diluted with MeOH, filtered, and the filtrate was concentrated in vacuo. The residue was purified by flash chromatography (silica gel, 24 g, 3% to 7% MeOH in DCM). Further purification by super fluid chromatography and freeze dry afforded a white foam as desired product (60.2 mg, 28% yield). MS +m/z: 517 (M+H)+

4'-(5-amino-1H-1,2,4-triazol-3-ylamino)-2'-chloro-4-methoxy-N-(piperidin-4-yl)-6'-(trifluoromethyl)biphenyl-3-sulfonamide hydrochloride (Compound 204)

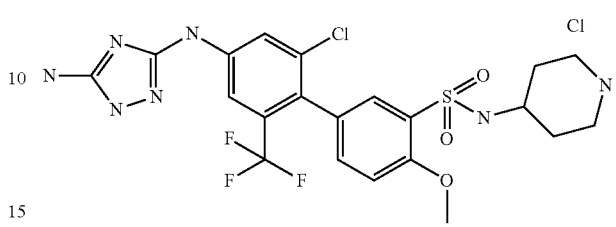

To anhydrous MeOH (5 ml) was quickly added acetyl chloride (552 mg, 0.5 ml, 7.03 mmol). The resulting solution was cooled with ice bath and was added to a solution of tert-butyl 4-(4'-(5-amino-1H-1,2,4-triazol-3-ylamino)-2'-chloro-4-methoxy-6'-(trifluoromethyl)biphenyl-3-ylsulfonamido)piperidine-1-carboxylate (175 mg, 271 mol, example 49) in MeOH (3 ml). The reaction was stirred at room temperature for 5 h. The reaction mixture was concentrated to a residue and was triturated with DCM (3×) to give a white solid as desired product (154 mg, 97% yield). MS +m/z: 546 (M+H)+ tert-butyl 3-(4'-(5-amino-1H-1,2,4-triazol-3-ylamino)-2'-chloro-6'-(trifluoromethyl)biphenyl-4-ylsulfonamido)-3-methylazetidine-1-carboxylate (Compound 205)

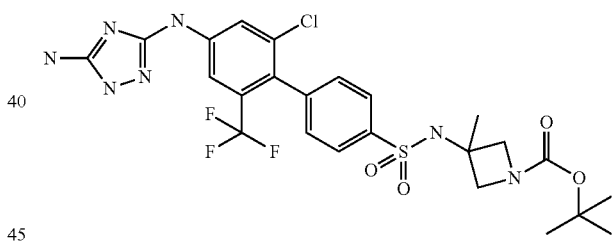

3-(4-bromo-benzenesulfonylamino)-3-methyl-azetidine-1-carboxylic acid tert-butyl ester

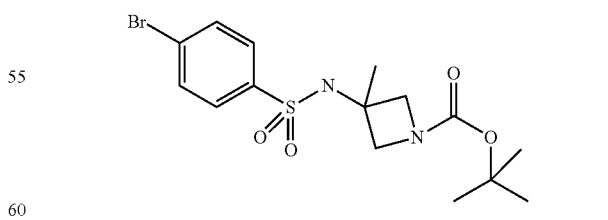

To a solution of 4-bromobenzene-1-sulfonyl chloride (1.3 g, 5.09 mmol, Aldrich) and 1-BOC-3-amino-3-methyl-azetine (995 mg, 5.34 mmol, A&C Pharmtech) in THF (10 ml) was added Et3N (1.42 ml, 10.2 mmol). The reaction was stirred at RT overnight. The reaction mixture was washed with 0.5 N HCl solution (2×20 ml), water (20 ml) and brine (15 ml), dried and concentrated to give a thick oil as desired product (2.01 g, ~90% pure, 88% yield).

tert-butyl 3-methyl-3-(4-(4,4,5,5-tetramethyl-1,3,2-dioxaborolan-2-yl)phenylsulfonamido)azetidine-1-carboxylate

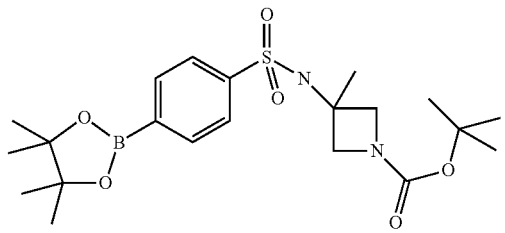 [SMILES: CC1(NS(=O)(=O)c2ccc(B3OC(C)(C)C(C)(C)O3)cc2)CN(C(=O)OC(C)(C)C)C1]

A mixture of bis(pinacolato)diboron (2.26 g, 8.88 mmol), tert-butyl 3-(4-bromophenylsulfonamido)-3-methylazetidine-1-carboxylate (2.0 g, 4.44 mmol) and potassium acetate (1.31 g, 13.3 mmol) in dioxane (30 ml) was degased with argon and then [1,1'-bis(diphenylphosphino)ferrocene]dichloropalladium(II) (162 mg, 222 μmol) was added. The reaction was heated at 105° C. for 18 hours. The reaction mixture was partitioned between EtOAc (35 ml) and 10% NaHCO3 (20 ml) and the layers were separated. The aqueous layer was extracted with EtOAc (2×25 ml). The combined organic solution was dried over Na2SO4, concentrated to give a residue.

The residue was purified by flash chromatography (silica gel, 40 g, 1% to 6% MeOH in DCM) and was triturated with hexanes (2×20 ml) to give a light brown solid as desired product (1.63 g, 81% yield).

tert-butyl 3-(4'-(5-amino-1H-1,2,4-triazol-3-ylamino)-2'-chloro-6'-(trifluoromethyl)biphenyl-4-ylsulfonamido)-3-methylazetidine-1-carboxylate (Compound 205)

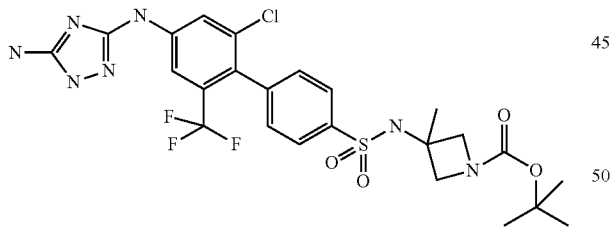

A mixture of N3-(4-bromo-3-chloro-5-(trifluoromethyl) phenyl)-1H-1,2,4-triazole-3,5-diamine Intermediate 1 (400 mg, 1.12 mmol), tert-butyl 3-methyl-3-(4-(4,4,5,5-tetramethyl-1,3,2-dioxaborolan-2-yl)phenylsulfonamido)azetidine-1-carboxylate (812 mg, 1.8 mmol) and K2CO3 (748 μl, 2.24 mmol) in dioxane (2.5 ml) and DME (2.5 ml) was degased with argon and then tetrakis(triphenylphosphine) palladium(0) (194 mg, 168 μmol) was added. The reaction was heated in a microwave at 128° C. for 3 hours. The reaction mixture was partitioned between water and EtOAc (10 ml/15 ml) and the layers were separated. The aqueous layer was extracted with EtOAc (3×10 ml). The combined organic solution was dried over Na2SO4, concentrated to give a residue which was purified by flash chromatography (silica gel, 24 g, 4% to 7% MeOH in DCM). Further purification by super fluid chromatography afforded a light brown solid as desired product (205 mg, 30% yield). MS +m/z: 502 (M+H)$^+$ 4'-(5-amino-1H-1,2,4-triazol-3-ylamino)-2'-chloro-N-(1-methylcyclopropyl)-6'-(trifluoromethyl)biphenyl-4-sulfonamide (Compound 206)

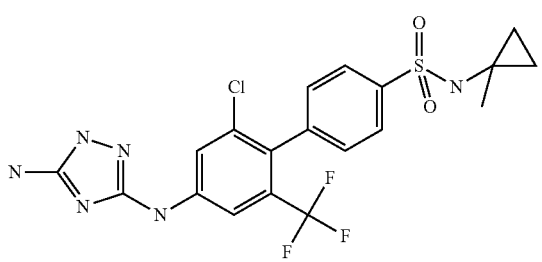 [SMILES: CC1(NS(=O)(=O)c2ccc(-c3c(Cl)cc(Nc4n[nH]c(N)n4)cc3C(F)(F)F)cc2)CC1]

4-bromo-N-(1-methylcyclopropyl)benzenesulfonamide

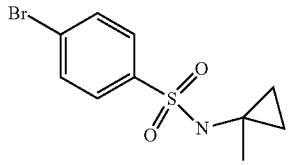

To a solution of 4-bromobenzene-1-sulfonyl chloride (1 g, 3.91 mmol, Aldrich) and Et3N (1.36 ml, 9.78 mmol) in THF (20 ml) was added 1-methylcyclopropanamine hydrochloride (477 mg, 4.69 mmol, Matrix) and the reaction was stirred at room temperature for 3 days. The reaction mixture was washed with 1 N HCl solution (2×15 ml), water (20 ml) and brine (15 ml), dried and concentrated to give a white solid as desired product (0.99 g, 87% yield).

N-(1-methylcyclopropyl)-4-(4,4,5,5-tetramethyl-1,3,2-dioxaborolan-2-yl)benzenesulfonamide

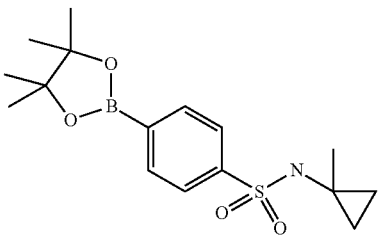 [SMILES: CC1(NS(=O)(=O)c2ccc(B3OC(C)(C)C(C)(C)O3)cc2)CC1]

A mixture of bis(pinacolato)diboron (1.72 g, 6.75 mmol), 4-bromo-N-(1-methylcyclopropyl)benzenesulfonamide (0.98 g, 3.38 mmo) and potassium acetate (994 mg, 10.1 mmol) in dioxane (15 ml) was degased with argon and then [1,1'-bis(diphenylphosphino)ferrocene]dichloropalladium (II) (148 mg, 203 μmol) was added. The reaction was heated at 105° C. for 18 hours. The reaction mixture was partitioned between EtOAc (35 ml) and 10% NaHCO3 (20 ml) and the layers were separated. The aqueous layer was extracted with EtOAc (2×25 ml). The combined organic solution was dried over Na2SO4, concentrated to give a residue.

The crude material was purified by flash chromatography (silica gel, 40 g, 0% to 4% MeOH in DCM). Recrystallized with hexanes afforded a white solid as desired product (0.681 g, 60% yield).

4'-amino-2'-chloro-N-(1-methylcyclopropyl)-6'-(trifluoromethyl)biphenyl-4-sulfonamide

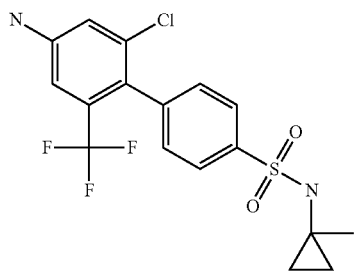 [SMILES: CC1(NS(=O)(=O)c2ccc(-c3c(Cl)cc(N)cc3C(F)(F)F)cc2)CC1]

A mixture of 4-bromo-3-chloro-5-(trifluoromethyl)aniline (250 mg, 911 µmol, APAC), 4-(N-(1-methylcyclopropyl)sulfamoyl)phenylboronic acid (290 mg, 1.14 mmol) and 2M Na2CO3 (911 µl, 1.82 mmol) in dioxane (8 ml) was degased with argon and tetrakis(triphenylphosphine)palladium(0) (105 mg, 91.1 µmol) was added. The reaction was heated at 105° C. for 18 hours. The reaction mixture was partitioned between EtOAc (20 ml) and water (10 ml) and the layers were separated. The aqueous layer was extracted with EtOAc (3×20 ml). The combined organic solution was washed with brine (20 ml), dried over Na2SO4, filtered and concentrated to give a residue. The residue was purified by flash chromatography (silica gel, 24 g, 20% to 35% EtOAc in hexanes) to give a light yellow solid as desired product (135 mg, 37% yield).

2'-chloro-4'-isothiocyanato-N-(1-methylcyclopropyl)-6'-(trifluoromethyl)biphenyl-4-sulfonamide

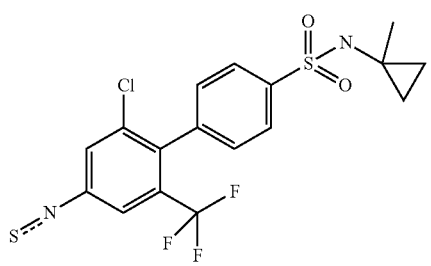

To a solution of 4'-amino-2'-chloro-N-(1-methylcyclopropyl)-6'-(trifluoromethyl)biphenyl-4-sulfonamide (130 mg, 321 µmol) in CH2Cl2 (4 ml) at 0° C. was added 1,1'-THIOCARBONYLDIIMIDAZOLE (68.7 mg, 385 µmol). The reaction was stirred at 0° C. for 30 minutes and then at room temperature for 5 hours. The reaction mixture was concentrated and the crude material was purified by flash chromatography (silica gel, 24 g, 5% to 30% EtOAc/Hexanes) to give a white solid as desired product (104 mg, 73% yield).

(Z)-methyl N-2-chloro-4'-(N-(1-methylcyclopropyl)sulfamoyl)-6-(trifluoromethyl)biphenyl-4-yl-N'-cyanocarbamimidothioate

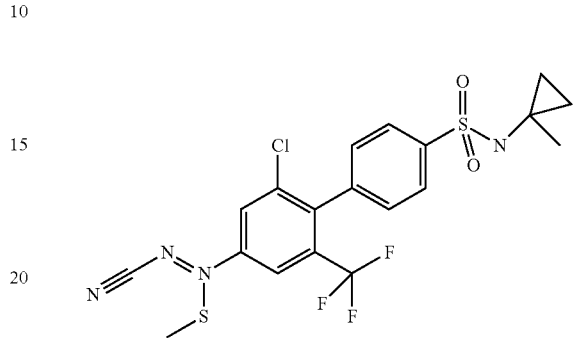

To a solution of 2'-chloro-4'-isothiocyanato-N-(1-methylcyclopropyl)-6'-(trifluoromethyl)biphenyl-4-sulfonamide (100 mg, 224 µmol) in DME (3 ml) was added sodium hydrogencyanamide (21.5 mg, 336 µmol) followed by MeOH (1 ml). The reaction was stirred at RT for 1.5 hours and methyl iodide (63.5 mg, 28.0 µl, 448 µmol) was added. After stirring for 2 hours the reaction mixture was concentrated to a small volume and acetonitrile (2 ml) and water (20 ml) was added to give a suspension. The suspension was filtered to afford a white solid as desired product (78 mg, 69% yield).

4'-(5-amino-1H-1,2,4-triazol-3-ylamino)-2'-chloro-N-(1-methylcyclopropyl)-6'-(trifluoromethyl)biphenyl-4-sulfonamide (Compound 206)

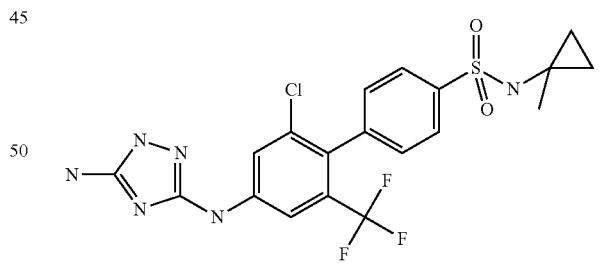

To a suspension of (Z)-methyl N-2-chloro-4'-(N-(1-methylcyclopropyl)sulfamoyl)-6-(trifluoromethyl)biphenyl-4-yl-N'-cyanocarbamimidothioate (76 mg, 151 µmol) in ethanol (2 ml) was added hydrazine (48.4 mg, 47.4 µl, 1.51 mmol) and the reaction was stirred at 70° C. for 3 hours. The reaction mixture was concentrated in vacuo. The crude material was purified by flash chromatography (silica gel, 12 g, column, 4% to 7% MeOH in DCM) to give a white solid as desired product (54 mg, 73% yield). MS +m/z: 487 (M+H)$^+$

4'-(5-amino-1H-1,2,4-triazol-3-ylamino)-2'-chloro-N-(3-methylazetidin-3-yl)-6'-(trifluoromethyl)biphenyl-4-sulfonamide hydrochloride (Compound 207)

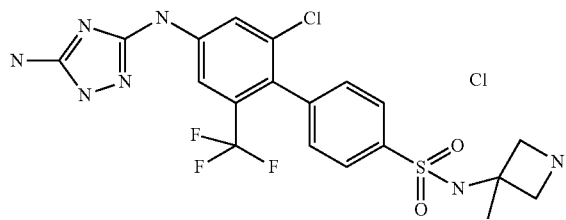 [SMILES: CC1(NS(=O)(=O)c2ccc(-c3c(Cl)cc(Nc4n[nH]c(N)n4)cc3C(F)(F)F)cc2)CNC1 ; Cl]

To anhydrous MeOH (5 ml) was quickly added acetyl chloride (552 mg, 0.5 ml, 7.03 mmol). The resulting solution was cooled with ice bath and was added to a solution of tert-butyl 3-(4'-(5-amino-1H-1,2,4-triazol-3-ylamino)-2'-chloro-6'-(trifluoromethyl)biphenyl-4-ylsulfonamido)-3-methylazetidine-1-carboxylate (155 mg, 257 µmol, example 52) in MeOH (3 ml). The reaction was stirred at room temperature for 4 hours. The reaction mixture was concentrated to a residue and was triturated with DCM (2×1 ml) to give a white solid as desired product (138 mg, 99% yield). MS +m/z: 502 (M+H)$^+$ tert-butyl 4-(4'-(5-amino-1H-1,2,4-triazol-3-ylamino)-2'-chloro-6'-(trifluoromethyl)biphenyl-4-ylsulfonyl)-4,7-diazaspiro[2.5]octane-7-carboxylate (Compound 208)

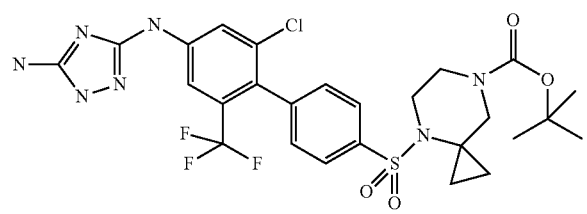 [SMILES: CC(C)(C)OC(=O)N1CCN(S(=O)(=O)c2ccc(-c3c(Cl)cc(Nc4n[nH]c(N)n4)cc3C(F)(F)F)cc2)C2(CC2)C1]

tert-butyl 4-(4-bromophenylsulfonyl)-4,7-diazaspiro[2.5]octane-7-carboxylate

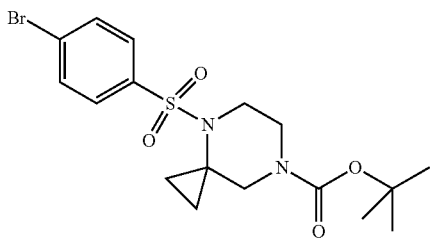 [SMILES: CC(C)(C)OC(=O)N1CCN(S(=O)(=O)c2ccc(Br)cc2)C2(CC2)C1]

To a solution of 4-bromobenzene-1-sulfonyl chloride (1.1 g, 4.31 mmol, Aldrich) and 4,7-diaza-spiro[2.5]octane-7-carboxylic acid tert-butyl ester (1.0 g, 4.71 mmol, Anichem Product List) in THF (20 ml) was added Et3N (1.36 ml, 9.78 mmol) and the reaction was stirred at room temperature for overnight. The reaction mixture was washed with 0.5 N HCl solution (2×20 ml), water (20 ml) and brine (15 ml), dried and concentrated to give a white solid as desired product (1.85 g, 90% pure, 90% yield).

tert-butyl 4-(4-(4,4,5,5-tetramethyl-1,3,2-dioxaborolan-2-yl)phenylsulfonyl)-4,7-diazaspiro[2.5]octane-7-carboxylate

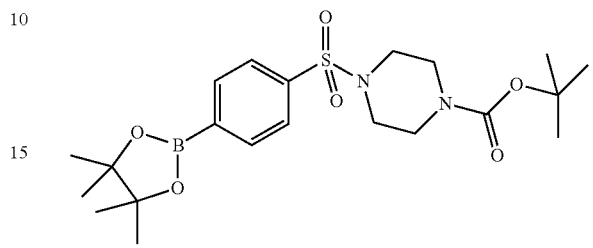

A mixture of bis(pinacolato)diboron (1.96 g, 7.72 mmol), tert-butyl 4-(4-bromophenylsulfonyl)-4,7-diazaspiro[2.5] octane-7-carboxylate (1.85 g, 3.86 mmol) and potassium acetate (1.14 g, 11.6 mmol) in dioxane (30.0 ml) was degased with argon and then [1,1'-bis(diphenylphosphino)ferrocene]dichloropalladium(II) (141 mg, 193 µmol) was added. The reaction was heated at 105° C. for 18 hours. The reaction mixture was partitioned between EtOAc (35 ml) and 10% NaHCO3 (20 ml) and the layers were separated. The aqueous layer was extracted with EtOAc (2×25 ml). The combined organic solution was dried over Na2SO4, filtered and concentrated in vacuo. The crude material was purified by flash chromatography (silica gel, 40 g, 1% to 6% MeOH in DCM) and was triturated with hexanes (2×20 ml) to give a light brown solid as desired product (2.6 g).

tert-butyl 4-(4'-(5-amino-1H-1,2,4-triazol-3-ylamino)-2'-chloro-6'-(trifluoromethyl)biphenyl-4-ylsulfonyl)-4,7-diazaspiro[2.5]octane-7-carboxylate (Compound 208)

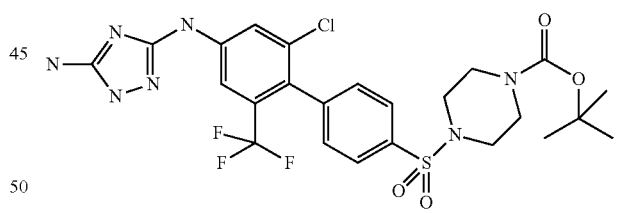

A mixture of N3-(4-bromo-3-chloro-5-(trifluoromethyl)phenyl)-1H-1,2,4-triazole-3,5-diamine Intermediate 1 (400 mg, 1.12 mmol), 7-(tert-butoxy(methoxy)methyl)-4-(4-(4,4,5,5-tetramethyl-1,3,2-dioxaborolan-2-yl)phenylsulfonyl)-4,7-diazaspiro[2.5]octane (1.11 g, 2.24 mmol) and K2CO3 (748 µl, 2.24 mmol) in dioxane (2.5 ml) and DME (2.5 ml) was degased with argon and then tetrakis(triphenylphosphine)palladium(0) (194 mg, 168 µmol) was added. The reaction was heated in a microwave at 128° C. for 3 hours. The reaction mixture was partitioned between water and EtOAc (10 ml/15 ml) and the layers were separated. The aqueous layer was extracted with EtOAc (3×10 ml). The combined organic solution was dried with Na2SO4, concentrated to give a residue which was purified by flash chromatography (silica gel, 24 g, 3.5% to 7% MeOH in DCM). Further purification by super fluid chromatography and freeze dry afforded a yellow foam as desired product (121 mg, 17% yield). MS +m/z: 528 (M+H−100)+ tert-butyl 2-(4'-(5-amino-1H-1,2,4-triazol-3-ylamino)-2'-chloro-6'-(trifluoromethyl)biphenyl-4-ylsulfonamido)ethyl(methyl)carbamate (Compound 209)

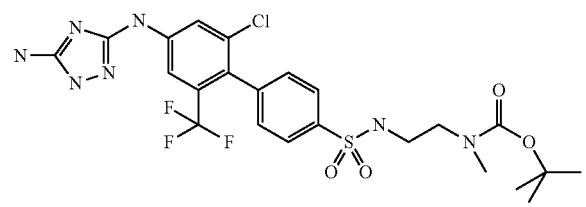 [SMILES: CN(CCNS(=O)(=O)c1ccc(-c2c(Cl)cc(Nc3n[nH]c(N)n3)cc2C(F)(F)F)cc1)C(=O)OC(C)(C)C]

tert-butyl 2-(4-bromophenylsulfonamido)ethyl(methyl)carbamate

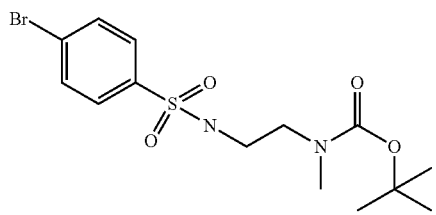 [SMILES: CN(CCNS(=O)(=O)c1ccc(Br)cc1)C(=O)OC(C)(C)C]

To a solution of 4-bromobenzene-1-sulfonyl chloride (1.3 g, 5.09 mmol, Aldrich) and N-(2-AMINOETHYL)-N-METHYL CARBAMIC ACID TERT-BUTYL ESTER (975 mg, 1.0 ml, 5.6 mmol, Chem-Impex Intl, Inc.) in THF (25 ml) was added Et3N (1.29 g, 1.77 ml, 12.7 mmol). The reaction was stirred at RT overnight. The reaction mixture was washed with 0.5 N HCl solution (2×20 ml), water (20 ml) and brine (15 ml), dried and concentrated to give a residue. The residue was purified by flash chromatography (silica gel, 40 g, 1% to 5% MeOH in DCM) to give a brown solid as desired product (2.0 g, quantitative yield).

tert-butyl methyl(2-(4-(4,4,5,5-tetramethyl-1,3,2-dioxaborolan-2-yl)phenylsulfonamido)ethyl)carbamate

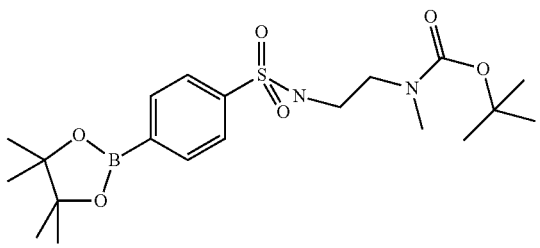 [SMILES: CN(CCNS(=O)(=O)c1ccc(B2OC(C)(C)C(C)(C)O2)cc1)C(=O)OC(C)(C)C]

A mixture of bis(pinacolato)diboron (2.45 g, 9.66 mmol), tert-butyl 2-(4-bromophenylsulfonamido)ethyl(methyl)carbamate (1.9 g, 4.83 mmol) and potassium acetate (1.42 g, 14.5 mmol) in dioxane (30 ml) was degased with argon and then 1,1'-bis(diphenylphosphino)ferrocene]dichloropalladium(II) (177 mg, 242 μmol) was added. The reaction was heated at 105° C. for 18 hours. The reaction was partitioned between EtOAc (35 ml) and 10% NaHCO3 (20 ml), and the layers were separated. The aqueous layer was extracted with EtOAc (2×25 ml). The combined organic solution was dried over Na2SO4, filtered and concentrated in vacuo.

The crude material was purified by flash chromatography (silica gel, 40 g, 10% to 30% EtOAc in DCM) and was tritrated with Hexanes to give a white solid as desired product (1.87 g, 88% yield).

tert-butyl 2-(4'-(5-amino-1H-1,2,4-triazol-3-ylamino)-2'-chloro-6'-(trifluoromethyl)biphenyl-4-ylsulfonamido)ethyl(methyl)carbamate (Compound 209)

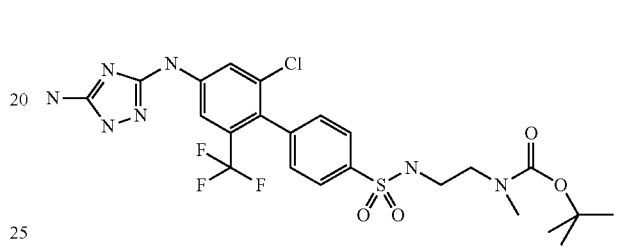

A mixture of N3-(4-bromo-3-chloro-5-(trifluoromethyl)phenyl)-1H-1,2,4-triazole-3,5-diamine Intermediate 1 (250 mg, 701 μmol), tert-butyl methyl(2-(4-(4,4,5,5-tetramethyl-1,3,2-dioxaborolan-2-yl)phenylsulfonamido)ethyl)carbamate (500 mg, 1.14 mmol) and K2CO3 (467 μl, 1.4 mmol) in dioxane (1.5 ml) and DME (1.5 ml) was degased with argon and then tetrakis(triphenylphosphine)palladium(0) (122 mg, 105 μmol) was added. The reaction was heated in a microwave at 125° C. for 3 hours.

The reaction mixture was partitioned between water and EtOAc (10 ml/15 ml), layers separated and the aqueous layer was extracted with EtOAc (3×10 ml). The combined organic solution was dried with Na2SO4, concentrated to give a residue which was purified by flash chromatography (silica gel, 24 g, 4% to 7% MeOH in DCM). Further purification by super fluid chromatography afforded a white solid as desired product (107 mg, 26% yield). MS +m/z: 490 (M+H−100)+

4'-(5-amino-1H-1,2,4-triazol-3-ylamino)-2'-chloro-N-(1-isopropyl-3-methylazetidin-3-yl)-6'-(trifluoromethyl)biphenyl-4-sulfonamide hydrochloride (Compound 210)

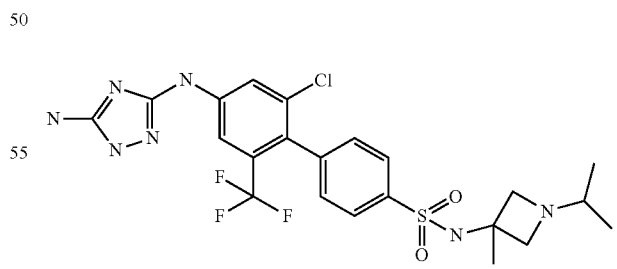

To a suspension of 4'-(5-amino-1H-1,2,4-triazol-3-ylamino)-2'-chloro-N-(3-methylazetidin-3-yl)-6'-(trifluoromethyl)biphenyl-4-sulfonamide hydrochloride (20 mg, 37.1 μmol, example 54) in Methanol (1 ml) was added acetone (8.63 mg, 10.9 μl, 149 μmol) and acetic acid (13.4 mg, 12.8 μl, 223 μmol), followed by sodium cyanoborohydride (4.67 mg, 74.3 μmol). The resulting solution was stirred at room temperature for overnight, and filtered to give a white solid as desired product (12.3 mg, 57% yield). MS +m/z: 544 (M+H)+

4'-(5-amino-1H-1,2,4-triazol-3-ylamino)-2'-chloro-N-(1-isopropyl-3-methylazetidin-3-yl)-6'-(trifluoromethyl)biphenyl-4-sulfonamide; compound with trifluoro-acetic acid (Compound 211)

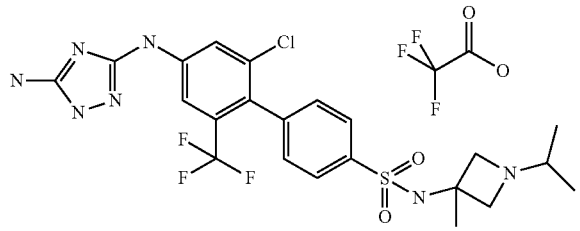

To a suspension of 4'-(5-amino-1H-1,2,4-triazol-3-ylamino)-2'-chloro-N-(3-methylazetidin-3-yl)-6'-(trifluoromethyl)biphenyl-4-sulfonamide hydrochloride (20 mg, 37.1 mol, example 54) in methanol (1 ml) was added acetone (8.63 mg, 149 μmol) and acetic acid (13.4 mg, 223 μmol), followed by sodium cyanoborohydride (4.67 mg, 74.3 μmol). The reaction was stirred at room temperature for overnight, then partitioned between EtOAc (4 ml) and 10% NaHCO₃ (2 ml), and the layers were separated. The aqueous layer was extracted with EtOAc (2×2 ml). The combined organic solution was concentrated to give a residue. Purification with reversed phase HPLC and freeze dry afforded a white foam as desired product (23 mg, 80% yield). MS + m/z: 544 (M+H)+ tert-butyl 3-(4'-(5-amino-1H-1,2,4-triazol-3-ylamino)-2'-chloro-4-methoxy-6'-(trifluoromethyl)biphenyl-3-ylsulfonamido)-3-methylazetidine-1-carboxylate (Compound 212)

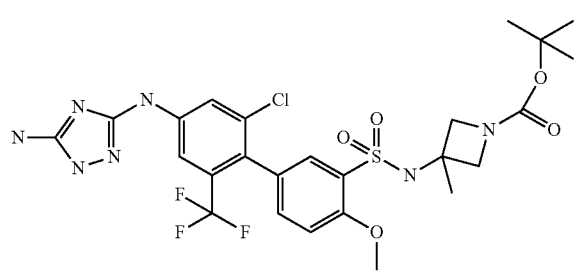 [SMILES: COc1ccc(-c2c(Cl)cc(Nc3n[nH]c(N)n3)cc2C(F)(F)F)cc1S(=O)(=O)NC1(C)CN(C(=O)OC(C)(C)C)C1]

tert-butyl 3-(5-bromo-2-methoxyphenylsulfonamido)-3-methylazetidine-1-carboxylate

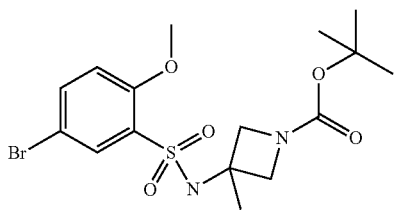 [SMILES: COc1ccc(Br)cc1S(=O)(=O)NC1(C)CN(C(=O)OC(C)(C)C)C1]

To a solution of 5-bromo-2-methoxybenzene-1-sulfonyl chloride (1.45 g, 5.08 mmol) and 1-Boc-3-amino-3-methylazetidine (1.0 g, 5.37 mmol) in THF (25 ml) was added Et3N (1.03 g, 1.42 ml, 10.2 mmol). The reaction was stirred at RT overnight. The reaction mixture was washed with 0.5 N HCl solution (2×20 ml), water (20 ml) and brine (25 ml). The organic solution was dried over Na2SO4, concentrated in vacuo to give a white solid as desired product (1.91 g, 86% yield).

tert-butyl 3-(2-methoxy-5-(4,4,5,5-tetramethyl-1,3,2-dioxaborolan-2-yl)phenylsulfonamido)-3-methylazetidine-1-carboxylate

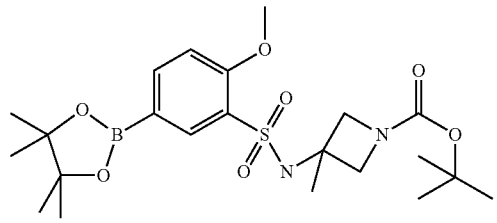 [SMILES: COc1ccc(B2OC(C)(C)C(C)(C)O2)cc1S(=O)(=O)NC1(C)CN(C(=O)OC(C)(C)C)C1]

A mixture of bis(pinacolato)diboron (2.22 g, 8.73 mmol), tert-butyl 3-(5-bromo-2-methoxyphenylsulfonamido)-3-methylazetidine-1-carboxylate (1.9 g, 4.36 mmol) and potassium acetate (1.29 g, 13.1 mmol) in dioxane (30 ml) was degased with argon and then [1,1'-bis(diphenylphosphino)ferrocene]dichloropalladium(II) (160 mg, 218 μmol) was added. The reaction was heated at 100° C. for 18 hours. The reaction was partitioned between EtOAc (35 ml) and 10% NaHCO3 (20 ml) and layers were separated. The aqueous layer was extracted with EtOAc (2×25 ml). The combined organic solution was dried over Na2SO4 and concentrated to give a residue.

The crude material was purified by flash chromatography (silica gel, 40 g, 15% to 30% EtOAc in DCM) and was triturated with hexanes (2×) to give a white solid as desired product (1.91 g, 90% yield).

tert-butyl 3-(4'-(5-amino-1H-1,2,4-triazol-3-ylamino)-2'-chloro-4-methoxy-6'-(trifluoromethyl)biphenyl-3-ylsulfonamido)-3-methylazetidine-1-carboxylate (Compound 212)

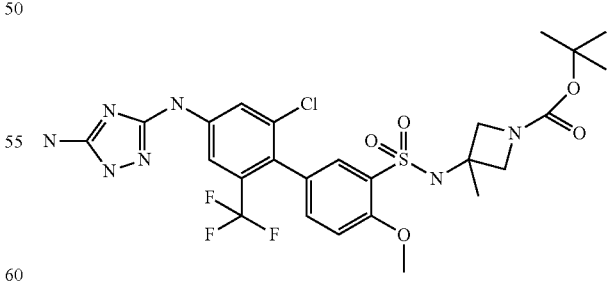

A mixture of N3-(4-bromo-3-chloro-5-(trifluoromethyl)phenyl)-1H-1,2,4-triazole-3,5-diamine Intermediate 1 (400 mg, 1.12 mmol), tert-butyl 3-(2'-chloro-4-methoxy-4'-(4,4,5,5-tetramethyl-1,3,2-dioxaborolan-2-yl)-6'-(trifluoromethyl)biphenyl-3-ylsulfonamido)-3-methylazetidine-1-carboxylate (1.19 g, 1.8 mmol) and 3M K2CO3 (748 μl, 2.24 mmol) in dioxane (2.5 ml) and DME (2.5 ml) was degased with argon and then tetrakis(triphenylphosphine)palladium (0) (194 mg, 168 µmol) was added. The reaction was heated in a microwave at 125° C. for 3 hours. The reaction mixture was partitioned between water and EtOAc (10 ml/15 ml) and the layers were separated. The aqueous layer was extracted with EtOAc (3×10 ml). The combined organic solution was dried over Na2SO4, concentrated to give a residue which was purified by flash chromatography (silica gel, 24 g, 3.5% to 7% MeOH in DCM). Further purification by super fluid chromatography afforded a white foam as desired product (194 mg, 27% yield). MS +m/z: 532 (M+H)+

4'-(5-amino-1H-1,2,4-triazol-3-ylamino)-2'-chloro-N-(2-(methylamino)ethyl)-6'-(trifluoromethyl)biphenyl-4-sulfonamide hydrochloride (Compound 213)

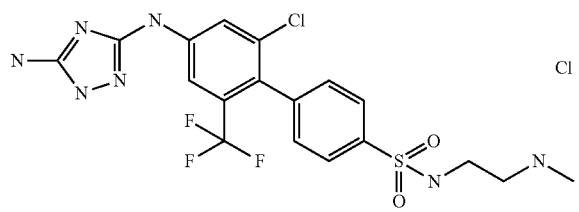 [SMILES: CNCCNS(=O)(=O)c1ccc(-c2c(Cl)cc(Nc3n[nH]c(N)n3)cc2C(F)(F)F)cc1 ; Cl]

To anhydrous MeOH (5 ml) was quickly added acetyl chloride (442 mg, 400 µl, 5.63 mmol). The resulting solution was cooled with ice bath and was added to a solution of tert-butyl 2-(4'-(5-amino-1H-1,2,4-triazol-3-ylamino)-2'-chloro-6'-(trifluoromethyl)biphenyl-4-ylsulfonamido)ethyl (methyl)carbamate (65 mg, 110 µmol, example 56) in MeOH (1 ml). The reaction was stirred at room temperature for 4 hours. The reaction mixture was concentrated to a residue and was triturated with diethyl ether (2×1 ml) to give an off white solid as desired product (60 mg, 99% yield). MS +m/z: 489.9 (M+H)+

N3-(4'-(4,7-diazaspiro[2.5]octan-4-ylsulfonyl)-2-chloro-6-(trifluoromethyl)biphenyl-4-yl)-1H-1,2,4-triazole-3,5-diamine hydrochloride (Compound 214)

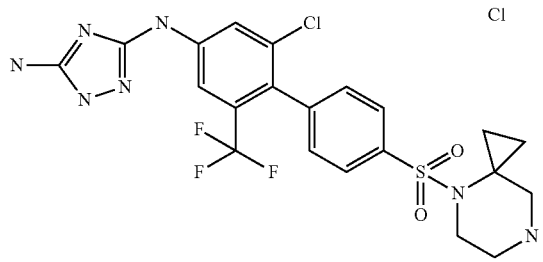 [SMILES: Cl ; Nc1nc(Nc2cc(Cl)c(-c3ccc(S(=O)(=O)N4CCNCC45CC5)cc3)c(C(F)(F)F)c2)n[nH]1]

To anhydrous MeOH (5 ml) was quickly added acetyl chloride (442 mg, 400 µl, 5.63 mmol). The resulting solution was cooled with ice bath and was added to a tert-butyl 4-(4'-(5-amino-1H-1,2,4-triazol-3-ylamino)-2'-chloro-6'-(trifluoromethyl)biphenyl-4-ylsulfonyl)-4,7-diazaspiro[2.5]octane-7-carboxylate (82 mg, 131 µmol, example 55) in MeOH (3 ml). The reaction was stirred at room temperature for 4 hours. The reaction mixture was concentrated to a residue and was triturated with diethyl ether (2×1 ml) to give an off white solid as desired product (72 mg, 98% yield). MS +m/z: 528 (M+H)+

4'-(5-amino-1H-1,2,4-triazol-3-ylamino)-2'-chloro-4-methoxy-N-(3-methylazetidin-3-yl)-6'-(trifluoromethyl)biphenyl-3-sulfonamide hydrochloride (Compound 215)

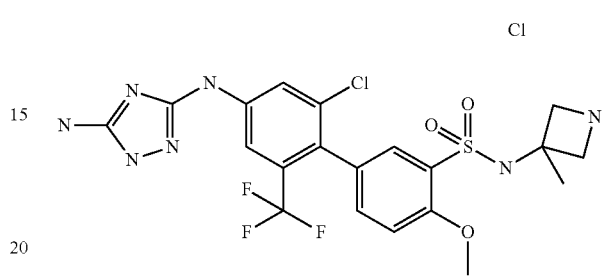

To anhydrous MeOH (5 ml) was quickly added acetyl chloride (552 mg, 500 µl, 7.03 mmol). The resulting solution was cooled with ice bath and was added to of tert-butyl 3-(4'-(5-amino-1H-1,2,4-triazol-3-ylamino)-2'-chloro-4-methoxy-6'-(trifluoromethyl)biphenyl-3-ylsulfonamido)-3-methylazetidine-1-carboxylate (140 mg, 221 µmol, example 59) in MeOH (1 ml). The reaction was stirred at room temperature for 4 hours. The reaction mixture was concentrated to a residue and was triturated with diethyl ether (2×1 ml) to give an off white solid as desired product (123 mg, 97% yield). MS +m/z: 532 (M+H)+

4'-(5-Amino-1H-[1,2,4]triazol-3-ylamino)-6'-chloro-4-methoxy-2'-trifluoromethyl-biphenyl-3-sulfonic acid tert-butylamide (Compound 216)

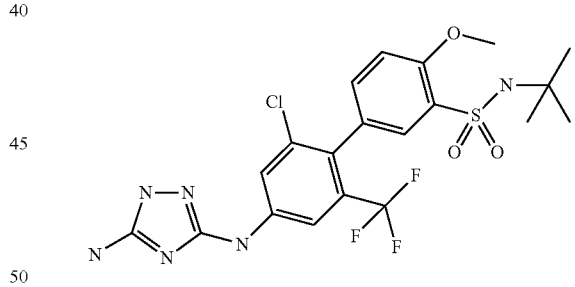

N-tert-Butyl-2-methoxy-5-(4,4,5,5-tetramethyl-[1,3,2]dioxaborolan-2-yl)-benzenesulfonamide

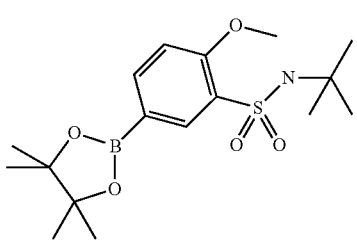 [SMILES: COc1ccc(B2OC(C)(C)C(C)(C)O2)cc1S(=O)(=O)NC(C)(C)C]

A mixture of 5-bromo-N-tert-butyl-2-methoxybenzenesulfonamide (966 mg, 3 mmol), 4,4,4',4',5,5,5',5'-octamethyl-2,2'-bi(1,3,2-dioxaborolane) (761 mg, 3 mmol), potassium acetate (900 mg, 9.17 mmol) and [1,1'-Bis(diphospheno)-ferrocene)dichloro Palladium(II) complex with methylene chloride (100 mg, 0.137 mmol) in 5 mL of 1,4-dioxane was bubbled with nitrogen and the mixture was sealed in a tube and heated in a microwave oven at 150° C. for 30 min. The reaction was diluted with ethyl acetate (15 mL) and water (20 mL). The organic layer was separated and dried with sodium sulfate. The solvent was removed and the residue was chromatographed (5% methanol/methylene chloride, 40 g column) to give a 960 mg (87%) of desired product as a white solid.

¹H NMR (300 MHz, CHLOROFORM-d) δ ppm 1.20 (s, 9H) 1.35 (s, 12H) 4.87 (br. s., 3H) 7.01 (d, J=8.29 Hz, 1H) 7.95 (dd, J=8.29, 1.51 Hz, 1H) 8.38 (d, J=1.51 Hz, 1H)

4'-(5-Amino-1H-[1,2,4]triazol-3-ylamino)-6'-chloro-4-methoxy-2'-trifluoromethyl-biphenyl-3-sulfonic acid tert-butylamide (Compound 216)

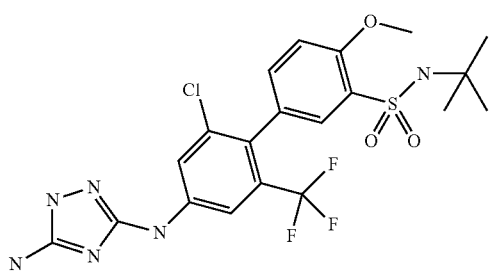 [SMILES: COc1ccc(-c2c(Cl)cc(Nc3n[nH]c(N)n3)cc2C(F)(F)F)cc1S(=O)(=O)NC(C)(C)C]

To a stirred solution of N3-(4-bromo-3-chloro-5-(trifluoromethyl)phenyl)-1H-1,2,4-triazole-3,5-diamine Intermediate 1 (200 mg, 0.56 mmol) in a mixture of DME and 1,4-dioxane (1:1, 2 ml each), was added tetrakis(triphenylphosphine)palladium(0) (50 mg, 0.043 mmol), potassium carbonate (233 mg, 1.68 mmol) in 0.5 mL of water and N-tert-butyl-2-methoxy-5-(4,4,5,5-tetramethyl-1,3,2-dioxaborolan-2-yl)benzenesulfonamide (207 mg, 0.56 mmol). The reaction mixture was bubbled with nitrogen and then heated in a microwave oven for 3 hrs for 140° C. The residue was diluted with 30 mL of water and extracted with ethyl acetate (3×10 mL). The organic extracts were dried with sodium sulfate and the solvent was removed. The residue was chromatographed (3-9% methanol/methylene chloride) on a 24 gram silica gel column, and further purified on a SFC machine to give 50 mg (17.2%) of product. MS +m/z: 519 (M+H)⁺

¹H NMR (300 MHz, DMSO-d₆) δ ppm 3.96 (s, 3H) 6.04 (br. s., 2H) 7.06 (s, 1H) 7.25 (d, J=8.67 Hz, 1H) 7.41 (d, J=8.67 Hz, 1H) 7.50 (s, 1H) 7.87-8.16 (m, 2H) 9.43 (s, 1H) 11.37 (s, 1H)

4'-(5-Amino-1H-[1,2,4]triazol-3-ylamino)-6'-chloro-3-trifluoromethoxy-2'-trifluoromethylbiphenyl-4-sulfonic acid tert-butylamide (Compound 217)

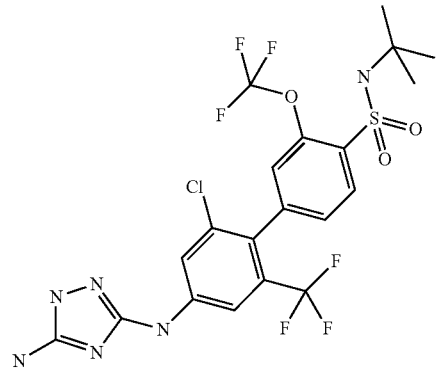 [SMILES: CC(C)(C)NS(=O)(=O)c1ccc(-c2c(Cl)cc(Nc3n[nH]c(N)n3)cc2C(F)(F)F)cc1OC(F)(F)F]

4-Bromo-N-tert-butyl-2-trifluoromethoxy-benzenesulfonamide

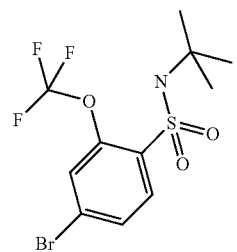 [SMILES: CC(C)(C)NS(=O)(=O)c1ccc(Br)cc1OC(F)(F)F]

To a stirred solution of 4-bromo-2-(trifluoromethoxy)benzene-1-sulfonyl chloride (680 mg, 2 mmol) in methylene chloride (5 mL), was added 2-methylpropan-2-amine (146 mg, 2 mmol) followed by triethylamine (0.30 mL). The mixture was stirred at rt overnight. The solvent was removed and the residue was chromatographed to give 430 mg (57%) of desired product as a white solid.

¹H NMR (300 MHz, CHLOROFORM-d) δ ppm 1.24 (s, 9H) 3.36 (d, J=7.16 Hz, 3H) 4.65 (s, 1H) 7.28 (s, 9H) 7.50-7.67 (m, 2H) 7.93 (d, J=8.67 Hz, 1H)

N-tert-Butyl-4-(4,4,5,5-tetramethyl-[1,3,2]dioxaborolan-2-yl)-2-trifluoromethoxybenzenesulfonamide

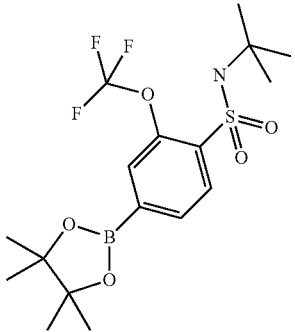 [SMILES: CC(C)(C)NS(=O)(=O)c1ccc(B2OC(C)(C)C(C)(C)O2)cc1OC(F)(F)F]

A mixture of 4-bromo-N-tert-butyl-2-(trifluoromethoxy)benzenesulfonamide (430 mg, 1.14 mmol), [1,1'-bis(diphenylphosphino)-ferrocine]dichloro palladium(II) complex with dichloromethane (90 mg, 0.123 mmol), 4,4,4',4',5,5,5',5'-octamethyl-2,2'-bi(1,3,2-dioxaborolane) (290 mg, 1.14 mmol) and KOAc (337 mg, 3.43 mmol) in 1,4-dioxane (4 mL) was flushed with N2, then sealed in a tube and heated at 130° C. for 30 min. The solvent was removed and the residue was chromatographed (20-40% EtOAc/Hexanes) to give a 476 mg (98%) of desired product as a white solid.

$^1$H NMR (300 MHz, CHLOROFORM-d) δ ppm 1.19-1.28 (m, 9H) 1.37 (s, 12H) 2.52-2.58 (m, 1H) 4.67 (s, 1H) 7.65-7.88 (m, 2H) 8.04 (d, J7.72 Hz, 1H)

4'-(5-Amino-1H-[1,2,4]triazol-3-ylamino)-6'-chloro-3-trifluoromethoxy-2'-trifluoromethylbiphenyl-4-sulfonic acid tert-butylamide (Compound 217)

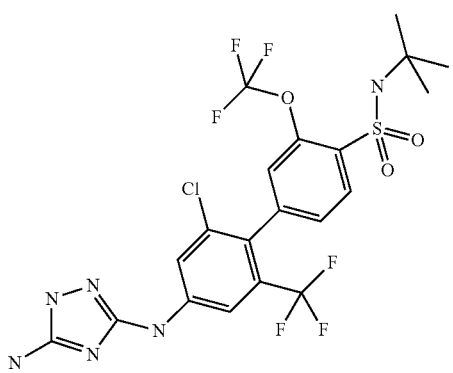 [SMILES: CC(C)(C)NS(=O)(=O)c1ccc(-c2c(Cl)cc(Nc3n[nH]c(N)n3)cc2C(F)(F)F)cc1OC(F)(F)F]

A mixture of 4-bromo-N-(1-cyanocyclopropyl)-2-methoxybenzenesulfonamide Intermediate 1 (250 mg, 0.70 mmol), N-tert-butyl-4-(4,4,5,5-tetramethyl-1,3,2-dioxaborolan-2-yl)-2-(trifluoromethoxy)benzenesulfonamide (297 mg, 0.70 mmol) and sodium carbonate (227 mg, 2.1 mmol) in a mixture of DME/1,4-dioxane (5 ml, 1:1) and tetrakis(triphenylphosphine)palladium(0) (80 mg, 0.069 mmol) was flushed with nitrogen and sealed into a sealed tube and heated on a microwave oven for 3 hrs at 140° C. The reaction was diluted with ethyl acetate (10 mL) and water (15 mL). The organic layer was dried with sodium sulfate and the solvent was removed. The residue was chromatographed to give the crude product, which was further purified on SFC to give 40 mg (10%) of desired product as a white solid. MS +m/z: 573.0 (M+H)$^+$ $^1$H NMR (300 MHz, DMSO-d$_6$) δ ppm 5.91-6.66 (m, 2H) 7.39 (s, 1H) 7.43 (d, J=8.29 Hz, 1H) 7.77 (s, 1H) 7.89-7.90 (m, 0H) 7.96 (s, 1H) 8.03 (d, J=8.10 Hz, 1H) 8.06 (s, 1H) 9.64 (s, 1H) 11.32-11.88 (m, 1H)

4'-(5-Amino-1H-[1,2,4]triazol-3-ylamino)-6'-chloro-4-methoxy-2'-trifluoromethyl-biphenyl-3-sulfonic acid (2-hydroxy-1,1-dimethyl-ethyl)-amide (Compound 218)

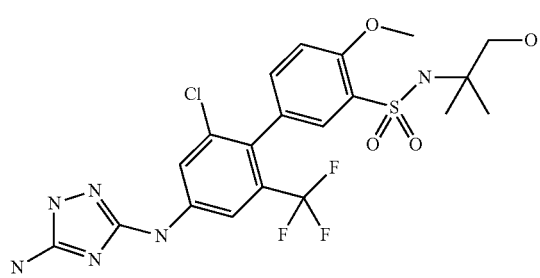 [SMILES: COc1ccc(-c2c(Cl)cc(Nc3n[nH]c(N)n3)cc2C(F)(F)F)cc1S(=O)(=O)NC(C)(C)CO]

5-Bromo-N-(2-hydroxy-1,1-dimethyl-ethyl)-2-methoxy-benzenesulfonamide

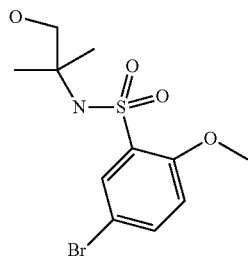 [SMILES: COc1ccc(Br)cc1S(=O)(=O)NC(C)(C)CO]

To a stirred solution of 5-bromo-2-methoxybenzene-1-sulfonyl chloride (1.29 g, 4.52 mmol) and 2-amino-2-methylpropan-1-ol (0.504 g, 5.65 mmol) in methylene chloride (10 mL) at rt, was added triethylamine (0.5 mL, 363 mg, 3.6 mmol) and the mixture was stirred overnight. The mixture was washed with 2N HCl (10 mL) and sodium bisulfate (10 mL) successively. The solution was dried with sodium sulfate and evaporated to give a 1.21 g (79%) of desired product as a white solid.

$^1$H NMR (300 MHz, CHLOROFORM-d) δ ppm 1.15 (s, 6H) 3.47 (s, 2H) 4.00 (s, 3H) 5.20 (br. s., 1H) 6.94 (d, J=8.67 Hz, 1H) 7.64 (d, J=10.74 Hz, 1H) 8.05 (d, J=2.07 Hz, 1H)

N-(2-Hydroxy-1,1-dimethyl-ethyl)-2-methoxy-5-(4,4,5,5-tetramethyl-[1,3,2]dioxaborolan-2-yl)-benzenesulfonamide

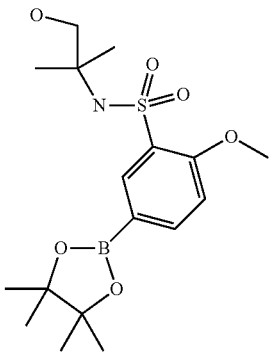

A mixture of 5-Bromo-N-(1-hydroxy-2-methylpropan-2-yl)-2-methoxybenzenesulfonamide (1.1 g, 3.25 mmoL) and 4,4,4',4',5,5,5',5'-octamethyl-2,2'-bi(1,3,2-dioxaborolane) (0.991 g, 3.90 mmol), Palladium ferrocene methylene chloride complex (80 mg, 0.109 mmol) in 1,4-dioxane (4 mL) was heated at 130° C. for 30 min with a microwave reactor. The reaction was diluted with brine (20 mL) and the mixture was extracted with ethyl acetate (3×10 mL). The extracts were combined and dried with sodium sulfate. The solvent was removed and the residue was loaded into a silica gel column and eluted with 2-5% methanol/methylene chloride to give 520 mg (42%) of desired product as a white solid.

4'-(5-Amino-1H-[1,2,4]triazol-3-ylamino)-6'-chloro-4-methoxy-2'-trifluoromethyl-biphenyl-3-sulfonic acid (2-hydroxy-1,1-dimethyl-ethyl)-amide (Compound 218)

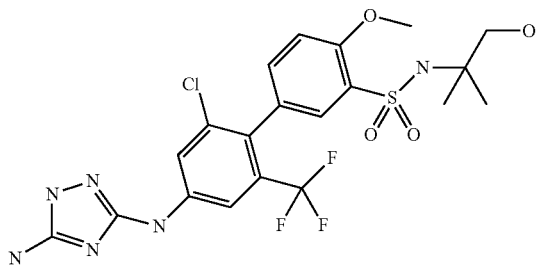 [SMILES: COc1ccc(-c2c(Cl)cc(Nc3n[nH]c(N)n3)cc2C(F)(F)F)cc1S(=O)(=O)NC(C)(C)CO]

A mixture of N3-(4-bromo-3-chloro-5-(trifluoromethyl)phenyl)-1H-1,2,4-triazole-3,5-diamine Intermediate 1 (250 mg, 0.701 mmol), N-(1-hydroxy-2-methylpropan-2-yl)-2-methoxy-5-(4,4,5,5-tetramethyl-1,3,2-dioxaborolan-2-yl)benzenesulfonamide (338 mg, 0.877 mmol), potassium carbonate (291 mg, 2.1 mmol) and tetrakistriphenylphosphine palladium (0)(100 mg, 0.087 mmol) in DME/1.4-dioxane (1:1) (4 mL) and water (0.2 mL) was heated with a microwave reactor at 135° C. for 3 hrs. The mixture was poured into water (20 mL) and extracted with ethyl acetate (3×10 mL). The organic extract was dried with sodium sulfate and concentrated. The residue was chromatographed on silica gel column (24 g, 2-7%) to give impure product, which was purified again on a SFC machine to give 46 mg (12%) of desired product as a white solid.

MS +m/z: 535.0 (M+H)$^+$ $^1$H NMR (300 MHz, DMSO-d$_6$) δ ppm 0.96 (d, J=10.36 Hz, 6H) 3.17 (d, J=5.84 Hz, 2H) 3.96 (s, 3H) 4.90 (t, J=5.75 Hz, 1H) 6.04 (s, 2H) 6.60 (s, 1H) 7.27 (d, J=8.67 Hz, 1H) 7.42 (d, J=8.85 Hz, 1H) 7.50 (s, 1H) 7.86-8.17 (m, 2H) 9.43 (s, 1H) 11.37 (s, 1H)

4'-(5-Amino-1H-[1,2,4]triazol-3-ylamino)-6'-chloro-2'-trifluoromethyl-biphenyl-4-sulfonic acid tert-butylamide (Compound 219)

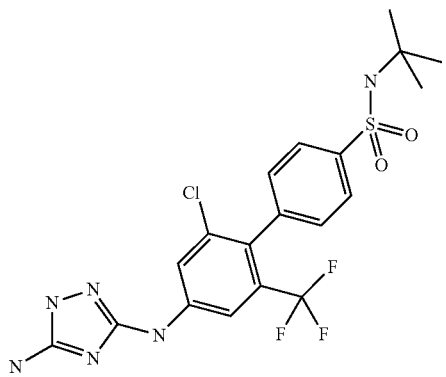 [SMILES: CC(C)(C)NS(=O)(=O)c1ccc(-c2c(Cl)cc(Nc3n[nH]c(N)n3)cc2C(F)(F)F)cc1]

To a sealed tube containing DME (5 mL), was added saturated sodium carbonate (0.5 mL), N3-(4-bromo-3-chloro-5-(trifluoromethyl)phenyl)-1H-1,2,4-triazole-3,5-diamine Intermediate 1 (104 mg, 0.292 mmol), 4-(N-tert-butylsulfamoyl)phenylboronic acid (90.0 mg, 0.35 mmol) and 1,1'-bis(diphenylphosphino)ferrocene-palladium(ii)dichloride dichloromethane complex (36 mg, 0.0438 mmol). The reaction mixture was flushed with N2, then sealed and heated at 115° C. for 2 hrs. The mixture was extracted with EtOAc (3×10 mL) and dried with sodium sulfate. The solvent was concentrated to give a residue which was chromatographed on a 12 g silica gel column to obtain a mixture of desired product and impurities. The mixture was separated on a HPLC (25-100%, 0.1% TFA) to give 22 mg (15%) of desired product as a white solid. MS +m/z: 488.9 (M+H)$^+$ $^1$H NMR (300 MHz, DMSO-d$_6$) δ ppm 1.09 (s, 9H) 6.26 (br. s., 2H) 7.41 (d, J=8.29 Hz, 2H) 7.60 (s, 1H) 7.87 (d, J=8.29 Hz, 2H) 7.96 (s, 1H) 8.06 (s, 1H) 9.56 (br. s., 1H) 11.59 (s, 1H)

N*3*-[2,6-Dichloro-4'-(pyrrolidine-1-sulfonyl)-biphenyl-4-yl]-1H-[1,2,4]triazole-3,5-diamine (Compound 220)

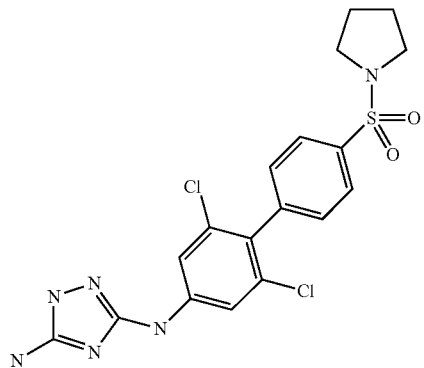 [SMILES: Nc1nc(Nc2cc(Cl)c(-c3ccc(S(=O)(=O)N4CCCC4)cc3)c(Cl)c2)n[nH]1]

To a stirred solution of N3-(4-bromo-3,5-dichlorophenyl)-1H-1,2,4-triazole-3,5-diamine Intermediate 2 (122 mg, 0.378 mmol) and 4-(pyrrolidin-1-ylsulfonyl)phenylboronic acid (193 mg, 0.755 mmol), 1,1'-bis(diphenylphosphino)ferrocene-palladium(ii)dichloride dichloromethane complex (50 mg, 0.16 mmol) and 10% Na2CO3 (0.5 mL), was added DME (6 mL) and the mixture was degassed and stirred at 115° C. for 3 hrs. The mixture was cooled to room temperature, diluted with water (10 mL) and extracted with EtOAc (3×10 mL). The organic extract was dried with sodium sulfate and concentrated. The residue was dissolved in 2 mL 6% MeOH/CH2Cl2 and loaded onto a silica gel column and eluted with 5% MeOH/CH2Cl2 solution to give 22 mg (13%) of desired product as a white solid. MS +m/z: 452.9 (M+H)$^+$

397

4-[4'-(5-Amino-1H-[1,2,4]triazol-3-ylamino)-6'-chloro-4-methoxy-2'-trifluoromethyl-biphenyl-3-sulfonylamino]-piperidine-1-carboxylic acid tert-butyl ester (Compound 221)

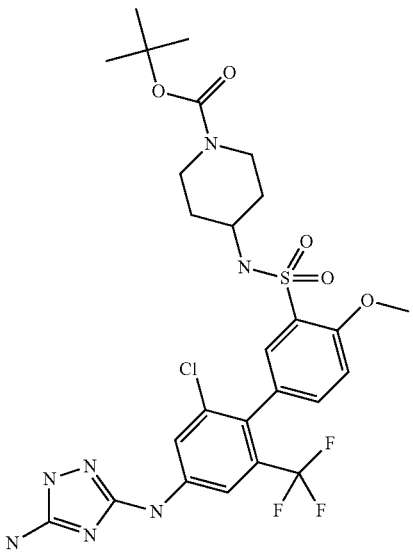 [SMILES: COc1ccc(-c2c(Cl)cc(Nc3n[nH]c(N)n3)cc2C(F)(F)F)cc1S(=O)(=O)NC1CCN(C(=O)OC(C)(C)C)CC1]

4-(5-Bromo-2-methoxy-benzenesulfonylamino)-piperidine-1-carboxylic acid tert-butyl ester

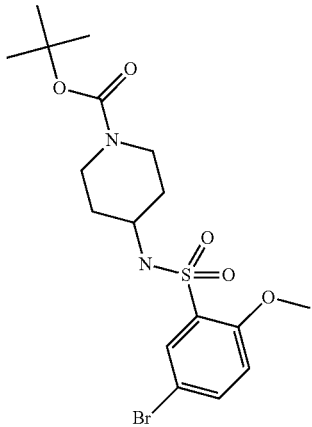 [SMILES: COc1ccc(Br)cc1S(=O)(=O)NC1CCN(C(=O)OC(C)(C)C)CC1]

To a stirred mixture of 5-bromo-2-methoxybenzene-1-sulfonyl chloride (1.14 g, 3.99 mmol) in methylene chloride (8 mL), was added tert-butyl 4-aminopiperidine-1-carboxylate (840 mg, 4.19 mmol) and triethylamine (0.565 mL, 3.99 mmol). The mixture was stirred at rt overnight. The mixture was washed with 1 N HCl and the extract was dried with sodium sulfate. The solvent was removed and the residue was chromatographed (20-40% EtOAc/hexanes) to give 1.5 g (84%) of desired product as a white solid. MS +m/z: 393.0 (M+H)$^+$ $^1$H NMR (300 MHz, DMSO-d$_6$) δ ppm 1.18-1.3 (m, 2H), 1.36 (s, 9H) 1.43-1.59 (m, 2H) 1.99 (s, 2H) 2.65-2.90 (m, 2H) 3.11-3.34 (m, 1H) 3.91 (s, 3H) 7.21 (d, J=9.04 Hz, 1H) 7.58 (d, J=7.91 Hz, 1H) 7.80 (s, 2H)

398

4-[2-Methoxy-5-(4,4,5,5-tetramethyl-[1,3,2]dioxaborolan-2-yl)-benzenesulfonylamino]-piperidine-1-carboxylic acid tert-butyl ester A mixture of tert-butyl 4-(5-bromo-2-methoxyphenylsulfonamido)piperidine-1-carboxylate (520 mg, 1.16 mmol), 4,4,4',4',5,5,5',5'-octamethyl-2,2'-bi(1,3,2-dioxaborolane) (338 mg, 1.33 mmol), potassium acetate (341 mg, 3.47 mmol) and [1,1'-bis(diphenylphosphino)-ferrocene]dichloro palladium(II) complex with dichloromethane (90 mg, 0.123 mmol) in 1,4-dioxane (4 mL) was bubbled with nitrogen and then the mixture was heated at 130° C. for 30 min with a microwave reactor. The solvent was removed and the residue was dissolved in methylene chloride (2.5 mL) and eluted on a silica gel column (24 g, 20-50% EtOAc/hexanes) to give a 402 mg (70%) of desried product as a white solid.

$^1$H NMR (300 MHz, CHLOROFORM-d) δ ppm 1.23-1.31 (m, 2H) 1.36 (s, 12H) 1.44 (s, 9H) 1.72 (d, J=10.17 Hz, 2H) 2.80 (t, J=11.68 Hz, 5H) 3.16-3.44 (m, 2H) 3.79-3.94 (m, 2H) 4.02 (s, 3H) 4.84 (d, J=7.16 Hz, 1H) 7.03 (d, J=8.29 Hz, 1H) 7.99 (d, J=8.29 Hz, 1H) 8.37 (s, 1H)

4-[4'-(5-Amino-1H-[1,2,4]triazol-3-ylamino)-6'-chloro-4-methoxy-2'-trifluoromethyl-biphenyl-3-sulfonylamino]-piperidine-1-carboxylic acid tert-butyl ester (Compound 221)

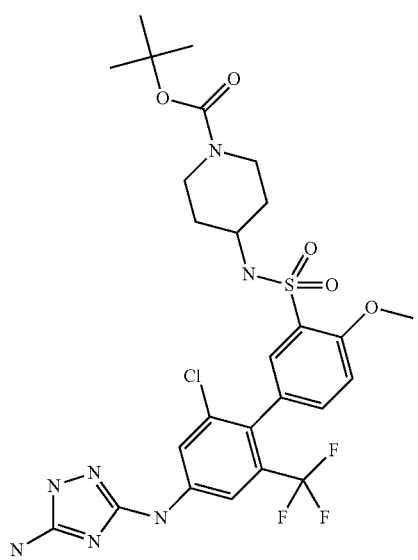 [SMILES: COc1ccc(-c2c(Cl)cc(Nc3n[nH]c(N)n3)cc2C(F)(F)F)cc1S(=O)(=O)NC1CCN(C(=O)OC(C)(C)C)CC1]

A mixture of tert-butyl 4-(5-bromo-2-methoxyphenylsulfonamido)piperidine-1-carboxylate (374 mg, 0.753 mmol), N3-(4-bromo-3-chloro-5-(trifluoromethyl)phenyl)-1H-1,2,4-triazole-3,5-diamine Intermediate 1 (269 mg, 0.753 mmol), tetrakistriphenlphosphine palladium(0)(86 mg, 0.074 mmol) and potassium carbonate (312 mg, 2.26 mmol) in 1,4-dioxane/DME/water (1:1:0.25, 4.5 mL) was bubbled with nitrogen and the mixture was heated with a microwave oven for 3 hrs at 140° C.

The mixture was poured into water (10 mL) and extracted with ethyl acetate (3×7 mL). The extract was dried with sodium sulfate and concentrated. The residue was dissolved in 2 mL of methylene chloride and eluted on a 24 g silica gel column on a Combiflash machine. The desired portion was collected and the solvent was removed. The crude product was further purified on SFC to give a 42 mg (9%) of desired product as a white solid. MS +m/z: 546.0 (M-boc)$^+$

4'-(5-Amino-1H-[1,2,4]triazol-3-ylamino)-6'-chloro-4-methoxy-2'-trifluoromethyl-biphenyl-3-sulfonic acid piperidin-4-ylamide; compound with trifluoroacetic acid (Compound 222)

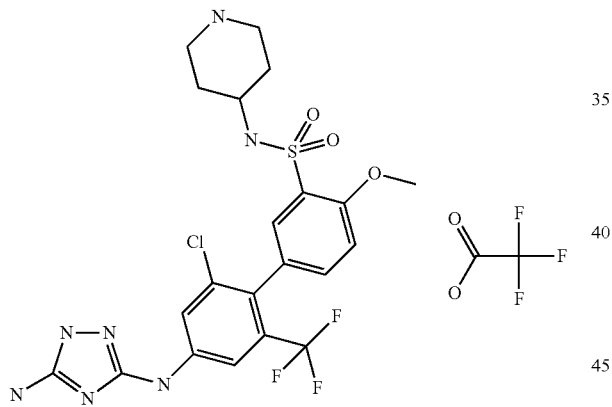

To a stirred solution of tert-Butyl 4-(4'-(5-amino-1H-1,2,4-triazol-3-ylamino)-2'-chloro-4-methoxy-6'-(trifluoromethyl)biphenyl-3-ylsulfonamido)piperidine-1-carboxylate (24 mg, 0.037 mmol) in methylene chloride (3 mL), was added trifluoroacetic acid (1 mL) was added and the mixture was stirred at rt for 1 hr. The solvent was removed and the residue was lyophilized to give 22 mg (90%) of desired product as a white solid. 22 mg (89.7%). MS +m/z: 588.0 (M+41)$^+$ $^1$H NMR (300 MHz, DMSO-d$_6$) δ ppm 1.39-1.90 (m, 4H) 2.76-3.01 (m, 2H) 3.04-3.26 (m, 2H) 3.27-3.51 (m, 1H) 4.0 (s, 3H) 5.87-6.62 (br, 2H) 7.21-7.37 (d, 1H) 7.42-7.49 (m, 1H) 7.52 (s, 1H) 7.79 (d, J=7.72 Hz, 1H) 7.95 (s, 1H) 8.04 (s, 1H) 8.13-8.34 (m, 1H) 8.36-8.62 (m, 1H) 9.56 (s, 1H) 10.99-12.01 (br, 1H)

4'-(5-Amino-1H-[1,2,4]triazol-3-ylamino)-6'-chloro-2'-trifluoromethyl-biphenyl-4-sulfonic acid tert-butyl-(2,2,2-trifluoro-ethyl)-amide (Compound 223)

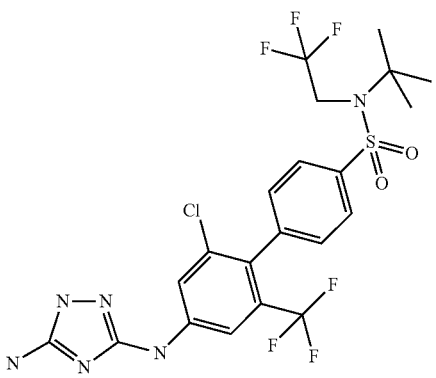 [SMILES: CC(C)(C)N(CC(F)(F)F)S(=O)(=O)c1ccc(-c2c(Cl)cc(Nc3n[nH]c(N)n3)cc2C(F)(F)F)cc1]

4-Bromo-N-tert-butyl-N-(2,2,2-trifluoro-ethyl)-benzenesulfonamide

To a solution of 4-Bromo-N-tert-butylbenzenesulfonamide (810 mg, 2.77 mol) in DMF (10 mL), was added potassium carbonate (972 mg, 6.93 mmol) and 2,2,2-trifluoroethyl trifluoromethanesulfonate (804 mg, 3.47 mmol) dropwise. The mixture was stirred at rt overnight. TLC indicated only partial completion. Added 2,2,2-trifluoroethyl trifluoromethanesulfonate (400 mg, 1.73 mmol) and potassium carbonate (450 mg, 3.26 mmol) and stirred for an additional 6 hrs. The reaction mixture was poured into water and extracted with ether (3×10 mL). Removal of solvent gave 980 mg (95%) of desired product as a white solid.

$^1$H NMR (300 MHz, CHLOROFORM-d) δ ppm 1.36 (s, 9H) 4.07-4.30 (m, 2H) 7.63-7.70 (m, 2H) 7.72-7.80 (m, 2H)

N-tert-Butyl-4-(4,4,5,5-tetramethyl-[1,3,2]dioxaborolan-2-yl)-N-(2,2,2-trifluoro-ethyl)-benzenesulfonamide

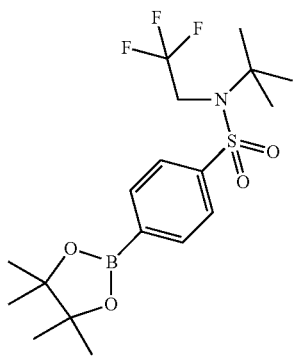 [SMILES: CC(C)(C)N(CC(F)(F)F)S(=O)(=O)c1ccc(B2OC(C)(C)C(C)(C)O2)cc1]

4-Bromo-N-tert-butyl-N-(2,2,2-trifluoroethyl)benzenesulfonamide (748 mg, 2 mmol), 4,4,4',4',5,5,5',5'-octamethyl-2,2'-bi(1,3,2-dioxaborolane) (508 mg, 2.0 mmol), potassium acetate (829 mmol, 6 mmol) and [1,1'-bis(diphenylphosphino)-ferrocine]dichloro palladium(II) complex with dichloromethane (90 mg, 0.123 mmol) were combined into a sealed tube containing 1,4-dioxane (4.5 mL). The mixture was stirred at 130° C. for 30 min in a microwave reactor. The reaction mixture was into water (15 mL) and extracted with EtOAc (3×10 mL). Removal of solvent gave the crude which was chromatographed with 2-5% methanol/DCM to give 356 mg (43%) of the desired product.

$^1$H NMR (300 MHz, CHLOROFORM-d) δ ppm 1.34 (s, 9H) 1.39 (s, 12H) 4.06-4.35 (m, 2H) 7.85-7.91 (m, 2H) 7.92-7.98 (m, 2H)

4'-(5-Amino-1H-[1,2,4]triazol-3-ylamino)-6'-chloro-2'-trifluoromethyl-biphenyl-4-sulfonic acid tert-butyl-(2,2,2-trifluoro-ethyl)-amide (Compound 223)

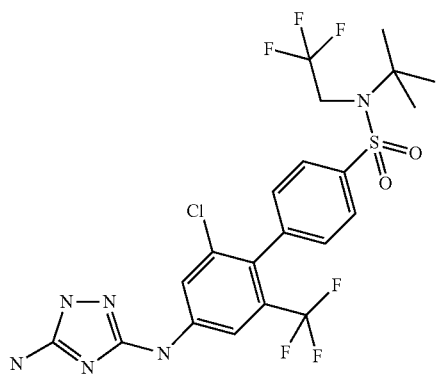 [SMILES: CC(C)(C)N(CC(F)(F)F)S(=O)(=O)c1ccc(-c2c(Cl)cc(Nc3n[nH]c(N)n3)cc2C(F)(F)F)cc1]

A suspension of N-tert-butyl-4-(4,4,5,5-tetramethyl-1,3,2-dioxaborolan-2-yl)-N-(2,2,2-trifluoroethyl)benzenesulfonamide (250 mg, 0.59 mmol), N3-(4-bromo-3-chloro-5-(trifluoromethyl)phenyl)-1H-1,2,4-triazole-3,5-diamine Intermediate 1 (212 mg, 0.59 mmol), potassium carbonate (3 eq, 276 mg, 1.57 mmol) and tetrakistriphenylphosphine palladium(0) (80 mg) were DME/1,4-dioxane (1:1, 4 mL) and water (0.5 mL) was flushed with nitrogen and sealed in a sealed tube. The reaction mixture was heated at 140° C. for 3.5 hrs, then poured into a mixture of water/EtOAc (1:1, 10 mL each). The organic layer was separated, dried, and concentrated. The crude residue was chromatographed on a silica gel column on a combiflash (5% methanol/methylene chloride) to give the crude, which was further purified by SFC to give 73 mg (22%) of desired product as a white solid. MS +m/z: 571.0 (M+H)$^+$ $^1$H NMR (300 MHz, DMSO-d$_6$) δ ppm 1.25 (s, 9H) 4.43 (q, J=8.79 Hz, 2H) 6.08 (br. s., 2H) 7.49 (d, J=8.10 Hz, 2H) 7.93 (d, J=8.29 Hz, 2H) 7.99 (s, 1H) 8.10 (s, 1H) 9.51 (s, 1H) 11.42 (br. s., 1H)

N*3*-[6-Chloro-4'-(3,3-difluoro-azetidine-1-sulfonyl)-2-trifluoromethyl-biphenyl-4-yl]-1H-[1,2,4]triazole-3,5-diamine (Compound 224)

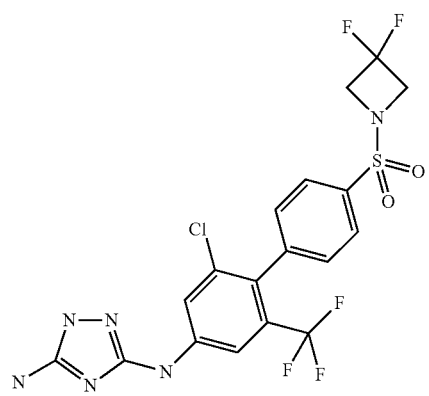 [SMILES: Nc1nc(Nc2cc(Cl)c(-c3ccc(S(=O)(=O)N4CC(F)(F)C4)cc3)c(C(F)(F)F)c2)n[nH]1]

1-(4-Bromo-benzenesulfonyl)-3,3-difluoro-azetidine

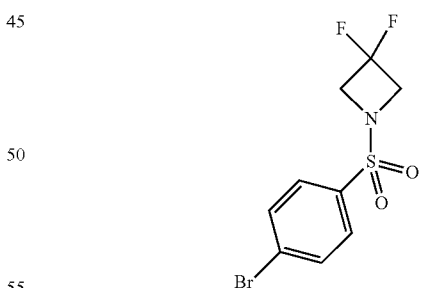

A solution of 4-bromobenzene-1-sulfonyl chloride (840 mg, 3.29 mmol), 3,3-difluoroazetidine hydrochloride (426 mg, 3.29 mmol) and triethylamine (1.83 mL, 13.13 mmol) in DCM (10 mL) was stirred for 1 hr. The reaction mixture was poured into 1N HCl (30 mL) and the extracted with DCM (2×10 mL). The extract was dried with sodium sulfate, filtered and concentrated to give 1.01 g (98%) of desired product as a white solid.

$^1$H NMR (300 MHz, CHLOROFORM-d) δ ppm 4.20 (t, J=11.96 Hz, 4H) 7.75 (s, 4H)

3,3-Difluoro-1-[4-(4,4,5,5-tetramethyl-[1,3,2]dioxaborolan-2-yl)-benzenesulfonyl]-azetidine

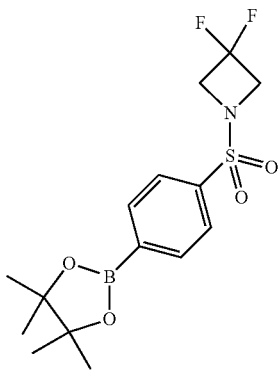 [SMILES: CC1(C)OB(c2ccc(S(=O)(=O)N3CC(F)(F)C3)cc2)OC1(C)C]

1-(4-Bromophenylsulfonyl)-3,3-difluoroazetidine (770 mg, 2.47 mmol), 4,4,4%4%5,5,5%5'-octamethyl-2,2'-bi(1,3,2-dioxaborolane) (752 mg, 2.96 mmol), potassium acetate (726 mg, 7.4 mmol) and [1,1'-Bis(diphospheno)-ferrocene) dichloro Palladium(II) complex with methylene chloride (100 mg, 0.137 mmol) were combined in a sealed tube containing Dioxane (5 mL). The mixture was bubbled with nitrogen and then heated at 130° C. for 30 min. The reaction was diluted with water (10 mL) and extracted with EtOAC (3×7 mL). Removal of solvent gave the crude, which was purified on a combiflash machine (2-5% methanol/DCM) to give a 825 mg (93%) of desired product as a light brown solid.

$^1$H NMR (300 MHz, CHLOROFORM-d) δ ppm 1.30 (s, 12H) 4.08 (t, J=11.87 Hz, 4H) 7.77 (d, J=8.29 Hz, 2H) 7.95 (d, J=8.10 Hz, 2H)

N*3*-[6-Chloro-4'-(3,3-difluoro-azetidine-1-sulfonyl)-2-trifluoromethyl-biphenyl-4-yl]-1H-[1,2,4]triazole-3,5-diamine (Compound 224)

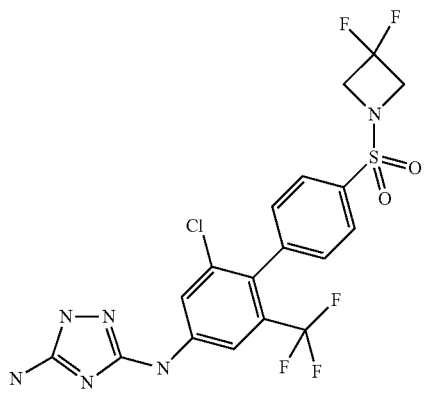 [SMILES: Nc1nc(Nc2cc(Cl)c(-c3ccc(S(=O)(=O)N4CC(F)(F)C4)cc3)c(C(F)(F)F)c2)n[nH]1]

3,3-Difluoro-1-(4-(4,4,5,5-tetramethyl-1,3,2-dioxaborolan-2-yl)phenylsulfonyl)azetidine (667 mg, 1.86 mmol), N3-(4-bromo-3-chloro-5-(trifluoromethyl)phenyl)-1H-1,2,4-triazole-3,5-diamine Intermediate 1 (662 mg, 1.86 mmol), potassium carbonate (3 eq, 276 mg, 1.57 mmol) and tetrakistriphenylphosphine palladium(0) (80 mg, 0.069 mmol) were suspended in 4 mL of DME/1,4-dioxane (1:1). 0.5 mL of water was added and the mixture was flushed with nitrogen and sealed in a seal tube. The reaction was heated at 140° C. for 3.5 hrs, then poured into a mixture of water/EtOAc (1:1, 10 mL each). The mixture was shaken thoroughly and the organic layer was separated. The solvent was removed and the residue was chromatographed on a silica gel column on a Combiflash (5% methanol/methylene chloride) to give the crude, which was further purified by SFC to give 162 mg (17%) of desired product as an off-white solid. MS +m/z: 509.0 (M+H)$^+$ $^1$H NMR (300 MHz, DMSO-d$_6$) δ ppm 4.31 (t, J=12.72 Hz, 4H) 5.92-6.37 (m, 2H) 7.59 (d, J=8.10 Hz, 2H) 7.99 (d, J=7.91 Hz, 3H) 8.10 (s, 1H) 9.55 (s, 1H) 11.27-11.66 (m, 1H)

4'-(5-Amino-1H-[1,2,4]triazol-3-ylamino)-6'-chloro-4-methoxy-2'-trifluoromethyl-biphenyl-3-sulfonic acid cyano-cyclopropyl)-amide (Compound 225)

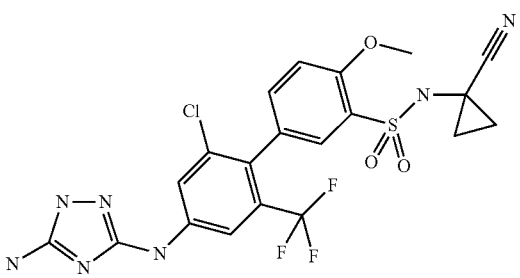 [SMILES: COc1ccc(-c2c(Cl)cc(Nc3n[nH]c(N)n3)cc2C(F)(F)F)cc1S(=O)(=O)NC1(C#N)CC1]

5-Bromo-N-(1-cyano-cyclopropyl)-2-methoxy-benzenesulfonamide

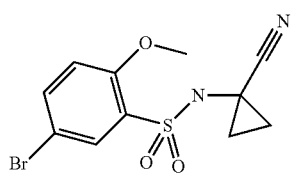 [SMILES: COc1ccc(Br)cc1S(=O)(=O)NC1(C#N)CC1]

To a stirred solution of 5-bromo-2-methoxybenzene-1-sulfonyl chloride (1.89 g, 6.63 mmol), 1-aminocyclopropanecarbonitrile (544 mg, 6.63 mmol) in methylene chloride (10 mL), was added Et3N (0.92 mL, 6.63 mmol). The reaction mixture was stirred at rt for 24 hrs. The mixture was diluted with 1 N HCl and the organic layer was separated and dried with sodium sulfate. The solvent was removed and the residue was chromatorgraphied on a silica gel column to give a 380 mg (17%) of desired product as a white solid.

$^1$H NMR (300 MHz, CHLOROFORM-d) δ ppm 1.31-1.49 (m, 2H) 1.62-1.77 (m, 2H) 4.06 (s, 3H) 5.75 (s, 1H) 7.01 (d, J=8.85 Hz, 1H) 7.74 (dd, J=8.67, 2.45 Hz, 1H) 8.11 (d, J=2.26 Hz, 1H)

N-(1-Cyano-cyclopropyl)-2-methoxy-5-(4,4,5,5-tetramethyl-[1,3,2]dioxaborolan-2-yl)-benzenesulfonamide

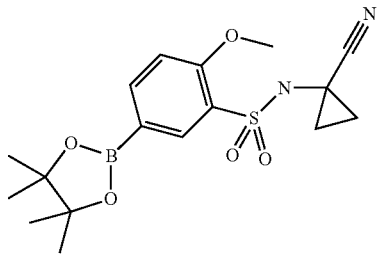 [SMILES: COc1ccc(B2OC(C)(C)C(C)(C)O2)cc1S(=O)(=O)NC1(C#N)CC1]

A mixture of 4-bromo-N-(1-cyanocyclopropyl)-2-methoxybenzenesulfonamide (520 mg, 1.16 mmol), 4,4,4',4',5,5,5',5'-octamethyl-2,2'-bi(1,3,2-dioxaborolane) (338 mg, 1.33 mmol), potassium acetate (341 mg, 3.47 mmol) and [1,1'-bis(diphenylphosphino)-ferrocine]dichloro palladium(II) complex with dichloromethane (90 mg, 0.123 mmol) in 1,4-dioxane (4 mL) was bubbled with nitrogen and then heated at 130° C. for 30 min with a microwave oven. The reaction was diluted with 10% sodium bicarbonate solution (10 mL) and extracted with ethyl acetate (2×7 mL). The extract was dried with sodium sulfate and the solvent was removed under reduced pressure. The residue was chromatographied to give 300 mg (69%) of desired product as a white solid.

$^1$H NMR (300 MHz, CHLOROFORM-d) δ ppm 1.26 (s, 6H) 1.36 (m, 8H) 1.61-1.70 (m, 2H) 4.09 (s, 3H) 5.75 (s, 1H) 7.09 (d, J=8.29 Hz, 1H) 8.07 (d, J=7.16 Hz, 1H) 8.42 (s, 1H)

4'-(5-Amino-1H-[1,2,4]triazol-3-ylamino)-6'-chloro-4-methoxy-2'-trifluoromethyl-biphenyl-3-sulfonic acid cyano-cyclopropyl)-amide (Compound 225)

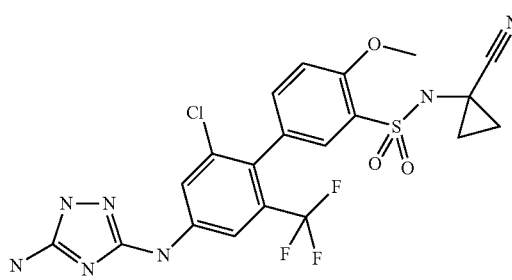

To a stirred suspension of N3-(4-bromo-3-chloro-5-(trifluoromethyl)phenyl)-1H-1,2,4-triazole-3,5-diamine Intermediate 1 (236 mg, 0.66 mmol), N-(1-cyanocyclopropyl)-2-methoxy-5-(4,4,5,5-tetramethyl-1,3,2-dioxaborolan-2-yl) benzenesulfonamide (250 mg, 0.66 mol) and potassium carbonate in a mixture of DME/THF (4 mL, 1:1), was added tetrakistriphenylphosphine palladium(0) (80 mg, 0.069 mmol) followed by 0.5 mL of water. The mixture was flushed with nitrogen and sealed and heated in a microwave oven for 3 hrs at 140° C. The reaction mixture was extracted with ethyl acetate (2×10 mL) and the extracts were dried with sodium sulfate. The solvent was removed and the residue was chromatographied on a silica gel column (20 g, 5% MeOH/CH2Cl2) to give the crude, which was further purified on SFC to give 43 mg (12%) of desired product as a white solid. MS +m/z: 528.0 (M+H)$^+$ $^1$H NMR (300 MHz, DMSO-d$_6$) δ ppm 1.04-1.39 (m, 4H) 3.96 (s, 3H) 6.05 (br. s., 2H) 7.31 (d, J=8.67 Hz, 1H) 7.50 (d, J=9.04 Hz, 1H) 7.55 (s, 1H) 7.96 (s, 1H) 8.06 (s, 1H) 8.61-9.09 (m, 1H) 9.45 (s, 1H) 11.38 (s, 1H)

4'-(5-Amino-1H-[1,2,4]triazol-3-ylamino)-6'-chloro-2'-trifluoromethyl-biphenyl-4-sulfonic acid (2-hydroxy-1,1-dimethyl-ethyl)-amide (Compound 226)

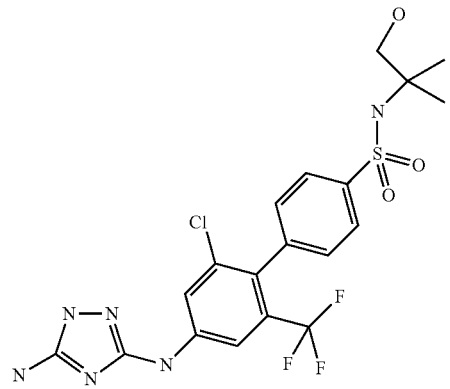 [SMILES: CC(C)(CO)NS(=O)(=O)c1ccc(-c2c(Cl)cc(Nc3n[nH]c(N)n3)cc2C(F)(F)F)cc1]

4-Bromo-N-(2-hydroxy-1,1-dimethyl-ethyl)-benzenesulfonamide

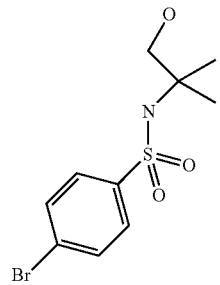 [SMILES: CC(C)(CO)NS(=O)(=O)c1ccc(Br)cc1]

To a stirred solution of 4-bromobenzene-1-sulfonyl chloride (1.5 g, 5.87 mmol) in methylene chloride (10 mL), was added 2-amino-2-methylpropan-1-ol (576 mg, 6.46 mmol) and triethylamine (594 mmol, 5.87 mmol). The reaction mixture was stirred at rt for 1 hr. The mixture was washed with 1 N HCl solution and the organic layer was separated and dried with sodium sulfate. Evaporation of solvent gave a white solid which was carried onto the next step.

$^1$H NMR (300 MHz, CHLOROFORM-d) δ ppm 1.17 (s, 6H) 3.47 (br. s., 2H) 5.08 (s, 1H) 7.58-7.71 (m, 2H) 7.79 (d, J=8.48 Hz, 2H)

N-(2-Hydroxy-1,1-dimethyl-ethyl)-4-(4,4,5,5-tetramethyl-[1,3,2]dioxaborolan-2-yl)-benzenesulfonamide

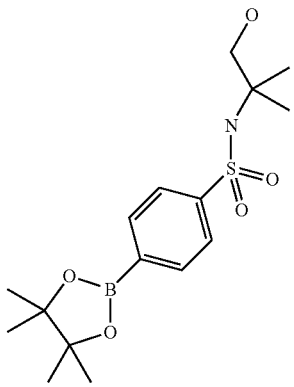 [SMILES: CC(C)(CO)NS(=O)(=O)c1ccc(B2OC(C)(C)C(C)(C)O2)cc1]

A mixture of 4-bromo-N-(1-hydroxy-2-methylpropan-2-yl)benzenesulfonamide (700 mg, 2.27 mmol), and 4-4,4,4',4',5,5,5',5'-octamethyl-2,2'-bi(1,3,2-dioxaborolane) (600 mg, 1.96 mmol) and potassium acetate (669 mg, 6.81 mmol) in 1,4-dioxane (6 mL) was heated at 140° C. in a microwave for 25 min. The mixture was diluted with water (10 mL), extracted with ethyl acetate (3×10 mL), and the extract was dried with sodium sulfate. The solvent was evaporated and the residue was chromatographed on a silica gel column (40 g) and eluted with 5% methanol/methylene chloride to give a 610 mg (76%) of solid.

$^1$H NMR (300 MHz, CHLOROFORM-d) δ ppm 1.11-1.36 (m, 18H) 3.52 (s, 2H) 4.86 (s, 1H) 7.75 (d, J=8.10 Hz, 2H) 8.03 (d, J=8.29 Hz, 2H)

4'-(5-Amino-1H-[1,2,4]triazol-3-ylamino)-6'-chloro-2'-trifluoromethyl-biphenyl-4-sulfonic acid (2-hydroxy-1,1-dimethyl-ethyl)-amide (Compound 226)

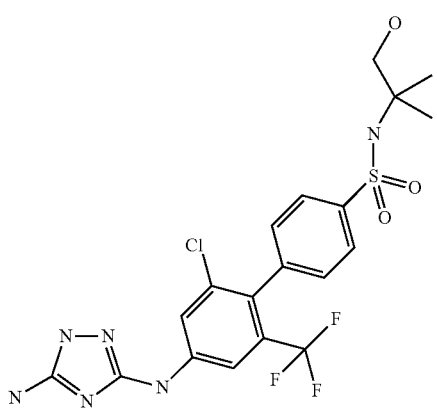 [SMILES: CC(C)(CO)NS(=O)(=O)c1ccc(-c2c(Cl)cc(Nc3n[nH]c(N)n3)cc2C(F)(F)F)cc1]

To a stirred solution of N3-(4-bromo-3-chloro-5-(trifluoromethyl)phenyl)-1H-1,2,4-triazole-3,5-diamine Intermediate 1 (200 mg, 0.56 mmol) in a mixture of DME and 1,4-dioxane (1:1, 2 ml each), was added tetrakis(triphenylphosphine)palladium(0) (50 mg, 0.043 mmol), potassium carbonate (233 mg, 1.68 mmol) and N-(1-hydroxy-2-methylpropan-2-yl)-4-(4,4,5,5-tetramethyl-1,3,2-dioxaborolan-2-yl)benzenesulfonamide (219 mg, 0.617 mmol). The reaction mixture was bubbled with nitrogen and then heated on a microwave oven for 3 hrs under 140° C. The reaction was washed with water (30 mL) and extracted with ethyl acetate (3×10 mL). The extracts were dried with sodium sulfate and the solvent was removed. The crude residue was chromatographed (3-9% methanol/methylene chloride) on a 24 gram silica gel column to give 72 mg (25%) of desired product. MS +m/z: 505.0 (M+H)$^+$ $^1$H NMR (300 MHz, DMSO-d$_6$) δ ppm 1.00 (s, 6H) 3.22 (d, J=5.84 Hz, 2H) 4.77 (t, J=5.84 Hz, 1H) 6.05 (br. s., 2H) 7.36-7.44 (m, 2H) 7.88 (d, J=8.29 Hz, 2H) 7.96 (br. s., 1H) 8.07 (s, 1H) 8.30 (s, 1H) 9.47 (s, 1H) 11.38 (s, 1H)

4'-(5-Amino-1H-[1,2,4]triazol-3-ylamino)-6'-chloro-4-methoxy-2'-trifluoromethyl-biphenyl-3-sulfonic acid (1-acetyl-piperidin-4-yl)-amide (Compound 227)

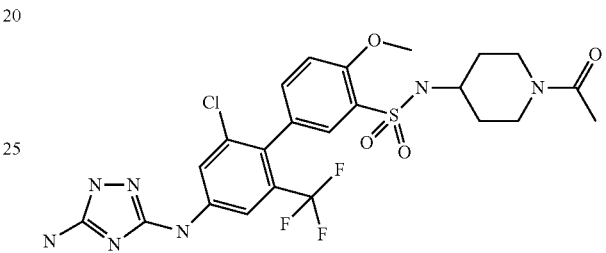

To a stirred suspension of 4'-(5-amino-1H-1,2,4-triazol-3-ylamino)-2'-chloro-4-methoxy-N-(piperidin-4-yl)-6'-(trifluoromethyl)biphenyl-3-sulfonamide trifluoro acetate (15 mg, 0.0275 mmol) in a mixture of THF/sat. NaHCO3 (2 mL, ratio: 1:1), was added acetic anhydride (3 mg, 0.029 mmol). The reaction mixture was stirred at rt for 1 hr. The mixture was extracted with ethyl acetate (3×5 mL) and the extracts were combined and dried with sodium sulfate. The solvent was removed under reduced pressure to give 12 mg (74%) of desired product as a white solid. MS +m/z: 588.0 (M+H)$^+$ $^1$H NMR (300 MHz, DMSO-d$_6$) δ ppm 1.39-1.90 (m, 4H) 1.90-2.0 (s, 3H) 2.76-3.01 (m, 2H) 3.04-3.26 (m, 2H) 3.27-3.51 (m, 1H) 3.9-4.0 (s, 3H) 6.0-6.1 (b, 2H) 7.2-7.3 (d, J=7.72 Hz, 1H) 7.40-60 (m, 3H) 8.04 (s, 1H) 7.90-8.0 (s, 1H) 8.14-8.10 (s, 1H) 9.46 (s, 1H) 10.99-12.01 (br, 1H)

N*3*-[6-Chloro-4'-(propane-2-sulfonyl)-2-trifluoromethyl-biphenyl-4-yl]-1H-[1,2,4]triazole-3,5-diamine (Compound 228)

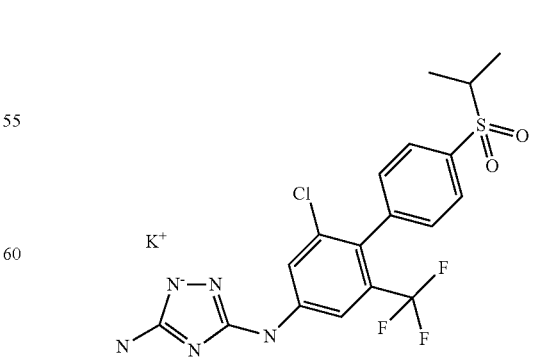

To a suspension of N3-(2-chloro-4'-(isopropylsulfonyl)-6-(trifluoromethyl)biphenyl-4-yl)-1H-1,2,4-triazole-3,5-diamine (46 mg, 0.1 mmol) in a mixture of acetonitrile/water (3:1, 1.5 mL), was added KOH (5.6 mg, 0.1 mmol and water (1 mL). The solution was cooled to −78° C. and lyophilized to give 49.5 mg (100%) of desired product. MS +m/z: 459.90 (M+H)⁺ with loss of K⁺.

¹H NMR (300 MHz, DMSO-$d_6$) δ ppm 1.17 (d, J=6.78 Hz, 6H) 3.42-3.61 (m, 1H) 5.66-6.43 (br, 2H) 7.53 (d, J=8.10 Hz, 2H) 7.91 (d, J=8.29 Hz, 3H) 8.05-8.22 (m, 1H) 8.99-9.87 (br, 1H)

N*3*-(6-Chloro-3'-isopropoxy-4'-methoxy-2-trifluoromethyl-biphenyl-4-yl)-1H-[1,2,4]triazole-3,5-diamine (Compound 229)

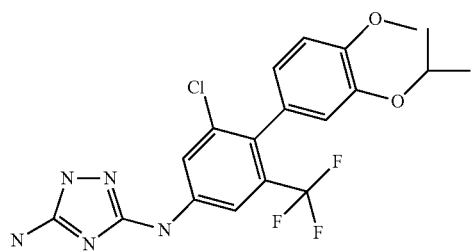 [SMILES: COc1ccc(-c2c(Cl)cc(Nc3n[nH]c(N)n3)cc2C(F)(F)F)cc1OC(C)C]

To a stirred suspension N3-(4-bromo-3-chloro-5-(trifluoromethyl)phenyl)-1H-1,2,4-triazole-3,5-diamine Intermediate 1 (250 mg, 0.701 mmol) in a mixture of DME/1,4-dioxane (1:1, 4 mL), was added 3-isopropoxy-4-methoxyphenylboronic acid (177 mg, 0.841 mmol), potassium carbonate (291 mg, 2.1 mmol) and tetrakistriphenylphosphine palladium (0) (80 mg, 0.069 mmol). The reaction mixture was stirred at rt for 3 hrs at 140° C. The reaction was extracted with ethyl acetate (2×10 mL) and the extracts were dried with sodium sulfate. The solvent was removed and the residue was chromatographed on a silica gel column (20 g, 5% MeOH/CH2Cl2) to give the crude, which was further purified on SFC to give 45 mg (15%) of an off-white solid.

MS +m/z: 442 (M+H)⁺

¹H NMR (300 MHz, DMSO-$d_6$) δ ppm 1.22 (t, J=5.84 Hz, 6H) 3.79 (s, 3H) 4.31-4.64 (m, 1H) 6.03 (br. s., 2H) 6.62-6.81 (m, 2H) 6.98 (d, J=8.10 Hz, 2H) 7.80-8.08 (m, 2H) 9.35 (s, 1H) 11.36 (br. s., 1H)

N*3*-(4'-tert-Butoxy-6-chloro-2-trifluoromethyl-biphenyl-4-yl)-1H-[1,2,4]triazole-3,5-diamine (Compound 230)

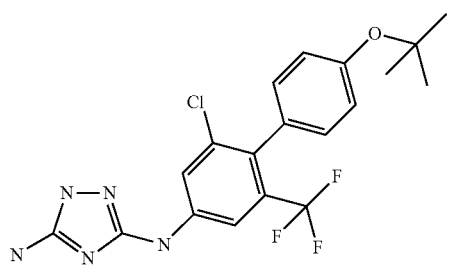 [SMILES: CC(C)(C)Oc1ccc(-c2c(Cl)cc(Nc3n[nH]c(N)n3)cc2C(F)(F)F)cc1]

To a suspension of N3-(4-bromo-3-chloro-5-(trifluoromethyl)phenyl)-1H-1,2,4-triazole-3,5-diamine Intermediate 1 (250 mg, 0.70 mmol), 4-tert-butoxyphenylboronic acid (204 mg, 1.05 mmol), tetrakistriphenylphosphine palladium(0) (80 mg, 0.069 mmol) and potassium carbonate (295 mg, 2.1 mmol) DME/1,4-dioxane (1:1, 4 mL), was added water (0.5 mL). The reaction mixture was purged with nitrogen, sealed in a seal tube and heated at 140° C. for 3.5 hrs. The mixture was poured into a mixture of water/EtOAc (1:1, 10 mL each) and the organic layer was separated. The solvent was removed and the residue was chromatographed on a silica gel column on a combiflash (5% methanol/methylene chloride) to give the crude, which was further purified by SFC to give 42 mg (14%) pure white solid. MS +m/z: 425.88 (M+H)⁺

¹H NMR (300 MHz, DMSO-$d_6$) δ ppm 1.33 (s, 9H) 6.03 (s, 2H) 6.81-7.24 (m, 4H) 7.78-7.97 (m, 1H) 7.97-8.13 (m, 1H) 9.37 (s, 1H) 11.35 (s, 1H)

N*3*-(6-Chloro-4'-methoxy-2,3'-bis-trifluoromethyl-biphenyl-4-yl)-1H-[1,2,4]triazole-3,5-diamine (Compound 231)

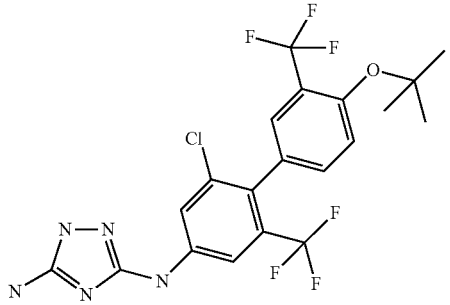 [SMILES: CC(C)(C)Oc1ccc(-c2c(Cl)cc(Nc3n[nH]c(N)n3)cc2C(F)(F)F)cc1C(F)(F)F]

A mixture of tetrakis(triphenylphosphine)palladium(0) (86 mg, 0.074 mmol), N3-(4-bromo-3-chloro-5-(trifluoromethyl)phenyl)-1H-1,2,4-triazole-3,5-diamine Intermediate 1 (280 mg, 0.785 mmol), 4-methoxy-3-(trifluoromethyl)phenylboronic acid (207 mg, 0.942 mmol) and sodium carbonate (250 mg, 2.36 mmol) in a 1:1 mixture of DME/1,4-dioxane (4 mL) was bubbled with nitrogen and sealed and heated on a microwave oven at 140° C. for 3 hrs. The mixture was treated with ethyl acetate (7 mL) and partioned with water. The organic layer was dried and the solvent was removed. The residue was chromatographed on a silica gel column (24 g, 2-7% methanol/methylene chloride) to give the crude, which was purified with SFC to give 99 mg (28%) white solid. MS +m/z: 451.90 (M+H)⁺

¹H NMR (300 MHz, DMSO-$d_6$) δ ppm 3.95 (s, 3H) 6.01-6.50 (m, 2H) 7.32 (d, J=8.85 Hz, 1H) 7.40 (s, 1H) 7.48 (d, J=8.29 Hz, 1H) 7.95 (d, J=2.07 Hz, 1H) 8.04 (d, J=1.88 Hz, 1H) 9.56 (s, 1H) 11.25-12.02 (m, 1H)

N*3*-[6'-Chloro-4,4"-bis-(pyrrolidine-1-sulfonyl)-[1,1';2',1"]terphenyl-4'-yl]-1H-[1,2,4]triazole-3,5-diamine (Compound 232

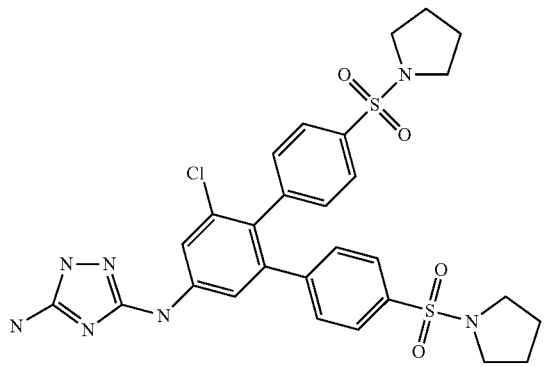 [SMILES: Nc1nc(Nc2cc(Cl)c(-c3ccc(S(=O)(=O)N4CCCC4)cc3)c(-c3ccc(S(=O)(=O)N4CCCC4)cc3)c2)n[nH]1]

A solution of N3-(4-bromo-3,5-dichlorophenyl)-1H-1,2,4-triazole-3,5-diamine Intermediate 1 (122 mg, 0.378 mmol) and 4-(pyrrolidin-1-ylsulfonyl)phenylboronic acid (193 mg, 0.755 mmol), 1,1'-bis(diphenylphosphino)ferrocene-palladium(ii)dichloride dichloromethane complex (50 mg, 0.16 mmol) and 10% $Na_2CO_3$ (0.5 mL) in DME (6 mL) was degassed and stirred at 115° C. for 3 hrs. The mixture was cooled and the mixture was treated with water (10 mL) and extracted with EtOAc (3×10 mL). The extracts were dried with sodium sulfate and concentrated. The residue was dissolved in 2 mL 6% $MeOH/CH_2Cl_2$ and loaded onto a silica gel column and eluted with 5% $MeOH/CH2Cl_2$ solution to give 10 mg (4%) of desired product as a white solid. MS +m/z: 628 $(M+H)^+$

N*3*-[6-Chloro-4'-(3-fluoro-azetidine-1-sulfonyl)-2-trifluoromethyl-biphenyl-4-yl]-1H-[1,2,4]triazole-3,5-diamine (Compound 233)

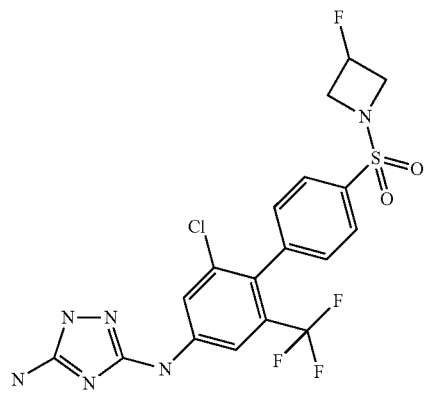 [SMILES: Nc1nc(Nc2cc(Cl)c(-c3ccc(S(=O)(=O)N4CC(F)C4)cc3)c(C(F)(F)F)c2)n[nH]1]

To a suspension of 3-Fluoro-1-(4-(4,4,5,5-tetramethyl-1,3,2-dioxaborolan-2-yl)phenylsulfonyl)azetidine (280 mg, 0.82 mmol), N3-(4-bromo-3-chloro-5-(trifluoromethyl)phenyl)-1H-1,2,4-triazole-3,5-diamine Intermediate 1 (293 mg, 0.82 mmol) potassium carbonate (3 eq, 340 mg, 2.46 mmol) and tetrakistriphenylphosphine palladium(0) (80 mg, 0.069 mmol) DME/1,4-dioxane (1:1, 4 mL), was added water (0.5 mL). The reaction mixture was bubbled with nitrogen, sealed in a seal tube, and heated at 140° C. for 3.5 hrs. The mixture was poured into water/EtOAc (1:1, 10 mL each), shaken thoroughly, and the organic layer was separated. The solvent was removed and the residue was chromatographed on a silica gel column on a Combiflash machine (5% methanol/methylene chloride) to give the crude, which was further purified by SFC to give 120 mg (30%) pure white solid. MS +m/z: 491 $(M+H)^+$ $^1$H NMR (300 MHz, DMSO-$d_6$) δ ppm 3.61-3.89 (m, 2H) 4.02-4.27 (m, 2H) 5.02-5.44 (m, 1H) 6.08 (br. s., 2H) 7.58 (d, J=8.10 Hz, 2H) 7.93 (d, J=8.29 Hz, 2H) 8.00 (s, 1H) 8.11 (s, 1H) 9.53 (s, 1H) 11.42 (br. s., 1H)

4'-(5-Amino-1H-[1,2,4]triazol-3-ylamino)-6'-chloro-4-methoxy-2'-trifluoromethyl-biphenyl-3-sulfonic acid piperidin-4-yl-(2,2,2-trifluoro-ethyl)-amide; compound with trifluoro-acetic acid (Compound 234)

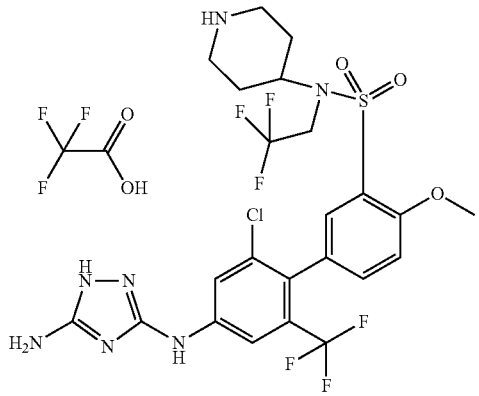 [SMILES: COc1ccc(-c2c(Cl)cc(Nc3n[nH]c(N)n3)cc2C(F)(F)F)cc1S(=O)(=O)N(CC(F)(F)F)C1CCNCC1 ; O=C(O)C(F)(F)F]

4-(5-Bromo-2-methoxy-benzenesulfonylamino)-piperidine-1-carboxylic acid tert-butyl ester

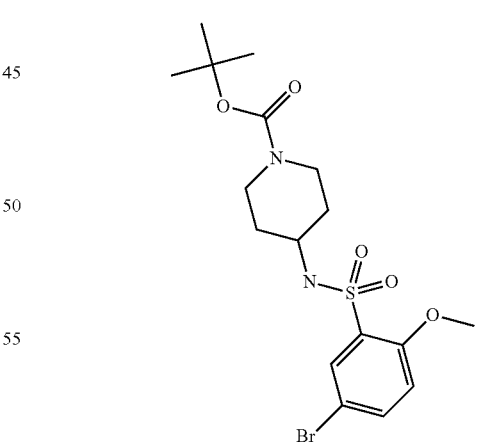

To a stirred solution of 5-bromo-2-methoxybenzene-1-sulfonyl chloride (1.14 g, 3.99 mmol) in methylene chloride (8 mL), was added tert-butyl 4-aminopiperidine-1-carboxylate (Aldrich, 840 mg, 4.19 mmol) and triethylamine (0.565 mL, 3.99 mmol). The mixture was stirred at rt overnight. The mixture was washed with 1 N HCl and the extract was dried with sodium sulfate. The solvent was removed and the residue was chromatographed (20-40% EtOAc/hexanes) to give 1.5 g (84%) of desired product as a white solid. MS +m/z: 393.0 (M+H)+

¹H NMR (300 MHz, DMSO-d₆) δ ppm 1.18-1.3 (m, 2H), 1.36 (s, 9H) 1.43-1.59 (m, 2H) 1.99 (s, 2H) 2.65-2.90 (m, 2H) 3.11-3.34 (m, 1H) 3.91 (s, 3H) 7.21 (d, J=9.04 Hz, 1H) 7.58 (d, J=7.91 Hz, 1H) 7.80 (s, 2H)

4-[(5-Bromo-2-methoxy-benzenesulfonyl)-(2,2,2-trifluoro-ethyl)-amino]-piperidine-1-carboxylic acid tert-butyl ester

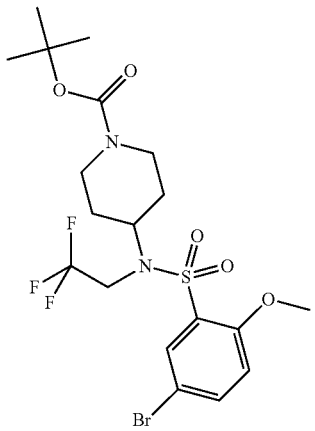 [SMILES: COc1ccc(Br)cc1S(=O)(=O)N(CC(F)(F)F)C1CCN(C(=O)OC(C)(C)C)CC1]

A solution of tert-butyl 4-(5-bromo-2-methoxyphenylsulfonamido)piperidine-1-carboxylate (740 mg, 1.65 mmol), 2,2,2-trifluoroethyl trifluoromethanesulfonate (764 mg, 3.29 mmol) and potassium carbonate (683 mg, 4.94 mmol) in DMF (10 mL) was stirred for 24 hours. The mixture was poured into water (25 ml) and extracted with diethyl ether (3×10 mL). The extract was washed with water and dried with sodium sulfate. Removal of solvent gave 660 mg (75%) of desired product as an off-white solid.

4-[2-Methoxy-5-(4,4,5,5-tetramethyl-[1,3,2]dioxaborolan-2-yl)-benzenesulfonylamino]-piperidine-1-carboxylic acid tert-butyl ester

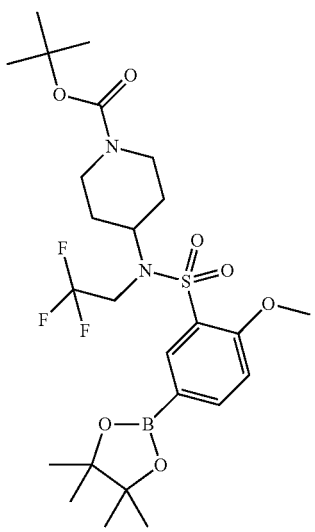 [SMILES: COc1ccc(B2OC(C)(C)C(C)(C)O2)cc1S(=O)(=O)N(CC(F)(F)F)C1CCN(C(=O)OC(C)(C)C)CC1]

Tert-butyl 4-(5-bromo-2-methoxy-N-(2,2,2-trifluoroethyl)phenylsulfonamido)piperidine-1-carboxylate (650 mg, 1.22 mmol), 4,4,4',4',5,5,5',5'-octamethyl-2,2'-bi(1,3,2-dioxaborolane) (311 mg, 1.22 mmol), potassium acetate (360 mg, 3.66 mmol) and [1,1'-bis(diphenylphosphino)-ferrocine]dichloro palladium(II) complex with dichloromethane (90 mg, 0.123 mmol) were combined into a sealed tube containing 1,4-dioxane (4.5 mL). The mixture was stirred at 140° C. for 30 min. on a microwave. The reaction mixture was diluted with EtOAc (10 mL) and washed with water (15 mL). The organic layer was dried with sodium sulfate and the solvent was removed. The residue was chromatographed (1.5-5% MeOH/DCM) to give 220 mg (31%) of desired product as a light brown solid.

4-[[4'-(5-Amino-1H-[1,2,4]triazol-3-ylamino)-2'-chloro-4-methoxy-6'-trifluoromethyl-biphenyl-3-sulfonyl]-(2,2,2-trifluoro-ethyl)-amino]-piperidine-1-carboxylic acid tert-butyl ester

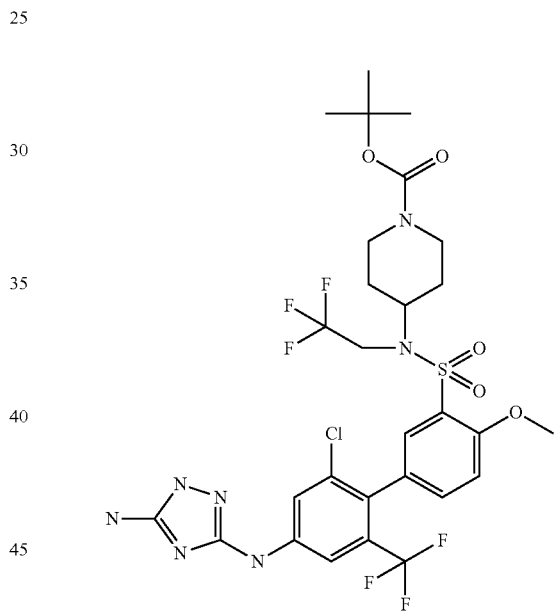

In a sealed tube containing a suspension of tert-butyl 4-(2-methoxy-5-(4,4,5,5-tetramethyl-1,3,2-dioxaborolan-2-yl)-N-(2,2,2-trifluoroethyl)phenylsulfonamido)piperidine-1-carboxylate (220 mg, 0.38 mmol), N3-(4-bromo-3-chloro-5-(trifluoromethyl)phenyl)-1H-1,2,4-triazole-3,5-diamine Intermediate 1 (136 mg, 0.38 mmol) potassium carbonate (3 eq, 53 mg, 1.14 mmol) and tetrakistriphenylphosphine palladium(0) (80 mg, 0.069 mmol) in DME/1,4-dioxane (1:1, 4 mL), was added water (0.5 mL). The reaction mixture was bubbled with nitrogen and heated at 140° C. for 3.5 hrs. The mixture was poured into water (10 mL) and the extracted with EtOAc (3×7 mL). The extract was dried with sodium sulfate and the solvent was removed under reduced pressure. The residue was purified by SFC to give 5 mg (2%) of desired product.

4'-(5-Amino-1H-[1,2,4]triazol-3-ylamino)-6'-chloro-4-methoxy-2'-trifluoromethyl-biphenyl-3-sulfonic acid piperidin-4-yl-(2,2,2-trifluoro-ethyl)-amide; compound with trifluoro-acetic acid (Compound 234)

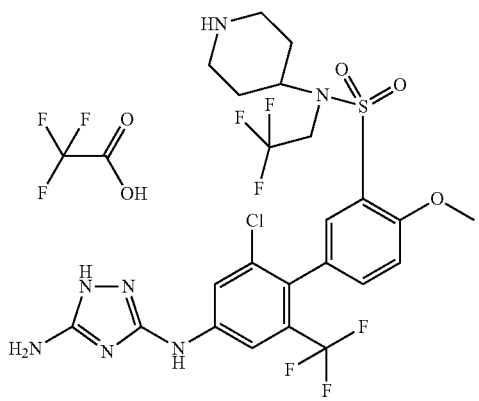 [SMILES: COc1ccc(-c2c(Cl)cc(Nc3n[nH]c(N)n3)cc2C(F)(F)F)cc1S(=O)(=O)N(CC(F)(F)F)C1CCNCC1 ; O=C(O)C(F)(F)F]

Tert-butyl 4-(4'-(5-amino-1H-1,2,4-triazol-3-ylamino)-2'-chloro-4-methoxy-N-(2,2,2-trifluoroethyl)-6'-(trifluoromethyl)biphenyl-3-ylsulfonamido)piperidine-1-carboxylate (5 mg) was dissolved in 30% trifluoro acetic acid in methylene chloride (3 mL) and the mixture was stirred at rt for 1 hr. The solvent was removed at reduced pressure and the residue was dissolved a mixture of acetonitrile/water and lyophilized to give 5 mg (98%) of desired product as a white powder. MS +m/z: 628.0 (M+H)⁺

4,4-Difluorocyclohexanecarboxylic acid [4'-(5-amino-1H-[1,2,4]triazol-3-ylamino)-2'-chloro-6'-trifluoromethyl-biphenyl-4-yl]-amide (Compound 235)

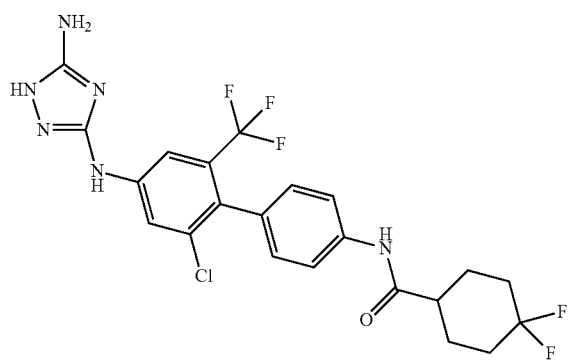 [SMILES: Nc1nc(Nc2cc(Cl)c(-c3ccc(NC(=O)C4CCC(F)(F)CC4)cc3)c(C(F)(F)F)c2)n[nH]1]

To a 15 mL microwave vial was added Intermediate 1 (70.7 mg, 198 µmol, Eq: 1.15), 4,4-difluoro-N-(4-(4,4,5,5-tetramethyl-1,3,2-dioxaborolan-2-yl)phenyl)cyclohexanecarboxamide (63 mg, 172 µmol, Eq: 1.00) and Pd(Ph₃P)₄ (19.9 mg, 17.2 µmol, Eq: 0.1) in Dioxane (4 ml) and 1M Na₂CO₃ (517 µl, 517 µmol, Eq: 3). The mixture was purged with argon, the vial was capped and heated in the microwave at 135° C. for 90 min. Diluted with methanol and filtered through celite. The filtrate was stripped and the crude material was purified by flash chromatography (silica gel, 24 g, 0% to 10% MeOH in DCM). The impure material was stripped to a light yellow powder and repurified by preparative HPLC (0.1% TFA in water/0.1% TFA in AcCN) 95% to 10% TFA water over 16 minutes. The material was dried overnight at 45° C. under vacuum to afford 24 mg (27%) of the desired product as an off-white solid.

MS +m/z: 515/517. (M+1)

[4'-(5-amino-1H-[1,2,4]triazol-3-ylamino)-2'-chloro-6'-trifluoromethyl-biphenyl-4-yl]-carbamic acid 1-tert-butyl-azetidin-3-yl ester (Compound 236)

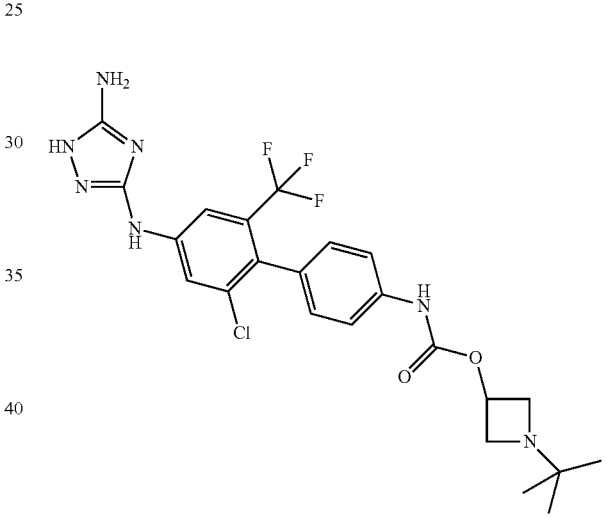

To a 15 mL microwave vial was added N3-(4-bromo-3-chloro-5-(trifluoromethyl)phenyl)-1H-1,2,4-triazole-3,5-diamine Intermediate 1 (47.1 mg, 132 µmol, Eq: 1.15), 1-tert-butylazetidin-3-yl 4-(4,4,5,5-tetramethyl-1,3,2-dioxaborolan-2-yl)phenylcarbamate (43 mg, 115 µmol, Eq: 1.00) and Pd(Ph₃P)₄ (13.3 mg, 11.5 µmol, Eq: 0.1) in Dioxane (2.5 ml) and Na₂CO₃ (345 µl, 345 µmol, Eq: 3). The mixture was purged with argon, the vial was capped and heated in the microwave at 135° C. for 60 min. Diluted with methanol and filtered. The filtrate was stripped and the crude material was purified by flash chromatography (silica gel, 24 g, 0% to 10% MeOH in DCM). The impure material was repurified by preparative HPLC (0.1% TFA in water/0.1% TFA in AcCN) 95% to 10% TFA water over 16 minutes. The material was dried overnight at 45° C. under vacuum to afford 4 mg (7%) of the desired product as a white solid.

MS +m/z: 522/524. (M+1)

[4'-(5-amino-1H-[1,2,4]triazol-3-ylamino)-2'-chloro-6'-trifluoromethyl-biphenyl-4-yl]-carbamic acid propyl ester (Compound 237)

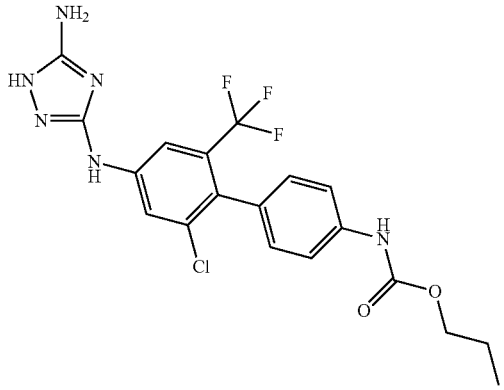 [SMILES: CCCOC(=O)Nc1ccc(-c2c(Cl)cc(Nc3n[nH]c(N)n3)cc2C(F)(F)F)cc1]

To a 15 mL microwave vial was added N3-(4-bromo-3-chloro-5-(trifluoromethyl)phenyl)-1H-1,2,4-triazole-3,5-diamine Intermediate 1 (97.0 mg, 272 μmol, Eq: 1.00), propyl 4-(4,4,5,5-tetramethyl-1,3,2-dioxaborolan-2-yl)phenylcarbamate (83 mg, 272 μmol, Eq: 1.00) and $Cs_2CO_3$ (266 mg, 816 μmol, Eq: 3) in n-butanol (2.5 ml) and water (500 μl). $PdCl_2$(DPPF) (22.2 mg, 27.2 μmol, Eq: 0.1) was added, the mixture was purged with argon, the vial was capped and heated in the microwave at 135° C. for 30 min. Diluted with dichloromethane, added $Na_2SO_4$ and filtered through celite. The filtrate was taken up in methanol, filtered and stripped in vacuo. The crude material was triturated with hot MeOH and filtered. The filtrate was stripped and the crude material was purified by preparative HPLC (0.1% TFA in water/0.1% TFA in AcCN) 95% to 10% TFA water over 16 mins. The isolated material was repurified by flash chromatography (silica gel, 40 g, 0% to 15% EtOH in DCM) to afford 5 mg (4%) of the desired product as a colorless oil.

MS +m/z: 455/457. (M+1)

[4'-(5-amino-1H-[1,2,4]triazol-3-ylamino)-2'-chloro-6'-trifluoromethyl-biphenyl-4-yl]-carbamic acid propyl ester (Compound 238)

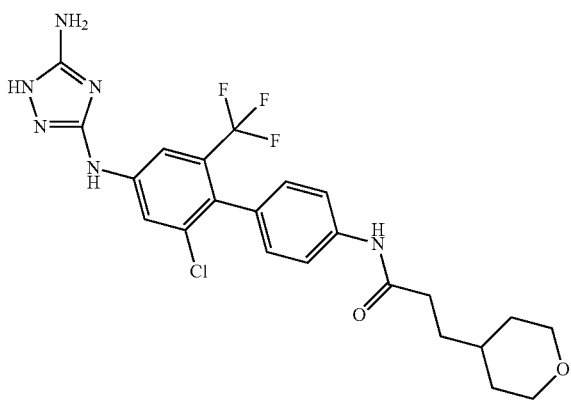 [SMILES: Nc1nc(Nc2cc(Cl)c(-c3ccc(NC(=O)CCC4CCOCC4)cc3)c(C(F)(F)F)c2)n[nH]1]

To a 15 mL microwave vial was added N3-(4-bromo-3-chloro-5-(trifluoromethyl)phenyl)-1H-1,2,4-triazole-3,5-diamine Intermediate 1 (99.2 mg, 278 μmol, Eq: 1.00), 3-(tetrahydro-2H-pyran-4-yl)-N-(4-(4,4,5,5-tetramethyl-1,3,2-dioxaborolan-2-yl)phenyl)propanamide (100 mg, 278 μmol, Eq: 1.00) and $Cs_2CO_3$ (272 mg, 835 μmol, Eq: 3) in n-butanol (2.5 ml) and water (500 μl). $PdCl_2$(DPPF) (22.2 mg, 27.2 μmol, Eq: 0.1) was added, the mixture was purged with argon, the vial was capped and heated in the microwave at 135° C. for 30 min. Diluted with dichloromethane, added $Na_2SO_4$ and filtered through celite. The filtrate was taken up in methanol, filtered and stripped in vacuo. The crude material was triturated with hot methanol and filtered. The filtrate was stripped and the crude material was purified by preparative HPLC (0.1% TFA in water/0.1% TFA in AcCN) 95% to 10% TFA water over 16 mins. The isolated material was repurified by preparative HPLC to afford 6 mg (4%) of the desired product as a white solid.

MS −m/z: 507/509. (M−1)

[4'-(5-amino-1H-[1,2,4]triazol-3-ylamino)-2'-chloro-6'-trifluoromethyl-biphenyl-4-yl]-1,1-dioxo-hexahydro-1$\lambda^6$-thiopyran-4-carboxylic acid (Compound 239)

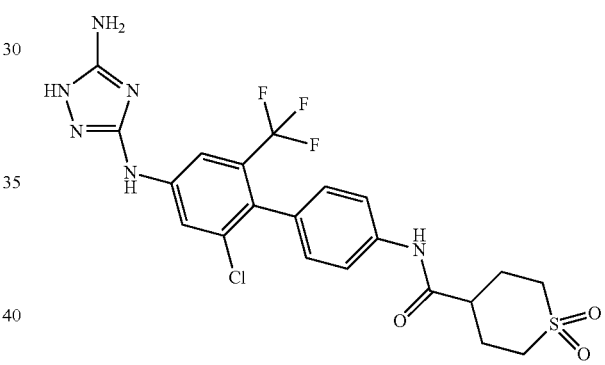

To a 15 mL microwave vial was added N3-(4-bromo-3-chloro-5-(trifluoromethyl)phenyl)-1H-1,2,4-triazole-3,5-diamine Intermediate 1 (136 mg, 380 μmol, Eq: 1.00), 4-(Tetrahydro-2H-thiopyran-4'-carboxamido-4'-yl)phenylboronic acid (113 mg, 380 μmol, Eq: 1.00) and $Cs_2CO_3$ (372 mg, 1.14 mmol, Eq: 3) in n-butanol (2.5 ml) and water (500 μl). $PdCl_2$(DPPF (31.1 mg, 38.0 μmol, Eq: 0.1) was added, the mixture was purged with argon, the vial was capped and heated in the microwave at 135° C. for 30 min. Diluted with dichloromethane, added $Na_2SO_4$ and filtered through celite. The filtrate was taken up in methanol, filtered and stripped in vacuo. The crude material was triturated with hot methanol and filtered. The filtrate was stripped and the crude material was purified by flash chromatography (silica gel, 80 g, 0% to 15% EtOH in DCM). The impure product was repurified by preparative HPLC (0.1% TFA in water/0.1% TFA in AcCN) 95% to 10% TEA water over 16 minutes to afford 4 mg (2%) of the desired product as a white solid.

MS +m/z: 529/531. (M+1)

[4'-(5-amino-1H-[1,2,4]triazol-3-ylamino)-2'-chloro-6'-trifluoromethyl-biphenyl-4-yl]-2-(1,1-dioxo-hexahydro-1λ⁶-thiopyran-4-yl)-acetamide (Compound 240)

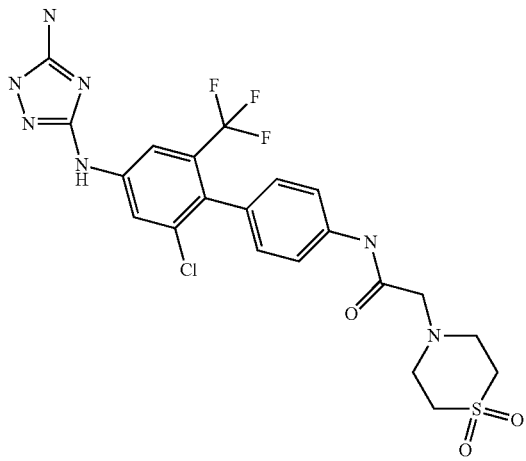 [SMILES: Nc1nc(Nc2cc(Cl)c(-c3ccc(NC(=O)CN4CCS(=O)(=O)CC4)cc3)c(C(F)(F)F)c2)n[nH]1]

Prepared by a similar procedure to Compound 235, except substituted 2-(1,1-Dioxothiomorpholin-4-yl)-N-(4-(4,4,5,5-tetramethyl-1,3,2-dioxaborolan-2-yl)phenyl)acetamide for 4,4-difluoro-N-(4-(4,4,5,5-tetramethyl-1,3,2-dioxaborolan-2-yl)phenyl)cyclohexanecarboxamide in step 1 to afford 37 mg (19%) of the desired material as a light yellow solid.

MS –m/z: 541.8/543.9. (M–1)

[4'-(5-amino-1H-[1,2,4]triazol-3-ylamino)-2'-chloro-6'-trifluoromethyl-biphenyl-4-yl]-2-morpholin-4-yl-acetamide (Compound 241)

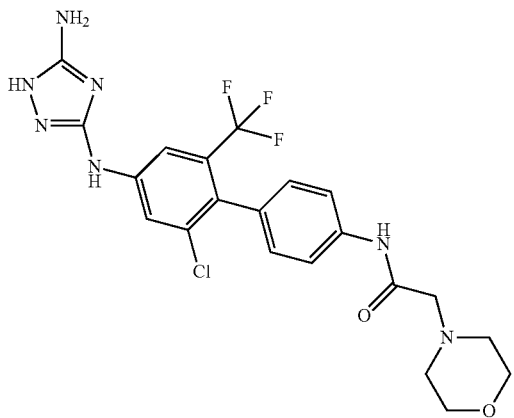 [SMILES: Nc1nc(Nc2cc(Cl)c(-c3ccc(NC(=O)CN4CCOCC4)cc3)c(C(F)(F)F)c2)n[nH]1]

Prepared by a similar procedure to Compound 235, except substituted 2-morpholino-N-(4-(4,4,5,5-tetramethyl-1,3,2-dioxaborolan-2-yl)phenyl)acetamide for 4,4-difluoro-N-(4-(4,4,5,5-tetramethyl-1,3,2-dioxaborolan-2-yl)phenyl)cyclohexanecarboxamide in step 1 to afford 15 mg (16%) of the desired material as an off white solid.

MS –m/z: 494/496. (M–1)

N-[4'-(5-Amino-2H-[1,2,4]-triazol-3-ylamino)-6'-fluoro-2'-trifluoromethyl-biphenyl-4-yl]-methanesulfonamide (Compound 242)

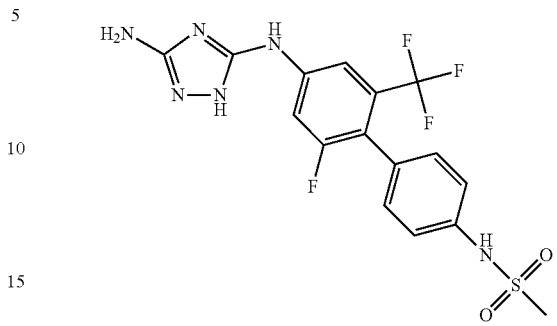

To a 15 mL microwave vial was added N3-(4-bromo-3-fluoro-5-(trifluoromethyl)phenyl)-1H-1,2,4-triazole-3,5-diamine Intermediate 3 (92 mg, 271 µmol, Eq: 1.00), 4-(methylsulfonamido)phenylboronic acid (58.2 mg, 271 µmol, Eq: 1.00) and Cs₂CO₃ (220 mg, 676 µmol, Eq: 2.5) in n-butanol (3 ml) and water (600 µl). PdCl₂(DPPF) (22.1 mg, 27.1 µmol, Eq: 0.1) was added and the mixture was purged with argon. The reaction was heated in the microwave at 135° C. for 30 min. The reaction was diluted with dichloromethane, Na2SO₄ was added and the mixture was filtered through celite. The filtrate was concentrated and the crude material was purified by preparative HPLC (20% ACN: 0.3% TFA in water to 100% ACN) to afford 11 mg (9%) of the desired material as a light brown solid.

MS –m/z: 428.9. (M–1)

N-[4'-(5-Amino-2H-[1,2,4]-triazol-3-ylamino)-6'-fluoro-2'-trifluoromethyl-biphenyl-3-yl]-methanesulfonamide (Compound 243)

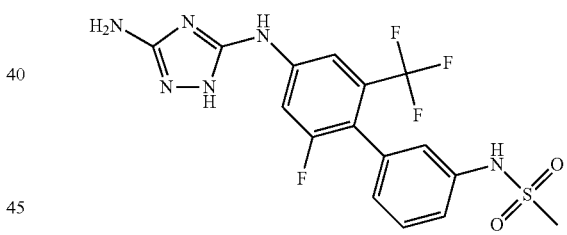

Prepared by a similar procedure to Compound 242, except substituted 3-(methylsulfonamido)phenylboronic acid acid for 4-(methylsulfonamido)phenylboronic acid to afford 4 mg (7%) of the desired material as a light brown solid.

MS –m/z: 428.9. (M–1)

N⁵-[6,3-Difluoro-2-trifluoromethylbiphenyl-4-yl]-1H-[1,2,4]-triazole-3,5-diamine (Compound 244)

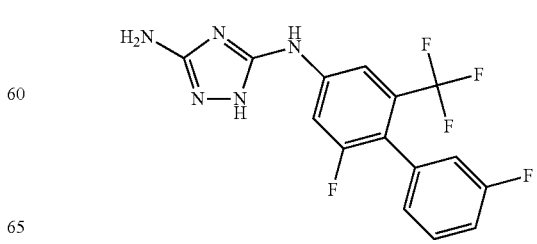

Prepared by a similar procedure to Compound 242, except substituted 3-fluorophenylboronic acid for 4-(methylsulfonamido)phenylboronic acid to afford 27 mg (40%) of the desired material as a white solid.
MS +m/z: 356.0. (M+1)

N⁵-[6,4'-Difluoro-2-trifluoromethylbiphenyl-4-yl]-1H-[1,2,4]-triazole-3,5-diamine (Compound 245)

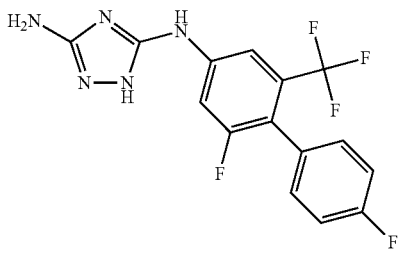 [SMILES: Nc1n[nH]c(Nc2cc(F)c(-c3ccc(F)cc3)c(C(F)(F)F)c2)n1]

Prepared by a similar procedure to Compound 242, except substituted 4-fluorophenylboronic acid for 4-(methylsulfonamido)phenylboronic acid to afford 30 mg (50%) of the desired material as a white solid.
MS +m/z: 356.0. (M+1)

N⁵-[6-Fluoro-2,4'-bis-trifluoromethylbiphenyl-4-yl]-1H-[1,2,4]-triazole-3,5-diamine (Compound 246)

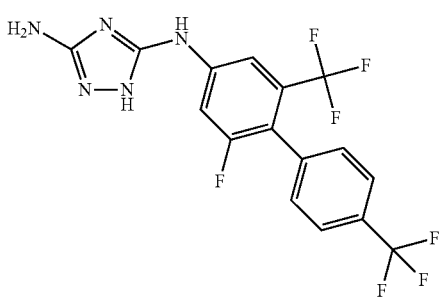 [SMILES: Nc1n[nH]c(Nc2cc(F)c(-c3ccc(C(F)(F)F)cc3)c(C(F)(F)F)c2)n1]

Prepared by a similar procedure to Compound 242, except substituted 4-trifluoromethylphenylboronic acid for 4-(methylsulfonamido)phenylboronic acid to afford 17 mg (24%) of the desired material as a white solid.
MS +m/z: 405.9. (M+1)

N⁵-[6-Fluoro-4'-methyl-2-trifluoromethylbiphenyl-4-yl]-1H-[1,2,4]-triazole-3,5-diamine (Compound 247)

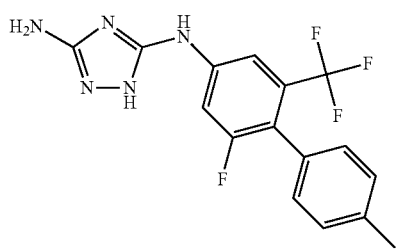 [SMILES: Cc1ccc(-c2c(F)cc(Nc3nc(N)n[nH]3)cc2C(F)(F)F)cc1]

Prepared by a similar procedure to Compound 242, except substituted 4-methylphenylboronic acid for 4-(methylsulfonamido)phenylboronic acid to afford 12 mg (23%) of the desired material as a white solid.
MS +m/z: 352.0. (M+1)

4'-(5-Amino-2H-[1,2,4]-triazol-3-ylamino)-6'-fluoro-2'-trifluoromethyl-biphenyl-43-carboxylic acid methylamide (Compound 248)

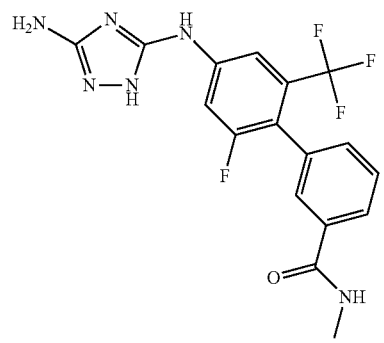 [SMILES: CNC(=O)c1cccc(-c2c(F)cc(Nc3nc(N)n[nH]3)cc2C(F)(F)F)c1]

Prepared by a similar procedure to Compound 242, except substituted 3-(methylcarbamoyl)-phenylboronic acid for 4-(methylsulfonamido)phenylboronic acid to afford 4 mg (4%) of the desired material as a colorless foam.
MS +m/z: 395.0. (M+1)

N⁵-(3-Fluoro-4-naphthalen-2-yl-5-trifluoromethyl-phenyl)-1H-[1,2,4]-triazole-3,5-diamine (Compound 249)

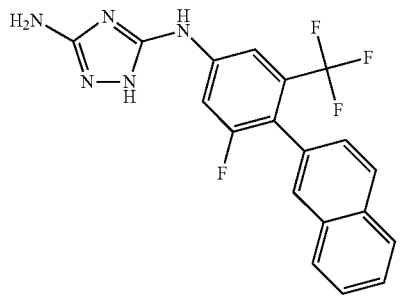 [SMILES: Nc1n[nH]c(Nc2cc(F)c(-c3ccc4ccccc4c3)c(C(F)(F)F)c2)n1]

Prepared by a similar procedure to Compound 242, except substituted naphthalen-2-ylboronic acid for 4-(methylsulfonamido)phenylboronic acid to afford 29 mg (57%) of the desired material as an off white solid.
MS +m/z: 387.9. (M+1)

4,4-Difluorocyclohexanecarboxylic acid [4'-(5-amino-1H-[1,2,4]triazol-3-ylamino)-2',6'-dichloro-biphenyl-4-yl]-amide (Compound 250)

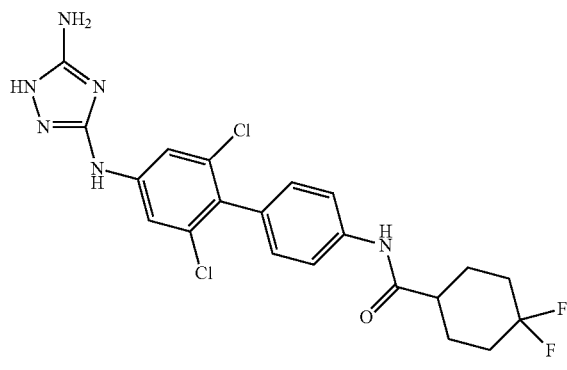 [SMILES: Nc1nc(Nc2cc(Cl)c(-c3ccc(NC(=O)C4CCC(F)(F)CC4)cc3)c(Cl)c2)n[nH]1]

To a 15 mL microwave vial was added N3-(4-bromo-3,5-dichlorophenyl)-1H-1,2,4-triazole-3,5-diamine Intermediate 2 (201 mg, 622 µmol, Eq: 1.00), 4,4-difluoro-N-(4-(4,4,5,5-tetramethyl-1,3,2-dioxaborolan-2-yl)phenyl)cyclohexanecarboxamide (227 mg, 622 µmol, Eq: 1.00) and Cs$_2$CO$_3$ (608 mg, 1.87 mmol, Eq: 3) in n-BuOH (3.00 ml) and Water (600 µl). PdCl$_2$(DPPF) (50.8 mg, 62.2 µmol, Eq: 0.1) was added, the mixture was purged with argon, the vial was capped and heated in the microwave at 135° C. for 30 min. Diluted with dichloromethane, added Na$_2$SO$_4$ and filtered through celite. The filtrate was taken up in MeOH, filtered and stripped of residual BuOH under vacuum with heating. The dark brown oily solid was dried under vacuum overnight. The crude material was triturated with hot MeOH. The tan solid was filtered and washed with MeOH. The filtrate was stripped and purified by preparative HPLC (0.1% TFA in water/0.1% TFA in AcCN) 95% to 10% TFA water over 16 mins. The purified material was combined with the isolated solid and dried at 45° C. under vacuum overnight to afford 32.8 mg (11%) of the desired product as an off-white solid.

MS +m/z: 481/483. (M+1)

N-[4'-(5-amino-1H-[1,2,4]triazol-3-ylamino)-2',6'-dichloro-biphenyl-4-yl]-isobutyramide (Compound 251)

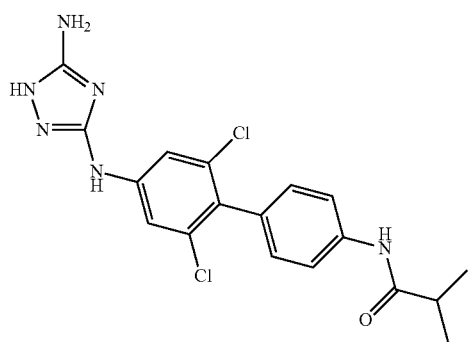 [SMILES: CC(C)C(=O)Nc1ccc(-c2c(Cl)cc(Nc3n[nH]c(N)n3)cc2Cl)cc1]

To a 15 mL microwave vial was added N3-(4-bromo-3,5-dichlorophenyl)-1H-1,2,4-triazole-3,5-diamine Intermediate 2 (201 mg, 622 µmol, Eq: 1.00), 4-isobutyramidophenylboronic acid (155 mg, 747 µmol, Eq: 1.2) and Cs$_2$CO$_3$ (608 mg, 1.87 mmol, Eq: 3) in n-BuOH (3.00 ml) and Water (600 µl). PdCl$_2$(DPPF) (50.8 mg, 62.2 µmol, Eq: 0.1) was added, the mixture was purged with argon, the vial was capped and heated in the microwave at 135° C. for 30 min. Diluted with dichloromethane, added. Na$_2$SO$_4$ and filtered through celite. The filtrate was taken up in MeOH, filtered and concentrated. The crude material was purified by preparative HPLC (0.1% TFA in water/0.1% TFA in AcCN) 95% to 10% TFA water over 25 mins. Dried under vacuum overnight to afford 71 mg (28%) of the desired product as an off white solid.

MS +m/z: 405.0/407.0. (M+1)

N-[4'-(5-amino-1H-[1,2,4]triazol-3-ylamino)-2',6'-dichloro-biphenyl-3-yl]-isobutyramide (Compound 252)

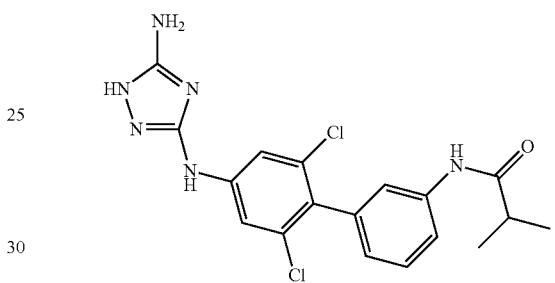

To a 15 mL microwave vial was added N3-(4-bromo-3,5-dichlorophenyl)-1H-1,2,4-triazole-3,5-diamine Intermediate 2 (100 mg, 310 µmol, Eq: 1.00), 3-isobutyramidophenylboronic acid and Cs$_2$CO$_3$ (303 mg, 929 µmol, Eq: 3) in n-BuOH (2 ml) and Water (400 µl). PdCl$_2$(DPPF) (25.3 mg, 31.0 µmol, Eq: 0.1) was added, the mixture was purged with argon, the vial was capped and heated in the microwave at 135° C. for 30 min. Diluted with dichloromethane, added Na$_2$SO$_4$ and filtered through celite. The filtrate was taken up in MeOH, filtered and concentrated. The crude material was purified by preparative HPLC (0.1% TFA in water/0.1% TFA in AcCN). 95% to 10% TFA water over 25 mins. Dried under vacuum overnight to afford 34 mg (27%) of the desired product as an off white solid.

MS +m/z: 405/407. (M+1)

N-[4'-(5-amino-1H-[1,2,4]triazol-3-ylamino)-2',6'-dichloro-biphenyl-4-sulfonic acid amide (Compound 253)

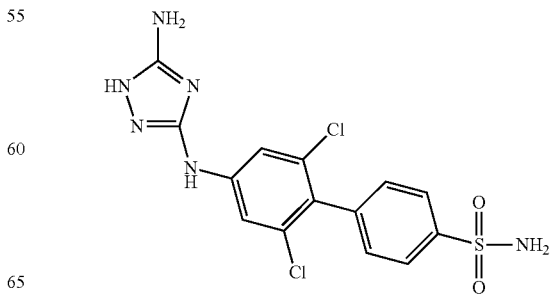

To a 15 mL microwave vial was added N3-(4-bromo-3,5-dichlorophenyl)-1H-1,2,4-triazole-3,5-diamine Intermediate 2 (392 mg, 1.21 mmol, Eq: 1.00), 4-(4,4,5,5-tetramethyl-1,3,2-dioxaborolan-2-yl)benzenesulfonamide (412 mg, 1.46 mmol, Eq: 1.2) and PdCl$_2$(DPPF) (49.6 mg, 60.7 μmol, Eq: 0.05) in Dioxane (3.00 ml) and 1M Na$_2$CO$_3$ (2 mL). The mixture was purged with argon, the vial was capped and heated in the microwave at 150° C. for 30 min. Diluted with dichloromethane, added Na$_2$SO$_4$ and filtered through celite. The filtrate was concentrated and the crude material was purified by preparative HPLC (0.1% TFA in water/0.1% TFA in AcCN) 95% to 10% TFA water over 25 mins. Dried under vacuum overnight to afford 68 mg (14%) of the desired product as an off white solid.

MS +m/z: 398.9/400.9. (M+1)

5-[4'-(5-amino-1H-[1,2,4]triazol-3-ylamino)-2',6'-dichlorophenyl-1,3-dihydroindol-2-one (Compound 254)

To a 15 mL microwave vial was added N3-(4-bromo-3,5-dichlorophenyl)-1H-1,2,4-triazole-3,5-diamine Intermediate 2 (201 mg, 622 μmol, Eq: 1.00), 5-(4,4,5,5-tetramethyl-1,3,2-dioxaborolan-2-yl)-1H-benzo[d]imidazol-2(3H)-one (162 mg, 622 μmol, Eq: 1.00) and Cs$_2$CO$_3$ (507 mg, 1.56 mmol, Eq: 2.5) in n-BuOH (3.00 ml) and Water (600 μl). PdCl$_2$(DPPF) (40.7 mg, 49.8 μmol, Eq: 0.08) was added, the mixture was purged with argon, the vial was capped and heated in the microwave at 135° C. for 30 min. Diluted with dichloromethane, added Na$_2$SO$_4$ and filtered through celite. The filtrate was concentrated and the crude material was purified by preparative HPLC (0.1% TFA in water/0.1% TFA in AcCN) 95% to 10% TFA water over 25 mins. Dried under vacuum overnight to afford 14 mg (6%) of the desired product as a light brown solid.

MS +m/z: 373.8/375.9. (M+1)

6-[4'-(5-amino-M-[1,2,4]triazol-3-ylamino)-2',6'-dichlorophenyl-1,3-dihydroindol-2-one (Compound 256)

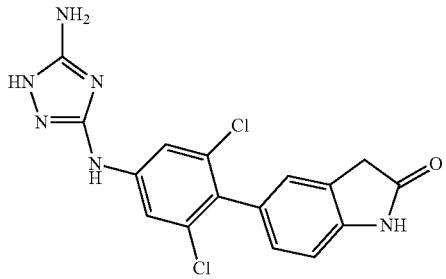 [SMILES: Nc1nc(Nc2cc(Cl)c(-c3ccc4c(c3)CC(=O)N4)c(Cl)c2)n[nH]1]

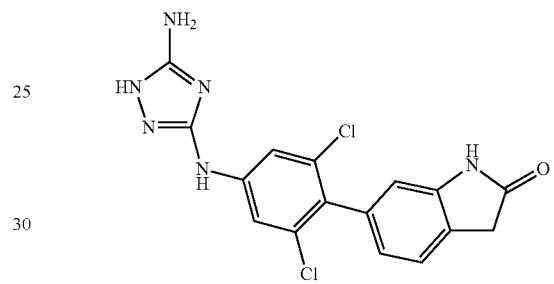

To a 15 mL microwave vial was added N3-(4-bromo-3,5-dichlorophenyl)-1H-1,2,4-triazole-3,5-diamine Intermediate 2 (201 mg, 622 μmol, Eq: 1.00), 5-(4,4,5,5-tetramethyl-1,3,2-dioxaborolan-2-yl)indolin-2-one (161 mg, 622 μmol, Eq: 1.00) and Cs$_2$CO$_3$ (507 mg, 1.56 mmol, Eq: 2.5) in n-BuOH (3.00 ml) and Water (600 μl). PdCl$_2$(DPPF) (40.7 mg, 49.8 μmol, Eq: 0.08) was added, the mixture was purged with argon, the vial was capped and heated in the microwave at 135° C. for 30 min. Diluted with dichloromethane, added Na$_2$SO$_4$ and filtered through celite. The filtrate was concentrated and the crude material was purified by preparative HPLC (0.1% TFA in water/0.1% TFA in AcCN) 95% to 10% TFA water over 25 mins to afford 23 mg (10%) of the desired product as an off white solid.

MS −m/z: 372.9/374.9. (M−1)

5-[4'-(5-amino-1H-[1,2,4]triazol-3-ylamino)-2',6'-dichlorophenyl-1,3-dihydrobenzimidazol-2-one (Compound 255)

To a 15 mL microwave vial was added N3-(4-bromo-3,5-dichlorophenyl)-1H-1,2,4-triazole-3,5-diamine Intermediate 2 (201 mg, 622 μmol, Eq: 1.00), 6-(4,4,5,5-tetramethyl-1,3,2-dioxaborolan-2-yl)indolin-2-one (161 mg, 622 μmol, Eq: 1.00) and Cs$_2$CO$_3$ (507 mg, 1.56 mmol, Eq: 2.5) in n-BuOH (3.00 ml) and Water (600 μl). PdCl$_2$(DPPF) (40.7 mg, 49.8 μmol, Eq: 0.08) was added, the mixture was purged with argon, the vial was capped and heated in the microwave at 135° C. for 30 min. Diluted with dichloromethane, added Na$_2$SO$_4$ and filtered through celite. The filtrate was concentrated and the crude material was purified by preparative HPLC (0.1% TFA in water/0.1% TFA in AcCN) 95% to 10% TFA water over 25 mins. Dried under vacuum overnight to afford 29 mg (12%) of the desired product as a light yellow solid.

MS −m/z: 372.9/374.9 (m−1)

N-3-[3',5'-dichlorophenyl-4'-(1H-indazol-5-yl)-phenyl]-1H-[1,2,4]triazole-3,5-diamine (Compound 257)

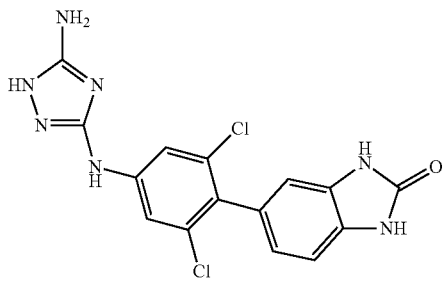 [SMILES: Nc1nc(Nc2cc(Cl)c(-c3ccc4[nH]c(=O)[nH]c4c3)c(Cl)c2)n[nH]1]

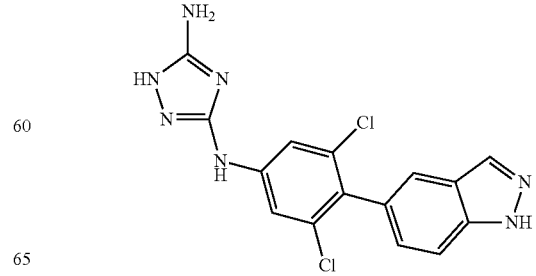

427

To a 15 mL microwave vial was added N3-(4-bromo-3,5-dichlorophenyl)-1H-1,2,4-triazole-3,5-diamine Intermediate 2 (201 mg, 622 μmol, Eq: 1.00), 1H-indazol-5-ylboronic acid (121 mg, 747 μmol, Eq: 1.2) and $Cs_2CO_3$ (507 mg, 1.56 mmol, Eq: 2.5) in Dioxane (3 ml) and Water (600 μl). $PdCl_2$(DPPF) (40.7 mg, 49.8 μmol, Eq: 0.08) was added, the mixture was purged with argon, the vial was capped and heated in the microwave at 120° C. for 30 min. Diluted with dichloromethane, added $Na_2SO_4$ and filtered through celite. The filtrate was concentrated and the crude material was purified by preparative HPLC (0.1% TFA in water/0.1% TFA in AcCN) 95% to 10% TFA water over 25 mins. Dried under vacuum overnight to afford 56 mg (25%) of the desired product as an off white solid.

MS −m/z: 359.9/362.0. (M−1)

$N^3$-2',6'-Dichlorobiphenyl-4-yl)-1H-[1,2,4]triazole-3,5-diamine (Compound 258)

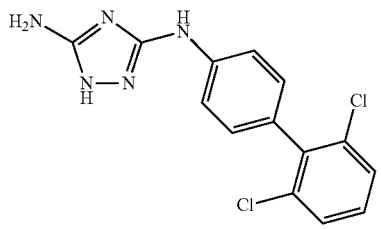 [SMILES: Nc1nc(Nc2ccc(-c3c(Cl)cccc3Cl)cc2)n[nH]1]

2',6'-Dichlorobiphenyl-4-ylamine

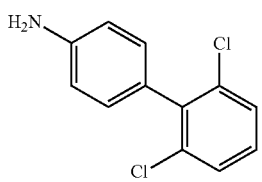 [SMILES: Nc1ccc(-c2c(Cl)cccc2Cl)cc1]

In a 100 mL round-bottomed flask, 4-(4,4,5,5-tetramethyl-1,3,2-dioxaborolan-2-yl)aniline (4.15 g, 18.9 mmol, Eq: 1.5), 2-bromo-1,3-dichlorobenzene (2.85 g, 12.6 mmol, Eq: 1.00) and NaOH (2.52 g, 63.1 mmol, Eq: 5) were combined with DME (50 ml) and Water (50.0 ml) to give a light brown turbid solution. $Pd(Ph_3P)_4$ (729 mg, 631 μmol, Eq: 0.05) was added and the reaction was evacuated and filled with argon. The yellow solution was heated to 90° C. and stirred for 19 h. The reaction was extracted with dichloromethane (3×100 mL). The organic layers were combined, washed with water (1×50 mL), brine (1×50 mL), dried over $Na_2SO_4$ and concentrated in vacuo. The crude material was purified by flash chromatography (silica gel, 80 g, 0% to 20% EtOAc in heptane) to afford 1.62 g (54%) of the desired product as a yellow oil.

MS +m/z: 237.9/240.0 (M+1)

428

2',6'-Dichloro-4'-isothiocyanato-biphenyl

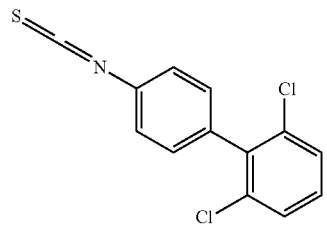 [SMILES: S=CC=Nc1ccc(-c2c(Cl)cccc2Cl)cc1]

In a 250 mL round-bottomed flask, 2',6'-dichlorobiphenyl-4-amine (1.62 g, 6.8 mmol, Eq: 1.00) and calcium carbonate (680 mg, 6.8 mmol, Eq: 1.00) were combined with dichloromethane (10 ml) and water (10.0 ml) to give a light brown two phase solution. Cooled to 0° C. and thiophosgene (859 mg, 573 μl, 7.47 mmol, Eq: 1.1) was added. The reaction was stirred at 0° C. for 30 mins then overnight at 25° C. TLC indicated total loss of SM. The reaction mixture was diluted with dichloromethane, separated and the aqueous layer was back-extracted with dichloromethane (1×25 mL). The organic layers were combined, washed with $H_2O$ (1×20 mL), dried over $Na_2SO_4$ and concentrated in vacuo. The dark orange oil was dried under vacuum at 25° C. for 1 hr. The oil was used without further purification.

N-Cyano-N'-2',6'-Dichlorobiphenyl-4-yl-carbamimidothioic acid methyl ester

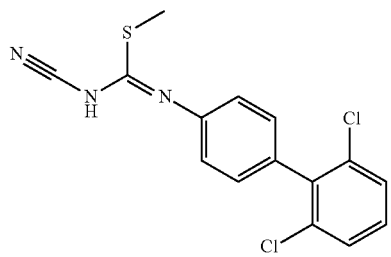 [SMILES: CSC(=Nc1ccc(-c2c(Cl)cccc2Cl)cc1)NC#N]

In a 250 mL round-bottomed flask, 2,6-dichloro-4'-isothiocyanatobiphenyl (1.841 g, 6.57 mmol, Eq: 1.00) was combined with MeOH (12 ml) to give an orange suspension. Sodium cyanamide (421 mg, 6.57 mmol, Eq: 1.00) was added and the reaction was stirred at 25° C. for 1.5 hours under argon. Methyl iodide (1.87 g, 822 μl, 13.1 mmol, Eq: 2) was added and the reaction became a light yellow suspension within 5 mins. The mixture was stirred at 25° C. for 44 hours under argon. The suspension was filtered and the filter cake was washed with methanol. The product was dried under vacuum to afford 1.74 g (79%) of the desired product as an off-white powder.

MS +m/z: 335.9/337.9 (M+1)

N³-2',6'-Dichlorobiphenyl-4-yl)-1H-[1,2,4]triazole-3,5-diamine (Compound 258)

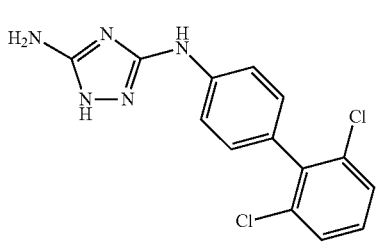 [SMILES: Nc1nc(Nc2ccc(-c3c(Cl)cccc3Cl)cc2)n[nH]1]

In a 250 mL round-bottomed flask N-Cyano-N'-2',6'-Dichlorobiphenyl-4-yl-carbamimidothioic acid methyl ester (1.74 g, 5.17 mmol, Eq: 1.00) was combined with ethanol (25 ml) to give an off-white suspension. Hydrazine monohydrate (2.59 g, 2.52 ml, 51.7 mmol, Eq: 10) was added and the reaction mixture was heated to 70° C. for 1.5 h. Concentrated to ~5 ml, diluted with water (20 ml) and stirred for 20 min. Filtered and washed the filter cake with water (~50 ml). The solid was dried under vacuum at 45° C. overnight vacuum to afford 1.61 g (97%) of the desired product as a white powder.

MS +m/z: 320.0/321.9 (M+1)

N*5*-[3,5-Dichloro-4-(piperidin-3-yloxy)-phenyl]-1H-[1,2,4]triazole-3,5-diamine (Compound 259)

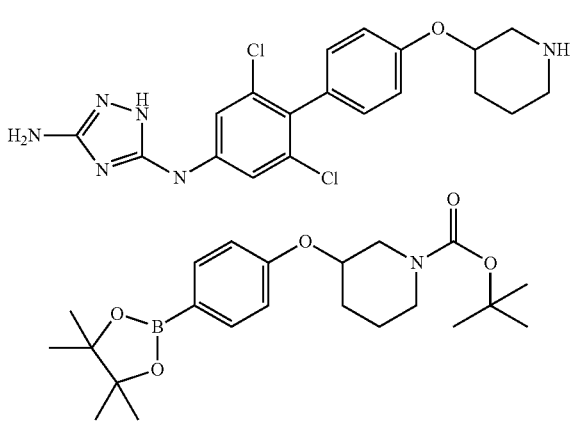

(E)-diazene-1,2-diylbis(piperidin-1-ylmethanone) (1.08 g, 4.1 mmol) was added to a solution of 4-(4,4,5,5-tetramethyl-1,3,2-dioxaborolan-2-yl)phenol (1.03, 4.1 mmol) and triphenylphosphine (902 mg, 4.1 mmol) in THF (30 mL). After stirring for 5 minutes, tert-butyl 3-hydroxypiperidine-1-carboxylate (750 mg, 3.73 mmol) was added and the reaction mixture was stirred for 16 hours. The resulting slurry was filtered and the all volatiles were removed from the filtrate under reduced pressure. tert-Butyl 3-(4-(4,4,5,5-tetramethyl-1,3,2-dioxaborolan-2-yl)phenoxy)piperidine-1-carboxylate was isolated in near pure form by column chromatography (5:1 hexane:EtOAc). Residual 4-(4,4,5,5-tetramethyl-1,3,2-dioxaborolan-2-yl)phenol was removed by dissolving the nearly-pure product in EtOAc and washing twice with 1M NaOH and once with brine. The organic phase was dried over MgSO₄. Filtration followed by removal of volatiles under reduced pressure gave pure tert-butyl 3-(4-(4,4,5,5-tetramethyl-1,3,2-dioxaborolan-2-yl)phenoxy)piperidine-1-carboxylate (279 mg, 18.6%).

N*5*-[3,5-Dichloro-4-(piperidin-3-yloxy)-phenyl]-1H-[1,2,4]triazole-3,5-diamine (Compound 259)

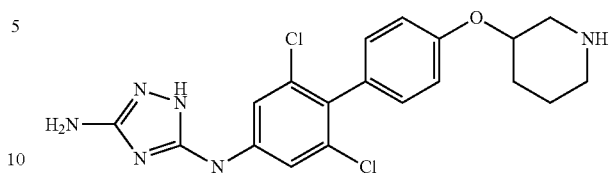

A solution of tert-butyl 3-(4-(4,4,5,5-tetramethyl-1,3,2-dioxaborolan-2-yl)phenoxy)piperidine-1-carboxylate (260 mg, 0.64 mmol), N5-(4-bromo-3,5-dichlorophenyl)-1H-1,2,4-triazole-3,5-diamine Intermediate 2 (208 mg, 0.64 mmol) and aqueous sodium carbonate solution (2.0M, 757 µL, 1.51 mmol) in dioxane (5 mL) was degassed for 10 minutes after which tetrakis triphenylphosphine palladium (74.5 mg, 64.5 mmol) was added. The reaction mixture was then sealed and heated to 135° C. for 72 hours. The reaction mixture was cooled, unsealed and poured into satd NaHCO₃ solution and extracted three times with EtOAc. The combined organic phases were washed with brine, dried over MgSO₄ and filtered. Removal of volatiles under reduced pressure gave a brown solid from which 3-[4-(5-Amino-2H-[1,2,4]triazol-3-ylamino)-2,6-dichloro-phenoxy]-piperidine-1-carboxylic acid tert-butyl ester was isolated as a white foam by column chromatography (15% EtOH in CHCl₃). This foam was dissolved in 10% HCl in CH₃OH and stirred for 1 hour. Evaporation of volatiles followed by trituration with diethyl ether gave N*5*-[3,5-Dichloro-4-(piperidin-3-yloxy)-phenyl]-1H-[1,2,4]triazole-3,5-diamine as a white solid (47 mg, 14%). MH+=419.0

3-[4'-(5-Amino-1H-[1,2,4]triazol-3-ylamino)-2',6'-dichloro-biphenyl-4-yloxymethyl]-azetidine-1-carboxylic acid tert-butyl ester (Compound 260)

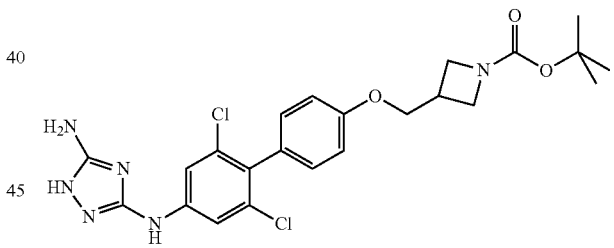

3-[4-(4,4,5,5-Tetramethyl-[1,3,2]dioxaborolan-2-yl)-phenoxymethyl]-azetidine-1-carboxylic acid tert-butyl ester

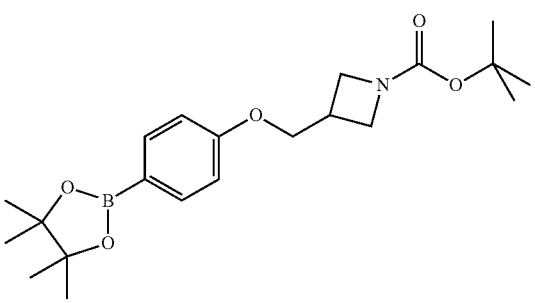 [SMILES: CC(C)(C)OC(=O)N1CC(COc2ccc(B3OC(C)(C)C(C)(C)O3)cc2)C1]

In a 100 mL round-bottomed flask, triphenylphosphine (1.25 g, 4.77 mmol, Eq: 1.05), tert-butyl 3-(hydroxymethyl)azetidine-1-carboxylate (851 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.85 g (48.1%) oil. MH+ 390.0

3-[4'-(5-Amino-1H-[1,2,4]triazol-3-ylamino)-2',6'-dichloro-biphenyl-4-yloxymethyl]-azetidine-1-carboxylic acid tert-butyl ester (Compound 260)

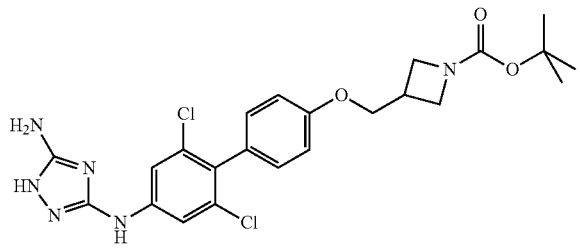 [SMILES: CC(C)(C)OC(=O)N1CC(COc2ccc(-c3c(Cl)cc(Nc4n[nH]c(N)n4)cc3Cl)cc2)C1]

In a 15 mL sealed tube, N3-(4-bromo-3,5-dichlorophenyl)-1H-1,2,4-triazole-3,5-diamine Intermediate 2 (200 mg, 619 mol, Eq: 1.00), tetrakis(triphenylphosphine)-palladium (0) (71.6 mg, 61.9 µmol, Eq: 0.1) and 3-[4-(4,4,5,5-tetramethyl-[1,3,2]dioxaborolan-2-yl)-phenoxymethyl]-azetidine-1-carboxylic acid tert-butyl ester (241 mg, 619 µmol, Eq: 1.00) were combined with a solution of 1,4-dioxane/H₂O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH₂Cl₂ (50 mL), washed with H₂O (25 mL) and brine (25 mL). The organic layer was dried over anhydrous MgSO₄, filtered and volatiles were removed under reduced pressure to yield an oil from which {2-[4'-(5-Amino-1H-[1,2,4]triazol-3-ylamino)-2',6'-dichloro-biphenyl-4-yloxy]-ethyl}-methyl-carbamic acid tert-butyl ester (Compound 261)

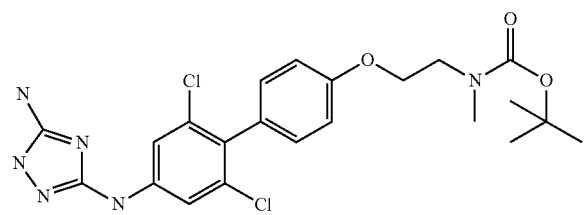 [SMILES: CN(CCOc1ccc(-c2c(Cl)cc(Nc3n[nH]c(N)n3)cc2Cl)cc1)C(=O)OC(C)(C)C]

Methyl-{2-[4-(4,4,5,5-tetramethyl-[1,3,2]dioxaborolan-2-yl)-phenoxy]-ethyl}-carbamic acid tert-butyl ester

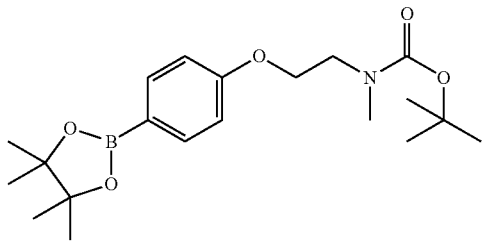 [SMILES: CN(CCOc1ccc(B2OC(C)(C)C(C)(C)O2)cc1)C(=O)OC(C)(C)C]

In a 100 mL round-bottomed flask, triphenylphosphine (1.25 g, 4.77 mmol, Eq: 1.05), tert-butyl 2-hydroxyethyl (methyl)carbamate (796 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound by column chromatography (Hexanes/EtOAc=70/30) to give 0.80 g (46.7%) oil.

{2-[4'-(5-Amino-1H-[1,2,4]triazol-3-ylamino)-2',6'-dichloro-biphenyl-4-yloxy]-ethyl}-methyl-carbamic acid tert-butyl ester (Compound 261)

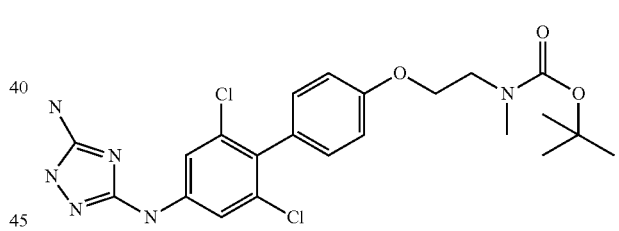

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and methyl-{2-[4-(4,4,5,5-tetramethyl-[1,3,2]dioxaborolan-2-yl)-phenoxy]-ethyl}-carbamic acid tert-butyl ester (234 mg, 619 µmol, Eq: 1.00) were combined with a solution of 1,4-dioxane/H₂O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH2Cl₂/MeOH=95/5) to give an off-white solid (28 mg, 9.2%). MH+ 493.0

433

N*3*-[2,6-Dichloro-4'-(piperidin-4-yloxy)-biphenyl-4-yl]-1H-[1,2,4]triazole-3,5-diamine, HCl salt (Compound 262)

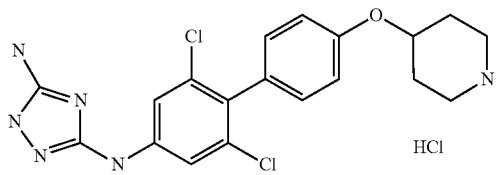 [SMILES: Nc1nc(Nc2cc(Cl)c(-c3ccc(OC4CCNCC4)cc3)c(Cl)c2)n[nH]1 ; Cl]

In a 25 mL round bottle, 1 mL acetyl chloride was added to 10 mL MeOH at room temperature, cool down the solution to RT, added to tert-butyl 4-(4'-(5-amino-1H-1,2,4-triazol-3-ylamino)-2',6'-dichlorobiphenyl-4-yloxy)piperidine-1-carboxylate (40 mg, 77.0 µmol), the reaction was allowed to stir at room temperature for 2 hours, filter out the solid to afford the product 28 mg (80%), MH+ 419.0.

N*3*-[2,6-Dichloro-4'-(2-methylamino-ethoxy)-biphenyl-4-yl]-1H-[1,2,4]triazole-3,5-diamine, HCl salt (Compound 263)

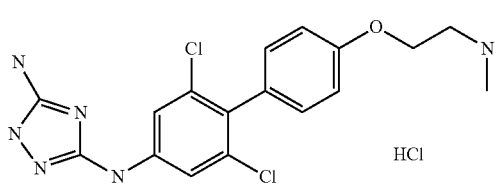 [SMILES: CNCCOc1ccc(-c2c(Cl)cc(Nc3n[nH]c(N)n3)cc2Cl)cc1 ; Cl]

In a 25 mL round bottle, 1 mL acetyl chloride was added to 10 mL MeOH at room temperature, cool down the solution to RT, added tert-butyl 2-(4'-(5-amino-1H-1,2,4-triazol-3-ylamino)-2',6'-dichlorobiphenyl-4-yloxy)ethyl(methyl)carbamate (23 mg, 46.6 µmol), the reaction was allowed to stir at room temperature for 2 hours, filter out the solid to afford the product 16 mg (80%), MH+ 393.0.

N*3*-[2,6-Dichloro-4'-(2-pyrrolidin-2-yl-ethoxy)-biphenyl-4-yl]-1H-[1,2,4]triazole-3,5-diamine, HCl salt (Compound 264)

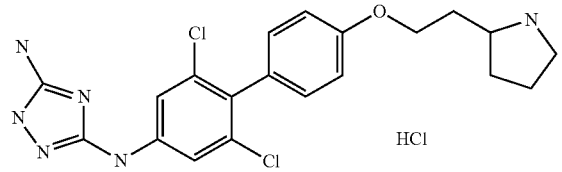 [SMILES: Nc1nc(Nc2cc(Cl)c(-c3ccc(OCCC4CCCN4)cc3)c(Cl)c2)n[nH]1 ; Cl]

In a 25 mL round bottle, 1 mL acetyl chloride was added to 10 mL MeOH at room temperature, cool down the solution to RT, added tert-butyl 2-(2-(4'-(5-amino-1H-1,2,4-triazol-3-ylamino)-2',6'-dichlorobiphenyl-4-yloxy)ethyl)pyrrolidine-1-carboxylate (30 mg, 56.2 µmol), the reaction was allowed to stir at room temperature for 2 hours, filter out the solid to afford the product 25 mg (95%), MH+ 433.0.

434

N*3*-[2,6-Dichloro-4'-((S)-1-pyrrolidin-2-yl-methoxy)-biphenyl-4-yl]-1H-[1,2,4]triazole-3,5-diamine (Compound 265)

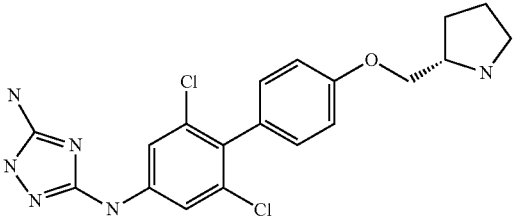 [SMILES: Nc1nc(Nc2cc(Cl)c(-c3ccc(OC[C@@H]4CCCN4)cc3)c(Cl)c2)n[nH]1]

In a 25 mL round bottle, (S)-tert-butyl 2-((4'-(5-amino-1H-1,2,4-triazol-3-ylamino)-2',6'-dichlorobiphenyl-4-yloxy)methyl)pyrrolidine-1-carboxylate (50 mg, 96.3 µmol) combined with CH2Cl2 (10.0 ml) to give a light yellow solution, TFA (1 mL) was added. Let the reaction stirred for 1 hour, concentrate the solution, added CH2Cl2 (50 mL), washed with saturated NaHCO3, filter out the solid to afford the product 35 mg (88%), MH+ 418.9.

2-{2-[4'-(5-Amino-1H-[1,2,4]triazol-3-ylamino)-2',6'-dichloro-biphenyl-4-yloxy]-ethyl}-pyrrolidine-1-carboxylic acid tert-butyl ester (Compound 266)

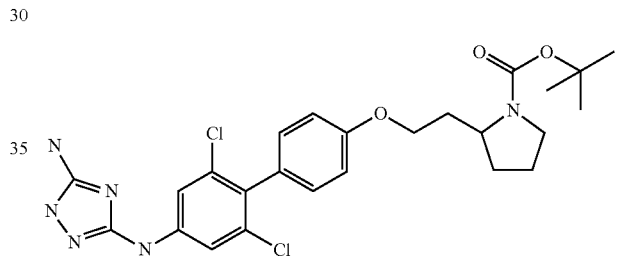

2-{2-[4-(4,4,5,5-Tetramethyl-[1,3,2]dioxaborolan-2-yl)-phenoxy]-ethyl}-pyrrolidine-1-carboxylic acid tert-butyl ester

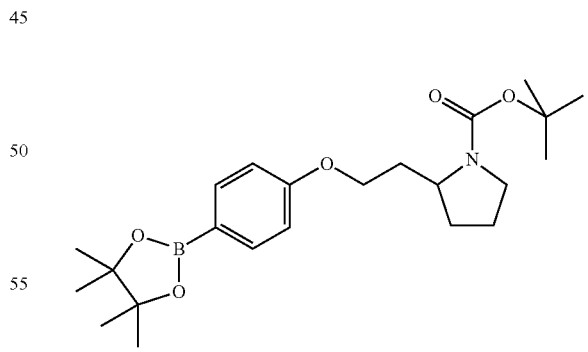

In a 100 mL round-bottomed flask, triphenylphosphine (1.25 g, 4.77 mmol, Eq: 1.05), tert-butyl 2-(2-hydroxyethyl)pyrrolidine-1-carboxylate (978 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.8 g (42%) oil.

2-{2-[4'-(5-Amino-1H-[1,2,4]triazol-3-ylamino)-2',6'-dichloro-biphenyl-4-yloxy]-ethyl}-pyrrolidine-1-carboxylic acid tert-butyl ester (Compound 266)

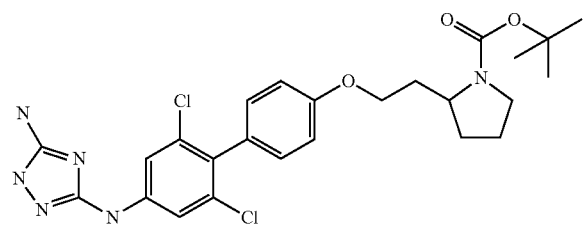 [SMILES: CC(C)(C)OC(=O)N1CCCC1CCOc1ccc(-c2c(Cl)cc(Nc3n[nH]c(N)n3)cc2Cl)cc1]

In a 15 mL sealed tube, N3-(4-bromo-3,5-dichlorophenyl)-1H-1,2,4-triazole-3,5-diamine Intermediate 2 (200 mg, 619 μmol, Eq: 1.00), tetrakis(triphenylphosphine)-palladium (0) (71.6 mg, 61.9 μmol, Eq: 0.1) and test-butyl 2-(2-(4-(4,4,5,5-tetramethyl-1,3,2-dioxaborolan-2-yl)phenoxy)ethyl) pyrrolidine-1-carboxylate (258 mg, 619 μmol, Eq: 1.00) were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH$_2$Cl$_2$/MeOH=95/5) to give an off-white solid (37 mg, 11.2%). MH+ 534.0

(R)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester (Compound 267)

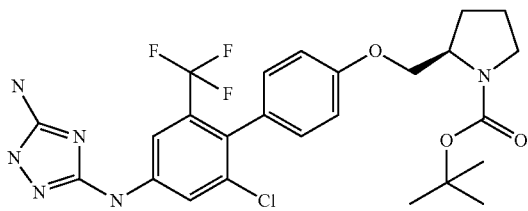 [SMILES: CC(C)(C)OC(=O)N1CCC[C@@H]1COc1ccc(-c2c(Cl)cc(Nc3n[nH]c(N)n3)cc2C(F)(F)F)cc1]

(R)-2-[4-(4,4,5,5-Tetramethyl-[1,3,2]dioxaborolan-2-yl)-phenoxymethyl]-pyrrolidine-1-carboxylic acid tert-butyl ester

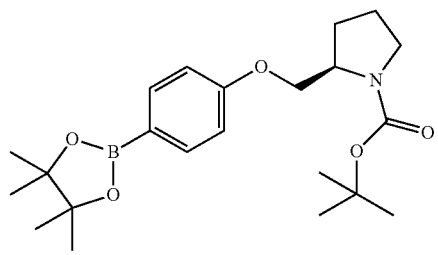 [SMILES: CC(C)(C)OC(=O)N1CCC[C@@H]1COc1ccc(B2OC(C)(C)C(C)(C)O2)cc1]

In a 100 mL round-bottomed flask, triphenylphosphine (1.25 g, 4.77 mmol, Eq: 1.05), N-boc-1-prolinol (915 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.8 g (46%) oil.

(R)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester (Compound 267)

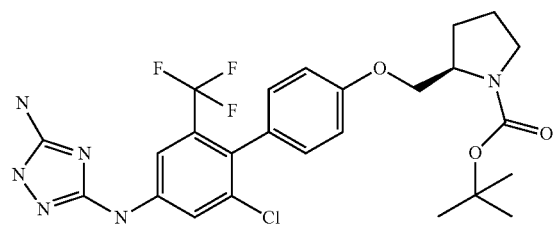 [SMILES: CC(C)(C)OC(=O)N1CCC[C@@H]1COc1ccc(-c2c(Cl)cc(Nc3n[nH]c(N)n3)cc2C(F)(F)F)cc1]

In a 15 mL sealed tube, N3-(4-bromo-3-chloro-5-(trifluoromethyl)phenyl)-1H-1,2,4-triazole-3,5-diamine Intermediate 1 (300 mg, 841 μmol, Eq: 1.00), tetrakis(triphenylphosphine)-palladium (0) (97.2 mg, 84.1 μmol, Eq: 0.1) and (R)-tert-butyl 2-((4-(4,4,5,5-tetramethyl-1,3,2-dioxaborolan-2-yl)phenoxy)methyl)pyrrolidine-1-carboxylate (407 mg, 1.01 mmol, Eq: 1.2), were combined with a solution of 1,4-dioxane/H$_2$O=4/1 (6.67 ml) to give a light yellow suspension. Potassium carbonate (465 mg, 3.37 mmol, Eq: 4) was added to the suspension. The reaction mixture was degassed with argon for 15 min, and then heated to 140° C. for overnight. The reaction mixture was cooled and diluted with CH2Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH2Cl$_2$/MeOH=95/5) to give an off-white solid (40 mg, 8.6%). MH+ 553.0

4-[4'-(5-Amino-1H-[1,2,4]triazol-3-ylamino)-2',6'-dichloro-biphenyl-4-yloxy]-piperidine-1-carboxylic acid tert-butyl ester (Compound 268)

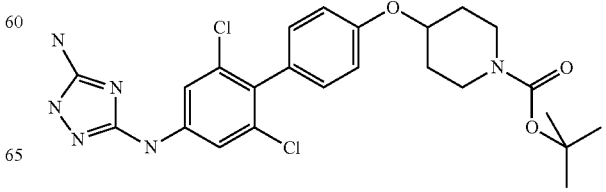

4-[4-(4,4,5,5-Tetramethyl-[1,3,2]dioxaborolan-2-yl)-phenoxy]-piperidine-1-carboxylic acid tert-butyl ester

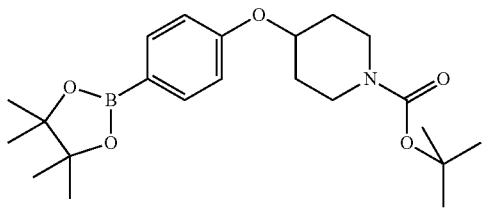 [SMILES: CC(C)(C)OC(=O)N1CCC(Oc2ccc(B3OC(C)(C)C(C)(C)O3)cc2)CC1]

In a 100 mL round-bottomed flask, triphenylphosphine (1.25 g, 4.77 mmol, Eq: 1.05), tert-butyl 4-hydroxypiperidine-1-carboxylate (915 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.7 g (38%) oil. MH+ 403.9

4-[4'-(5-Amino-1H-[1,2,4]triazol-3-ylamino)-2',6'-dichloro-biphenyl-4-yloxy]-piperidine-1-carboxylic acid tert-butyl ester (Compound 268)

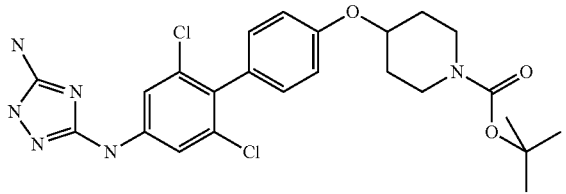 [SMILES: CC(C)(C)OC(=O)N1CCC(Oc2ccc(-c3c(Cl)cc(Nc4n[nH]c(N)n4)cc3Cl)cc2)CC1]

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and tert-butyl 4-(4-(4,4,5,5-tetramethyl-1,3,2-dioxaborolan-2-yl)phenoxy)piperidine-1-carboxylate (250 mg, 619 µmol, Eq: 1.00), were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH2Cl$_2$/MeOH=95/5) to give an off-white solid (45 mg, 14%). MH+ 519.0

N*3*-[2,6-Dichloro-4'-(2-dimethylamino-ethoxy)-biphenyl-4-yl]-1H-[1,2,4]triazole-3,5-diamine (Compound 269)

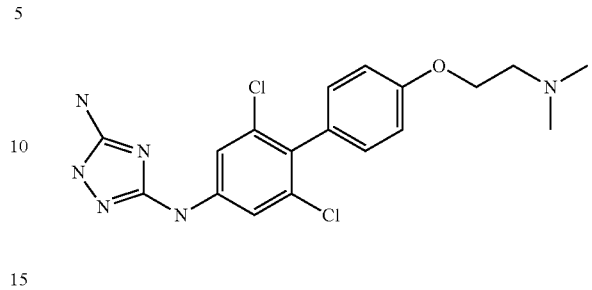

Dimethyl-{2-[4-(4,4,5,5-tetramethyl-[1,3,2]dioxaborolan-2-yl)-phenoxy]-ethyl}-amine

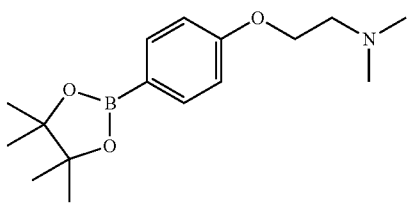

In a 100 mL round-bottomed flask, triphenylphosphine (1.25 g, 4.77 mmol, Eq: 1.05), tert-butyl 4-hydroxypiperidine-1-carboxylate (405 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.19 g (14%) oil. MH+ 292.1

N*3*-[2,6-Dichloro-4'-(2-dimethylamino-ethoxy)-biphenyl-4-yl]-1H-[1,2,4]triazole-3,5-diamine (Compound 269)

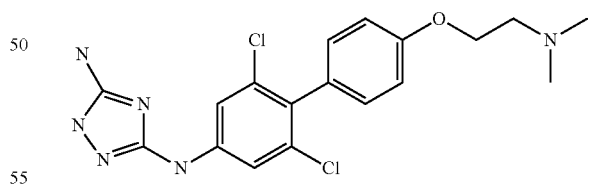

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and N,N-dimethyl-2-(4-(4,4,5,5-tetramethyl-1,3,2-dioxaborolan-2-yl)phenoxy) ethanamine (180 mg, 619 µmol, Eq: 1.00), were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH$_2$Cl$_2$/MeOH=95/5) to give an off-white solid (12.8 mg, 5%). MH+ 406.9

N*3*-[6-Chloro-4'-((S)-1-pyrrolidin-2-ylmethoxy)-2-trifluoromethyl-biphenyl-4-yl]-1H-[1,2,4]triazole-3,5-diamine (Compound 270)

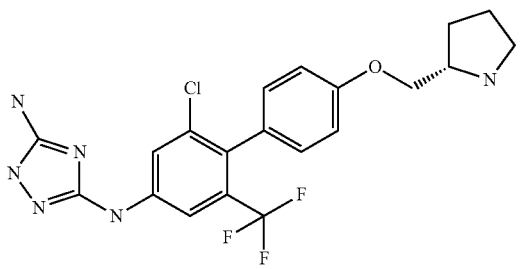 [SMILES: Nc1nc(Nc2cc(Cl)c(-c3ccc(OC[C@@H]4CCCN4)cc3)c(C(F)(F)F)c2)n[nH]1]

In a 25 mL round bottle, (S)-tert-butyl 2-((4'-(5-amino-1H-1,2,4-triazol-3-ylamino)-2',6'-dichlorobiphenyl-4-yloxy)methyl)pyrrolidine-1-carboxylate (73 mg, 132 µmol) combined with CH2Cl2 (10.0 ml) to give a light yellow solution, TFA (1 mL) was added. Let the reaction stirred for 1 hour, concentrate the solution, added CH2Cl2 (50 mL), washed with saturated NaHCO3, filter out the solid to afford the product 50 mg (84%), MH+ 453.0.

N*3*-[2,6-Dichloro-4'-((S)-pyrrolidin-3-yloxy)-biphenyl-4-yl]-1H-[1,2,4]triazole-3,5-diamine, HCl salt (Compound 271)

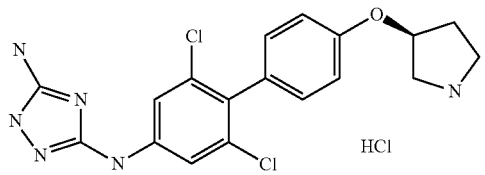 [SMILES: Nc1nc(Nc2cc(Cl)c(-c3ccc(O[C@H]4CCNC4)cc3)c(Cl)c2)n[nH]1 ; Cl]

In a 25 mL round bottle, 1 mL acetyl chloride was added to 10 mL MeOH at room temperature, cool down the solution to RT, (S)-tert-butyl 3-(4'-(5-amino-1H-1,2,4-triazol-3-ylamino)-2',6'dichlorobiphenyl-4-yloxy)pyrrolidine-1-carboxylate (45 mg, 89 µmol), the reaction was allowed to stir at room temperature for 2 hours, filter out the solid to afford the product 15 mg (38%), MH+ 404.9.

N*3*-[2,6-Dichloro-4'-((R)-1-pyrrolidin-2-ylmethoxy)-biphenyl-4-yl]-1H-[1,2,4]triazole-3,5-diamine (Compound 272)

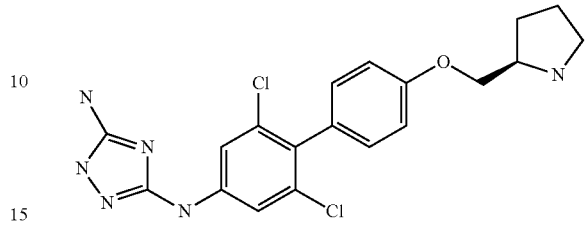

In a 25 mL round bottle, (R)-tert-butyl 2-((4'-(5-amino-1H-1,2,4-triazol-3-ylamino) dichlorobiphenyl-4-yloxy)methyl)pyrrolidine-1-carboxylate (70 mg, 135 µmol) combined with CH2Cl2 (10.0 ml) to give a light yellow solution, TEA (1 mL) was added. Let the reaction stirred for 1 hour, concentrate the solution, added CH2Cl2 (50 mL), washed with saturated NaHCO3, filter out the solid to afford the product 33 mg (58%), MH+ 418.9.

(S)-3-[4'-(5-Amino-1H-[1,2,4]triazol-3-ylamino)-2',6'-dichloro-biphenyl-4-yloxy]-pyrrolidine-1-carboxylic acid tert-butyl ester (Compound 273)

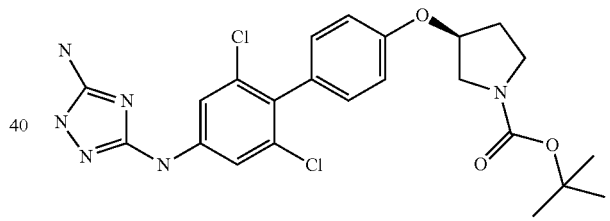

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and (S)-tert-butyl 3-(4-(4,4,5,5-tetramethyl-1,3,2-dioxaborolan-2-yl)phenoxy)pyrrolidine-1-carboxylate (241 mg, 619 µmol, Eq: 1.00) were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH$_2$Cl$_2$/MeOH=95/5) to give an off-white solid (53 mg, 16.9%).

N*3*-[2,6-Dichloro-4'-(2,2-dimethyl-[1,3]dioxolan-4-ylmethoxy)-biphenyl-4-yl]-1H-[1,2,4]triazole-3,5-diamine (Compound 274)

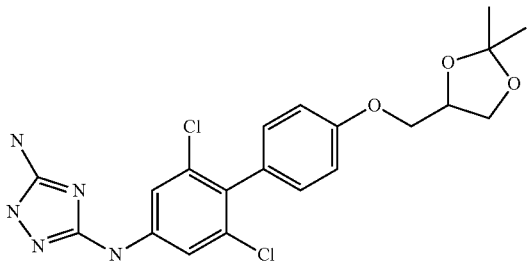 [SMILES: CC1(C)OCC(COc2ccc(-c3c(Cl)cc(Nc4n[nH]c(N)n4)cc3Cl)cc2)O1]

2-[4-(2,2-Dimethyl-[1,3]dioxolan-4-ylmethoxy)-phenyl]-4,4,5,5-tetramethyl-[1,3,2]dioxaborolane

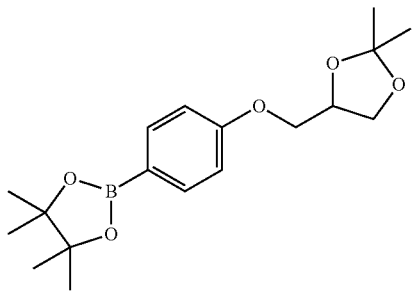

In a 100 mL round-bottomed flask, triphenylphosphine (2.5 g, 9.54 mmol, Eq: 1.05), (2,2-dimethyl-1,3-dioxolan-4-yl)methanol (1.2 g, 9.09 mmol, Eq: 1.00) and 4-(4,4,5,5,-tetramethyl-1,3,2-dioxaborolan-2-yl)phenol (2 g, 9.09 mmol, Eq: 1.00) were combined with THF (25.0 ml) to give a colorless suspension. Cooled the reaction to 0° C., 1,1'-(azodicarbonyl)dipiperidine (2.4 g, 9.54 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 1.4 g (46.1%) oil. MH+ 335.0

N*3*-[2,6-Dichloro-4'-(2,2-dimethyl-[1,3]dioxolan-4-ylmethoxy)-biphenyl-4-yl]-1H-[1,2,4]triazole-3,5-diamine (Compound 274)

In a 15 mL sealed tube, N3-(4-bromo-3,5-dichlorophenyl)-1H-1,2,4-triazole-3,5-diamine Intermediate 2 (500 mg, 1.55 mol, Eq: 1.00), tetrakis(triphenylphosphine)-palladium (0) (179 mg, 155 μmol, Eq: 0.1) and 2-(4-((2,2-dimethyl-1,3-dioxolan-4-yl)methoxy)phenyl)-4,4,5,5-tetramethyl-1,3,2-dioxaborolane (517 mg, 1.55 mmol, Eq: 1.00) were combined with a solution of 1,4-dioxane/H₂O=4/1 (10 ml) to give a light yellow suspension. Potassium carbonate (856 mg, 6.19 mmol, Eq: 4) was added to the suspension. The reaction mixture was degassed with argon for 15 min, and then heated to 140° C. for overnight. The reaction mixture was cooled and diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH₂Cl₂/MeOH=95/5) to give an off-white solid (80 mg, 11.5%). MH+ 449.9

(R)-2-[4'-(5-Amino-1H-[1,2,4]triazol-3-ylamino)-2',6'-dichloro-biphenyl-4-yloxymethyl]-pyrrolidine-1-carboxylic acid tert-butyl ester (Compound 275)

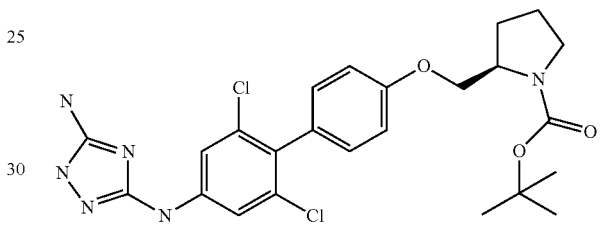

In a 15 mL sealed tube, N3-(4-bromo-3,5-dichlorophenyl)-1H-1,2,4-triazole-3,5-diamine Intermediate 2 (500 mg, 1.55 mmol, Eq: 1.00), tetrakis(triphenylphosphine)-palladium (0) (179 mg, 155 μmol, Eq: 0.1) and (R)-tert-butyl 2-((4-(4,4,5,5-tetramethyl-1,3,2-dioxaborolan-2-yl)phenoxy)methyl)pyrrolidine-1-carboxylate (937 mg, 2.32 mmol, Eq: 1.5), were combined with a solution of 1,4-dioxane/H₂O=4/1 (6.67 ml) to give a light yellow suspension. Potassium carbonate (856 mg, 6.19 mmol, Eq: 4) was added to the suspension. The reaction mixture was degassed with argon for 15 min, and then heated to 140° C. for overnight. The reaction mixture was cooled and diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH₂Cl₂/MeOH=95/5) to give an off-white solid (80 mg, 10%). MH+ 518.9

[4'-(5-Amino-1H-[1,2,4]triazol-3-ylamino)-2',6'-dichloro-biphenyl-4-yloxy]-acetic acid tert-butyl ester (Compound 276)

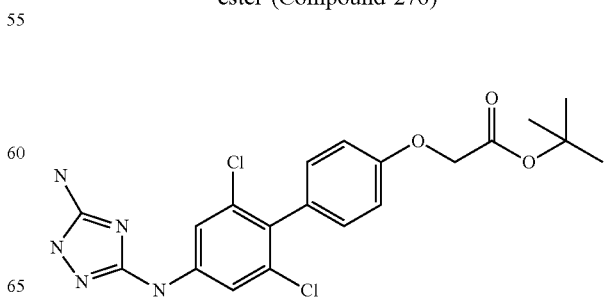

[4-(4,4,5,5-Tetramethyl-[1,3,2]dioxaborolan-2-yl)-phenoxy]-acetic acid tert-butyl ester

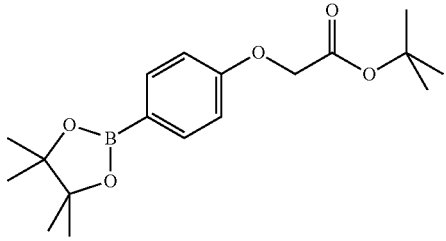 [SMILES: CC(C)(C)OC(=O)COc1ccc(B2OC(C)(C)C(C)(C)O2)cc1]

In a 100 mL round-bottomed flask, cesium carbonate (5.92 g, 18.2 mmol, Eq: 2.00), tert-butyl 2-bromoacetate (2.13 g, 10.9 mmol, Eq: 1.20) and 4-(4,4,5,5-tetramethyl-1,3,2-dioxaborolan-2-yl)phenol (2 g, 9.09 mmol, Eq: 1.00) were combined with DMF (25.0 ml) to give a colorless suspension. Let the reaction stir overnight. Added CH2Cl2 (50 mL), washed with $H_2O$ (30 mL) and Brine (30 mL), dried the organic layer, purify the compound by column (Hexanes/EtOAc=70/30) to afford the product 2.5 g (82%)

[4'-(5-Amino-1H-[1,2,4]triazol-3-ylamino)-2',6'-dichloro-biphenyl-4-yloxy]-acetic acid tert-butyl ester (Compound 276)

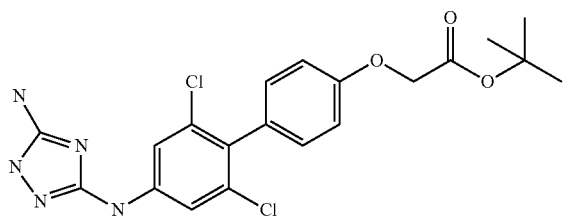 [SMILES: CC(C)(C)OC(=O)COc1ccc(-c2c(Cl)cc(Nc3n[nH]c(N)n3)cc2Cl)cc1]

In a 15 mL sealed tube, N3-(4-bromo-3,5-dichlorophenyl)-1H-1,2,4-triazole-3,5-diamine Intermediate 2 (400 mg, 1.24 mol, Eq: 1.00), tetrakis(triphenylphosphine)-palladium (0) (143 mg, 124 µmol, Eq: 0.1) and tert-butyl 2-(4-(4,4,5,5-tetramethyl-1,3,2-dioxaborolan-2-yl)phenoxy)acetate (828 mg, 2.48 mmol, Eq: 2.00) were combined with a solution of 1,4-dioxane/$H_2O$=4/1 (10 ml) to give a light yellow suspension. Potassium carbonate (685 mg, 4.95 mmol, Eq: 4) was added to the suspension. The reaction mixture was degassed with argon for 15 min, and then heated to 140° C. for overnight. The reaction mixture was cooled and diluted with $CH_2Cl_2$ (50 mL), washed with $H_2O$ (25 mL) and brine (25 mL). The organic layer was dried over anhydrous $MgSO_4$, filtered and volatiles were removed under reduced pressure to yield an oil from which the compound was isolated by column chromatography ($CH_2Cl_2$/MeOH=95/5) to give an off-white solid (90 mg, 16.1%). MH+ 449.8

(S)-2-[4'-(5-Amino-M-[1,2,4]triazol-3-ylamino)-2'-chloro-6'-trifluoromethyl-biphenyl-4-yloxymethyl]-pyrrolidine-1-carboxylic acid tert-butyl ester (Compound 277)

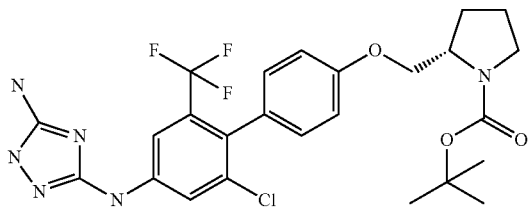 [SMILES: CC(C)(C)OC(=O)N1CCC[C@H]1COc1ccc(-c2c(Cl)cc(Nc3n[nH]c(N)n3)cc2C(F)(F)F)cc1]

(S)-2-[4-(4,4,5,5-Tetramethyl-[1,3,2]dioxaborolan-2-yl)-phenoxymethyl]-pyrrolidine-1-carboxylic acid tert-butyl ester

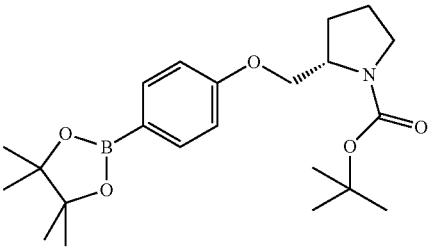 [SMILES: CC(C)(C)OC(=O)N1CCC[C@H]1COc1ccc(B2OC(C)(C)C(C)(C)O2)cc1]

In a 100 mL round-bottomed flask, triphenylphosphine (1.57 g, 6.00 mmol, Eq: 1.05), (R)-tert-butyl 2-(hydroxymethyl)pyrrolidine-1-carboxylate (1.15 g, 5.71 mmol, Eq: 1.00) and 4-(4,4,5,5,-tetramethyl-1,3,2-dioxaborolan-2-yl)phenol (1.26 g, 5.71 mmol, Eq: 1.00) were combined with THF (25.0 ml) to give a colorless suspension. Cooled the reaction to 0° C., 1,1'-(azodicarbonyl)dipiperidine (1.51 g, 6.00 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 1.4 g (60%) oil.

(S)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester (Compound 277)

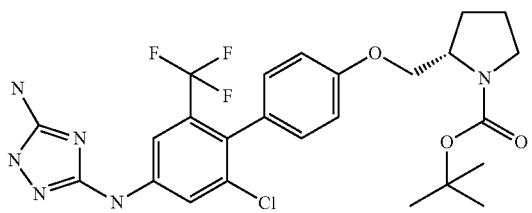 [SMILES: CC(C)(C)OC(=O)N1CCC[C@H]1COc1ccc(-c2c(Cl)cc(Nc3n[nH]c(N)n3)cc2C(F)(F)F)cc1]

In a 15 mL sealed tube, N3-(4-bromo-3-chloro-5-(trifluoromethyl)phenyl)-1H-1,2,4-triazole-3,5-diamine Intermediate 1 (300 mg, 841 µmol, Eq: 1.00), tetrakis(triphenylphosphine)-palladium (0) (97.2 mg, 84.1 µmol, Eq: 0.1) and (S)-tert-butyl 2-((4-(4,4,5,5-tetramethyl-1,3,2-dioxaborolan-2-yl)phenoxy)methyl)pyrrolidine-1-carboxylate (407 mg, 1.01 mmol, Eq: 1.2), were combined with a solution of 1,4-dioxane/H₂O=4/1 (6.67 ml) to give a light yellow suspension. Potassium carbonate (465 mg, 3.37 mmol, Eq: 4) was added to the suspension. The reaction mixture was degassed with argon for 15 min, and then heated to 140° C. for overnight. The reaction mixture was cooled and diluted with CH2Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH₂Cl₂/MeOH=95/5) to give an off-white solid (80 mg, 17.2%). MH+553.1

N*3*-[2,6-Dichloro-4'-(2-methoxy-ethoxy)-biphenyl-4-yl]-1H-[1,2,4]triazole-3,5-diamine (Compound 278)

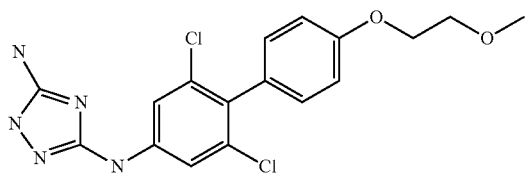 [SMILES: COCCOc1ccc(-c2c(Cl)cc(Nc3n[nH]c(N)n3)cc2Cl)cc1]

In a 15 mL sealed tube, N3-(4-bromo-3,5-dichlorophenyl)-1H-1,2,4-triazole-3,5-diamine Intermediate 2 (200 mg, 619 μmol, Eq: 1.00), tetrakis(triphenylphosphine)-palladium (0) (71.6 mg, 61.9 μmol, Eq: 0.1) and 2-(4-(2-methoxy-ethoxyl)phenyl)-4,4,5,5-tetramethyl-1,3,2-dioxaborolane (172 mg, 619 μmol, Eq: 1.00), were combined with a solution of 1,4-dioxane/H₂O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH2Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH₂Cl₂/MeOH=95/5) to give an off-white solid (30 mg, 12.3%). MH+ 393.9

2-[4-(2-Methoxy-ethoxy)-phenyl]-4,4,5,5-tetramethyl-[1,3,2]dioxaborolane

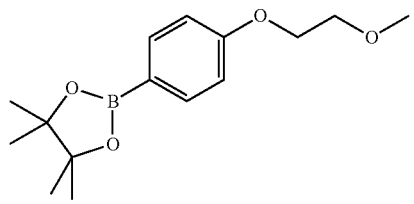

In a 100 mL round-bottomed flask, triphenylphosphine (1.25 g, 4.77 mmol, Eq: 1.05), 2-methoxyethanol (346 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.60 g (48%) oil.

N*3*-[2,6-Dichloro-4'-(2-methoxy-ethoxy)-biphenyl-4-yl]-1H-[1,2,4]triazole-3,5-diamine (Compound 278)

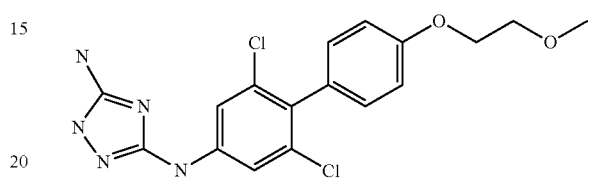

In a 15 mL sealed tube, N3-(4-bromo-3,5-dichlorophenyl)-1H-1,2,4-triazole-3,5-diamine Intermediate 2 (200 mg, 619 μmol, Eq: 1.00), tetrakis(triphenylphosphine)-palladium (0) (71.6 mg, 61.9 μmol, Eq: 0.1) and 2-(4-(2-methoxy-ethoxyl)phenyl)-4,4,5,5-tetramethyl-1,3,2-dioxaborolane (172 mg, 619 μmol, Eq: 1.00), were combined with a solution of 1,4-dioxane/H₂O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH2Cl₂/MeOH=95/5) to give an off-white solid (30 mg, 12.3%). MH+ 393.9

N*3*-[6-Chloro-4'-(pyrrolidin-2-ylmethoxy)-2-trifluoromethyl-biphenyl-4-yl]-1H-[1,2,4]triazole-3,5-diamine, HCl salt (Compound 279)

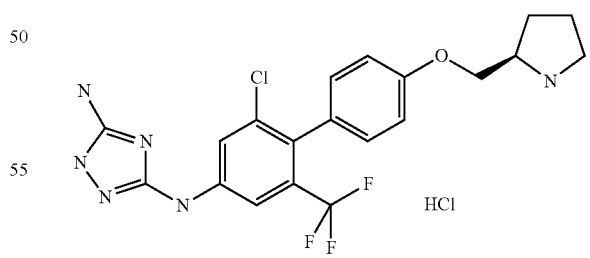

In a 25 mL round bottle, 1 mL acetyl chloride was added to 10 mL MeOH at room temperature, cool down the solution to RT, added to tert-butyl 4-(4'-(5-amino-1H-1,2,4-triazol-3-ylamino)-2',6'-dichlorobiphenyl-4-yloxy)piperidine-1-carboxylate (40 mg, 77.0 μmol), the reaction was allowed to stir at room temperature for 2 hours, filter out the solid to afford the product 17 mg (60%), MH+ 452.9.

(S)-2-[4'-(5-Amino-1H-[1,2,4]triazol-3-ylamino)-2',
6'-dichloro-biphenyl-4-yloxymethyl]-pyrrolidine-1-
carboxylic acid tert-butyl ester (Compound 280)

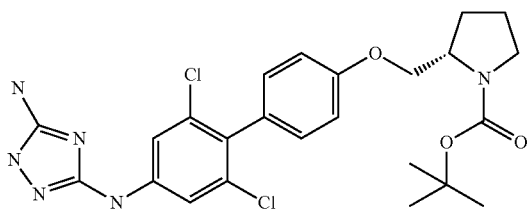 [SMILES: CC(C)(C)OC(=O)N1CCC[C@H]1COc1ccc(-c2c(Cl)cc(Nc3n[nH]c(N)n3)cc2Cl)cc1]

(S)-2-[4-(4,4,5,5-Tetramethyl-[1,3,2]dioxaborolan-2-
yl)-phenoxymethyl]-pyrrolidine-1-carboxylic acid
tert-butyl ester

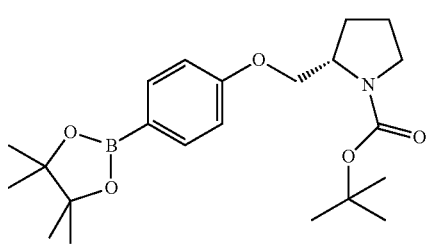 [SMILES: CC(C)(C)OC(=O)N1CCC[C@H]1COc1ccc(B2OC(C)(C)C(C)(C)O2)cc1]

In a 100 mL round-bottomed flask, triphenylphosphine (1.25 g, 4.77 mmol, Eq: 1.05), N-boc-L-prolinol (915 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.84 g (46%) oil.

(S)-2-[4'-(5-Amino-M-[1,2,4]triazol-3-ylamino)-2',
6'-dichloro-biphenyl-4-yloxymethyl]-pyrrolidine-1-
carboxylic acid tert-butyl ester (Compound 280)

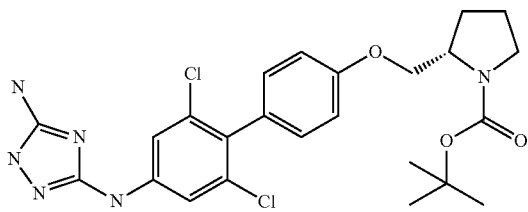 [SMILES: CC(C)(C)OC(=O)N1CCC[C@H]1COc1ccc(-c2c(Cl)cc(Nc3n[nH]c(N)n3)cc2Cl)cc1]

In a 15 mL sealed tube, N3-(4-bromo-3,5-dichlorophenyl)-1H-1,2,4-triazole-3,5-diamine Intermediate 2 (200 mg, 619 μmol, Eq: 1.00), tetrakis(triphenylphosphine)-palladium (0) (71.6 mg, 61.9 mol, Eq: 0.1) and (S)-tert-butyl 2-((4-(4,4,5,5-tetramethyl-1,3,2-dioxaborolan-2-yl)phenoxy)methyl) pyrrolidine-1-carboxylate (375 mg, 929 mol, Eq: 1.50), were combined with a solution of 1,4-dioxane/H₂O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH₂Cl₂ (50 mL), washed with H₂O (25 mL) and brine (25 mL). The organic layer was dried over anhydrous MgSO₄, filtered and volatiles were removed under reduced pressure to yield an oil from which the compound was isolated by column chromatography (CH₂Cl₂/MeOH=95/5) to give an off-white solid (16 mg, 5%). MH+ 519.0

N*3*-[2,6-Dichloro-4'-(2-morpholin-4-yl-ethoxy)-
biphenyl-4-yl]-1H-[1,2,4]triazole-3,5-diamine
(Compound 281)

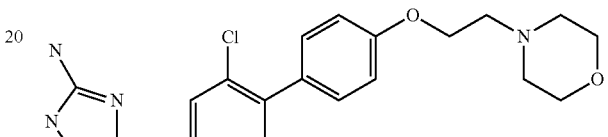

4-{2-[4-(4,4,5,5-Tetramethyl-[1,3,2]dioxaborolan-2-
yl)-phenoxy]-ethyl}-morpholine

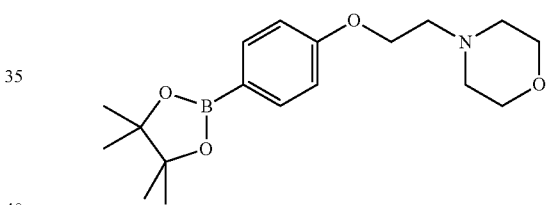

In a 100 mL round-bottomed flask, triphenylphosphine (1.25 g, 4.77 mmol, Eq: 1.05), 2-morpholinoethanol (596 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.80 g (53%) oil.

N*3*-[2,6-Dichloro-4'-(2-morpholin-4-yl-ethoxy)-
biphenyl-4-yl]-1H-[1,2,4]triazole-3,5-diamine
(Compound 281)

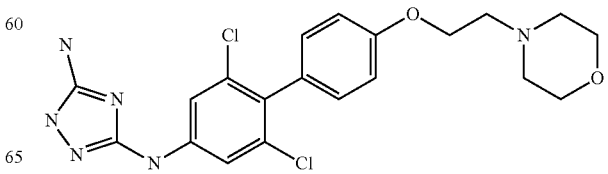

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and 4-(2-(4-(4,4,5,5-tetramethyl-1,3,2-dioxaborolan-2-yl)phenoxy)ethyl)morpholine (248 mg, 743 µmol, Eq: 1.20), were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH$_2$Cl$_2$/MeOH=95/5) to give an off-white solid (18 mg, 6.5%). MH+ 448.9

3-[4'-(5-Amino-1H-[1,2,4]triazol-3-ylamino)-2',6'-dichloro-biphenyl-4-yloxy]-propane-1,2-diol-diamine (Compound 282)

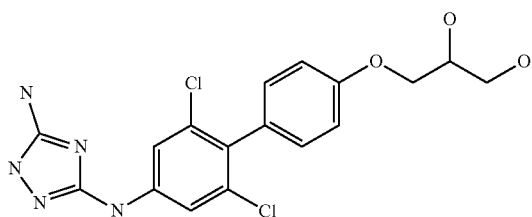 [SMILES: Nc1nc(Nc2cc(Cl)c(-c3ccc(OCC(O)CO)cc3)c(Cl)c2)n[nH]1]

In a 25 mL round bottle, Compound 274 N3-(2,6-dichloro-4'-((2,2-dimethyl-1,3-dioxolan-4-yl)methoxy)biphenyl-4-yl)-1H-1,2,4-triazole-3,5-diamine (70 mg, 155 µmol) combined with CH2Cl2 (10.0 ml) to give a light yellow solution, TFA (1 mL) was added. Let the reaction stirred for 1 hour, concentrate the solution, added CH2Cl2 (50 mL), washed with saturated NaHCO3, filter out the solid to afford the product 54 mg (85%), MH+ 411.7.

N*3*-[2,6-Dichloro-4'-(3-morpholin-4-yl-propoxy)-biphenyl-4-yl]-1H-[1,2,4]triazole-3,5-diamine (Compound 283)

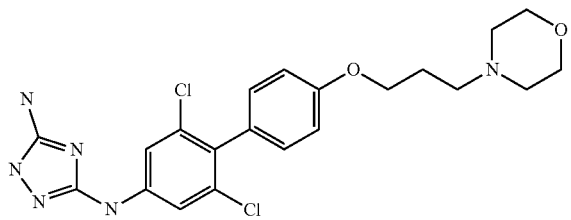 [SMILES: Nc1nc(Nc2cc(Cl)c(-c3ccc(OCCCN4CCOCC4)cc3)c(Cl)c2)n[nH]1]

4-{3-[4-(4,4,5,5-Tetramethyl-[1,3,2]dioxaborolan-2-yl)-phenoxy]-propyl}-morpholine

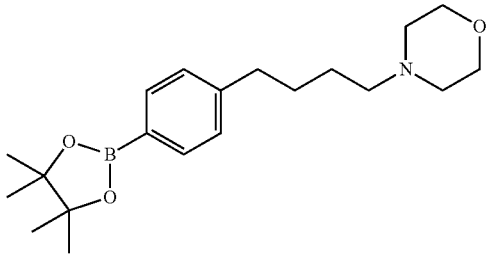 [SMILES: CC1(C)OB(c2ccc(CCCCN3CCOCC3)cc2)OC1(C)C]

In a 100 mL round-bottomed flask, triphenylphosphine (1.25 g, 4.77 mmol, Eq: 1.05), 3-morpholinopropan-1-ol (596 mg, 4.54 mmol, Eq: 1.00) and 4-(4,4,5,5,-tetramethyl-1,3,2-dioxaborolan-2-yl)phenol (1 g, 4.54 mmol, Eq: 1.00) were combined with THF (25.0 ml) to give a colorless suspension. Cooled the reaction to 0° C., 1,1'-(azodicarbonyl)dipiperidine (1.2 g, 4.77 mmol, Eq: 1.05) in THF (5 mL) was added. The reaction mixture was slowly raised to room temperature and stirred overnight, concentrate the solution. The compound was purified by column chromatography (Hexanes/EtOAc=70/30) to give 0.90 g (57%) oil. MH+ 348.1

N*3*-[2,6-Dichloro-4'-(3-morpholin-4-yl-propoxy)-biphenyl-4-yl]-1H-[1,2,4]triazole-3,5-diamine (Compound 283)

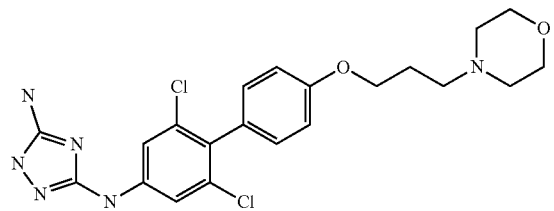 [SMILES: Nc1nc(Nc2cc(Cl)c(-c3ccc(OCCCN4CCOCC4)cc3)c(Cl)c2)n[nH]1]

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and 4-(3-(4-(4,4,5,5-tetramethyl-1,3,2-dioxaborolan-2-yl)phenoxy)propyl)morpholine (215 mg, 619 µmol, Eq: 1.00), were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH$_2$Cl$_2$/MeOH=95/5) to give an off-white solid 73 mg, (26%). MH+ 462.8

N*3*-[2,6-Dichloro-4'-(pyridin-2-ylmethoxy)-biphenyl-4-yl]-1H-[1,2,4]triazole-3,5-diamine (Compound 284)

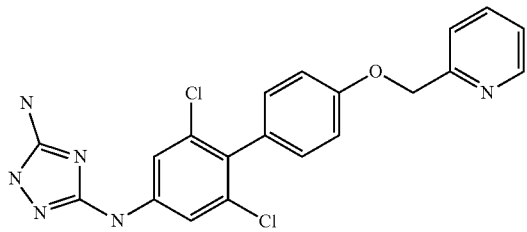 [SMILES: Nc1nc(Nc2cc(Cl)c(-c3ccc(OCc4ccccn4)cc3)c(Cl)c2)n[nH]1]

2-[4-(4,4,5,5-Tetramethyl-[1,3,2]dioxaborolan-2-yl)-phenoxymethyl]-pyridine

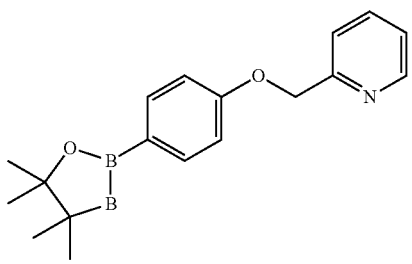

In a 50 mL round-bottomed flask, cesium carbonate (2.96 g, 9.09 mmol, Eq: 2.00), 4-(4,4,5,5-TETRAMETHYL-1,3,2-DIOXABOROLAN-2-YL)PHENOL (1 g, 4.54 mmol, Eq: 1.00) and 2-(bromomethyl)pyridine hydrobromide (1.15 g, 4.54 mmol, Eq: 1.00) were combined with DMF (20 mL) to give a light yellow suspension. Let the reaction stir at rt overnight, concentrate the solution. Purify the compound by column (Hexanes/EtOAc=70/30) to afford the product 1.15 g (81%) MH+ 312.0

N*3*-[2,6-Dichloro-4'-(pyridin-2-ylmethoxy)-biphenyl-4-yl]-1H-[1,2,4]triazole-3,5-diamine (Compound 284)

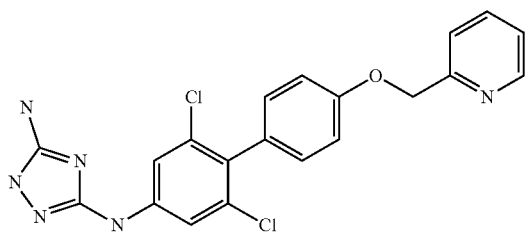 [SMILES: Nc1nc(Nc2cc(Cl)c(-c3ccc(OCc4ccccn4)cc3)c(Cl)c2)n[nH]1]

In a 15 mL sealed tube, N3-(4-bromo-3,5-dichlorophenyl)-1H-1,2,4-triazole-3,5-diamine Intermediate 2 (200 mg, 619 µmol, Eq: 1.00), tetrakis(triphenylphosphine)-palladium (0) (71.6 mg, 61.9 µmol, Eq: 0.1) and 2-((4-(4,4,5,5-tetramethyl-1,3,2-dioxaborolan-2-yl)phenoxy)methyl)pyridine (289 mg, 929 µmol, Eq: 1.50), were combined with a solution of 1,4-dioxane/H$_2$O=4/1 (6.67 ml) to give a light yellow suspension. Potassium carbonate (342 mg, 2.48 mmol, Eq: 4) was added to the suspension. The reaction mixture was degassed with argon for 15 min, and then heated to 140° C. for overnight. The reaction mixture was cooled and diluted with CH$_2$Cl$_2$ (50 mL), washed with H$_2$O (25 mL) and brine (25 mL). The organic layer was dried over anhydrous MgSO$_4$, filtered and volatiles were removed under reduced pressure to yield an oil from which the compound was isolated by column chromatography (CH$_2$Cl$_2$/MeOH=95/5) to give an off-white solid 21 mg, (8%). MH+ 426.9

[4'-(5-Amino-1H-[1,2,4]triazol-3-ylamino)-2',6'-dichloro-biphenyl-4-yloxy]-acetic acid (Compound 285)

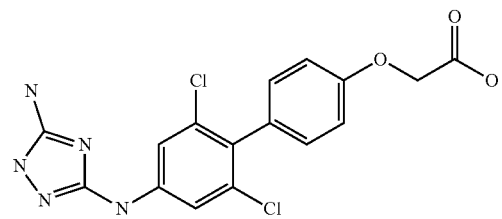 [SMILES: Nc1nc(Nc2cc(Cl)c(-c3ccc(OCC(=O)O)cc3)c(Cl)c2)n[nH]1]

In a 25 mL round bottle, Compound 276 tert-butyl 2-(4'-(5-amino-1H-1,2,4-triazol-3-ylamino)-2',6'-dichlorobiphenyl-4-yloxy)acetate (40 mg, 89 µmol) combined with CH2Cl2 (10.0 ml) to give a light yellow solution, TFA (1 mL) was added. Let the reaction stirred for 1 hour, concentrate the solution, added CH2Cl2 (50 mL), washed with saturated NaHCO3, filter out the solid to afford the product 12 mg (33%), MH+ 393.8.

N3-(2,6-dichloro-4'-fluorobiphenyl-4-yl)-1H-1,2,4-triazole-3,5-diamine (Compound 286)

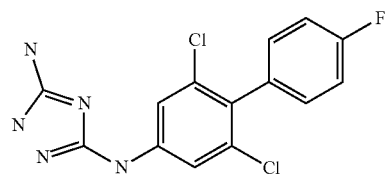 [SMILES: N=C(N=C(N)N)Nc1cc(Cl)c(-c2ccc(F)cc2)c(Cl)c1]

2,6-Dichloro-4'-fluoro-4-nitro-biphenyl

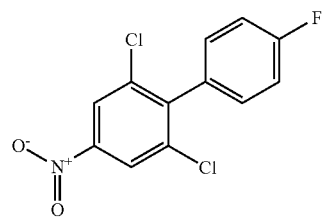 [SMILES: O=[N+]([O-])c1cc(Cl)c(-c2ccc(F)cc2)c(Cl)c1]

A solution of 1,3-dichloro-2-iodo-5-nitrobenzene (500 mg, 1.57 mmol, Eq: 1.00), 4-fluorophenylboronic acid (330 mg, 2.36 mmol, Eq: 1.5), sodium carbonate (420 mg, 3.96 mmol, Eq: 2.52) and bis(triphenylphosphine)palladium (II)

chloride (112 mg, 159 µmol, Eq: 0.101) in methanol (2 mL) and dichloromethane (0.5 mL) were placed in a microwave vial and heated 110 for 30 min. The reaction was concentrated, diluted with ethyl acetate, washed with brine and dried over sodium sulfate. The crude residue was chromatographed (60 g Analogix, 100% hex to 5% EtOAc/hex) to give 266 mg (59%) of desired product as a white solid.

2,6-Dichloro-4'-fluoro-biphenyl-4-ylamine

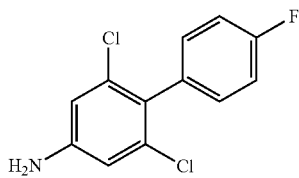 [SMILES: Nc1cc(Cl)c(-c2ccc(F)cc2)c(Cl)c1]

A solution of 2,6-dichloro-4'-fluoro-4-nitrobiphenyl (647 mg, 2.26 mmol, Eq: 1.00), iron (631 mg, 11.3 mmol, Eq: 5) and ammonium chloride (1.21 g, 22.6 mmol, Eq: 10) in methanol (10 mL)/water (5 mL) was heated at 50° o/n. The reaction was filtered over Celite and washed with methanol and ethyl acetate. The solution was concentrated and partitioned with ethyl acetate. The organic extract was washed with water and dried over sodium sulfate to give 579 mg (100%) of desired product as a pale yellow gummy oil.

2,6-Dichloro-4'-fluoro-4-isothiocyanato-biphenyl

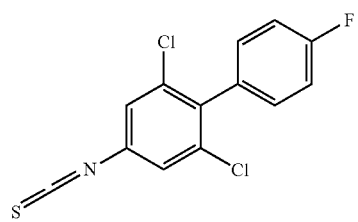

To a solution of 2,6-dichloro-4'-fluorobiphenyl-4-amine (421 mg, 1.64 mmol, Eq: 1.00) in DCM at 0° C., was added di(1H-imidazol-1-yl)methanethione (352 mg, 1.97 mmol, Eq: 1.2). The reaction mixture was gradually warmed to room temperature overnight. The reaction was concentrated and chromatographed (40 g Analogix, 100% hex) to give 307 mg (63%) of desired product as a colorless oil.

(Z)-methyl N'-cyano-N-(2,6-dichloro-4'-fluorobiphenyl-4-yl)carbamimidothioate

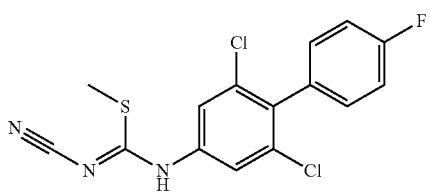 [SMILES: CS/C(=N\C#N)Nc1cc(Cl)c(-c2ccc(F)cc2)c(Cl)c1]

Sodium methoxide (0.5M in methanol) (2.6 mL, 1.3 mmol, Eq 1.21) was added to cyanamide (50 mg, 1.19 mmol, Eq: 1.16). After 15 minutes, the solution was added to a solution 2,6-dichloro-4'-fluoro-4-isothiocyanatobiphenyl (307 mg, 1.03 mmol, Eq: 1.00) in methanol (5 mL). After 1 hr, methyl iodide (295 mg, 130 µl, 2.08 mmol, Eq: 2.02) was added and the reaction was stirred overnight at room temperature to give a white precipitate. The precipitate was filtered and the solid was absorbed onto silica gel and purified (24 g Analogix, 100% hex to 5% EtOAc/hex) to give 225 mg (62%) of desired product as a yellow solid.

N3-(2,6-dichloro-4'-fluorobiphenyl-4-yl)-1H-1,2,4-triazole-3,5-diamine (Compound 286)

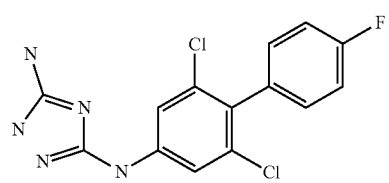 [SMILES: N=C(N=C(N)N)Nc1cc(Cl)c(-c2ccc(F)cc2)c(Cl)c1]

A solution of (Z)-methyl N'-cyano-N-(2,6-dichloro-4'-fluorobiphenyl-4-yl)carbamimidothioate (220 mg, 621 µmol, Eq: 1.00) and hydrazine (204 mg, 200 µl, 6.37 mmol, Eq: 10.3) in dry ethanol (6 ml) was stirred overnight at 70° C.

The reaction mixture was purified on silicagel (column 12 g, dichloromethane/methanol 100:0 to 80:20). One fraction was isolated and dried in vacuo to afford 190 mg (77%) of the desired product as a foam containing 15% w/w of ethyl acetate.

MS +m/z: 338.0 (M+H)$^+$

N3-(2,6-dichloro-2'-fluorobiphenyl-4-yl)-1H-1,2,4-triazole-3,5-diamine (Compound 287)

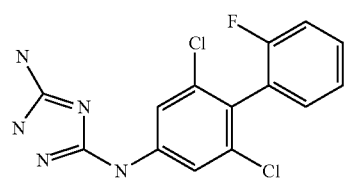

2,6-Dichloro-2'-fluoro-4-nitro-biphenyl

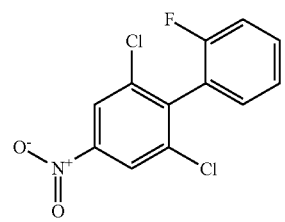 [SMILES: O=[N+]([O-])c1cc(Cl)c(-c2ccccc2F)c(Cl)c1]

A solution of 1,3-dichloro-2-iodo-5-nitrobenzene (800 mg, 2.52 mmol, Eq: 1.00), 2-fluorophenylboronic acid (528 mg, 3.77 mmol, Eq: 1.5), sodium carbonate (672 mg, 6.34 mmol, Eq: 2.52) and bis(triphenylphosphine)palladium (II) chloride (179 mg, 255 µmol, Eq: 0.101) in methanol (4 mL)

and dichloromethane (1 mL) were placed in a microwave vial and heated 110 for 30 min. The reaction was concentrated, diluted with ethyl acetate, washed with brine and dried over sodium sulfate. The crude residue was chromatographed (60 g Analogix, 100% hex to 5% EtOAc/hex) to give 575 mg (80%) of desired product as a colorless oil.

2,6-Dichloro-2'-fluoro-biphenyl-4-ylamine

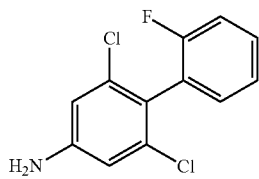 [SMILES: Nc1cc(Cl)c(-c2ccccc2F)c(Cl)c1]

A solution of 2,6-dichloro-2'-fluoro-4-nitrobiphenyl (575 mg, 2.01 mmol, Eq: 1.00), iron (565 mg, 10.1 mmol, Eq: 5.03) and ammonium chloride (1.085 g, 20.3 mmol, Eq: 10.1) in methanol/water was heated at 50° o/n. The reaction was filtered over Celite and was with methanol and ethyl acetate. The solution was concentrated and partitioned with ethyl acetate. The organic extract was washed with water and dried over sodium sulfate. The crude residue was chromatographed (40 g Analogix, 10 to 20% EtOAc/hex) to give 201 mg (39%) of desired product as a purple oil.

2,6-Dichloro-2'-fluoro-4-isothiocyanato-biphenyl

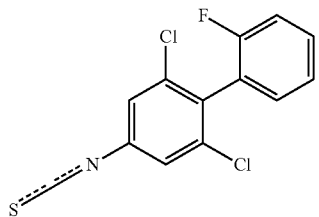

To a solution of 2,6-dichloro-2'-fluorobiphenyl-4-amine (201 mg, 785 µmol, Eq: 1.00) in DCM at 0° C., was added di(1H-imidazol-1-yl)methanethione (168 mg, 942 µmol, Eq: 1.2). The reaction mixture was gradually warmed to room temperature overnight. The reaction was concentrated and chromatographed (24 g Analogix, 100% hex) to give 179 mg (77%) off-white solid.

(Z)-methyl N'-cyano-N-(2,6-dichloro-2'-fluorobiphenyl-4-yl)carbamimidothioate

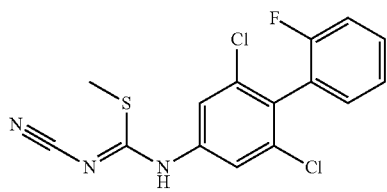 [SMILES: CS/C(=N\C#N)Nc1cc(Cl)c(-c2ccccc2F)c(Cl)c1]

Sodium methoxide (0.5M in methanol) (1.5 ml, 750 µmol, Eq: 1.25) was added to cyanamide (30 mg, 714 µmol, Eq: 1.19). After 15 minutes, the solution was added to a solution of 2,6-dichloro-2'-fluoro-4-isothiocyanatobiphenyl (179 mg, 600 µmol, Eq: 1.00) in methanol (5 mL). After 1 hr, methyl iodide (182 mg, 80 µl, 1.28 mmol, Eq: 2.13) was added and the reaction was stirred overnight at room temperature. The yellow solution was absorbed onto silica gel and purified (12 g Analogix, 85% hex to 45% EtOAc/hex) to give 50 mg (26%) of desired product as a white solid.

N3-(2,6-dichloro-2'-fluorobiphenyl-4-yl)-1H-1,2,4-triazole-3,5-diamine (Compound 287)

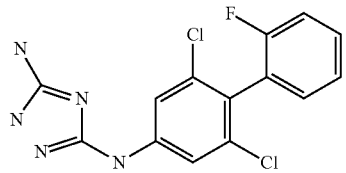 [SMILES: N=C(N=C(N)N)Nc1cc(Cl)c(-c2ccccc2F)c(Cl)c1]

A solution of (Z)-methyl N'-cyano-N-(2,6-dichloro-2'-fluorobiphenyl-4-yl)carbamimidothioate (50 mg, 141 µmol, Eq: 1.00) and hydrazine (51 mg, 50 µl, 1.59 mmol, Eq: 11.3) in dry ethanol (2 ml) was stirred overnight at 70° C. The reaction mixture was purified on silicagel (column 4 g, dichloromethane/methanol 100:0 to 80:20). One fraction was isolated and dried in vacuo to afford 40 mg (72%) of the desired product as a white solid containing 14% w/w of ethyl acetate.

MS +m/z: 338.0 (M+H)$^+$

N*3*-(4'-Methanesulfonyl-2-pentafluorosulfur-biphenyl-4-yl)-1H-[1,2,4]triazole-3,5-diamine (Compound 288)

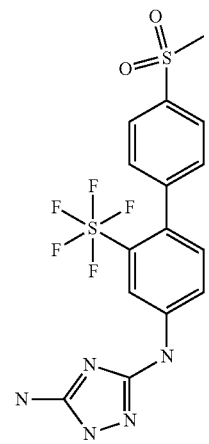

3-pentafluorosulfur-4-bromo-aniline

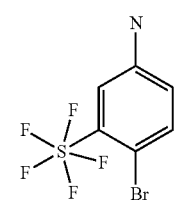

To a mixture of 3-pentafluorosulfuraniline (0.3 g, 1.37 mmol, Eq: 1.00) in dimethyl sulfoxide (3.5 ml) was added N-bromosuccinimide (270 mg, 1.52 mmol, Eq: 1.11) in 3 portions over 3 h. After 1 h, the reaction mixture was partitioned between 10% aqueous sodium sulfite and ethyl acetate. The organic layer was washed with aqueous sat. sodium hydrogenocarbonate, water (3 times) and brine then adsorbed unto silica (1.8 g) and purified on silicagel (column 25 g, Hexane/ethyl acetate 95:5 to 60:40). One fraction was isolated and dried in vacuo to afford 209 mg (51%) of the desired product as a yellow oil.

3-pentafluorsulfur-4-bromo-isothiocyanatobenzene

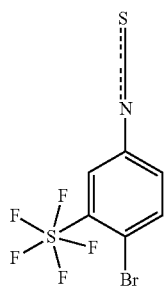

To a cold (0° C.) suspension of 3-pentafluorosulfur-4-bromo-aniline (260 mg, 872 µmol, Eq: 1.00) and calcium carbonate (175 mg, 1.74 mmol, Eq: 2) in water (2 ml) and dichloromethane (2.00 ml) was added thiophosgene (110 mg, 73.3 µl, 960 µmol, Eq: 1.1).

The reaction mixture was allowed to warm to room temperature and was vigorously stirred for 24 h.

1N HCl (2.0 mL) was added to adjust the pH to ca. 3 and the reaction mixture was partitioned between water and ethyl acetate. The organic layer was washed with water and brine, adsorbed unto silica (0.8 g), and purified on silicagel (column 11 g, Hexane/ethyl acetate 1:0 to 85:15).

One fraction was isolated and dried in vacuo to afford 276 mg (93%) of the desired product as a colorless oil.

(Z)-methyl N-3-pentafluorosulphur-4-bromo-phenyl-N'-cyanocarbamimidothioate

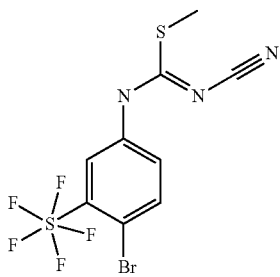 [SMILES: CS/C(=N\C#N)Nc1ccc(Br)c(S(F)(F)(F)(F)F)c1]

To a solution of 3-pentafluorsulfur-4-bromo-isothiocyanatobenzene (270 mg, 794 µmol, Eq: 1.00) in dry methanol (3 ml) was added sodium hydrogencyanamide (53.4 mg, 834 µmol, Eq: 1.05). The light yellow reaction solution was stirred 1 h at room temperature then iodomethane (225 mg, 110 µl, 1.59 mmol, Eq: 2) was added and the reaction mixture was stirred overnight at room temperature.

The clear reaction mixture was adsorbed unto silica (0.8 g) and purified on silica gel (silica 11 g, dichloromethane/ethyl acetate 100:0 to 85:15). One Fraction was isolated and dried in vacuo to afford 207 mg (66%) of the desired product as a white solid.

N*3*-(4-Bromo-3-pentafluorosulfur-phenyl)-1H-[1,2,4]triazole-3,5-diamine

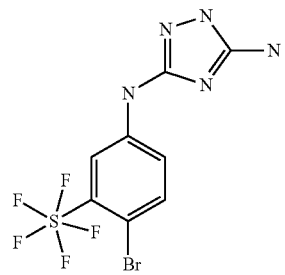 [SMILES: Nc1nc(Nc2ccc(Br)c(S(F)(F)(F)(F)F)c2)n[nH]1]

A solution of (Z)-methyl N-3-pentafluorosulphur-4-bromo-phenyl-N'-cyanocarbamimidothioate (205 mg, 517 µmol, Eq: 1.00) and hydrazine (166 mg, 162 µl, 5.17 mmol, Eq: 10) in dry ethanol (5 ml) was stirred overnight at 70° C.

The reaction mixture was adsorbed unto silica (0.8 g) and purified on silicagel (column 12 g, dichloromethane/methanol 100:0 to 70:30). One fraction was isolated and dried in vacuo to afford 176 mg (90%) of the desired product as a white solid.

MS +m/z: 380.0 (M+H)$^+$

N*3*-(4'-Methanesulfonyl-2-pentafluorosulfur-biphenyl-4-yl)-1H-[1,2,4]triazole-3,5-diamine (Compound 288)

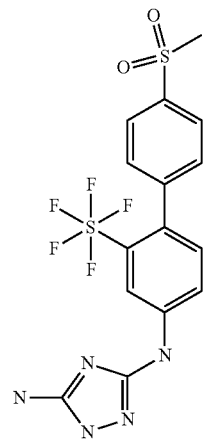

To a mixture of N*3*-(4-Bromo-3-pentafluorosulfur-phenyl)-1H-[1,2,4]triazole-3,5-diamine (60 mg, 158 µmol, Eq: 1.00), 4-(methylsulfonyl)phenylboronic acid (63.1 mg, 316 µmol, Eq: 2) and tetrakis(triphenylphosphine)palladium (0) (14.6 mg, 12.6 µmol, Eq: 0.08) was added degassed (nitrogen bubbling with sonication)dioxane dry (1000 µl) and degassed (nitrogen bubbling with sonication) potassium carbonate 2M in water (158 µl, 316 µmol, Eq: 2). The mixture was sealed and stirred at 100° C. for 16 h.

The reaction mixture was adsorbed unto silica (0.6 g) and purified on silicagel (column 12 g, dichloromethane/methanol 100:0 to 70:30). One fraction was isolated and dried in vacuo to afford 50 mg of a yellow solid. This solid was further purified by reverse phase HLPC to afford 11 mg (15%) of the desired product as a white solid.

MS +m/z: 456.1 (M+H)+

N-3-[2,6-Dichloro-4'-(1,1-dioxo-1,6-isothiazolidin-2-yl)-biphenyl-4-yl]-1H-[1,2,4]triazole-3,5-diamine (Compound 289)

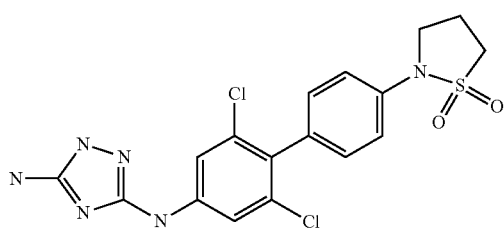 [SMILES: Nc1nc(Nc2cc(Cl)c(-c3ccc(N4CCCS4(=O)=O)cc3)c(Cl)c2)n[nH]1]

2-[4-(4,4,5,5-Tetramethyl-[1,3,2]dioxaborolan-2-yl)-phenyl]-isothiazolidine 1,1-dioxide

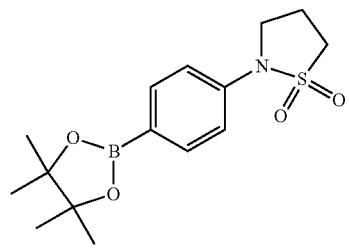 [SMILES: CC1(C)OB(c2ccc(N3CCCS3(=O)=O)cc2)OC1(C)C]

To a cold (ice bath) mixture of 4-(4,4,5,5-tetramethyl-1,3,2-dioxaborolan-2-yl)aniline (3 g, 13.7 mmol, Eq: 1.00) in dry dichloromethane (90 ml) and triethylamine (1.66 g, 2.29 ml, 16.4 mmol, Eq: 1.2) was slowly added 3-chloropropane-1-sulfonyl chloride (2.55 g, 1.75 ml, 14.4 mmol, Eq: 1.05). The reaction mixture was stirred at room temperature overnight.

The reaction mixture was diluted with dichloromethane (150 mL), washed with aqueous sat. sodium hydrogenocarbonate, water (3 times) then brine. The organic layer was then dried over sodium sulfate, filtered and concentrated in vacuo, to afford 6.19 g of a white solid.

The white solid was dissolved in dry dimethylformamide (100 ml) and cooled to 0° C. (ice bath). Sodium hydride dispersion in oil (800 mg, 20.0 mmol, Eq: 1.46) was added in 4 portions of 200 mg each, over 1 h30. The reaction mixture was stirred at room temperature for 3 h then diluted in ethyl acetate, washed with HCl 0.1N, water (3 times) and brine then dried over sodium sulfate, filtered and dried in vacuo to afford 3.3 g of a solid.

The solid was purified on silicagel (column 120 g, dichloromethane/ethyl acetate 1:0 to 90:10). One fraction was isolated and dried in vacuo to afford 590 mg (13%) of the desired product as a white solid.

N-3-[2,6-Dichloro-4'-(1,1-dioxo-1,6-isothiazolidin-2-yl)-biphenyl-4-yl]-1H-[1,2,4]triazole-3,5-diamine (Compound 289)

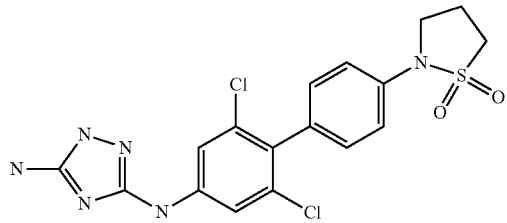 [SMILES: Nc1nc(Nc2cc(Cl)c(-c3ccc(N4CCCS4(=O)=O)cc3)c(Cl)c2)n[nH]1]

To a mixture of N3-(4-bromo-3,5-dichlorophenyl)-1H-1,2,4-triazole-3,5-diamine Intermediate 2 (100 mg, 310 µmol, Eq: 1.00), 2-[4-(4,4,5,5-Tetramethyl-[1,3,2]dioxaborolan-2-yl)-phenyl]-isothiazolidine 1,1-dioxide (150 mg, 464 µmol, Eq: 1.5) and tetrakis(triphenylphosphine)palladium (0) (28.6 mg, 24.8 µmol, Eq: 0.08) was added degassed (nitrogen bubbling with sonication) dry dioxane (1.96 ml) and a degassed (nitrogen bubbling with sonication) solution of potassium Carbonate in water (2M, 310 µl, 619 µmol, Eq: 2). The reaction mixture was sealed and stirred at 100° C. for 16 h.

The reaction mixture was adsorbed unto silica (0.6 g) and purified on silicagel (column 12 g, dichloromethane/methanol 100:0 to 70:30). One fraction was isolated and dried in vacuo to afford 119 mg of a yellow solid. The yellow solid was further purified on reverse phase HLPC (CN column). One fraction was isolated to afford 16 mg (12%) of the desired product as a brown solid.

MS +m/z: 439.1 (M+H)+

N-(4'-(5-amino-1H-1,2,4-triazol-3-ylamino)-2'-chloro-6'-(trifluoromethyl)biphenyl-3-yl)methanesulfonamide (Compound 290)

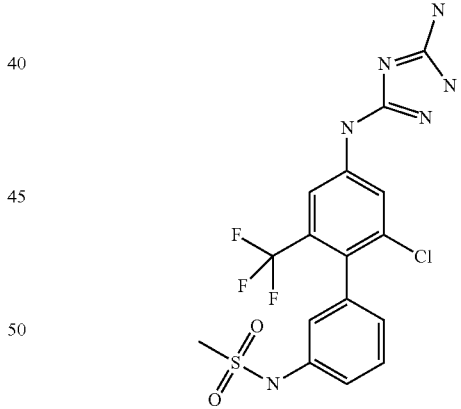

4-bromo-3-chloro-5-(trifluoromethyl)aniline

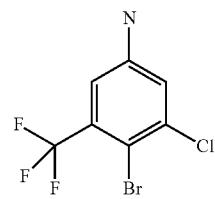 [SMILES: Nc1cc(Cl)c(Br)c(C(F)(F)F)c1]

To a mixture of 3-chloro-5-(trifluoromethyl)aniline (3.25 g, 16.6 mmol, Eq: 1.00) in dimethylsulfoxide (43.4 ml) was added N-bromosuccinimide (3.11 g, 17.4 mmol, Eq: 1.05) in 5 portions over 2 h30 (622 mg each 30 min). 2 h after the last addition, the reaction mixture was partitioned between 10% aqueous sodium sulfite and ethyl acetate. The organic layer was washed with aqueous sat. sodium carbonate, water (3 times) and brine then adsorbed unto silica (6 g) and purified on silicagel (column 120 g, Hexane/ethyl acetate 90:10 to 65:35). One fraction was isolated and dried in vacuo to afford 4.36 g (96%) of a yellow solid.

MS +m/z: 275.8 (M+H)$^+$

N-(4'-amino-2'-chloro-6'-(trifluoromethyl)biphenyl-3-yl)methanesulfonamide

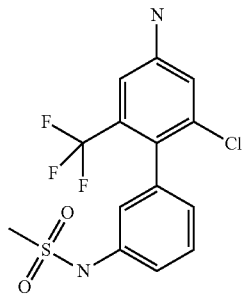 [SMILES: CS(=O)(=O)Nc1cccc(-c2c(Cl)cc(N)cc2C(F)(F)F)c1]

A mixture of 4-bromo-3-chloro-5-(trifluoromethyl)aniline (573 mg, 2.09 mmol, Eq: 1.00), 3-(methylsulfonamido)phenylboronic acid (529 mg, 2.46 mmol, Eq: 1.18) and tetrakis(triphenylphosphine)palladium (0) (211 mg, 183 µmol, Eq: 0.0875) was degassed (vacuum/nitrogen cycles) then degassed dioxane (6.87 ml) (nitrogen bubbling with sonication) and a degassed (nitrogen bubbling with sonication) 2M solution of sodium carbonate in water (1.83 ml, 3.66 mmol, Eq: 1.75) were added. The mixture was stirred at 100° C. for 18 h. The reaction mixture was adsorbed unto silica (2 g), concentrated and purified on silica gel (silica 40 g, dichloromethane/ethyl acetate 100:0 to 80:20). One fraction was isolated and dried in vacuo to afford 574 mg (75 mg) of the desired product as a yellow solid.

MS +m/z: 365.0 (M+H)$^+$

N-(2'-chloro-4'-isothiocyanato-6'-(trifluoromethyl)biphenyl-3-yl)methanesulfonamide

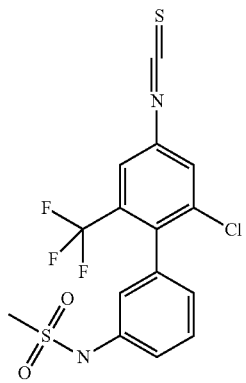 [SMILES: CS(=O)(=O)Nc1cccc(-c2c(Cl)cc(N=C=S)cc2C(F)(F)F)c1]

To a cold (0° C.) suspension of N-(4'-amino-2'-chloro-6'-(trifluoromethyl)biphenyl-3-yl)methanesulfonamide (570 mg, 1.56 mmol, Eq: 1.00) and calcium carbonate (313 mg, 3.13 mmol, Eq: 2) in dichloromethane (3.38 ml) and water (3.38 ml) was added thiophosgene (198 mg, 131 µl, 1.72 mmol, Eq: 1.1). The reaction mixture was allowed to warm up to room temperature and was vigorously stirred for 16 h. 1N HCl was added to adjust the pH to ca. 2. The reaction mixture was partitioned between water and ethyl acetate.

The organic layer was separated and washed with water then brine and purified on silicagel (column 24 g, dichlormethane/ethyl acetate 1:0 to 85:15).

One fraction was isolated and dried in vacuo to afford 565 mg (89%) of the desired product as a colorless oil.

(E)-methyl N-2-chloro-3'-(methylsulfonamido)-6-(trifluoromethyl)biphenyl-4-yl-N'-cyanocarbamimidothioate

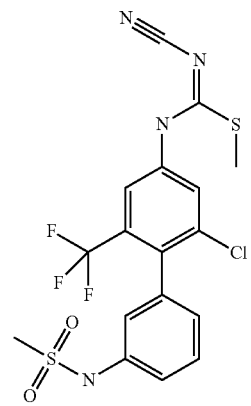

To a solution of N-(2'-chloro-4'-isothiocyanato-6'-(trifluoromethyl)biphenyl-3-yl)methanesulfonamide (560 mg, 1.38 mmol, Eq: 1.00) in dry methanol (5 ml) was added sodium hydrogencyanamide (92.5 mg, 1.45 mmol, Eq: 1.05). The reaction mixture was stirred 30 min at room temperature then iodomethane (408 mg, 200 µl, 2.87 mmol, Eq: 2.09) was added and the reaction mixture was stirred 1 h30 at room temperature then adsorbed unto silica (1 g), concentrated and purified on silica gel (silica 24 g, dichloromethane/ethyl acetate 100:0 to 60:40). One fraction was isolated and dried in vacuo to afford 436 mg (68%) of the desired product as a yellow foam.

N-(4'-(5-amino-1H-1,2,4-triazol-3-ylamino)-2'-chloro-6'-(trifluoromethyl)biphenyl-3-yl)methanesulfonamide (Compound 290)

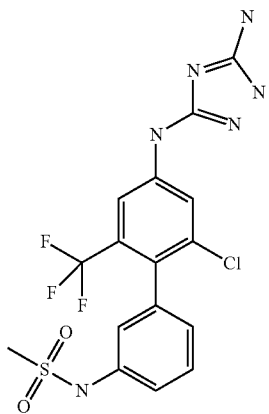 [SMILES: CS(=O)(=O)Nc1cccc(-c2c(Cl)cc(NC(=N)N=C(N)N)cc2C(F)(F)F)c1]

To a suspension of (E)-methyl N-2-chloro-3'-(methylsulfonamido)-6-(trifluoromethyl)biphenyl-4-yl-N'-cyanocarbamimidothioate (100 mg, 216 µmol, Eq: 1.00) in dry ethanol (1.58 ml) was added hydrazine (69.2 mg, 67.8 µl, 2.16 mmol, Eq: 10). The reaction mixture was stirred 1 h30 at 70° C. then was adsorbed unto silica (0.5 g) and purified on silicagel (column 12 g, dichloromethane/methanol 100:0 to 75:25). One fraction was isolated and dried in vacuo to afford 86 mg (89%) of the desired product as a white solid.

MS +m/z: 446.9 (M+H)+

4'-(5-amino-1H-1,2,4-triazol-3-ylamino)-2'-chloro-3-fluoro-N-methyl-6'-(trifluoromethyl)biphenyl-4-carboxamide (Compound 291)

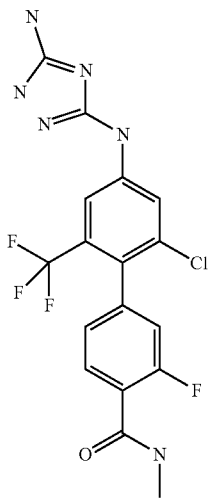 [SMILES: CNC(=O)c1ccc(-c2c(Cl)cc(NC(=N)N=C(N)N)cc2C(F)(F)F)cc1F]

A mixture of N3-(4-bromo-3-chloro-5-(trifluoromethyl)phenyl)-1H-1,2,4-triazole-3,5-diamine Intermediate 1 (130 mg, 365 µmol, Eq: 1.00), 3-fluoro-4-(methylcarbamoyl)phenylboronic acid [849833-86-9] (97.0 mg, 492 µmol, Eq: 1.35) and tetrakis(triphenylphosphine)palladium (0) (37.9 mg, 32.8 µmol, Eq: 0.09) was degassed (vacuum/nitrogen cycles) then degassed dry dioxane (1.2 ml) (nitrogen bubbling with sonication) and a degassed (nitrogen bubbling with sonication) 2M solution of sodium carbonate in water (365 µl, 729 µmol, Eq: 2) were added. The reaction mixture sealed and stirred at 105° C. for 18 h. The reaction mixture was adsorbed unto silica (1 g), concentrated and purified on silica gel (silica 12 g, dichloromethane/methanol 98:2 to 70:30). One fraction was isolated and dried in vacuo to afford 73 mg (47%) of the desired product as a brown solid.

MS +m/z: 429.0 (M+H)+

4'-(5-amino-1H-1,2,4-triazol-3-ylamino)-2'-chloro-4-fluoro-N-methyl-6'-(trifluoromethyl)biphenyl-3-carboxamide (Compound 292)

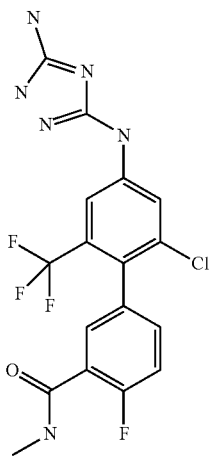 [SMILES: CNC(=O)c1cc(-c2c(Cl)cc(NC(=N)N=C(N)N)cc2C(F)(F)F)ccc1F]

A mixture of N3-(4-bromo-3-chloro-5-(trifluoromethyl)phenyl)-1H-1,2,4-triazole-3,5-diamine Intermediate 1 (200 mg, 561 µmol, Eq: 1.00), 4-fluoro-3-(methylcarbamoyl)phenylboronic acid [874219-19-9] (149 mg, 757 µmol, Eq: 1.35) and tetrakis(triphenylphosphine)palladium (0) (64.8 mg, 56.1 µmol, Eq: 0.1) was degassed (vacuum/nitrogen cycles) then degassed dry dioxane (2 ml) (nitrogen bubbling with sonication) and a degassed (nitrogen bubbling with sonication) 2M solution of sodium carbonate in water (600 µl, 1.2 mmol, Eq: 2.14) were added. The mixture was sealed and stirred at 105° C. for 18 h. The reaction mixture was adsorbed unto silica (1 g), concentrated and purified on silica gel (silica 24 g, dichloromethane/methanol 98:2 to 70:30). One fraction was isolated and dried in vacuo to afford 95 mg (40%) of the desired product as a brown solid.

MS +m/z: 428.9 (M+H)+

4'-(5-amino-1H-1,2,4-triazol-3-ylamino)-2'-chloro-3-fluoro-N-(2-hydroxyethyl)-6'-(trifluoromethyl)biphenyl-4-carboxamide (Compound 293)

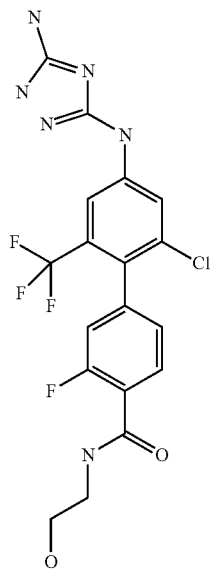 [SMILES: N=C(N=C(N)N)Nc1cc(Cl)c(-c2ccc(C(=O)NCCO)c(F)c2)c(C(F)(F)F)c1]

A mixture of N3-(4-bromo-3-chloro-5-(trifluoromethyl)phenyl)-1H-1,2,4-triazole-3,5-diamine Intermediate 1 (200 mg, 561 µmol, Eq: 1.00), 3-fluoro-4-(2-hydroxyethylcarbamoyl)phenylboronic acid [874289-21-1] (172 mg, 757 µmol, Eq: 1.35) and tetrakis(triphenylphosphine)palladium (0) (64.8 mg, 56.1 µmol, Eq: 0.1) was degassed (vacuum/nitrogen cycles) then degassed dry dioxane (1.85 ml) (nitrogen bubbling with sonication) and a degassed (nitrogen bubbling with sonication) 2M solution of sodium carbonate in water (561 µl, 1.12 mmol, Eq: 2) were added. The reaction mixture was sealed and stirred at 105° C. for 18 h. The reaction mixture was adsorbed unto silica (1 g), concentrated and purified on silica gel (silica 24 g, dichloromethane/methanol 97:3 to 70:30). One fraction was isolated and dried in vacuo to afford 106 mg (41%) of the desired product as a brown solid.

MS +m/z: 458.9 (M+H)+

4'-(5-amino-1H-1,2,4-triazol-3-ylamino)-2'-chloro-4-fluoro-N-(2-hydroxyethyl)-6'-(trifluoromethyl)biphenyl-3-carboxamide (Compound 294)

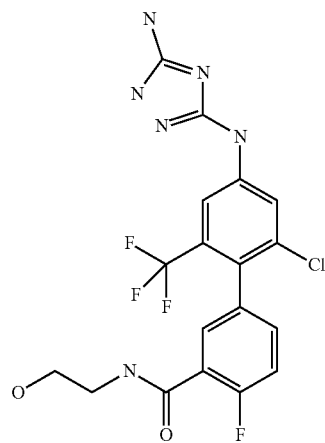 [SMILES: N=C(N=C(N)N)Nc1cc(Cl)c(-c2ccc(F)c(C(=O)NCCO)c2)c(C(F)(F)F)c1]

A mixture of N3-(4-bromo-3-chloro-5-(trifluoromethyl)phenyl)-1H-1,2,4-triazole-3,5-diamine Intermediate 1 (200 mg, 561 µmol, Eq: 1.00), 4-fluoro-3-(2-hydroxyethylcarbamoyl)phenylboronic acid [874219-25-7] (172 mg, 757 µmol, Eq: 1.35) and tetrakis(triphenylphosphine)palladium (0) (64.8 mg, 56.1 µmol, Eq: 0.1) was degassed (vacuum/nitrogen cycles) then degassed dry dioxane (1.85 ml) (nitrogen bubbling with sonication) and a degassed (nitrogen bubbling with sonication) 2M solution of sodium carbonate in water (561 µl, 1.12 mmol, Eq: 2) were added. The reaction mixture was sealed and stirred at 105° C. for 18 h. The reaction mixture was adsorbed unto silica (1 g), concentrated and purified on silica gel (silica 24 g, dichloromethane/methanol 97:3 to 70:30). One fraction was isolated and dried in vacuo to afford 99 mg (39%) of the desired product as a yellow semi-solid solid.

MS +m/z: 458.9 (M+H)$^+$

4'-(5-amino-1H-1,2,4-triazol-3-ylamino)-2'-chloro-N-(oxetan-3-yl)-6'-(trifluoromethyl)biphenyl-4-sulfonamide (Compound 295)

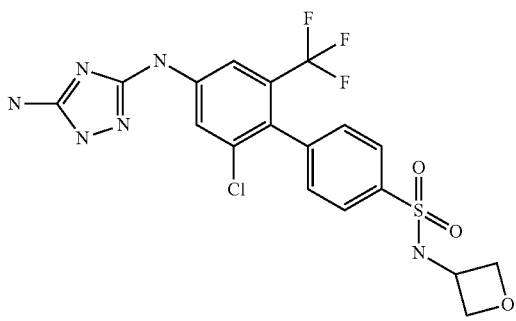 [SMILES: Nc1nc(Nc2cc(Cl)c(-c3ccc(S(=O)(=O)NC4COC4)cc3)c(C(F)(F)F)c2)n[nH]1]

4-bromo-N-(oxetan-3-yl)benzenesulfonamide

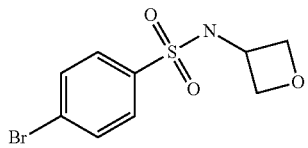 [SMILES: O=S(=O)(NC1COC1)c1ccc(Br)cc1]

To a cold (0° C.) mixture of oxetan-3-amine (190 mg, 2.6 mmol, Eq: 1.3) and triethylamine (504 mg, 700 µl, 4.98 mmol, Eq: 2.49) in dichloromethane (10 ml) was added 4-bromobenzene-1-sulfonyl chloride (511 mg, 2 mmol, Eq: 1.00). The reaction mixture was allowed to warm up to room temperature and was stirred 16 h. The reaction mixture was diluted with dichloromethane, washed with HCl 1N, water and brine then concentrated in vacuo. The residue was adsorbed on silica (1 g) and purified on silica gel (silica 24 g, dichloromethane/ethyl acetate 100:0 to 85:15). One fraction was isolated and dried in vacuo to afford 360 mg (62%) of the desired product as a white solid.

N-(oxetan-3-yl)-4-(4,4,5,5-tetramethyl-1,3,2-dioxaborolan-2-yl)benzenesulfonamide

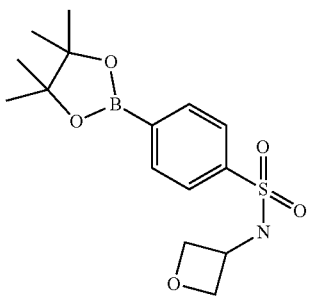 [SMILES: CC1(C)OB(c2ccc(S(=O)(=O)NC3COC3)cc2)OC1(C)C]

A mixture of 4-bromo-N-(oxetan-3-yl)benzenesulfonamide (360 mg, 1.23 mmol, Eq: 1.00), 4,4,4',4',5,5,5',5'-octamethyl-2,2'-bi(1,3,2-dioxaborolane) (782 mg, 3.08 mmol, Eq: 2.5), potassium acetate (544 mg, 5.55 mmol, Eq: 4.5) and dichloro[1,1'-bis(diphenylphosphino)ferrocene] palladium (II) (90.2 mg, 123 µmol, Eq: 0.1) was degassed (vacuum/nitrogen cycles) then degassed (nitrogen bubbling with sonication)dioxane dry (8 ml) was added. The mixture was stirred at 80° C. for 18 h in the sealed vial.

The reaction mixture was adsorbed unto silica (2 g), concentrated and purified on silica gel (silica 40 g, dichloromethane/methanol 100:0 to 70:30). One fraction was isolated and dried in vacuo to afford 347 mg (83%) of the desired product as a white solid.

4'-(5-amino-1H-1,2,4-triazol-3-ylamino)-2'-chloro-N-(oxetan-3-yl)-6'-(trifluoromethyl)biphenyl-4-sulfonamide (Compound 295)

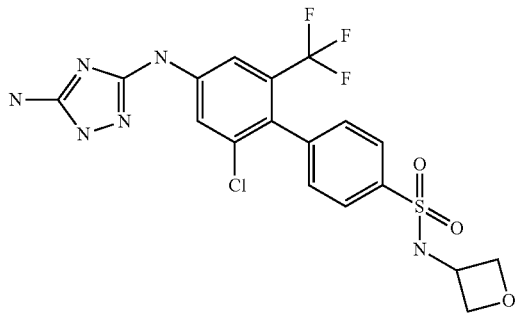 [SMILES: Nc1nc(Nc2cc(Cl)c(-c3ccc(S(=O)(=O)NC4COC4)cc3)c(C(F)(F)F)c2)n[nH]1]

A mixture of N3-(4-bromo-3-chloro-5-(trifluoromethyl)phenyl)-1H-1,2,4-triazole-3,5-diamine Intermediate 1 (200 mg, 561 μmol, Eq: 1.00), N-(oxetan-3-yl)-4-(4,4,5,5-tetramethyl-1,3,2-dioxaborolan-2-yl)benzenesulfonamide (257 mg, 757 μmol, Eq: 1.35) and tetrakis(triphenylphosphine)palladium (0) (64.8 mg, 56.1 μmol, Eq: 0.1) was degassed (vacuum/nitrogen cycles) then degassed (nitrogen bubbling with sonication) dry dioxane (2 ml) and a degassed (nitrogen bubbling with sonication) 2M solution of sodium carbonate in water (600 μl, 1.2 mmol, Eq: 2.14) were added and the reaction mixture was sealed and stirred at 100° C. for 18 h.

The reaction mixture was adsorbed unto silica (1 g), concentrated and purified on silica gel (column 24 g, dichloromethane/methanol 95:5 to 65:35). One fraction was isolated and dried in vacuo to afford 130 mg of a yellow solid. This solid was further purified by reverse phase HLPC to afford 108 mg (39%) of the desired product as an off white solid.

MS +m/z: 488.9 (M+H)+

BIOLOGICAL EXAMPLES

Determination of compounds HCV GT1b and GT1a entry inhibitory activity using the pseudotyped HCV particle (HCVpp) reporter assay.

Mammalian expression plasmids for the generation of pseudotyped virus particles.

Plasmids expressing HCV E1 and E2 envelope proteins of GT1a H77 strain (Proc Natl Acad Sci USA 1997 94:8738-43) or GT1b Con1 strain (Science 1999 285:110-3) were constructed by cloning the nucleic acids encoding the last 60 amino acids of HCV core protein and all of the HCV E1 and E2 proteins into pcDNA3.1(+) vector. Plasmid pVSV-G expressing the glycoprotein G of the vesicular stomatitis virus (VSV G) is from Clontech (cat #631530). The HIV packaging construct expressing the firefly luciferase reporter gene was modified based on the envelope defective pNL.4.3.Luc-R−.E− vector (Virology 1995 206:935-44) by further deleting part of the HIV envelope protein.

Generation of pseudotyped virus particles in transiently transfected HEK-293T cells.

Pseudotyped HCV GT1a and GT1b particles (HCVpp) and the pseudotyped VSV G particles (VSVpp) were generated from transiently transfected HEK-293T cells (ATCC cat# CRL-573). For generating HCVpp, the HEK-293T cells were transfected with equal amounts of plasmids expressing the HCV envelope proteins and the HIV packaging genome by using polyethylenimine (Polysciences cat#23966) as transfection reagent. For generating VSVpp, the HEK-293T cells were transfected with equal amounts of plasmids expressing VSV G and the HIV packaging genome by using polyethylenimine. 24 hours after the transfection, the cell culture medium containing the transfection mixture was replaced with fresh Dulbecco's Modified Eagle Medium (DMEM-Glutamax™-I; Invitrogen cat #10569-010) supplemented with 10% Fetal Bovine Serum (Invitrogen cat #10082-147) and 2 mM L-glutamine (Invitrogen cat #25030-081). The supernatant was collected 48 hours after the transfection and filtered through a sterile 0.45 μm filter. Aliquots of the supernatant was frozen and stored at −80° C. until use.

Huh7-high CD81 cells with high CD81 expression level were enriched by flow cytometry sorting using FITC-labeled CD81 antibody JS-81 (BD Biosciences cat#561956) to allow more efficient HCV entry. The Huh7-high CD81 cells were cultured in Dulbecco's Modified Eagle Medium (DMEM-Glutamax™-I; Invitrogen cat #10569-010). The medium was supplemented with 10% Fetal Bovine Serum (Invitrogen cat #10082-147) and 1% penicillin/streptomycin (Invitrogen cat #15070-063). Cells were maintained at 37° C. in a humidified 5% $CO_2$ atmosphere.

Determination of compound HCVpp entry inhibitory activity in Huh7-high CD81 cells.

Huh7-high CD81 cells were plated at a cell density of 8000 cells per well in 96 well plates (Perkin Elmer, cat #6005660). Cells were plated in 100 μl of Dulbecco's Modified Eagle Medium (DMEM-Glutamax™-I, Invitrogen Cat #10569-010) supplemented with 10% Fetal Bovine Serum (Invitrogen Cat #10082-147) and 1% penicillin/streptomycin (Invitrogen cat #15070-063). Cells were allowed to equilibrate for 24 hours at 37° C. and 5% CO2 at which time compounds and pseudotyped viruses were added. On the day of the assay, HCVpp aliquots were thawed in 37° C. water bath and kept at 4° C. until use. Compounds (or medium as a control) were diluted in 3 fold dilution series in DMEM-Glutamax™-I with 2% DMSO and 2% penicillin/streptomycin. The 100 μl plating medium in each culture well was removed followed by the addition of 50 μl compound dilutions and 50 μl thawed HCVpp. Firefly luciferase reporter signal was read 72 hours after the addition of compounds and HCVpp using the Steady-Glo luciferase Assay System (Promega, cat # E2520) following the manufacturer's instruction. EC50 values were defined as the compound concentration at which a 50% reduction in the levels of firefly luciferase reporter was observed as compared to control samples in the absence of compound and was determined by non-linear fitting of compound dose-response data.

Determination of compound selectivity in Huh7-high CD81 cells.

Huh7 hCD81 cell assay plates and compound dilutions were set up in the same format as in the HCVpp assay. 24 hours after cell plating, thawed VSVpp was diluted by 800 fold in DMEM-Glutamax™-I supplemented with 10% fetal bovine serum. After removal of the cell plating medium from the culture wells, 50 μl compound dilutions and 50 μl diluted VSVpp were added to the wells. Firefly luciferase reporter signal was read 72 hours after the addition of compounds and VSVpp using the Steady-Glo luciferase Assay System (Promega, cat # E2520). EC50 values were defined as the compound concentration at which a 50% reduction in the levels of firefly luciferase reporter was observed as compared to control samples in the absence of compound and was determined by non-linear fitting of compound dose-response data. The EC50 was approximated if maximum percentage inhibition was less than 90% and more than 70%. Representative assay data can be found in Table II below:

TABLE II

| Compound # | HCVpp GT-1b (EC$_{50}$, μM) | HCVpp GT-1a (EC$_{50}$, μM) | VSVpp (EC$_{50}$, μM) |
| --- | --- | --- | --- |
| 1 | 0.001 | 0.014 | >10 |
| 2 | 0.005 | | 6.10 |
| 3 | 0.005 | | 4.37 |
| 4 | 0.005 | | >10.00 |
| 5 | 0.005 | | >10.00 |
| 6 | 0.008 | | 2.56 |
| 7 | 0.017 | | 3.09 |
| 8 | 0.013 | | >10.00 |
| 9 | 0.014 | | 5.05 |
| 10 | 0.015 | | >10.00 |
| 11 | 0.017 | | 6.78 |
| 12 | 0.035 | 0.003 | 18.26 |
| 13 | 0.027 | | 20.99 |
| 14 | 0.052 | | 0.12 |
| 15 | 0.05 | | 0.23 |
| 16 | 0.03 | | >10.00 |
| 17 | 0.043 | | 4.90 |
| 18 | 0.032 | | 3.47 |
| 19 | 0.049 | | >10.00 |
| 20 | 0.053 | | 3.46 |
| 21 | 0.039 | | >10.00 |
| 22 | 0.053 | | 13.50 |
| 23 | 0.092 | 0.023 | >10.00 |
| 24 | 0.058 | | >10.00 |
| 25 | 0.059 | | >10.00 |
| 26 | 0.116 | 0.008 | 3.79 |
| 27 | 0.052 | | 30.09 |
| 28 | 0.083 | | 4.02 |
| 29 | 0.09 | | 3.53 |
| 30 | 0.107 | | 1.53 |
| 31 | 0.086 | 0.004 | 3.23 |
| 32 | 0.116 | 0.006 | 6.10 |
| 33 | 0.099 | 0.019 | 34.26 |
| 34 | 0.122 | 0.028 | >10.00 |
| 35 | 0.127 | | 4.79 |
| 36 | 0.096 | | 14.18 |
| 37 | 0.107 | | >10.00 |
| 38 | 0.087 | | 7.01 |
| 39 | 0.09 | 0.002 | >10.00 |
| 40 | 0.073 | | 31.74 |
| 41 | 0.166 | | >10.00 |
| 42 | 0.212 | | 2.27 |
| 43 | 0.169 | | 15.42 |
| 44 | 0.236 | | 4.92 |
| 45 | 0.101 | | >10.00 |
| 46 | 0.414 | | >10.00 |
| 47 | 0.544 | | 0.82 |
| 48 | 0.533 | 0.01 | 30.48 |
| 49 | 0.455 | | >10.00 |
| 50 | 0.689 | | >10.00 |
| 51 | 0.678 | | >10.00 |
| 52 | 0.64 | | >10.00 |
| 53 | 5.611 | | 4.38 |
| 54 | 10 | 5.732 | >10.00 |
| 55 | 100 | 25.147 | 100.00 |
| 56 | 0.046 | | 3.74 |
| 57 | 0.049 | | 2.45 |
| 58 | 0.086 | | 4.56 |
| 59 | 0.008 | | 5.78 |
| 60 | 0.014 | | >10.00 |
| 61 | 0.013 | | >10.00 |
| 62 | 0.02 | | >10.00 |
| 63 | 0.018 | | 3.86 |
| 64 | 0.023 | | 9.54 |
| 65 | 0.026 | | >10.00 |
| 66 | 0.101 | | 7.32 |
| 67 | 0.107 | | >10.00 |
| 68 | 0.05 | | 8.73 |
| 69 | 0.033 | | >10 |
| 70 | 0.064 | | 5.15 |
| 71 | 0.153 | | >10.00 |
| 72 | 0.154 | | >10.00 |
| 73 | 0.113 | | 24.10 |
| 74 | 0.169 | 0.055 | 16.86 |
| 75 | 0.164 | | 12.58 |
| 76 | 0.246 | | >10.00 |
| 77 | 0.19 | | 24.74 |
| 78 | 0.346 | | 8.18 |
| 79 | 0.483 | | 8.11 |
| 80 | 0.286 | | >10.00 |
| 81 | 0.549 | | 34.92 |
| 82 | 0.39 | | >10.00 |
| 83 | 0.532 | | 4.34 |
| 84 | 0.43 | | 16.82 |
| 85 | 0.568 | | >10.00 |
| 86 | 0.525 | | 8.87 |
| 87 | 0.696 | | >10.00 |
| 88 | 1.948 | | 25.23 |
| 89 | 25.066 | | 33.30 |
| 90 | 0.875 | | 15.74 |
| 91 | 1.128 | 0.065 | 23.29 |
| 92 | 0.57 | 0.034 | 35.50 |
| 93 | 0.364 | 0.015 | 14.82 |
| 94 | 0.174 | 0.007 | 2.00 |
| 95 | 0.229 | 0.028 | 24.10 |
| 96 | 0.927 | 0.009 | 4.27 |
| 97 | 0.704 | 0.007 | 9.33 |
| 98 | 0.353 | 0.01 | 5.25 |
| 99 | 1.575 | 0.056 | 20.64 |
| 100 | 0.839 | 0.062 | 14.33 |
| 101 | 0.514 | 0.037 | 13.18 |
| 102 | 0.931 | 0.062 | 6.33 |
| 103 | 0.269 | 0.025 | 13.35 |
| 104 | 1.28 | 0.072 | 17.79 |
| 105 | 0.472 | 0.039 | 16.84 |
| 106 | 23.388 | 1.171 | 100.00 |
| 107 | 0.228 | 0.008 | 11.13 |
| 108 | 0.014 | | 29.00 |
| 109 | 0.74 | | 46.49 |
| 110 | 0.1 | | 24.98 |
| 111 | 0.039 | 0.003 | 7.53 |
| 112 | 0.048 | 0.006 | 15.30 |
| 113 | 0.079 | | 43.20 |
| 114 | 0.069 | 0.01 | 18.17 |
| 115 | 0.107 | 0.007 | 34.76 |
| 116 | 0.086 | 0.002 | 29.35 |
| 117 | 0.218 | 0.011 | 26.06 |
| 118 | 0.013 | 0.004 | 4.24 |
| 119 | 0.046 | | 3.94 |
| 120 | 0.181 | | 1.12 |
| 121 | 0.068 | | 0.08 |
| 122 | 0.024 | 0.004 | 12.09 |
| 123 | 0.042 | 0.002 | 10.97 |
| 124 | 1.006 | | 4.49 |
| 125 | 0.096 | | >10.00 |
| 126 | 0.088 | | >10.00 |
| 127 | 0.144 | | 9.69 |
| 128 | 0.011 | | 9.26 |
| 129 | 0.017 | | 9.62 |
| 130 | 0.055 | | 8.67 |
| 131 | 0.095 | | 7.02 |
| 132 | 0.088 | | 6.13 |
| 133 | 0.13 | | >10 |
| 134 | 0.081 | | >10 |
| 135 | 0.077 | | >10 |
| 136 | 0.005 | | 3.08 |
| 137 | 0.062 | | >10 |
| 138 | 0.162 | | >10 |
| 139 | 0.042 | | 5.66 |
| 140 | 0.111 | | >10 |
| 141 | 0.194 | | >10 |
| 142 | 0.242 | | >10 |
| 143 | 0.231 | | 8.98 |
| 144 | 2.921 | 0.333 | 34.76 |
| 145 | 6.023 | 0.532 | 39.13 |
| 146 | 2.879 | | 29.35 |
| 147 | 6.124 | 0.621 | 47.22 |
| 148 | 3.343 | 0.301 | 33.77 |

TABLE II-continued

| Compound # | HCVpp GT-1b (EC$_{50}$, μM) | HCVpp GT-1a (EC$_{50}$, μM) | VSVpp (EC$_{50}$, μM) |
|---|---|---|---|
| 149 | 0.581 | | 29.19 |
| 150 | 0.866 | | 21.28 |
| 151 | 0.356 | | 26.49 |
| 152 | 0.575 | | 20.35 |
| 153 | 1.812 | | 9.61 |
| 154 | 2.47 | | 16.39 |
| 155 | 1.655 | | 7.46 |
| 156 | 3.769 | | 11.30 |
| 157 | 1.33 | | 5.16 |
| 158 | 0.539 | | >10.00 |
| 159 | 0.164 | 0.005 | 4.62 |
| 160 | 0.063 | | 10.57 |
| 161 | 0.058 | | 26.78 |
| 162 | 0.126 | | >10.00 |
| 163 | 0.005 | | >10.00 |
| 164 | 0.004 | | 7.06 |
| 165 | 0.009 | | >10.00 |
| 166 | 0.005 | 0.003 | >10.00 |
| 167 | 0.009 | | >10.00 |
| 168 | 0.011 | | |
| 169 | 0.011 | | 3.55 |
| 170 | 0.026 | 0.02 | 14.14 |
| 171 | 0.028 | | 5.23 |
| 172 | 0.032 | | 45.12 |
| 173 | 0.019 | 0.007 | >10.00 |
| 174 | 0.038 | | >10.00 |
| 175 | 0.018 | | >10.00 |
| 176 | 0.019 | | 9.60 |
| 177 | 0.018 | 0.003 | 23.42 |
| 178 | 0.023 | | >10.00 |
| 179 | 0.02 | 0.002 | 8.55 |
| 180 | 0.036 | | |
| 181 | 0.059 | 0.021 | |
| 182 | 0.044 | | >10.00 |
| 183 | 0.048 | | 8.19 |
| 184 | 0.05 | 0.028 | >10.00 |
| 185 | 0.052 | 0.015 | 11.74 |
| 186 | 0.038 | 0.011 | 19.72 |
| 187 | 0.046 | 0.016 | 1.58 |
| 188 | 0.089 | | 0.09 |
| 189 | 0.08 | | 36.84 |
| 190 | 0.046 | | 56.14 |
| 191 | 0.069 | | 25.04 |
| 192 | 0.084 | | 17.18 |
| 193 | 0.075 | | 4.97 |
| 194 | 0.115 | | 22.84 |
| 195 | 0.212 | | 39.69 |
| 196 | 0.126 | | >10.00 |
| 197 | 0.249 | | >10.00 |
| 198 | 0.268 | | 21.26 |
| 199 | 0.196 | | 31.77 |
| 200 | 0.574 | | >10.00 |
| 201 | 0.405 | | 58.30 |
| 202 | 1.252 | | >10.00 |
| 203 | 0.008 | | 10.55 |
| 204 | 0.011 | | >10 |
| 205 | 0.011 | | 9.26 |
| 206 | 0.017 | | 9.62 |
| 207 | 0.029 | | >10 |
| 208 | 0.049 | | >10 |
| 209 | 0.005 | | 7.09 |
| 210 | 0.021 | | 4.41 |
| 211 | 0.012 | | 3.65 |
| 212 | 0.005 | | 1.42 |
| 213 | 0.062 | | >10 |
| 214 | 0.048 | | 3.36 |
| 215 | 0.111 | | >10 |
| 216 | 0.004 | | 6.48 |
| 217 | | 0.003 | 7.50 |
| 218 | 0.005 | 0.003 | 20.30 |
| 219 | | 0.011 | 16.23 |
| 220 | 0.028 | | 24.75 |
| 221 | 0.003 | | 4.55 |
| 222 | 0.014 | | >10.00 |
| 223 | 0.029 | | 9.80 |
| 224 | 0.02 | | 4.57 |
| 225 | 0.031 | | >10.00 |
| 226 | 0.032 | | 5.39 |
| 227 | 0.042 | | >10.00 |
| 228 | 0.042 | | 7.52 |
| 229 | 0.072 | | 6.47 |
| 230 | 0.332 | | >10.00 |
| 231 | 0.41 | | >10.00 |
| 232 | | | |
| 233 | 0.051 | | >10 |
| 234 | 0.005 | | >10 |
| 235 | 0.012 | | >10.00 |
| 236 | 0.045 | | >10.00 |
| 237 | 0.058 | | 3.67 |
| 238 | 0.078 | | 24.87 |
| 239 | 0.122 | | >10.00 |
| 240 | 0.171 | 0.011 | >10.00 |
| 241 | 0.123 | | >10.00 |
| 242 | 0.113 | 0.061 | >10.00 |
| 243 | 0.213 | | >10.00 |
| 244 | 0.689 | | 33.37 |
| 245 | 1.466 | | 17.05 |
| 246 | 3.542 | | 37.88 |
| 247 | 1.704 | | 10.66 |
| 248 | 1.02 | | >10.00 |
| 249 | 0.991 | | 17.22 |
| 250 | 0.013 | | 14.01 |
| 251 | 0.041 | | 32.54 |
| 252 | 0.067 | | >10.00 |
| 253 | 0.026 | | 0.60 |
| 254 | 0.051 | 0.003 | 12.89 |
| 255 | 0.42 | | >10.00 |
| 256 | 0.594 | | 8.69 |
| 257 | 0.343 | | 2.73 |
| 258 | 20.23 | | 26.16 |
| 259 | 0.089 | | 4.27 |
| 260 | 0.022 | | 17.49 |
| 261 | 0.033 | | 4.26 |
| 262 | 0.05 | | 4.87 |
| 263 | 0.059 | | 3.75 |
| 264 | 0.048 | | 6.50 |
| 265 | 0.063 | 0.005 | 17.87 |
| 266 | 0.103 | | >10.00 |
| 267 | 0.048 | | 9.62 |
| 268 | 0.17 | | >10.00 |
| 269 | 0.122 | | 6.09 |
| 270 | 0.117 | | 33.29 |
| 271 | 0.12 | | 4.39 |
| 272 | 0.147 | | 4.49 |
| 273 | 0.28 | | >10.00 |
| 274 | 0.121 | | 34.07 |
| 275 | 0.285 | | >10.00 |
| 276 | 0.168 | | >10.00 |
| 277 | 0.312 | | 27.92 |
| 278 | 0.264 | | 5.31 |
| 279 | 0.193 | | 36.96 |
| 280 | 0.401 | | >10.00 |
| 281 | 0.244 | | 23.37 |
| 282 | 0.213 | | 39.71 |
| 283 | 0.523 | | >10.00 |
| 284 | 0.576 | | >10.00 |
| 285 | 4.967 | | >10.00 |
| 286 | 0.64 | 0.018 | 13.572 |
| 287 | 0.366 | 0.005 | 12.971 |
| 288 | 1.232 | | 8.933 |
| 289 | 0.046 | 0.002 | 17.811 |
| 290 | 0.149 | | 14.406 |
| 291 | 0.325 | | 21.524 |
| 292 | 0.647 | | 29.24 |
| 293 | 0.139 | | 15.669 |
| 294 | 0.544 | | 38.332 |
| 295 | 0.022 | | 10 |

The foregoing invention has been described in some detail by way of illustration and example, for purposes of clarity and understanding. It will be obvious to one of skill in the art that changes and modifications may be practiced within the scope of the appended claims.

Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:
1. A compound of formula I:

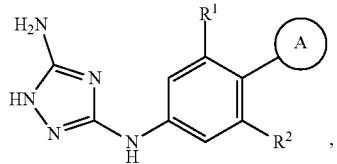

wherein:
A is phenyl, naphthyl, or bicyclic unsaturated or partially saturated heteroaryl, substituted with one or more A;
each A is independently lower alkyl, halo, lower alkoxy, $S(=O)_2(CH_2)_m$ A", $C(=O)NHA"$, $NHC(O)A"$, $—O(CH_2)_mA"$, $(CHA^1)_mNHS(=O)_2A^1$; or $S(=O)_2NHA"$;
each A" is independently, heterocycloalkyl or heteroaryl, optionally substituted with one or more A'";
each A'" is independently hydroxy, lower alkyl, oxo, $C(=O)OA^1$, halo loweralkyl,
each $A^1$ is independently H, lower alkyl, halo loweralkyl, amino, lower alkoxy,
each m is independently 0, 1, 2, or 3;
$R^1$ is H, halo, lower alkyl, halo loweralkyl, $SF_5$, and
$R^2$ is H, halo, lower alkyl, halo loweralkyl,
or a pharmaceutically acceptable salt thereof.
2. The compound of claim 1, wherein A is phenyl.
3. The compound of claim 2, wherein $R^1$ is halo loweralkyl.
4. The compound of claim 3, wherein $R^2$ is halo.
5. The compound of claim 2, wherein $R^1$ is halo.
6. The compound of claim 5, wherein $R^2$ is halo.
7. The compound of claim 1, wherein A' is $S(=O)_2(CH_2)_mA"$ or $(CH_2)_mS(=O)_2$ A".
8. The compound of claim 1, wherein A' is lower alkyl, halo, or lower alkoxy.
9. The compound of claim 1, wherein A' is $C(=O)NHA"$ or $NHC(=O)A"$.
10. The compound of claim 1, wherein A' is $(CHA^1)_m NHS(=O)_2A^1$ or $S(=O)_2NHA"$.
11. The compound of claim 1, wherein A' is $O(CH_2)_mA"$.
12. A compound selected from the group consisting of:
4-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester;
3-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester;
(S)-1-[4'-(5-Amino-1H-[1,2,4]triazol-3-ylamino)-2'-chloro-6'-trifluormethyl-biphenyl-4-sulfonyl]-pyrrolidine-2-carboxylic acid tert-butyl ester;
$N^3$-{6-Chloro-2-trifluoromethyl-4'-[1-(3,3,3-trifluoro-propyl)-piperidine-4-sulfonyl]-biphenyl-4-yl}-1H-[1,2,4]triazole-3,5-diamine;
$N^3$-{6-Chloro-4'-[1-(3,3-dimethyl-butyl)-piperidine-4-sulfonyl]-2-trifluoromethyl-biphenyl-4-yl}-H-[1,2,4]triazole-3,5-diamine;
3-[4'-(5-Amino-1H-[1,2,4]triazol-3-ylamino)-2'-chloro-6'-trifluoromethyl-biphenyl-4-sulfonyl]-piperidine-1-carboxylic acid tert-butyl ester;
4-[4'-(5-Amino-1H-[1,2,4]triazol-3-ylamino)-2'-chloro-6'-trifluoromethyl-biphenyl-4-sulfonylmethyl]-piperidine-1-carboxylic acid tert-butyl ester;
4'-(5-Amino-1H-[1,2,4]triazol-3-ylamino)-2',6'-dichloro-biphenyl-4-carboxylic acid tert-butylamide;
Pentanoic acid [4'-(5-amino-1H-[1,2,4]triazol-3-ylamino)-2',6'-dichloro-biphenyl-4-yl]-amide;
$N^3$-[4-(2-tert-Butyl-1,1-dioxo-2,3-dihydro-1H-1$\lambda^6$-benzo[d]isothiazol-6-yl)-3-chloro-5-trifluoromethyl-phenyl]-1H-[1,2,4]triazole-3,5-diamine;
$N^3$-{6-Chloro-2-trifluoromethyl-4'-[1-(3,3,3-trifluoro-propyl)-piperidine-3-sulfonyl]-biphenyl-4-yl}-1H-[1,2,4]triazole-3,5-diamine;
N-[4'-(5-Amino-1H-[1,2,4]triazol-3-ylamino)-2',6'-dichloro-biphenyl-4-ylmethyl]-methanesulfonamide;
N—{(S)-1-[4'-(5-Amino-1H-[1,2,4]triazol-3-ylamino)-2'-chloro-6'-trifluoromethyl-biphenyl-4-yl]-ethyl}-methanesulfonamide;
$N^3$-(2,6-Dichloro-4'-methanesulfonyl-3'-trifluoromethyl-biphenyl-4-yl)-1H-[1,2,4]triazole-3,5-diamine;
$N^3$-[3,5-Dichloro-4-(1-methanesulfonyl-1H-indol-4-yl)-phenyl]-1H-[1,2,4]triazole-3,5-diamine;
4-[4'-(5-Amino-1H-[1,2,4]triazol-3-ylamino)-2'-chloro-6'-trifluoromethyl-biphenyl-4-sulfonyl]-piperazine-1-carboxylic acid tert-butyl ester;
$N^3$-{6-Chloro-4'-[1-(3,3-dimethyl-butyl)-piperidine-3-sulfonyl]-2-trifluoromethyl-biphenyl-4-yl}-1H-[1,2,4]triazole-3,5-diamine;
4'-(5-Amino-1H-[1,2,4]triazol-3-ylamino)-2'-chloro-4-methyl-6'-trifluoromethyl-biphenyl-3-sulfonic acid tert-butylamide;
$N^3$-[2-Chloro-4'-methoxy-3'-(propane-2-sulfonyl)-6-trifluoromethyl-biphenyl-4-yl]-1H-[1,2,4]triazole-3,5-diamine;
$N^3$-[2-Chloro-4'-(piperidine-4-sulfonyl)-6-trifluoromethyl-biphenyl-4-yl]-1H-[1,2,4]triazole-3,5-diamine;
4-[4'-(5-Amino-1H-[1,2,4]triazol-3-ylamino)-2'-chloro-6'-trifluoromethyl-biphenyl-3-yloxy]-piperidine-1-carboxylic acid tert-butyl ester;
$N^3$-[2-Chloro-4'-(4-methyl-piperazine-1-sulfonyl)-6-trifluoromethyl-biphenyl-4-yl]-1H-[1,2,4]triazole-3,5-diamine;
$N^3$-[2-Chloro-6-fluoro-4'-(propane-2-sulfonyl)-biphenyl-4-yl]-1H-[1,2,4]triazole-3,5-diamine;
N—{(R)-1-[4'-(5-Amino-1H-[1,2,4]triazol-3-ylamino)-2'-chloro-6'-trifluoromethyl-biphenyl-4-yl]-ethyl}-methanesulfonamide;
$N^3$-[2-Chloro-4'-(piperidin-3-ylmethanesulfonyl)-6-trifluoromethyl-biphenyl-4-yl]-1H-[1,2,4]triazole-3,5-diamine;
4-[4'-(5-Amino-1H-[1,2,4]triazol-3-ylamino)-2',6'-dichloro-biphenyl-4-yloxy]-butyronitrile;
4'-(5-Amino-1H-[1,2,4]triazol-3-ylamino)-2'-chloro-6'-trifluoromethyl-biphenyl-4-sulfonic acid ((S)-1-pyrolidin-2-ylmethyl)-amide;
N-[4'-(5-Amino-1H-[1,2,4]triazol-3-ylamino)-2',6'-dichloro-2-fluoro-biphenyl-4-yl]-methanesulfonamide;

N³-[2-Chloro-4'-(piperidine-3-sulfonyl)-6-trifluorom-ethyl-biphenyl-4-yl]-1H-[1,2,4]triazole-3,5-diamine;
N³-(2-Chloro-6-fluoro-4'-methanesulfonyl-biphenyl-4-yl)-1H-[1,2,4]triazole-3,5-diamine;
N³-(2,6-Dichloro-4'-methanesufonylmethyl-biphenyl-4-yl)-1H-[1,2,4]triazole-3,5-diamine;
N³-[4'-(Azetidin-3-ylmethoxy)-2,6-dichloro-biphenyl-4-yl]-1H-[1,2,4]triazole-3,5-diamine;
N³-[2-Chloro-4'-(piperazine-1-sulfonyl)-6-trifluorom-ethyl-biphenyl-4-yl]-1H-[1,2,4]triazole-3,5-diamine;
4'(5-Amino-1H-[1,2,4]triazol-3-ylamino)-2'-chloro-6'-fluoro-biphenyl-4-sulfonic acid dimethylamide;
N³-[2-Chloro-4'-((S)-1-pyrrolidin-2-ylmethanesulfonyl)-6-trifluoromethyl-biphenyl-4-yl]-1H-[1,2,4]triazole-3,5-diamine;
N³-[2-Chloro-4'-(morpholine-4-sulfonyl)-6-trifluorom-ethyl-biphenyl-4-yl]-1H-[1,2,4]triazole-3,5-diamine;
N³-[4'-(Azetidin-3-ylmethoxy)-2-chloro-6-trifluorom-ethyl-biphenyl-4-yl]-1H-[1,2,4]triazole-3,5-diamine;
N-{2-[4'-(5-Amino-1H-[1,2,4]triazol-3-ylamino)-2'-chloro-6'-trifluoromethyl-biphenyl-4-yl]-ethyl}-meth-anesulfonamide;
5-((3aR,6S,6aS)-2-Oxo-hexahydro-thieno[3,4-d]imida-zol-6-yl)-pentanoic acid [4'-(5-amino-1H-[1,2,4]tri-azol-3-ylamino)-2',6'-dichloro-biphenyl-4-yl]-amide;
N³-[2-Chloro-4'-(piperidin-4-ylmethanesulfonyl)-6-trif-luoromethyl-biphenyl-4-yl]-1H-[1,2,4]triazole-3,5-di-amine;
N³-[2-Chloro-3'-(piperidin-4-yloxy)-6-trifluoromethyl-biphenyl-4-yl]-1H-[1,2,4]triazole-3,5-diamine;
N³-[3,5-Dichloro-4-(1-methanesulfonyl-1H-indol-5-yl)-phenyl]-1H-[1,2,4]triazole-3,5-diamine;
1-[4'-(5-Amino-1H-[1,2,4]triazol-3-ylamino)-2',6'-di-chloro-biphenyl-4-yl]-pyrrolidin-2-one;
N³-[3-Chloro-4-(4-methanesulfonyl-3,4-dihydro-2H-benzo[1,4]oxazin-6-yl)-5-trifluoromethyl-phenyl]-1H-[1,2,4]triazole-3,5-diamine;
N³-[2-Chloro-4'-(1,1-dioxo-1λ⁶-thiomorpholine-4-sulfo-nyl)-6-trifluoromethyl-biphenyl-4-yl]-1H-[1,2,4]triaz-ole-3,5-diamine;
N-[4'-(5-Amino-1H-[1,2,4]triazol-3-ylamino)-2',6'-di-chloro-3-fluoro-biphenyl-4-yl]-methanesulfonamide;
6-[4-(5-Amino-1H-[1,2,4]triazol-3-ylamino)-2-chloro-6-trifluoromethyl-phenyl]-4H-benzo[1,4]oxazin-3-one;
N³-(2,6-Dichloro-biphenyl-4-yl)-1H-[1,2,4]triazole-3,5-diamine;
N³-[4'-(4-Amino-butoxy)-2,6-dichloro-biphenyl-4-yl]-1H-[1,2,4]triazole-3,5-diamine;
compound with trifluoro-acetic acid;
N³-(4'-Amino-2,6-dichloro-biphenyl-4-yl)-1H-[1,2,4]tri-azole-3,5-diamine;
(S)-1-[4'-(5-Amino-1H-[1,2,4]triazol-3-ylamino)-2'-chloro-6'-trifluoromethyl-biphenyl-4-sulfonyl]-pyrro-lidine-2-carboxylic acid;
N³-[3,5-Dichloro-4-(2,2-dimethyl-4,4-dioxo-3,4-di-hydro-2H-4λ⁶-benzo[1,4]oxathiin-6-yl)-phenyl]-1H-[1,2,4]triazole-3,5-diamine;
Pentanoic acid [4'-(5-amino-1H-[1,2,4]triazol-3-ylamino)-biphenyl-4-yl]-amide;
5-((3aR,6S,6aS)-2-Oxo-hexahydro-thieno[3,4-d]imida-zol-6-yl)-pentanoic acid [4'-(5-amino-1H-[1,2,4]tri-azol-3-ylamino)-biphenyl-4-yl]-amide;
N³-Biphenyl-4-yl-1H-[1,2,4]triazole-3,5-diamine;
N³-{6-Chloro-4'-[1-(3,3-dimethyl-butyl)-piperidin-3-yl-methanesulfonyl]-2-trifluoromethyl-biphenyl-4-yl}-1H-[1,2,4]triazole-3,5-diamine;
N³-{6-Chloro-4'-[1-(3,3-dimethyl-butyl)-piperidin-4-yl-methanesulfonyl]-2-trifluoromethyl-biphenyl-4-yl}-1H-[1,2,4]triazole-3,5-diamine;
N³-[4'-(tert-Butylamino-methyl)-2-chloro-6-trifluorom-ethyl-biphenyl-4-yl]-1H-[1,2,4]triazole-3,5-diamine;
3-[4'-(5-Amino-1H-[1,2,4]triazol-3-ylamino)-6'-cloro-2'-trifluoromethyl-biphenyl-4-sulfonyl]-azetidine-1-car-boxylic acid tert-butyl ester;
4'-(5-Amino-1H-[1,2,4]triazol-3-ylamino)-6'-chloro-2'-trifluoromethyl-biphenyl-4-sulfonic acid (3-methyl-ox-etan-3-yl)-amide;
N³-[6-Chloro-4'-(3-methyl-butane-1-sulfonyl)-2-trifluo-romethyl-biphenyl-4-yl]-1H-[1,2,4]triazole-3,5-di-amine;
N³-[6-Chloro-4'-(3,3-difluoro-pyrrolidine-1-sulfonyl)-2-trifluoromethyl-biphenyl-4-yl]-1H-[1,2,4]triazole-3,5-diamine;
1-[4'-(5-Amino-1H-[1,2,4]triazol-3-ylamino)-6'-chloro-2'-trifluoromethyl-biphenyl-4-sulfonyl]-3-methyl-aze-tidin-3-ol;
N³-(6-Chloro-4'-cyclopropylmethanesulfonyl-2-trifluo-romethyl-biphenyl-4-yl)-1H-[1,2,4]triazole-3,5-di-amine;
N³-[6-Chloro-4'-(2-methyl-propane-1-sulfonyl)-2-trifluo-romethyl-biphenyl-4-yl]-1H-[1,2,4]triazole-3,5-di-amine;
1-[4'-(5-Amino-1H-[1,2,4]triazol-3-ylamino)-6'-chloro-2'-trifluoromethyl-biphenyl-4-sulfonyl]-4-methyl-pip-eridin-4-ol;
N³-[4'-(Azetidine-3-sulfonyl)-6-chloro-2-trifluorom-ethyl-biphenyl-4-yl]-1H-[1,2,4]triazole-3,5-diamine;
1-[4'-(5-Amino-1H-[1,2,4]triazol-3-ylamino)-6'-chloro-2'-trifluoromethyl-biphenyl-4-sulfonyl]-3-methyl-pyr-rolidin-3-ol;
N³-[6-Chloro-4'-(2-oxa-6-aza-spiro[3.3]heptane-6-sulfo-nyl)-2-trifluoromethyl-biphenyl-4-yl]-1H-[1,2,4]triaz-ole-3,5-diamine;
N⁵-(2-Fluoro-4'-methanesulfonyl-6-trifluoromethyl-bi-phenyl-4-yl)-1H-[1,2,4]triazole-3,5-diamine;
N⁵-[2-Fluoro-4'-(propane-2-sulfonyl)-6-trifluoromethyl-biphenyl-4-yl]-1H-[1,2,4]triazole-3,5-diamine;
4'-(5-Amino-2H-[1,2,4]triazol-3-ylamino)-2'-fluoro-6'-trifluoromethyl-biphenyl-4-sulfonic acid methylamide;
N-[4'-(5-Amino-1H-[1,2,4]triazol-3-ylamino)-2',6'-di-chloro-biphenyl-4-yl]-2-methoxy-acetamide;
N⁵-(2-Fluoro-3'-methanesulfonyl-6-trifluoromethyl-bi-phenyl-4-yl)-1H-[1,2,4]triazole-3,5-diamine;
4'-(5-Amino-2H-[1,2,4]triazol-3-ylamino)-2'-fluoro-6'-trifluoromethyl-biphenyl-4-sulfonic acid dimethylam-ide;
N⁵-(2,6-Difluoro-4'-methanesulfonyl-biphenyl-4-yl)-1H-[1,2,4]triazole-3,5-diamine;
N⁵-[2,6-Difluoro-4'-(morpholine-4-sulfonyl)-biphenyl-4-yl]-1H-[1,2,4]triazole-3,5-diamine;
N⁵-[2-Fluoro-4'-(morpholine-4-sulfonyl)-6-trifluorom-ethyl-biphenyl-4-yl]-1H-[1,2,4]triazole-3,5-diamine;
4'-(5-Amino-2H-[1,2,4]triazol-3-ylamino)-2'-fluoro-6'-trifluoromethyl-biphenyl-4-carbonitrile;
N⁵-(2,6-Difluoro-3'-methanesulfonyl-biphenyl-4-yl)-1H-[1,2,4]triazole-3,5-diamine;
4'-(5-Amino-2H-[1,2,4]triazol-3-ylamino)-2'-fluoro-6'-trifluoromethyl-biphenyl-3-sulfonic acid methylamide;
Tetrahydro-pyran-4-carboxylic acid [4'-(5-amino-1H-[1,2,4]triazol-3-ylamino)-2',6'-dichloro-biphenyl-4-yl]-amide;
N³-(2,6-Dichloro-4'-nitro-biphenyl-4-yl)-1H-[1,2,4]triaz-ole-3,5-diaminetrifluoro-acetic acid;

4'-(5-Amino-2H-[1,2,4]triazol-3-ylamino)-2'-fluoro-6'-trifluoromethyl-biphenyl-3-sulfonic acid dimethylamide;

4'-(5-Amino-2H-[1,2,4]triazol-3-ylamino)-2'-fluoro-6'-trifluoromethyl-biphenyl-4-carboxylic acid dimethylamide;

$N^5$-(2-Fluoro-4'-methoxy-6-trifluoromethyl-biphenyl-4-yl)-1H-[1,2,4]triazole-3,5-diamine;

4'-(5-Amino-2H-[1,2,4]triazol-3-ylamino)-2',6'-difluoro-biphenyl-4-carbonitrile;

$N^5$-(2-Fluoro-4'-trifluoromethanesulfonyl-6-trifluoromethyl-biphenyl-4-yl)-1H-[1,2,4]triazole-3,5-diamine;

4'-(5-Amino-2H-[1,2,4]triazol-3-ylamino)-2'-fluoro-6'-trifluoromethyl-biphenyl-3-carbonitrile;

$N^3$-(4-Methanesulfonyl-2-trifluoromethyl-biphenyl-4-yl)-1H-[1,2,4]triazole-3,5-diamine;

$N^3$-(2,6-Dichloro-4'-trifluoromethoxy-biphenyl-4-yl)-1H-[1,2,4]triazole-3,5-diamine;

$N^3$-(2,6,3'-Trichloro-biphenyl-4-yl)-1H-[1,2,4]triazole-3,5-diamine;

4'-(5-Amino-1H-[1,2,4]triazol-3-ylamino)-2',6'-dichloro-biphenyl-4-carbonitrile;

$N^3$-(2,6-Dichloro-4'-methanesulfonyl-biphenyl-4-yl)-1H-[1,2,4]triazole-3,5-diamine;

$N^3$-(3,5-Dichloro-4-naphthalen-1-yl-phenyl)-1H-[1,2,4]triazole-3,5-diamine;

$N^3$-(2,6,4'-Trichloro-biphenyl-4-yl)-1H-[1,2,4]triazole-3,5-diamine;

$N^3$-(2,6-Dichloro-4'-methyl-biphenyl-4-yl)-1H-[1,2,4]triazole-3,5-diamine;

$N^3$-(2,6-Dichloro-4'-methoxy-biphenyl-4-yl)-1H-[1,2,4]triazole-3,5-diamine;

$N^3$-(2,6-Dichloro-4'-trifluoromethyl-biphenyl-4-yl)-1H-[1,2,4]triazole-3,5-diamine;

$N^3$-(2,6-Dichloro-3'-methoxy-biphenyl-4-yl)-1H-[1,2,4]triazole-3,5-diamine;

$N^3$-(2,6,2'-Trichloro-biphenyl-4-yl)-1H-[1,2,4]triazole-3,5-diamine;

$N^3$-(2,6,3',4'-Tetrachloro-biphenyl-4-yl)-1H-[1,2,4]triazole-3,5-diamine;

4'-(5-Amino-1H-[1,2,4]triazol-3-ylamino)-2',6'-dichloro-biphenyl-3-carbonitrile;

4'-(5-Amino-1H-[1,2,4]triazol-3-ylamino)-2',6'-dichloro-biphenyl-2-carbonitrile;

4'-(5-Amino-1H-[1,2,4]triazol-3-ylamino)-4,2',6'-trichloro-biphenyl-3-carbonitrile;

4'-(5-Amino-1H-[1,2,4]triazol-3-ylamino)-2',6'-dichloro-biphenyl-3-carboxylic acid;

1-[4'-(5-Amino-1H-[1,2,4]triazol-3-ylamino)-2',6'-dichloro-biphenyl-4-yl]-ethanone;

$N^3$-(2,6-Dichloro-3'-trifluoromethyl-biphenyl-4-yl)-1H-[1,2,4]triazole-3,5-diamine;

$N^3$-(2,6,2',3'-Tetrachloro-biphenyl-4-yl)-1H-[1,2,4]triazole-3,5-diamine;

4'-(5-Amino-1H-[1,2,4]triazol-3-ylamino)-2',6'-dichloro-biphenyl-4-carboxylic acid methyl ester;

N-[4'-(5-Amino-1H-[1,2,4]triazol-3-ylamino)-2',6'-dichloro-biphenyl-4-yl]-methanesulfonamide;

N-[4'-(5-Amino-1H-[1,2,4]triazol-3-ylamino)-2',6'-dichloro-biphenyl-3-yl]-methanesulfonamide;

4'-(5-Amino-1H-[1,2,4]triazol-3-ylamino)-2',6'-dichloro-biphenyl-4-carboxylic acid dimethylamide;

$N^3$-(2,6-Dichloro-3'-methanesulfonyl-biphenyl-4-yl)-1H-[1,2,4]triazole-3,5-diamine;

4'-(5-Amino-1H-[1,2,4]triazol-3-ylamino)-2',6'-dichloro-biphenyl-3-carboxylic acid dimethylamide;

4'-(5-Amino-1H-[1,2,4]triazol-3-ylamino)-2',6'-dichloro-biphenyl-4-carboxylic acid methylamide;

4'-(5-Amino-1H-[1,2,4]triazol-3-ylamino)-2',6'-dichloro-biphenyl-3-carboxylic acid methylamide;

4'-(5-Amino-1H-[1,2,4]triazol-3-ylamino)-2',6'-dichloro-biphenyl-4-sulfonic acid methylamide;

4'-(5-Amino-1H-[1,2,4]triazol-3-ylamino)-2',6'-dichloro-biphenyl-3-sulfonic acid methylamide;

$N^3$-(2,6-Dichloro-2'-methoxy-biphenyl-4-yl)-1H-[1,2,4]triazole-3,5-diamine;

$N^3$-(2,6-Dichloro-3'-fluoro-4'-methanesulfonyl-biphenyl-4-yl)-1H-[1,2,4]triazole-3,5-diamine;

$N^3$-[2,6-Dichloro-4'-(propane-2-sulfonyl)-biphenyl-4-yl]-1H-[1,2,4]triazole-3,5-diamine;

4'-(5-Amino-1H-[1,2,4]triazol-3-ylamino)-2',6'-dichloro-biphenyl-4-sulfonic acid dimethylamide;

$N^3$-(2,6,2',4'-Tetrachloro-biphenyl-4-yl)-1H-[1,2,4]triazole-3,5-diamine;

{2-[4'-(5-Amino-1H-[1,2,4]triazol-3-ylamino)-6'-chloro-2'-trifluoromethyl-biphenyl-4-yloxy]-ethyl}-methyl-carbamic acid tert-butyl ester;

$N^3$-[6-Chloro-4'-(2-methylamino-ethoxy)-2-trifluoromethyl-biphenyl-4-yl]-1H-[1,2,4]triazole-3,5-diamine;

$N^3$-[6-Chloro-4'-(1,2,2,6,6-pentamethyl-piperidin-4-ylsulfanyl)-2-trifluoromethyl-biphenyl-4-yl]-1H-[1,2,4]triazole-3,5-diamine;

{2-[4'-(5-Amino-1H-[1,2,4]triazol-3-ylamino)-6'-cloro-2'-trifluoromethyl-biphenyl-4-yloxy]-1,1-dimethyl-ethyl}-methyl-carbamic acid tert-butyl ester;

3-[4'-(5-Amino-1H-[1,2,4]triazol-3-ylamino)-6'-chloro-2'-trifluoromethyl-biphenyl-4-yloxy]-piperidine-1-carboxylic acid tert-butyl ester;

$N^3$-[6-Chloro-4'-(piperidin-3-yloxy)-2-trifluoromethyl-biphenyl-4-yl]-1H-[1,2,4]triazole-3,5-diamine;

$N^3$-{6-Chloro-4'-[1-(3,3-dimethyl-butyl)-piperidin-3-yloxy]-2-trifluoromethyl-biphenyl-4-yl}-1H-[1,2,4]triazole-3,5-diamine;

$N^3$-[6-Chloro-4'-(1-methyl-piperidin-3-yloxy)-2-trifluoromethyl-biphenyl-4-yl]-1H-[1,2,4]triazole-3,5-diamine;

$N^3$-{6-Chloro-2-trifluoromethyl-4'-[1-(3,3,3-trifluoropropyl)-piperidin-3-yloxy]-biphenyl-4-yl}-1H-[1,2,4]triazole-3,5-diamine;

{2-[4'-(5-Amino-1H-[1,2,4]triazol-3-ylamino)-6'-chloro-2'-trifluoromethyl-biphenyl-4-yloxy]-ethyl}-carbamic acid tert-butyl ester;

$N^3$-[4'-(2-Amino-ethoxy)-6-chloro-2-trifluoromethyl-biphenyl-4-yl]-1H-[1,2,4]triazole-3,5-diamine;

$N^3$-{6-Chloro-4'-[2-(3,3-dimethyl-butylamino)-ethoxy]-2-trifluoromethyl-biphenyl-4-yl}-1H-[1,2,4]triazole-3,5-diamine;

$N^3$-(4'-{2-[Bis-(3,3-dimethyl-butyl)-amino]-ethoxy}-6-chloro-2-trifluoromethyl-biphenyl-4-yl)-1H-[1,2,4]triazole-3,5-diamine;

4-[4'-(5-Amino-1H-[1,2,4]triazol-3-ylamino)-6'-chloro-2'-trifluoromethyl-biphenyl-4-yloxy]-piperidine-1-carboxylic acid tert-butyl ester;

$N^3$-[6-Chloro-4'-(piperidin-4-yloxy)-2-trifluoromethyl-biphenyl-4-yl]-1H-[1,2,4]triazole-3,5-diamine;

$N^3$-{6-Chloro-2-trifluoromethyl-4'-[1-(3,3,3-trifluoropropyl)-piperidin-4-yloxy]-biphenyl-4-yl}-1H-[1,2,4]triazole-3,5-diamine;

$N^3$-{6-Chloro-4'-[1-(2-methanesulfonyl-ethyl)-piperidin-4-yloxy]-2-trifluoromethyl-biphenyl-4-yl}-1H-[1,2,4]triazole-3,5-diamine;

N³-{6-Chloro-4'-[1-(3-methanesulfonyl-propyl)-piperidin-4-yloxy]-2-trifluoromethyl-biphenyl-4-yl}-1H-[1,2,4]triazole-3,5-diamine;
N³-{6-Chloro-4'-[1-(2-methoxy-ethyl)-piperidin-4-yloxy]-2-trifluoromethyl-biphenyl-4-yl}-1H-[1,2,4]triazole-3,5-diamine;
N³-(2-Chloro-biphenyl-4-yl)-1H-[1,2,4]triazole-3,5-diamine;
N³-(2-Chloro-4'-fluoro-biphenyl-4-yl)-1H-[1,2,4]triazole-3,5-diamine;
N³-(2-Chloro-2'-fluoro-biphenyl-4-yl)-1H-[1,2,4]triazole-3,5-diamine;
N³-(2-Chloro-3',4'-difluoro-biphenyl-4-yl)-1H-[1,2,4]triazole-3,5-diamine;
N³-(2-Chloro-3'-fluoro-biphenyl-4-yl)-1H-[1,2,4]triazole-3,5-diamine;
N³-(2-Trifluoromethyl-biphenyl-4-yl)-1H-[1,2,4]triazole-3,5-diamine;
N³-(2'-Fluoro-2-trifluoromethyl-biphenyl-4-yl)-1H-[1,2,4]triazole-3,5-diamine;
N³-(4'-Fluoro-2-trifluoromethyl-biphenyl-4-yl)-1H-[1,2,4]triazole-3,5-diamine;
N³-(3',4'-Difluoro-2-trifluoromethyl-biphenyl-4-yl)-1H-[1,2,4]triazole-3,5-diamine;
N³-(2'-Chloro-2-trifluoromethyl-biphenyl-4-yl)-1H-[1,2,4]triazole-3,5-diamine;
N³-(2-Chloro-4'-methanesulfonyl-biphenyl-4-yl)-1H-[1,2,4]triazole-3,5-diamine;
N³-(2,2'-Dichloro-biphenyl-4-yl)-1H-[1,2,4]triazole-3,5-diamine;
N³-(2-Chloro-2'-fluoro-4'-methylsulfanyl-biphenyl-4-yl)-H-[1,2,4]triazole-3,5-diamine;
N³-(2-Chloro-2'-fluoro-4'-methanesulfonyl-biphenyl-4-yl)-1H-[1,2,4]triazole-3,5-diamine;
4'-(5-Amino-1H-[1,2,4]triazol-3-ylamino)-2',6'-dichloro-biphenyl-3-carboxylic acid amide;
4'-(5-Amino-1H-[1,2,4]triazol-3-ylamino)-2',6'-dichloro-biphenyl-4-carboxylic acid amide;
4'-(5-Amino-1H-[1,2,4]triazol-3-ylamino)-2',6'-dichloro-biphenyl-4-sulfonic acid (2-hydroxy-ethyl)-amide;
4'-(5-Amino-1H-[1,2,4]triazol-3-ylamino)-2'-chloro-6'-trifluoromethyl-biphenyl-4-sulfonic acid (2-hydroxy-ethyl)-amide;
2-[4'-(5-Amino-1H-[1,2,4]triazol-3-ylamino)-2'-chloro-6'-trifluoromethyl-biphenyl-4-sulfonyl]-ethanol;
4-[4'-(5-Amino-1H-[1,2,4]triazol-3-ylamino)-6'-chloro-3-methoxy-2'-trifluoromethyl-biphenyl-4-sulfonyl amino]-piperidine-1-carboxylic acid tert-butyl ester;
4'-(5-Amino-1H-[1,2,4]triazol-3-ylamino)-2',6'-dichloro-biphenyl-4-sulfonic acid tert-butylamide;
4'-(5-Amino-1H-[1,2,4]triazol-3-ylamino)-6'-chloro-2'-trifluoromethyl-biphenyl-4-sulfonic acid (2,2,2-trifluoro-1,1-dimethyl-ethyl)-amide;
4-[4'-(5-Amino-1H-[1,2,4]triazol-3-ylamino)-6'-chloro-4-methoxy-2'-trifluoromethyl-biphenyl-3-sulfonyl]-piperazine-1-carboxylic acid tert-butyl ester;
4'-(5-Amino-1H-[1,2,4]triazol-3-ylamino)-6'-chloro-3-methoxy-2'-trifluoromethyl-biphenyl-4-sulfonic acid (4-hydroxy-cyclohexyl)-amide;
4'-(5-Amino-1H-[1,2,4]triazol-3-ylamino)-6'-chloro-4-methoxy-2'-trifluoromethyl-biphenyl-3-sulfonic acid (tetrahydro-pyran-4-yl)-amide;
4'-(5-Amino-1H-[1,2,4]triazol-3-ylamino)-6'-chloro-2'-trifluoromethyl-biphenyl-4-sulfonic acid cyclopropylamide;
N³-[6-Chloro-4'-(pyrrolidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-2'-trifluoromethyl-biphenyl-4-sulfonic acid amide;
4'-(5-Amino-1H-[1,2,4]triazol-3-ylamino)-6'-chloro-2'-trifluoromethyl-biphenyl-4-sulfonic acid (3-hydroxy-cyclobutyl)-amide;
4'-(5-Amino-1H-[1,2,4]triazol-3-ylamino)-6'-chloro-2'-trifluoromethyl-biphenyl-4-sulfonic acid (3-hydroxy-cyclobutyl)-amide;
4'-(5-Amino-1H-[1,2,4]triazol-3-ylamino)-6'-chloro-2'-trifluoromethyl-biphenyl-4-sulfonic acid (3-hydroxy-cyclobutyl)-amide;
4'-(5-amino-1H-1,2,4-triazol-3-ylamino)-2'-chloro-N-(2-hydroxyethyl)-4-methoxy-6'-(trifluoromethyl)biphenyl-3-sulfonamide
4'-(5-Amino-1H-[1,2,4]triazol-3-ylamino)-6'-chloro-4-methoxy-2'-trifluoromethyl-biphenyl-3-sulfonic acid (2-hydroxy-ethyl)-amide;
4'-(5-Amino-1H-[1,2,4]triazol-3-ylamino)-6'-chloro-2'-trifluoromethyl-biphenyl-3-sulfonic acid tert-butylamide;
N³-[6-Chloro-4'-methoxy-3'-(morpholine-4-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-3-methoxy-2'-trifluoromethyl-biphenyl-4-sulfonic acid piperidin-4-ylamide;
4'-(5-Amino-1H-[1,2,4]triazol-3-ylamino)-6'-chloro-4-methoxy-2'-trifluoromethyl-biphenyl-3-sulfonic acid amide;
N³-[6-Chloro-4'-(propane-2-sulfonyl)-2-trifluoromethyl-biphenyl-4-yl]-1H-[1,2,4]triazole-3,5-diamine;
N³-[6-Chloro-4'-methoxy-3'-(piperazine-1-sulfonyl)-2-trifluoromethyl-biphenyl-4-yl]-1H-[1,2,4]triazole-3,5-diamine;
N³-[6-Chloro-4'-(4,4-difluoro-piperidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-2'-trifluoromethyl-biphenyl-4-sulfonic acid (4-hydroxy-cyclohexyl)-amide;
4'-(5-Amino-1H-[1,2,4]triazol-3-ylamino)-6'-chloro-2'-trifluoromethyl-biphenyl-4-sulfonic acid dimethylamide;
N-[4'-(5-Amino-1H-[1,2,4]triazol-3-ylamino)-6'-chloro-2'-trifluoromethyl-biphenyl-4-ylmethyl]-methanesulfonamide;
N³-(6-Chloro-4'-methanesulfonyl-2-trifluoromethyl-biphenyl-4-yl)-1H-[1,2,4]triazole-3,5-diamine;
N³-(6-Chloro-4'-cyclopropanesulfonyl-2-trifluoromethyl-biphenyl-4-yl)-1H-[1,2,4]triazole-3,5-diamine;
4'-(5-Amino-1H-[1,2,4]triazol-3-ylamino)-6'-chloro-2'-trifluoromethyl-biphenyl-4-carboxylic acid methylamide;
4'-(5-Amino-1H-[1,2,4]triazol-3-ylamino)-6'-chloro-4-methoxy-2'-trifluoromethyl-biphenyl-3-sulfonic acid (4-hydroxy-cyclohexyl)-amide;
1-[4'-(5-Amino-1H-[1,2,4]triazol-3-ylamino)-6'-chloro-2'-trifluoromethyl-biphenyl-4-sulfonyl]-azetidin-3-ol;
N³-[6-Chloro-3'-(pyrrolidine-1-sulfonyl)-2-trifluoromethyl-biphenyl-4-yl]-1H-[1,2,4]triazole-3,5-diamine;
4'-(5-Amino-1H-[1,2,4]triazol-3-ylamino)-6'-chloro-4-trifluoromethoxy-2'-trifluoromethyl-biphenyl-3-sulfonic acid tert-butylamide;
1-[4'-(5-Amino-1H-[1,2,4]triazol-3-ylamino)-6'-chloro-2'-trifluoromethyl-biphenyl-4-sulfonyl]-piperidin-4-ol;
N³-(6-Chloro-3'-methanesulfonyl-2-trifluoromethyl-biphenyl-4-yl)-H-[1,2,4]triazole-3,5-diamine;

4'-(5-Amino-1H-[1,2,4]triazol-3-ylamino)-6'-chloro-2'-trifluoromethyl-biphenyl-3-sulfonic acid tert-butyl-methyl-amide;

4'-(5-Amino-1H-[1,2,4]triazol-3-ylamino)-6'-chloro-2'-trifluoromethyl-biphenyl-3-sulfonic acid amide;

4'-(5-Amino-1H-[1,2,4]triazol-3-ylamino)-6'-chloro-2'-trifluoromethyl-biphenyl-3-sulfonic acid dimethylamide;

N-[4'-(5-Amino-1H-[1,2,4]triazol-3-ylamino)-6'-chloro-2'-trifluoromethyl-biphenyl-3-ylmethyl]-methanesulfonamide;

4'-(5-Amino-1H-[1,2,4]triazol-3-ylamino)-6'-chloro-2'-trifluoromethyl-biphenyl-4-carboxylic acid tert-butyl ester;

$N^3$-(6-Chloro-2-trifluoromethyl-biphenyl-4-yl)-1H-[1,2,4]triazole-3,5-diamine;

4'-(5-Amino-1H-[1,2,4]triazol-3-ylamino)-6'-chloro-2'-trifluoromethyl-biphenyl-4-carboxylic acid;

$N^3$-[6-Chloro-4'-methoxy-3'-(pyrrolidine-1-sulfonyl)-2-trifluoromethyl-biphenyl-4-yl]-1H-[1,2,4]triazole-3,5-diamine;

4'-(5-Amino-1H-[1,2,4]triazol-3-ylamino)-6'-chloro-4-methoxy-2'-trifluoromethyl-biphenyl-3-sulfonic acid piperidin-4-ylamide 3-[4'-(5-Amino-1H-[1,2,4]triazol-3-ylamino)-6'-chloro-2'-trifluoromethyl-biphenyl-4-sulfonylamino]-3-methyl-azetidine-1-carboxylic acid tert-butyl ester;

4'-(5-Amino-1H-[1,2,4]triazol-3-ylamino)-6'-chloro-2'-trifluoromethyl-biphenyl-4-sulfonic acid (1-methyl-cyclopropyl)-amide;

4'-(5-Amino-1H-[1,2,4]triazol-3-ylamino)-6'-chloro-2'-trifluoromethyl-biphenyl-4-sulfonic acid (3-methyl-azetidin-3-yl)-amide;

4-[4'-(5-Amino-1H-[1,2,4]triazol-3-ylamino)-6'-chloro-2'-trifluoromethyl-biphenyl-4-sulfonyl]-4,7-diaza-spiro[2.5]octane-7-carboxylic acid tert-butyl ester;

{2-[4'-(5-Amino-1H-[1,2,4]triazol-3-ylamino)-6'-chloro-2'-trifluoromethyl-biphenyl-4-sulfonylamino]-ethyl}-methyl-carbamic acid tert-butyl ester;

4'-(5-Amino-1H-[1,2,4]triazol-3-ylamino)-6'-chloro-2'-trifluoromethyl-biphenyl-4-sulfonic acid (1-isopropyl-3-methyl-azetidin-3-yl)-amide;

4'-(5-Amino-1H-[1,2,4]triazol-3-ylamino)-6'-chloro-2'-trifluoromethyl-biphenyl-4-sulfonic acid (1-isopropyl-3-methyl-azetidin-3-yl)-amide;

3-[4'-(5-Amino-1H-[1,2,4]triazol-3-ylamino)-6'-chloro-4-methoxy-2'-trifluoromethyl-biphenyl-3-sulfonylamino]-3-methyl-azetidine-1-carboxylic acid tert-butyl ester;

4'-(5-Amino-1H-[1,2,4]triazol-3-ylamino)-6'-chloro-2'-trifluoromethyl-biphenyl-4-sulfonic acid (2-methyl-amino-ethyl)-amide;

$N^3$-[6-Chloro-4'-(4,7-diaza-spiro[2.5]octane-4-sulfonyl)-2-trifluoromethyl-biphenyl-4-yl]-1H-[1,2,4]triazole-3,5-diamine;

4'-(5-Amino-1H-[1,2,4]triazol-3-ylamino)-6'-chloro-4-methoxy-2'-trifluoromethyl-biphenyl-3-sulfonic acid (3-methyl-azetidin-3-yl)-amide;

4'-(5-Amino-1H-[1,2,4]triazol-3-ylamino)-6'-chloro-4-methoxy-2'-trifluoromethyl-biphenyl-3-sulfonic acid tert-butylamide;

4'-(5-Amino-1H-[1,2,4]triazol-3-ylamino)-6'-chloro-trifluoromethoxy-2'-trifluoromethyl-biphenyl-4-sulfonic acid tert-butylamide;

4'-(5-Amino-1H-[1,2,4]triazol-3-ylamino)-6'-chloro-4-methoxy-2'-trifluoromethyl-biphenyl-3-sulfonic acid (2-hydroxy-1,1-dimethyl-ethyl)-amide;

4'-(5-Amino-1H-[1,2,4]triazol-3-ylamino)-2'-chloro-6'-trifluoromethyl-biphenyl-4-sulfonic acid tert-butylamide;

$N^3$-[2,6-Dichloro-4'-(pyrrolidine-1-sulfonyl)-biphenyl-4-yl]-1H-[1,2,4]triazole-3,5-diamine;

4-[4'-(5-Amino-1H-[1,2,4]triazol-3-ylamino)-6'-chloro-4-methoxy-2'-trifluoromethyl-biphenyl-3-sulfonylamino]-piperidine-1-carboxylic acid tert-butyl ester;

4'-(5-Amino-1H-[1,2,4]triazol-3-ylamino)-2'-chloro-4-methoxy-6'-trifluoromethyl-biphenyl-3-sulfonic acid piperidin-4-ylamide;

4'-(5-Amino-1H-[1,2,4]triazol-3-ylamino)-6'-chloro-2'-trifluoromethyl-biphenyl-4-sulfonic acid tert-butyl-(2,2,2-trifluoro-ethyl)-amide;

$N^3$-[6-Chloro-4'-(3,3-difluoro-azetidine-1-sulfonyl)-2-trifluoromethyl-biphenyl-4-yl]-1H-[1,2,4]triazole-3,5-diamine;

4'-(5-Amino-1H-[1,2,4]triazol-3-ylamino)-6'-chloro-4-methoxy-2'-trifluoromethyl-biphenyl-3-sulfonic acid (1-cyano-cyclopropyl)-amide;

4'-(5-Amino-1H-[1,2,4]triazol-3-ylamino)-6'-chloro-2'-trifluoromethyl-biphenyl-4-sulfonic acid (2-hydroxy-1,1-dimethyl-ethyl)-amide;

4'-(5-Amino-1H-[1,2,4]triazol-3-ylamino)-2'-chloro-4-methoxy-6'-trifluoromethyl-biphenyl-3-sulfonic acid (1-acetyl-piperidin-4-yl)-amide;

N*3*-[6-Chloro-4'-(propane-2-sulfonyl)-2-trifluoromethyl-biphenyl-4-yl]-1H-[1,2,4]triazole-3,5-diamine $N^3$-(6-Chloro-3'-isopropoxy-4'-methoxy-2-trifluoromethyl-biphenyl-4-yl)-1H-[1,2,4]triazole-3,5-diamine;

$N^3$-(4'-tert-Butoxy-6-chloro-2-trifluoromethyl-biphenyl-4-yl)-1H-[1,2,4]triazole-3,5-diamine;

$N^3$-(6-Chloro-4'-methoxy-2,3'-bis-trifluoromethyl-biphenyl-4-yl)-1H-[1,2,4]triazole-3,5-diamine;

$N^3$-[6'-Chloro-4,4"-bis-(pyrrolidine-1-sulfonyl)-[1,1';2',1"]terphenyl-4'-yl]-1H-[1,2,4]triazole-3,5-diamine;

$N^3$-[6-Chloro-4'-(3-fluoro-azetidine-1-sulfonyl)-2-trifluoromethyl-biphenyl-4-yl]-1H-[1,2,4]triazole-3,5-diamine;

4'-(5-Amino-1H-[1,2,4]triazol-3-ylamino)-6'-chloro-4-methoxy-2'-trifluoromethyl-biphenyl-3-sulfonic acid piperidin-4-yl-(2,2,2-trifluoro-ethyl)-amide;

4,4-Difluoro-cyclohexanecarboxylic acid [4'-(5-amino-1H-[1,2,4]triazol-3-ylamino)-6'-chloro-2'-trifluoromethyl-biphenyl-4-yl]-amide;

[4'-(5-Amino-1H-[1,2,4]triazol-3-ylamino)-6'-chloro-2'-trifluoromethyl-biphenyl-4-yl]-carbamic acid 1-tert-butyl-azetidin-3-yl ester;

[4'-(5-Amino-1H-[1,2,4]triazol-3-ylamino)-6'-chloro-2'-trifluoromethyl-biphenyl-4-yl]-carbamic acid propyl ester;

N-[4'-(5-Amino-1H-[1,2,4]triazol-3-ylamino)-6'-chloro-2'-trifluoromethyl-biphenyl-4-yl]-3-(tetrahydro-pyran-4-yl)-propionamide;

1,1-Dioxo-hexahydro-1$\lambda^6$-thiopyran-4-carboxylic acid [4'-(5-amino-1H-[1,2,4]triazol-3-ylamino)-6'-chloro-2'-trifluoromethyl-biphenyl-4-yl]-amide;

N-[4'-(5-Amino-1H-[1,2,4]triazol-3-ylamino)-6'-chloro-2'-trifluoromethyl-biphenyl-4-yl]-2-(1,1-dioxo-1$\lambda^6$-thiomorpholin-4-yl)-acetamide;

N-[4'-(5-Amino-1H-[1,2,4]triazol-3-ylamino)-6'-chloro-2'-trifluoromethyl-biphenyl-4-yl]-2-morpholin-4-yl-acetamide;

N-[4'-(5-Amino-2H-[1,2,4]triazol-3-ylamino)-6'-fluoro-2'-trifluoromethyl-biphenyl-4-yl]-methanesulfonamide;

N-[4'-(5-Amino-2H-[1,2,4]triazol-3-ylamino)-6'-fluoro-2'-trifluoromethyl-biphenyl-3-yl]-methanesulfonamide;

$N^5$-(6,3'-Difluoro-2-trifluoromethyl-biphenyl-4-yl)-H-[1,2,4]triazole-3,5-diamine;

$N^5$-(6,4'-Difluoro-2-trifluoromethyl-biphenyl-4-yl)-1H-[1,2,4]triazole-3,5-diamine;

$N^5$-(6-Fluoro-2,4'-bis-trifluoromethyl-biphenyl-4-yl)-1H-[1,2,4]triazole-3,5-diamine;

$N^5$-(6-Fluoro-4'-methyl-2-trifluoromethyl-biphenyl-4-yl)-1H-[1,2,4]triazole-3,5-diamine;

4'-(5-Amino-2H-[1,2,4]triazol-3-ylamino)-6'-fluoro-2'-trifluoromethyl-biphenyl-3-carboxylic acid methylamide;

$N^5$-(3-Fluoro-4-naphthalen-2-yl-5-trifluoromethyl-phenyl)-1H-[1,2,4]triazole-3,5-diamine;

4,4-Difluoro-cyclohexanecarboxylic acid [4'-(5-amino-1H-[1,2,4]triazol-3-ylamino)-2',6'-dichloro-biphenyl-4-yl]-amide;

N-[4'-(5-Amino-1H-[1,2,4]triazol-3-ylamino)-2',6'-dichloro-biphenyl-4-yl]-isobutyramide;

N-[4'-(5-Amino-1H-[1,2,4]triazol-3-ylamino)-2',6'-dichloro-biphenyl-3-yl]-isobutyramide;

4'-(5-Amino-1H-[1,2,4]triazol-3-ylamino)-2',6'-dichloro-biphenyl-4-sulfonic acid amide;

5-[4-(5-Amino-2H-[1,2,4]triazol-3-ylamino)-2,6-dichloro-phenyl]-1,3-dihydro-indol-2-one;

5-[4-(5-Amino-2H-[1,2,4]triazol-3-ylamino)-2,6-dichloro-phenyl]-1,3-dihydro-benzoimidazol-2-one;

6-[4-(5-Amino-2H-[1,2,4]triazol-3-ylamino)-2,6-dichloro-phenyl]-1,3-dihydro-indol-2-one;

$N^5$-[3,5-Dichloro-4-(1H-indazol-5-yl)-phenyl]-1H-[1,2,4]triazole-3,5-diamine;

$N^3$-(2',6'-Dichloro-biphenyl-4-yl)-1H-[1,2,4]triazole-3,5-diamine;

$N^5$-[2,6-Dichloro-4'-(piperidin-3-yloxy)-biphenyl-4-yl]-1H-[1,2,4]triazole-3,5-diamine;

3-[4'-(5-Amino-1H-[1,2,4]triazol-3-ylamino)-2',6'-dichloro-biphenyl-4-yloxymethyl]-azetidine-1-carboxylic acid tert-butyl ester;

{2-[4'-(5-Amino-1H-[1,2,4]triazol-3-ylamino)-2',6'-dichloro-biphenyl-4-yloxy]-ethyl}-methyl-carbamic acid tert-butyl ester;

$N^3$-[2,6-Dichloro-4'-(piperidin-4-yloxy)-biphenyl-4-yl]-1H-[1,2,4]triazole-3,5-diamine;

$N^3$-[2,6-Dichloro-4'-(2-methylamino-ethoxy)-biphenyl-4-yl]-1H-[1,2,4]triazole-3,5-diamine;

$N^3$-[2,6-Dichloro-4'-(2-pyrrolidin-2-yl-ethoxy)-biphenyl-4-yl]-1H-[1,2,4]triazole-3,5-diamine;

$N^3$-[2,6-Dichloro-4'-((S)-1-pyrrolidin-2-ylmethoxy)-biphenyl-4-yl]-1H-[1,2,4]triazole-3,5-diamine;

2-{2-[4'-(5-Amino-1H-[1,2,4]triazol-3-ylamino)-2',6'-dichloro-biphenyl-4-yloxy]-ethyl}-pyrrolidine-1-carboxylic acid tert-butyl ester;

(R)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester;

4-[4'-(5-Amino-1H-[1,2,4]triazol-3-ylamino)-2',6'-dichloro-biphenyl-4-yloxy]-piperidine-1-carboxylic acid tert-butyl ester;

$N^3$-[2,6-Dichloro-4'-(2-dimethylamino-ethoxy)-biphenyl-4-yl]-1H-[1,2,4]triazole-3,5-diamine;

$N^3$-[6-Chloro-4'-((S)-1-pyrrolidin-2-ylmethoxy)-2-trifluoromethyl-biphenyl-4-yl]-1H-[1,2,4]triazole-3,5-diamine;

$N^3$-[2,6-Dichloro-4'-((S)-pyrrolidin-3-yloxy)-biphenyl-4-yl]-1H-[1,2,4]triazole-3,5-diamine;

$N^3$-[2,6-Dichloro-4'-((R)-1-pyrrolidin-2-ylmethoxy)-biphenyl-4-yl]-1H-[1,2,4]triazole-3,5-diamine;

(S)-3-[4'-(5-Amino-1H-[1,2,4]triazol-3-ylamino)-2',6'-dichloro-biphenyl-4-yloxy]-pyrrolidine-1-carboxylic acid tert-butyl ester;

$N^3$-[2,6-Dichloro-4'-(2,2-dimethyl-[1,3]dioxolan-4-ylmethoxy)-biphenyl-4-yl]-1H-[1,2,4]triazole-3,5-diamine;

(R)-2-[4'-(5-Amino-1H-[1,2,4]triazol-3-ylamino)-2',6'-dichloro-biphenyl-4-yloxymethy]-pyrrolidine-1-carboxylic acid tert-butyl ester;

[4'-(5-Amino-1H-[1,2,4]triazol-3-ylamino)-2',6'-dichloro-biphenyl-4-yloxy]-acetic acid tert-butyl ester;

(S)-2-[4'-(5-Amino-1H-[1,2,4]triazol-3-ylamino)-2'-chloro-6'-trifluoromethyl-biphenyl-4-yloxymethyl]-pyrrolidine-1-carboxylic acid tert-butyl ester;

$N^3$-[2,6-Dichloro-4'-(2-methoxy-ethoxy)-biphenyl-4-yl]-1H-[1,2,4]triazole-3,5-diamine $N^3$-[6-Chloro-4'-((R)-1-pyrrolidin-2-ylmethoxy)-2-trifluoromethyl-biphenyl-4-yl]-1H-[1,2,4]triazole-3,5-diamine;

(S)-2-[4'-(5-Amino-1H-[1,2,4]triazol-3-ylamino)-2',6'-dichloro-biphenyl-4-yloxymethyl]-pyrrolidine-1-carboxylic acid tert-butyl ester;

$N^3$-[2,6-Dichloro-4'-(2-morpholin-4-yl-ethoxy)-biphenyl-4-yl]-1H-[1,2,4]triazole-3,5-diamine;

3-[4'-(5-Amino-1H-[1,2,4]triazol-3-ylamino)-2',6'-dichloro-biphenyl-4-yloxy]-propane-1,2-diol;

$N^3$-[2,6-Dichloro-4'-(3-morpholin-4-yl-propoxy)-biphenyl-4-yl]-1H-[1,2,4]triazole-3,5-diamine;

$N^3$-[2,6-Dichloro-4'-(pyridin-2-ylmethoxy)-biphenyl-4-yl]-1H-[1,2,4]triazole-3,5-diamine;

[4'-(5-Amino-1H-[1,2,4]triazol-3-ylamino)-2',6'-dichloro-biphenyl-4-yloxy]-acetic acid;

$N^3$-(2,6-Dichloro-4'-fluoro-biphenyl-4-yl)-1H-[1,2,4]triazole-3,5-diamine;

$N^3$-(2,6-Dichloro-2'-fluoro-biphenyl-4-yl)-1H-[1,2,4]triazole-3,5-diamine;

N*3*-(4'-Methanesulfonyl-2-pentafluorosulfur-biphenyl-4-yl)-1H-[1,2,4]triazole-3,5-diamine $N^3$-[2,6-Dichloro-4'-(1,1-dioxo-$\lambda^6$-isothiazolidin-2-yl)-biphenyl-4-yl]-H-[1,2,4]triazole-3,5-diamine;

N-[4'-(5-Amino-1H-[1,2,4]triazol-3-ylamino)-6'-chloro-2'-trifluoromethyl-biphenyl-3-yl]-methanesulfonamide;

4'-(5-Amino-1H-[1,2,4]triazol-3-ylamino)-6'-chloro-3-fluoro-2'-trifluoromethyl-biphenyl-4-carboxylic acid methylamide;

4'-(5-Amino-1H-[1,2,4]triazol-3-ylamino)-6'-chloro-4-fluoro-2'-trifluoromethyl-biphenyl-3-carboxylic acid methylamide;

4'-(5-Amino-1H-[1,2,4]triazol-3-ylamino)-6'-chloro-3-fluoro-2'-trifluoromethyl-biphenyl-4-carboxylic acid (2-hydroxy-ethyl)-amide;

4'-(5-Amino-1H-[1,2,4]triazol-3-ylamino)-6'-chloro-4-fluoro-2'-trifluoromethyl-biphenyl-3-carboxylic acid (2-hydroxy-ethyl)-amide;

4'-(5-Amino-1H-[1,2,4]triazol-3-ylamino)-2'-chloro-6'-trifluoromethyl-biphenyl-4-sulfonic acid oxetan-3-yl-amide; and 4'-(5-Amino-1H-[1,2,4]triazol-3-ylamino)-6'-chloro-4-methoxy-2'-trifluoromethyl-biphenyl-3-sulfonic acid (1-isopropyl-piperidin-4-yl)-amide, or a pharmaceutically acceptable salt thereof.

13. A pharmaceutical composition, comprising a therapeutically effective amount of a compound of claim 1, or a pharmaceutically acceptable salt thereof, and a pharmaceutically acceptable excipient.

14. A pharmaceutical composition, comprising a therapeutically effective amount of a compound of claim 12, or a pharmaceutically acceptable salt thereof, and a pharmaceutically acceptable excipient.

15. A method for treating a Hepatitis C Virus (HCV) infection, comprising the step of administering to a patient in need thereof a therapeutically effective amount of a compound of claim 1 or a pharmaceutically acceptable salt thereof.

16. The method of claim 15, further comprising the step administering a combination of antiviral agents that inhibits replication of HCV.

17. The method of claim 15, further comprising the step of administering an immune system modulator or an antiviral agent that inhibits replication of HCV, or a combination thereof.

18. The method of claim 17, wherein the immune system modulator is an interferon or a chemically derivatized interferon.

19. The method of claim 17, wherein the antiviral agent is selected from the group consisting of a HCV protease inhibitor, a HCV polymerase inhibitor, a HCV helicase inhibitor and a HCV NS5A inhibitor, or any combination thereof.

* * * * *